US012667615B2

(12) United States Patent
Robinson

(10) Patent No.: US 12,667,615 B2
(45) Date of Patent: *Jun. 30, 2026

(54) TREATMENT FOR BONE DISEASES

(71) Applicant: UCB PHARMA S.A., Brussels (BE)

(72) Inventor: Martyn K. Robinson, Shaftesbury (GB)

(73) Assignee: UCB PHARMA S.A., Brussels (BE)

( * ) Notice: Subject to any disclaimer, the term of this patent is extended or adjusted under 35 U.S.C. 154(b) by 19 days.

This patent is subject to a terminal disclaimer.

(21) Appl. No.: 18/406,593

(22) Filed: Jan. 8, 2024

(65) Prior Publication Data

US 2024/0269274 A1 Aug. 15, 2024

Related U.S. Application Data

(63) Continuation of application No. 17/020,108, filed on Sep. 14, 2020, now Pat. No. 11,896,667, which is a continuation of application No. 15/887,299, filed on Feb. 2, 2018, now Pat. No. 10,799,583, which is a continuation of application No. 13/934,433, filed on Jul. 3, 2013, now Pat. No. 9,925,260.

(60) Provisional application No. 61/782,072, filed on Mar. 14, 2013, provisional application No. 61/668,210, filed on Jul. 5, 2012.

(51) Int. Cl.

| | |
|---|---|
| ***A61K 39/395*** | (2006.01) |
| ***A61K 33/42*** | (2006.01) |
| ***A61K 45/06*** | (2006.01) |
| ***A61P 19/08*** | (2006.01) |
| ***C07K 16/22*** | (2006.01) |
| *A61K 39/00* | (2006.01) |
| *C07K 16/18* | (2006.01) |

(52) U.S. Cl.

CPC .......... *A61K 39/3955* (2013.01); *A61K 33/42* (2013.01); *A61K 45/06* (2013.01); *A61P 19/08* (2018.01); *C07K 16/22* (2013.01); *A61K 2039/505* (2013.01); *C07K 16/18* (2013.01); *C07K 2317/94* (2013.01)

(58) Field of Classification Search

CPC ..... A61K 39/3955; C07K 16/22; A61P 19/08; A61P 19/10

See application file for complete search history.

(56) References Cited

U.S. PATENT DOCUMENTS

| | | | |
|---|---|---|---|
| 4,331,647 | A | 5/1982 | Goldenberg |
| 4,376,110 | A | 3/1983 | David et al. |
| 4,411,993 | A | 10/1983 | Gillis |
| 4,427,115 | A | 1/1984 | Laipply |
| 4,543,439 | A | 9/1985 | Frackelton, Jr. et al. |
| RE32,011 | E | 10/1985 | Zimmerman et al. |
| 4,837,440 | A | 6/1989 | Burtscher et al. |
| 4,902,614 | A | 2/1990 | Wakabayashi et al. |
| 5,070,108 | A | 12/1991 | Margolis |
| 5,145,684 | A | 9/1992 | Liversidge et al. |
| 5,223,409 | A | 6/1993 | Ladner et al. |
| 5,399,363 | A | 3/1995 | Liversidge et al. |
| 5,453,492 | A | 9/1995 | Butzow et al. |
| 5,466,468 | A | 11/1995 | Schneider et al. |
| 5,543,158 | A | 8/1996 | Gref et al. |
| 5,552,157 | A | 9/1996 | Yagi et al. |
| 5,565,213 | A | 10/1996 | Nakamori et al. |
| 5,567,434 | A | 10/1996 | Szoka, Jr. |
| 5,571,714 | A | 11/1996 | Dasch et al. |
| 5,627,052 | A | 5/1997 | Schrader |
| 5,641,515 | A | 6/1997 | Ramtoola |
| 5,698,426 | A | 12/1997 | Huse |
| 5,738,868 | A | 4/1998 | Shinkarenko |
| 5,780,263 | A | 7/1998 | Hastings et al. |
| 5,795,587 | A | 8/1998 | Gao et al. |
| 5,795,965 | A | 8/1998 | Tsuchiya et al. |
| 5,811,238 | A | 9/1998 | Stemmer et al. |
| 5,830,721 | A | 11/1998 | Stemmer et al. |
| 5,837,458 | A | 11/1998 | Minshull et al. |
| 5,877,397 | A | 3/1999 | Lonberg et al. |

(Continued)

FOREIGN PATENT DOCUMENTS

| | | | |
|---|---|---|---|
| JP | 4-141095 | B2 | 8/2008 |
| JP | 2008539726 | A | 11/2008 |

(Continued)

OTHER PUBLICATIONS

A diagram of a relevant part of the human genome (D64), citation in Appeal, European Patent No. 1133558, dated Apr. 15, 2010.

Abbas et al. (Eds.), Cellular and Molecular Immunology, Third Edition, Section II, p. 54 (1997).

Alberts et al. (Eds.), Moelcular Biology of the Cell, Third Edition, Chapter 23, p. 1212 (1994).

(Continued)

*Primary Examiner* — Xiaozhen Xie

(74) *Attorney, Agent, or Firm* — MARSHALL, GERSTEIN & BORUN LLP

(57) ABSTRACT

The invention relates to the treatment of bone disorders. In particular, the invention is directed to the use of a dosing holiday to help overcome the resistance to anti-sclerostin antibodies which develops over time when a plurality of doses of antibody are given to a subject. By giving the subject to be treated such a dosing holiday, the subject may subsequently display an increased response to a subsequent dose of the anti-sclerostin antibody. The subject may be given multiple cycles of a batch of at least two doses of anti-sclerostin antibody and a dosing holiday. In some instances, the subject may be monitored to help determine when to give the dosing holiday. Further, the subject may be given a different treatment for the bone disorder during the dosing holiday from the anti-sclerostin antibody.

13 Claims, 177 Drawing Sheets

Specification includes a Sequence Listing.

(56) References Cited

U.S. PATENT DOCUMENTS

| | | | |
|---|---|---|---|
| 6,015,801 | A | 1/2000 | Daifotis et al. |
| 6,054,561 | A | 4/2000 | Ring |
| 6,057,421 | A | 5/2000 | Muller et al. |
| 6,117,911 | A | 9/2000 | Grainger et al. |
| 6,133,426 | A | 10/2000 | Gonzalez et al. |
| 6,180,370 | B1 | 1/2001 | Queen et al. |
| 6,207,153 | B1 | 3/2001 | Dan et al. |
| 6,395,511 | B1 | 5/2002 | Brunkow et al. |
| 6,489,445 | B1 | 12/2002 | Brunkow et al. |
| 6,495,736 | B1 | 12/2002 | Brunkow et al. |
| 6,703,199 | B1 | 3/2004 | Koide |
| 6,803,453 | B1 | 10/2004 | Brunkow et al. |
| 6,806,055 | B2 | 10/2004 | Berman et al. |
| 6,815,201 | B2 | 11/2004 | Pinter |
| 6,818,748 | B2 | 11/2004 | Fulton et al. |
| 7,192,583 | B2 | 3/2007 | Brunkow et al. |
| 7,226,902 | B2 | 6/2007 | Winkler et al. |
| 7,381,409 | B2 | 6/2008 | Winkler et al. |
| 7,572,899 | B2 | 8/2009 | Brunkow et al. |
| 7,578,999 | B2 | 8/2009 | Winkler et al. |
| 7,592,429 | B2 | 9/2009 | Paszty et al. |
| 7,642,238 | B2 | 1/2010 | Shaughnessy |
| 7,744,874 | B2 | 6/2010 | Korytko et al. |
| 7,758,858 | B2 | 7/2010 | Brunkow et al. |
| 7,868,134 | B2 | 1/2011 | Winkler et al. |
| 7,872,106 | B2 | 1/2011 | Paszty et al. |
| 8,003,108 | B2 | 8/2011 | Lu et al. |
| 8,017,120 | B2 | 9/2011 | Padhi et al. |
| 8,178,099 | B2 | 5/2012 | Ellies |
| 2003/0166247 | A1 | 9/2003 | Brunkow et al. |
| 2003/0186915 | A1 | 10/2003 | Pan et al. |
| 2003/0229041 | A1 | 12/2003 | Sutherland et al. |
| 2004/0009535 | A1 | 1/2004 | Brunkow et al. |
| 2004/0023356 | A1 | 2/2004 | Krumlauf et al. |
| 2004/0058321 | A1 | 3/2004 | Brunkow et al. |
| 2004/0141875 | A1 | 7/2004 | Doshi |
| 2004/0146888 | A1 | 7/2004 | Paszty et al. |
| 2004/0158045 | A1 | 8/2004 | Brunkow et al. |
| 2005/0014650 | A1 | 1/2005 | Seitz et al. |
| 2005/0085418 | A1 | 4/2005 | Winkler et al. |
| 2005/0106683 | A1 | 5/2005 | Winkler et al. |
| 2005/0238646 | A1 | 10/2005 | Ledbetter et al. |
| 2006/0233801 | A1 | 10/2006 | Brunkow et al. |
| 2007/0072797 | A1 | 3/2007 | Robinson et al. |
| 2007/0110747 | A1 | 5/2007 | Paszty et al. |
| 2007/0292444 | A1 | 12/2007 | Krumlauf et al. |
| 2008/0182788 | A1 | 7/2008 | Brunkow et al. |
| 2008/0234219 | A1 | 9/2008 | Brunkow et al. |
| 2009/0074763 | A1* | 3/2009 | Padhi ........................ A61P 5/00 424/139.1 |
| 2009/0117118 | A1 | 5/2009 | Winkler et al. |
| 2009/0304713 | A1 | 12/2009 | Paszty et al. |
| 2010/0015665 | A1 | 1/2010 | Latham et al. |
| 2010/0036091 | A1 | 2/2010 | Robinson et al. |
| 2010/0151524 | A1 | 6/2010 | Winkler et al. |
| 2011/0044978 | A1 | 2/2011 | Ke |
| 2011/0097342 | A1 | 4/2011 | Paszty et al. |
| 2011/0150866 | A1 | 6/2011 | Brunkow et al. |

FOREIGN PATENT DOCUMENTS

| | | | | |
|---|---|---|---|---|
| WO | WO-91/013152 | | 9/1991 | |
| WO | WO-91/013152 | A1 | 9/1991 | |
| WO | WO-1992/001047 | | 1/1992 | |
| WO | WO-1992/001047 | A1 | 1/1992 | |
| WO | WO-92/002551 | A1 | 2/1992 | |
| WO | WO-92/006693 | | 4/1992 | |
| WO | WO-92/006693 | A1 | 4/1992 | |
| WO | WO-95/030003 | A2 | 11/1995 | |
| WO | WO-1996/004375 | | 2/1996 | |
| WO | WO-1996/004375 | A1 | 2/1996 | |
| WO | WO-98/021335 | A1 | 5/1998 | |
| WO | WO-99/003996 | A1 | 1/1999 | |
| WO | WO-99/006554 | A2 | 2/1999 | |
| WO | WO-99/015556 | A1 | 4/1999 | |
| WO | WO-2000/032773 | | 6/2000 | |
| WO | WO-2000/044777 | | 8/2000 | |
| WO | WO-2000/044777 | A1 | 8/2000 | |
| WO | WO-00/075317 | A2 | 12/2000 | |
| WO | WO-01/064885 | A1 | 9/2001 | |
| WO | WO-01/092308 | A2 | 12/2001 | |
| WO | WO-01/098491 | A2 | 12/2001 | |
| WO | WO-2002/024888 | | 3/2002 | |
| WO | WO-02/030463 | A2 | 4/2002 | |
| WO | WO-03/050513 | A2 | 6/2003 | |
| WO | WO-03/087763 | A2 | 10/2003 | |
| WO | WO-03/106657 | A2 | 12/2003 | |
| WO | WO-2004/082608 | A2 | 9/2004 | |
| WO | WO-2004/094477 | A1 | 11/2004 | |
| WO | WO-2004/098491 | A2 | 11/2004 | |
| WO | WO-2005/003158 | A2 | 1/2005 | |
| WO | WO-2005/014650 | A2 | 2/2005 | |
| WO | WO-2005/115356 | A2 | 12/2005 | |
| WO | WO-2006/015373 | A2 | 2/2006 | |
| WO | WO-2006/065746 | A2 | 6/2006 | |
| WO | WO-2006/102070 | A2 | 9/2006 | |
| WO | WO-2006/119062 | A2 | 11/2006 | |
| WO | WO-2006/119107 | A2 | 11/2006 | |
| WO | WO-2007/080129 | A1 | 7/2007 | |
| WO | WO-2008/061013 | A2 | 5/2008 | |
| WO | WO-2008/092894 | A1 | 8/2008 | |
| WO | WO-2008/115732 | A2 | 9/2008 | |
| WO | WO-2008/133722 | A2 | 11/2008 | |
| WO | WO-2009/039175 | A2 | 3/2009 | |
| WO | WO-2009047356 | A1 * | 4/2009 | .............. A61P 43/00 |
| WO | WO-2009/056634 | A2 | 5/2009 | |
| WO | WO-2009/079471 | A1 | 6/2009 | |
| WO | WO-2009/131553 | A2 | 10/2009 | |
| WO | WO-2009/149189 | A2 | 12/2009 | |
| WO | WO-2010/100179 | A2 | 9/2010 | |
| WO | WO-2010/100200 | A2 | 9/2010 | |
| WO | WO-2010/115932 | | 10/2010 | |
| WO | WO-2010/115932 | A1 | 10/2010 | |
| WO | WO-2010/130830 | A2 | 11/2010 | |
| WO | WO-2012/028683 | | 3/2012 | |
| WO | WO-2012/028683 | A1 | 3/2012 | |
| WO | WO-2012/058393 | A2 | 5/2012 | |

OTHER PUBLICATIONS

Albertsen et al., A physical map and candidate genes in the BRCA1 region on chromosome 17q12-21. *Nat. Genet.*, 7:472-9 (1994).

Alting-Mees et al., Monoclonal antibody expression libraries: A rapid alternative to hybridomas. *Strat. Molec. Biol.*, 3:1-9 (1990).

Alves et al., Sclerosteosis: A marker of Dutch ancestry? *Rev. Bras. Genet.*, 4:825-34 (1982).

Andersson et al., Molecular genetics and pathophysiology of 17β-hydroxysteriod dehydrogenase 3 deficiency. *J. Clin. Endrocrinol. Metab.*, 81(1): 130-6 (1996).

Angal et al., A single amino acid substitution abolishes the heterogeneity of chimeric mouse/human (IgG4) antibody. *Mol. Immunol.*, 30(1):105-8 (1993).

Annex EW6 to Declaration filed in connection with the European Patent EP 1133558 Opposition, Expert opinion of Prof. Dr. Edgar Wingender, dated Sep. 24, 2009.

Annex regarding the purported relevance of gene/peptides mentioned by Professor Arnett.

Anonymous, Amgen presents denosumab and sclerostin antibody data at American Society for Bone and Mineral Research Annual Meeting. Amgen Media Press Release. <www.amgen.com/media/media_pr_detail.jsp?releaseID=907028> (2006).

Anonymous, UCB on track. UCB News <http://hugin.info/133973/R/1176122/233395.pdf> (2007).

Arnett et al., Effect of pH on bone resorption by rat osteoclasts in vitro. *Endocrinol.*, 119(1): 119-124 (1986).

Attana Application Example, cited in Opposition against European Patent No. 1721979 by Opponent: Novartis AG, dated Jun. 15, 2011.

Avsian-Kretchmer et al., Comparative genomic analysis of the eight-membered ring cystine knot-containing bone morphogenetic protein antagonists. *Molec. Endocrinol.*, 18(1):1-12 (2004).

(56) References Cited

OTHER PUBLICATIONS

Babcook et al., A novel strategy for generating monoclonal antibodies from single, isolated lymphocytes producing antibodies of defined specificities, *Proc. Natl. Acad. Sci. USA*, 93:7843-8 (1996).
Baines et al., Purification of immunoglobulin G (IgG). *Meth. Molec. Biol.*, 10:79-104 (1992).
Balemans et al., Extracellular regulation of BMP signaling in vertebrates: A cocktail of modulators. *Dev. Biol.*, 250:231-50 (2002).
Balemans et al., Increased bone density in sclerosteosis is due to the deficiency of a novel secreted protein (SOST). *Hum. Mol. Genet.*, 10:537-43 (2001).
Balemans et al., Localization of the gene for sclerosteosis to the van Buchem disease-gene region on chromosome 17q12-q21. *Am. J. Hum. Genet.*, 64:1661-9 (1999).
Balint et al., Antibody engineering by parsimonious mutagenesis. *Gene*, 137(1):109-18 (1993).
Bateman et al., Granulins: The structure and function of an emerging family of growth factors. *J. Endocrinol.*, 158: 145-51 (1998).
Baxevanis (Ed.) et al., Bioinformatics: A practical guide to the analysis of genes and proteins, John Wiley & Sons, Inc. p. 234 (1998).
Beighton et al., Heterzygous manifestations in the heritable disorders of the skeleton. *Pediatr. Radiol.*, 27:397-401 (1997).
Beighton et al., The clinical features of sclerosteosis. *Clin. Genet.*, 25:175-81 (1984).
Beighton et al., The syndromic status of sclerosteosis and van Buchem disease. *Ann. Intern. Med.*, 84:393-7 (1976).
Bellows et al., Parathyroid hormone reversibly suppresses the differentiation of osteoprogenitor cells in functional osteoblasts. *Endocrinol.*, 127(6):3111-6 (1990).
Bendayan, Possibilities of false immunocytochemical results generated by the use of monoclonal antibodies: The example of the anti-proinsulin antibody. *J. Histochem. Cytochem.*, 43(9):881-6 (1995).
Bendig, Humanization of rodent monoclonal antibodies by CDR grafting. *Methods*, 8:83-93 (1995).
Bergfeld et al., Release of ATP from human erythrocytes in response to a brief period of hypoxia and hypercapnia. *Cardiovascular Res.*, 26: 40-7 (1992).
Berman et al., The Protein Data Bank. *Acta. Cryst.*, 58(1):899-907 (2002).
Bigger versions of Figures from Declaration of Professor Teresa Attwood, citation in Appeal, European Patent No. 1133558, dated Apr. 13, 2010.
Bird et al., Single-Chain Antigen-Binding Proteins. *Science*, 242:423-6 (1988).
Birren et al., EMBL Sequence Database Accession No. AC003098. 2, Nov. 14, 1997.
Bishop (Ed.), Guide to Human Genome Computing, Second Edition, Academic Press, Chapter 1: Introduction to human genome computer via the world wide web, pp. 1-14 (2003).
Black et al., A somatic cell hybrid map of the long arm of human chromosome 17, containing the familial breast cancer ILocus (BRCAI). *Am. J. Hum. Genet.*, 52:702-10 (1993).
Blum et al., Study plan for German students in the summer of 1998, University Bioinformatik lecture announcement (1998).
Boden et al., Glucocorticoid-induced differentiation of fetal rat calvarial osteoblasts is mediated by bone morphogenetic protein-6. *Endocrinology*, 138(7):2820-8 (1997).
Boerner et al., Production of antigen-specific human monoclonal antibodies from in vitro-primed human splenocytes. *J. Immunol.*, 147:86-95 (1991).
Bonaldo et al., EMBL Sequence Database Accession No. Al113131, Sep. 4, 1998.
Bonaldo et al., Normalization and subtraction: Two approaches to facilitate gene discovery. *Genome Res.*, 6(9):791-806 (1996).
Bondestam, Ligands & Signaling Components of the Transforming Growth Factor, Helsinki University Biomedical Dissertations (2002).
Bone et al., Effects of denosumab on bone mineral density and bone turnover in postmenopausal women. *J. Clin. Endocrinol. Metab.* 93: 2149-57 (2008).
Bork et al., Go hunting in sequence databases by watch out for the traps. *Trends Genet.* 12: 425-7 (1996).
Bos et al., ras ongogenes in human cancer: A review, *Cancer Res.*, 49: 4682-9 (1989).
Bost et al., Antibodies against a peptide sequence within the HIV envelope protein crossreacts with human interleukin-2. *Immunol. Invest.*, 17(6&7):577-86 (1988).
Bostrom et al., Ligand and signaling components of the transforming growth factor β family. *J. Orth. Res.*, 13:357-67 (1995).
Bottcher et al., NCBI Sequence Database Accession No. NM_004329, Aug. 2, 2009.
Bouffard et al., A physical map of human chromosome 7: An integrated YAC contig map with average STS spacing of 79 kb. *Genome Res.*, 7: 673-92 (1997).
Bowie et al., A method to identify protein sequences that fold into a known three-dimensional structure. *Science*, 253:164-70 (1991).
Bowie et al., Deciphering the message in protein sequences: Tolerance to amino acid substitutions. *Science*, 247(4948):1306-10 (1990).
Bradley et al., Modifying the mouse: Design and desire. *Bio/Technology*, 10:534-9 (1992).
Brandao-Burch et al., Acidosis inhibits bone formation by osteoblasts in vitro by preventing mineralization. *Calcif. Tissue Int.*, 77: 167-74 (2005).
Brenner et al., Population statistics of protein structures: Lessons from structural classifications. *Curr. Op. Struct. Biol.*, 7(3):369-76 (1997).
Brommage et al., High-throughput screening of mouse gene knockouts identifies established and novel skeletal phenotypes, Bone Res., 14034 (2014).
Brown, Hybridization Analysis of DNA Blots, *Current Protocols in Protein Science*, 13:A.4H.1-A.4H.9 (1990).
Brown, Hybridization Analysis of DNA Blots, *Current Protocols in Protein Science*, 2.10.1-2.10.16 (2000).
Bruggemann et al., Production of human antibody repertoires in transgenic mice. *Curr. Opin. Biotechnol.*, 8:455-8 (1997).
Brunkow et al., Bone dysplasia sclerosteosis results from loss of the SOST gene product, a novel cysteine knot-containing protein. *Am. J. Hum. Genet.*, 68:577-89 (2001).
Burton et al., Human antibodies from combinatorial libraries. *Adv. Immunol.*, 57:191-280 (1994).
Butcher et al., Increased salt concentration reversibly destabilizes p53 quaternary structure and sequence-specific DNA binding. *Biochem. J.*, 298: 513-6 (1994).
Byrne et al., CD4+CD45RBHi T cell transfer induced colitis in mice is accompanied by osteopenia which is treatable with recombinant human osteoprotegerin. *Gut*, 54:78-86 (2005).
Campbell et al., Totipotency or multipotentiality of cultured cells: Applications and progress. *Theriogenology*, 47:63-72 (1997).
Caverzasio et al., Characteristics and regulation of Pi transport in osteogenic cells for bone metabolism. *Kindey Int.*, 49: 975-80 (1996).
Chan et al., A new paradigm in the treatment of osteoporosis: Wnt pathway proteins and their antagonists. *Curr. Opin. Invest. Drugs.*, 8:293-8 (2007).
Chandran et al., Recent trends in drug delivery systems: Liposomal drug delivery system—Preparation and characterisation. *Indian J. Exp. Biol.*, 35(8):801-9 (1997).
Charlier et al., A pore mutation in a novel KQT-like potassium channel gene in an idiopathic epilepsy family. *Nat. Genet.*, 18:53-5 (1998).
Chenu et al., Glutamate receptors are expressed by bone cells and are involved in bone resorption. *Bone*, 22(4): 295-9 (1998).
Chou et al., Empirical predication of protein conformation. *Ann. Rev. Biochem.*, 47:251-76 (1979).
Chou et al., Prediction of the secondary structure of proteins from their amino acid sequence. *Adv. Enzymol. Relat. Areas Mol. Biol.*, 47:145-8 (1978).
Clark, Antibody humanization: A case of the 'Emperor's New Clothes'?. *Immunology Today*, 21(8):397-402 (2000).

(56) References Cited

OTHER PUBLICATIONS

Cogan et al., NCBI Sequence Database Accession No. NM_033346, Jul. 19, 2005.
Collins, Identifying human disease genes by positional cloning. *The Harvey Lectures*, Series 86:149-64 (1992).
Collins, Positional cloning moves from perditional to traditional. *Nat. Genet.*, 9:347-50 (1995).
Colman, Effects of amino acid sequence changes on antibody-antigen interactions. *Biomolec.Res. Inst.*,55:33-6 (1994).
Communication from the European Patent Office providing an "Observation by a Third Party according to Article 115 EPC" submitted in connection with the Opposition to European Patent No. 1 133 558, dated Dec. 3, 2008.
Cook et al., Structural basis for a functional antagonist in the transforming growth factor β superfamily. *J. Biol. Chem.*, 280(48):40177-86 (2005).
Cormier, Markers of bone metabolism. *Curr. Opin. in Rheu.*, 7:243-8 (1995).
Cosman et al., Roosozumab Treatment in Postmenopausal Women with Osteoporosis, N. Engl. J. Med., 375(16):1532-4 (2016).
Couvreur et al., Polyalkylcyanoacrylates as colloidal drug carriers. *Crit. Rev. Ther. Drug Carrier Syst.*, 5(1):1-20 (1988).
Craig et al., Sclerostin binds and regulates the activity of cysteine rich protein 61. *Biochem. Biophys. Res. Commun.*, 293(1): 36-40 (2010).
Craig et al., Sclerostin-erbB-3 interactions: Modulation of erbB-3 activity by sclerostin. *Biochem. Biophys. Res. Commun.*, 402: 421-4 (2010).
Crameri et al., DNA shuffling of a family of genes from diverse species accelerates directed evolution. *Nature*, 391:288-91 (1998).
Dall'Acqua et al., Antibody humanization by framework shuffling. *Methods*, 36(1):43-60 (2005).
Davies, et al., Affinity improvement of single antibody VH domains: Residues in all three hypervariable regions affect antigen binding. *Immunotechnology*, 2(3): 169-79 (1996).
De Jong et al., Evolution of the α-crystallin/small heat-shock protein family. *Mol. Biol. Evol.*, 10(1): 103-26 (1993).
Dean et al., Matrix vesicles produced by osteoblast-like cells in culture become significantly enriched in proteoglycan-degrading metalloproteinases after addition of β-glycerophosphate and ascorbic acid. *Calcif. Tissue*, 54: 399-408 (1994).
Declaration filed in connection with the European Patent EP 1133558 Opposition, Expert opinion of Dr. Auristela Freire de Paes Alves, Ph.D., dated Sep. 9, 2009.
Declaration filed in connection with the European Patent EP 1133558 Opposition, Expert opinion of Dr. Walter Sebald, dated Sep. 24, 2009.
Declaration filed in connection with the European Patent EP 1133558 Opposition, Expert opinion of Prof. Dr. Edgar Wingender, dated Sep. 24, 2009.
Declaration filed in connection with the European Patent EP 1133558 Opposition, Expert opinion of Prof. Dr. Thomas Muller, dated Sep. 23, 2009.
Declaration of Alistair J. Henry, citation in Appeal, European Patent No. 1133558, dated Apr. 2, 2010.
Declaration of Dr. Martyn Robinson, including C.V., and Figure A with experimental results, filed on EP 1373322.5 dated Apr. 8, 2019.
Declaration of Dr. Martyn Robinson, submitted in Opposition to European Patent No. 1133558.
Declaration of Dr. Mary E. Brunkow, submitted in Opposition to European Patent No. 1133558.
Declaration of Dr. Raymond Dalgleish dated Dec. 8, 2011, citation in Appeal, European Patent No. 1133558.
Declaration of Prof. Edgar Wingender filed in connection with that Opposition regarding European Patent EP 1133558 B1, dated Mar. 10, 2011.
Declaration of Professor Teresa Attwood, citation in Appeal, European Patent No. 1133558, dated Apr. 13, 2010.
Declaration of Tim Arnett, citation in Appeal, European Patent No. 1133558, dated Apr. 2, 2010.
Delmas et al., The use of biochemical markers of bone turnover in osteoporosis. Osteoporosis International., Suppl. 6:S2-17 (2000).
Diagram of the candidate interval, citation by Propriator in Opposition against European Patent No. 1721979 on Feb. 20, 2012.
Ducy et al., 5-HT and bone biology. *Curr. Opin. Pharmacol.*, 11: 34-8 (2011).
Ducy et al., Genetic control of cell differentiation in the skeleton. *Curr. Opin. Cell Biol.*, 10: 614-9 (1998).
Durham et al., Alterations in insulin-like growth factor (IGF)-dependent IGF-binding protein-4 proteolysis in transformed osteoblastic cells. *Endocrinology*, 136(4):1374-80 (1995).
Ebara et al., Mechanism for the action of bone morphogenetic proteins and regulation of their activity. *Spine*, 27(165):S10-5 (2002).
Eddleston et al., A short treatment with an antibody to sclerostin can inhibit bone loss in an ongoing model of colitis., J. Bone Miner. Res., 24:1662-71 (2009).
Eli Lilly Statement of Grounds of Appeal, Opposition to European Patent Application No. 1133558 B1, dated Sep. 28, 2009.
Eli Lilly, Biacore experiment comparison results, Setup assay to measure BMP binding to captured SOST, referenced on p. 41 of reference C193, dated Sep. 28, 2009.
Epstein et al., Endocrine function in sclerosteosis. *S. Afr. Med. J.*, 55:1105-10 (1979).
European Patent Office Communication, Opposition to European Patent No. 1133558, dated Nov. 4, 2008.
European Patent Office, "Opinion of the Enlarged Board of Appeal dated Dec. 1992 G 1/92", available from [http://documents.epo.org/projects/babylon/eponet.nsf/0/907016FA57B46FD0C12572C8006CD2E2/$File/g920001.pdf], cited Jun. 15, 2011.
Expert Opinion from Dr. Catalina Lopez-Correa, submitted in Opposition to European Patent No. 1133558, dated Mar. 6, 2009.
Expert opinion of Professor Dr.-Ing Ulrich Vollrath, citation in Appeal of European Patent No. 1133558, dated Apr. 12, 2005.
Extract from Sigma Aldrich catalogue, cited in Opposition against European Patent No. 1721979 by Opponent: Laudens, dated Jun. 15, 2011.
Extract of NCT00896532 from clinicaltrials.gov showing the original clinical trial protocol of May 7, 2009 compared to the amended clinical trial protocol of Jun. 27, 2012.
Eyre et al., Characterization of aromatase and 17β-hydroxysteroid dehydrogenase expression in rat osteoblastic cells. *J. Bone Miner. Res.*, 13(6): 996-1004 (1998).
Finkelstein et al., J. Clin. Endocrinol. Metab. 94)7):2495-2501 (Jul. 2009).
Foster et al., Establishment of interference in osteoblasts by an osteopetrosis-inducing Avian Leukosis virus. *Virology*, 205: 376-8 (1994).
Fouser et al., Feedback regulation of collagen gene expression: A Trojan horse approach. *Proc. Natl. Acad. Sci. USA*, 88: 10158-62 (1991).
Frost et al., On the rat model of human osteopenias and osteoporoses. *Bone and Mineral*, 18:227-36 (1992).
Fujiwara et al., GenBank Sequence Database Accession No. D79813, Feb. 9, 1996.
Gardner et al., Bone mineral density in sclerosteosis; Affected individuals and gene carriers. *J. Clin. Endocrinol. Metab.*, 90(12): 6392-5 (2005).
Gavarini et al., Opposite effects of PSD-95 and MPP3 Pdz proteins on serotonin 5-hydroxytryptamine2C receptor desensitization and membrane stability. *Molec. Biol.*, 17: 4619-31 (2006).
Gazzerro et al., Bone morphogenetic proteins induce the expression of noggin which limits their activity in cultured rat osteoblasts. *J. Clin. Invest.*, 102(12):2106-14 (1998).
Gazzerro et al., Potential drug targets within bone morphogenetic protein signaling pathways. *Curr. Opin. Pharmacol.*, 7: 325-3 (2007).
Geissler et la., Male pseudohermaphroditism caused by mutations of testicular 17β-hydroxysteroid hehydrogenase 3. *Nat. Genetics*, 7: 34-9 (1994).

(56) References Cited

OTHER PUBLICATIONS

Gencic et al., Conservative amino acid substitution in the myelin proteolipid protein of Jimpymsd mice. *J. Neurosci.*, 10(1):117-24 (1990).
Getts, Have we overestimated the benefit of human(ized) antibodies?, (2010).
Geysen et al., Cognitive features of continuous antigenic determinants. *J. Molec. Recog.*, 1(1):32-41 (1988).
Gitelman et al., Vgr-1/BMP-6 induces osteoblastic differentiation of pluripotential mesenchymal cells. *Cell Growth & Differentiation*, 6:827-36 (1995).
Glasky et al., Stability of specific immunoglobulin secretion by EBV-transformed lymphoblastoid cells and human-murine heterohybridomas. *Hybridoma*, 8:377-89 (1989).
Gowen et al., Actions of recombinant human $\gamma$-interferon and tumor necrosis factor a on the proliferation and osteoblastic characteristics of human trabecular bone cells in vitro. *Arthritis Rheumatism*, 31(12): 1500-7 (1988).
Graner et al., Splice variants of the *Drosophila* PS2 integrins differentially interact with RGD-containing fragments of the extracellular proteins tiggrin, Ten-m and D-laminin $\alpha 2$. *J. Biol. Chem.*, 273(29): 18235-41 (1998).
Green et al., Antigen-specific human monoclonal antibodies from mice engineered with human Ig heavy and light chain YACs. *Nat. Genet.*, 7:13 (1994).
Green et al., Cytosolic pH regulation in osteoblasts. *J. Gen. Physiol.*, 95: 121-45 (1990).
Greene et al., Screening Recombinant DNA Libraries. *Current Protocols in Molecular Biology*, Ch. 6(1) (1990).
Gribskov et al., Profile analysis. *Meth. Enzym.*, 183:146-59 (1990).
Gribskov et al., Profile analysis: Detection of distantly related proteins. *Proc. Nat. Acad. Sci. USA*, 84(13):4355-8 (1987).
Groeneveld et al., Bone morphogenetic proteins in human bone regeneration. *Eur. J. Endocrinol.*, 142:9-21 (2000).
Gronthos et al., Integrin expression and function on human osteoblast-like cells. *J. Bone Miner. Res.*, 12(8): 1189-97 (1997).
Groppe et al., Structural basis of BMP signalling inhibition by the cystine knot protein noggin. *Nature*, 420:636-42 (2002).
Guinness-Hey, Increased trabecular bone mass in rats treated with human synthetic parathyroid hormone. *Metab. Bone Dis. Relat. Res.*, 5:177-81 (1984).
Hardling et al., The immunogenicity of humanized and fully human antibodies: Residual immunogenicity resides in the CDR regions, mAbs, 2(3):256-65 2010.
Harlow et al., Antibodies: A Laboratory Manual, Cold Spring Harbor Laboratory, 141-157 (1988).
Harris, Processing of C-terminal lysine and arginine residues of proteins isolated from mammalian cell culture. *J. Chromatogr.*, 705:129-34 (1995).
Hart et al., Crystal structure of the human T$\beta$R2 ectodomain-TGF-$\beta$3 complex. *Nat. Struc. Biol.*, 9(3):203-8 (2002).
Hay et al., ATCC Cell Line and Hybridomas, American Type Culture Collection, 8th Ed., pp. 149, 258, 428 (1994).
He et al., High-throughput dynamic light scattering method for measuring viscosity of concentrated protein solutions. *Anal. Biochem.*, 399(1): 141-3 (2010).
Heinecke et al., Receptor oligomerization and beyond: A case study in bone morphogenetic proteins, *BMC Biol.*, 7: 59 (2009).
Hill et al., Multiple extracellular signals promote osteoblast survival and apoptosis. *Endocrinology*, 138(9):3849-58 (1997).
Hillier et al., EMBL Sequence Database Accession No. AA393939, May 19, 1997.
Hillier et al., GenBank Sequence Database Accession No. AA393768, Apr. 24, 1997.
Hillier et al., Generation and analysis of 280,000 human expressed sequence tags. *Genome Res.*, 6: 807-28 (1996).
Hilliker et al., Truncation of the amino terminus of PTH alters its anabolic activity on bone in vivo. *Bone*, 19(5): 469-77 (1996).
Hirschhorn, Letter to the Editor: Dominance and Homozygosity in Man. *Am. J. Med. Genetics*, 18: 541 (1984).
Hock et al., Perspective: Osteoblast apoptosis and bone turnover. *J. Bone Miner. Res.*, 16(6):975-84 (2001).
Hoffman et al., BMP Signaling Pathways in Cartilage and Bone Formation, Critical Review in Eukaryotic Gene Expression, 11(1-3):23-45 (2001).
Hoggard et al., Localization of leptin receptor mRNA splice variants in murine peripheral tissues by RT-PCR and in situ hybridization. *Biochem. Biophys. Res. Commun.*, 232: 383-7 (1997).
Holdsworth et al., Dampening of the bone formation response following repeat dosing with sclerostin antibody in mice is associated with up-regulation of Wnt antagonists, Bone, 107:93-103 (2018).
Hollinger et al., Engineered antibody fragments and the rise of single domains. *Nat. Biotech.*, 23(9):1126-36 (2005).
Holm et al., Protein folds and families: Sequence and structure alignments. *Nucl. Acid Res.*, 27(1):244-7 (1999).
Holt, et al., Domain antibodies: proteins for therapy. *Trends Biotechnol.*, 21(11):484-90 (2003).
Hoogenboom et al., By-passing immunisation: Human antibodies from synthetic repertoires of germline VH gene segmens rearranged in vitro. *J. Molec. Biol.*, 227:381-8 (1992).
Hoogewerf et al., Glycosaminoglycans mediate cell surface oligomerization of chemokines. *Biochemistry*, 36: 13570-8 (1997).
Horton et al., Arg-Gly-Asp (RGD) peptides and the anti-vitronectin receptor antibody 23C6 inhibit dentine resorption and cell spreading by osteoclats. *Exp. Cell Res.*, 195: 368-75 (1991).
Hsu et al., The Xenopus dorsalizing factor gremlin indentified a novel family of secreted proteins that antagonize BMP activities. *Molecular Cell*, 1:673-83 (1998).
Hufner et al., Evidence for an osteoblast-activating factor in a patient with peripheral T-cell lymphoma and osteosclerosis. *Klin. Wochenscher.*, 67: 402-7 (1989).
Hulley et al., Inhibition of mitogen-activated protein kinase activity and proliferation of an early osteoblast cell line (MBA 15.4) by dexamethasone: Role of protein phosphatases. *Endocrinol.*, 139(5): 2423-31 (1998).
Huse et al., Generation of a large combinatorial library of the immunoglobulin repertoire in phage lambda. *Science*, 246:1275-81 (1989).
Hwang et al., Use of human germline genes in a CDR homoloy-based approach to antibody humanization. *Methods*, 36(1):35-42 (2005).
Ide et al., GenBank Sequence Database Accession No. BAA19765, Feb. 7, 1999.
Ide et al., GenBank Sequence Datacase Accession No. D89675, Feb. 7, 1999.
Iemura et al., Direct binding of follistatin to a complex of bone-morphogenetic protein and its receptor inhibits ventral and epidermal cell fates in early Xenopus embryo. *Proc. Natl. Acad. Sci. USA*, 95:9337-42 (1998).
Innis et al., Evolutionary trace analysis of TGF-B and related growth factors: Implications for stie-directed mutagenesis. *Protein Engineering*, 13(12):839-47 (2000).
International Search Report and Written Opinion of the European Patent Office, PCT/EP2013/064052, dated Oct. 23, 2013.
Jakobovits et al., Production of antigen-specific human antibodies from mice engineered with human heavy and light chain YACsa. *Ann. N.Y. Acad. Sci.*, 764:525-35 (1995).
Jee et al., Overview: Animal models of osteopenia and osteoporosis. *J. Musculoskel. Neuron. Interact.*, 1:193-207 (2001).
Jilka et al., Increased bone formation by prevention of osteoblast apoptosis with parathyroid hormone. *J. Clin. Invest.*, 104:439-46 (1999).
Jilka et al., Osteoblast programmed cell death (apoptosis): Modulation by growth factors and cytokines. *J. Bone Miner. Res.*, 13(5): 793-802 (1998).
Jones, Progress in protein structure predication. *Curr. Opin. Struct. Biol.*, 7(3):377-387 (1997).
Kabat et al., Sequences of Proteins of Immunological Interest, U.S. Department of Health and Human Services, NIH, USA (1987) (Table of Contents).
Kalu, The ovariectomized rat model of postmenopausal bone loss. *Bone and Mineral*, 15:175-92 (1991).

(56) References Cited

OTHER PUBLICATIONS

Kang et al., Linkage of recognition and replication functions by assembling combinatorial antibody Fab libraries along phage surfaces. *Proc. Natl. Acad. Sci. USA*, 88:4363-6 (1991).
Katagiri et al., The non-osteogenic mouse pluripotent cell line, C3H10T1/2, is induced to differentiate into osteoblastic cells by recombinant human bone morphogenetic protein-2. *Biochem. Biophys. Res. Comm.*, 172(1):295-9 (1990).
Kawabata et al., Signal transduction by bone morphogenetic proteins. *Cytokine and Growth Factor Reviews*, 9(1):49-61 (1998).
Ke et al., Sclerostin and Dickkopf-1 as therapeutic targets in bone disease. *Endocrine Rev.* 33(5): 747-83 (2012).
Keller et al., Molecular recognition of BMP-2 and BMP receptor IA. *Nat. Struct. Mol. Biol.*, 11(5):481-488 (2004).
Kendler et al., OR08-1: Retreatment of Romosozumab after 12 months of Placebo Demonstrates Similar BMD Efficacy Compared with Initial Romosozumab Treatment, Presented at Endocrine Society Meeting in Orlando, Florida (2017).
Khalil, TGF-β: From latent to active. *Microbes and Infection*, 1(15):1255-63 (1999).
Khosla et al., Concise review for primary-care physicians. Treatment pptions for osteoporosis. *Mayo Clin. Proc.*, 70:978-82 (1995).
Kirsch et al., BMP-2 antagonists emerge from alterations in the low-affinity binding epitope for receptor BMPR-II, *EMBO J.* 19(13): 3314-24 (2000).
Kohler et al., Continuous cultures of fused cells secreting antibody of predefined specificity. *Nature*, 256:495 (1975).
Koli et al., Latency, activation, and binding proteins of TGF-. *Microscopy Res. Tech.*, 52:354-62 (2001).
Kopylov et al., The efficacy of shortening the dosing interval to once every six weeks in Chron's patients losing resposing to maintenance does of infliximab, Alimentary Pharmacol, 33(3):349-57 (2010).
Koreth et al., Microsatellites and PCR genomic analysis. *J. Pathology*, 178:239-48 (1996).
Kramer et al., The gapped duplex DNA approach to oligonucleotide-directed mutation construction. *Nucleic Acids Res.*, 12:9441 (1984).
Krause et al., Distinct modes of inhibition by sclerostin on bone morphogenetic protein and Wnt signaling pathways. *J. Biol. Chem.* ,285(53): 41614-26 (2010).
Kunkel et al., Rapid and efficient site-specific mutagenesis without phenoypic selection. *Meth. Enzymol.*, 154:367-82 (1987).
Kunkel, Rapid and efficient site-specific mutagenesis without phenotypic selection. *Proc. Natl. Acad. Sci. USA*, 82:488-92 (1985).
Kurahashi et al., Regions of genomic instability on 22q11 and 11q23 as the etiology for the recurrent constitutional t (11;22). *Hum. Molec. Genet.*, 9: 1665-70 (2000).
Kusu et al., Sclerostin is a novel secreted osteoclast-dervied bone morphogenetic protein antagonist with unique ligand specificity. *J. Biol. Chem.*, 278:24113-7 (2003).
Labat et al., Retroviral expression in mononuclear blood cells isolated from a patient with osteopetrosis (Albers-Schonberg disease). *J. Bone Miner. Res.*, 5(5): 425-35 (1989).
Labat, A new approach to the study of the origin of genetic disease: Retroviral etiology of osteopetrosis. *Biomed. Pharmacother.*, 45: 23-7 (1991).
Lasic, Novel applications of liposomes. *Trends Biotechnol.*, 16(7):307-21 (1998).
Latham, The biochemical and cellular characterization of sclerostin, The causative gene for sclerostenosis. *Calcified Tissue International*, 70(4):244 (2002).
Leppert et al., Benign familial neonatal epilepsy with mutations in two potassium channel genes. *Curr. Opin. Neurol.*, 12: 143-7 (1999).
Lewiecki et al., A Phase 3 Randomized Placebo-controlled Trial to evaluate Efficacy and Safety of Romosozumab I Men with Osteoporosis, J. Clin. Endocrinol. Met., (2018).
Lewiecki et al., RANK ligand inhibition with denosumab for the management of osteoporosis, Exp. Opin. Biol. Ther. 6(10):1041-50 (2006).
Lewiecki et al., Sclerostin monoclonal antibody therapy with AMG 785: A potential treatment for osteoporosis. *Exp. Opin. Biol. Ther.*, 11(1): 117-27 (2011).
Li et al., Sclerostin binds to LRP5/6 and antagonizes canonical Wnt signaling. *J. Biol. Chem.*, 280: 19883-7 (2005).
Li et al., Treatment with an anti-sclerostin antibody directly stimulates bone formation in a dose- dependent manner in ovariectomized rats with established osteopenia. *J. Bone Min. Res.*, 22(Suppl. S1): S65 (2007).
Lian et al., Bone Formation: Osteoblast Lineage Cells, Growth Factors, Matrix Proteins, and the Mineralization Process, Primer on the Metabolic Bone Diseases and Disorders of Mineral Metabolism, 4th Edition, 14-29 (1999).
Lierop et al., Van Buchem disease: Clinical, biochemical and densitometric features of patients and disease carriers. *J. Bone Miner. Res.* Accepted Article (2012).
Lin et al., Sclerostin Mediates Bo9ne Response to Mechanical Unloading Through Antagonizing Wnt/B-Catenin Signaling, J. Bone. Min Res., 24(10):1651-61 (2009).
Liu et al., GenBank Sequence Database Accession No. U25110, Feb. 2, 1996.
Liu et al., Human type II receptor for bone morphogenic proteins (BMPs): Extension of the two-kinase receptor model to the BMPs. *Molec. Cell. Biol.*, 15(7):3479-86 (1995).
Lonberg et al., Antigen-specific human antibodies from mice comprising four distinct genetic modifications. *Nature*, 368:856 (1994).
Loots et al., Genomic deletion of a long-range bone enhancer misregulates sclerostin in Van Buchem disease. *Genome Res.*, 15: 928-35 (2005).
Low et al., Mimicking somatic hypermutation: Affinity maturation of antibodies displayed on bacteriophage using a bacterial mutator strain. *J. Mol. Biol.*, 250:350-68 (1996).
Lowik et al., Wnt signaling is involved in the inhibitory action of sclerostin on BMP-stimulated bone formation. *J. Musculoskeleton Neuronal Interact.* 6: 357 (2006).
Luckman et al., Heterocycle-containing bisphosphonates cause apoptosis and inhibit bone resorption by preventing protein prenylation: Evidence from structure-activity relationships in J774 macrophages. *J. Bone Miner. Res.*, 13(11): 1668-78 (1998).
Luckman et al., Nitrogen-containing bisphosphonates inhibit the mevalonate pathway and prevent post-translational prenylation of GTP-binding proteins, including Ras. *J. Bone Miner. Res.*, 13(4): 581-9 (1998).
Malone et al., Bone anabolism achieved by reducing sclerostin bioavailability with an anti-sclerostin antibody. 37th International Sun Valley Workshop on Skeletal Tissue Biology. Aug. 5-8, 2007.
Mango et al., Carboxy-terminal truncation activates glp-1 protein to specify vulval fates in *Caenorhabditis elegans*. Lett. Nature, 352: 811-15 (1991).
Margalit et al., Comparative analysis of structurally defined herparin binding sequences reveals a distinct spatial distribution of basic residues. *J. Biol. Chem.*, 268 (26): 19228-31 (1993).
Margalit, Liposome-mediated drug targeting in topical and regional therapies. *Crit. Rev. Ther. Drug Carrier Syst.*, 12(2-3):233-61 (1995).
Marks et al., By-passing immunization: Building high affinity human antibodies by chain shuffling. Bio/Technology, 10:779-83 (1992).
Matthews et al., Adenovirus protein-protein interactions: Hexon and protein VI. *J. Gen. Virol.*, 75: 3365-74 (1994).
Mayer et al., Differentiation of osteogenetic cells: Systems and regulators, *Z. Orthop.*, 130: 276-84 (1992)—Abstract Only.
McClung et al., Effects of 24 Months of Treatment with Romosozumab Followed by 12 Months of Denosumab or Placebo in Postmenopausal Women with Low Bone Mineral Density: A Randomized , Double-Blind, Phase 2, Parallel Group Study, J. Bone Min. Res., 1-11 (2018).
McClung et al., Inhibition of sclerostin with AMG 785 in postmenopausal women with low bone mineral density: Phase 2 trial results—Abstract presented at the 2012 meeting of the American Society for Bone and Mineral Reasearch (2012).
Meeting Highlights from the Committee for Medicinal Products for Human Use (CHMP) Jun. 24-27, 2019.

(56) References Cited

OTHER PUBLICATIONS

Memorandum C, Munich Diplomatic Conference, September 1 to Oct. 6, 1973.
Miller, Current Osteoporosis Reports 7:18-22 (2009).
Minabe-Saegusa et al., Genbank Sequence Database Accession No. AB011030, Jun. 23, 1998.
Minutes of the oral proceedings before the opposition division for Opposition against European Patent No. 1721979, dated May 10, 2013.
Miyazono et al., Divergence and convergence of TGF-β/BMP signaling. *J. Cell. Physiol.*, 187:265-76 (2001).
Miyazono et al., TGF-β signaling by Smad proteins. *Adv. Immunology*, 75:115-57 (2000).
Morais et al., In vitro biomineralization by osteoblast-like cells I. Retardation of tissue mineralization by metal salts. *Biomaterials*, 19: 13-21 (1998).
Mori et al., A novel amino acid substitution a the receptor-binding site on the hemaglutinin of H3N2 influenza A viruses isolated from 6 cases with acute encephalopathy during 1997-1998 season in Tokyo. *Arch. Virol.*, 144: 147-55 (1999).
Morrison et al., ATP is a potent stimulator of the activiation and formation of rodent osteoclasts. *J. Physiol.*, 511.2: 495-500 (1998).
Mosekilde et al., Assessing bone quality—Animcal models in preclinincal osteoporosis research. *Bone*, 17 (4): 343S-52S (1995).
Moult, The current state of the art in protein structure predicion. *Curr. Opin. Biotech.*, 7(4):422-7 (1996).
Moustafa et al., Mechanical loading-related changes in osteocyte sclerostin expression in mice are more closely associated with the subsequent osteogenic response than the peak strains engendered, Osteoporos. Int. 23:1255-34 (2012).
Mullins et al., Perspectives series: Molecular medicine in genetically engineered animals; Transgenesis in the rat and larger mammals. *J. Clin. Invest.*, 97(7):1557-60 (1996).
Muntoni et al., A mutation in the dystrophin gene selectively affecting dystrophin expression in the heart. *J. Clin. Invest.*, 96: 693-9 (1995).
Nagaraja et al., X chromosome map at 75-kb STS resolution, revealing extremes of recombination and GC content. *Genome Res.* 7: 210-22 (1997).
Nakase et al., Transient and localized expression of bone morphogenetic protein 4 messenger RNA during fracture healing. *J. Bone Miner. Res.*, 9(5):651-9 (1994).
Nelson, Positional cloning reaches maturity. *Curr. Opin. Genet. Devel.*, 5:298-303 (1995).
Nickel et al., The crystal structure of the BMP-2: BMPR-1A complex and the generation of BMP-2 antagonists. *J. Bone Joint Surg.*, 83-A:S1-7-S1-14 (2001).
Nicolas et al., An age-related decrease in the concentration of insulin-like growth factor binding protein-5 in human cortical bone. *Calcif. Tissue Int.*, 57:206-12 (1995).
Nifuji et al., Coordinated expression of noggin and bone morphogenetic proteins (BMPs) during early skeletogenesi and induction of noggin expression by BMP-7. *J. Bone Miner. Res.*, 14(12):2057-66 (1999).
Nisonoff et al., Separation of univalent fragments from the bivalent rabbit antidody molecule by reduction of disulfide bonds. *Arch. Biochem. Biophys.*, 89:230-44 (1960).
Niu et al., Sclerostin inhibition leads to increased periosteal and endocortical bone formation as well as decreased cortical porosity in aged ovariectomized rats. *J. Bone Min. Res.*, 22(Suppl. S1) S65 (2007).
Nordsletten et al., The neuronal regulation of fracture healing. *Acta Orthop Scand.*, 65(3): 299-304 (1994).
Notice of Opposition against European Patent No. 1133558, Opponent: Eli Lilly and Company, dated May 31, 2007.
Notice of Opposition against European Patent No. 1721979, Opponent: Eli Lilly & Company, dated Jun. 15, 2011.
Notice of Opposition against European Patent No. 1721979, Opponent: Laudens, dated Jun. 15, 2011.
Notice of Opposition against European Patent No. 1721979, Opponent: Novartis AG, dated Jun. 15, 2011.
Notice of Opposition to European Patent No. 1 133 558, dated May 29, 2007.
Nygren et al., Scaffolds for engineering novel binding sites in proteins. *Curr. Opin. Struct. Biol.*, 7:463-9 (1997).
Observations of Opponent: Laudens in response to summons to oral proceedings in Opposition against European Patent No. 1721979, dated Feb. 25, 2013.
Oelgeschlager et al., The evolutionarily conserved BMP-binding protein twisted gastrulation promotes BMP signalling. *Nature*, 405:757-63 (2000).
OMIM #607625, Niemann-pick disease, type C2 (2007).
Ominsky et al., Two doses of sclerostin antibody in cynomolgus monkeys increases bone formation, bone mineral density, and bone strength, *J. Bone Min. Res.*, 25(5):948-59 (2010).
Ominsky, et al., Sclerostin monoclonal antibody treatment increases bone strength in aged osteopenic ovariectomozed rats. J. Bone Min. Res., 21(1): S44 PRES1161 (2006). Abstract.
Opposition Decision for Opposition against European Patent No. 1721979, dated Aug. 2, 2013.
Opposition Statement of May 20, 2007 filed by Opponent 2 (Eli Lilly) against European Patent No. 1133558.
Oreffo et al., Human bone marrow osteoprogenitors express estrogen receptor-alpha and bone morphogenetic proteins 2 and 4 mRNA during osteoblastic differentiation. *J. Cell. Biochem.*, 75:382-92 (1999).
Orriss et al., Purinergic signaling and bone remodeling. Curr. Opin. Pharmacol., 10:322-30 (2010).
Oshima et al., TGF-β receoptor type II deficiency results in defects of yolk Sac hematopoiesis and vasculogenesis. *Dev. Biol.*, 179:297-302 (1996).
Padhi et al., Anti-sclerostin antibody increases markers of bone formation in healthy postmenopausal women. *J. Bone Min. Res.*, 22: S37 (2007).
Padhi et al., OC35—Effects of anti-sclerostin monoclonal antibody in healthy postmenopausal women. *Osteoporosis Int.*, 19: Suppl. 1: S19 (2008).
Padhi et al., Presentation at ECTS 2012, 39th Annual Congress, Stockholm, Sweden, Abstract OC17 (May 2012).
Padhi et al., Single-dose placebo-controlled, randomized study of AMG 785, a sclerostin monoclonal antibody, *J. Bone. Min. Res.*, 26(1):19-26 (2011).
Padlan et al., Structure of an antibody-antigen complex; Crystal structure of the HyHEL-10 Feb-lysozyme complex. *Proc. Natl. Acad. Sci. USA*, 86:5938-42 (1989).
Palokangas et al., Endocytic pathway from the basal plasma membrane to the ruffled border membrane in bone-resorbing osteoclasts. *J. Cell Sci.*, 110: 1767-80 (1997).
Pandey et al., Nucleotide sequence database: A gold mine for biologists. *TIBS*. 24: 276-80 (1999).
Papapoulos et al., Targeting sclerostin as potential treatment of osteoporosis. *Ann. Rheum. Dis.*, 70(Suppl. 1): 1119-22 (2011).
Patel et al., Current and potential future drug treatments for osteoporosis. *Ann. Rheumatic Dis.*, 55: 700-14 (1996).
Patten et al., Applications of DNA shuffling to pharmaceuticals and vaccines. *Curr. Opin. Biotechnol.*, 8:724-33 (1997).
Pearson et al., Effective protein sequence comparison. Chapter 15, pp. 227-258 (1996).
Piao et al., The proximal promotor region of the gene encoding human 17β-hydroxysteroid dehydrogenase type 1 contains GATA, AP-2, and Sp1 response elements: Analysis of promotor function in choriocarcinoma cells. *Endrocrinol.*, 138(8): 3417-25 (1997).
Piccolo et al., The head inducer Cerberus is a multifunctional antagonist of nodal, BMP and Wnt signals. *Nature*, 397: 707-10 (1999).
Piek et al., Specificity, diversity, and regulation of TGF-β superfamily signaling. *FASEB J.*, 13:2105-24 (1999).
Pietromonaco et al., Protein kinase C-Θ phosphorylation of moesin in the actin-binding sequence. *J. Biol. Chem.*, 273:7594-603 (1998).
Pignatti et al., Tracking disease genes by reverse genetics. *J. Psychiar. Res.*, 26(4):287-98 (1992).

(56) References Cited

OTHER PUBLICATIONS

Pittenger et al., Multilineage potential of adult human mesenchymal stem cells. *Science*, 284:143-7 (1999).
Pluckthun et al., Expression of functional anitbody Fv and Fab fragments in *Escherichia coli. Meth. Enzymol.*, 178:497-515 (1989).
Pockwinse et al., Expression of cell growth and bone specific genes at single cell resolution during development of bone tissue-like organization in primary osteoblast cultures. *J. Cell. Biol.*, 49:310-23 (1992).
Poole et al., Sclerostin is a delayed secreted product of osteocytes that inhibit bone formation. *FESEB J.* 19: 1842-4 (2005).
Porter, The hydrolysis of rabbit γ-globulin and antibodies with crystalline papain. *Biochem. J.*, 73:119-26 (1959).
Proprietor's Response to Opponent's Statement of Grounds of Appeal, European Patent No. 1133558, dated Apr. 15, 2010.
Proprietor's Response to Oppositions against European Patent No. 1721979, UCB Pharma S.A., dated Feb. 20, 2012.
Proprietor's Written submission in preparation for oral proceedings in Opposition against European Patent No. 1721979, Proprietor: UCB Pharma S.A., dated Feb. 25, 2013.
Quintanar-Guerrero et al., Preparation techniques and mechanisms of formation of biodegradable nanoparticles from preformed polymers. *Drug Dev. Ind. Pharm.*, 24(12):1113-28 (1998).
Rachner et al., Osteoporosis: Now and the future. *Lancet*, 377(9773): 1276-87 (2011).
Rawadi et al., BMP-2 controls alkaline phosphatase expression and osteoblast mineralization by a Wnt autocrine loop. *J. Bone Min. Res.* 18: 1842-53 (2003).
Reb, Antikorpergegen Sclerostin, *Medical Tribune*, 39:12 (2007).
Reddi et al., The *Escherichia coli* chaperonin 60 (groEL) is a potent stimulator of osteoclast formation. *J. Bone Miner. Res.*, 13(8): 1260-6 (1998).
Reddi, Interplay between bone morphogenetic proteins and cognate binding proteins in bone and cartilage development: Noggin, chordin and DAN. *Arthritis Res.*, 3(1):1-5 (2000).
Response to Proprietor's brief of Apr. 15, 2010, European Patent Opposition, EP-1133558 B1, dated Mar. 18, 2011.
Riggs, Overview of osteoporosis. *West J. Med.*, 154:63-77 (1991).
Ritter et al., Serological analysis of human anti-human antibody responses in colon cancer patients treated with repeated doses of humanized monoclonal antibody A33, *Can. Res.*, 61:6851-9 (2001).
RnD Systems catalogue excerpt, cited in Opposition against European Patent No. 1721979 by Opponent: Novartis AG dated Jun. 15, 2011.
Roberts et al., Essential functional interactions of SAFA, a *Saccharomyces cerevisiae* complex of Spt, Ada, and Gon5 proteins, with the Snf/Swi and Srb/Mediator complexes. *Genetics*, 147: 451-65 (1997).
Robinson et al., The sclerostin antibody project. *Hum. Antibodies*, 16: 36 (2007).
Roitt et la., Roitt's Essential Immunology, 9th Edition, pp. 90-91 (1997).
Rosenzweig et al., Cloning and characterization of a human type II receptor for bone morphogenetic proteins. *Proc. Natl. Acad. Sci, USA*, 92:7632-7636 (1995).
Rosenzweig et al., GenBank Sequence Database Accession No. CAA88759, Oct. 7, 2008.
Rosenzweig et al., GenBank Sequence Database Accession No. Z48923, Oct. 7, 2008.
Rudikoff, et al., Single amino acid substitution altering antigen-binding specificity. *Proc. Natl. Acad. Sci. USA*, 79:1979-83 (1982).
Ruppert et al., Human bone morphogenetic protein 2 contains a heparin-binding site which modifies its biological activity. *Eur. J. Biochem.*, 237: 295-302 (1996).
Sada et al., Adsorption equilibirum in immuno-affinity chromatography with polyclonal and monoclonal antibodies. *Biotechnol. Bioengin.*, 28 (1986). Abstract.
Sali et al., Comparative protein modeling by satisfaction of spatial restraints. *J. Mol. Biol.*, 234(3):779-815 (1993).
Sambrook et al., Synthetic Oligonucleotide Probes, *Molecular Cloning—A Laboratory Manual*, Ch.11:11.1-11.19 and 11.58-11.61 (1989).
Sanger et al., DNA sequencing with chain-terminating inhibitors. *Proc. Natl. Acad. Sci. USA*, 74:5463-7 (1997).
Sastry et al., Cloning of the immunological repertoire in *Escherichia coli* for generation of monoclonal catalytic antibodies: Construction of a heavy chain variable region-specific cDNA library. *Proc. Natl. Acad. Sci. USA*, 86:5728-32 (1989).
Scatchard et al., The attractions of proteins for small molecules and ions. *Ann. N. Y. Acad. Sci.*, 51:660-72 (1949).
Scheufler et al., Crystal structure of human bone morphogenetic protein-2 at 2.7 A resolution. *J. Mol. Biol.*, 287(1):101-15 (1999).
Schlebusch et al., Production of a single-chain fragment of the murine anti-idiotypic antibody ACA125 as phage-displayed and soluble antibody by recombinant phage antibody technique. *Hybridoma*, 16:47-52 (1997).
Schlunegger et al., Refined crystal structure of human transforming growth factor β2 at 1.95 A Resolution*J. Mol. Biol.*, 231(2):445-458 (1993).
Schmidt et al., Retrovirus-induced osteopetrosis in mice: Effects of viral infection on osteogenic differentiation in skeletoblast cell cultures. *Am. J. Pathol.*, 129(3): 503-10 (1987).
Schmitt et al., Bone morphogenetic proteins: An update on basic biology and clinical relevance. *J. Orth. Res.*, 17:269-78 (1999).
Schwappacher et al., NCBI Sequence Database Accession No. NM_001204, Aug. 16, 2009.
Scully et al., BRCA1 is a component of the RNA polymerase II holoenzyme. *Proc. Natl. Acad. Sci. USA*, 94: 5605-10 (1997).
Second declaration of Martyn Robinson, citation in Appeal, European Patent No. 1133558, dated Apr. 15, 2010.
Serra et al., Expression of a truncated, kinase-defective TGF-β type II receptor in mouse skeletal tissue promotes terminal chondrocyte differentiation and osteoarthritis. *J. Cell. Biol.*, 139(2):541-52 (1997).
Sigmund, Viewpoint: Are studies in genetically altered mice out of control? *Arterioscler. Thromb. Vasc.* Biol., 20:1425-9 (2000).
Silverman et al., Sclerostin, *J. Osteoporosis*, 2010: 1-3 (2010).
Sippl et al., Threading thrills and threats. *Structure*, 4(1):15-19 (1996).
Siris, Clinical Review: Paget's disease of bone. *J. Bone Miner. Res.*, 13(7): 1061-5 (1998).
Sivakumar et al., New insights into extracellular matrix assembly and reorganization from dynamic imaging of extracellular matrix proteins in living osteoblasts. *J. Cell. Sci.*, 119(7):1350-60 (2006).
Skiple Skjerpen et al., Binding of FGF-1 variants to protein kinase CK2 correlates with mitogenicity. *EMBO J.* 21(15): 4058-69 (2002).
Slater et al., Involvement of platelets in stimulating osteogenic activity. *J. Orthopaedic Res.*, 13: 655-63 (1995).
Smith et al., Glucocorticoids inhibit development stage-specific osteoblast cell cycle. *J. Biol. Chem.*, 275:19992-20001 (2000).
Smith, TGF β inhibitors, new and unexpected requirements in vertebrate development. *TIG*, 15(1):3-5 (1999).
Sohocki et al., A range of clinical phenotypes associated with mutations in CRX, a photoreceptor transcription-factor gene. *Am. J. Hum. Genet.*, 63: 1307-15 (1998).
Spranger, International classification of osteochondrodysplasias, *Eur. J. Pediatr.*, 151: 407-15 (1992).
Staehling-Hampton et al., A 52-kb delection in the SOST-MEOX1 intergenic region on 17q12-q21 is associated with van Buchem disease in the Dutch population. *Am. J. Med. Gen.* 110: 144-52 (2002).
Stanley et al., DAN is a secreted glycopeotein related to *Xenopus cerberus. Mech. Dev.*, 77: 173-84 (1998).
Statement of Grounds of Appeal to Decision of Opposition against European Patent No. 1133558, dated Sep. 28, 2009.
Stenmark et al., Distinct structural elements of rab5 define its functional specificity. *EMBO J.*, 13(3): 575-83 (1994).
Strachan et al. (Eds.), Diagram from text book entitled Human Molecular Genetics, 2nd Edition (1999).
Strachan et al. (Eds.), Human Molecular Genetics, 1st Edition, p. 420 (1996).
Strachan et al., Human Molecular Genetics, 2nd Edition, Figure 15.4 (1999).

(56) References Cited

OTHER PUBLICATIONS

Submission in response to oral proceedings in Opposition against European Patent No. 1721979, Opponent: Eli Lilly, dated Apr. 24, 2013.
Sudo et al., In vitro differentiation and calcification in a new clonal osteogenic cell line derived from newborn mouse calvaria. *J. Cell Biol.*, 96:191-8 (1983).
Summary of CHMP opinion of Oct. 17, 2019.
Summons to attend oral proceedings for Opposition against European Patent No. 1133558, dated Nov. 4, 2008.
Summons to attend oral proceedings in Opposition against European Patent No. 1721979, dated Nov. 12, 2012.
Sutherland et al., Sclerostin romotes the apoptosis of human osteoblastic cells: A novel regulation of bone formation. *Bone*, 35:828-35 (2004).
Suzawa et al., Extracellular matrix-associated bone morphogenetic proteins are essential for differentiation of murine osteoblastic cells in vitro. *Endocrinology*, 140:2125-33 (1999).
Sverdlov et al., Perpetually mobile footprints of ancient infections in human genome. *FEBS Lett.*, 428: 1-6 (1998).
Sylatron label, cited in Opposition against European Patent No. 1721979 by Opponent: Novartis AG, dated Jun. 15, 2011.
Takakura, Drug delivery systems in gene therapy. *Nippon Rinsho*, 56(3):691-5 (1998) (Abstract Only).
Takeda et al., GenBank Sequence Database Accession No. AAB33865, May 27, 1995.
Takeda et al., GenBank Sequence Database Accession No. D38082, dated Dec. 27, 2006.
Takeda et al., GenBank Sequence Database Accession No. S75359, May 27, 1995.
Takeda et al., NCBI Sequence Database Accession No. NM_030849, Feb. 11, 2009.
Takeda, Expression of serine/threonine kinase receptors during ectopic bone formation induced by bone morphogenetic protein (BMP). *Kokubyo Gakkai Zasshi*, 61(4):512-26 (1994).
Tam et al., TGF-β receptor expression on human keratinocytes: A 150 kDa GPI-anchored TGF-β1 binding protein forms a heteromeric complex with type I and type II receptors. *J. Cellular Biochem.*, 70:573-56 (1998).
Taylor et al., Differential time-dependent transcriptional changes in the osteoblast lineage in cortical bone associated with sclerostin antibody treatment in ovariectomized rats, Bone Report., 8:95-103 (2018).
Taylor et al., Human immunoglobulin transgenes undergo rearrangement, somatic mutation and class switching in mice that lack endogenous IgM. *Int. Immun.*, 6:579 (1994).
The Merck Manual-Second Home Edition, Ch. 61:1-3 (2005).
Thompson et al., Affinity maturation of a high-affinity human monoclonal antibody against the third hypervariable loop of human immunodeficiency virus: Use of phage display to improve affinity and broaden strain reactivity. *J. Mol. Biol.*, 256:7-88 (1996).
Thornton et al., Prediction of progress at last. *Nature*, 354:105-6 (1991).
Tjaderhane et al., A high sucrose diet decreases the mechanical strength of bones in growing rats. *J. Nutr.*, 128: 1807-10 (1998).
Tuncay et al., Oxygen tension regulates osteoblast function. *Am. J. Orthod. Dentofac. Orthop.*, 105: 457-63 (1994).
UCB and Amgen announce positive phase 2 results of CDP7851/AMG785 in patients with post menopausal osteoporosis (PMO), dated Apr. 21, 2011—Citation in Opposition against European Patent No. 1721979.
Uitterlinden et al., Relation of alleles of the collagen type lα1 gene to bone density and the risk of osteoporotic fractures in postmenopausal women. *New Engl. J. Med.*, 338: 1016-21 (1998).
Utting et al., Hypoxia stimulates osteoclast formation from human peripheral blood. *Cell Biochem. Funct.*, 28:374-80 (2010). Orriss et al., Osteoblast cultures. *Methods Molec. Med.*, (2010b).
Valero et al., Quaternary structure of casein kinase 2. *J. Biol. Chem.*, 27(14): 8345-52 (1995).
Van Assche et al., Management of loss of response to anti-TNF drugs, Change the dose or change the drug? J. Crohns and Colitis, 2(4):348-51 (2008).
Van Bezooijen et al., Sclerostin is an osteocyte-expressed negative regulator of bone formation, but not a classical BMP antagonist. *J. Exp. Med.*, 199: 805-14 (2004).
Van Bezooijen et al., SOST/sclerostin, an osteocyte-derived negative regulator of bone formation, *Cytokine Growth Factor Rev.*, 16: 319-27 (2005).
Van Bezooijen et al., Wnt but not BMP signaling is involved in the inhibitory action of sclerostin on BMP-stimulated bone formation. *J. Bone. Miner. Res.* 22:19-28 (2007).
Van Hul et al., Van Buchem Disease (hyperostosis corticalis generalisata) maps to chromosome 17q12-a21. *Am. J. Hum. Genet.*, 2:391-9 (1998).
Van Lierop et al., Serum Dickkopf 1 Levels in Sclerostin Deficiency, J. Clin. Endocrinol. Metab., 99(2):E252 (2014).
Vanier et al., Recent advances in elucidating Niemann-Pick C disease. *Brain Pathol.* 8: 163-74 (1998).
Veverka et al., Characterization of the structural features and interactions of sclerostin. *J. Biol. Chem.*, 284(16): 10890-900 (2009).
Viter et al., Analysis of antigenic structure of potato virus M Ukrainian strains. *Biopolimery I Kletka, Naukova Dumka, Kiev K, UK*, 16: 312-9 (2000).
Von Bubnoff et al., Intracellular BMP signaling regulation in vertebrates: Pathway or network? *Dev. Biol.*, 239:1-14 (2001).
Wall, Transgenic livestock: Progress and prospects for the future. *Theriogenology*, 45:57-68 (1996).
Wang et al., IFP 35 forms complexes with B-ATF, a member of the AP1 family of transcription factors. *Biochem. Biophys. Res. Commun.*, 229: 316-22 (1996).
Wang, Bone morphogenetic proteins (BMPs): Therapeutic potential in healing bony defects. *TIBTECH*, 11:379-83 (1993).
Warmington et al., American Society for Bone and Mineral Research, 30th Annual Meeting 2008, Montreal Quebec Canada, Abstract 1211.
Warmington et al., Sclerostin antagonism in adult rodents, via monoclonal antibody mediated blockade, increases bone mineral density and implicates sclerostia as a key regulator of bone mass during adulthood. *J. Bone Min. Res.*, 19:S56-7 (2004).
Warmington et al., Sclerostin monoclonal antibody treatment of osteoporotic rats completely reverses one year of overiectomy-induced systemic bone loss, *J. Bone Min. Res.*, 20:S22 (2005).
Watts et al., Endocr. Pract. 16(3):1-37 (2010).
Wijenayaka et al., Sclerostin stimulates osteocyte support of osteoclast activity by a RANKL-dependent pathway, *PLoS One*, 6(10):e25900 (2011).
Winkler et al., Noggin and sclerostin bone morphogenetic protein antagonists form a mutually inhibitory complex. *J. Biol. Chem.*, 279(35): 36296-8 (2004).
Winkler et al., Osteocyte control of bone formation via sclerostin, a novel BMP antagonist. *EMBO J.* 22: 6267-76 (2003).
Winkler et al., Sclerostin inhibition of Wnt-3a-induced C3H10T1/2 cell differentiation is indirect and mediated by bone morphogenetic proteins. *J. Biol. Chem.* 280: 2498-502 (2005).
Winter et al., Making antibodies by phase display technology. *Annu. Rev. Immunol.*, 12:433-55 (1994).
Wolff et al., Monoclonal antibody homodimers: Enhanced antitumor activity in nude mice. *Cancer Res.*, 53:2560-5 (1993).
Wollenberger et al. (Eds.), Analytische Biochemie, Chapter 3, pp. 47-49 (2003).
World Health Organization Scientific Group on the Prevention and Management of Osteoporosis, "Prevention and management of osteoporosis: report of a WHO scientific group." *WHO Technical Report Series*, 921 (2000).
Written submission—Observation by a Third Party According to Art. 115 EPC, Opposition to European Patent No. 1133558, dated Nov. 25, 2008.
Written submission in response to summons to oral proceedings in Opposition against European Patent No. 1721979, Opponent: Eli Lilly Company, dated Feb. 25, 2013.

(56) References Cited

OTHER PUBLICATIONS

Written submission in response to summons to oral proceedings in Opposition against European Patent No. 1721979, Opponent: Norvartis AG, dated Feb. 25, 2013.
Written submission of Eli Lilly & Company to European Patent Office, Opposition to European Patent No. 1133558, dated May 29, 2007.
Written Submission of Eli Lilly & Company, Opposition to European Patent No. 1133558, dated Mar. 9, 2009.
Written submission of UCB S.A., Proprietor's Preliminary Response to the Opponent's submission of Mar. 9, 2009, Opposition to European Patent No. 1133558, dated Mar. 20, 2009.
Written submission of UCB S.A., Proprietor's Response to Opposition against European Patent No. 1133558, dated Mar. 14, 2008.
Yanagita et al., USAG-1: A bone morphogenetic protein antagonist abundantly expressed in the kidney. *Biochem. Biophys. Res. Comm.* 316: 490-550 (2004).
Yang et al., CDR walking mutagenesis for the affinity maturation of a potent human Anti-HIV-1 antibody into the picomolar range. *J. Mol. Biol.*, 254:392-403 (1995).
Yates et al., Inhibition of bone resorption by inorganic phosphate in mediated by both reduced osteoclast formation and decreased activity of mature osteoclasts. *J. Bone Miner. Res.*, 6(5): 476-8 (1990).
Yerges et al., NCBI Sequence Database Accession No. NM_001203, Jul. 12, 2009.
Yerges et al., NCBI Sequence Database Accession No. NP_001194, Jul. 12, 2009.
Yoshida et al., Osteoinduction capability of recombinant human bone morphogenetic protein-2 in intramuscular and subcutaneous sites: An experimental study. *J. Cranio-Maxillofac. Surg.*, 26: 112-5 (1998).
Zambaux et al., Influence of experimental parameters on the characteristics of poly(lactic acid) nanoparticles prepared by a double emulsion method. *J. Controlled Rel.*, 50(1-3):31-40 (1998).
Zhang et al., Humanization of an anti-human TNF-β antibody by variable region resurfacing with the aid of molecular modeling. *Molec. Immunol.*, 42(12):1445-51 (2005).
Zimmerman et al., The spemann organizer signal noggin binds and inactives bone morphogenetic protein 4. *Cell*, 86(4):599-606 (1996).
Zlotogora et al., Dominance and homozygosity, *Am. J. Med. Genet.*, 68: 412-6 (1997).
Zur Muhlen et al., Solid lipid nanoparticles (SLN) for controlled drug delivery—Drug release and release mechanism. *Eur. J. Pharm. Biopharm.*, 45(2):149-55 (1998).
Andersson et al., Molecular genetics and pathophysiology of 17P-hydroxysteriod dehydrogenase 3 deficiency. *J. Clin. Endrocrinol. Metab.*, 81(1): 130-6 (1996).
Anonymous, Amgen presents denosumab and sclerostin antibody data at American Society for Bone and Mineral Research Annual Meeting. Amgen Media Press Release. <www.amgen.com/media/media_pr_detail.jsp?releaseID=907028 <http://www.amgen.com/media/media_pr_detail.jsp?releaseID=907028>> (2006).
Bonaldo et al., EMBL Sequence Database Accession No. A1113131, Sep. 4, 1998.
Bostrom et al., Ligand and signaling components of the transforming growth factor 13 family. *J. Orth. Res.*, 13:357-67 (1995).
Cook et al., Structural basis for a functional antagonist in the transforming growth factor 13 superfamily. *J. Biol. Chem.*, 280(48):40177-86 (2005).
De Jong et al., Evolution of the a-crystallin/small heat-shock protein family. *Mol Biol. Evol.*, 10(1): 103-26 (1993).
Dean et al., Matrix vesicles produced by osteoblast-like cells in culture become significantly enriched in proteoglycan-degrading metalloproteinases after addition of 6-glycerophosphate and ascorbic acid. *Calcif. Tissue*, 54: 399-408 (1994).
Declaration of Prof. Edgar Wingender filed in connection with that Opposition regarding European Patent EP 1133558 BI, dated Mar. 10, 2011.
Eli Lilly Statement of Grounds of Appeal, Opposition to European Patent Application No. 1133558 BI, dated Sep. 28, 2009.
Eyre et al., Characterization of aromatase and 173-hydroxysteroid dehydrogenase expression in rat osteoblastic cells. *J. Bone Miner. Res.*, 13(6): 996-1004 (1998).
Geissler et la., Male pseudohermaphroditism caused by mutations of testicular 17P-hydroxysteroid hehydrogenase 3. *Nat. Genetics*, 7: 34-9 (1994).
Gowen et al., Actions of recombinant human y-interferon and tumor necrosis factor a on the proliferation and osteoblastic characteristics of human trabecular bone cells in vitro. *Arthritis Rheumatism*, 31(12): 1500-7 (1988).
Graner et al., Splice variants of the *Drosophila* PS2 integrins differentially interact with RGD-containing fragments of the extracellular proteins tiggrin, Ten-m and D-laminin a2. *J. Biol. Chem.*, 273(29): 18235-41 (1998).
Hart et al., Crystal structure of the human T[3R2 ectodomain-TGF-133 complex. *Nat. Struc. Biol.*, 9(3):203-8 (2002).
Holm et al., Protein folds and families: Sequence and structure alignments. *Nuci. Acid Res.*, 27(1):244-7 (1999).
Khalil, TGF-[3: From latent to active. *Microbes and Infection*, 1(15):1255-63 (1999).
Lane, Epidemiology, etiology, and diagnosis of osteoporosis, Am. J. Obstet. Gynecol., 194(2 Suppl.):S2-11, (2006).

* cited by examiner

THE DECLINE IN P1NP LEVELS AFTER MULTIPLE DOSING IS NOT DUE TO REDUCED EXPOSURE OF Scl-Ab (DATA FOR DAY 32)

P1NP TACHYPHYLAXIS OCCURS AFTER REPEATED Scl-Ab BUT RECOVERS AFTER A "DOSING HOLIDAY"

FIGURE 7

| Sequence Description | Sequence |
|---|---|
| Ab-A and Ab-1 CDR-L1 | QSSQSVYDNNWLA (SEQ ID NO: 54) |
| Ab-A and Ab-1 CDR-L2 | DASDLAS (SEQ ID NO: 55) |
| Ab-A and Ab-1 CDR-L3 | QGAYNDVIYA (SEQ ID NO: 56) |
| Ab-A and Ab-1 CDR-H1 | SYWMN (SEQ ID NO: 51) |
| Ab-A and Ab-1 CDR-H2 | TIDSGGRTDYASWAKG (SEQ ID NO: 52) |
| Ab-A and Ab-1 CDR-H3 | NWNL (SEQ ID NO: 53) |
| Ab-A light chain | SEQ ID NO: 23 |
| Ab-A heavy chain | SEQ ID NO: 27 |
| Ab-1 light variable region (with signal sequence) | SEQ ID NO: 75 |
| Ab-1 heavy variable region (with signal sequence) | SEQ ID NO: 77 |
| Ab-B CDR-L1 | SASSSVSFVD (SEQ ID NO: 60) |
| Ab-B CDR-L2 | RTSNLGF (SEQ ID NO: 61) |
| Ab-B CDR-L3 | QQRSTYPPT (SEQ ID NO: 62) |
| Ab-B CDR-H1 | TSGMGVG (SEQ ID NO: 57) |
| Ab-B CDR-H2 | HIWWDDVKRYNPVLKS (SEQ ID NO: 58) |
| Ab-B CDR-H3 | EDFDYDEEYYAMDY (SEQ ID NO: 59) |
| Ab-B light chain | SEQ ID NO: 31 |
| Ab-B heavy chain | SEQ ID NO: 35 |
| Ab-C CDR-L1 | KASQSVDYDGDSYMN (SEQ ID NO: 48) |
| Ab-C CDR-L2 | AASNLES (SEQ ID NO: 49) |
| Ab-C CDR-L3 | QQSNEDPWT (SEQ ID NO: 50) |
| Ab-C CDR-H1 | DCYMN (SEQ ID NO: 45) |
| Ab-C CDR-H2 | DINPFNGGTTYNQKFKG (SEQ ID NO: 46) |
| Ab-C CDR-H3 | SHYYFDGRVPWDAMDY (SEQ ID NO: 47) |
| Ab-C light chain | SEQ ID NO: 15 |
| Ab-C heavy chain | SEQ ID NO: 19 |
| Ab-D CDR-L1 | QASQGTSINLN (SEQ ID NO: 42) |
| Ab-D CDR-L2 | GSSNLED (SEQ ID NO: 43) |
| Ab-D CDR-L3 | LQHSYLPYT (SEQ ID NO: 44) |
| Ab-D CDR-H1 | DHYMS (SEQ ID NO: 39) |
| Ab-D CDR-H2 | DINPYSGETTYNQKFKG (SEQ ID NO: 40 ) |
| Ab-D CDR-H3 | DDYDASPFAY (SEQ ID NO: 41) |
| Ab-D light chain | SEQ ID NO: 7 |
| Ab-D heavy chain | SEQ ID NO: 11 |
| Ab-2 CDR-L1 | RASSSVYYYMH (SEQ ID NO: 275) |
| Ab-2 CDR-L2 | ATSNLAS (SEQ ID NO: 276 ) |
| Ab-2 CDR-L3 | QQWSSDPLT (SEQ ID NO: 277) |
| Ab-2 CDR-H1 | DYFIH (SEQ ID NO: 287) |
| Ab-2 CDR-H2 | RLDPEDGESDYAPKFQD (SEQ ID NO: 288) |
| Ab-2 CDR-H3 | EDYDGTYTFFPY (SEQ ID NO: 289) |
| Ab-2 light chain | SEQ ID NO: 117 |
| Ab-2 heavy chain | SEQ ID NO: 121 |
| Ab-3 and Ab-15 CDR-L1 | SVSSTISSNHLH (SEQ ID NO: 278) |

FIGURE 7 (cont.)

| Sequence Description | Sequence |
|---|---|
| Ab-3 and Ab-15 CDR-L2 | GTSNLAS (SEQ ID NO: 279) |
| Ab-3 and Ab-15 CDR-L3 | QQWSSYPLT (SEQ ID NO: 280) |
| Ab-3 and Ab-15 CDR-H1 | DFYLH (SEQ ID NO: 290) |
| Ab-3 and Ab-15 CDR-H2 | RIDPENGDTLYDPKFQD (SEQ ID NO: 291) |
| Ab-3 and Ab-15 CDR-H3 | EADYFHDGTSYWYFDV (SEQ ID NO: 292) |
| Ab-3 light chain | SEQ ID NO: 125 |
| Ab-3 heavy chain | SEQ ID NO: 129 |
| Ab-15 light variable region | SEQ ID NO: 384 |
| Ab-15 heavy variable region | SEQ ID NO: 386 |
| Ab-15 light chain | SEQ ID NO: 221 |
| AB-15 heavy chain | SEQ ID NO: 225 |
| Ab-4 and Ab-5 CDR-L1 | RASQDISNYLN (SEQ ID NO: 78) |
| Ab-4 and Ab-5 CDR-L2 | YTSRLLS (SEQ ID NO: 79) |
| Ab-4 and Ab-5 CDR-L3 | QQGDTLPYT (SEQ ID NO: 80) |
| Ab-4 and Ab-5 CDR-H1 | DYNMH (SEQ ID NO: 245) |
| Ab-4 and Ab-5 CDR-H2 | EINPNSGGAGYNQKFKG (SEQ ID NO: 246) |
| Ab-4 and Ab-5 CDR-H3 | LGYDDIYDDWYFDV (SEQ ID NO: 247) |
| Ab-4 light chain | SEQ ID NO: 133 |
| Ab-4 heavy chain | SEQ ID NO: 137 |
| Ab-5 light variable region | SEQ ID NO: 376 |
| Ab-5 heavy variable region | SEQ ID NO: 378 |
| Ab-5 light chain | SEQ ID NO: 141 |
| Ab-5 heavy chain | SEQ ID NO: 145 |
| Ab-6 CDR-L1 | RASQDISNYLN (SEQ ID NO: 81) |
| Ab-6 CDR-L2 | YTSRLHS (SEQ ID NO: 99) |
| Ab-6 CDR-L3 | QQGDTLPYT (SEQ ID NO: 100) |
| Ab-6 CDR-H1 | DYNMH (SEQ ID NO: 248) |
| Ab-6 CDR-H2 | EINPNSGGSGYNQKFKG (SEQ ID NO: 249) |
| Ab-6 CDR-H3 | LVYDGSYEDWYFDV (SEQ ID NO: 250) |
| Ab-6 light chain | SEQ ID NO: 149 |
| Ab-6 heavy chain | SEQ ID NO: 153 |
| Ab-7 CDR-L1 | RASQVITNYLY (SEQ ID NO: 101) |
| Ab-7 CDR-L2 | YTSRLHS (SEQ ID NO: 102) |
| Ab-7 CDR-L3 | QQGDTLPYT (SEQ ID NO: 103) |
| Ab-7 CDR-H1 | DYNMH (SEQ ID NO: 251) |
| Ab-7 CDR-H2 | EINPNSGGAGYNQQFKG (SEQ ID NO: 252) |
| Ab-7 CDR-H3 | LGYVGNYEDWYFDV (SEQ ID NO: 253) |
| Ab-7 light chain | SEQ ID NO: 157 |
| Ab-7 heavy chain | SEQ ID NO: 161 |
| Ab-8 CDR-L1 | RASQDISNYLN (SEQ ID NO: 104) |
| Ab-8 CDR-L2 | YTSRLLS (SEQ ID NO: 105) |
| Ab-8 CDR-L3 | QQGDTLPYT (SEQ ID NO: 106) |
| Ab-8 CDR-H1 | DYNMH (SEQ ID NO: 254) |
| Ab-8 CDR-H2 | EINPNSGGAGYNQKFKG (SEQ ID NO: 255) |
| Ab-8 CDR-H3 | LGYDDIYDDWYFDV (SEQ ID NO: 256) |

FIGURE 7 (cont.)

| Sequence Description | Sequence |
|---|---|
| Ab-8 light chain | SEQ ID NO: 165 |
| Ab-8 heavy chain | SEQ ID NO: 169 |
| Ab-9 CDR-L1 | RASQDISNYLN (SEQ ID NO: 107) |
| Ab-9 CDR-L2 | YTSRLFS (SEQ ID NO: 108) |
| Ab-9 CDR-L3 | QQGDTLPYT (SEQ ID NO: 109) |
| Ab-9 CDR-H1 | DYNMH (SEQ ID NO: 257) |
| Ab-9 CDR-H2 | EINPNSGGAGYNQKFKG (SEQ ID NO: 258) |
| Ab-9 CDR-H3 | LGYDDIYDDWYFDV (SEQ ID NO: 259) |
| Ab-9 light chain | SEQ ID NO: 173 |
| Ab-9 heavy chain | SEQ ID NO: 177 |
| Ab-10 CDR-L1 | RASQDISNYLN (SEQ ID NO: 110) |
| Ab-10 CDR-L2 | YTSRLLS (SEQ ID NO: 111) |
| Ab-10 CDR-L3 | QQGDTLPYT (SEQ ID NO: 112) |
| Ab-10 CDR-H1 | DYNMH (SEQ ID NO: 260) |
| Ab-10 CDR-H2 | EINPNSGGAGYNQKFKG (SEQ ID NO: 261) |
| Ab-10 CDR-H3 | LGYDDIYDDWYFDV (SEQ ID NO: 262) |
| Ab-10 light chain | SEQ ID NO: 181 |
| Ab-10 heavy chain | SEQ ID NO: 185 |
| Ab-11 and Ab-16 CDR-L1 | RASSSISYIH (SEQ ID NO: 281) |
| Ab-11 and Ab-16 CDR-L2 | ATSNLAS (SEQ ID NO: 282) |
| Ab-11 and Ab-16 CDR-L3 | QQWSSDPLT (SEQ ID NO: 283) |
| Ab-11 and Ab-16 CDR-H1 | DYYIH (SEQ ID NO: 293) |
| Ab-11 and Ab-16 CDR-H2 | RVDPDNGETEFAPKFPG (SEQ ID NO: 294) |
| Ab-11 and Ab-16 CDR-H3 | EDYDGTYTWFPY (SEQ ID NO: 295) |
| Ab-11 light chain | SEQ ID NO: 189 |
| Ab-11 heavy chain | SEQ ID NO: 193 |
| Ab-16 light variable region | SEQ ID NO: 388 |
| Ab-16 heavy variable region | SEQ ID NO: 390 |
| Ab-16 light chain | SEQ ID NO: 229 |
| Ab-16 heavy chain | SEQ ID NO: 233 |
| Ab-12 CDR-L1 | RASQDISNYLN (SEQ ID NO: 113) |
| Ab-12 CDR-L2 | YTSTLQS (SEQ ID NO: 114) |
| Ab-12 CDR-L3 | QQGDTLPYT(SEQ ID NO: 115) |
| Ab-12 CDR-H1 | DYNMH (SEQ ID NO: 263) |
| Ab-12 CDR-H2 | EINPNSGGSGYNQKFKG (SEQ ID NO: 264) |
| Ab-12 CDR-H3 | LGYYGNYEDWYFDV (SEQ ID NO: 265) |
| Ab-12 light chain | SEQ ID NO: 197 |
| Ab-12 heavy chain | SEQ ID NO: 201 |
| Ab-13 and Ab-14 CDR-L1 | RASSSVTSSYLN (SEQ ID NO: 284) |
| Ab-13 and Ab-14 CDR-L2 | STSNLAS (SEQ ID NO: 285) |
| Ab-13 and Ab-14 CDR-L3 | QQYDFFPST (SEQ ID NO: 286) |
| Ab-13 and Ab-14 CDR-H1 | DYYMN (SEQ ID NO: 296) |
| Ab-13 and Ab-14 CDR-H2 | DINPYNDDTTYNHKFKG (SEQ ID NO: 297) |
| Ab-13 and Ab-14 CDR-H3 | ETAVITTNAMD (SEQ ID NO: 298) |
| Ab-13 light chain | SEQ ID NO: 205 |

FIGURE 7 (cont.)

| Sequence Description | Sequence |
|---|---|
| Ab-13 heavy chain | SEQ ID NO: 209 |
| Ab-14 light variable region | SEQ ID NO: 380 |
| Ab-14 heavy variable region | SEQ ID NO: 382 |
| Ab-14 light chain | SEQ ID NO: 213 |
| Ab-14 heavy chain | SEQ ID NO: 217 |
| Ab-17 and Ab-18 CDR-L1 | SVSSSISSSNLH (SEQ ID NO: 116) |
| Ab-17 and Ab-18 CDR-L2 | GTSNLAS (SEQ ID NO: 237) |
| Ab-17 and Ab-18 CDR-L3 | QQWTTTYT (SEQ ID NO: 238) |
| Ab-17 and Ab-18 CDR-H1 | DYYIH (SEQ ID NO: 266) |
| Ab-17 and Ab-18 CDR-H2 | RIDPDNGESTYVPKFQG (SEQ ID NO: 267) |
| Ab-17 and Ab-18 CDR-H3 | EGLDYGDYYAVDY (SEQ ID NO: 268) |
| Ab-17 light variable region (with signal sequence) | SEQ ID NO: 299 |
| Ab-17 heavy variable region (with signal sequence) | SEQ ID NO: 301 |
| Ab-18 light variable region (with signal sequence) | SEQ ID NO: 303 |
| Ab-18 heavy variable region (with signal sequence) | SEQ ID NO: 305 |
| Ab-19, Ab-20 and Ab-23 CDR-L1 | RASQDISSYLN (SEQ ID NO: 239) |
| Ab-19, Ab-20 and Ab-23 CDR-L2 | STSRLNS (SEQ ID NO: 240) |
| Ab-19, Ab-20 and Ab-23 CDR-L3 | QQDIKHPT (SEQ ID NO: 241) |
| Ab-19, Ab-20 and Ab-23 CDR-H1 | DYIMH (SEQ ID NO: 269) |
| Ab-19, Ab-20 and Ab-23 CDR-H2 | YINPYNDDTEYNEKFKG (SEQ ID NO: 270) |
| Ab-19, Ab-20 and Ab-23 CDR-H3 | SIYYYDAPFAY (SEQ ID NO: 271) |
| Ab-19 light variable region | SEQ ID NO: 314 |
| Ab-19 heavy variable region | SEQ ID NO: 327 |
| Ab-19 light chain (with signal sequence) | SEQ ID NO: 307 |
| Ab-19 heavy chain (with signal sequence) | SEQ ID NO: 309 |
| Ab-20 light variable region (with signal sequence) | SEQ ID NO: 311 |
| Ab-20 heavy variable region (with signal sequence) | SEQ ID NO: 313 |
| Ab-23 light variable region | SEQ ID NO: 364 |
| Ab-23 heavy variable region | SEQ ID NO: 366 |
| Ab-23 light chain | SEQ ID NO: 341 |
| Ab-23 heavy chain | SEQ ID NO: 345 |
| Ab-21 and Ab-22 CDR-L1 | KASQDVFTAVA (SEQ ID NO: 242) |
| Ab-21 and Ab-22 CDR-L2 | WASTRHT (SEQ ID NO: 243) |
| Ab-21 and Ab-22 CDR-L3 | QQYSSYPLT (SEQ ID NO: 244) |
| Ab-21 and Ab-22 CDR-H1 | DYYMH (SEQ ID NO: 272) |
| Ab-21 and Ab-22 CDR-H2 | RIDPENGDIIYDPKFQG (SEQ ID NO: 273) |
| Ab-21 and Ab-22 CDR-H3 | DAGDPAWFTY (SEQ ID NO: 274) |
| Ab-21 light variable region (with signal sequence) | SEQ ID NO: 315 |
| Ab-21 heavy variable region (with signal | SEQ ID NO: 317 |

FIGURE 7 (cont.)

| Sequence Description | Sequence |
|---|---|
| sequence) | |
| Ab-22 light variable region | SEQ ID NO: 368 |
| Ab-22 heavy variable region | SEQ ID NO: 370 |
| Ab-24 CDR-L1 | KASQSVDYDGTSYMN (SEQ ID NO: 351) |
| Ab-24 CDR-L2 | AASNLES (SEQ ID NO: 352) |
| Ab-24 CDR-L3 | QQSNEDPFT (SEQ ID NO: 353) |
| Ab-24 CDR-H1 | TYWMN (SEQ ID NO: 358) |
| Ab-24 CDR-H2 | MIHPSASEIRLDQKFKD (SEQ ID NO: 359) |
| Ab-24 CDR-H3 | SGEWGSMDY (SEQ ID NO: 360) |
| Ab-24 light chain | SEQ ID NO: 350 |
| Ab-24 heavy chain | SEQ ID NO: 357 |

FIGURE 8

SEQUENCE LISTING

```
<110>  Eli Lilly and Company
       Korytko, Andrew I.
       Marquis, David  Matthew
       Smith , Eric  Michael
       Swanson , Barbara  Anne

<120>  Anti-Sclerostin Antibodies

<130>  X17563

<150>  US 60/895813
<151>  2007-03-20

<160>  43

<170>  PatentIn version 3.4

<210>  1
<211>  213
<212>  PRT
<213>  Homo sapiens

<400>  1

Met Gln Leu Pro Leu Ala Leu Cys Leu Val Cys Leu Leu Val His Thr
1               5                   10                  15


Ala Phe Arg Val Val Glu Gly Gln Gly Trp Gln Ala Phe Lys Asn Asp
            20                  25                  30


Ala Thr Glu Ile Ile Pro Glu Leu Gly Glu Tyr Pro Glu Pro Pro Pro
        35                  40                  45


Glu Leu Glu Asn Asn Lys Thr Met Asn Arg Ala Glu Asn Gly Gly Arg
    50                  55                  60


Pro Pro His His Pro Phe Glu Thr Lys Asp Val Ser Glu Tyr Ser Cys
65                  70                  75                  80


Arg Glu Leu His Phe Thr Arg Tyr Val Thr Asp Gly Pro Cys Arg Ser
                85                  90                  95


Ala Lys Pro Val Thr Glu Leu Val Cys Ser Gly Gln Cys Gly Pro Ala
            100                 105                 110


Arg Leu Leu Pro Asn Ala Ile Gly Arg Gly Lys Trp Trp Arg Pro Ser
        115                 120                 125


Gly Pro Asp Phe Arg Cys Ile Pro Asp Arg Tyr Arg Ala Gln Arg Val
    130                 135                 140
```

FIGURE 8 Continued…

```
Gln Leu Leu Cys Pro Gly Gly Glu Ala Pro Arg Ala Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Thr Glu Ala Ala Arg Pro Gln Lys Gly
            180                 185                 190

Arg Lys Pro Arg Pro Arg Ala Arg Ser Ala Lys Ala Asn Gln Ala Glu
        195                 200                 205

Leu Glu Asn Ala Tyr
    210


<210>  2
<211>  444
<212>  PRT
<213>  Artificial

<220>
<223>  Miscellaneous construct

<400>  2

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Phe Leu Asn Trp Val Arg Gln Ala Pro Gly Gln Gly Leu Glu Trp Met
        35                  40                  45

Gly Thr Ile Tyr Pro Tyr His Asp Gly Thr Thr Tyr Ser Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Glu Glu Asp Gly Gln Phe Asp Tyr Trp Gly Gln Gly Thr
            100                 105                 110

Thr Val Thr Val Ser Ser Ala Ser Thr Lys Gly Pro Ser Val Phe Pro
        115                 120                 125
```

FIGURE 8 Continued…

```
Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365
```

FIGURE 8 Continued…

Gly Phe Tyr Pro Ser Asp Ile Ala Val Glu Trp Glu Ser Asn Gly Gln
370 375 380

Pro Glu Asn Asn Tyr Lys Thr Thr Pro Pro Val Leu Asp Ser Asp Gly
385 390 395 400

Ser Phe Phe Leu Tyr Ser Arg Leu Thr Val Asp Lys Ser Arg Trp Gln
405 410 415

Glu Gly Asn Val Phe Ser Cys Ser Val Met His Glu Ala Leu His Asn
420 425 430

His Tyr Thr Gln Lys Ser Leu Ser Leu Ser Leu Gly
435 440

<210> 3
<211> 444
<212> PRT
<213> Artificial

<220>
<223> Miscellaneous construct

<400> 3

Gln Val Gln Leu Val Gln Ser Gly Ala Glu Val Lys Lys Pro Gly Ala
1 5 10 15

Ser Val Lys Val Ser Cys Lys Val Ser Gly Phe Pro Ile Lys Asp Thr
20 25 30

Phe Gln His Trp Val Arg Gln Ala Pro Gly Lys Gly Leu Glu Trp Met
35 40 45

Gly Trp Ser Asp Pro Glu Ile Gly Asp Thr Glu Tyr Ala Ser Lys Phe
50 55 60

Gln Gly Arg Val Thr Met Thr Glu Asp Thr Ser Thr Asp Thr Ala Tyr
65 70 75 80

Met Glu Leu Ser Ser Leu Arg Ser Glu Asp Thr Ala Val Tyr Tyr Cys
85 90 95

Ala Thr Gly Asp Thr Thr Tyr Lys Phe Asp Phe Trp Gly Gln Gly Thr
100 105 110

Thr Val Thr Val Ser Ser Ala Ser Thr Lys Gly Pro Ser Val Phe Pro
115 120 125

FIGURE 8 Continued…

```
Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365
```

FIGURE 8 Continued...

Gly Phe Tyr Pro Ser Asp Ile Ala Val Glu Trp Glu Ser Asn Gly Gln
370 375 380

Pro Glu Asn Asn Tyr Lys Thr Thr Pro Pro Val Leu Asp Ser Asp Gly
385 390 395 400

Ser Phe Phe Leu Tyr Ser Arg Leu Thr Val Asp Lys Ser Arg Trp Gln
405 410 415

Glu Gly Asn Val Phe Ser Cys Ser Val Met His Glu Ala Leu His Asn
420 425 430

His Tyr Thr Gln Lys Ser Leu Ser Leu Ser Leu Gly
435 440

<210> 4
<211> 450
<212> PRT
<213> Artificial

<220>
<223> Miscellaneous construct

<400> 4

Glu Val Gln Leu Val Gln Ser Gly Ala Glu Val Lys Lys Pro Gly Glu
1 5 10 15

Ser Leu Lys Ile Ser Cys Lys Gly Ser Asp Phe Glu Ile Lys Asp Tyr
20 25 30

Tyr Ile His Trp Val Arg Gln Met Pro Gly Lys Gly Leu Glu Trp Met
35 40 45

Gly Gln Ile Asp Ala Glu Asp Gly Glu Thr Glu Tyr Ala Pro Arg Phe
50 55 60

Gln Gly Gln Val Thr Ile Ser Ala Asp Lys Ser Ile Ser Thr Ala Tyr
65 70 75 80

Leu Gln Trp Ser Ser Leu Lys Ala Ser Asp Thr Ala Met Tyr Tyr Cys
85 90 95

Ala Arg Glu Gly Tyr Tyr Tyr Asp Gly Arg Asp Tyr Trp Tyr Phe Asp
100 105 110

Val Trp Gly Gln Gly Thr Thr Val Thr Val Ser Ser Ala Ser Thr Lys
115 120 125

FIGURE 8 Continued…

```
Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365
```

FIGURE 8 Continued...

```
Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly
    450


<210>  5
<211>  214
<212>  PRT
<213>  Artificial

<220>
<223>  Miscellaneous construct

<400>  5

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Gln Trp Tyr
            20                  25                  30

Leu Asn Trp Tyr Gln Gln Lys Pro Gly Lys Ala Pro Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Ser Lys Leu Pro Arg
                85                  90                  95

Thr Phe Gly Gly Gly Thr Lys Val Glu Ile Lys Arg Thr Val Ala Ala
            100                 105                 110
```

FIGURE 8 Continued…

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> 6
<211> 214
<212> PRT
<213> Artificial

<220>
<223> Miscellaneous construct

<400> 6

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Val His Thr Ala
20 25 30

Val Ala Trp Tyr Gln Gln Lys Pro Gly Lys Ala Pro Lys Leu Leu Ile
35 40 45

Tyr Trp Ala Ser Thr Arg Trp Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Ser Asp Tyr Pro Trp
85 90 95

FIGURE 8 Continued…

```
Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210>  7
<211>  213
<212>  PRT
<213>  Artificial

<220>
<223>  Miscellaneous construct

<400>  7

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Ile
            20                  25                  30

His Trp Tyr Gln Gln Lys Pro Gly Gln Ala Pro Arg Leu Leu Ile Tyr
        35                  40                  45

Ser Thr Ser Glu Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
```

```
65                  70                  75                  80

Asp Phe Ala Val Tyr Tyr Cys Gln Gln Leu Ser His Leu Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210>  8
<211>  1332
<212>  DNA
<213>  Artificial

<220>
<223>  Miscellaneous construct

<400>  8
caggtgcagc tggtgcagtc tggggctgag gtgaagaagc ctgggtcctc agtgaaggtt      60

tcctgcaagg catctggata cacattcact gactactttc tgaactgggt gcgacaggcc     120

cctggacaag ggcttgagtg gatgggaact atttatcctt accatgatgg tactacctac     180

tctcagaagt tcaagggcag agtcaccatt accgcggaca aatccacgag cacagcctac     240

atggagctga gcagcctgag atctgaggac acggccgtgt attactgtgc gagagaggaa     300

gaggatggtc agttcgacta ctggggccaa ggaaccacgg tcaccgtctc ctcagcctcc     360

accaagggcc catcggtctt cccgctagcg ccctgctcca ggagcacctc cgagagcaca     420
```

FIGURE 8 Continued… gccgccctgg gctgcctggt caaggactac ttccccgaac cggtgacggt gtcgtggaac 480
tcaggcgccc tgaccagcgg cgtgcacacc ttcccggctg tcctacagtc ctcaggactc 540
tactccctca gcagcgtggt gaccgtgccc tccagcagct tgggcacgaa gacctacacc 600
tgcaacgtag atcacaagcc cagcaacacc aaggtggaca agagagttga gtccaaatat 660
ggtcccccat gcccaccctg cccagcacct gagttcctgg ggggaccatc agtcttcctg 720
ttccccccaa aacccaagga cactctcatg atctcccgga cccctgaggt cacgtgcgtg 780
gtggtggacg tgagccagga agaccccgag gtccagttca actggtacgt ggatggcgtg 840
gaggtgcata atgccaagac aaagccgcgg gaggagcagt tcaacagcac gtaccgtgtg 900
gtcagcgtcc tcaccgtcct gcaccaggac tggctgaacg gcaaggagta caagtgcaag 960
gtctccaaca aaggcctccc gtcctccatc gagaaaacca tctccaaagc caaagggcag 1020
ccccgagagc cacaggtgta caccctgccc ccatcccagg aggagatgac caagaaccag 1080
gtcagcctga cctgcctggt caaaggcttc taccccagcg acatcgccgt ggagtgggaa 1140
agcaatgggc agccggagaa caactacaag accacgcctc ccgtgctgga ctccgacggc 1200
tccttcttcc tctacagcag gctaaccgtg gacaagagca ggtggcagga ggggaatgtc 1260
ttctcatgct ccgtgatgca tgaggctctg cacaaccact acacacagaa gagcctctcc 1320
ctgtctctgg gt 1332

<210> 9
<211> 1332
<212> DNA
<213> Artificial

<220>
<223> Miscellaneous construct

<400> 9
caggttcagc tggtgcagtc tggggctgag gtgaagaagc ctggggcctc agtgaaggtc 60
tcctgcaagg tttccggctt ccccattaag gacacctttc agcactgggt gcgacaggct 120
cctggaaaag ggcttgagtg gatgggatgg agcgatcctg agatcggtga tactgaatat 180
gcctcgaagt tccagggcag agtcaccatg accgaggaca catctacaga cacagcctac 240
atggagctga gcagcctgag atctgaggac acggccgtgt attactgtgc aacaggcgac 300
accacataca agtttgactt ctgggggcaa gggaccacgg tcaccgtctc ctcagcctcc 360
accaagggcc catcggtctt cccgctagcg ccctgctcca ggagcacctc cgagagcaca 420
gccgccctgg gctgcctggt caaggactac ttccccgaac cggtgacggt gtcgtggaac 480
tcaggcgccc tgaccagcgg cgtgcacacc ttcccggctg tcctacagtc ctcaggactc 540

FIGURE 8 Continued...

```
tactccctca gcagcgtggt gaccgtgccc tccagcagct tgggcacgaa gacctacacc    600
tgcaacgtag atcacaagcc cagcaacacc aaggtggaca agagagttga gtccaaatat    660
ggtcccccat gcccaccctg cccagcacct gagttcctgg ggggaccatc agtcttcctg    720
ttccccccaa aacccaagga cactctcatg atctcccgga cccctgaggt cacgtgcgtg    780
gtggtggacg tgagccagga agaccccgag gtccagttca actggtacgt ggatggcgtg    840
gaggtgcata atgccaagac aaagccgcgg gaggagcagt tcaacagcac gtaccgtgtg    900
gtcagcgtcc tcaccgtcct gcaccaggac tggctgaacg gcaaggagta caagtgcaag    960
gtctccaaca aaggcctccc gtcctccatc gagaaaacca tctccaaagc caaagggcag   1020
ccccgagagc cacaggtgta caccctgccc ccatcccagg aggagatgac caagaaccag   1080
gtcagcctga cctgcctggt caaaggcttc taccccagcg acatcgccgt ggagtgggaa   1140
agcaatgggc agccggagaa caactacaag accacgcctc ccgtgctgga ctccgacggc   1200
tccttcttcc tctacagcag gctaaccgtg gacaagagca ggtggcagga ggggaatgtc   1260
ttctcatgct ccgtgatgca tgaggctctg cacaaccact acacacagaa gagcctctcc   1320
ctgtctctgg gt                                                       1332
```

<210> 10
<211> 1350
<212> DNA
<213> Artificial

<220>
<223> Miscellaneous construct

<400> 10

```
gaggtgcagc tggtgcagtc tggagcagag gtgaaaaagc ccggggagtc tctgaagatc     60
tcctgtaagg gttctgactt cgagattaaa gactactata tacattgggt gcgccagatg    120
cccgggaaag gcctggagtg gatggggcag attgatgctg aggatggtga aactgaatat    180
gccccgaggt tccagggcca ggtcaccatc tcagccgaca agtccatcag caccgcctac    240
ctgcagtgga gcagcctgaa ggcctcggac accgccatgt attactgtgc gagagagggt    300
tattactacg atgggcgcga ctactggtac ttcgatgtct ggggccaagg gaccacggtc    360
accgtctcct cagcctccac caagggccca tcggtcttcc cgctagcgcc ctgctccagg    420
agcacctccg agagcacagc cgccctgggc tgcctggtca aggactactt ccccgaaccg    480
gtgacggtgt cgtggaactc aggcgccctg accagcggcg tgcacacctt cccggctgtc    540
ctacagtcct caggactcta ctccctcagc agcgtggtga ccgtgccctc cagcagcttg    600
ggcacgaaga cctacacctg caacgtagat cacaagccca gcaacaccaa ggtggacaag    660
agagttgagt ccaaatatgg tcccccatgc ccaccctgcc cagcacctga gttcctgggg    720
```

FIGURE 8 Continued...

ggaccatcag tcttcctgtt ccccccaaaa cccaaggaca ctctcatgat ctcccggacc 780
cctgaggtca cgtgcgtggt ggtggacgtg agccaggaag accccgaggt ccagttcaac 840
tggtacgtgg atggcgtgga ggtgcataat gccaagacaa agccgcggga ggagcagttc 900
aacagcacgt accgtgtggt cagcgtcctc accgtcctgc accaggactg gctgaacggc 960
aaggagtaca agtgcaaggt ctccaacaaa ggcctcccgt cctccatcga gaaaaccatc 1020
tccaaagcca aagggcagcc ccgagagcca caggtgtaca ccctgccccc atcccaggag 1080
gagatgacca agaaccaggt cagcctgacc tgcctggtca aaggcttcta ccccagcgac 1140
atcgccgtgg agtgggaaag caatgggcag ccggagaaca actacaagac cacgcctccc 1200
gtgctggact ccgacggctc cttcttcctc tacagcaggc taaccgtgga caagagcagg 1260
tggcaggagg ggaatgtctt ctcatgctcc gtgatgcatg aggctctgca caaccactac 1320
acacagaaga gcctctccct gtctctgggt 1350

<210> 11
<211> 642
<212> DNA
<213> Artificial

<220>
<223> Miscellaneous construct

<400> 11
gacatccaga tgacccagtc tccatcctct ctgtctgcat ctgtaggaga cagagtcacc 60
atcacttgca gtgcaagtca gggcattcag tggtatttaa actggtatca gcagaaacca 120
gggaaagccc ctaagctcct gatctattac acatcaagtt tacactcagg ggtcccatca 180
aggttcagtg gcagtggatc tgggacagat ttcactctca ccatcagcag tctgcaacct 240
gaagattttg caacttacta ctgtcagcag catagtaaac ttcctcggac gttcggcgga 300
gggaccaagg tggagatcaa acggactgtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gc 642

<210> 12
<211> 642
<212> DNA
<213> Artificial

FIGURE 8 Continued…

<220>
<223> Miscellaneous construct

<400> 12
gacatccaga tgacccagtc tccatcctcc ctgtctgcat ctgtaggaga cagagtcacc 60
atcacttgca aggccagtca ggatgtgcac actgctgtag cctggtatca gcagaaacca 120
gggaaagccc ctaagctcct gatctattgg gcatccaccc ggtggactgg agtcccatca 180
aggttcagtg gcagtggatc tgggacagat ttcactctca ccatcagcag tctgcaacct 240
gaagattttg caacttacta ctgtcagcaa tatagcgatt atccgtggac gttcggcgga 300
gggaccaagg tggagatcaa acggactgtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gc 642

<210> 13
<211> 639
<212> DNA
<213> Artificial

<220>
<223> Miscellaneous construct

<400> 13
gaaattgtgt tgacacagtc tccagccacc ctgtctttgt ctccagggga aagagccacc 60
ctctcctgca gtgccagctc aagtgtaagt tacatccact ggtaccaaca gaaacctggc 120
caggctccca ggctcctcat ctatagcaca tccgagctgg cttctggcat cccagccagg 180
ttcagtggca gtgggtctgg gacagacttc actctcacca tcagcagcct agagcctgaa 240
gattttgcag tttattactg tcagcagctt agtcatctcc cgctcacgtt cggcggaggg 300
accaaggtgg agatcaaacg aactgtggct gcaccatctg tcttcatctt cccgccatct 360
gatgagcagt tgaaatctgg aactgcctct gttgtgtgcc tgctgaataa cttctatccc 420
agagaggcca aagtacagtg gaaggtggat aacgccctcc aatcgggtaa ctcccaggag 480
agtgtcacag agcaggacag caaggacagc acctacagcc tcagcagcac cctgacgctg 540
agcaaagcag actacgagaa acacaaagtc tacgcctgcg aagtcaccca tcagggcctg 600
agctcgcccg tcacaaagag cttcaacagg ggagagtgc 639

<212> PRT
<213> Artificial

<220>
<223> Miscellaneous construct

<400> 14

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asp Tyr
20 25 30

Phe Leu Asn Trp Val Arg Gln Ala Pro Gly Gln Gly Leu Glu Trp Met
35 40 45

Gly Thr Ile Tyr Pro Tyr His Asp Gly Thr Thr Tyr Ser Gln Lys Phe
50 55 60

Lys Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Glu Glu Glu Asp Gly Gln Phe Asp Tyr Trp Gly Gln Gly Thr
100 105 110

Thr Val Thr Val Ser Ser
115

<210> 15
<211> 118
<212> PRT
<213> Artificial

<220>
<223> Miscellaneous construct

<400> 15

Gln Val Gln Leu Val Gln Ser Gly Ala Glu Val Lys Lys Pro Gly Ala
1 5 10 15

Ser Val Lys Val Ser Cys Lys Val Ser Gly Phe Pro Ile Lys Asp Thr
20 25 30

Phe Gln His Trp Val Arg Gln Ala Pro Gly Lys Gly Leu Glu Trp Met
35 40 45

FIGURE 8 Continued…

```
Gly Trp Ser Asp Pro Glu Ile Gly Asp Thr Glu Tyr Ala Ser Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Asp Thr Thr Tyr Lys Phe Asp Phe Trp Gly Gln Gly Thr
            100                 105                 110

Thr Val Thr Val Ser Ser
        115


<210>  16
<211>  124
<212>  PRT
<213>  Artificial

<220>
<223>  Miscellaneous construct

<400>  16

Glu Val Gln Leu Val Gln Ser Gly Ala Glu Val Lys Lys Pro Gly Glu
1               5                   10                  15

Ser Leu Lys Ile Ser Cys Lys Gly Ser Asp Phe Glu Ile Lys Asp Tyr
            20                  25                  30

Tyr Ile His Trp Val Arg Gln Met Pro Gly Lys Gly Leu Glu Trp Met
        35                  40                  45

Gly Gln Ile Asp Ala Glu Asp Gly Glu Thr Glu Tyr Ala Pro Arg Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Gly Tyr Tyr Tyr Asp Gly Arg Asp Tyr Trp Tyr Phe Asp
            100                 105                 110

Val Trp Gly Gln Gly Thr Thr Val Thr Val Ser Ser
        115                 120
```

FIGURE 8 Continued…

<210> 17
<211> 107
<212> PRT
<213> Artificial

<220>
<223> Miscellaneous construct

<400> 17

Asp Ile Gln Met Thr Gln Ser Pro Ser Ser Leu Ser Ala Ser Val Gly
1 5 10 15

Asp Arg Val Thr Ile Thr Cys Ser Ala Ser Gln Gly Ile Gln Trp Tyr
20 25 30

Leu Asn Trp Tyr Gln Gln Lys Pro Gly Lys Ala Pro Lys Leu Leu Ile
35 40 45

Tyr Tyr Thr Ser Ser Leu His Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln His Ser Lys Leu Pro Arg
85 90 95

Thr Phe Gly Gly Gly Thr Lys Val Glu Ile Lys
100 105

<210> 18
<211> 107
<212> PRT
<213> Artificial

<220>
<223> Miscellaneous construct

<400> 18

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Val His Thr Ala
20 25 30

Val Ala Trp Tyr Gln Gln Lys Pro Gly Lys Ala Pro Lys Leu Leu Ile
35 40 45

FIGURE 8 Continued…

```
Tyr Trp Ala Ser Thr Arg Trp Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Asp Tyr Pro Trp
                85                  90                  95

Thr Phe Gly Gly Gly Thr Lys Val Glu Ile Lys
            100                 105


<210>  19
<211>  106
<212>  PRT
<213>  Artificial

<220>
<223>  Miscellaneous construct

<400>  19

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Ile
            20                  25                  30

His Trp Tyr Gln Gln Lys Pro Gly Gln Ala Pro Arg Leu Leu Ile Tyr
        35                  40                  45

Ser Thr Ser Glu Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Leu Ser His Leu Pro Leu Thr
                85                  90                  95

Phe Gly Gly Gly Thr Lys Val Glu Ile Lys
            100                 105


<210>  20
<211>  10
<212>  PRT
<213>  Artificial

<220>
```

```
<223>  Miscellaneous construct

<400>  20

Gly Tyr Thr Phe Thr Asp Tyr Phe Leu Asn
1               5                   10


<210>  21
<211>  17
<212>  PRT
<213>  Artificial

<220>
<223>  Miscellaneous construct

<400>  21

Thr Ile Tyr Pro Tyr His Asp Gly Thr Thr Tyr Ser Gln Lys Phe Lys
1               5                   10                  15


Gly



<210>  22
<211>  9
<212>  PRT
<213>  Artificial

<220>
<223>  Miscellaneous construct

<400>  22

Glu Glu Glu Asp Gly Gln Phe Asp Tyr
1               5


<210>  23
<211>  11
<212>  PRT
<213>  Artificial

<220>
<223>  Miscellaneous construct

<400>  23

Ser Ala Ser Gln Gly Ile Gln Trp Tyr Leu Asn
1               5                   10


<210>  24
<211>  7
<212>  PRT
<213>  Artificial

<220>
<223>  Miscellaneous construct
```

Tyr Thr Ser Ser Leu His Ser
1 5

<210> 25
<211> 9
<212> PRT
<213> Artificial

<220>
<223> Miscellaneous construct

<400> 25

Gln Gln His Ser Lys Leu Pro Arg Thr
1 5

<210> 26
<211> 10
<212> PRT
<213> Artificial

<220>
<223> Miscellaneous construct

<400> 26

Gly Phe Pro Ile Lys Asp Thr Phe Gln His
1 5 10

<210> 27
<211> 17
<212> PRT
<213> Artificial

<220>
<223> Miscellaneous construct

<400> 27

Trp Ser Asp Pro Glu Ile Gly Asp Thr Glu Tyr Ala Ser Lys Phe Gln
1 5 10 15

Gly

<210> 28
<211> 9
<212> PRT
<213> Artificial

<220>
<223> Miscellaneous construct

```
<400>  28

Gly Asp Thr Thr Tyr Lys Phe Asp Phe
1               5


<210>  29
<211>  11
<212>  PRT
<213>  Artificial

<220>
<223>  Miscellaneous construct

<400>  29

Lys Ala Ser Gln Asp Val His Thr Ala Val Ala
1               5                   10


<210>  30
<211>  7
<212>  PRT
<213>  Artificial

<220>
<223>  Miscellaneous construct

<400>  30

Trp Ala Ser Thr Arg Trp Thr
1               5


<210>  31
<211>  9
<212>  PRT
<213>  Artificial

<220>
<223>  Miscellaneous construct

<400>  31

Gln Gln Tyr Ser Asp Tyr Pro Trp Thr
1               5


<210>  32
<211>  10
<212>  PRT
<213>  Artificial

<220>
<223>  Miscellaneous construct

<400>  32

Asp Phe Glu Ile Lys Asp Tyr Tyr Ile His
1               5                   10
```

FIGURE 8 Continued…

<210> 33
<211> 17
<212> PRT
<213> Artificial

<220>
<223> Miscellaneous construct

<400> 33

Gln Ile Asp Ala Glu Asp Gly Glu Thr Glu Tyr Ala Pro Arg Phe Gln
1 5 10 15

Gly

<210> 34
<211> 17
<212> PRT
<213> Artificial

<220>
<223> Miscellaneous construct

<400> 34

Gln Ile Asp Ala Glu Asp Gly Glu Thr Glu Tyr Ala Pro Arg Phe Gln
1 5 10 15

Gly

<210> 35
<211> 17
<212> PRT
<213> Artificial

<220>
<223> Miscellaneous construct

<400> 35

Gln Ile Asp Ala Glu Asp Gly Glu Thr Glu Tyr Ala Pro Arg Phe Gln
1 5 10 15

Gly

<210> 36
<211> 7
<212> PRT
<213> Artificial

```
<223>  Miscellaneous construct

<400>  36

Ser Thr Ser Glu Leu Ala Ser
1               5


<210>  37
<211>  9
<212>  PRT
<213>  Artificial

<220>
<223>  Miscellaneous construct

<400>  37

Gln Gln Leu Ser His Leu Pro Leu Thr
1               5


<210>  38
<211>  322
<212>  PRT
<213>  Artificial

<220>
<223>  Miscellaneous construct

<400>  38

Gly Pro Ser Val Phe Pro Leu Ala Pro Cys Ser Arg Ser Thr Ser Glu
1               5                   10                  15

Ser Thr Ala Ala Leu Gly Cys Leu Val Lys Asp Tyr Phe Pro Glu Pro
            20                  25                  30

Val Thr Val Ser Trp Asn Ser Gly Ala Leu Thr Ser Gly Val His Thr
        35                  40                  45

Phe Pro Ala Val Leu Gln Ser Ser Gly Leu Tyr Ser Leu Ser Ser Val
    50                  55                  60

Val Thr Val Pro Ser Ser Ser Leu Gly Thr Lys Thr Tyr Thr Cys Asn
65                  70                  75                  80

Val Asp His Lys Pro Ser Asn Thr Lys Val Asp Lys Arg Val Glu Ser
                85                  90                  95

Lys Tyr Gly Pro Pro Cys Pro Pro Cys Pro Ala Pro Glu Phe Leu Gly
            100                 105                 110

Gly Pro Ser Val Phe Leu Phe Pro Pro Lys Pro Lys Asp Thr Leu Met
```

```
        115                 120                 125

Ile Ser Arg Thr Pro Glu Val Thr Cys Val Val Val Asp Val Ser Gln
    130                 135                 140

Glu Asp Pro Glu Val Gln Phe Asn Trp Tyr Val Asp Gly Val Glu Val
145                 150                 155                 160

His Asn Ala Lys Thr Lys Pro Arg Glu Glu Gln Phe Asn Ser Thr Tyr
                165                 170                 175

Arg Val Val Ser Val Leu Thr Val Leu His Gln Asp Trp Leu Asn Gly
            180                 185                 190

Lys Glu Tyr Lys Cys Lys Val Ser Asn Lys Gly Leu Pro Ser Ser Ile
        195                 200                 205

Glu Lys Thr Ile Ser Lys Ala Lys Gly Gln Pro Arg Glu Pro Gln Val
    210                 215                 220

Tyr Thr Leu Pro Pro Ser Gln Glu Glu Met Thr Lys Asn Gln Val Ser
225                 230                 235                 240

Leu Thr Cys Leu Val Lys Gly Phe Tyr Pro Ser Asp Ile Ala Val Glu
                245                 250                 255

Trp Glu Ser Asn Gly Gln Pro Glu Asn Asn Tyr Lys Thr Thr Pro Pro
            260                 265                 270

Val Leu Asp Ser Asp Gly Ser Phe Phe Leu Tyr Ser Arg Leu Thr Val
        275                 280                 285

Asp Lys Ser Arg Trp Gln Glu Gly Asn Val Phe Ser Cys Ser Val Met
    290                 295                 300

His Glu Ala Leu His Asn His Tyr Thr Gln Lys Ser Leu Ser Leu Ser
305                 310                 315                 320

Leu Gly


<210>  39
<211>  970
<212>  DNA
<213>  Artificial

<220>
```

<223> Miscellaneous construct

<400> 39

```
ggcccatcgg tcttcccgct agcgccctgc tccaggagca cctccgagag cacagccgcc      60

ctgggctgcc tggtcaagga ctacttcccc gaaccggtga cggtgtcgtg gaactcaggc     120

gccctgacca gcggcgtgca caccttcccg gctgtcctac agtcctcagg actctactcc     180

gctcagcagc gtggtgaccg tgccctccag cagcttgggc acgaagacct acacctgcaa     240

cgtagatcac aagcccagca acaccaaggt ggacaagaga gttgagtcca aatatggtcc     300

cccatgccca ccctgcccag cacctgagtt cctgggggga ccatcagtct tcctgttccc     360

cccaaaaccc aaggacactc tcatgatctc ccggacccct gaggtcacgt gcgtggtggt     420

ggacgtgagc caggaagacc ccgaggtcca gttcaactgg tacgtggatg gcgtggaggt     480

gcataatgcc aagacaaagc cgcgggagga gcagttcaac agcacgtacc gtgtggtcag     540

cgtcctcacc gtcctgcacc aggactggct gaacggcaag gagtacaagt gcaaggtctc     600

caacaaaggc ctcccgtcct ccatcgagaa aaccatctcc aaagccaaag ggcagccccg     660

agagccacag gtgtacaccc tgcccccatc ccaggaggag atgaccaaga accaggtcag     720

cctgacctgc ctggtcaaag gcttctaccc cagcgacatc gccgtggagt gggaaagcaa     780

tgggcagccg gagaacaact acaagaccac gcctcccgtg ctggactccg acggctcctt     840

cttcctctac agcaggctaa ccgtggacaa gagcaggtgg caggagggga atgtcttctc     900

atgctccgtg atgcatgagg ctctgcacaa ccactacaca cagaagagcc tctccctgtc     960

tctgggttga                                                            970
```

<210> 40
<211> 444
<212> PRT
<213> Artificial

<220>
<223> Miscellaneous construct

<400> 40

```
Glu Val Gln Leu Gln Gln Ser Val Ala Glu Leu Val Arg Pro Gly Ala
1               5                   10                  15

Ser Val Lys Leu Ser Cys Thr Ala Ser Gly Phe Asn Ile Lys Ser Thr
            20                  25                  30

Phe Met His Trp Val Lys Gln Arg Pro Asp Gln Gly Leu Glu Trp Ile
        35                  40                  45

Gly Trp Ile Asp Pro Glu Asn Gly Asp Thr Glu Tyr Ala Ser Lys Phe
```

```
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Thr Gly Glu Ser Asn Tyr Asp Phe Asp Phe Trp Gly Leu Gly Thr
            100                 105                 110

Thr Leu Thr Val Ser Ser Ala Lys Thr Thr Pro Pro Ser Val Tyr Pro
        115                 120                 125

Leu Ala Pro Gly Thr Ala Leu Lys Ser Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ala Leu Ser Ser Gly Val His Thr Phe Pro Ala Val Leu Gln
                165                 170                 175

Ser Gly Leu Tyr Thr Leu Thr Ser Ser Val Thr Val Pro Ser Ser Thr
            180                 185                 190

Trp Pro Ser Gln Thr Val Thr Cys Asn Val Ala His Pro Ala Ser Ser
        195                 200                 205

Thr Lys Val Asp Lys Lys Ile Val Pro Arg Asn Cys Gly Gly Asp Cys
    210                 215                 220

Lys Pro Cys Ile Cys Thr Gly Ser Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Gln Asp Asp Pro Glu Val His Phe
            260                 265                 270

Ser Trp Phe Val Asp Asp Val Glu Val His Thr Ala Gln Thr Arg Pro
        275                 280                 285

Pro Glu Glu Gln Phe Asn Ser Thr Phe Arg Ser Val Ser Glu Leu Pro
    290                 295                 300
```

FIGURE 8 Continued…

```
Ile Leu His Gln Asp Trp Leu Asn Gly Arg Thr Phe Arg Cys Lys Val
305                 310                 315                 320

Thr Ser Ala Ala Phe Pro Ser Pro Ile Glu Lys Thr Ile Ser Lys Pro
                325                 330                 335

Glu Gly Arg Thr Gln Val Pro His Val Tyr Thr Met Ser Pro Thr Lys
            340                 345                 350

Glu Glu Met Thr Gln Asn Glu Val Ser Ile Thr Cys Met Val Lys Gly
        355                 360                 365

Phe Tyr Pro Pro Asp Ile Tyr Val Glu Trp Gln Met Asn Gly Gln Pro
    370                 375                 380

Gln Glu Asn Tyr Lys Asn Thr Pro Pro Thr Met Asp Thr Asp Gly Ser
385                 390                 395                 400

Tyr Phe Leu Tyr Ser Lys Leu Asn Val Lys Lys Glu Lys Trp Gln Gln
                405                 410                 415

Gly Asn Thr Phe Thr Cys Ser Val Leu His Glu Gly Leu His Asn His
            420                 425                 430

His Thr Glu Lys Ser Leu Ser His Ser Pro Gly Lys
        435                 440


<210>  41
<211>  214
<212>  PRT
<213>  Artificial

<220>
<223>  Miscellaneous construct

<400>  41

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
```

```
    50                  55                  60

Ser Gly Ser Gly Thr Asp Tyr Thr Leu Thr Ile Ser Asp Val Gln Ser
65                  70                  75                  80

Glu Asp Leu Ala Asp Tyr Phe Cys Gln Gln Tyr Ser Asn Tyr Pro Trp
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Thr Glu Gln Leu Ala Thr Gly
        115                 120                 125

Gly Ala Ser Val Val Cys Leu Met Asn Asn Phe Tyr Pro Arg Asp Ile
    130                 135                 140

Ser Val Lys Trp Lys Ile Asp Gly Thr Glu Arg Arg Asp Gly Val Leu
145                 150                 155                 160

Asp Ser Val Thr Asp Gln Asp Ser Lys Asp Ser Thr Tyr Ser Met Ser
                165                 170                 175

Ser Thr Leu Ser Leu Ser Lys Ala Asp Tyr Glu Ser His Asn Leu Tyr
            180                 185                 190

Thr Cys Glu Val Val His Lys Thr Ser Ser Ser Pro Val Val Lys Ser
        195                 200                 205

Phe Asn Arg Asn Glu Cys
    210

<210>  42
<211>  450
<212>  PRT
<213>  Artificial

<220>
<223>  Miscellaneous construct

<400>  42

Glu Val Gln Leu Gln Gln Ser Gly Ala Glu His Val Lys Pro Gly Ala
1               5                   10                  15

Ser Val Lys Leu Ser Cys Thr Ala Ser Asp Phe Asn Ile Lys Asp Tyr
            20                  25                  30
```

FIGURE 8 Continued…

```
Tyr Ile His Trp Val Lys Gln Arg Thr Ala Gln Gly Leu Glu Trp Ile
        35                  40                  45

Gly Arg Ile Asp Pro Glu Asp Gly Glu Thr Glu Tyr Ala Pro Arg Phe
    50                  55                  60

Gln Gly Lys Ala Thr Ile Ile Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Glu Gly Tyr Tyr Tyr Asp Ser Arg Asp Tyr Trp Tyr Phe Asp
            100                 105                 110

Val Trp Gly Thr Gly Thr Thr Val Thr Val Ser Ser Ala Lys Thr Thr
        115                 120                 125

Pro Pro Ser Val Tyr Pro Leu Ala Pro Gly Thr Ala Leu Lys Ser Asn
    130                 135                 140

Ser Met Val Thr Leu Gly Cys Leu Val Lys Gly Tyr Phe Pro Glu Pro
145                 150                 155                 160

Val Thr Val Thr Trp Asn Ser Gly Ala Leu Ser Ser Gly Val His Thr
                165                 170                 175

Phe Pro Ala Val Leu Gln Ser Gly Leu Tyr Thr Leu Thr Ser Ser Val
            180                 185                 190

Thr Val Pro Ser Ser Thr Trp Pro Ser Gln Thr Val Thr Cys Asn Val
        195                 200                 205

Ala His Pro Ala Ser Ser Thr Lys Val Asp Lys Lys Ile Val Pro Arg
    210                 215                 220

Asn Cys Gly Gly Asp Cys Lys Pro Cys Ile Cys Thr Gly Ser Glu Val
225                 230                 235                 240

Ser Ser Val Phe Ile Phe Pro Pro Lys Pro Lys Asp Val Leu Thr Ile
                245                 250                 255

Thr Leu Thr Pro Lys Val Thr Cys Val Val Val Asp Ile Ser Gln Asp
            260                 265                 270

Asp Pro Glu Val His Phe Ser Trp Phe Val Asp Asp Val Glu Val His
```

```
        275                 280                 285

Thr Ala Gln Thr Arg Pro Pro Glu Glu Gln Phe Asn Ser Thr Phe Arg
    290                 295                 300

Ser Val Ser Glu Leu Pro Ile Leu His Gln Asp Trp Leu Asn Gly Arg
305                 310                 315                 320

Thr Phe Arg Cys Lys Val Thr Ser Ala Ala Phe Pro Ser Pro Ile Glu
                325                 330                 335

Lys Thr Ile Ser Lys Pro Glu Gly Arg Thr Gln Val Pro His Val Tyr
            340                 345                 350

Thr Met Ser Pro Thr Lys Glu Glu Met Thr Gln Asn Glu Val Ser Ile
        355                 360                 365

Thr Cys Met Val Lys Gly Phe Tyr Pro Pro Asp Ile Tyr Val Glu Trp
    370                 375                 380

Gln Met Asn Gly Gln Pro Gln Glu Asn Tyr Lys Asn Thr Pro Pro Thr
385                 390                 395                 400

Met Asp Thr Asp Gly Ser Tyr Phe Leu Tyr Ser Lys Leu Asn Val Lys
                405                 410                 415

Lys Glu Lys Trp Gln Gln Gly Asn Thr Phe Thr Cys Ser Val Leu His
            420                 425                 430

Glu Gly Leu His Asn His His Thr Glu Lys Ser Leu Ser His Ser Pro
        435                 440                 445

Gly Lys
    450

<210>  43
<211>  213
<212>  PRT
<213>  Artificial

<220>
<223>  Miscellaneous construct

<400>  43

Glu Ile Val Leu Thr Gln Ser Pro Ala Leu Met Ser Ala Ser Pro Gly
1               5                   10                  15
```

FIGURE 8 Continued…

```
Glu Lys Val Thr Met Thr Cys Ser Ala Ser Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg Ala Asp Ala Ala Pro
            100                 105                 110

Thr Val Ser Ile Phe Pro Pro Ser Thr Glu Gln Leu Ala Thr Gly Gly
        115                 120                 125

Ala Ser Val Val Cys Leu Met Asn Asn Phe Tyr Pro Arg Asp Ile Ser
    130                 135                 140

Val Lys Trp Lys Ile Asp Gly Thr Glu Arg Arg Asp Gly Val Leu Asp
145                 150                 155                 160

Ser Val Thr Asp Gln Asp Ser Lys Asp Ser Thr Tyr Ser Met Ser Ser
                165                 170                 175

Thr Leu Ser Leu Ser Lys Ala Asp Tyr Glu Ser His Asn Leu Tyr Thr
            180                 185                 190

Cys Glu Val Val His Lys Thr Ser Ser Ser Pro Val Val Lys Ser Phe
        195                 200                 205

Asn Arg Asn Glu Cys
    210
```

FIGURE 9

SEQUENCE LISTING

<110> Novartis AG

<120> COMPOSITIONS AND METHODS OF USE FOR ANTIBODIES AGAINST SCLEROSTIN

<130> 52279

<160> 171

<170> PatentIn version 3.2

<210> 1
<211> 10
<212> PRT
<213> Homo sapiens

<400> 1

Gly Phe Thr Phe Ser Ser Tyr Val Met Asn
1 5 10

<210> 2
<211> 10
<212> PRT
<213> Homo sapiens

<400> 2

Gly Phe Thr Phe Arg Ser His Trp Leu Ser
1 5 10

<210> 3
<211> 10
<212> PRT
<213> Homo sapiens

<400> 3

Gly Phe Thr Phe Ser Ser Tyr Val Met Asn
1 5 10

<210> 4
<211> 10
<212> PRT
<213> Homo sapiens

Gly Phe Thr Phe Arg Ser His Trp Leu Ser
1 5 10

<210> 5
<211> 10
<212> PRT
<213> Homo sapiens

<400> 5

Gly Phe Thr Phe Arg Ser His Trp Leu Ser
1 5 10

<210> 6
<211> 10
<212> PRT
<213> Homo sapiens

<400> 6

Gly Phe Thr Phe Arg Ser His Trp Leu Ser
1 5 10

<210> 7
<211> 10
<212> PRT
<213> Homo sapiens

<400> 7

Gly Phe Thr Phe Arg Ser His Trp Leu Ser
1 5 10

<210> 8
<211> 10
<212> PRT
<213> Homo sapiens

<400> 8

Gly Phe Thr Phe Arg Ser His Trp Leu Ser
1 5 10

<210> 9
<211> 10
<212> PRT
<213> Homo sapiens

<400> 9

Gly Phe Thr Phe Arg Ser His Trp Leu Ser
1 5 10

FIGURE 9 Continued…

<210> 10
<211> 10
<212> PRT
<213> Homo sapiens

<400> 10

Gly Phe Thr Phe Arg Ser His Trp Leu Ser
1 5 10

<210> 11
<211> 10
<212> PRT
<213> Homo sapiens

<400> 11

Gly Phe Thr Phe Arg Ser His Trp Leu Ser
1 5 10

<210> 12
<211> 20
<212> PRT
<213> Homo sapiens

<400> 12

Trp Val Ser Phe Ile Ser Gly Asp Ser Ser Asn Thr Tyr Tyr Ala Asp
1 5 10 15

Ser Val Lys Gly
20

<210> 13
<211> 20
<212> PRT
<213> Homo sapiens

<400> 13

Trp Val Ser Asn Ile Asn Tyr Asp Gly Ser Ser Thr Tyr Tyr Ala Asp
1 5 10 15

Ser Val Lys Gly
20

<210> 14
<211> 20
<212> PRT
<213> Homo sapiens

<400> 14

Trp Val Ser Phe Ile Ser Gly Asp Ser Ser Asn Thr Tyr Tyr Ala Asp

```
1               5                   10                  15


Ser Val Lys Gly
            20


<210>  15
<211>  20
<212>  PRT
<213>  Homo sapiens

<400>  15

Trp Val Ser Asn Ile Asn Tyr Asp Gly Ser Ser Thr Tyr Tyr Ala Asp
1               5                   10                  15


Ser Val Lys Gly
            20


<210>  16
<211>  19
<212>  PRT
<213>  Homo sapiens

<400>  16

Trp Val Ser Val Thr Gly Val His Gly Asp Thr Tyr Tyr Ala Asp Ser
1               5                   10                  15


Val Lys Gly



<210>  17
<211>  19
<212>  PRT
<213>  Homo sapiens

<400>  17

Trp Val Ser Val Ile Gly Asn Trp Gly Asp Thr Tyr Tyr Ala Asp Ser
1               5                   10                  15


Val Lys Gly



<210>  18
<211>  19
<212>  PRT
<213>  Homo sapiens

<400>  18

Trp Val Ser Val Thr Thr His Gln Gly Tyr Thr Tyr Tyr Ala Asp Ser
1               5                   10                  15
```

FIGURE 9 Continued…

Val Lys Gly

<210> 19
<211> 19
<212> PRT
<213> Homo sapiens

<400> 19

Trp Val Ser Ala Thr Asn Arg Tyr Gly Tyr Thr Tyr Tyr Ala Asp Ser
1 5 10 15

Val Lys Gly

<210> 20
<211> 20
<212> PRT
<213> Homo sapiens

<400> 20

Trp Val Ser Asn Ile Asn Tyr Asp Gly Ser Ser Thr Tyr Tyr Ala Asp
1 5 10 15

Ser Val Lys Gly
20

<210> 21
<211> 19
<212> PRT
<213> Homo sapiens

<400> 21

Trp Val Ser Val Ile Thr Pro Tyr Gly Asp Thr Tyr Tyr Ala Asp Ser
1 5 10 15

Val Lys Gly

<210> 22
<211> 19
<212> PRT
<213> Homo sapiens

<400> 22

Trp Val Ser Val Ile Thr Pro Tyr Gly Asp Thr Tyr Tyr Ala Asp Ser
1 5 10 15

FIGURE 9 Continued…

Val Lys Gly

<210> 23
<211> 15
<212> PRT
<213> Homo sapiens

<400> 23

Thr Phe Met His Gly His Leu Gly Gly Gly Leu Ser Met Asp Phe
1 5 10 15

<210> 24
<211> 8
<212> PRT
<213> Homo sapiens

<400> 24

Asp Thr Tyr Leu His Phe Asp Tyr
1 5

<210> 25
<211> 15
<212> PRT
<213> Homo sapiens

<400> 25

Thr Phe Met His Gly His Leu Gly Gly Gly Leu Ser Met Asp Phe
1 5 10 15

<210> 26
<211> 8
<212> PRT
<213> Homo sapiens

<400> 26

Asp Thr Tyr Leu His Phe Asp Tyr
1 5

<210> 27
<211> 8
<212> PRT
<213> Homo sapiens

<400> 27

Asp Thr Tyr Leu His Phe Asp Tyr
1 5

<211> 8
<212> PRT
<213> Homo sapiens

<400> 28

Asp Thr Tyr Leu His Phe Asp Tyr
1 5

<210> 29
<211> 8
<212> PRT
<213> Homo sapiens

<400> 29

Asp Thr Tyr Leu His Phe Asp Tyr
1 5

<210> 30
<211> 8
<212> PRT
<213> Homo sapiens

<400> 30

Asp Thr Tyr Leu His Phe Asp Tyr
1 5

<210> 31
<211> 8
<212> PRT
<213> Homo sapiens

<400> 31

Asp Thr Tyr Leu His Phe Asp Tyr
1 5

<210> 32
<211> 8
<212> PRT
<213> Homo sapiens

<400> 32

Asp Thr Tyr Leu His Phe Asp Tyr
1 5

<210> 33
<211> 8
<212> PRT
<213> Homo sapiens

Asp Thr Tyr Leu His Phe Asp Tyr
1 5

<210> 34
<211> 11
<212> PRT
<213> Homo sapiens

<400> 34

Ser Gly Asp Asn Ile Gly Ser Phe Tyr Val His
1 5 10

<210> 35
<211> 20
<212> PRT
<213> Homo sapiens

<400> 35

Trp Val Ser Asn Ile Asn Tyr Asp Gly Ser Ser Thr Tyr Tyr Ala Asp
1 5 10 15

Ser Val Lys Gly
20

<210> 36
<211> 11
<212> PRT
<213> Homo sapiens

<400> 36

Ser Gly Asp Asn Ile Gly Ser Phe Tyr Val His
1 5 10

<210> 37
<211> 14
<212> PRT
<213> Homo sapiens

<400> 37

Thr Gly Thr Ser Ser Asp Val Gly Asp Ile Asn Asp Val Ser
1 5 10

<210> 38
<211> 14
<212> PRT
<213> Homo sapiens

<400> 38

Thr Gly Thr Ser Ser Asp Val Gly Asp Ile Asn Asp Val Ser
1 5 10

FIGURE 9 Continued...

<210> 39
<211> 14
<212> PRT
<213> Homo sapiens

<400> 39

Thr Gly Thr Ser Ser Asp Val Gly Asp Ile Asn Asp Val Ser
1 5 10

<210> 40
<211> 14
<212> PRT
<213> Homo sapiens

<400> 40

Thr Gly Thr Ser Ser Asp Val Gly Asp Ile Asn Asp Val Ser
1 5 10

<210> 41
<211> 14
<212> PRT
<213> Homo sapiens

<400> 41

Thr Gly Thr Ser Ser Asp Val Gly Asp Ile Asn Asp Val Ser
1 5 10

<210> 42
<211> 14
<212> PRT
<213> Homo sapiens

<400> 42

Thr Gly Thr Ser Ser Asp Val Gly Asp Ile Asn Asp Val Ser
1 5 10

<210> 43
<211> 14
<212> PRT
<213> Homo sapiens

<400> 43

Thr Gly Thr Ser Ser Asp Val Gly Asp Ile Asn Asp Val Ser
1 5 10

<210> 44
<211> 14
<212> PRT
<213> Homo sapiens

Thr Gly Thr Ser Ser Asp Val Gly Asp Ile Asn Asp Val Ser
1 5 10

<210> 45
<211> 11
<212> PRT
<213> Homo sapiens

<400> 45

Leu Val Ile Tyr Asp Asp Asn Asn Arg Pro Ser
1 5 10

<210> 46
<211> 11
<212> PRT
<213> Homo sapiens

<400> 46

Leu Met Ile Tyr Asp Val Asn Asn Arg Pro Ser
1 5 10

<210> 47
<211> 11
<212> PRT
<213> Homo sapiens

<400> 47

Leu Val Ile Tyr Asp Asp Asn Asn Arg Pro Ser
1 5 10

<210> 48
<211> 11
<212> PRT
<213> Homo sapiens

<400> 48

Leu Met Ile Tyr Asp Val Asn Asn Arg Pro Ser
1 5 10

<210> 49
<211> 11
<212> PRT
<213> Homo sapiens

<400> 49

Leu Met Ile Tyr Asp Val Asn Asn Arg Pro Ser
1 5 10

FIGURE 9 Continued...

<210> 50
<211> 11
<212> PRT
<213> Homo sapiens

<400> 50

Leu Met Ile Tyr Asp Val Asn Asn Arg Pro Ser
1 5 10

<210> 51
<211> 11
<212> PRT
<213> Homo sapiens

<400> 51

Leu Met Ile Tyr Asp Val Asn Asn Arg Pro Ser
1 5 10

<210> 52
<211> 11
<212> PRT
<213> Homo sapiens

<400> 52

Leu Met Ile Tyr Asp Val Asn Asn Arg Pro Ser
1 5 10

<210> 53
<211> 11
<212> PRT
<213> Homo sapiens

<400> 53

Leu Met Ile Tyr Asp Val Asn Asn Arg Pro Ser
1 5 10

<210> 54
<211> 11
<212> PRT
<213> Homo sapiens

<400> 54

Leu Met Ile Tyr Asp Val Asn Asn Arg Pro Ser
1 5 10

<210> 55
<211> 11
<212> PRT
<213> Homo sapiens

Leu Met Ile Tyr Asp Val Asn Asn Arg Pro Ser
1 5 10

<210> 56
<211> 10
<212> PRT
<213> Homo sapiens

<400> 56

Gly Ser Trp Ala Gly Ser Ser Gly Ser Tyr
1 5 10

<210> 57
<211> 10
<212> PRT
<213> Homo sapiens

<400> 57

Ser Ser Tyr Gly Glu Ser Leu Thr Ser Tyr
1 5 10

<210> 58
<211> 10
<212> PRT
<213> Homo sapiens

<400> 58

Ala Ser Trp Thr Gly Val Glu Pro Asp Tyr
1 5 10

<210> 59
<211> 10
<212> PRT
<213> Homo sapiens

<400> 59

Gln Ser Tyr Ala Gly Ser Tyr Leu Ser Glu
1 5 10

<210> 60
<211> 10
<212> PRT
<213> Homo sapiens

<400> 60

Ser Ser Tyr Gly Glu Ser Leu Thr Ser Tyr
1 5 10

FIGURE 9 Continued…

<210> 61
<211> 10
<212> PRT
<213> Homo sapiens

<400> 61

Ser Ser Tyr Gly Glu Ser Leu Thr Ser Tyr
1 5 10

<210> 62
<211> 10
<212> PRT
<213> Homo sapiens

<400> 62

Ser Ser Tyr Gly Glu Ser Leu Thr Ser Tyr
1 5 10

<210> 63
<211> 10
<212> PRT
<213> Homo sapiens

<400> 63

Ser Ser Tyr Gly Glu Ser Leu Thr Ser Tyr
1 5 10

<210> 64
<211> 10
<212> PRT
<213> Homo sapiens

<400> 64

Ser Thr Tyr Asp Gly Pro Gly Leu Ser Glu
1 5 10

<210> 65
<211> 10
<212> PRT
<213> Homo sapiens

<400> 65

Ser Ser Tyr Gly Glu Ser Leu Thr Ser Tyr
1 5 10

<210> 66
<211> 10
<212> PRT
<213> Homo sapiens

```
Ser Ser Tyr Gly Glu Ser Leu Thr Ser Tyr
1               5                   10


<210>  67
<211>  124
<212>  PRT
<213>  Homo sapiens

<400>  67

Gln Val Gln Leu Val Glu Ser Gly Gly Gly Leu Val Gln Pro Gly Gly
1               5                   10                  15


Ser Leu Arg Leu Ser Cys Ala Ala Ser Gly Phe Thr Phe Ser Ser Tyr
            20                  25                  30


Val Met Asn Trp Val Arg Gln Ala Pro Gly Lys Gly Leu Glu Trp Val
        35                  40                  45


Ser Phe Ile Ser Gly Asp Ser Ser Asn Thr Tyr Tyr Ala Asp Ser Val
    50                  55                  60


Lys Gly Arg Phe Thr Ile Ser Arg Asp Asn Ser Lys Asn Thr Leu Tyr
65                  70                  75                  80


Leu Gln Met Asn Ser Leu Arg Ala Glu Asp Thr Ala Val Tyr Tyr Cys
                85                  90                  95


Ala Arg Thr Phe Met His Gly His Leu Gly Gly Gly Leu Ser Met Asp
            100                 105                 110


Phe Trp Gly Gln Gly Thr Leu Val Thr Val Ser Ser
        115                 120


<210>  68
<211>  117
<212>  PRT
<213>  Homo sapiens

<400>  68

Gln Val Gln Leu Val Glu Ser Gly Gly Gly Leu Val Gln Pro Gly Gly
1               5                   10                  15


Ser Leu Arg Leu Ser Cys Ala Ala Ser Gly Phe Thr Phe Arg Ser His
            20                  25                  30


Trp Leu Ser Trp Val Arg Gln Ala Pro Gly Lys Gly Leu Glu Trp Val
        35                  40                  45
```

FIGURE 9 Continued…

```
Ser Asn Ile Asn Tyr Asp Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Tyr Leu His Phe Asp Tyr Trp Gly Gln Gly Thr Leu
            100                 105                 110

Val Thr Val Ser Ser
        115


<210>  69
<211>  124
<212>  PRT
<213>  Homo sapiens

<400>  69

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Asn Trp Val Arg Gln Ala Pro Gly Lys Gly Leu Glu Trp Val
        35                  40                  45

Ser Phe Ile Ser Gly Asp Ser Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Phe Met His Gly His Leu Gly Gly Gly Leu Ser Met Asp
            100                 105                 110

Phe Trp Gly Gln Gly Thr Leu Val Thr Val Ser Ser
        115                 120
```

FIGURE 9 Continued…

<210> 70
<211> 117
<212> PRT
<213> Homo sapiens

<400> 70

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Arg Ser His
20 25 30

Trp Leu Ser Trp Val Arg Gln Ala Pro Gly Lys Gly Leu Glu Trp Val
35 40 45

Ser Asn Ile Asn Tyr Asp Gly Ser Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Thr Tyr Leu His Phe Asp Tyr Trp Gly Gln Gly Thr Leu
100 105 110

Val Thr Val Ser Ser
115

<210> 71
<211> 116
<212> PRT
<213> Homo sapiens

<400> 71

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Arg Ser His
20 25 30

Trp Leu Ser Trp Val Arg Gln Ala Pro Gly Lys Gly Leu Glu Trp Val
35 40 45

Ser Val Thr Gly Val His Gly Asp Thr Tyr Tyr Ala Asp Ser Val Lys
50 55 60

FIGURE 9 Continued...

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Asp Thr Tyr Leu His Phe Asp Tyr Trp Gly Gln Gly Thr Leu Val
100 105 110

Thr Val Ser Ser
115

<210> 72
<211> 116
<212> PRT
<213> Homo sapiens

<400> 72

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Arg Ser His
20 25 30

Trp Leu Ser Trp Val Arg Gln Ala Pro Gly Lys Gly Leu Glu Trp Val
35 40 45

Ser Val Ile Gly Asn Trp Gly Asp Thr Tyr Tyr Ala Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Asp Thr Tyr Leu His Phe Asp Tyr Trp Gly Gln Gly Thr Leu Val
100 105 110

Thr Val Ser Ser
115

<210> 73
<211> 116
<212> PRT
<213> Homo sapiens

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Arg Ser His
20 25 30

Trp Leu Ser Trp Val Arg Gln Ala Pro Gly Lys Gly Leu Glu Trp Val
35 40 45

Ser Val Thr Thr His Gln Gly Tyr Thr Tyr Tyr Ala Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Asp Thr Tyr Leu His Phe Asp Tyr Trp Gly Gln Gly Thr Leu Val
100 105 110

Thr Val Ser Ser
115

<210> 74
<211> 116
<212> PRT
<213> Homo sapiens

<400> 74

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Arg Ser His
20 25 30

Trp Leu Ser Trp Val Arg Gln Ala Pro Gly Lys Gly Leu Glu Trp Val
35 40 45

Ser Ala Thr Asn Arg Tyr Gly Tyr Thr Tyr Tyr Ala Asp Ser Val Lys
50 55 60

Gly Arg Phe Thr Ile Ser Arg Asp Asn Ser Lys Asn Thr Leu Tyr Leu
65 70 75 80

FIGURE 9 Continued…

Gln Met Asn Ser Leu Arg Ala Glu Asp Thr Ala Val Tyr Tyr Cys Ala
85 90 95

Arg Asp Thr Tyr Leu His Phe Asp Tyr Trp Gly Gln Gly Thr Leu Val
100 105 110

Thr Val Ser Ser
115

<210> 75
<211> 117
<212> PRT
<213> Homo sapiens

<400> 75

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Arg Ser His
20 25 30

Trp Leu Ser Trp Val Arg Gln Ala Pro Gly Lys Gly Leu Glu Trp Val
35 40 45

Ser Asn Ile Asn Tyr Asp Gly Ser Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Thr Tyr Leu His Phe Asp Tyr Trp Gly Gln Gly Thr Leu
100 105 110

Val Thr Val Ser Ser
115

<210> 76
<211> 116
<212> PRT
<213> Homo sapiens

<400> 76

Gln Val Gln Leu Val Glu Ser Gly Gly Gly Leu Val Gln Pro Gly Gly
1 5 10 15

FIGURE 9 Continued...

```
Ser Leu Arg Leu Ser Cys Ala Ala Ser Gly Phe Thr Phe Arg Ser His
            20                  25                  30

Trp Leu Ser Trp Val Arg Gln Ala Pro Gly Lys Gly Leu Glu Trp Val
        35                  40                  45

Ser Val Ile Thr Pro Tyr Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Thr Tyr Leu His Phe Asp Tyr Trp Gly Gln Gly Thr Leu Val
            100                 105                 110

Thr Val Ser Ser
        115


<210>  77
<211>  116
<212>  PRT
<213>  Homo sapiens

<400>  77

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser His
            20                  25                  30

Trp Leu Ser Trp Val Arg Gln Ala Pro Gly Lys Gly Leu Glu Trp Val
        35                  40                  45

Ser Val Ile Thr Pro Tyr Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Thr Tyr Leu His Phe Asp Tyr Trp Gly Gln Gly Thr Leu Val
```

```
                100                 105                 110

Thr Val Ser Ser
        115


<210>  78
<211>  110
<212>  PRT
<213>  Homo sapiens

<400>  78

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Ser Phe Tyr Val
            20                  25                  30

His Trp Tyr Gln Gln Lys Pro Gly Gln Ala Pro Val Leu Val Ile Tyr
        35                  40                  45

Asp Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gly Ser Trp Ala Gly Ser Ser Gly Ser
                85                  90                  95

Tyr Val Phe Gly Gly Arg Thr Lys Leu Thr Val Leu Gly Gln
            100                 105                 110


<210>  79
<211>  113
<212>  PRT
<213>  Homo sapiens

<400>  79

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asp Ile
            20                  25                  30

Asn Asp Val Ser Trp Tyr Gln Gln His Pro Gly Lys Ala Pro Lys Leu
        35                  40                  45
```

FIGURE 9 Continued…

```
Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Gly Glu Ser
                85                  90                  95

Leu Thr Ser Tyr Val Phe Gly Gly Gly Thr Lys Leu Thr Val Leu Gly
            100                 105                 110

Gln


<210>  80
<211>  110
<212>  PRT
<213>  Homo sapiens

<400>  80

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Ser Phe Tyr Val
            20                  25                  30

His Trp Tyr Gln Gln Lys Pro Gly Gln Ala Pro Val Leu Val Ile Tyr
        35                  40                  45

Asp Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ala Ser Trp Thr Gly Val Glu Pro Asp
                85                  90                  95

Tyr Val Phe Gly Gly Gly Thr Lys Leu Thr Val Leu Gly Gln
            100                 105                 110


<210>  81
<211>  113
<212>  PRT
<213>  Homo sapiens

<400>  81
```

Asp Ile Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Asp Ile
20 25 30

Asn Asp Val Ser Trp Tyr Gln Gln His Pro Gly Lys Ala Pro Lys Leu
35 40 45

Met Ile Tyr Asp Val Asn Asn Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Gln Ser Tyr Ala Gly Ser
85 90 95

Tyr Leu Ser Glu Val Phe Gly Gly Gly Thr Lys Leu Thr Val Leu Gly
100 105 110

Gln

<210> 82
<211> 113
<212> PRT
<213> Homo sapiens

<400> 82

Asp Ile Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Asp Ile
20 25 30

Asn Asp Val Ser Trp Tyr Gln Gln His Pro Gly Lys Ala Pro Lys Leu
35 40 45

Met Ile Tyr Asp Val Asn Asn Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ser Ser Tyr Gly Glu Ser

```
                85                  90                  95

Leu Thr Ser Tyr Val Phe Gly Gly Gly Thr Lys Leu Thr Val Leu Gly
            100                 105                 110

Gln



<210>  83
<211>  113
<212>  PRT
<213>  Homo sapiens

<400>  83

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asp Ile
            20                  25                  30

Asn Asp Val Ser Trp Tyr Gln Gln His Pro Gly Lys Ala Pro Lys Leu
        35                  40                  45

Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Gly Glu Ser
                85                  90                  95

Leu Thr Ser Tyr Val Phe Gly Gly Gly Thr Lys Leu Thr Val Leu Gly
            100                 105                 110

Gln



<210>  84
<211>  113
<212>  PRT
<213>  Homo sapiens

<400>  84

Asp Ile Ala Leu Thr Gln Pro Ala Ser Val Ser Gly Ser Pro Gly Gln
1               5                   10                  15
```

FIGURE 9 Continued…

Ser Ile Thr Ile Ser Cys Thr Gly Thr Ser Ser Asp Val Gly Asp Ile
20 25 30

Asn Asp Val Ser Trp Tyr Gln Gln His Pro Gly Lys Ala Pro Lys Leu
35 40 45

Met Ile Tyr Asp Val Asn Asn Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ser Ser Tyr Gly Glu Ser
85 90 95

Leu Thr Ser Tyr Val Phe Gly Gly Gly Thr Lys Leu Thr Val Leu Gly
100 105 110

Gln

<210> 85
<211> 113
<212> PRT
<213> Homo sapiens

<400> 85

Asp Ile Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Asp Ile
20 25 30

Asn Asp Val Ser Trp Tyr Gln Gln His Pro Gly Lys Ala Pro Lys Leu
35 40 45

Met Ile Tyr Asp Val Asn Asn Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ser Ser Tyr Gly Glu Ser
85 90 95

Leu Thr Ser Tyr Val Phe Gly Gly Gly Thr Lys Leu Thr Val Leu Gly
100 105 110

FIGURE 9 Continued…

Gln

<210> 86
<211> 113
<212> PRT
<213> Homo sapiens

<400> 86

Asp Ile Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Asp Ile
20 25 30

Asn Asp Val Ser Trp Tyr Gln Gln His Pro Gly Lys Ala Pro Lys Leu
35 40 45

Met Ile Tyr Asp Val Asn Asn Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ser Thr Tyr Asp Gly Pro
85 90 95

Gly Leu Ser Glu Val Phe Gly Gly Gly Thr Lys Leu Thr Val Leu Gly
100 105 110

Gln

<210> 87
<211> 113
<212> PRT
<213> Homo sapiens

<400> 87

Asp Ile Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Asp Ile
20 25 30

Asn Asp Val Ser Trp Tyr Gln Gln His Pro Gly Lys Ala Pro Lys Leu

```
        35                  40                  45

Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Gly Glu Ser
                85                  90                  95

Leu Thr Ser Tyr Val Phe Gly Gly Gly Thr Lys Leu Thr Val Leu Gly
            100                 105                 110

Gln


<210>  88
<211>  113
<212>  PRT
<213>  Homo sapiens

<400>  88

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asp Ile
            20                  25                  30

Asn Asp Val Ser Trp Tyr Gln Gln His Pro Gly Lys Ala Pro Lys Leu
        35                  40                  45

Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Thr Tyr Asp Gly Pro
                85                  90                  95

Gly Leu Ser Glu Val Phe Gly Gly Gly Thr Lys Leu Thr Val Leu Gly
            100                 105                 110

Gln
```

FIGURE 9 Continued...

<210> 89
<211> 372
<212> DNA
<213> Homo sapiens

<400> 89
caggtgcaat tggtggaaag cggcggcggc ctggtgcaac cgggcggcag cctgcgtctg 60
agctgcgcgg cctccggatt tacctttttct tcttatgtta tgaattgggt gcgccaagcc 120
cctgggaagg gtctcgagtg ggtgagcttt atctctggtg attctagcaa tacctattat 180
gcggatagcg tgaaaggccg ttttaccatt tcacgtgata attcgaaaaa caccctgtat 240
ctgcaaatga acagcctgcg tgcggaagat acggccgtgt attattgcgc gcgtactttt 300
atgcatggtc atcttggtgg tggtctttct atggattttt ggggccaagg caccctggtg 360
acggttagct ca 372

<210> 90
<211> 351
<212> DNA
<213> Homo sapiens

<400> 90
caggtgcaat tggtggaaag cggcggcggc ctggtgcaac cgggcggcag cctgcgtctg 60
agctgcgcgg cctccggatt tacctttcgt tctcattggc tttcttgggt gcgccaagcc 120
cctgggaagg gtctcgagtg ggtgagcaat atcaattatg atggtagctc tacctattat 180
gcggatagcg tgaaaggccg ttttaccatt tcacgtgata attcgaaaaa caccctgtat 240
ctgcaaatga acagcctgcg tgcggaagat acggccgtgt attattgcgc gcgtgatact 300
tatcttcatt ttgattattg gggccaaggc accctggtga cggttagctc a 351

<210> 91
<211> 372
<212> DNA
<213> Homo sapiens

<400> 91
caggtgcaat tggtggaaag cggcggcggc ctggtgcaac cgggcggcag cctgcgtctg 60
agctgcgcgg cctccggatt tacctttttct tcttatgtta tgaattgggt gcgccaagcc 120
cctgggaagg gtctcgagtg ggtgagcttt atctctggtg attctagcaa tacctattat 180
gcggatagcg tgaaaggccg ttttaccatt tcacgtgata attcgaaaaa caccctgtat 240
ctgcaaatga acagcctgcg tgcggaagat acggccgtgt attattgcgc gcgtactttt 300
atgcatggtc atcttggtgg tggtctttct atggattttt ggggccaagg caccctggtg 360
acggttagct ca 372

FIGURE 9 Continued...

<210> 92
<211> 351
<212> DNA
<213> Homo sapiens

<400> 92
caggtgcaat tggtggaaag cggcggcggc ctggtgcaac cgggcggcag cctgcgtctg 60
agctgcgcgg cctccggatt tacctttcgt tctcattggc tttcttgggt gcgccaagcc 120
cctgggaagg gtctcgagtg ggtgagcaat atcaattatg atggtagctc tacctattat 180
gcggatagcg tgaaaggccg ttttaccatt tcacgtgata attcgaaaaa caccctgtat 240
ctgcaaatga acagcctgcg tgcggaagat acggccgtgt attattgcgc gcgtgatact 300
tatcttcatt ttgattattg gggccaaggc accctggtga cggttagctc a 351

<210> 93
<211> 348
<212> DNA
<213> Homo sapiens

<400> 93
caggtgcaat tggtggaaag cggcggcggc ctggtgcaac cgggcggcag cctgcgtctg 60
agctgcgcgg cctccggatt tacctttcgt tctcattggc tttcttgggt gcgccaagcc 120
cctgggaagg gtctcgagtg ggtgagcgtt actggtgttc atggtgatac ttattatgct 180
gattctgtta agggtcgttt taccatttca cgtgataatt cgaaaaacac cctgtatctg 240
caaatgaaca gcctgcgtgc ggaagatacg gccgtgtatt attgcgcgcg tgatacttat 300
cttcattttg attattgggg ccaaggcacc ctggtgacgg ttagctca 348

<210> 94
<211> 348
<212> DNA
<213> Homo sapiens

<400> 94
caggtgcaat tggtggaaag cggcggcggc ctggtgcaac cgggcggcag cctgcgtctg 60
agctgcgcgg cctccggatt tacctttcgt tctcattggc tttcttgggt gcgccaagcc 120
cctgggaagg gtctcgagtg ggtgagcgtt attggtaatt ggggtgatac ttattatgct 180
gattctgtta agggtcgttt taccatttca cgtgataatt cgaaaaacac cctgtatctg 240
caaatgaaca gcctgcgtgc ggaagatacg gccgtgtatt attgcgcgcg tgatacttat 300
cttcattttg attattgggg ccaaggcacc ctggtgacgg ttagctca 348

<210> 95
<211> 348
<212> DNA

FIGURE 9 Continued...

<213> Homo sapiens

<400> 95
caggtgcaat tggtggaaag cggcggcggc ctggtgcaac cgggcggcag cctgcgtctg 60
agctgcgcgg cctccggatt tacctttcgt tctcattggc tttcttgggt gcgccaagcc 120
cctgggaagg gtctcgagtg ggtgagcgtt actactcatc agggttatac ttattatgct 180
gattctgtta agggtcgttt taccatttca cgtgataatt cgaaaaacac cctgtatctg 240
caaatgaaca gcctgcgtgc ggaagatacg gccgtgtatt attgcgcgcg tgatacttat 300
cttcattttg attattgggg ccaaggcacc ctggtgacgg ttagctca 348

<210> 96
<211> 348
<212> DNA
<213> Homo sapiens

<400> 96
caggtgcaat tggtggaaag cggcggcggc ctggtgcaac cgggcggcag cctgcgtctg 60
agctgcgcgg cctccggatt tacctttcgt tctcattggc tttcttgggt gcgccaagcc 120
cctgggaagg gtctcgagtg ggtgagcgct actaatcgtt atggttatac ttattatgct 180
gattctgtta agggtcgttt taccatttca cgtgataatt cgaaaaacac cctgtatctg 240
caaatgaaca gcctgcgtgc ggaagatacg gccgtgtatt attgcgcgcg tgatacttat 300
cttcattttg attattgggg ccaaggcacc ctggtgacgg ttagctca 348

<210> 97
<211> 351
<212> DNA
<213> Homo sapiens

<400> 97
caggtgcaat tggtggaaag cggcggcggc ctggtgcaac cgggcggcag cctgcgtctg 60
agctgcgcgg cctccggatt tacctttcgt tctcattggc tttcttgggt gcgccaagcc 120
cctgggaagg gtctcgagtg ggtgagcaat atcaattatg atggtagctc tacctattat 180
gcggatagcg tgaaaggccg ttttaccatt tcacgtgata attcgaaaaa caccctgtat 240
ctgcaaatga acagcctgcg tgcggaagat acggccgtgt attattgcgc gcgtgatact 300
tatcttcatt ttgattattg gggccaaggc accctggtga cggttagctc a 351

<210> 98
<211> 348
<212> DNA
<213> Homo sapiens

<400> 98
caggtgcaat tggtggaaag cggcggcggc ctggtgcaac cgggcggcag cctgcgtctg 60

FIGURE 9 Continued...

```
agctgcgcgg cctccggatt tacctttcgt tctcattggc tttcttgggt gcgccaagcc    120

cctgggaagg gtctcgagtg ggtgagcgtt attactcctt atggtgatac ttattatgct    180

gattctgtta agggtcgttt taccatttca cgtgataatt cgaaaaacac cctgtatctg    240

caaatgaaca gcctgcgtgc ggaagatacg gccgtgtatt attgcgcgcg tgatacttat    300

cttcattttg attattgggg ccaaggcacc ctggtgacgg ttagctca                348


<210>  99
<211>  348
<212>  DNA
<213>  Homo sapiens

<400>  99
caggtgcaat tggtggaaag cggcggcggc ctggtgcaac cgggcggcag cctgcgtctg     60

agctgcgcgg cctccggatt tacctttcgt tctcattggc tttcttgggt gcgccaagcc    120

cctgggaagg gtctcgagtg ggtgagcgtt attactcctt atggtgatac ttattatgct    180

gattctgtta agggtcgttt taccatttca cgtgataatt cgaaaaacac cctgtatctg    240

caaatgaaca gcctgcgtgc ggaagatacg gccgtgtatt attgcgcgcg tgatacttat    300

cttcattttg attattgggg ccaaggcacc ctggtgacgg ttagctca                348


<210>  100
<211>  330
<212>  DNA
<213>  Homo sapiens

<400>  100
gatatcgaac tgacccagcc gccttcagtg agcgttgcac caggtcagac cgcgcgtatc     60

tcgtgtagcg gcgataatat tggttctttt tatgttcatt ggtaccagca gaaacccggg    120

caggcgccag ttcttgtgat ttatgatgat aataatcgtc cctcaggcat cccggaacgc    180

tttagcggat ccaacagcgg caacaccgcg accctgacca ttagcggcac tcaggcggaa    240

gacgaagcgg attattattg cggttcttgg gctggttctt ctggttctta tgtgtttggc    300

ggccgcacga agttaaccgt tcttggccag                                     330


<210>  101
<211>  339
<212>  DNA
<213>  Homo sapiens

<400>  101
gatatcgcac tgacccagcc agcttcagtg agcggctcac caggtcagag cattaccatc     60

tcgtgtacgg gtactagcag cgatgttggt gatattaatg atgtgtcttg gtaccagcag    120

catcccggga aggcgccgaa acttatgatt tatgatgtta ataatcgtcc ctcaggcgtg    180
```

FIGURE 9 Continued...

```
agcaaccgtt ttagcggatc caaaagcggc aacaccgcga gcctgaccat tagcggcctg    240

caagcggaag acgaagcgga ttattattgc tcttcttatg gtgagtctct tacttcttat    300

gtgtttggcg gcggcacgaa gttaaccgtt cttggccag                           339


<210>  102
<211>  330
<212>  DNA
<213>  Homo sapiens

<400>  102
gatatcgaac tgacccagcc gccttcagtg agcgttgcac caggtcagac cgcgcgtatc     60

tcgtgtagcg gcgataatat tggttctttt tatgttcatt ggtaccagca gaaacccggg    120

caggcgccag ttcttgtgat ttatgatgat aataatcgtc cctcaggcat cccggaacgc    180

tttagcggat ccaacagcgg caacaccgcg accctgacca ttagcggcac tcaggcggaa    240

gacgaagcgg attattattg cgcttcttgg actggtgttg agcctgatta tgtgtttggc    300

ggcggcacga agttaaccgt tcttggccag                                     330


<210>  103
<211>  339
<212>  DNA
<213>  Homo sapiens

<400>  103
gatatcgcac tgacccagcc agcttcagtg agcggctcac caggtcagag cattaccatc     60

tcgtgtacgg gtactagcag cgatgttggt gatattaatg atgtgtcttg gtaccagcag    120

catcccggga aggcgccgaa acttatgatt tatgatgtta ataatcgtcc ctcaggcgtg    180

agcaaccgtt ttagcggatc caaaagcggc aacaccgcga gcctgaccat tagcggcctg    240

caagcggaag acgaagcgga ttattattgc cagtcttatg ctggttctta tctttctgag    300

gtgtttggcg gcggcacgaa gttaaccgtt cttggccag                           339


<210>  104
<211>  339
<212>  DNA
<213>  Homo sapiens

<400>  104
gatatcgcac tgacccagcc agcttcagtg agcggctcac caggtcagag cattaccatc     60

tcgtgtacgg gtactagcag cgatgttggt gatattaatg atgtgtcttg gtaccagcag    120

catcccggga aggcgccgaa acttatgatt tatgatgtta ataatcgtcc ctcaggcgtg    180

agcaaccgtt ttagcggatc caaaagcggc aacaccgcga gcctgaccat tagcggcctg    240

caagcggaag acgaagcgga ttattattgc tcttcttatg gtgagtctct tacttcttat    300
```

FIGURE 9 Continued… gtgtttggcg gcggcacgaa gttaaccgtt cttggccag 339

<210> 105
<211> 339
<212> DNA
<213> Homo sapiens

<400> 105
gatatcgcac tgacccagcc agcttcagtg agcggctcac caggtcagag cattaccatc 60
tcgtgtacgg gtactagcag cgatgttggt gatattaatg atgtgtcttg gtaccagcag 120
catcccggga aggcgccgaa acttatgatt tatgatgtta ataatcgtcc ctcaggcgtg 180
agcaaccgtt ttagcggatc caaaagcggc aacaccgcga gcctgaccat tagcggcctg 240
caagcggaag acgaagcgga ttattattgc tcttcttatg gtgagtctct tacttcttat 300
gtgtttggcg gcggcacgaa gttaaccgtt cttggccag 339

<210> 106
<211> 339
<212> DNA
<213> Homo sapiens

<400> 106
gatatcgcac tgacccagcc agcttcagtg agcggctcac caggtcagag cattaccatc 60
tcgtgtacgg gtactagcag cgatgttggt gatattaatg atgtgtcttg gtaccagcag 120
catcccggga aggcgccgaa acttatgatt tatgatgtta ataatcgtcc ctcaggcgtg 180
agcaaccgtt ttagcggatc caaaagcggc aacaccgcga gcctgaccat tagcggcctg 240
caagcggaag acgaagcgga ttattattgc tcttcttatg gtgagtctct tacttcttat 300
gtgtttggcg gcggcacgaa gttaaccgtt cttggccag 339

<210> 107
<211> 339
<212> DNA
<213> Homo sapiens

<400> 107
gatatcgcac tgacccagcc agcttcagtg agcggctcac caggtcagag cattaccatc 60
tcgtgtacgg gtactagcag cgatgttggt gatattaatg atgtgtcttg gtaccagcag 120
catcccggga aggcgccgaa acttatgatt tatgatgtta ataatcgtcc ctcaggcgtg 180
agcaaccgtt ttagcggatc caaaagcggc aacaccgcga gcctgaccat tagcggcctg 240
caagcggaag acgaagcgga ttattattgc tcttcttatg gtgagtctct tacttcttat 300
gtgtttggcg gcggcacgaa gttaaccgtt cttggccag 339

FIGURE 9 Continued...

<210> 108
<211> 339
<212> DNA
<213> Homo sapiens

<400> 108
gatatcgcac tgacccagcc agcttcagtg agcggctcac caggtcagag cattaccatc 60
tcgtgtacgg gtactagcag cgatgttggt gatattaatg atgtgtcttg gtaccagcag 120
catcccggga aggcgccgaa acttatgatt tatgatgtta ataatcgtcc ctcaggcgtg 180
agcaaccgtt ttagcggatc caaaagcggc aacaccgcga gcctgaccat tagcggcctg 240
caagcggaag acgaagcgga ttattattgc tctacttatg atggtcctgg tctttctgag 300
gtgtttggcg gcggcacgaa gttaaccgtt cttggccag 339

<210> 109
<211> 339
<212> DNA
<213> Homo sapiens

<400> 109
gatatcgcac tgacccagcc agcttcagtg agcggctcac caggtcagag cattaccatc 60
tcgtgtacgg gtactagcag cgatgttggt gatattaatg atgtgtcttg gtaccagcag 120
catcccggga aggcgccgaa acttatgatt tatgatgtta ataatcgtcc ctcaggcgtg 180
agcaaccgtt ttagcggatc caaaagcggc aacaccgcga gcctgaccat tagcggcctg 240
caagcggaag acgaagcgga ttattattgc tcttcttatg gtgagtctct tacttcttat 300
gtgtttggcg gcggcacgaa gttaaccgtt cttggccag 339

<210> 110
<211> 339
<212> DNA
<213> Homo sapiens

<400> 110
gatatcgcac tgacccagcc agcttcagtg agcggctcac caggtcagag cattaccatc 60
tcgtgtacgg gtactagcag cgatgttggt gatattaatg atgtgtcttg gtaccagcag 120
catcccggga aggcgccgaa acttatgatt tatgatgtta ataatcgtcc ctcaggcgtg 180
agcaaccgtt ttagcggatc caaaagcggc aacaccgcga gcctgaccat tagcggcctg 240
caagcggaag acgaagcgga ttattattgc tctacttatg atggtcctgg tctttctgag 300
gtgtttggcg gcggcacgaa gttaaccgtt cttggccag 339

<210> 111
<211> 469
<212> PRT
<213> Homo sapiens

```
Met Ala Trp Val Trp Thr Leu Pro Phe Leu Met Ala Ala Ala Gln Ser
1               5                   10                  15

Val Gln Ala Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Val Met Asn Trp Val Arg Gln Ala Pro Gly Lys Gly Leu
    50                  55                  60

Glu Trp Val Ser Phe Ile Ser Gly Asp Ser Ser Asn Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Thr Phe Met His Gly His Leu Gly Gly Gly Leu
        115                 120                 125

Ser Met Asp Phe Trp Gly Gln Gly Thr Leu Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Asn Phe Gly Thr Gln Thr Tyr
    210                 215                 220

Thr Cys Asn Val Asp His Lys Pro Ser Asn Thr Lys Val Asp Lys Thr
225                 230                 235                 240
```

FIGURE 9 Continued…

```
Val Glu Arg Lys Cys Cys Val Glu Cys Pro Pro Cys Pro Ala Pro Pro
                245                 250                 255

Val Ala Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Gln Phe Asn Trp Tyr Val Asp Gly Val
    290                 295                 300

Glu Val His Asn Ala Lys Thr Lys Pro Arg Glu Glu Gln Phe Asn Ser
305                 310                 315                 320

Thr Phe Arg Val Val Ser Val Leu Thr Val Val His Gln Asp Trp Leu
                325                 330                 335

Asn Gly Lys Glu Tyr Lys Cys Lys Val Ser Asn Lys Gly Leu Pro Ala
            340                 345                 350

Pro Ile Glu Lys Thr Ile Ser Lys Thr Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Met Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465
```

FIGURE 9 Continued…

<210> 112
<211> 462
<212> PRT
<213> Homo sapiens

<400> 112

```
Met Ala Trp Val Trp Thr Leu Pro Phe Leu Met Ala Ala Ala Gln Ser
1               5                   10                  15

Val Gln Ala Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Arg Ser His Trp Leu Ser Trp Val Arg Gln Ala Pro Gly Lys Gly Leu
    50                  55                  60

Glu Trp Val Ser Asn Ile Asn Tyr Asp Gly Ser Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Thr Tyr Leu His Phe Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Asn Phe Gly Thr Gln Thr Tyr Thr Cys Asn Val Asp His Lys
```

```
    210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Phe Arg Val Val Ser Val
305                 310                 315                 320

Leu Thr Val Val His Gln Asp Trp Leu Asn Gly Lys Glu Tyr Lys Cys
                325                 330                 335

Lys Val Ser Asn Lys Gly Leu Pro Ala Pro Ile Glu Lys Thr Ile Ser
            340                 345                 350

Lys Thr Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Met Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460
```

FIGURE 9 Continued…

<210> 113
<211> 469
<212> PRT
<213> Homo sapiens

<400> 113

```
Met Ala Trp Val Trp Thr Leu Pro Phe Leu Met Ala Ala Ala Gln Ser
1               5                   10                  15

Val Gln Ala Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Val Met Asn Trp Val Arg Gln Ala Pro Gly Lys Gly Leu
    50                  55                  60

Glu Trp Val Ser Phe Ile Ser Gly Asp Ser Ser Asn Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Thr Phe Met His Gly His Leu Gly Gly Gly Leu
        115                 120                 125

Ser Met Asp Phe Trp Gly Gln Gly Thr Leu Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205
```

FIGURE 9 Continued…

```
Ser Ser Val Val Thr Val Pro Ser Ser Asn Phe Gly Thr Gln Thr Tyr
    210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Pro
                245                 250                 255

Val Ala Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Gln Phe Asn Trp Tyr Val Asp Gly Val
    290                 295                 300

Glu Val His Asn Ala Lys Thr Lys Pro Arg Glu Glu Gln Phe Asn Ser
305                 310                 315                 320

Thr Phe Arg Val Val Ser Val Leu Thr Val Val His Gln Asp Trp Leu
                325                 330                 335

Asn Gly Lys Glu Tyr Lys Cys Lys Val Ser Asn Lys Gly Leu Pro Ala
            340                 345                 350

Pro Ile Glu Lys Thr Ile Ser Lys Thr Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Met Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
```

```
    450                 455                 460

Leu Ser Pro Gly Lys
465


<210>  114
<211>  462
<212>  PRT
<213>  Homo sapiens

<400>  114

Met Ala Trp Val Trp Thr Leu Pro Phe Leu Met Ala Ala Ala Gln Ser
1               5                   10                  15

Val Gln Ala Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Arg Ser His Trp Leu Ser Trp Val Arg Gln Ala Pro Gly Lys Gly Leu
    50                  55                  60

Glu Trp Val Ser Asn Ile Asn Tyr Asp Gly Ser Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Thr Tyr Leu His Phe Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190
```

FIGURE 9 Continued...

```
Leu Gln Ser Ser Gly Leu Tyr Ser Leu Ser Ser Val Val Thr Val Pro
        195                 200                 205

Ser Ser Asn Phe Gly Thr Gln Thr Tyr Thr Cys Asn Val Asp His Lys
    210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Phe Arg Val Val Ser Val
305                 310                 315                 320

Leu Thr Val Val His Gln Asp Trp Leu Asn Gly Lys Glu Tyr Lys Cys
                325                 330                 335

Lys Val Ser Asn Lys Gly Leu Pro Ala Pro Ile Glu Lys Thr Ile Ser
            340                 345                 350

Lys Thr Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Met Leu Asp Ser Asp
                405                 410                 415

Gly Ser Phe Phe Leu Tyr Ser Lys Leu Thr Val Asp Lys Ser Arg Trp
            420                 425                 430
```

FIGURE 9 Continued…

```
Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460


<210>  115
<211>  461
<212>  PRT
<213>  Homo sapiens

<400>  115

Met Ala Trp Val Trp Thr Leu Pro Phe Leu Met Ala Ala Ala Gln Ser
1               5                   10                  15

Val Gln Ala Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Arg Ser His Trp Leu Ser Trp Val Arg Gln Ala Pro Gly Lys Gly Leu
    50                  55                  60

Glu Trp Val Ser Val Thr Gly Val His Gly Asp Thr Tyr Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Asp Thr Tyr Leu His Phe Asp Tyr Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190
```

FIGURE 9 Continued...

```
Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
    210                 215                 220

Ser Asn Thr Lys Val Asp Lys Thr Val Glu Arg Lys Cys Cys Val Glu
225                 230                 235                 240

Cys Pro Pro Cys Pro Ala Pro Pro Val Ala Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Gln
        275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Phe Arg Val Val Ser Val Leu
305                 310                 315                 320

Thr Val Val His Gln Asp Trp Leu Asn Gly Lys Glu Tyr Lys Cys Lys
                325                 330                 335

Val Ser Asn Lys Gly Leu Pro Ala Pro Ile Glu Lys Thr Ile Ser Lys
            340                 345                 350

Thr Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Met Leu Asp Ser Asp Gly
                405                 410                 415

Ser Phe Phe Leu Tyr Ser Lys Leu Thr Val Asp Lys Ser Arg Trp Gln
            420                 425                 430
```

FIGURE 9 Continued…

```
Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460


<210>  116
<211>  461
<212>  PRT
<213>  Homo sapiens

<400>  116

Met Ala Trp Val Trp Thr Leu Pro Phe Leu Met Ala Ala Ala Gln Ser
1               5                   10                  15

Val Gln Ala Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Arg Ser His Trp Leu Ser Trp Val Arg Gln Ala Pro Gly Lys Gly Leu
    50                  55                  60

Glu Trp Val Ser Val Ile Gly Asn Trp Gly Asp Thr Tyr Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Asp Thr Tyr Leu His Phe Asp Tyr Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
```

```
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
    210                 215                 220

Ser Asn Thr Lys Val Asp Lys Thr Val Glu Arg Lys Cys Cys Val Glu
225                 230                 235                 240

Cys Pro Pro Cys Pro Ala Pro Pro Val Ala Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Gln
        275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Phe Arg Val Val Ser Val Leu
305                 310                 315                 320

Thr Val Val His Gln Asp Trp Leu Asn Gly Lys Glu Tyr Lys Cys Lys
                325                 330                 335

Val Ser Asn Lys Gly Leu Pro Ala Pro Ile Glu Lys Thr Ile Ser Lys
            340                 345                 350

Thr Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Met Leu Asp Ser Asp Gly
                405                 410                 415

Ser Phe Phe Leu Tyr Ser Lys Leu Thr Val Asp Lys Ser Arg Trp Gln
            420                 425                 430
```

FIGURE 9 Continued...

```
Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460


<210>  117
<211>  461
<212>  PRT
<213>  Homo sapiens

<400>  117

Met Ala Trp Val Trp Thr Leu Pro Phe Leu Met Ala Ala Ala Gln Ser
1               5                   10                  15

Val Gln Ala Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Arg Ser His Trp Leu Ser Trp Val Arg Gln Ala Pro Gly Lys Gly Leu
    50                  55                  60

Glu Trp Val Ser Val Thr Thr His Gln Gly Tyr Thr Tyr Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Asp Thr Tyr Leu His Phe Asp Tyr Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175
```

FIGURE 9 Continued…

```
Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
    210                 215                 220

Ser Asn Thr Lys Val Asp Lys Thr Val Glu Arg Lys Cys Cys Val Glu
225                 230                 235                 240

Cys Pro Pro Cys Pro Ala Pro Pro Val Ala Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Gln
        275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Phe Arg Val Val Ser Val Leu
305                 310                 315                 320

Thr Val Val His Gln Asp Trp Leu Asn Gly Lys Glu Tyr Lys Cys Lys
                325                 330                 335

Val Ser Asn Lys Gly Leu Pro Ala Pro Ile Glu Lys Thr Ile Ser Lys
            340                 345                 350

Thr Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Met Leu Asp Ser Asp Gly
                405                 410                 415

Ser Phe Phe Leu Tyr Ser Lys Leu Thr Val Asp Lys Ser Arg Trp Gln
```

Gln Gly Asn Val Phe Ser Cys Ser Val Met His Glu Ala Leu His Asn
435 440 445

His Tyr Thr Gln Lys Ser Leu Ser Leu Ser Pro Gly Lys
450 455 460

<210> 118
<211> 465
<212> PRT
<213> Homo sapiens

<400> 118

Met Lys His Leu Trp Phe Phe Leu Leu Leu Val Ala Ala Pro Arg Trp
1 5 10 15

Val Leu Ser Gln Val Gln Leu Val Glu Ser Gly Gly Gly Leu Val Gln
20 25 30

Pro Gly Gly Ser Leu Arg Leu Ser Cys Ala Ala Ser Gly Phe Thr Phe
35 40 45

Arg Ser His Trp Leu Ser Trp Val Arg Gln Ala Pro Gly Lys Gly Leu
50 55 60

Glu Trp Val Ser Ala Thr Asn Arg Tyr Gly Tyr Thr Tyr Tyr Ala Asp
65 70 75 80

Ser Val Lys Gly Arg Phe Thr Ile Ser Arg Asp Asn Ser Lys Asn Thr
85 90 95

Leu Tyr Leu Gln Met Asn Ser Leu Arg Ala Glu Asp Thr Ala Val Tyr
100 105 110

Tyr Cys Ala Arg Asp Thr Tyr Leu His Phe Asp Tyr Trp Gly Gln Gly
115 120 125

Thr Leu Val Thr Val Ser Ser Ala Lys Thr Thr Ala Pro Ser Val Tyr
130 135 140

Pro Leu Ala Pro Val Cys Gly Asp Thr Thr Gly Ser Ser Val Thr Leu
145 150 155 160

Gly Cys Leu Val Lys Gly Tyr Phe Pro Glu Pro Val Thr Leu Thr Trp
165 170 175

FIGURE 9 Continued…

```
Asn Ser Gly Ser Leu Ser Ser Gly Val His Thr Phe Pro Ala Val Leu
            180                 185                 190

Gln Ser Asp Leu Tyr Thr Leu Ser Ser Ser Val Thr Val Thr Ser Ser
        195                 200                 205

Thr Trp Pro Ser Gln Ser Ile Thr Cys Asn Val Ala His Pro Ala Ser
    210                 215                 220

Ser Thr Lys Val Asp Lys Lys Ile Glu Pro Arg Gly Pro Thr Ile Lys
225                 230                 235                 240

Pro Cys Pro Pro Cys Lys Cys Pro Ala Pro Asn Leu Leu Gly Gly Pro
                245                 250                 255

Ser Val Phe Ile Phe Pro Pro Lys Ile Lys Asp Val Leu Met Ile Ser
            260                 265                 270

Leu Ser Pro Ile Val Thr Cys Val Val Val Asp Val Ser Glu Asp Asp
        275                 280                 285

Pro Asp Val Gln Ile Ser Trp Phe Val Asn Asn Val Glu Val His Thr
    290                 295                 300

Ala Gln Thr Gln Thr His Arg Glu Asp Tyr Asn Ser Thr Leu Arg Val
305                 310                 315                 320

Val Ser Ala Leu Pro Ile Gln His Gln Asp Trp Met Ser Gly Lys Glu
                325                 330                 335

Phe Lys Cys Lys Val Asn Asn Lys Asp Leu Pro Ala Pro Ile Glu Arg
            340                 345                 350

Thr Ile Ser Lys Pro Lys Gly Ser Val Arg Ala Pro Gln Val Tyr Val
        355                 360                 365

Leu Pro Pro Pro Glu Glu Glu Met Thr Lys Lys Gln Val Thr Leu Thr
    370                 375                 380

Cys Met Val Thr Asp Phe Met Pro Glu Asp Ile Tyr Val Glu Trp Thr
385                 390                 395                 400

Asn Asn Gly Lys Thr Glu Leu Asn Tyr Lys Asn Thr Glu Pro Val Leu
                405                 410                 415
```

FIGURE 9 Continued…

```
Asp Ser Asp Gly Ser Tyr Phe Met Tyr Ser Lys Leu Arg Val Glu Lys
            420                 425                 430

Lys Asn Trp Val Glu Arg Asn Ser Tyr Ser Cys Ser Val Val His Glu
        435                 440                 445

Gly Leu His Asn His His Thr Thr Lys Ser Phe Ser Arg Thr Pro Gly
    450                 455                 460

Lys
465


<210>  119
<211>  462
<212>  PRT
<213>  Homo sapiens

<400>  119

Met Ala Trp Val Trp Thr Leu Pro Phe Leu Met Ala Ala Ala Gln Ser
1               5                   10                  15

Val Gln Ala Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Arg Ser His Trp Leu Ser Trp Val Arg Gln Ala Pro Gly Lys Gly Leu
    50                  55                  60

Glu Trp Val Ser Asn Ile Asn Tyr Asp Gly Ser Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Thr Tyr Leu His Phe Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160
```

FIGURE 9 Continued...

```
Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Asn Phe Gly Thr Gln Thr Tyr Thr Cys Asn Val Asp His Lys
    210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Phe Arg Val Val Ser Val
305                 310                 315                 320

Leu Thr Val Val His Gln Asp Trp Leu Asn Gly Lys Glu Tyr Lys Cys
                325                 330                 335

Lys Val Ser Asn Lys Gly Leu Pro Ala Pro Ile Glu Lys Thr Ile Ser
            340                 345                 350

Lys Thr Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400
```

FIGURE 9 Continued...

Gln Pro Glu Asn Asn Tyr Lys Thr Thr Pro Pro Met Leu Asp Ser Asp
405 410 415

Gly Ser Phe Phe Leu Tyr Ser Lys Leu Thr Val Asp Lys Ser Arg Trp
420 425 430

Gln Gln Gly Asn Val Phe Ser Cys Ser Val Met His Glu Ala Leu His
435 440 445

Asn His Tyr Thr Gln Lys Ser Leu Ser Leu Ser Pro Gly Lys
450 455 460

<210> 120
<211> 461
<212> PRT
<213> Homo sapiens

<400> 120

Met Ala Trp Val Trp Thr Leu Pro Phe Leu Met Ala Ala Ala Gln Ser
1 5 10 15

Val Gln Ala Gln Val Gln Leu Val Glu Ser Gly Gly Gly Leu Val Gln
20 25 30

Pro Gly Gly Ser Leu Arg Leu Ser Cys Ala Ala Ser Gly Phe Thr Phe
35 40 45

Arg Ser His Trp Leu Ser Trp Val Arg Gln Ala Pro Gly Lys Gly Leu
50 55 60

Glu Trp Val Ser Val Ile Thr Pro Tyr Gly Asp Thr Tyr Tyr Ala Asp
65 70 75 80

Ser Val Lys Gly Arg Phe Thr Ile Ser Arg Asp Asn Ser Lys Asn Thr
85 90 95

Leu Tyr Leu Gln Met Asn Ser Leu Arg Ala Glu Asp Thr Ala Val Tyr
100 105 110

Tyr Cys Ala Arg Asp Thr Tyr Leu His Phe Asp Tyr Trp Gly Gln Gly
115 120 125

Thr Leu Val Thr Val Ser Ser Ala Ser Thr Lys Gly Pro Ser Val Phe
130 135 140

Pro Leu Ala Pro Cys Ser Arg Ser Thr Ser Glu Ser Thr Ala Ala Leu

```
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
    210                 215                 220

Ser Asn Thr Lys Val Asp Lys Thr Val Glu Arg Lys Cys Cys Val Glu
225                 230                 235                 240

Cys Pro Pro Cys Pro Ala Pro Pro Val Ala Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Gln
        275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Phe Arg Val Val Ser Val Leu
305                 310                 315                 320

Thr Val Val His Gln Asp Trp Leu Asn Gly Lys Glu Tyr Lys Cys Lys
                325                 330                 335

Val Ser Asn Lys Gly Leu Pro Ala Pro Ile Glu Lys Thr Ile Ser Lys
            340                 345                 350

Thr Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400
```

FIGURE 9 Continued…

Pro Glu Asn Asn Tyr Lys Thr Thr Pro Pro Met Leu Asp Ser Asp Gly
405 410 415

Ser Phe Phe Leu Tyr Ser Lys Leu Thr Val Asp Lys Ser Arg Trp Gln
420 425 430

Gln Gly Asn Val Phe Ser Cys Ser Val Met His Glu Ala Leu His Asn
435 440 445

His Tyr Thr Gln Lys Ser Leu Ser Leu Ser Pro Gly Lys
450 455 460

<210> 121
<211> 461
<212> PRT
<213> Homo sapiens

<400> 121

Met Ala Trp Val Trp Thr Leu Pro Phe Leu Met Ala Ala Ala Gln Ser
1 5 10 15

Val Gln Ala Gln Val Gln Leu Val Glu Ser Gly Gly Gly Leu Val Gln
20 25 30

Pro Gly Gly Ser Leu Arg Leu Ser Cys Ala Ala Ser Gly Phe Thr Phe
35 40 45

Arg Ser His Trp Leu Ser Trp Val Arg Gln Ala Pro Gly Lys Gly Leu
50 55 60

Glu Trp Val Ser Val Ile Thr Pro Tyr Gly Asp Thr Tyr Tyr Ala Asp
65 70 75 80

Ser Val Lys Gly Arg Phe Thr Ile Ser Arg Asp Asn Ser Lys Asn Thr
85 90 95

Leu Tyr Leu Gln Met Asn Ser Leu Arg Ala Glu Asp Thr Ala Val Tyr
100 105 110

Tyr Cys Ala Arg Asp Thr Tyr Leu His Phe Asp Tyr Trp Gly Gln Gly
115 120 125

Thr Leu Val Thr Val Ser Ser Ala Ser Thr Lys Gly Pro Ser Val Phe
130 135 140

FIGURE 9 Continued…

```
Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
    210                 215                 220

Ser Asn Thr Lys Val Asp Lys Thr Val Glu Arg Lys Cys Cys Val Glu
225                 230                 235                 240

Cys Pro Pro Cys Pro Ala Pro Pro Val Ala Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Gln
        275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Phe Arg Val Val Ser Val Leu
305                 310                 315                 320

Thr Val Val His Gln Asp Trp Leu Asn Gly Lys Glu Tyr Lys Cys Lys
                325                 330                 335

Val Ser Asn Lys Gly Leu Pro Ala Pro Ile Glu Lys Thr Ile Ser Lys
            340                 345                 350

Thr Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
```

```
385                 390                 395                 400

Pro Glu Asn Asn Tyr Lys Thr Thr Pro Pro Met Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460


<210>  122
<211>  130
<212>  PRT
<213>  Homo sapiens

<400>  122

Met Ser Val Leu Thr Gln Val Leu Ala Leu Leu Leu Leu Trp Leu Thr
1               5                   10                  15

Gly Thr Arg Cys Asp Ile Glu Leu Thr Gln Pro Pro Ser Val Ser Val
            20                  25                  30

Ala Pro Gly Gln Thr Ala Arg Ile Ser Cys Ser Gly Asp Asn Ile Gly
        35                  40                  45

Ser Phe Tyr Val His Trp Tyr Gln Gln Lys Pro Gly Gln Ala Pro Val
    50                  55                  60

Leu Val Ile Tyr Asp Asp Asn Asn Arg Pro Ser Gly Ile Pro Glu Arg
65                  70                  75                  80

Phe Ser Gly Ser Asn Ser Gly Asn Thr Ala Thr Leu Thr Ile Ser Gly
                85                  90                  95

Thr Gln Ala Glu Asp Glu Ala Asp Tyr Tyr Cys Gly Ser Trp Ala Gly
            100                 105                 110

Ser Ser Gly Ser Tyr Val Phe Gly Gly Arg Thr Lys Leu Thr Val Leu
        115                 120                 125

Gly Gln
    130
```

FIGURE 9 Continued…

<210> 123
<211> 237
<212> PRT
<213> Homo sapiens

<400> 123

Met Ser Val Leu Thr Gln Val Leu Ala Leu Leu Leu Leu Trp Leu Thr
1 5 10 15

Gly Thr Arg Cys Asp Ile Ala Leu Thr Gln Pro Ala Ser Val Ser Gly
20 25 30

Ser Pro Gly Gln Ser Ile Thr Ile Ser Cys Thr Gly Thr Ser Ser Asp
35 40 45

Val Gly Asp Ile Asn Asp Val Ser Trp Tyr Gln Gln His Pro Gly Lys
50 55 60

Ala Pro Lys Leu Met Ile Tyr Asp Val Asn Asn Arg Pro Ser Gly Val
65 70 75 80

Ser Asn Arg Phe Ser Gly Ser Lys Ser Gly Asn Thr Ala Ser Leu Thr
85 90 95

Ile Ser Gly Leu Gln Ala Glu Asp Glu Ala Asp Tyr Tyr Cys Ser Ser
100 105 110

Tyr Gly Glu Ser Leu Thr Ser Tyr Val Phe Gly Gly Gly Thr Lys Leu
115 120 125

Thr Val Leu Gly Gln Pro Lys Ala Ala Pro Ser Val Thr Leu Phe Pro
130 135 140

Pro Ser Ser Glu Glu Leu Gln Ala Asn Lys Ala Thr Leu Val Cys Leu
145 150 155 160

Ile Ser Asp Phe Tyr Pro Gly Ala Val Thr Val Ala Trp Lys Ala Asp
165 170 175

Ser Ser Pro Val Lys Ala Gly Val Glu Thr Thr Thr Pro Ser Lys Gln
180 185 190

Ser Asn Asn Lys Tyr Ala Ala Ser Ser Tyr Leu Ser Leu Thr Pro Glu
195 200 205

Gln Trp Lys Ser His Arg Ser Tyr Ser Cys Gln Val Thr His Glu Gly

```
        210                 215                 220

Ser Thr Val Glu Lys Thr Val Ala Pro Thr Glu Cys Ser
225                 230                 235


<210>  124
<211>  234
<212>  PRT
<213>  Homo sapiens

<400>  124

Met Ser Val Leu Thr Gln Val Leu Ala Leu Leu Leu Leu Trp Leu Thr
1               5                   10                  15


Gly Thr Arg Cys Asp Ile Glu Leu Thr Gln Pro Pro Ser Val Ser Val
            20                  25                  30


Ala Pro Gly Gln Thr Ala Arg Ile Ser Cys Ser Gly Asp Asn Ile Gly
        35                  40                  45


Ser Phe Tyr Val His Trp Tyr Gln Gln Lys Pro Gly Gln Ala Pro Val
    50                  55                  60


Leu Val Ile Tyr Asp Asp Asn Asn Arg Pro Ser Gly Ile Pro Glu Arg
65                  70                  75                  80


Phe Ser Gly Ser Asn Ser Gly Asn Thr Ala Thr Leu Thr Ile Ser Gly
                85                  90                  95


Thr Gln Ala Glu Asp Glu Ala Asp Tyr Tyr Cys Ala Ser Trp Thr Gly
            100                 105                 110


Val Glu Pro Asp Tyr Val Phe Gly Gly Gly Thr Lys Leu Thr Val Leu
        115                 120                 125


Gly Gln Pro Lys Ala Ala Pro Ser Val Thr Leu Phe Pro Pro Ser Ser
    130                 135                 140


Glu Glu Leu Gln Ala Asn Lys Ala Thr Leu Val Cys Leu Ile Ser Asp
145                 150                 155                 160


Phe Tyr Pro Gly Ala Val Thr Val Ala Trp Lys Ala Asp Ser Ser Pro
                165                 170                 175


Val Lys Ala Gly Val Glu Thr Thr Thr Pro Ser Lys Gln Ser Asn Asn
            180                 185                 190
```

FIGURE 9 Continued…

```
Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230

<210>  125
<211>  237
<212>  PRT
<213>  Homo sapiens

<400>  125

Met Ser Val Leu Thr Gln Val Leu Ala Leu Leu Leu Leu Trp Leu Thr
1               5                   10                  15

Gly Thr Arg Cys Asp Ile Ala Leu Thr Gln Pro Ala Ser Val Ser Gly
            20                  25                  30

Ser Pro Gly Gln Ser Ile Thr Ile Ser Cys Thr Gly Thr Ser Ser Asp
        35                  40                  45

Val Gly Asp Ile Asn Asp Val Ser Trp Tyr Gln Gln His Pro Gly Lys
    50                  55                  60

Ala Pro Lys Leu Met Ile Tyr Asp Val Asn Asn Arg Pro Ser Gly Val
65                  70                  75                  80

Ser Asn Arg Phe Ser Gly Ser Lys Ser Gly Asn Thr Ala Ser Leu Thr
                85                  90                  95

Ile Ser Gly Leu Gln Ala Glu Asp Glu Ala Asp Tyr Tyr Cys Gln Ser
            100                 105                 110

Tyr Ala Gly Ser Tyr Leu Ser Glu Val Phe Gly Gly Gly Thr Lys Leu
        115                 120                 125

Thr Val Leu Gly Gln Pro Lys Ala Ala Pro Ser Val Thr Leu Phe Pro
    130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
```

```
                165                 170                 175

Ser Ser Pro Val Lys Ala Gly Val Glu Thr Thr Thr Pro Ser Lys Gln
            180                 185                 190

Ser Asn Asn Lys Tyr Ala Ala Ser Ser Tyr Leu Ser Leu Thr Pro Glu
        195                 200                 205

Gln Trp Lys Ser His Arg Ser Tyr Ser Cys Gln Val Thr His Glu Gly
    210                 215                 220

Ser Thr Val Glu Lys Thr Val Ala Pro Thr Glu Cys Ser
225                 230                 235


<210>  126
<211>  237
<212>  PRT
<213>  Homo sapiens

<400>  126

Met Ser Val Leu Thr Gln Val Leu Ala Leu Leu Leu Leu Trp Leu Thr
1               5                   10                  15

Gly Thr Arg Cys Asp Ile Ala Leu Thr Gln Pro Ala Ser Val Ser Gly
            20                  25                  30

Ser Pro Gly Gln Ser Ile Thr Ile Ser Cys Thr Gly Thr Ser Ser Asp
        35                  40                  45

Val Gly Asp Ile Asn Asp Val Ser Trp Tyr Gln Gln His Pro Gly Lys
    50                  55                  60

Ala Pro Lys Leu Met Ile Tyr Asp Val Asn Asn Arg Pro Ser Gly Val
65                  70                  75                  80

Ser Asn Arg Phe Ser Gly Ser Lys Ser Gly Asn Thr Ala Ser Leu Thr
                85                  90                  95

Ile Ser Gly Leu Gln Ala Glu Asp Glu Ala Asp Tyr Tyr Cys Ser Ser
            100                 105                 110

Tyr Gly Glu Ser Leu Thr Ser Tyr Val Phe Gly Gly Gly Thr Lys Leu
        115                 120                 125

Thr Val Leu Gly Gln Pro Lys Ala Ala Pro Ser Val Thr Leu Phe Pro
    130                 135                 140
```

FIGURE 10

SEQUENCE LISTING

<110> Ablynx N.V.

<120> Amino acid sequences directed against sclerostin and polypeptides comprising the same for the treatment of bone diseases and disorders

<130> P09-013-PCT-1

<150> US 61/178,679
<151> 2009-05-15

<160> 199

<170> PatentIn version 3.5

<210> 1
<211> 102
<212> PRT
<213> Artificial Sequence

<220>
<223> KERE-class Nanobody

<220>
<221> misc_feature
<222> (31)..(35)
<223> CDR

<220>
<221> misc_feature
<222> (50)..(54)
<223> CDR

<220>
<221> misc_feature
<222> (87)..(91)
<223> CDR

<400> 1

```
Glu Val Gln Leu Val Glu Ser Gly Gly Gly Leu Val Gln Pro Gly Gly
1               5                   10                  15


Ser Leu Arg Leu Ser Cys Ala Ala Ser Gly Ile Pro Phe Ser Xaa Xaa
            20                  25                  30


Xaa Xaa Xaa Trp Phe Arg Gln Ala Pro Gly Lys Gln Arg Asp Ser Val
        35                  40                  45


Ala Xaa Xaa Xaa Xaa Xaa Arg Phe Thr Ile Ser Arg Asp Asn Ala Lys
    50                  55                  60


Asn Thr Val Tyr Leu Gln Met Asn Ser Leu Lys Pro Glu Asp Thr Ala
65                  70                  75                  80
```

FIGURE 10 Continued...

```
Val Tyr Arg Cys Tyr Phe Xaa Xaa Xaa Xaa Xaa Trp Gly Gln Gly Thr
                85                  90                  95

Gln Val Thr Val Ser Ser
            100

<210>  2
<211>  102
<212>  PRT
<213>  Artificial Sequence

<220>
<223>  KERE-class Nanobody


<220>
<221>  misc_feature
<222>  (31)..(35)
<223>  CDR

<220>
<221>  misc_feature
<222>  (50)..(54)
<223>  CDR

<220>
<221>  misc_feature
<222>  (87)..(91)
<223>  CDR

<400>  2

Gln Val Lys Leu Glu Glu Ser Gly Gly Gly Leu Val Gln Ala Gly Gly
1               5                   10                  15

Ser Leu Arg Leu Ser Cys Val Gly Ser Gly Arg Thr Phe Ser Xaa Xaa
            20                  25                  30

Xaa Xaa Xaa Trp Phe Arg Leu Ala Pro Gly Lys Glu Arg Glu Phe Val
        35                  40                  45

Ala Xaa Xaa Xaa Xaa Xaa Arg Phe Thr Ile Ser Arg Asp Thr Ala Ser
    50                  55                  60

Asn Arg Gly Tyr Leu His Met Asn Asn Leu Thr Pro Glu Asp Thr Ala
65                  70                  75                  80

Val Tyr Tyr Cys Ala Ala Xaa Xaa Xaa Xaa Xaa Trp Gly Gln Gly Thr
                85                  90                  95

Gln Val Thr Val Ser Ser
            100
```

FIGURE 10 Continued...

<210> 3
<211> 102
<212> PRT
<213> Artificial Sequence

<220>
<223> KERE-class Nanobody

<220>
<221> misc_feature
<222> (31)..(35)
<223> CDR

<220>
<221> misc_feature
<222> (50)..(54)
<223> CDR

<220>
<221> misc_feature
<222> (87)..(91)
<223> CDR

<400> 3

```
Ala Val Gln Leu Val Asp Ser Gly Gly Gly Leu Val Gln Ala Gly Asp
1               5                   10                  15

Ser Leu Lys Leu Ser Cys Ala Leu Thr Gly Gly Ala Phe Thr Xaa Xaa
            20                  25                  30

Xaa Xaa Xaa Trp Phe Arg Gln Thr Pro Gly Arg Glu Arg Glu Phe Val
        35                  40                  45

Ala Xaa Xaa Xaa Xaa Xaa Arg Phe Thr Ile Ser Arg Asp Asn Ala Lys
    50                  55                  60

Asn Met Val Tyr Leu Arg Met Asn Ser Leu Ile Pro Glu Asp Ala Ala
65                  70                  75                  80

Val Tyr Ser Cys Ala Ala Xaa Xaa Xaa Xaa Xaa Trp Gly Gln Gly Thr
                85                  90                  95

Leu Val Thr Val Ser Ser
            100
```

<210> 4
<211> 102
<212> PRT
<213> Artificial Sequence

FIGURE 10 Continued...

<220>
<223> KERE-class Nanobody

<220>
<221> misc_feature
<222> (31)..(35)
<223> CDR

<220>
<221> misc_feature
<222> (50)..(54)
<223> CDR

<220>
<221> misc_feature
<222> (87)..(91)
<223> CDR

<400> 4

```
Gln Val Gln Leu Val Glu Ser Gly Gly Gly Leu Val Glu Ala Gly Gly
1               5                   10                  15

Ser Leu Arg Leu Ser Cys Thr Ala Ser Glu Ser Pro Phe Arg Xaa Xaa
            20                  25                  30

Xaa Xaa Xaa Trp Phe Arg Gln Thr Ser Gly Gln Glu Arg Glu Phe Val
        35                  40                  45

Ala Xaa Xaa Xaa Xaa Xaa Arg Phe Thr Ile Ser Arg Asp Asp Ala Lys
    50                  55                  60

Asn Thr Val Trp Leu His Gly Ser Thr Leu Lys Pro Glu Asp Thr Ala
65                  70                  75                  80

Val Tyr Tyr Cys Ala Ala Xaa Xaa Xaa Xaa Xaa Trp Gly Gln Gly Thr
                85                  90                  95

Gln Val Thr Val Ser Ser
            100
```

<210> 5
<211> 102
<212> PRT
<213> Artificial Sequence

<220>
<223> KERE-class Nanobody

<220>
<221> misc_feature
<222> (31)..(35)

FIGURE 10 Continued...

<223> CDR

<220>
<221> misc_feature
<222> (50)..(54)
<223> CDR

<220>
<221> misc_feature
<222> (87)..(91)
<223> CDR

<400> 5

```
Ala Val Gln Leu Val Glu Ser Gly Gly Gly Leu Val Gln Gly Gly Gly
1               5                   10                  15

Ser Leu Arg Leu Ala Cys Ala Ala Ser Glu Arg Ile Phe Asp Xaa Xaa
            20                  25                  30

Xaa Xaa Xaa Trp Tyr Arg Gln Gly Pro Gly Asn Glu Arg Glu Leu Val
        35                  40                  45

Ala Xaa Xaa Xaa Xaa Xaa Arg Phe Thr Ile Ser Met Asp Tyr Thr Lys
    50                  55                  60

Gln Thr Val Tyr Leu His Met Asn Ser Leu Arg Pro Glu Asp Thr Gly
65                  70                  75                  80

Leu Tyr Tyr Cys Lys Ile Xaa Xaa Xaa Xaa Xaa Trp Gly Gln Gly Thr
                85                  90                  95

Gln Val Thr Val Ser Ser
            100
```

<210> 6
<211> 102
<212> PRT
<213> Artificial Sequence

<220>
<223> KERE-class Nanobody

<220>
<221> misc_feature
<222> (31)..(35)
<223> CDR

<220>
<221> misc_feature
<222> (50)..(54)
<223> CDR

FIGURE 10 Continued…

<220>
<221> misc_feature
<222> (87)..(91)
<223> CDR

<400> 6

Asp Val Lys Phe Val Glu Ser Gly Gly Gly Leu Val Gln Ala Gly Gly
1 5 10 15

Ser Leu Arg Leu Ser Cys Val Ala Ser Gly Phe Asn Phe Asp Xaa Xaa
20 25 30

Xaa Xaa Xaa Trp Phe Arg Gln Ala Pro Gly Lys Glu Arg Glu Glu Val
35 40 45

Ala Xaa Xaa Xaa Xaa Xaa Arg Phe Thr Ile Ser Ser Glu Lys Asp Lys
50 55 60

Asn Ser Val Tyr Leu Gln Met Asn Ser Leu Lys Pro Glu Asp Thr Ala
65 70 75 80

Leu Tyr Ile Cys Ala Gly Xaa Xaa Xaa Xaa Xaa Trp Gly Arg Gly Thr
85 90 95

Gln Val Thr Val Ser Ser
100

<210> 7
<211> 102
<212> PRT
<213> Artificial Sequence

<220>
<223> KERE-class Nanobody

<220>
<221> misc_feature
<222> (31)..(35)
<223> CDR

<220>
<221> misc_feature
<222> (50)..(54)
<223> CDR

<220>
<221> misc_feature
<222> (87)..(91)
<223> CDR

```
Gln Val Arg Leu Ala Glu Ser Gly Gly Gly Leu Val Gln Ser Gly Gly
1               5                   10                  15

Ser Leu Arg Leu Ser Cys Val Ala Ser Gly Ser Thr Tyr Thr Xaa Xaa
            20                  25                  30

Xaa Xaa Xaa Trp Tyr Arg Gln Tyr Pro Gly Lys Gln Arg Ala Leu Val
        35                  40                  45

Ala Xaa Xaa Xaa Xaa Xaa Arg Phe Thr Ile Ala Arg Asp Ser Thr Lys
    50                  55                  60

Asp Thr Phe Cys Leu Gln Met Asn Asn Leu Lys Pro Glu Asp Thr Ala
65                  70                  75                  80

Val Tyr Tyr Cys Tyr Ala Xaa Xaa Xaa Xaa Xaa Trp Gly Gln Gly Thr
                85                  90                  95

Gln Val Thr Val Ser Ser
            100


<210>  8
<211>  102
<212>  PRT
<213>  Artificial Sequence

<220>
<223>  KERE-class Nanobody


<220>
<221>  misc_feature
<222>  (31)..(35)
<223>  CDR

<220>
<221>  misc_feature
<222>  (50)..(54)
<223>  CDR

<220>
<221>  misc_feature
<222>  (87)..(91)
<223>  CDR

<400>  8

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Ser Asp Xaa Xaa
            20                  25                  30
```

FIGURE 10 Continued…

```
Xaa Xaa Xaa Trp Phe Arg Gln Ala Pro Gly Lys Pro Arg Glu Gly Val
        35                  40                  45

Ser Xaa Xaa Xaa Xaa Xaa Arg Phe Thr Ile Ser Thr Asp Asn Ala Lys
    50                  55                  60

Asn Thr Val His Leu Leu Met Asn Arg Val Asn Ala Glu Asp Thr Ala
65                  70                  75                  80

Leu Tyr Tyr Cys Ala Val Xaa Xaa Xaa Xaa Xaa Trp Gly Arg Gly Thr
                85                  90                  95

Arg Val Thr Val Ser Ser
            100


<210>  9
<211>  102
<212>  PRT
<213>  Artificial Sequence

<220>
<223>  KERE-class Nanobody


<220>
<221>  misc_feature
<222>  (31)..(35)
<223>  CDR

<220>
<221>  misc_feature
<222>  (50)..(54)
<223>  CDR

<220>
<221>  misc_feature
<222>  (87)..(91)
<223>  CDR

<400>  9

Gln Val Gln Leu Val Glu Ser Gly Gly Gly Leu Val Gln Pro Gly Gly
1               5                   10                  15

Ser Leu Arg Leu Ser Cys Gln Ala Ser Gly Asp Ile Ser Thr Xaa Xaa
            20                  25                  30

Xaa Xaa Xaa Trp Tyr Arg Gln Val Pro Gly Lys Leu Arg Glu Phe Val
        35                  40                  45

Ala Xaa Xaa Xaa Xaa Xaa Arg Phe Thr Ile Ser Gly Asp Asn Ala Lys
    50                  55                  60
```

FIGURE 10 Continued...

Arg Ala Ile Tyr Leu Gln Met Asn Asn Leu Lys Pro Asp Asp Thr Ala
65 70 75 80

Val Tyr Tyr Cys Asn Arg Xaa Xaa Xaa Xaa Xaa Trp Gly Gln Gly Thr
85 90 95

Gln Val Thr Val Ser Pro
100

<210> 10
<211> 102
<212> PRT
<213> Artificial Sequence

<220>
<223> KERE-class Nanobody

<220>
<221> misc_feature
<222> (31)..(35)
<223> CDR

<220>
<221> misc_feature
<222> (50)..(54)
<223> CDR

<220>
<221> misc_feature
<222> (87)..(91)
<223> CDR

<400> 10

Gln Val Pro Val Val Glu Ser Gly Gly Gly Leu Val Gln Ala Gly Asp
1 5 10 15

Ser Leu Arg Leu Phe Cys Ala Val Pro Ser Phe Thr Ser Thr Xaa Xaa
20 25 30

Xaa Xaa Xaa Trp Phe Arg Gln Ala Pro Gly Lys Glu Arg Glu Phe Val
35 40 45

Ala Xaa Xaa Xaa Xaa Xaa Arg Phe Thr Ile Ser Arg Asn Ala Thr Lys
50 55 60

Asn Thr Leu Thr Leu Arg Met Asp Ser Leu Lys Pro Glu Asp Thr Ala
65 70 75 80

Val Tyr Tyr Cys Ala Ala Xaa Xaa Xaa Xaa Xaa Trp Gly Gln Gly Thr

```
                85                  90                  95

Gln Val Thr Val Ser Ser
            100


<210>  11
<211>  102
<212>  PRT
<213>  Artificial Sequence

<220>
<223>  KERE-class Nanobody


<220>
<221>  misc_feature
<222>  (31)..(35)
<223>  CDR

<220>
<221>  misc_feature
<222>  (50)..(54)
<223>  CDR

<220>
<221>  misc_feature
<222>  (87)..(91)
<223>  CDR

<400>  11

Glu Val Gln Leu Val Glu Ser Gly Gly Gly Leu Val Gln Ala Gly Asp
1               5                   10                  15


Ser Leu Arg Leu Phe Cys Thr Val Ser Gly Gly Thr Ala Ser Xaa Xaa
            20                  25                  30


Xaa Xaa Xaa Trp Phe Arg Gln Ala Pro Gly Glu Lys Arg Glu Phe Val
        35                  40                  45


Ala Xaa Xaa Xaa Xaa Xaa Arg Phe Thr Ile Ala Arg Glu Asn Ala Gly
    50                  55                  60


Asn Met Val Tyr Leu Gln Met Asn Asn Leu Lys Pro Asp Asp Thr Ala
65                  70                  75                  80


Leu Tyr Thr Cys Ala Ala Xaa Xaa Xaa Xaa Xaa Trp Gly Arg Gly Thr
                85                  90                  95


Gln Val Thr Val Ser Ser
            100
```

FIGURE 10 Continued...

<210> 12
<211> 102
<212> PRT
<213> Artificial Sequence

<220>
<223> KERE-class Nanobody

<220>
<221> misc_feature
<222> (31)..(35)
<223> CDR

<220>
<221> misc_feature
<222> (50)..(54)
<223> CDR

<220>
<221> misc_feature
<222> (87)..(91)
<223> CDR

<400> 12

Ala Val Gln Leu Val Glu Ser Gly Gly Asp Ser Val Gln Pro Gly Asp
1 5 10 15

Ser Gln Thr Leu Ser Cys Ala Ala Ser Gly Arg Thr Asn Ser Xaa Xaa
20 25 30

Xaa Xaa Xaa Trp Phe Arg Gln Ala Pro Gly Lys Glu Arg Val Phe Leu
35 40 45

Ala Xaa Xaa Xaa Xaa Xaa Arg Phe Thr Ile Ser Arg Asp Ser Ala Lys
50 55 60

Asn Met Met Tyr Leu Gln Met Asn Asn Leu Lys Pro Gln Asp Thr Ala
65 70 75 80

Val Tyr Tyr Cys Ala Ala Xaa Xaa Xaa Xaa Xaa Trp Gly Gln Gly Thr
85 90 95

Gln Val Thr Val Ser Ser
100

<210> 13
<211> 102
<212> PRT
<213> Artificial Sequence

<220>
<223> KERE-class Nanobody

FIGURE 10 Continued...

<220>
<221> misc_feature
<222> (31)..(35)
<223> CDR

<220>
<221> misc_feature
<222> (50)..(54)
<223> CDR

<220>
<221> misc_feature
<222> (87)..(91)
<223> CDR

<400> 13

Ala Val Gln Leu Val Glu Ser Gly Gly Gly Leu Val Gln Ala Gly Gly
1 5 10 15

Ser Leu Arg Leu Ser Cys Val Val Ser Gly Leu Thr Ser Ser Xaa Xaa
20 25 30

Xaa Xaa Xaa Trp Phe Arg Gln Thr Pro Trp Gln Glu Arg Asp Phe Val
35 40 45

Ala Xaa Xaa Xaa Xaa Xaa Arg Phe Thr Ile Ser Arg Asp Asn Tyr Lys
50 55 60

Asp Thr Val Leu Leu Glu Met Asn Phe Leu Lys Pro Glu Asp Thr Ala
65 70 75 80

Ile Tyr Tyr Cys Ala Ala Xaa Xaa Xaa Xaa Xaa Trp Gly Gln Gly Thr
85 90 95

Gln Val Thr Val Ser Ser
100

<210> 14
<211> 102
<212> PRT
<213> Artificial Sequence

<220>
<223> KERE-class Nanobody

<220>
<221> misc_feature
<222> (31)..(35)
<223> CDR

FIGURE 10 Continued...

<220>
<221> misc_feature
<222> (50)..(54)
<223> CDR

<220>
<221> misc_feature
<222> (87)..(91)
<223> CDR

<400> 14

Ala Val Gln Leu Val Glu Ser Gly Gly Gly Leu Val Gln Ala Gly Ala
1 5 10 15

Ser Leu Arg Leu Ser Cys Ala Thr Ser Thr Arg Thr Leu Asp Xaa Xaa
20 25 30

Xaa Xaa Xaa Trp Phe Arg Gln Ala Pro Gly Arg Asp Arg Glu Phe Val
35 40 45

Ala Xaa Xaa Xaa Xaa Xaa Arg Phe Thr Val Ser Arg Asp Ser Ala Glu
50 55 60

Asn Thr Val Ala Leu Gln Met Asn Ser Leu Lys Pro Glu Asp Thr Ala
65 70 75 80

Val Tyr Tyr Cys Ala Ala Xaa Xaa Xaa Xaa Xaa Trp Gly Gln Gly Thr
85 90 95

Arg Val Thr Val Ser Ser
100

<210> 15
<211> 102
<212> PRT
<213> Artificial Sequence

<220>
<223> KERE-class Nanobody

<220>
<221> misc_feature
<222> (31)..(35)
<223> CDR

<220>
<221> misc_feature
<222> (50)..(54)
<223> CDR

<220>
<221> misc_feature

FIGURE 10 Continued…

<222> (87)..(91)
<223> CDR

<400> 15

Gln Val Gln Leu Val Glu Ser Gly Gly Gly Leu Val Gln Pro Gly Gly
1 5 10 15

Ser Leu Arg Leu Ser Cys Thr Val Ser Arg Leu Thr Ala His Xaa Xaa
20 25 30

Xaa Xaa Xaa Trp Phe Arg Gln Ala Pro Gly Lys Glu Arg Glu Ala Val
35 40 45

Ser Xaa Xaa Xaa Xaa Xaa Arg Phe Thr Ile Ser Arg Asp Tyr Ala Gly
50 55 60

Asn Thr Ala Phe Leu Gln Met Asp Ser Leu Lys Pro Glu Asp Thr Gly
65 70 75 80

Val Tyr Tyr Cys Ala Thr Xaa Xaa Xaa Xaa Xaa Trp Gly Gln Gly Thr
85 90 95

Gln Val Thr Val Ser Ser
100

<210> 16
<211> 102
<212> PRT
<213> Artificial Sequence

<220>
<223> KERE-class Nanobody

<220>
<221> misc_feature
<222> (31)..(35)
<223> CDR

<220>
<221> misc_feature
<222> (50)..(54)
<223> CDR

<220>
<221> misc_feature
<222> (87)..(91)
<223> CDR

<400> 16

Glu Val Gln Leu Val Glu Ser Gly Gly Glu Leu Val Gln Ala Gly Gly
1 5 10 15

FIGURE 10 Continued...

```
Ser Leu Lys Leu Ser Cys Thr Ala Ser Gly Arg Asn Phe Val Xaa Xaa
            20                  25                  30

Xaa Xaa Xaa Trp Phe Arg Arg Ala Pro Gly Lys Glu Arg Glu Phe Val
        35                  40                  45

Ala Xaa Xaa Xaa Xaa Xaa Arg Phe Thr Val Ser Arg Asp Asn Gly Lys
    50                  55                  60

Asn Thr Ala Tyr Leu Arg Met Asn Ser Leu Lys Pro Glu Asp Thr Ala
65                  70                  75                  80

Asp Tyr Tyr Cys Ala Val Xaa Xaa Xaa Xaa Xaa Leu Gly Ser Gly Thr
                85                  90                  95

Gln Val Thr Val Ser Ser
            100


<210>  17
<211>  102
<212>  PRT
<213>  Artificial Sequence

<220>
<223>  GLEW-class Nanobody


<220>
<221>  misc_feature
<222>  (31)..(35)
<223>  CDR

<220>
<221>  misc_feature
<222>  (50)..(54)
<223>  CDR

<220>
<221>  misc_feature
<222>  (87)..(91)
<223>  CDR

<400>  17

Ala Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Xaa Xaa
            20                  25                  30

Xaa Xaa Xaa Trp Val Arg Gln Ala Pro Gly Lys Val Leu Glu Trp Val
```

```
        35                  40                  45

Ser Xaa Xaa Xaa Xaa Xaa Arg Phe Thr Ile Ser Arg Asp Asn Ala Lys
    50                  55                  60

Asn Thr Leu Tyr Leu Gln Met Asn Ser Leu Lys Pro Glu Asp Thr Ala
65                  70                  75                  80

Val Tyr Tyr Cys Val Lys Xaa Xaa Xaa Xaa Xaa Gly Ser Gln Gly Thr
                85                  90                  95

Gln Val Thr Val Ser Ser
            100


<210>  18
<211>  102
<212>  PRT
<213>  Artificial Sequence

<220>
<223>  GLEW-class Nanobody


<220>
<221>  misc_feature
<222>  (31)..(35)
<223>  CDR

<220>
<221>  misc_feature
<222>  (50)..(54)
<223>  CDR

<220>
<221>  misc_feature
<222>  (87)..(91)
<223>  CDR

<400>  18

Glu Val Gln Leu Val Glu Ser Gly Gly Gly Leu Val Gln Pro Gly Gly
1               5                   10                  15

Ser Leu Arg Leu Ser Cys Val Cys Val Ser Ser Gly Cys Thr Xaa Xaa
            20                  25                  30

Xaa Xaa Xaa Trp Val Arg Gln Ala Pro Gly Lys Ala Glu Glu Trp Val
        35                  40                  45

Ser Xaa Xaa Xaa Xaa Xaa Arg Phe Lys Ile Ser Arg Asp Asn Ala Lys
    50                  55                  60
```

FIGURE 10 Continued...

```
Lys Thr Leu Tyr Leu Gln Met Asn Ser Leu Gly Pro Glu Asp Thr Ala
65                  70                  75                  80

Met Tyr Tyr Cys Gln Arg Xaa Xaa Xaa Xaa Xaa Arg Gly Gln Gly Thr
                85                  90                  95

Gln Val Thr Val Ser Ser
            100


<210>  19
<211>  102
<212>  PRT
<213>  Artificial Sequence

<220>
<223>  GLEW-class Nanobody


<220>
<221>  misc_feature
<222>  (31)..(35)
<223>  CDR

<220>
<221>  misc_feature
<222>  (50)..(54)
<223>  CDR

<220>
<221>  misc_feature
<222>  (87)..(91)
<223>  CDR

<400>  19

Glu Val Gln Leu Val Glu Ser Gly Gly Gly Leu Ala Leu Pro Gly Gly
1               5                   10                  15

Ser Leu Thr Leu Ser Cys Val Phe Ser Gly Ser Thr Phe Ser Xaa Xaa
            20                  25                  30

Xaa Xaa Xaa Trp Val Arg His Thr Pro Gly Lys Ala Glu Glu Trp Val
        35                  40                  45

Ser Xaa Xaa Xaa Xaa Xaa Arg Phe Thr Ile Ser Arg Asp Asn Ala Lys
    50                  55                  60

Asn Thr Leu Tyr Leu Glu Met Asn Ser Leu Ser Pro Glu Asp Thr Ala
65                  70                  75                  80

Met Tyr Tyr Cys Gly Arg Xaa Xaa Xaa Xaa Xaa Arg Ser Lys Gly Ile
                85                  90                  95
```

FIGURE 10 Continued…

```
Gln Val Thr Val Ser Ser
            100


<210>  20
<211>  102
<212>  PRT
<213>  Artificial Sequence

<220>
<223>  P,R,S 103-class Nanobody


<220>
<221>  misc_feature
<222>  (31)..(35)
<223>  CDR

<220>
<221>  misc_feature
<222>  (50)..(54)
<223>  CDR

<220>
<221>  misc_feature
<222>  (87)..(91)
<223>  CDR

<400>  20

Ala Val Gln Leu Val Glu Ser Gly Gly Gly Leu Val Gln Ala Gly Gly
1               5                   10                  15


Ser Leu Arg Leu Ser Cys Ala Ala Ser Gly Arg Thr Phe Ser Xaa Xaa
            20                  25                  30


Xaa Xaa Xaa Trp Phe Arg Gln Ala Pro Gly Lys Glu Arg Glu Phe Val
        35                  40                  45


Ala Xaa Xaa Xaa Xaa Xaa Arg Phe Thr Ile Ser Arg Asp Asn Ala Lys
    50                  55                  60


Asn Thr Val Tyr Leu Gln Met Asn Ser Leu Lys Pro Glu Asp Thr Ala
65                  70                  75                  80


Val Tyr Tyr Cys Ala Ala Xaa Xaa Xaa Xaa Xaa Arg Gly Gln Gly Thr
                85                  90                  95


Gln Val Thr Val Ser Ser
            100


<210>  21
<211>  102
```

```
<212>  PRT
<213>  Artificial Sequence

<220>
<223>  P,R,S 103-class Nanobody


<220>
<221>  misc_feature
<222>  (31)..(35)
<223>  CDR

<220>
<221>  misc_feature
<222>  (50)..(54)
<223>  CDR

<220>
<221>  misc_feature
<222>  (87)..(91)
<223>  CDR

<400>  21

Asp Val Gln Leu Val Glu Ser Gly Gly Asp Leu Val Gln Pro Gly Gly
1               5                   10                  15


Ser Leu Arg Leu Ser Cys Ala Ala Ser Gly Phe Ser Phe Asp Xaa Xaa
            20                  25                  30


Xaa Xaa Xaa Trp Leu Arg Gln Thr Pro Gly Lys Gly Leu Glu Trp Val
        35                  40                  45


Gly Xaa Xaa Xaa Xaa Xaa Arg Phe Thr Ile Ser Arg Asp Asn Ala Lys
    50                  55                  60


Asn Met Leu Tyr Leu His Leu Asn Asn Leu Lys Ser Glu Asp Thr Ala
65                  70                  75                  80


Val Tyr Tyr Cys Arg Arg Xaa Xaa Xaa Xaa Xaa Leu Gly Gln Gly Thr
                85                  90                  95


Gln Val Thr Val Ser Ser
            100


<210>  22
<211>  102
<212>  PRT
<213>  Artificial Sequence

<220>
<223>  P,R,S 103-class Nanobody
```

FIGURE 10 Continued...

<220>
<221> misc_feature
<222> (31)..(35)
<223> CDR

<220>
<221> misc_feature
<222> (50)..(54)
<223> CDR

<220>
<221> misc_feature
<222> (87)..(91)
<223> CDR

<400> 22

```
Glu Val Gln Leu Val Glu Ser Gly Gly Gly Leu Val Gln Pro Gly Gly
1               5                   10                  15

Ser Leu Arg Leu Ser Cys Val Cys Val Ser Ser Gly Cys Thr Xaa Xaa
            20                  25                  30

Xaa Xaa Xaa Trp Val Arg Gln Ala Pro Gly Lys Ala Glu Glu Trp Val
        35                  40                  45

Ser Xaa Xaa Xaa Xaa Xaa Arg Phe Lys Ile Ser Arg Asp Asn Ala Lys
    50                  55                  60

Lys Thr Leu Tyr Leu Gln Met Asn Ser Leu Gly Pro Glu Asp Thr Ala
65                  70                  75                  80

Met Tyr Tyr Cys Gln Arg Xaa Xaa Xaa Xaa Xaa Arg Gly Gln Gly Thr
                85                  90                  95

Gln Val Thr Val Ser Ser
            100
```

<210> 23
<211> 30
<212> PRT
<213> Artificial Sequence

<220>
<223> KERE-class Nanobody FW1 sequence

<400> 23

```
Gln Val Gln Arg Val Glu Ser Gly Gly Gly Leu Val Gln Ala Gly Gly
1               5                   10                  15

Ser Leu Arg Leu Ser Cys Ala Ala Ser Gly Arg Thr Ser Ser
            20                  25                  30
```

FIGURE 10 Continued…

<210> 24
<211> 30
<212> PRT
<213> Artificial Sequence

<220>
<223> KERE-class Nanobody FW1 sequence

<400> 24

Gln Val Gln Leu Val Glu Ser Gly Gly Gly Leu Val Gln Thr Gly Asp
1 5 10 15

Ser Leu Ser Leu Ser Cys Ser Ala Ser Gly Arg Thr Phe Ser
20 25 30

<210> 25
<211> 30
<212> PRT
<213> Artificial Sequence

<220>
<223> KERE-class Nanobody FW1 sequence

<400> 25

Gln Val Lys Leu Glu Glu Ser Gly Gly Gly Leu Val Gln Ala Gly Asp
1 5 10 15

Ser Leu Arg Leu Ser Cys Ala Ala Thr Gly Arg Ala Phe Gly
20 25 30

<210> 26
<211> 30
<212> PRT
<213> Artificial Sequence

<220>
<223> KERE-class Nanobody FW1 sequence

<400> 26

Ala Val Gln Leu Val Glu Ser Gly Gly Gly Leu Val Gln Pro Gly Glu
1 5 10 15

Ser Leu Gly Leu Ser Cys Val Ala Ser Gly Arg Asp Phe Val
20 25 30

<210> 27
<211> 30
<212> PRT
<213> Artificial Sequence

FIGURE 10 Continued...

<220>
<223> KERE-class Nanobody FW1 sequence

<400> 27

Glu Val Gln Leu Val Glu Ser Gly Gly Gly Leu Val Gln Ala Gly Gly
1 5 10 15

Ser Leu Arg Leu Ser Cys Glu Val Leu Gly Arg Thr Ala Gly
20 25 30

<210> 28
<211> 30
<212> PRT
<213> Artificial Sequence

<220>
<223> KERE-class Nanobody FW1 sequence

<400> 28

Gln Val Gln Leu Val Glu Ser Gly Gly Gly Trp Val Gln Pro Gly Gly
1 5 10 15

Ser Leu Arg Leu Ser Cys Ala Ala Ser Glu Thr Ile Leu Ser
20 25 30

<210> 29
<211> 30
<212> PRT
<213> Artificial Sequence

<220>
<223> KERE-class Nanobody FW1 sequence

<400> 29

Gln Val Gln Leu Val Glu Ser Gly Gly Gly Thr Val Gln Pro Gly Gly
1 5 10 15

Ser Leu Asn Leu Ser Cys Val Ala Ser Gly Asn Thr Phe Asn
20 25 30

<210> 30
<211> 30
<212> PRT
<213> Artificial Sequence

<220>
<223> KERE-class Nanobody FW1 sequence

<400> 30

Glu Val Gln Leu Val Glu Ser Gly Gly Gly Leu Ala Gln Pro Gly Gly
1 5 10 15

FIGURE 10 Continued…

```
Ser Leu Gln Leu Ser Cys Ser Ala Pro Gly Phe Thr Leu Asp
            20                  25                  30


<210>  31
<211>  30
<212>  PRT
<213>  Artificial Sequence

<220>
<223>  KERE-class Nanobody FW1 sequence

<400>  31

Ala Gln Glu Leu Glu Glu Ser Gly Gly Gly Leu Val Gln Ala Gly Gly
1               5                   10                  15


Ser Leu Arg Leu Ser Cys Ala Ala Ser Gly Arg Thr Phe Asn
            20                  25                  30


<210>  32
<211>  22
<212>  PRT
<213>  Artificial Sequence

<220>
<223>  KERE-class Nanobody FW1 sequence

<400>  32

Val Glu Ser Gly Gly Gly Leu Val Gln Pro Gly Gly Ser Leu Arg Leu
1               5                   10                  15


Ser Cys Ala Ala Ser Gly
            20


<210>  33
<211>  22
<212>  PRT
<213>  Artificial Sequence

<220>
<223>  KERE-class Nanobody FW1 sequence

<400>  33

Val Asp Ser Gly Gly Gly Leu Val Gln Ala Gly Asp Ser Leu Lys Leu
1               5                   10                  15


Ser Cys Ala Leu Thr Gly
            20


<210>  34
```

<211> 22
<212> PRT
<213> Artificial Sequence

<220>
<223> KERE-class Nanobody FW1 sequence

<400> 34

Val Asp Ser Gly Gly Gly Leu Val Gln Ala Gly Asp Ser Leu Arg Leu
1 5 10 15

Ser Cys Ala Ala Ser Gly
20

<210> 35
<211> 22
<212> PRT
<213> Artificial Sequence

<220>
<223> KERE-class Nanobody FW1 sequence

<400> 35

Val Asp Ser Gly Gly Gly Leu Val Glu Ala Gly Gly Ser Leu Arg Leu
1 5 10 15

Ser Cys Gln Val Ser Glu
20

<210> 36
<211> 22
<212> PRT
<213> Artificial Sequence

<220>
<223> KERE-class Nanobody FW1 sequence

<400> 36

Gln Asp Ser Gly Gly Gly Ser Val Gln Ala Gly Gly Ser Leu Lys Leu
1 5 10 15

Ser Cys Ala Ala Ser Gly
20

<210> 37
<211> 22
<212> PRT
<213> Artificial Sequence

<220>
<223> KERE-class Nanobody FW1 sequence

Val Gln Ser Gly Gly Arg Leu Val Gln Ala Gly Asp Ser Leu Arg Leu
1 5 10 15

Ser Cys Ala Ala Ser Glu
20

<210> 38
<211> 22
<212> PRT
<213> Artificial Sequence

<220>
<223> KERE-class Nanobody FW1 sequence

<400> 38

Val Glu Ser Gly Gly Thr Leu Val Gln Ser Gly Asp Ser Leu Lys Leu
1 5 10 15

Ser Cys Ala Ser Ser Thr
20

<210> 39
<211> 22
<212> PRT
<213> Artificial Sequence

<220>
<223> KERE-class Nanobody FW1 sequence

<400> 39

Met Glu Ser Gly Gly Asp Ser Val Gln Ser Gly Gly Ser Leu Thr Leu
1 5 10 15

Ser Cys Val Ala Ser Gly
20

<210> 40
<211> 22
<212> PRT
<213> Artificial Sequence

<220>
<223> KERE-class Nanobody FW1 sequence

<400> 40

Gln Ala Ser Gly Gly Gly Leu Val Gln Ala Gly Gly Ser Leu Arg Leu
1 5 10 15

Ser Cys Ser Ala Ser Val

<210> 41
<211> 14
<212> PRT
<213> Artificial Sequence

<220>
<223> KERE-class Nanobody FW2 sequence

<400> 41

Trp Phe Arg Gln Ala Pro Gly Lys Glu Arg Glu Phe Val Ala
1 5 10

<210> 42
<211> 14
<212> PRT
<213> Artificial Sequence

<220>
<223> KERE-class Nanobody FW2 sequence

<400> 42

Trp Phe Arg Gln Thr Pro Gly Arg Glu Arg Glu Phe Val Ala
1 5 10

<210> 43
<211> 14
<212> PRT
<213> Artificial Sequence

<220>
<223> KERE-class Nanobody FW2 sequence

<400> 43

Trp Tyr Arg Gln Ala Pro Gly Lys Gln Arg Glu Met Val Ala
1 5 10

<210> 44
<211> 14
<212> PRT
<213> Artificial Sequence

<220>
<223> KERE-class Nanobody FW2 sequence

<400> 44

Trp Tyr Arg Gln Gly Pro Gly Lys Gln Arg Glu Leu Val Ala
1 5 10

<212> PRT
<213> Artificial Sequence

<220>
<223> KERE-class Nanobody FW2 sequence

<400> 45

Trp Ile Arg Gln Ala Pro Gly Lys Glu Arg Glu Gly Val Ser
1 5 10

<210> 46
<211> 14
<212> PRT
<213> Artificial Sequence

<220>
<223> KERE-class Nanobody FW2 sequence

<400> 46

Trp Phe Arg Glu Ala Pro Gly Lys Glu Arg Glu Gly Ile Ser
1 5 10

<210> 47
<211> 14
<212> PRT
<213> Artificial Sequence

<220>
<223> KERE-class Nanobody FW2 sequence

<400> 47

Trp Tyr Arg Gln Ala Pro Gly Lys Glu Arg Asp Leu Val Ala
1 5 10

<210> 48
<211> 14
<212> PRT
<213> Artificial Sequence

<220>
<223> KERE-class Nanobody FW2 sequence

<400> 48

Trp Phe Arg Gln Ala Pro Gly Lys Gln Arg Glu Glu Val Ser
1 5 10

<210> 49
<211> 14
<212> PRT
<213> Artificial Sequence

<220>
<223> KERE-class Nanobody FW2 sequence

Trp Phe Arg Gln Pro Pro Gly Lys Val Arg Glu Phe Val Gly
1 5 10

<210> 50
<211> 32
<212> PRT
<213> Artificial Sequence

<220>
<223> KERE-class Nanobody FW3 sequence

<400> 50

Arg Phe Thr Ile Ser Arg Asp Asn Ala Lys Asn Thr Val Tyr Leu Gln
1 5 10 15

Met Asn Ser Leu Lys Pro Glu Asp Thr Ala Val Tyr Arg Cys Tyr Phe
20 25 30

<210> 51
<211> 32
<212> PRT
<213> Artificial Sequence

<220>
<223> KERE-class Nanobody FW3 sequence

<400> 51

Arg Phe Ala Ile Ser Arg Asp Asn Asn Lys Asn Thr Gly Tyr Leu Gln
1 5 10 15

Met Asn Ser Leu Glu Pro Glu Asp Thr Ala Val Tyr Tyr Cys Ala Ala
20 25 30

<210> 52
<211> 32
<212> PRT
<213> Artificial Sequence

<220>
<223> KERE-class Nanobody FW3 sequence

<400> 52

Arg Phe Thr Val Ala Arg Asn Asn Ala Lys Asn Thr Val Asn Leu Glu
1 5 10 15

Met Asn Ser Leu Lys Pro Glu Asp Thr Ala Val Tyr Tyr Cys Ala Ala
20 25 30

FIGURE 10 Continued...

<210> 53
<211> 32
<212> PRT
<213> Artificial Sequence

<220>
<223> KERE-class Nanobody FW3 sequence

<400> 53

Arg Phe Thr Ile Ser Arg Asp Ile Ala Lys Asn Thr Val Asp Leu Leu
1 5 10 15

Met Asn Asn Leu Glu Pro Glu Asp Thr Ala Val Tyr Tyr Cys Ala Ala
20 25 30

<210> 54
<211> 32
<212> PRT
<213> Artificial Sequence

<220>
<223> KERE-class Nanobody FW3 sequence

<400> 54

Arg Leu Thr Ile Ser Arg Asp Asn Ala Val Asp Thr Met Tyr Leu Gln
1 5 10 15

Met Asn Ser Leu Lys Pro Glu Asp Thr Ala Val Tyr Tyr Cys Ala Ala
20 25 30

<210> 55
<211> 32
<212> PRT
<213> Artificial Sequence

<220>
<223> KERE-class Nanobody FW3 sequence

<400> 55

Arg Phe Thr Ile Ser Arg Asp Asn Ala Lys Asn Thr Val Tyr Leu Gln
1 5 10 15

Met Asp Asn Val Lys Pro Glu Asp Thr Ala Ile Tyr Tyr Cys Ala Ala
20 25 30

<210> 56
<211> 32
<212> PRT
<213> Artificial Sequence

<220>
<223> KERE-class Nanobody FW3 sequence

Arg Phe Thr Ile Ser Lys Asp Ser Gly Lys Asn Thr Val Tyr Leu Gln
1 5 10 15

Met Thr Ser Leu Lys Pro Glu Asp Thr Ala Val Tyr Tyr Cys Ala Thr
20 25 30

<210> 57
<211> 32
<212> PRT
<213> Artificial Sequence

<220>
<223> KERE-class Nanobody FW3 sequence

<400> 57

Arg Phe Thr Ile Ser Arg Asp Ser Ala Lys Asn Met Met Tyr Leu Gln
1 5 10 15

Met Asn Asn Leu Lys Pro Gln Asp Thr Ala Val Tyr Tyr Cys Ala Ala
20 25 30

<210> 58
<211> 32
<212> PRT
<213> Artificial Sequence

<220>
<223> KERE-class Nanobody FW3 sequence

<400> 58

Arg Phe Thr Ile Ser Arg Glu Asn Asp Lys Ser Thr Val Tyr Leu Gln
1 5 10 15

Leu Asn Ser Leu Lys Pro Glu Asp Thr Ala Val Tyr Tyr Cys Ala Ala
20 25 30

<210> 59
<211> 32
<212> PRT
<213> Artificial Sequence

<220>
<223> KERE-class Nanobody FW3 sequence

<400> 59

Arg Phe Thr Ile Ser Arg Asp Tyr Ala Gly Asn Thr Ala Tyr Leu Gln
1 5 10 15

FIGURE 10 Continued…

```
Met Asn Ser Leu Lys Pro Glu Asp Thr Gly Val Tyr Tyr Cys Ala Thr
            20                  25                  30


<210>  60
<211>  11
<212>  PRT
<213>  Artificial Sequence

<220>
<223>  KERE-class Nanobody FW4 sequence

<400>  60

Trp Gly Gln Gly Thr Gln Val Thr Val Ser Ser
1               5                   10


<210>  61
<211>  11
<212>  PRT
<213>  Artificial Sequence

<220>
<223>  KERE-class Nanobody FW4 sequence

<400>  61

Trp Gly Lys Gly Thr Leu Val Thr Val Ser Ser
1               5                   10


<210>  62
<211>  11
<212>  PRT
<213>  Artificial Sequence

<220>
<223>  KERE-class Nanobody FW4 sequence

<400>  62

Arg Gly Gln Gly Thr Arg Val Thr Val Ser Ser
1               5                   10


<210>  63
<211>  11
<212>  PRT
<213>  Artificial Sequence

<220>
<223>  KERE-class Nanobody FW4 sequence

<400>  63

Trp Gly Leu Gly Thr Gln Val Thr Ile Ser Ser
1               5                   10


<210>  64
```

<211> 30
<212> PRT
<213> Artificial Sequence

<220>
<223> GLEW-class Nanobody FW1 sequence

<400> 64

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser
20 25 30

<210> 65
<211> 30
<212> PRT
<213> Artificial Sequence

<220>
<223> GLEW-class Nanobody FW1 sequence

<400> 65

Glu Val His Leu Val Glu Ser Gly Gly Gly Leu Val Arg Pro Gly Gly
1 5 10 15

Ser Leu Arg Leu Ser Cys Ala Ala Phe Gly Phe Ile Phe Lys
20 25 30

<210> 66
<211> 30
<212> PRT
<213> Artificial Sequence

<220>
<223> GLEW-class Nanobody FW1 sequence

<400> 66

Gln Val Lys Leu Glu Glu Ser Gly Gly Gly Leu Ala Gln Pro Gly Gly
1 5 10 15

Ser Leu Arg Leu Ser Cys Val Ala Ser Gly Phe Thr Phe Ser
20 25 30

<210> 67
<211> 30
<212> PRT
<213> Artificial Sequence

<220>
<223> GLEW-class Nanobody FW1 sequence

Glu Val Gln Leu Val Glu Ser Gly Gly Gly Leu Val Gln Pro Gly Gly
1 5 10 15

Ser Leu Arg Leu Ser Cys Val Cys Val Ser Ser Gly Cys Thr
20 25 30

<210> 68
<211> 30
<212> PRT
<213> Artificial Sequence

<220>
<223> GLEW-class Nanobody FW1 sequence

<400> 68

Glu Val Gln Leu Val Glu Ser Gly Gly Gly Leu Ala Leu Pro Gly Gly
1 5 10 15

Ser Leu Thr Leu Ser Cys Val Phe Ser Gly Ser Thr Phe Ser
20 25 30

<210> 69
<211> 22
<212> PRT
<213> Artificial Sequence

<220>
<223> GLEW-class Nanobody FW1 sequence

<400> 69

Val Glu Ser Gly Gly Gly Leu Val Gln Pro Gly Gly Ser Leu Arg Leu
1 5 10 15

Ser Cys Ala Ala Ser Gly
20

<210> 70
<211> 22
<212> PRT
<213> Artificial Sequence

<220>
<223> GLEW-class Nanobody FW1 sequence

<400> 70

Glu Glu Ser Gly Gly Gly Leu Ala Gln Pro Gly Gly Ser Leu Arg Leu
1 5 10 15

Ser Cys Val Ala Ser Gly

<210> 71
<211> 22
<212> PRT
<213> Artificial Sequence

<220>
<223> GLEW-class Nanobody FW1 sequence

<400> 71

Val Glu Ser Gly Gly Gly Leu Ala Leu Pro Gly Gly Ser Leu Thr Leu
1 5 10 15

Ser Cys Val Phe Ser Gly
20

<210> 72
<211> 14
<212> PRT
<213> Artificial Sequence

<220>
<223> GLEW-class Nanobody FW2 sequence

<400> 72

Trp Val Arg Gln Ala Pro Gly Lys Val Leu Glu Trp Val Ser
1 5 10

<210> 73
<211> 14
<212> PRT
<213> Artificial Sequence

<220>
<223> GLEW-class Nanobody FW2 sequence

<400> 73

Trp Val Arg Arg Pro Pro Gly Lys Gly Leu Glu Trp Val Ser
1 5 10

<210> 74
<211> 14
<212> PRT
<213> Artificial Sequence

<220>
<223> GLEW-class Nanobody FW2 sequence

<400> 74

Trp Val Arg Gln Ala Pro Gly Met Gly Leu Glu Trp Val Ser
1 5 10

FIGURE 10 Continued...

<210> 75
<211> 14
<212> PRT
<213> Artificial Sequence

<220>
<223> GLEW-class Nanobody FW2 sequence

<400> 75

Trp Val Arg Gln Ala Pro Gly Lys Glu Pro Glu Trp Val Ser
1 5 10

<210> 76
<211> 14
<212> PRT
<213> Artificial Sequence

<220>
<223> GLEW-class Nanobody FW2 sequence

<400> 76

Trp Val Arg Gln Ala Pro Gly Lys Asp Gln Glu Trp Val Ser
1 5 10

<210> 77
<211> 14
<212> PRT
<213> Artificial Sequence

<220>
<223> GLEW-class Nanobody FW2 sequence

<400> 77

Trp Val Arg Gln Ala Pro Gly Lys Ala Glu Glu Trp Val Ser
1 5 10

<210> 78
<211> 14
<212> PRT
<213> Artificial Sequence

<220>
<223> GLEW-class Nanobody FW2 sequence

<400> 78

Trp Val Arg Gln Ala Pro Gly Lys Gly Leu Glu Trp Val Ala
1 5 10

<210> 79
<211> 14
<212> PRT

FIGURE 10 Continued...

<213> Artificial Sequence

<220>
<223> GLEW-class Nanobody FW2 sequence

<400> 79

Trp Val Arg Gln Ala Pro Gly Arg Ala Thr Glu Trp Val Ser
1 5 10

<210> 80
<211> 32
<212> PRT
<213> Artificial Sequence

<220>
<223> GLEW-class Nanobody FW3 sequence

<400> 80

Arg Phe Thr Ile Ser Arg Asp Asn Ala Lys Asn Thr Leu Tyr Leu Gln
1 5 10 15

Met Asn Ser Leu Lys Pro Glu Asp Thr Ala Val Tyr Tyr Cys Val Lys
20 25 30

<210> 81
<211> 32
<212> PRT
<213> Artificial Sequence

<220>
<223> GLEW-class Nanobody FW3 sequence

<400> 81

Arg Phe Thr Ile Ser Arg Asp Asn Ala Arg Asn Thr Leu Tyr Leu Gln
1 5 10 15

Met Asp Ser Leu Ile Pro Glu Asp Thr Ala Leu Tyr Tyr Cys Ala Arg
20 25 30

<210> 82
<211> 32
<212> PRT
<213> Artificial Sequence

<220>
<223> GLEW-class Nanobody FW3 sequence

<400> 82

Arg Phe Thr Ser Ser Arg Asp Asn Ala Lys Ser Thr Leu Tyr Leu Gln
1 5 10 15

FIGURE 10 Continued...

```
Met Asn Asp Leu Lys Pro Glu Asp Thr Ala Leu Tyr Tyr Cys Ala Arg
            20                  25                  30


<210>  83
<211>  32
<212>  PRT
<213>  Artificial Sequence

<220>
<223>  GLEW-class Nanobody FW3 sequence

<400>  83

Arg Phe Ile Ile Ser Arg Asp Asn Ala Lys Asn Thr Leu Tyr Leu Gln
1               5                   10                  15


Met Asn Ser Leu Gly Pro Glu Asp Thr Ala Met Tyr Tyr Cys Gln Arg
            20                  25                  30


<210>  84
<211>  32
<212>  PRT
<213>  Artificial Sequence

<220>
<223>  GLEW-class Nanobody FW3 sequence

<400>  84

Arg Phe Thr Ala Ser Arg Asp Asn Ala Lys Asn Thr Leu Tyr Leu Gln
1               5                   10                  15


Met Asn Ser Leu Lys Ser Glu Asp Thr Ala Arg Tyr Tyr Cys Ala Arg
            20                  25                  30


<210>  85
<211>  32
<212>  PRT
<213>  Artificial Sequence

<220>
<223>  GLEW-class Nanobody FW3 sequence

<400>  85

Arg Phe Thr Ile Ser Arg Asp Asn Ala Lys Asn Thr Leu Tyr Leu Gln
1               5                   10                  15


Met Asp Asp Leu Gln Ser Glu Asp Thr Ala Met Tyr Tyr Cys Gly Arg
            20                  25                  30


<210>  86
<211>  11
<212>  PRT
```

FIGURE 10 Continued...

<213> Artificial Sequence

<220>
<223> GLEW-class Nanobody FW4 sequence

<400> 86

Gly Ser Gln Gly Thr Gln Val Thr Val Ser Ser
1 5 10

<210> 87
<211> 11
<212> PRT
<213> Artificial Sequence

<220>
<223> GLEW-class Nanobody FW4 sequence

<400> 87

Leu Arg Gly Gly Thr Gln Val Thr Val Ser Ser
1 5 10

<210> 88
<211> 11
<212> PRT
<213> Artificial Sequence

<220>
<223> GLEW-class Nanobody FW4 sequence

<400> 88

Arg Gly Gln Gly Thr Leu Val Thr Val Ser Ser
1 5 10

<210> 89
<211> 11
<212> PRT
<213> Artificial Sequence

<220>
<223> GLEW-class Nanobody FW4 sequence

<400> 89

Arg Ser Arg Gly Ile Gln Val Thr Val Ser Ser
1 5 10

<210> 90
<211> 11
<212> PRT
<213> Artificial Sequence

<220>
<223> GLEW-class Nanobody FW4 sequence

```
<400>  90

Trp Gly Lys Gly Thr Gln Val Thr Val Ser Ser
1               5                   10


<210>  91
<211>  11
<212>  PRT
<213>  Artificial Sequence

<220>
<223>  GLEW-class Nanobody FW4 sequence

<400>  91

Trp Gly Gln Gly Thr Gln Val Thr Val Ser Ser
1               5                   10


<210>  92
<211>  30
<212>  PRT
<213>  Artificial Sequence

<220>
<223>  P,R,S 103-class Nanobody FW1 sequence

<400>  92

Ala Val Gln Leu Val Glu Ser Gly Gly Gly Leu Val Gln Ala Gly Gly
1               5                   10                  15


Ser Leu Arg Leu Ser Cys Ala Ala Ser Gly Arg Thr Phe Ser
            20                  25                  30


<210>  93
<211>  30
<212>  PRT
<213>  Artificial Sequence

<220>
<223>  P,R,S 103-class Nanobody FW1 sequence

<400>  93

Gln Val Gln Leu Gln Glu Ser Gly Gly Gly Met Val Gln Pro Gly Gly
1               5                   10                  15


Ser Leu Arg Leu Ser Cys Ala Ala Ser Gly Phe Asp Phe Gly
            20                  25                  30


<210>  94
<211>  30
<212>  PRT
<213>  Artificial Sequence
```

FIGURE 10 Continued...

<220>
<223> P,R,S 103-class Nanobody FW1 sequence

<400> 94

Glu Val His Leu Val Glu Ser Gly Gly Gly Leu Val Arg Pro Gly Gly
1 5 10 15

Ser Leu Arg Leu Ser Cys Ala Ala Phe Gly Phe Ile Phe Lys
20 25 30

<210> 95
<211> 30
<212> PRT
<213> Artificial Sequence

<220>
<223> P,R,S 103-class Nanobody FW1 sequence

<400> 95

Gln Val Gln Leu Ala Glu Ser Gly Gly Gly Leu Val Gln Pro Gly Gly
1 5 10 15

Ser Leu Lys Leu Ser Cys Ala Ala Ser Arg Thr Ile Val Ser
20 25 30

<210> 96
<211> 30
<212> PRT
<213> Artificial Sequence

<220>
<223> P,R,S 103-class Nanobody FW1 sequence

<400> 96

Gln Glu His Leu Val Glu Ser Gly Gly Gly Leu Val Asp Ile Gly Gly
1 5 10 15

Ser Leu Arg Leu Ser Cys Ala Ala Ser Glu Arg Ile Phe Ser
20 25 30

<210> 97
<211> 30
<212> PRT
<213> Artificial Sequence

<220>
<223> P,R,S 103-class Nanobody FW1 sequence

<400> 97

Gln Val Lys Leu Glu Glu Ser Gly Gly Gly Leu Ala Gln Pro Gly Gly
1 5 10 15

FIGURE 10 Continued…

```
Ser Leu Arg Leu Ser Cys Val Ala Ser Gly Phe Thr Phe Ser
            20                  25                  30


<210>  98
<211>  30
<212>  PRT
<213>  Artificial Sequence

<220>
<223>  P,R,S 103-class Nanobody FW1 sequence

<400>  98

Glu Val Gln Leu Val Glu Ser Gly Gly Gly Leu Val Gln Pro Gly Gly
1               5                   10                  15


Ser Leu Arg Leu Ser Cys Val Cys Val Ser Ser Gly Cys Thr
            20                  25                  30


<210>  99
<211>  30
<212>  PRT
<213>  Artificial Sequence

<220>
<223>  P,R,S 103-class Nanobody FW1 sequence

<400>  99

Glu Val Gln Leu Val Glu Ser Gly Gly Gly Leu Ala Leu Pro Gly Gly
1               5                   10                  15


Ser Leu Thr Leu Ser Cys Val Phe Ser Gly Ser Thr Phe Ser
            20                  25                  30


<210>  100
<211>  22
<212>  PRT
<213>  Artificial Sequence

<220>
<223>  P,R,S 103-class Nanobody FW1 sequence

<400>  100

Val Glu Ser Gly Gly Gly Leu Val Gln Ala Gly Gly Ser Leu Arg Leu
1               5                   10                  15


Ser Cys Ala Ala Ser Gly
            20


<210>  101
```

<211> 22
<212> PRT
<213> Artificial Sequence

<220>
<223> P,R,S 103-class Nanobody FW1 sequence

<400> 101

Ala Glu Ser Gly Gly Gly Leu Val Gln Pro Gly Gly Ser Leu Lys Leu
1 5 10 15

Ser Cys Ala Ala Ser Arg
20

<210> 102
<211> 14
<212> PRT
<213> Artificial Sequence

<220>
<223> P,R,S 103-class Nanobody FW2 sequence

<400> 102

Trp Phe Arg Gln Ala Pro Gly Lys Glu Arg Glu Phe Val Ala
1 5 10

<210> 103
<211> 14
<212> PRT
<213> Artificial Sequence

<220>
<223> P,R,S 103-class Nanobody FW2 sequence

<400> 103

Trp Val Arg Gln Ala Pro Gly Lys Val Leu Glu Trp Val Ser
1 5 10

<210> 104
<211> 14
<212> PRT
<213> Artificial Sequence

<220>
<223> P,R,S 103-class Nanobody FW2 sequence

<400> 104

Trp Val Arg Arg Pro Pro Gly Lys Gly Leu Glu Trp Val Ser
1 5 10

<212> PRT
<213> Artificial Sequence

<220>
<223> P,R,S 103-class Nanobody FW2 sequence

<400> 105

Trp Ile Arg Gln Ala Pro Gly Lys Glu Arg Glu Gly Val Ser
1 5 10

<210> 106
<211> 14
<212> PRT
<213> Artificial Sequence

<220>
<223> P,R,S 103-class Nanobody FW2 sequence

<400> 106

Trp Val Arg Gln Tyr Pro Gly Lys Glu Pro Glu Trp Val Ser
1 5 10

<210> 107
<211> 14
<212> PRT
<213> Artificial Sequence

<220>
<223> P,R,S 103-class Nanobody FW2 sequence

<400> 107

Trp Phe Arg Gln Pro Pro Gly Lys Glu His Glu Phe Val Ala
1 5 10

<210> 108
<211> 14
<212> PRT
<213> Artificial Sequence

<220>
<223> P,R,S 103-class Nanobody FW2 sequence

<400> 108

Trp Tyr Arg Gln Ala Pro Gly Lys Arg Thr Glu Leu Val Ala
1 5 10

<210> 109
<211> 14
<212> PRT
<213> Artificial Sequence

<220>
<223> P,R,S 103-class Nanobody FW2 sequence

Trp Leu Arg Gln Ala Pro Gly Gln Gly Leu Glu Trp Val Ser
1 5 10

<210> 110
<211> 14
<212> PRT
<213> Artificial Sequence

<220>
<223> P,R,S 103-class Nanobody FW2 sequence

<400> 110

Trp Leu Arg Gln Thr Pro Gly Lys Gly Leu Glu Trp Val Gly
1 5 10

<210> 111
<211> 14
<212> PRT
<213> Artificial Sequence

<220>
<223> P,R,S 103-class Nanobody FW2 sequence

<400> 111

Trp Val Arg Gln Ala Pro Gly Lys Ala Glu Glu Phe Val Ser
1 5 10

<210> 112
<211> 32
<212> PRT
<213> Artificial Sequence

<220>
<223> P,R,S 103-class Nanobody FW3 sequence

<400> 112

Arg Phe Thr Ile Ser Arg Asp Asn Ala Lys Asn Thr Val Tyr Leu Gln
1 5 10 15

Met Asn Ser Leu Lys Pro Glu Asp Thr Ala Val Tyr Tyr Cys Ala Ala
20 25 30

<210> 113
<211> 32
<212> PRT
<213> Artificial Sequence

<220>
<223> P,R,S 103-class Nanobody FW3 sequence

Arg Phe Thr Ile Ser Arg Asp Asn Ala Arg Asn Thr Leu Tyr Leu Gln
1 5 10 15

Met Asp Ser Leu Ile Pro Glu Asp Thr Ala Leu Tyr Tyr Cys Ala Arg
20 25 30

<210> 114
<211> 32
<212> PRT
<213> Artificial Sequence

<220>
<223> P,R,S 103-class Nanobody FW3 sequence

<400> 114

Arg Phe Thr Ile Ser Arg Asp Asn Ala Lys Asn Glu Met Tyr Leu Gln
1 5 10 15

Met Asn Asn Leu Lys Thr Glu Asp Thr Gly Val Tyr Trp Cys Gly Ala
20 25 30

<210> 115
<211> 32
<212> PRT
<213> Artificial Sequence

<220>
<223> P,R,S 103-class Nanobody FW3 sequence

<400> 115

Arg Phe Thr Ile Ser Ser Asp Ser Asn Arg Asn Met Ile Tyr Leu Gln
1 5 10 15

Met Asn Asn Leu Lys Pro Glu Asp Thr Ala Val Tyr Tyr Cys Ala Ala
20 25 30

<210> 116
<211> 32
<212> PRT
<213> Artificial Sequence

<220>
<223> P,R,S 103-class Nanobody FW3 sequence

<400> 116

Arg Phe Thr Ile Ser Arg Asp Asn Ala Lys Asn Met Leu Tyr Leu His
1 5 10 15

Leu Asn Asn Leu Lys Ser Glu Asp Thr Ala Val Tyr Tyr Cys Arg Arg

<210> 117
<211> 32
<212> PRT
<213> Artificial Sequence

<220>
<223> P,R,S 103-class Nanobody FW3 sequence

<400> 117

Arg Phe Thr Ile Ser Arg Asp Asn Ala Lys Lys Thr Val Tyr Leu Arg
1 5 10 15

Leu Asn Ser Leu Asn Pro Glu Asp Thr Ala Val Tyr Ser Cys Asn Leu
20 25 30

<210> 118
<211> 32
<212> PRT
<213> Artificial Sequence

<220>
<223> P,R,S 103-class Nanobody FW3 sequence

<400> 118

Arg Phe Lys Ile Ser Arg Asp Asn Ala Lys Lys Thr Leu Tyr Leu Gln
1 5 10 15

Met Asn Ser Leu Gly Pro Glu Asp Thr Ala Met Tyr Tyr Cys Gln Arg
20 25 30

<210> 119
<211> 32
<212> PRT
<213> Artificial Sequence

<220>
<223> P,R,S 103-class Nanobody FW3 sequence

<400> 119

Arg Phe Thr Val Ser Arg Asp Asn Gly Lys Asn Thr Ala Tyr Leu Arg
1 5 10 15

Met Asn Ser Leu Lys Pro Glu Asp Thr Ala Asp Tyr Tyr Cys Ala Val
20 25 30

<210> 120
<211> 11
<212> PRT
<213> Artificial Sequence

FIGURE 10 Continued...

<220>
<223> P,R,S 103-class Nanobody FW4 sequence

<400> 120

Arg Gly Gln Gly Thr Gln Val Thr Val Ser Ser
1 5 10

<210> 121
<211> 11
<212> PRT
<213> Artificial Sequence

<220>
<223> P,R,S 103-class Nanobody FW4 sequence

<400> 121

Leu Arg Gly Gly Thr Gln Val Thr Val Ser Ser
1 5 10

<210> 122
<211> 11
<212> PRT
<213> Artificial Sequence

<220>
<223> P,R,S 103-class Nanobody FW4 sequence

<400> 122

Gly Asn Lys Gly Thr Leu Val Thr Val Ser Ser
1 5 10

<210> 123
<211> 11
<212> PRT
<213> Artificial Sequence

<220>
<223> P,R,S 103-class Nanobody FW4 sequence

<400> 123

Ser Ser Pro Gly Thr Gln Val Thr Val Ser Ser
1 5 10

<210> 124
<211> 11
<212> PRT
<213> Artificial Sequence

<220>
<223> P,R,S 103-class Nanobody FW4 sequence

Ser Ser Gln Gly Thr Leu Val Thr Val Ser Ser
1 5 10

<210> 125
<211> 11
<212> PRT
<213> Artificial Sequence

<220>
<223> P,R,S 103-class Nanobody FW4 sequence

<400> 125

Arg Ser Arg Gly Ile Gln Val Thr Val Ser Ser
1 5 10

<210> 126
<211> 30
<212> PRT
<213> Artificial Sequence

<220>
<223> FR1 sequence

<400> 126

Glu Val Gln Leu Val Glu Ser Gly Gly Gly Leu Val Gln Pro Gly Gly
1 5 10 15

Ser Leu Arg Leu Ser Cys Ala Ala Ser Gly Ser Ile Phe Ser
20 25 30

<210> 127
<211> 30
<212> PRT
<213> Artificial Sequence

<220>
<223> FR1 sequence

<400> 127

Glu Val Gln Leu Val Glu Ser Gly Gly Gly Leu Val Gln Ala Gly Asp
1 5 10 15

Ser Leu Arg Leu Ser Cys Thr Ala Thr Gly Arg Thr Ser Ser
20 25 30

<210> 128
<211> 30
<212> PRT
<213> Artificial Sequence

<223> FR1 sequence

<400> 128

```
Glu Val Gln Leu Val Glu Ser Gly Gly Gly Leu Val Gln Ala Gly Gly
1               5                   10                  15


Ser Leu Arg Leu Ser Cys Ala Thr Ser Gly Phe Thr Phe Ser
            20                  25                  30
```

<210> 129
<211> 30
<212> PRT
<213> Artificial Sequence

<220>
<223> FR1 sequence

<400> 129

```
Lys Val Gln Leu Val Glu Ser Gly Gly Gly Leu Val Gln Ala Gly Gly
1               5                   10                  15


Ser Leu Arg Leu Ser Cys Ala Ala Ser Gly Arg Thr Phe Ser
            20                  25                  30
```

<210> 130
<211> 30
<212> PRT
<213> Artificial Sequence

<220>
<223> FR1 sequence

<400> 130

```
Glu Val Gln Leu Val Glu Ser Gly Gly Gly Leu Val Gln Ala Gly Asp
1               5                   10                  15


Ser Leu Arg Leu Ser Cys Ala Ala Thr Gly Arg Thr Ser Ser
            20                  25                  30
```

<210> 131
<211> 30
<212> PRT
<213> Artificial Sequence

<220>
<223> FR1 sequence

<400> 131

```
Glu Val Gln Leu Val Glu Ser Gly Gly Gly Leu Val Gln Ala Gly Gly
1               5                   10                  15
```

FIGURE 10 Continued...

Ser Leu Arg Leu Ser Cys Val Ala Ser Gly Arg Thr Leu Arg
20 25 30

<210> 132
<211> 30
<212> PRT
<213> Artificial Sequence

<220>
<223> FR1 sequence

<400> 132

Glu Val Gln Leu Val Glu Ser Gly Gly Gly Leu Val Gln Ala Gly Gly
1 5 10 15

Ser Leu Arg Leu Thr Cys Ala Ala Ser Gly Arg Thr Phe Ser
20 25 30

<210> 133
<211> 30
<212> PRT
<213> Artificial Sequence

<220>
<223> FR1 sequence

<400> 133

Glu Val Gln Leu Val Glu Ser Gly Gly Gly Leu Val Gln Ala Gly Gly
1 5 10 15

Ser Leu Arg Leu Ser Cys Ala Ala Ser Gly Leu Thr Phe Asn
20 25 30

<210> 134
<211> 30
<212> PRT
<213> Artificial Sequence

<220>
<223> FR1 sequence

<400> 134

Glu Val Gln Leu Val Glu Ser Gly Gly Gly Leu Val Gln Ala Gly Asp
1 5 10 15

Ser Leu Arg Leu Ser Cys Ala Ala Thr Gly Arg Thr Ser Ser
20 25 30

```
<212>  PRT
<213>  Artificial Sequence

<220>
<223>  CDR sequence

<400>  135

Asp Asn Val Met Gly
1               5


<210>  136
<211>  5
<212>  PRT
<213>  Artificial Sequence

<220>
<223>  CDR sequence

<400>  136

Ile Tyr Asn Met Asp
1               5


<210>  137
<211>  5
<212>  PRT
<213>  Artificial Sequence

<220>
<223>  CDR sequence

<400>  137

Arg Phe Asp Met Ser
1               5


<210>  138
<211>  5
<212>  PRT
<213>  Artificial Sequence

<220>
<223>  CDR sequence

<400>  138

Ser Tyr Phe Met Gly
1               5


<210>  139
<211>  5
<212>  PRT
<213>  Artificial Sequence

<220>
<223>  CDR sequence
```

Ile Tyr Asn Met Asp
1 5

<210> 140
<211> 5
<212> PRT
<213> Artificial Sequence

<220>
<223> CDR sequence

<400> 140

Arg Tyr Val Thr Gly
1 5

<210> 141
<211> 5
<212> PRT
<213> Artificial Sequence

<220>
<223> CDR sequence

<400> 141

Ser Phe Val Ile Gly
1 5

<210> 142
<211> 5
<212> PRT
<213> Artificial Sequence

<220>
<223> CDR sequence

<400> 142

Gln Tyr Thr Ile Thr
1 5

<210> 143
<211> 5
<212> PRT
<213> Artificial Sequence

<220>
<223> CDR sequence

<400> 143

Ile Tyr Asn Met Asp
1 5

FIGURE 10 Continued...

<210> 144
<211> 14
<212> PRT
<213> Artificial Sequence

<220>
<223> FR2 sequence

<400> 144

Trp Tyr Arg Gln Ala Pro Gly Lys Gln Arg Glu Leu Val Ala
1 5 10

<210> 145
<211> 14
<212> PRT
<213> Artificial Sequence

<220>
<223> FR2 sequence

<400> 145

Trp Phe Arg Gln Thr Pro Gly Lys Glu Arg Glu Leu Ile Ala
1 5 10

<210> 146
<211> 14
<212> PRT
<213> Artificial Sequence

<220>
<223> FR2 sequence

<400> 146

Trp Phe Arg Gln Ala Pro Gly Lys Gln Arg Glu Phe Ile Ala
1 5 10

<210> 147
<211> 14
<212> PRT
<213> Artificial Sequence

<220>
<223> FR2 sequence

<400> 147

Trp Phe Arg Gln Ala Pro Gly Lys Glu Arg Glu Val Val Ala
1 5 10

<210> 148
<211> 14
<212> PRT

FIGURE 10 Continued...

<213> Artificial Sequence

<220>
<223> FR2 sequence

<400> 148

Trp Phe Leu Gln Ala Pro Gly Lys Glu Arg Glu Leu Ile Ala
1 5 10

<210> 149
<211> 14
<212> PRT
<213> Artificial Sequence

<220>
<223> FR2 sequence

<400> 149

Trp Phe Arg Gln Ala Pro Gly Lys Glu Arg Glu Val Val Ala
1 5 10

<210> 150
<211> 14
<212> PRT
<213> Artificial Sequence

<220>
<223> FR2 sequence

<400> 150

Trp Phe Arg Gln Ala Pro Gly Lys Gln Arg Glu Val Val Ala
1 5 10

<210> 151
<211> 14
<212> PRT
<213> Artificial Sequence

<220>
<223> FR2 sequence

<400> 151

Trp Phe Arg Gln Ala Pro Gly Lys Glu Arg Glu Phe Val Ala
1 5 10

<210> 152
<211> 14
<212> PRT
<213> Artificial Sequence

<220>
<223> FR2 sequence

Trp Phe Arg Gln Gly Ser Gly Lys Gly Arg Glu Leu Ile Ala
1 5 10

<210> 153
<211> 16
<212> PRT
<213> Artificial Sequence

<220>
<223> CDR sequence

<400> 153

Thr Ile Trp Ser Ser Gly His Thr Asn Tyr Ala Asp Ser Val Lys Gly
1 5 10 15

<210> 154
<211> 17
<212> PRT
<213> Artificial Sequence

<220>
<223> CDR sequence

<400> 154

Arg Leu Trp Trp Arg Ser Gly Ser Thr Tyr Tyr Ala Asp Ser Val Lys
1 5 10 15

Gly

<210> 155
<211> 16
<212> PRT
<213> Artificial Sequence

<220>
<223> CDR sequence

<400> 155

Thr Ile Phe Ser Gly Gly Asp Thr Asp Tyr Ile Asp Ser Val Lys Gly
1 5 10 15

<210> 156
<211> 17
<212> PRT
<213> Artificial Sequence

<220>
<223> CDR sequence

Thr Ile Arg Trp Ser Asp Gly Ser Thr Tyr Tyr Glu Asp Ser Val Lys
1 5 10 15

Gly

<210> 157
<211> 17
<212> PRT
<213> Artificial Sequence

<220>
<223> CDR sequence

<400> 157

Arg Ile Trp Trp Arg Ser Gly Ala Thr Tyr Tyr Ala Asp Ser Val Lys
1 5 10 15

Gly

<210> 158
<211> 17
<212> PRT
<213> Artificial Sequence

<220>
<223> CDR sequence

<400> 158

Ser Ile Ser Trp Ser Gly Glu Ser Thr Tyr Tyr Ala Asp Ser Val Lys
1 5 10 15

Gly

<210> 159
<211> 16
<212> PRT
<213> Artificial Sequence

<220>
<223> CDR sequence

<400> 159

Ser Ile Thr Ser Gly Gly Ser Thr Tyr Tyr Glu Asp Ser Gly Lys Gly
1 5 10 15

<212> PRT
<213> Artificial Sequence

<220>
<223> CDR sequence

<400> 160

Ala Val Ser Trp Ser Gly Ser Ser Glu Ser Val Ser Asn Ser Val Lys
1 5 10 15

Gly

<210> 161
<211> 17
<212> PRT
<213> Artificial Sequence

<220>
<223> CDR sequence

<400> 161

Arg Ile Trp Trp Arg Ser Gly Glu Thr Tyr Tyr Ala Asp Ser Val Lys
1 5 10 15

Gly

<210> 162
<211> 32
<212> PRT
<213> Artificial Sequence

<220>
<223> FR3 sequence

<400> 162

Arg Phe Thr Ile Ser Arg Asp Asn Ala Lys Asn Thr Val Tyr Leu Gln
1 5 10 15

Met Asn Ser Leu Lys Pro Glu Asp Thr Ala Val Tyr Tyr Cys Asn Leu
20 25 30

<210> 163
<211> 32
<212> PRT
<213> Artificial Sequence

<220>
<223> FR3 sequence

Arg Phe Thr Ile Ser Arg Asp Asn Ala Lys Asn Thr Val Tyr Leu Gln
1 5 10 15

Met Asn Ser Leu Lys Pro Glu Asp Thr Ser Val Tyr Ile Cys Thr Ala
20 25 30

<210> 164
<211> 32
<212> PRT
<213> Artificial Sequence

<220>
<223> FR3 sequence

<400> 164

Arg Phe Thr Ile Ser Arg Asp Asn Ala Lys Asn Thr Val Tyr Leu Gln
1 5 10 15

Met Asn Ser Leu Lys Pro Glu Asp Thr Ala Val Tyr Tyr Cys Cys Pro
20 25 30

<210> 165
<211> 32
<212> PRT
<213> Artificial Sequence

<220>
<223> FR3 sequence

<400> 165

Arg Phe Thr Ile Ser Arg Asp Asn Ala Lys Asn Thr Val Tyr Leu Gln
1 5 10 15

Met Asn Ser Leu Lys Pro Glu Asp Thr Ala Val Tyr Tyr Cys Ala Ala
20 25 30

<210> 166
<211> 32
<212> PRT
<213> Artificial Sequence

<220>
<223> FR3 sequence

<400> 166

Arg Phe Thr Ile Ser Arg Gly Asn Ala Lys Asn Thr Val Tyr Leu Gln
1 5 10 15

Met Asn Ser Leu Lys Pro Glu Asp Thr Gly Val Tyr His Cys Thr Ala
20 25 30

FIGURE 10 Continued…

<210> 167
<211> 32
<212> PRT
<213> Artificial Sequence

<220>
<223> FR3 sequence

<400> 167

```
Arg Phe Ala Ile Ser Arg Asp Asn Ala Lys Asn Ala Val Tyr Leu Gln
1               5                   10                  15

Met Asn Ser Leu Asn Leu Glu Asp Thr Gly Val Tyr Tyr Cys Ala Glu
            20                  25                  30
```

<210> 168
<211> 32
<212> PRT
<213> Artificial Sequence

<220>
<223> FR3 sequence

<400> 168

```
Arg Phe Thr Ile Ser Arg Asp Asn Ala Lys Asn Arg Val Tyr Leu Gln
1               5                   10                  15

Met Asn Ser Leu Arg Pro Glu Asp Thr Ala Val Tyr Tyr Cys Ala Ala
            20                  25                  30
```

<210> 169
<211> 32
<212> PRT
<213> Artificial Sequence

<220>
<223> FR3 sequence

<400> 169

```
Arg Phe Thr Ile Ser Arg Asp Asn Ala Lys Asn Thr Ala Tyr Leu Ala
1               5                   10                  15

Met Asn Ser Leu Lys Pro Glu Asp Thr Ala Val Tyr Tyr Cys Ala Ala
            20                  25                  30
```

<210> 170
<211> 32
<212> PRT
<213> Artificial Sequence

FIGURE 10 Continued...

<220>
<223> FR3 sequence

<400> 170

Arg Phe Thr Ile Ser Arg Asp Asn Ala Lys Asn Thr Val Tyr Leu Gln
1 5 10 15

Met Asn Ser Leu Lys Pro Glu Asp Thr Asn Val Tyr His Cys Ala Ala
20 25 30

<210> 171
<211> 12
<212> PRT
<213> Artificial Sequence

<220>
<223> CDR sequence

<400> 171

Gly Thr Ile Val Thr Gly Thr Trp Arg Ser Asp Tyr
1 5 10

<210> 172
<211> 10
<212> PRT
<213> Artificial Sequence

<220>
<223> CDR sequence

<400> 172

Gly Asp Thr Gly Gly Ala Ala Tyr Gly Tyr
1 5 10

<210> 173
<211> 6
<212> PRT
<213> Artificial Sequence

<220>
<223> CDR sequence

<400> 173

Leu Gly Ile Glu Tyr Ala
1 5

<210> 174
<211> 9
<212> PRT
<213> Artificial Sequence

<223> CDR sequence

<400> 174

Ala Lys Gly Ile Gly Val Tyr Gly Tyr
1 5

<210> 175
<211> 10
<212> PRT
<213> Artificial Sequence

<220>
<223> CDR sequence

<400> 175

Gly Val Thr Gly Gly Ala Ala Tyr Gly Tyr
1 5 10

<210> 176
<211> 9
<212> PRT
<213> Artificial Sequence

<220>
<223> CDR sequence

<400> 176

Ala Glu Leu Pro Gly Thr Tyr Asp Tyr
1 5

<210> 177
<211> 9
<212> PRT
<213> Artificial Sequence

<220>
<223> CDR sequence

<400> 177

Ala Glu Pro Ala Gly Val Tyr Asp Val
1 5

<210> 178
<211> 15
<212> PRT
<213> Artificial Sequence

<220>
<223> CDR sequence

<400> 178

Asp Arg Arg Gly Leu Ala Ser Thr Arg Ala Ala Asp Tyr Asp Tyr

<210> 179
<211> 10
<212> PRT
<213> Artificial Sequence

<220>
<223> CDR sequence

<400> 179

Gly Asp Thr Gly Gly Ala Ser Tyr Gly Tyr
1 5 10

<210> 180
<211> 11
<212> PRT
<213> Artificial Sequence

<220>
<223> FR4 sequence

<400> 180

Trp Gly Gln Gly Thr Gln Val Thr Val Ser Ser
1 5 10

<210> 181
<211> 11
<212> PRT
<213> Artificial Sequence

<220>
<223> FR4 sequence

<400> 181

Trp Gly Gln Gly Thr Gln Val Thr Val Ser Ser
1 5 10

<210> 182
<211> 11
<212> PRT
<213> Artificial Sequence

<220>
<223> FR4 sequence

<400> 182

Trp Gly Gln Gly Thr Gln Val Thr Val Ser Ser
1 5 10

<212> PRT
<213> Artificial Sequence

<220>
<223> FR4 sequence

<400> 183

Trp Gly Gln Gly Thr Gln Val Thr Val Ser Ser
1 5 10

<210> 184
<211> 11
<212> PRT
<213> Artificial Sequence

<220>
<223> FR4 sequence

<400> 184

Trp Gly Gln Gly Thr Gln Val Thr Val Ser Ser
1 5 10

<210> 185
<211> 11
<212> PRT
<213> Artificial Sequence

<220>
<223> FR4 sequence

<400> 185

Trp Gly Gln Gly Thr Gln Val Thr Val Ser Ser
1 5 10

<210> 186
<211> 11
<212> PRT
<213> Artificial Sequence

<220>
<223> FR4 sequence

<400> 186

Trp Gly Gln Gly Thr Gln Val Thr Val Ser Ser
1 5 10

<210> 187
<211> 11
<212> PRT
<213> Artificial Sequence

<220>
<223> FR4 sequence

Trp Gly Gln Gly Thr Gln Val Thr Val Ser Ser
1 5 10

<210> 188
<211> 11
<212> PRT
<213> Artificial Sequence

<220>
<223> FR4 sequence

<400> 188

Trp Gly Gln Gly Thr Gln Val Thr Val Ser Ser
1 5 10

<210> 189
<211> 120
<212> PRT
<213> Artificial Sequence

<220>
<223> Nanobody

<400> 189

Glu Val Gln Leu Val Glu Ser Gly Gly Gly Leu Val Gln Pro Gly Gly
1 5 10 15

Ser Leu Arg Leu Ser Cys Ala Ala Ser Gly Ser Ile Phe Ser Asp Asn
20 25 30

Val Met Gly Trp Tyr Arg Gln Ala Pro Gly Lys Gln Arg Glu Leu Val
35 40 45

Ala Thr Ile Trp Ser Ser Gly His Thr Asn Tyr Ala Asp Ser Val Lys
50 55 60

Gly Arg Phe Thr Ile Ser Arg Asp Asn Ala Lys Asn Thr Val Tyr Leu
65 70 75 80

Gln Met Asn Ser Leu Lys Pro Glu Asp Thr Ala Val Tyr Tyr Cys Asn
85 90 95

Leu Gly Thr Ile Val Thr Gly Thr Trp Arg Ser Asp Tyr Trp Gly Gln
100 105 110

Gly Thr Gln Val Thr Val Ser Ser
115 120

FIGURE 10 Continued…

<210> 190
<211> 119
<212> PRT
<213> Artificial Sequence

<220>
<223> Nanobody

<400> 190

Glu Val Gln Leu Val Glu Ser Gly Gly Gly Leu Val Gln Ala Gly Asp
1               5                   10                  15

Ser Leu Arg Leu Ser Cys Thr Ala Thr Gly Arg Thr Ser Ser Ile Tyr
            20                  25                  30

Asn Met Asp Trp Phe Arg Gln Thr Pro Gly Lys Glu Arg Glu Leu Ile
        35                  40                  45

Ala Arg Leu Trp Trp Arg Ser Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ser Val Tyr Ile Cys
                85                  90                  95

Thr Ala Gly Asp Thr Gly Gly Ala Ala Tyr Gly Tyr Trp Gly Gln Gly
            100                 105                 110

Thr Gln Val Thr Val Ser Ser
        115

<210> 191
<211> 114
<212> PRT
<213> Artificial Sequence

<220>
<223> Nanobody

<400> 191

Glu Val Gln Leu Val Glu Ser Gly Gly Gly Leu Val Gln Ala Gly Gly
1               5                   10                  15

Ser Leu Arg Leu Ser Cys Ala Thr Ser Gly Phe Thr Phe Ser Arg Phe
            20                  25                  30

FIGURE 10 Continued…

Asp Met Ser Trp Phe Arg Gln Ala Pro Gly Lys Gln Arg Glu Phe Ile
35 40 45

Ala Thr Ile Phe Ser Gly Gly Asp Thr Asp Tyr Ile Asp Ser Val Lys
50 55 60

Gly Arg Phe Thr Ile Ser Arg Asp Asn Ala Lys Asn Thr Val Tyr Leu
65 70 75 80

Gln Met Asn Ser Leu Lys Pro Glu Asp Thr Ala Val Tyr Tyr Cys Cys
85 90 95

Pro Leu Gly Ile Glu Tyr Ala Trp Gly Gln Gly Thr Gln Val Thr Val
100 105 110

Ser Ser

<210> 192
<211> 118
<212> PRT
<213> Artificial Sequence

<220>
<223> Nanobody

<400> 192

Lys Val Gln Leu Val Glu Ser Gly Gly Gly Leu Val Gln Ala Gly Gly
1 5 10 15

Ser Leu Arg Leu Ser Cys Ala Ala Ser Gly Arg Thr Phe Ser Ser Tyr
20 25 30

Phe Met Gly Trp Phe Arg Gln Ala Pro Gly Lys Glu Arg Glu Val Val
35 40 45

Ala Thr Ile Arg Trp Ser Asp Gly Ser Thr Tyr Tyr Glu Asp Ser Val
50 55 60

Lys Gly Arg Phe Thr Ile Ser Arg Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Ala Lys Gly Ile Gly Val Tyr Gly Tyr Trp Gly Gln Gly Thr
100 105 110

FIGURE 10 Continued...

Gln Val Thr Val Ser Ser
115

<210> 193
<211> 119
<212> PRT
<213> Artificial Sequence

<220>
<223> Nanobody

<400> 193

Glu Val Gln Leu Val Glu Ser Gly Gly Gly Leu Val Gln Ala Gly Asp
1 5 10 15

Ser Leu Arg Leu Ser Cys Ala Ala Thr Gly Arg Thr Ser Ser Ile Tyr
20 25 30

Asn Met Asp Trp Phe Leu Gln Ala Pro Gly Lys Glu Arg Glu Leu Ile
35 40 45

Ala Arg Ile Trp Trp Arg Ser Gly Ala Thr Tyr Tyr Ala Asp Ser Val
50 55 60

Lys Gly Arg Phe Thr Ile Ser Arg Gly Asn Ala Lys Asn Thr Val Tyr
65 70 75 80

Leu Gln Met Asn Ser Leu Lys Pro Glu Asp Thr Gly Val Tyr His Cys
85 90 95

Thr Ala Gly Val Thr Gly Gly Ala Ala Tyr Gly Tyr Trp Gly Gln Gly
100 105 110

Thr Gln Val Thr Val Ser Ser
115

<210> 194
<211> 118
<212> PRT
<213> Artificial Sequence

<220>
<223> Nanobody

<400> 194

Glu Val Gln Leu Val Glu Ser Gly Gly Gly Leu Val Gln Ala Gly Gly
1 5 10 15

FIGURE 10 Continued...

Ser Leu Arg Leu Ser Cys Val Ala Ser Gly Arg Thr Leu Arg Arg Tyr
20 25 30

Val Thr Gly Trp Phe Arg Gln Ala Pro Gly Lys Glu Arg Glu Val Val
35 40 45

Ala Ser Ile Ser Trp Ser Gly Glu Ser Thr Tyr Tyr Ala Asp Ser Val
50 55 60

Lys Gly Arg Phe Ala Ile Ser Arg Asp Asn Ala Lys Asn Ala Val Tyr
65 70 75 80

Leu Gln Met Asn Ser Leu Asn Leu Glu Asp Thr Gly Val Tyr Tyr Cys
85 90 95

Ala Glu Ala Glu Leu Pro Gly Thr Tyr Asp Tyr Trp Gly Gln Gly Thr
100 105 110

Gln Val Thr Val Ser Ser
115

<210> 195
<211> 117
<212> PRT
<213> Artificial Sequence

<220>
<223> Nanobody

<400> 195

Glu Val Gln Leu Val Glu Ser Gly Gly Gly Leu Val Gln Ala Gly Gly
1 5 10 15

Ser Leu Arg Leu Thr Cys Ala Ala Ser Gly Arg Thr Phe Ser Ser Phe
20 25 30

Val Ile Gly Trp Phe Arg Gln Ala Pro Gly Lys Gln Arg Glu Val Val
35 40 45

Ala Ser Ile Thr Ser Gly Gly Ser Thr Tyr Tyr Glu Asp Ser Gly Lys
50 55 60

Gly Arg Phe Thr Ile Ser Arg Asp Asn Ala Lys Asn Arg Val Tyr Leu
65 70 75 80

Gln Met Asn Ser Leu Arg Pro Glu Asp Thr Ala Val Tyr Tyr Cys Ala
85 90 95

FIGURE 10 Continued…

```
Ala Ala Glu Pro Ala Gly Val Tyr Asp Val Trp Gly Gln Gly Thr Gln
            100                 105                 110

Val Thr Val Ser Ser
        115

<210>  196
<211>  124
<212>  PRT
<213>  Artificial Sequence

<220>
<223>  Nanobody

<400>  196

Glu Val Gln Leu Val Glu Ser Gly Gly Gly Leu Val Gln Ala Gly Gly
1               5                   10                  15

Ser Leu Arg Leu Ser Cys Ala Ala Ser Gly Leu Thr Phe Asn Gln Tyr
            20                  25                  30

Thr Ile Thr Trp Phe Arg Gln Ala Pro Gly Lys Glu Arg Glu Phe Val
        35                  40                  45

Ala Ala Val Ser Trp Ser Gly Ser Ser Glu Ser Val Ser Asn Ser Val
    50                  55                  60

Lys Gly Arg Phe Thr Ile Ser Arg Asp Asn Ala Lys Asn Thr Ala Tyr
65                  70                  75                  80

Leu Ala Met Asn Ser Leu Lys Pro Glu Asp Thr Ala Val Tyr Tyr Cys
                85                  90                  95

Ala Ala Asp Arg Arg Gly Leu Ala Ser Thr Arg Ala Ala Asp Tyr Asp
            100                 105                 110

Tyr Trp Gly Gln Gly Thr Gln Val Thr Val Ser Ser
        115                 120

<210>  197
<211>  119
<212>  PRT
<213>  Artificial Sequence

<220>
<223>  Nanobody

<400>  197
```

Glu Val Gln Leu Val Glu Ser Gly Gly Gly Leu Val Gln Ala Gly Asp
1 5 10 15

Ser Leu Arg Leu Ser Cys Ala Ala Thr Gly Arg Thr Ser Ser Ile Tyr
20 25 30

Asn Met Asp Trp Phe Arg Gln Gly Ser Gly Lys Gly Arg Glu Leu Ile
35 40 45

Ala Arg Ile Trp Trp Arg Ser Gly Glu Thr Tyr Tyr Ala Asp Ser Val
50 55 60

Lys Gly Arg Phe Thr Ile Ser Arg Asp Asn Ala Lys Asn Thr Val Tyr
65 70 75 80

Leu Gln Met Asn Ser Leu Lys Pro Glu Asp Thr Asn Val Tyr His Cys
85 90 95

Ala Ala Gly Asp Thr Gly Gly Ala Ser Tyr Gly Tyr Trp Gly Gln Gly
100 105 110

Thr Gln Val Thr Val Ser Ser
115

<210> 198
<211> 213
<212> PRT
<213> Homo sapiens

<400> 198

Met Gln Leu Pro Leu Ala Leu Cys Leu Val Cys Leu Leu Val His Thr
1 5 10 15

Ala Phe Arg Val Val Glu Gly Gln Gly Trp Gln Ala Phe Lys Asn Asp
20 25 30

Ala Thr Glu Ile Ile Pro Glu Leu Gly Glu Tyr Pro Glu Pro Pro Pro
35 40 45

Glu Leu Glu Asn Asn Lys Thr Met Asn Arg Ala Glu Asn Gly Gly Arg
50 55 60

Pro Pro His His Pro Phe Glu Thr Lys Asp Val Ser Glu Tyr Ser Cys
65 70 75 80

Arg Glu Leu His Phe Thr Arg Tyr Val Thr Asp Gly Pro Cys Arg Ser

```
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Gly Lys Trp Trp Arg Pro Ser
        115                 120                 125

Gly Pro Asp Phe Arg Cys Ile Pro Asp Arg Tyr Arg Ala Gln Thr Val
    130                 135                 140

Gln Leu Leu Cys Pro Gly Gly Glu Ala Pro Arg Ala Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Thr Glu Ala Ala Arg Pro Gln Lys Gly
            180                 185                 190

Arg Lys Pro Arg Pro Arg Ala Arg Ser Ala Lys Ala Asn Gln Ala Glu
        195                 200                 205

Leu Glu Asn Ala Tyr
    210


<210>  199
<211>  213
<212>  PRT
<213>  Artificial Sequence

<220>
<223>  Recombinant sclerostin

<400>  199

Met Pro Leu Leu Leu Leu Leu Pro Leu Leu Trp Ala Gly Ala Leu Ala
1               5                   10                  15

His His His His His His His Gln Gly Trp Gln Ala Phe Lys Asn Asp
            20                  25                  30

Ala Thr Glu Ile Ile Pro Glu Leu Gly Glu Tyr Pro Glu Pro Pro Pro
        35                  40                  45

Glu Leu Glu Asn Asn Lys Thr Met Asn Arg Ala Glu Asn Gly Gly Arg
    50                  55                  60
```

FIGURE 10 Continued...

```
Pro Pro His His Pro Phe Glu Thr Lys Asp Val Ser Glu Tyr Ser Cys
65                  70                  75                  80

Arg Glu Leu His Phe Thr Arg Tyr Val Thr Asp Gly Pro Cys Arg Ser
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Gly Lys Trp Trp Arg Pro Ser
        115                 120                 125

Gly Pro Asp Phe Arg Cys Ile Pro Asp Arg Tyr Arg Ala Gln Arg Val
    130                 135                 140

Gln Leu Leu Cys Pro Gly Gly Glu Ala Pro Arg Ala Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Thr Glu Ala Ala Arg Pro Gln Lys Gly
            180                 185                 190

Arg Lys Pro Arg Pro Arg Ala Arg Ser Ala Lys Ala Asn Gln Ala Glu
        195                 200                 205

Leu Glu Asn Ala Tyr
    210
```

TREATMENT FOR BONE DISEASES

CROSS-REFERENCE TO RELATED APPLICATIONS

This application is a continuation of U.S. Pat. Application No. 17,020,108, filed Sep. 14, 2020, now U.S. Pat. No. 11,896,667, which is a continuation of U.S. patent application Ser. No. 15/887,299, filed Feb. 2, 2018, now U.S. Pat. No. 10,799,583, which is a continuation of U.S. patent application Ser. No. 13/934,433, filed Jul. 3, 2013, now U.S. Pat. No. 9,925,960, which claims priority to U.S. Provisional Application 61/668,210, filed on Jul. 5, 2012, and U.S. Provisional Application 61/782,072, filed on Mar. 14, 2013, the disclosures of which are hereby incorporated by reference in their entirety.

TECHNICAL FIELD OF THE INVENTION

The invention generally relates to methods of treating bone disorders using anti-sclerostin antibodies.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: ASCII (text) file named “40016E_SeqListing.xml,” 1,072,396 bytes, created Jan. 8, 2024.

CROSS-REFERENCE TO RELATED APPLICATIONS AND INCORPORATION BY REFERENCE

This application is a continuation of Ser. No. 13/934,433, filed Jul. 3, 2013, which claims priority to U.S. Provisional Patent Application No. 61/668,210, filed Jul. 5, 2012, and U.S. Provisional Patent Application No. 61/782,072, filed Mar. 14, 2013, the disclosures of which are hereby incorporated by reference in their entirety.

The following applications are hereby incorporated by reference in their entirety: U.S. patent application Ser. No. 11/410,540 (issued as U.S. Pat. No. 8,003,108), filed Apr. 25, 2006, which claims priority to U.S. Provisional Patent Application No. 60/792,645, filed Apr. 17, 2006, U.S. Provisional Patent Application No. 60/782,244, filed Mar. 13, 2006, U.S. Provisional Patent Application No. 60/776,847, filed Feb. 24, 2006, and U.S. Provisional Patent Application No. 60/677,583, filed May 3, 2005; and U.S. patent application Ser. No. 11/411,003 (issued as U.S. Pat. No. 7,592,429), filed Apr. 25, 2006, which claims priority to U.S. Provisional Patent Application No. 60/792,645, filed Apr. 17, 2006, U.S. Provisional Patent Application No. 60/782,244, filed Mar. 13, 2006, U.S. Provisional Patent Application No. 60/776,847, filed Feb. 24, 2006, and U.S. Provisional Patent Application No. 60/677,583, filed May 3, 2005. The following applications also are hereby incorporated by reference: U.S. Provisional Patent Application No. 61/668,210, filed Jul. 5, 2012; U.S. patent application Ser. No. 12/212,327 (issued as U.S. Pat. No. 8,017,120), filed Sep. 17, 2008, which claims priority to U.S. Provisional Patent Application No. 60/973,024, filed Sep. 17, 2007; and U.S. patent application Ser. No 12/811,171, filed Jun. 29, 2010, which is a U.S. National Phase Application pursuant to 35 U.S.C. § 371 of International Patent Application No. PCT/US08/86864, filed on Dec. 15, 2008, which claims priority to U.S. Provisional Patent Application No. 61/013,917, filed Dec. 14, 2007.

BACKGROUND OF THE INVENTION

Loss of bone mineral content can be caused by a wide variety of conditions and may result in significant medical problems. For example, osteoporosis is a debilitating disease in humans and is characterized by marked decreases in skeletal bone mass and mineral density, structural deterioration of bone, including degradation of bone microarchitecture and corresponding increases in bone fragility (i.e., decreases in bone strength), and susceptibility to fracture in afflicted individuals. Osteoporosis in humans is generally preceded by clinical osteopenia (bone mineral density that is greater than one standard deviation but less than 2.5 standard deviations below the mean value for young adult bone), a condition found in approximately 25 million people in the United States. Another 7-8 million patients in the United States have been diagnosed with clinical osteoporosis (defined as bone mineral content greater than 2.5 standard deviations below that of mature young adult bone). The frequency of osteoporosis in the human population increases with age. Among Caucasians, osteoporosis is predominant in women who, in the United States, comprise 80% of the osteoporosis patient pool. The increased fragility and susceptibility to fracture of skeletal bone in the aged is aggravated by the greater risk of accidental falls in this population. Fractured hips, wrists, and vertebrae are among the most common injuries associated with osteoporosis. Hip fractures in particular are extremely uncomfortable and expensive for the patient, and for women, correlate with high rates of mortality and morbidity.

SUMMARY OF THE INVENTION

The summary below is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document. With respect to aspects of the invention described or claimed with “a” or “an,” it should be understood that these terms mean “one or more” unless context unambiguously requires a more restricted meaning. The term “or” should be understood to encompass items in the alternative or together, unless context unambiguously requires otherwise. If aspects of the invention are described as “comprising” a feature, embodiments also are contemplated “consisting of” or “consisting essentially of” the feature. Where the term “about” is used the application also discloses employing the exact value specified.

Antibodies against sclerostin may be used to treat bone disorders, as they both promote bone formation and inhibit bone resorption. After multiple doses of anti-sclerostin antibody are administered, resistance to the antibody may though develop, where the response to the antibody is diminished and is lower than the “naïve” response seen when the anti-sclerostin antibody is administered for the first time to a subject. Such resistance may reduce the efficacy of treatment, particularly for subjects who have chronic conditions that require long term treatment.

Unexpectedly, it has now been shown that the development of such resistance is reversible. In particular, by allowing patients a dosing holiday, where they are not administered the anti-sclerostin antibody, the subject may once again show a higher response to a subsequent dose of the anti-sclerostin antibody. In some cases, multiple cycles of a batch of at least two doses of the anti-sclerostin antibody, followed by a dosing holiday, are performed, so that the subject may be given anti-sclerostin antibody treatment over a prolonged period, whilst minimizing the development of resistance to the antibody.

The method may be, in some instances, combined with monitoring for resistance to the antibody, such as by monitoring the response seen, to help optimize when best to give the patient the dosing holiday. Further, in some instances, the patient may be treated with a different therapy for the bone disorder in the dosing holiday for the anti-sclerostin antibody. In particular, the subject may be administered bisphosphonates during the dosing holiday. That has the further advantage that it means the subject is not treated continuously with the other therapy. For instance, it may be beneficial for subjects to have a break from treatment with another therapeutic, such as bisphosphonates, and cycling between antibody and bisphosphonate treatment also helps avoid continuous treatment with bisphosphonates. In some instances, the different therapy may be an anti-resorptive which is not a bisphosphonate, including any of those discussed herein.

Hence, the present invention provides a method for treating a bone disorder associated with at least one of low bone formation, low bone mineral density, low bone mineral content, low bone mass, low bone quality and low bone strength in a mammalian subject, which method comprises:

(a) administering a batch of at least two doses of anti-sclerostin antibody to a subject in need of such treatment;

(b) then allowing the subject a dosing holiday, which is greater in length than the time interval been two successive doses in the batch of (a); and (c) administering to the subject at least one further dose of anti-sclerostin antibody after the dosing holiday of (b).

The invention further provides a method for treating a bone disorder associated with at least one of low bone formation, low bone mineral density, low bone mineral content, low bone mass, low bone quality and low bone strength in a mammalian subject, which method comprises:

(a) administering at least one dose of anti-sclerostin antibody to the subject and monitoring the subject to identify whether the subject shows a reduced response to a dose of the anti-sclerostin antibody; and (b) if such a reduced response is identified, allowing the subject a dosing holiday which is at least four weeks in length.

The invention also provides a method for treating a bone disorder associated with at least one of low bone formation, low bone mineral density, low bone mineral content, low bone mass, low bone quality and low bone strength in a mammalian subject, which method comprises:

(a) administering a batch of at least two doses of anti-sclerostin antibodies to a subject in need of such treatment and monitoring the subject to identify when the subject shows a reduced response to a dose of the anti-sclerostin antibody;

(b) when such a reduced response is identified, allowing the subject a dosing holiday which is greater in length than the time interval been two successive doses in the batch of (a); and (c) administering to the subject at least one further dose of anti-sclerostin antibody after the dosing holiday of (b).

The invention also provides a method for treating a bone disorder associated with at least one of low bone formation, low bone mineral density, low bone mineral content, low bone mass, low bone quality and low bone strength in a mammalian subject, which method comprises:

(a) administering to a subject in need of such treatment a batch of at least two doses of anti-sclerostin antibody;

(b) then allowing the subject a dosing holiday which is greater in length than the interval been two successive doses in the batch of (a), where during that interval the subject is administered a different treatment for the bone disorder; and (c) after the dosing holiday of (b) administering to the subject at least one further dose of anti-sclerostin antibody.

The invention further provides an anti-sclerostin antibody for use in a method of treating a bone disorder associated with at least one of low bone formation, low bone mineral density, low bone mineral content, low bone mass, low bone quality and low bone strength in a mammalian subject, which method comprises:

(a) administering a batch of at least two doses of anti-sclerostin antibody to a subject in need of such treatment;

(b) then allowing the subject a dosing holiday, which is greater in length than the time interval been two successive doses in the batch of (a); and (c) administering to the subject at least one further dose of anti-sclerostin antibody after the dosing holiday of (b).

Also provided by the invention is an anti-sclerostin antibody for use in a method for treating a bone disorder associated with at least one of low bone formation, low bone mineral density, low bone mineral content, low bone mass, low bone quality and low bone strength in a mammalian subject, which method comprises:

(a) administering at least one dose of anti-sclerostin antibody to a subject in need of such treatment and monitoring the subject to identify whether the subject shows a reduced response to a dose of the anti-sclerostin antibody; and (b) if such a reduced response is identified, allowing the subject a dosing holiday which is at least four weeks in length.

Further provided by the invention is an anti-sclerostin antibody for use in a method of treating a bone disorder associated with at least one of low bone formation, low bone mineral density, low bone mineral content, low bone mass, low bone quality and low bone strength in a mammalian subject, which method comprises:

(a) administering a batch of at least two doses of anti-sclerostin antibody to a subject in need of such treatment and monitoring the subject to identify when the subject shows a reduced response to a dose of the anti-sclerostin antibody;

(b) when such a reduced response is identified, allowing the subject a dosing holiday which is greater in length than the time interval been two successive doses in the batch of (a); and (c) administering to the subject at least one further dose of anti-sclerostin antibody after the dosing holiday of (b).

The invention also provides for the use of an anti-sclerostin antibody in the manufacture of a medicament for use in treating a bone disorder associated with at least one of low bone formation, low bone mineral density, low bone mineral content, low bone mass, low bone quality and low bone strength in a mammalian subject, where the medicament is to be administered in a method comprising:

(a) administering a batch of at least two doses of anti-sclerostin antibody to a subject in need of such treatment;
(b) then allowing the subject a dosing holiday, which is greater in length than the time interval been two successive doses in the batch of (a); and
(c) administering to the subject at least one further dose of anti-sclerostin antibody after the dosing holiday of (b).

Additionally, the invention provides for the use of an anti-sclerostin antibody in the manufacture of a medicament for use in treating a bone disorder associated with at least one of low bone formation, low bone mineral density, low bone mineral content, low bone mass, low bone quality and low bone strength in a mammalian subject, where the medicament is to be administered in a method comprising:

(a) administering at least one dose of anti-sclerostin antibody to a subject in need of such treatment and monitoring the subject to identify whether the subject shows a reduced response to a dose of the anti-sclerostin antibody; and
(b) if such a reduced response is identified, allowing the subject a dosing holiday which is at least four weeks in length.

The invention further provides for the use of an anti-sclerostin antibody in the manufacture of a medicament for use in treating a bone disorder associated with at least one of low bone formation, low bone mineral density, low bone mineral content, low bone mass, low bone quality and low bone strength in a mammalian subject, where the medicament is to be administered in a method comprising:

(a) administering a batch of at least two doses of anti-sclerostin antibody to a subject in need of such treatment and monitoring the subject to identify when the subject shows a reduced response to a dose of the anti-sclerostin antibody;
(b) when such a reduced response is identified, allowing the subject a dosing holiday which is greater in length than the time interval been two successive doses in the batch of (a); and
(c) administering to the subject at least one further dose of anti-sclerostin antibody after the dosing holiday of (b).

The invention also provides for the use of an anti-sclerostin antibody in the manufacture of a medicament for use in treating a bone disorder associated with at least one of low bone formation, low bone mineral density, low bone mineral content, low bone mass, low bone quality and low bone strength in a mammalian subject, where the medicament is to be administered in a method comprising:

(a) administering to a subject in need of such treatment a batch of at least two doses of anti-sclerostin antibody;
(b) then allowing the subject a dosing holiday which is greater in length than the interval been two successive doses in the batch of (a), where during that interval the subject is administered a different treatment for the bone disorder; and
(c) after the dosing holiday of (b) administering to the subject at least one further dose of anti-sclerostin antibody.

BRIEF DESCRIPTION OF THE FIGURES

FIG. 7 is a chart listing amino acid sequences and sequence identifiers for amino acid sequences of various anti-sclerostin antibodies described herein. The sequence identifiers refer to amino acid sequences provided in the Sequence Listing submitted herewith. The amino acid sequences also are set forth in U.S. Patent Publication No. 20070110747, hereby incorporated by reference.

FIG. 8 is a listing of amino acid sequences and nucleotide sequences set forth in International Patent Publication No. WO 2008/115732, referred to herein.

FIG. 9 is a listing of amino acid sequences and nucleotide sequences set forth in International Patent Publication No. WO 2009/047356, referred to herein.

FIG. 10 is a listing of amino acid sequences and nucleotide sequences set forth in International Patent Publication No. WO 2010/130830, referred to herein.

DETAILED DESCRIPTION OF THE INVENTION

Figure 1:
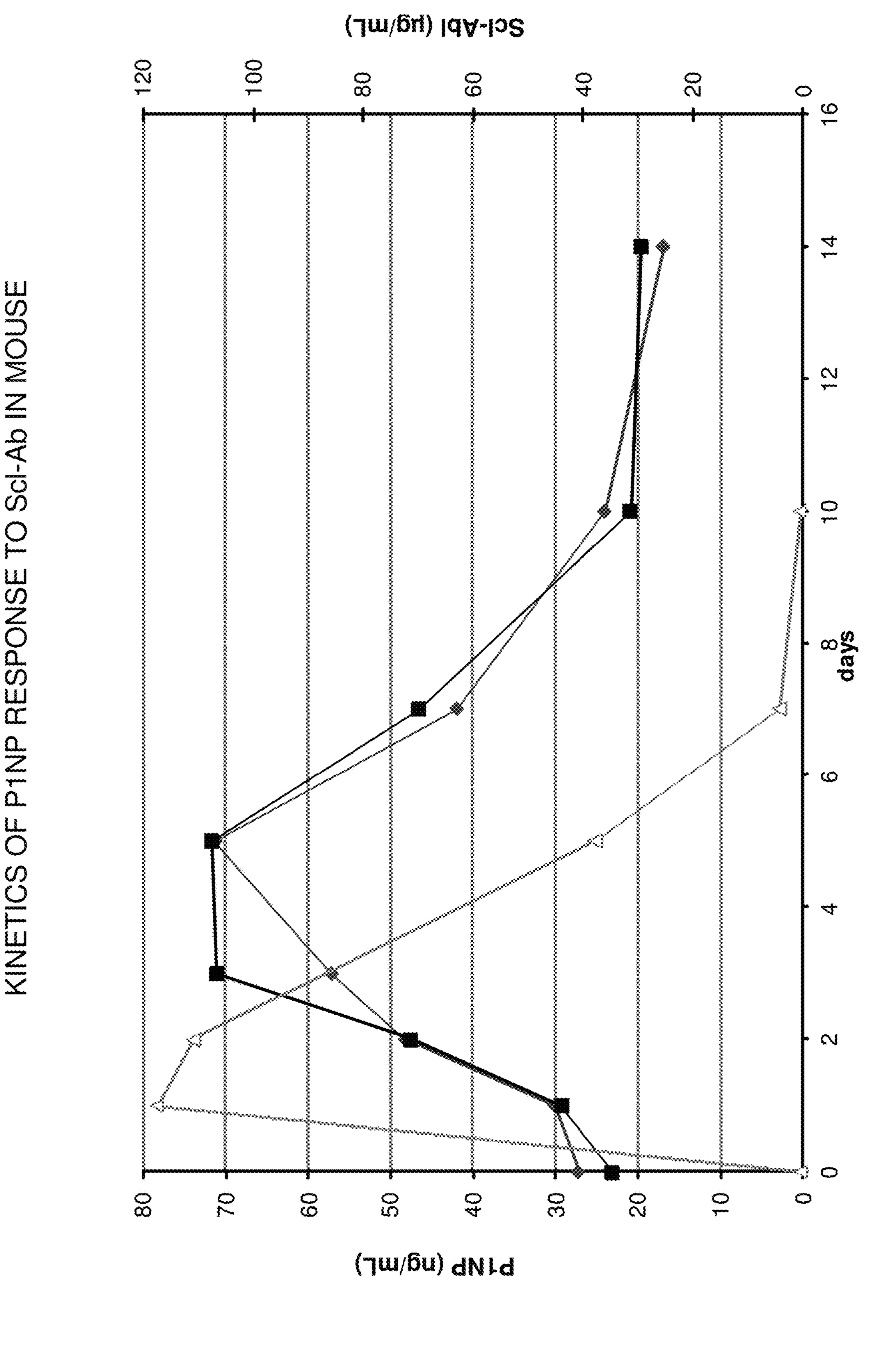
FIG. 1 shows the results of a preliminary experiment to measure the kinetics of P1NP response after subcutaneous administration of anti-sclerostin antibody to help gauge when best to measure P1NP levels in the subsequent experiments. Circulating P1NP levels for two mice dosed subcutaneously with 10 mg/kg on day 0 are shown (square and diamond symbols) along with the level of anti-sclerostin antibody in a similarly dosed mouse (triangular symbols).

Unexpectedly, it has been shown that it is possible to reverse, or reduce, the resistance which develops when multiple doses of anti-sclerostin antibody are administered by allowing the subject a dosing holiday where they are not administered the antibody. After the dosing holiday, the subject typically shows an increased response to the anti-sclerostin antibody in comparison to a response prior to the dosing holiday.

Dosing

Prior to being given a dosing holiday, the subject will have been administered at least one dose of anti-sclerostin antibody. Typically, the subject will have been given a plurality of doses prior to the holiday. For instance, the subject may have been given a batch of at least two doses of the anti-sclerostin antibody prior to the dosing holiday. Preferably, the subject may have been administered three, four, five, or at least those numbers of doses of antibody before being given a dosing holiday. The administration of such a batch of doses may form part of the invention.

In some cases, the subject may be given a batch of two, three, four, five, six, seven, eight, nine or more doses prior to the dosing holiday, or at least that number of doses. In some instances, the subject may have been given a batch of ten, eleven, twelve, thirteen, fourteen, fifteen, sixteen or more doses of the antibody. In some instances the subject may have been given a batch of ten or less, nine or less, eight or less, seven or less, six or less or five or less doses, where the number of doses given is at least two, preferably at least three and more preferably at least four doses. It may be that the subject is given a batch of from two to sixteen doses, such as from two to fourteen doses or from two to twelve doses. In some instances, the subject may have been given a batch of from two to seven, from two to six, from two to five, or from two to four doses prior to the holiday. In other instances, the number of doses may be from three to eight, seven, six, five or four doses. In other instances, the number of doses in the batch may be from four to eight, seven, six, or five doses. In some instances, the subject may have been given twelve doses of the antibody. In one instance, the subject will have been administered, or is administered, a batch of doses, where the overall time period for the batch is at least two, three, four, five, six, seven, eight, nine, ten, eleven or twelve months or, for example, at least about 4, 8, 12, 16, 20 or 24 weeks in length. In one instance, the overall duration of a batch of doses may be about six months, twelve months (i.e., one year) or eighteen months.

In some instances, the interval between individual doses in a batch may be about two weeks. In other cases, the interval may be longer. For instance, the interval may be about a month, 2 months, 3 months, 4 months, 5 months, 6 months or longer. In some cases, the interval between doses in a batch may be about every two, three, four, five, six, seven, or eight weeks. In some cases, the interval between doses in a batch may be about from one week to six months, from two weeks to four months, from three weeks to six weeks, or from four to five weeks. In one preferred instance, the interval between doses may be about a month or may be about four weeks. In other instances, the interval may be about 7 days, a week, 2 weeks, 3 weeks, four weeks, 1 month, 5 weeks, 6 weeks, 7 weeks, 2 months, 8 weeks, 9 weeks, 10 weeks, 11 weeks, 12 weeks or 3 months. In some instances, the interval between doses in a batch may be about a day, two days, three days, four days, five days, six days, seven days or longer. In some instances, the doses may be given once, twice, three, four, five, six or seven times a week.

In some instances, the doses in a batch may be administered every week, two weeks, four weeks, six weeks or eight weeks, or about such intervals. The intervals between doses in a batch may be, for instance, monthly, two monthly or three monthly, or about those intervals. In some cases individual doses of antibody may be given more than once a week, such as two, three or four times a week. For instance, doses may be administered in some cases every two, three, four, five, six, seven or eight days to the subject.

In some instances, the invention may entail administering any of the above specified batches of dosages, for instance as part of the method of the invention. In some instances, the subject may have been known to have been administered such a number of doses, but the administration of the batch of the doses does not form part of the method, rather the subject is simply given a dosing holiday prior to being administered a further batch of doses.

In some cases the number of doses given to the subject is such that a drop of the response of the subject to the antibody is seen for at least one of the doses given in a batch, for instance for the last dose prior to the holiday being initiated. The dosing holiday may begin when the subject first shows a reduction in the response to the antibody. In some instances, the dosing holiday may begin after one, two or three doses showing a reduced effect. For instance, in some cases the dosing holiday may be started where a subsequent dose shows a reduced effect in comparison to the response seen with the first dose of the antibody given to the subject. In some cases, it may be that the average response seen for at least two doses is reduced in comparison to that seen for two earlier doses, particularly the first two doses.

In some instances, the subject may be actively monitored to determine the best time for the dosing holiday, in other cases the subject is not monitored for resistance. In some cases, the dosing holiday may be initiated when the response seen for a dose of antibody falls below 90%, 80%, 70%, 60%, 50%, 40%, 30% or less than the response seen with an earlier dose, such as for the first dose. In some instances, the dosing holiday may be initiated when the response to a dose is below such a percentage in comparison to what would be expected for a naive subject with the same disorder, such as an age and gender matched subject. In some instances, the drop in response may be at least 5%, 15%, 20%, 25%, 30%, 40%, 50% or more. In some course the parameter used to gauge how much the response is reduced is any of those mentioned herein. In one preferred instance, the response may be that defined by reference to P1NP levels, though any of the markers discussed herein may be employed.

In some instances, the response may be that gauged using change in bone mineral density (BMD). The rate, or amount, of bone formation, the rate, or amount, of bone resorption, or any combination thereof may also be used as a parameter to define the response to the antibody. It may be that the anti-sclerostin antibody still brings about an increase in BMD, but the increase is less than that for a naïve subject. Hence, a reduced response may be one with a smaller increase than would be expected for a naïve subject, including for any of the markers discussed herein.

Dosing Holidays

Typically a dosing holiday is a time period where no anti-sclerostin antibody is administered to a subject. Such a dosing holiday may help reduce, reverse or prevent the reduced response to an anti-sclerostin antibody seen in subjects given a plurality of doses of the antibody and hence help improve the efficiency of treatment of bone disorders with anti-sclerostin antibodies. Typically, the dosing holiday will result in reversal or reduction of the reduced response displayed by the subject to the anti-sclerostin antibody. Hence, the subject may display a higher response to the antibody than prior to the dosing holiday. The subject may, for instance, display a response to the anti-sclerostin antibody which is closer to the "naïve" response to the antibody when the subject was first administered the anti-sclerostin antibody. For at least about 50%, 60%, 70%, 80%, 90%, 95%, or 99% of the naïve response or even about 100% of the naïve response. In a preferred instance, the dosing holiday will result in a higher response to the anti-sclerostin antibody as measured by a bone marker, such as a marker of bone resorption and/or formation, including any of those mentioned herein, particularly P1NP.

Typically, the administration of a batch of doses, followed by a dosing holiday and then administration of at least one dose of antibody, means that the dosing regimen followed is one of irregular dosing. Hence, the treatment may be characterized by irregular dosing, such as over the treatment period as a whole. The length of a dosing holiday may vary. A dosing holiday will be typically longer in length than the interval between individual doses in a batch, for instance the interval between doses in a batch of doses known to have been administered to the subject or administered to the subject as part of the invention. In some instances, the dosing holiday may be any of the above specified lengths as long as the interval between doses in the preceding batch is shorter. In some instances, the dosing holiday may be any of at least 4, 5, 6, 7, 8, 19, 10, 11 or 12 weeks or about such duration. It may be the dosing holiday is at least 14, 16, 18, 20, 22, 24, 26, 28, 30, 35, 40, 45 or 50 weeks in length or may be of about such duration. In some instances, the dosing holiday may be from about four weeks to 52 weeks, for example from six weeks to 24 weeks, in some cases from eight weeks to 12 weeks. In some instances of the invention, the dosing holiday may be about two months, three months, four months, five months, six months, seven months, eight months, nine months, ten months, eleven months or twelve months or at least those time periods. In some cases the dosing holiday may be about, or at least, eighteen months in length. For instance, the dosing holiday may be about four weeks, six weeks, eight weeks, ten weeks, or twelve weeks longer than the interval between doses in a batch of doses. In some instances, the dosing holiday may be equivalent to the total duration of a batch of doses, such as any of those specified herein, or in other instances it may be equivalent to the overall duration of a batch of doses, plus an additional two, four, six, eight, twelve or more weeks in length.

It may be that the dosing holiday is at least two, three, four, five, six, seven, eight, nine or ten weeks longer than the interval between two doses in the preceding batch, or the dosing interval may be of such length. In some cases the dosing holiday may be such a length longer than the average interval for three, four, five, six, seven or more doses in a batch or, for example, than the average interval between all of the doses in a batch. The total length of the dosing holiday may be, for example, four, five, six, seven, eight, nine, ten or more weeks. For instance, the dosing holiday may be one, two, three, four, five or six months in length and in some cases may be at least a year, or eighteen months in length. In some cases, the dosing holiday may be from a month to a year, such as from two to six months in length. In some cases, the dosing holiday may be from four to sixteen weeks, for instance, from six to twelve weeks, for example from eight to ten weeks in length. In other instances, the dosing holiday may be about from six to eighteen months, for instance about a year. In some cases the dosing holiday may be about twice, three times, four times, five times, six times, seven times, eight times, nine times or more in duration than the interval between doses in a batch administered to the subject. In some instances, where a different treatment is administered during the dosing holiday, the duration of the dosing holiday may be the normal duration for a course of a different treatment for the disorder to be administered in the dosing holiday.

In some cases, the subject is given more than one dosing holiday. In particular, after the first dosing holiday, the subject is given at least two doses of the antibody and may, for instance, benefit from a further dosing holiday. In some cases, it may be that the subject is given two, three, four, five, six, seven, or more dosing holidays in the course of their treatment. The administration of at least two doses of the antibody, followed by a dosing holiday, may be referred to as a cycle and in some instances, one, two, three, four, five, six, seven, eight, nine, ten or more such cycles may be used. In other instances, the overall total treatment period may be at least six months, nine months, a year, eighteen months, twenty-four months, or more. It may be that the overall treatment is at least 4, 8, 12, 16, 20, 24, 28, 32, 36, 40, 44, 48 or 52 weeks, or longer, or about such periods. In some instances, where the subject is being treated indefinitely with the antibody, it may be that the approach of batches of doses combined with dosing holidays is continued as long as the treatment lasts. In some instances, it may simply be that a set regimen of batch doses alternating with dosing holidays is administered. For instance, any combination of those batches and dosing holidays specified herein, for example for two, three, four, five, six or more cycles of a batch of doses followed by a dosing holiday may be administered.

In some instances, any of the batches of doses specified herein may be combined with any of the dosing holidays specified herein, as long as the dosing holiday is longer than the interval between doses in a batch. For instance, a batch of doses administered at daily, weekly, fortnightly, four weekly, six weekly or eight weekly intervals may be combined with a dosing holiday of at least six weeks, at least eight weeks, at least twelve weeks, at least 16 weeks, at least 20 weeks or at least 24 weeks, where the dosing holiday is longer than the interval between batches. In some instances, the doses in the batch may be given at about monthly or two monthly intervals and may be combined with a dosing holiday of at least three, four, five, six, eight, ten, twelve or more months in length. In some cases, the batch of doses may comprise three to fourteen doses at daily, weekly, fortnightly, four weekly or six weekly intervals, combined with a dosing holiday of at least six, eight, ten, twelve, fourteen or more weeks in length, where the dosing holiday is longer than the interval between the doses in the batch. In one instance, a batch of monthly doses is combined with a dosing holiday of at least two, three, four, five, six, twelve or more months in length. In some instances, it may be that the doses in the batch are given about every four weeks.

In some cases, the interval between earlier doses will not be known and the subject will simply be one who is displaying a reduced response to the anti-sclerostin antibody in comparison to what would be expected for the subject. Hence, it may be that the length of the dosing holiday given is simply one of the above time periods without reference to the time between administration of earlier doses or the response to earlier doses. For example, the dosing holiday may be six weeks, eight weeks, twelve weeks, sixteen weeks, twenty weeks, twenty four weeks or more in length or any of the other possible lengths referred to. In some cases the subject may have been identified as one showing resistance to anti-sclerostin antibody, for example, even though the precise regimen previously administered is not known. It may be that they have been administered the antibody for at least about two, three, four, five, six or more months in length and hence be identified as a candidate for a dosing holiday. In some cases they may have been administered the antibody for at least about nine, twelve or eighteen months in length and hence be identified as a candidate for a dosing holiday. The subject may be displaying reduced or diminishing therapy from the existing therapy.

A fixed regimen of batch dosing and dosing holiday may be applied in some instances including any of those specified herein. It may be the fix regimen is designed with reference to age, gender, weight, the nature of the disorder, the severity of the disorder and so on.

Responses and Monitoring

In one instance, the response is the response as defined by a bone marker, for instance a bone formation and/or bone resorption marker, particularly any of those referred to herein. For instance, whether or not a response can be considered reduced may be, in some instances, defined by whether the response of the bone marker to administration of the anti-sclerostin antibody is reduced. Similarly, whether a dosing holiday may be said to prevent, or reverse, resistance to an anti-sclerostin antibody may be defined by the response of a bone marker and, for instance, the level of that marker. In a preferred instance, the response to the antibody is defined by P1NP level, particularly serum P1NP level.

In one instance, the response of the subject to a dose of anti-sclerostin antibody is measured to help gauge whether the subject is displaying resistance to the anti-sclerostin antibody. Any suitable means of measuring the response to the anti-sclerostin antibody may be employed. For instance, the level of a bone marker may be measured, in particular a marker of bone formation and/or mineralization may be measured in the subject. Markers of bone resorption may also be employed. In other instances, the invention itself does not entail measurement, or monitoring, of the response, but the response in question is that defined by a bone marker, such as, the level of any of the bone markers referred to herein.

Markers indicative of bone resorption (or osteoclast activity) which may be used include, for example, C-telopeptide (e.g., C-terminal telopeptide of type 1 collagen (CTX) or serum cross-linked C-telopeptide), N-telopeptide (N-terminal telopeptide of type 1 collagen (NTX)), deoxypyridinoline (DPD), pyridinoline, urinary hydroxyproline, galactosyl hydroxylysine, and tartrate-resistant acid phosphatase (e.g., serum tartrate-resistant acid phosphatase isoform 5b). Bone formation/mineralization markers which may be used include, but are not limited to, bone-specific alkaline phosphatase (BSAP), peptides released from N- and C-terminal extension of type I procollagen (P1NP, PICP), and osteocalcin (OstCa). Several kits are commercially-available to detect and quantify markers in clinical samples, such as urine and blood. In one preferred instance, the marker used is selected from the serum level of C-telopeptide of type I collagen (CTX), bone-specific alkaline phosphatase (BSAP), osteocalcin (OstCa), and/or N-terminal extension of procollagen type 1 (P1NP). In a preferred instance, the response is the response to such a marker.

Other approaches for measuring the effect of the anti-sclerostin antibody include assessing bone mineral content and/or bone density. In some instances, the response in question may be defined by reference to bone mineral density (BMD) or bone mineral content (BMC). In some cases, it may be that the reduced response is a reduced rate of increase of BMD and/or BMC following administration of the antibody. In other words, administration of the antibody still results in an increase in bone formation and/or a reduction of bone absorption, for example in terms of BMD/BMC, but at a reduced rate compared to a naïve subject. The use of a dosing holiday may mean the subject again displays the same size of increase in such parameters as a naïve subject, or at least closer to a naïve subject.

Bone mineral density may be, for instance, measured using techniques, such as, single- and dual-energy X-ray absorptometry, ultrasound, computed tomography, radiography, and magnetic resonance imaging. The amount of bone mass may also be calculated from body weights or by using other methods (see Guinness-Hey, *Metab. Bone Dis. Relat. Res.,* 5:177-181 (1984)). In humans, bone mineral density may be, for instance, determined clinically using dual x-ray absorptiometry (DXA) of, for example, the hip and spine. Other techniques include quantitative computed tomography (QCT), ultrasonography, single-energy x-ray absorptiometry (SXA), and radiographic absorptiometry. Common central skeletal sites for measurement include the spine and hip; peripheral sites include the forearm, finger, wrist and heel. Except for ultrasonography, the American Medical Association notes that BMD techniques typically involve the use of x-rays and are based on the principle that attenuation of the radiation depends on thickness and composition of the tissues in the radiation path. All techniques may employ the comparison of results to a normative database or control subject.

In some instances, the bone mineral density (BMD) of the subject is compared to the peak density of a 30-year old healthy adult (i.e., a "young adult"), creating the so-called "T-score." A patient's BMD also may be compared to an "age-matched" bone density (see, e.g., World Health Organization Scientific Group on the Prevention and Management of Osteoporosis, "Prevention and management of osteoporosis: report of a WHO scientific group." WHO Technical Report Series; 921, Geneva, Switzerland (2000)). The difference between a patient's BMD and that of a healthy, young adult is conventionally referred to in terms of the multiple of a "standard deviation," which typically equals about 10% to about 12% decrease in bone density. The World Health Organization proposed four diagnostic categories based on BMD T-scores. A BMD value within 1 standard deviation of the young adult reference mean (T-score>−1) is "normal." Low bone mass (osteopenia) is indicated by a BMD value more than 1 standard deviation below the young adult mean, but less than 2.5 standard deviations (T-score<−1 and >−2.5). A T-score of more than 2.5 standard deviations below the norm supports a diagnosis of osteoporosis. If a patient additionally suffers from one or more fragility fractures, the patient qualifies as having severe osteoporosis. Hence, the invention may entail calculating the T-score for the subject, for instance, in response to a dose of anti-sclerostin antibody and determining whether there is a reduced improvement in the T-score following administration of a dose of the anti-sclerostin antibody.

In some instances, the decision as to when to initiate the dosing holiday may therefore be based on assessing the response of the subject to a dose of the anti-sclerostin antibody and determining whether the response is lower than expected. The dosing holiday may be, for instance, initiated when monitoring shows a reduced response to a dose, or two consecutive doses, particularly in comparison to earlier doses, such as the first dose, or in comparison to the average response seen for the doses in the batch. The dosing holiday may be, for instance, begun, when the positive results seen with the treatment plateau or begin to tail-off for the batch of doses administered. It may be that the dosing holiday is administered when administration of the antibody results in a smaller increase of the particular parameter or marker than would be expected. For instance, when the response is less than 90%, 80%, 70%, 60%, 50%, 40%, 30%, 25% or less than that which would be expected from the equivalent naïve subject or displayed to an earlier dose by the same subject.

In some instances of the invention the subject may be administered a test dose of anti-sclerostin to gauge their response to the antibody. In particular, where the subject is known to have been administered at least two, three, four, five, or six doses of anti-sclerostin antibody previously or indeed any of the types of batch of doses specified herein. The test dose may be given, the response measured, and, if considered reduced, the subject will be given a dosing holiday. If the subject does not display a reduced response, they may be given further doses of anti-sclerostin antibody. In some cases, rather than a single test dose, the subject is administered at least two, three, four, five, or six doses and their response measured.

It may be, for instance, that a subject is monitored continuously, for example after each dose of anti-sclerostin antibody. It may be that the subject is monitored, for instance, about once a month, once about every two months, once about every three months, once about every four months, once about every six months or about once a year. It may be that the subject is monitored immediately before a dose is administered and then, for example, about one, two, three, four, five or six weeks later. It may be, for example, that the response seen for at least one, two, three, four, five or more doses is monitored. In some cases, the dosing holiday may be initiated when the monitoring shows the response is below an expected level for the subject or below a set cut-off value.

For instance, the dosing holiday may be initiated when the response for a dose is less than the response seen for an earlier dose, such as that for the first dose, or for the first dose in a batch of doses. The size of the response as a percentage of the response to an earlier dose may be determined, particularly the first dose, and it may be that when the percentage value falls to, or below, one of the percentage values specified herein the dosing holiday is begun.

In some cases, the response to a dose may be measured without any reference to earlier doses and simply the fact it falls below an expected value means a dosing holiday is initiated. Hence, in one instance, the method of the invention may comprise: (a) administering a dose of anti-sclerostin antibody to a subject who has previously been administered anti-sclerostin antibody; (b) measuring the response to the dose; and (c) assessing whether the dose is lower than that expected. If the response is lower than that expected, for instance below a threshold, then a dosing holiday may be given. If the response to the test dose is not though reduced, then the method may optionally comprise administering at least one further dose of the anti-sclerostin antibody to the subject and measuring until a reduced response is seen, then giving a dosing holiday. In some instances, it may be that the subject has already been administered at least three, four, five or six doses before the test dose.

A dosing holiday may include the administration of one or more test doses of anti-sclerostin antibody, where the test dose is used to determine if the resistance displayed to the antibody has diminished or been eliminated. In particular, where the test dose is used to determine whether to terminate the dosing holiday and again begin treatment with the anti-sclerostin antibody or continue the dosing holiday. Hence, in some cases, it may be that the subject may be given a dosing holiday and the end of the dosing holiday may be defined by when the subject displays an increased response to a test dose of anti-sclerostin antibody or, for instance, the subject displays resistance below a defined threshold, such as any of those mentioned herein.

In one case, the subject may be given a set pattern of a batch of at least two doses, followed by a set dosing holiday, without monitoring to determine when to initiate the dosing holiday. Such fixed batches of doses and dosing holidays may be, for example, based on the disorder to be treated, age, gender and weight of the subject. In other instances, it may be that a suitable cycle of a batch of doses and dosing holiday is determined on a particular cycle by monitoring and then adhered to on subsequent cycles to the same regimen.

In a preferred instance, where a test dose is given, what will be monitored, or how the response is defined, will be reference to a bone formation and/or resorption marker, including any of those referred to herein, particularly P1NP levels. It may be that the level of the marker is measured before administration of the dose, then, for instance, four, five, six, seven, eight, ten, eleven or twelve days after administration of the test dose.

In some cases, rather than determining the response to an individual dose, it may be that any of the parameters referred to herein are measured during a course of treatment to determine if they are less than expected or show a slower, or less marked, increase in the marker. It may be that the subject is assessed clinically to determine whether the effect of the treatment is less and so that a dosing holiday may be of benefit. It may be that the subject has regular checks, such as about monthly, three monthly, four monthly, six monthly or yearly intervals and such checks entail checking or measuring the effect of the anti-sclerostin antibody and/or dosing holiday, for instance to decide whether to commence a dosing holiday.

In some cases the invention may be administered to a patient group thought to be displaying resistance to anti-sclerostin antibodies, or thought likely to display such resistance to the antibody. In some cases, the invention may be applied to a patient group displaying a higher than average resistance to anti-sclerostin antibodies. It may be that such a patient population is identified using monitoring, such any of the monitoring means discussed herein, particularly any of the markers discussed herein. Identification of such patients may entail administration of a test dose as described herein, followed by measurement of the response and assessment of whether the response seen is less than expected. It may be though that the patients are identified due to the fact that they have been receiving anti-sclerostin antibodies and the improvement initially seen has diminished. It may be that whilst the subject still shows an improvement in bone mineral density, that the improvement is less than first seen or would be expected for a naïve subject. Hence, whilst administration of anti-sclerostin antibody may still promote bone formation and/or inhibit resorption, the effect may be less pronounced. In one instance, the invention may be applied to a subject who has been administered anti-sclerostin antibodies, but the treatment has been discontinued, particularly where the treatment has been discontinued because the subject is displaying a reduced response to the anti-sclerostin antibodies.

Any of the methods of the invention, and other aspects, may comprise first assessing whether a subject is one displaying resistance to anti-sclerostin antibodies and then applying the invention if the subject does display such resistance. Hence, if such resistance is displayed, the invention may then entail allowing the subject a dosing holiday to reverse or reduce that resistance.

Some markers may display diurnal variation, i.e., display variation in their level during the day. Hence, a marker may be measured at a specific time, or time period, in the day. In some instances, where a particular marker is measured more than once, it may be that the marker is measured each time at, or approximately at, the same time in the day, or in about a one hour, two hour, or three hour window. For instance, the marker may be consistently measured in the morning or consistently in the afternoon. In one case, any of the markers measured herein may be measured in such a manner, particularly including those known to show diurnal variation. In some instances, P1NP levels may be measured in such a manner. In some cases, where a marker is measured and compared to a standard, or expected value, the value is measured at a time in the day, or time period, consistent with the standard or expected value.

Doses

The amount of anti-sclerostin antibody administered as an individual dose to the subject may, for instance, comprise at least about 70 mg of the anti-sclerostin antibody. For example, in various aspects, the amount of anti-sclerostin antibody administered is at least about 120 mg (e.g., 180 mg) or at least about 140 mg, e.g., at least about 210 mg anti-sclerostin antibody. The amount of anti-sclerostin antibody administered may be, for instance, no more than about 350 mg anti-sclerostin antibody, e.g., no more than about 280 mg anti-sclerostin antibody (e.g., 270 mg), no more than about 210 mg of anti-sclerostin antibody, no more than about 140 mg anti-sclerostin antibody, or no more than about 120 mg anti-sclerostin antibody (e.g., about 120 mg of antibody). Put another way, a single administration or dose of anti-sclerostin comprises, for example, no more than about 350 mg of the antibody.

In some instances, the subject is administered a dose of anti-sclerostin antibody in an amount of about 70 mg to about 350 mg, such as about 70 mg to about 280 mg, or about 120 mg to about 350 mg, or about 140 mg to about 350 mg, or about 210 mg to about 350 mg, or about 280 mg to about 350 mg. Optionally, a single dose of anti-sclerostin antibody comprises about 70 mg to about 210 mg of anti-sclerostin antibody, such as about 70 mg to about 120 mg (e.g., about 70 mg) anti-sclerostin antibody, or about 70 mg to about 140 mg of anti-sclerostin antibody, or about 120 mg to about 210 mg anti-sclerostin antibody, or about 120 mg to about 140 mg of anti-sclerostin antibody. Optionally, a single dose of anti-sclerostin antibody comprises about 140 mg to about 210 mg (e.g., about 140 mg or about 210 mg) of anti-sclerostin antibody.

In some instances, the dose administered is between about 0.1 to about 20 mg/kg, or about 0.1 to about 12 mg/kg, or about 0.5 to about 12 mg/kg, or about 1 to about 10 mg/kg, or about 1 to about 8 mg/kg, or about 2 to about 8 mg/kg, or about 3 to about 8 mg/kg. In some instances, a dose is about 1 mg/kg to about 10 mg/kg (e.g., about 2 mg/kg or about 9 mg/kg), about 1 mg/kg to about 3 mg/kg, or about 3 mg/kg to about 8 mg/kg (e.g., about 4 mg/kg, 5 mg/kg, 6 mg/kg, or 7 mg/kg). In the case of individuals with significantly lower or higher weight than average, it may some times be that the dose is calculated based on a per weight basis specifically for that subject.

In some instances, particularly where the interval between doses is short, it may be that a low dose is employed. For instance, a lower dose may be employed where an interval between doses of less than two weeks, such as less than one week, in particular any of the time periods specified herein shorter than a week, is employed. For example, in some cases, the dose may be any of the above specified doses of 2 mg/kg or under. In some cases, the dose may be about, or under, 1 mg/kg, 0.75 mg/kg, 0.5 mg/kg, 0.25 mg/kg or 0.1 mg/kg. In some instances, a fixed dose is administered, such as any of about 1 to about 50 mg, about 1 to about 25 mg, about 1 to about 10 mg, about 1 to about 5 mg or about 1 to about 3 mg. For example, a fixed dose of from about 2 to about 5 mg, about 2 to about 7 mg or about 3 to about 8 mg may be employed.

Reference herein to a single dose may include multiple contemporaneous injections be administered to achieve delivery of the dose. For instance, several injections within the space of an hour, day or week.

Typically, the subject will be administered a plurality of doses of anti-sclerostin antibody and in particular a batch of doses. In some instances, all of the doses within a batch will be approximately the same amount, or actually the same amount. In some instances, the doses administered in the different batches will be the same. In others, the dose may vary between different batches. For instance, it may be that the dose is varied according to how the patient is responding to the treatment.

Anti-Sclerostin Antibodies

Any suitable anti-sclerostin antibody may be employed in the present invention. The term "antibody" refers to an intact antibody, or a binding fragment thereof. An antibody may comprise a complete antibody (immunoglobulin) molecule (including polyclonal, monoclonal, chimeric, humanized, and/or human versions having full length heavy and/or light chains), or comprise an antigen binding fragment thereof. Antibody fragments include $F(ab')_2$, Fab, Fab', Fv, Fc, and Fd fragments, and can be incorporated into single domain antibodies (e.g., nanobodies), single-chain antibodies, maxibodies, minibodies, intrabodies, diabodies, triabodies, tetrabodies, v-NAR and bis-scFv (sec, e.g., Hollinger and Hudson, *Nature Biotechnology,* 23(9):1126-1136 (2005)). Antibody polypeptides, including fibronectin polypeptide monobodies, also are disclosed in U.S. Pat. No. 6,703,199. Other antibody polypeptides are disclosed in U.S. Patent Publication No. 20050238646. U.S. Pat. Nos. 6,395,511 and 6,803,453, and U.S. Patent Publication Nos. 20040009535 and 20050106683 (incorporated in their entirety by reference for their disclosure of anti-sclerostin antibodies) refer to anti-sclerostin antibodies generally. The amino acid sequence of human sclerostin is set forth in SEQ ID NO: 1 of the Sequence Listing and is provided as SEQ ID NO: 1 of U.S. Patent Publication No. 20070110747 (which patent publication is incorporated in its entirety for its description of sclerostin and sclerostin binding agents and Sequence Listing). Sclerostin also is described in Brunkow et al., *Am. J. Hum. Genet.,* 68:577-589 (2001); and Balemans et al., *Hum. Mol. Genet.,* 10:537-543 (2001). Additional information regarding materials and methods for generating anti-sclerostin antibodies can be found in U.S. Patent Publication No. 20040158045 (hereby incorporated by reference in its entirety).

An antibody fragment may be any synthetic or genetically engineered protein. For example, antibody fragments include isolated fragments consisting of the light chain variable region, "Fv" fragments consisting of the variable regions of the heavy and light chains, and recombinant single chain polypeptide molecules in which light and heavy variable regions are connected by a peptide linker (scFv proteins).

The antibody may be any class of antibody, but in a preferred instance the antibody is an IgG antibody.

Another form of an antibody fragment is a peptide comprising one or more complementarity determining regions (CDRs) of an antibody. CDRs (also termed "minimal recognition units" or "hypervariable region") can be obtained by constructing polynucleotides that encode the CDR of interest. Such polynucleotides are prepared, for example, by using the polymerase chain reaction to synthesize the variable region using mRNA of antibody-producing cells as a template (see, for example, Larrick et al., *Methods: A Companion to Methods in Enzymology,* 2:106 (1991); Courtenay-Luck, "Genetic Manipulation of Monoclonal Antibodies," in *Monoclonal Antibodies Production, Engineering and Clinical Application*, Ritter et al. (eds.), page 166, Cambridge University Press (1995); and Ward et al., "Genetic Manipulation and Expression of Antibodies," in *Monoclonal Antibodies: Principles and Applications*, Birch et al., (eds.), page 137, Wiley-Liss, Inc. (1995)).

Anti-sclerostin antibodies may, for instance, bind to sclerostin of SEQ ID NO: 1, or a naturally occurring variant thereof, with an affinity (Kd) of less than or equal to $1\times10^{-7}$ M, less than or equal to $1\times10^{-8}$ M, less than or equal to $1\times10^{-9}$M, less than or equal to $1\times10^{-10}$ M, less than or equal to $1\times10^{-11}$ M, or less than or equal to $1\times10^{-12}$ M. Affinity is determined using a variety of techniques, an example of which is an affinity ELISA assay. In various embodiments, affinity is determined by a BIAcore assay (a surface plasmon resonance assay). In various embodiments, affinity is determined by a kinetic method. In various embodiments, affinity is determined by an equilibrium/solution method. U.S. Patent Publication No. 20070110747 contains additional description of affinity assays suitable for determining the affinity (Kd) of an antibody for sclerostin.

Anti-sclerostin antibodies for use in the inventive method preferably modulate sclerostin function in the cell-based assay described in U.S. Patent Publication No. 20070110747 and/or the in vivo assay described in U.S. Patent Publication No. 20070110747 and/or bind to one or more of the epitopes described in U.S. Patent Publication No. 20070110747 and/or cross-block the binding of one of the antibodies described in U.S. Patent Publication No. 20070110747 and/or are cross-blocked from binding sclerostin by one of the antibodies described in U.S. Patent Publication No. 20070110747 (incorporated by reference in its entirety and for its description of assays for characterizing an anti-sclerostin antibody).

In various embodiments, the anti-sclerostin antibody binds to a sclerostin polypeptide comprising the amino acid sequence set forth in SEQ ID NO: 1 of the Sequence Listing and binds the sequence of SEQ ID NO: 6 (C4GPARLLPNAIGRGKWWRPSGPDFRC5; corresponding to amino acids 86-111 of SEQ ID NO: 1). Alternatively, or in addition, the anti-sclerostin antibody binds to a sclerostin polypeptide comprising the amino acid sequence set forth in SEQ ID NO: 1 and binds the sequence of at least one of SEQ ID NO: 2 (DVSEYSC1RELHFTR; corresponding to amino acids 51-64 of SEQ ID NO: 1), SEQ ID NO: 3 (SAKPVTELVC3SGQC4GPAR; corresponding to amino acids 73-90 of SEQ ID NO: 1), SEQ ID NO: 4 (WWRPSGPDFRC5IPDRYR; corresponding to amino acids 101-117 of SEQ ID NO: 1), SEQ ID NO: 5 (LVASC7KC8KRLTR; corresponding to amino acids 138-149 of SEQ ID NO: 1), SEQ ID NO: 70 (SAKPVTELVC3SGQC4; corresponding to amino acids 73-86 of SEQ ID NO: 1), SEQ ID NO: 71 (LVASC7KC8; corresponding to amino acids 138-144 of SEQ ID NO: 1), SEQ ID NO: 72 (C1RELHFTR; corresponding to amino acids 57-64 of SEQ ID NO: 1), or SEQ ID NO: 73 (C5IPDRYR; corresponding to amino acids 111-117 of SEQ ID NO: 1) within SEQ ID NO: 1. For example, in one aspect, the anti-sclerostin antibody binds a subregion of sclerostin of SEQ ID NO: 1 comprising SEQ ID NOs: 2-5 (and/or SEQ ID NOs: 70-73), optionally in its native three-dimensional conformation. Optionally, the anti-sclerostin antibody binds a peptide consisting of one or more of SEQ ID NO: 2, SEQ ID NO: 3, SEQ ID NO: 4, SEQ ID NO: 5, SEQ ID NO: 6, SEQ ID NO: 70, SEQ ID NO: 71, SEQ ID NO: 72, or SEQ ID NO: 73 of the Sequence Listing (e.g., a peptide consisting of SEQ ID NO: 2, SEQ ID NO: 3, SEQ ID NO: 4, and SEQ ID NO: 5 or a peptide consisting of SEQ ID NO: 70, SEQ ID NO: 71, SEQ ID NO: 72, and SEQ ID NO: 73).

In various aspects, the anti-sclerostin antibody is capable of neutralizing human sclerostin in a MC3T3 cell-based mineralization assay when there is less than a 6-fold excess of moles of sclerostin binding sites per well as compared to the number of moles of sclerostin per well. Mineralization by osteoblast-lineage cells in culture, either primary cells or cell lines, is used as an in vitro model of bone formation. An exemplary cell-based mineralization assay is described in U.S. Patent Publication No. 20070110747 at, e.g., Example 8 (hereby incorporated by reference). MC3T3-E1 cells (Sudo et al., *J. Cell Biol.,* 96:191-198 (1983)) and subclones of the original cell line can form mineral in culture upon growth in the presence of differentiating agents. Such subclones include MC3T3-E1-BF (Smith et al., *J. Biol. Chem.,* 275:19992-20001 (2000)). For both the MC3T3-E1-BF subclone as well as the original MC3T3-E1 cells, sclerostin can inhibit one or more of the sequence of events leading up to and including mineral deposition (i.e., sclerostin inhibits mineralization). Anti-sclerostin antibodies that are able to neutralize sclerostin's inhibitory activity allow for mineralization of the culture in the presence of sclerostin such that there is a statistically significant increase in, e.g., deposition of calcium phosphate (measured as calcium) as compared to the amount of calcium measured in the sclerostin-only (i.e., no antibody) treatment group.

When running the assay with the goal of determining whether a particular anti-sclerostin antibody can neutralize sclerostin, the amount of sclerostin used in the assay desirably is the minimum amount of sclerostin that causes at least a 70%, statistically significant, reduction in deposition of calcium phosphate (measured as calcium) in the sclerostin-only group, as compared to the amount of calcium measured in the no sclerostin group. An anti-sclerostin neutralizing antibody is defined as one that causes a statistically significant increase in deposition of calcium phosphate (measured as calcium) as compared to the amount of calcium measured in the sclerostin-only (i.e., no antibody) treatment group. To determine whether an anti-sclerostin antibody is neutralizing or not, the amount of anti-sclerostin antibody used in the assay needs to be such that there is an excess of moles of sclerostin binding sites per well as compared to the number of moles of sclerostin per well. Depending on the potency of the antibody, the fold excess that may be required can be 24, 18, 12, 6, 3, or 1.5, and one of skill is familiar with the routine practice of testing more than one concentration of binding agent (antibody). For example, a very potent anti-sclerostin neutralizing antibody will neutralize sclerostin when there is less than a 6-fold excess of moles of sclerostin binding sites per well as compared to the number of moles of sclerostin per well. A less potent anti-sclerostin neutralizing antibody will neutralize sclerostin only at a 12, 18 or 24 fold excess.

The anti-sclerostin antibody optionally has an $IC_{50}$ of 100 nM or less, or 75 nM or less, or 50 nM or less, or 25 nM or less for neutralizing human sclerostin in a cell-based assay, such as a bone specific alkaline phosphatase assay, e.g., the bone specific alkaline phosphatase assay described in International Patent Publication No. WO 2008/115732 and U.S. Pat. No. 7,744,874 (incorporated herein by reference in its entirety for its description of cell-based assays and anti-sclerostin antibodies). The bone specific alkaline phosphatase assay is predicated on the ability of sclerostin to decrease BMP-4 and Wnt3a-stimulated alkaline phosphatase levels in the multipotential murine cell line, C2C12. According to WO 2008/115732, a neutralizing anti-sclerostin antibody mediates a dose-dependent increase of alkaline phosphatase activity in this assay.

Alternatively or in addition, the anti-sclerostin antibody has an $IC_{50}$ of 100 nM or less (e.g., 75 nM or less, or 50 nM or less) for neutralizing human sclerostin in a cell-based Wnt signalling assay in HEK293 cell lines, such as the Wnt assay involving Wnt1-mediated induction of STF reporter gene described in, e.g., International Patent Publication No. WO 2009/047356 (incorporated by reference for its discussion of anti-sclerostin antibodies and cell-based assays). Alternatively or in addition, the anti-sclerostin antibody has an $IC_{50}$ of 500 nM or less (e.g., 250 nM or less, 150 nM or less, 100 nM or less, or 50 nM or less) for neutralizing human sclerostin in a BMP2-induced mineralization assay in MC3T3 cells, such as the mineralization assay described in, e.g., International Patent Publication No. WO 2009/047356.

Examples of anti-sclerostin antibodies suitable for use in the context of the invention are described in U.S. Patent Publication Nos. 20070110747 and 20070072797, which are hereby incorporated by reference. In one embodiment of the invention, the anti-sclerostin antibody cross-blocks the binding of at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, or Ab-24 (all of which are described in U.S. Patent Publication No. 20070110747) to sclerostin. Alternatively or in addition, the anti-sclerostin antibody is cross-blocked from binding to sclerostin by at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, or Ab-24 (all of which are described in U.S. Patent Publication No. 20070110747). The terms "cross-block," "cross-blocked," and "cross-blocking" are used interchangeably herein to mean the ability of an antibody to interfere with the binding of other antibodies to sclerostin. The extent to which an antibody is able to interfere with the binding of another to sclerostin, and therefore whether it can be said to cross-block, can be determined using competition binding assays. In some aspects of the invention, a cross-blocking antibody or fragment thereof reduces sclerostin binding of a reference antibody between about 40% and about 100%, such as about 60% and about 100%, specifically between 70% and 100%, and more specifically between 80% and 100%. A particularly suitable quantitative assay for detecting cross-blocking uses a Biacore machine which measures the extent of interactions using surface plasmon resonance technology. Another suitable quantitative cross-blocking assay uses an ELISA-based approach to measure competition between antibodies in terms of their binding to sclerostin.

Examples of suitable anti-sclerostin antibodies and fragments thereof include antibodies and antibody fragments having one or more of CDR-H1, CDR-H2, CDR-H3, CDR-L1, CDR-L2 and CDR-L3 specifically disclosed in U.S. Patent Publication No. 20070110747. At least one of the regions of CDR-H1, CDR-H2, CDR-H3, CDR-L1, CDR-L2, and CDR-L3 may have at least one amino acid substitution, provided that the antibody retains the binding specificity of the non-substituted CDR. Preferably, the anti-sclerostin antibody is Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, or Ab-24 of U.S. Patent Publication No. 20070110747.

In addition, the anti-sclerostin antibody can comprise at least one CDR sequence having at least 75% identity (e.g., 100% identity) to a CDR selected from SEQ ID NOs: 39, 40, 41, 42, 43, 44, 45, 46, 47, 48, 49, 50, 51, 52, 53, 54, 55, 56, 57, 58, 59, 60, 61, 62, 78, 79, 80, 81, 99, 100, 101, 102, 103, 104, 105, 106, 107, 108, 109, 110, 111, 112, 113, 114, 115, 116, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 351, 352, 353, 358, 359, and 360 provided in the Sequence Listing and disclosed in U.S. Patent Publication No. 20070110747. Preferably, the anti-sclerostin antibody comprises at least one CDR sequence having at least 75% identity to a CDR selected from SEQ ID NOs: 245, 246, 247, 78, 79, 80, 269, 270, 271, 239, 240, and 241, all of which is provided in the Sequence Listing and described in U.S. Patent Publication No. 20070110747. As described in U.S. Patent Publication No. 20070110747, the anti-sclerostin antibody can comprise: a) CDR sequences of SEQ ID NOs:54, 55, and 56 and CDR sequences of SEQ ID NOs:51, 52, and 53; b) CDR sequences of SEQ ID NOs:60, 61, and 62 and CDR sequences of SEQ ID NOs:57, 58, and 59; c) CDR sequences of SEQ ID NOs:48, 49, and 50 and CDR sequences of SEQ ID NOs:45, 46, and 47; d) CDR sequences of SEQ ID NOs:42, 43, and 44 and CDR sequences of SEQ ID NOs:39, 40, and 41; e) CDR sequences of SEQ ID NOs:275, 276, and 277 and CDR sequences of SEQ ID NOs:287, 288, and 289; f) CDR sequences of SEQ ID NOs:278, 279, and 280 and CDR sequences of SEQ ID NOs:290, 291, and 292; g) CDR sequences of SEQ ID NOs: 78, 79, and 80 and CDR sequences of SEQ ID NOs: 245, 246, and 247; h) CDR sequences of SEQ ID NOs:81, 99, and 100 and CDR sequences of SEQ ID NOs:248, 249, and 250; i) CDR sequences of SEQ ID NOs: 101, 102, and 103 and CDR sequences of SEQ ID NOs:251, 252, and 253; j) CDR sequences of SEQ ID NOs: 104, 105, and 106 and CDR sequences of SEQ ID NOs:254, 255, and 256; k) CDR sequences of SEQ ID NOs: 107, 108, and 109 and CDR sequences of SEQ ID NOs:257, 258, and 259; l) CDR sequences of SEQ ID NOs:110, 111, and 112 and CDR sequences of SEQ ID NOs:260, 261, and 262; m) CDR sequences of SEQ ID NOs:281, 282, and 283 and CDR sequences of SEQ ID NOs:293, 294, and 295; n) CDR sequences of SEQ ID NOs: 113, 114, and 115 and CDR sequences of SEQ ID NOs:263, 264, and 265; o) CDR sequences of SEQ ID NOs:284, 285, and 286 and CDR sequences of SEQ ID NOs:296, 297, and 298; p) CDR sequences of SEQ ID NOs: 116, 237, and 238 and CDR sequences of SEQ ID NOs:266, 267, and 268; q) CDR sequences of SEQ ID NOs:239, 240, and 241 and CDR sequences of SEQ ID NOs:269, 270, and 271; r) CDR sequences of SEQ ID NOs:242, 243, and 244 and CDR sequences of SEQ ID NOs:272, 273, and 274; or s) CDR sequences of SEQ ID NOs:351, 352, and 353 and CDR sequences of SEQ ID NOs:358, 359, and 360.

The anti-sclerostin antibody also can comprise at least one CDR sequence having at least 75% identity (e.g., 100% identical) to a CDR selected from CDR-H1, CDR-H2, CDR-H3, CDR-L1, CDR-L2, and CDR-L3 wherein CDR-H1 has the sequence given in SEQ ID NO: 245, CDR-H2 has the sequence given in SEQ ID NO: 246, CDR-H3 has the sequence given in SEQ ID NO: 247, CDR-L1 has the sequence given in SEQ ID NO: 78, CDR-L2 has the sequence given in SEQ ID NO: 79 and CDR-L3 has the sequence given in SEQ ID NO: 80, all of which is provided in the Sequence Listing and described in U.S. Patent Publication No. 20070110747. The anti-sclerostin antibody, in various aspects, comprises two of the CDRs or six of the CDRs. Optionally, the anti-sclerostin antibody comprises heavy chains comprising SEQ ID NO: 378 and light chains comprising SEQ ID NO 376 provided in the Sequence Listing.

The anti-sclerostin antibody also can comprise at least one CDR sequence having at least 75% identity (e.g., 100% identical) to a CDR selected from CDR-H1, CDR-H2, CDR-H3, CDR-L1, CDR-L2, and CDR-L3 wherein CDR-H1 has the sequence given in SEQ ID NO: 269, CDR-H2 has the sequence given in SEQ ID NO: 270, CDR-H3 has the sequence given in SEQ ID NO: 271, CDR-L1 has the sequence given in SEQ ID NO: 239, CDR-L2 has the sequence given in SEQ ID NO: 240 and CDR-L3 has the sequence given in SEQ ID NO 241, all of which is provided in the Sequence Listing and described in U.S. Patent Publication No. 20070110747. The anti-sclerostin antibody, in various aspects, comprises two of the CDRs or six of the CDRs. Optionally, the anti-sclerostin antibody comprises heavy chains comprising SEQ ID NO: 366 and light chains comprising SEQ ID NO 364 provided in the Sequence Listing.

Alternatively, the anti-sclerostin antibody can have a heavy chain comprising CDR's H1, H2, and H3 and comprising a polypeptide having the sequence provided in SEQ ID NO: 137 or a variant thereof in which said CDR's are at least 75% identical (e.g., 100% identical) to SEQ ID NO: 245, 246, and 247, respectively, and a light chain comprising CDR's L1, L2 and L3 and comprising a polypeptide having the sequence provided in SEQ ID NO: 133 or a variant thereof in which said CDR's are at least 75% identical (e.g., 100% identical) to SEQ ID NO: 78, 79, and 80, respectively (as described in U.S. Patent Publication No. 20070110747).

The anti-sclerostin antibody may have a heavy chain comprising CDR's H1, H2, and H3 and comprising a polypeptide having the sequence provided in SEQ ID NO: 145 or 392 or a variant thereof in which said CDR's are at least 75% identical (e.g., 100% identical) to SEQ ID NO: 245, 246, and 247, respectively, and a light chain comprising CDR's L1, L2, and L3 and comprising a polypeptide having the sequence provided in SEQ ID NO: 141 or a variant thereof in which said CDR's are at least 75% identical (e.g., 100% identical) to SEQ ID NO: 78, 79, and 80, respectively (as described in U.S. Patent Publication No. 20070110747).

The anti-sclerostin antibody may have a heavy chain comprising CDR's H1, H2, and H3 and comprising a polypeptide having the sequence provided in SEQ ID NO: 335, 331, 345, or 396 (provided in the Sequence Listing) or a variant of any of the foregoing in which said CDR's are at least 75% (e.g., 100% identical) identical to SEQ ID NO: 269, 270, and 271, respectively, and a light chain comprising CDR's L1, L2, and L3 and comprising a polypeptide having the sequence provided in SEQ ID NO: 334 or 341 (provided in the Sequence Listing) or a variant of any of the foregoing in which said CDR's are at least 75% identical (e.g., 100% identical) to SEQ ID NO: 239, 240, and 241, respectively (as described in U.S. Patent Publication No. 20070110747). All combinations of the heavy and light chain sequences are contemplated (e.g., heavy chains comprising SEQ ID NO: 335 and light chains comprising SEQ ID NO: 334; heavy chains comprising SEQ ID NO: 331 and light chains comprising SEQ ID NO: 334 or 341; and heavy chains comprising SEQ ID NO: 345 or 396 and light chains comprising SEQ ID NO: 341).

Alternatively, the anti-sclerostin antibody has a heavy chain comprising a polypeptide having the sequence provided in SEQ ID NO:137, and a light chain comprising a polypeptide having the sequence provided in SEQ ID NO: 133; a heavy chain comprising a polypeptide having the sequence provided in SEQ ID NO: 145 or 392, and a light chain comprising a polypeptide having the sequence provided in SEQ ID NO: 141; a heavy chain comprising a polypeptide having the sequence provided in SEQ ID NO:335, and a light chain comprising a polypeptide having the sequence provided in SEQ ID NO:334; a heavy chain comprising a polypeptide having the sequence provided in SEQ ID NO:331, and a light chain comprising a polypeptide having the sequence provided in SEQ ID NO:341; or a heavy chain comprising a polypeptide having the sequence provided in SEQ ID NO:345 or 396, and a light chain comprising a polypeptide having the sequence provided in SEQ ID NO:341 (provided in the Sequence Listing and as described in U.S. Patent Publication No. 20070110747).

Examples of anti-sclerostin antibodies also include, but are not limited to, the anti-sclerostin antibodies disclosed in International Patent Publication Nos. WO 2008/092894, WO 2008/115732, WO 2009/056634, WO 2009/047356, WO 2010/100200, WO 2010/100179, WO 2010/115932, and WO 2010/130830 (each of which is incorporated by reference herein in its entirety), such as an anti-sclerostin antibody comprising CDRs of SEQ ID NOs: 20-25 of International Patent Publication No. WO 2008/115732 (FIG. 8), an anti-sclerostin antibody comprising CDRs of SEQ ID NOs: 26-31 of International Patent Publication No. WO 2008/115732 (FIG. 8), an anti-sclerostin antibody comprising CDRs of SEQ ID NOs: 32-37 of International Patent Publication No. WO 2008/115732 (FIG. 8), an anti-sclerostin antibody comprising CDRs of SEQ ID NOs: 4, 15, 26, 37, 48, and 59 of International Patent Publication No. WO 2009/047356 (FIG. 9), or an anti-sclerostin antibody comprising the amino acid sequence of at least one of SEQ ID NOs: 135-143, 153-161, or 171-179 of International Patent Publication No. WO 2010/130830 (FIG. 10).

In one instance, the antibody employed comprises CDRs of SEQ ID NOs: 20-25 of International Patent Publication No. WO 2008/115732 (FIG. 8), CDRs of SEQ ID NOs: 26-31 of International Patent Publication No. WO 2008/115732 (FIG. 8), or CDRs of SEQ ID NOs: 32-37 of International Patent Publication No. WO 2008/115732 (FIG. 8). In another instance, the antibody comprises CDRs of SEQ ID NOs: 4, 15, 26, 37, 48, and 59 of International Patent Publication No. WO 2009/047356 (FIG. 9). In a further instance, the antibody comprises the amino acid sequence of at least one of SEQ ID NOs: 135-143, 153-161, or 171-179 of International Patent Publication No. WO 2010/130830 (FIG. 10). The disclosure of WO 2008/115732, WO 2009/047356 and WO 2010/130830 is incorporated herein in its entirety, including specifically the referenced CDR sequences and description of antibodies comprising the CDR sequences.

In one instance, the antibody employed may be an antibody capable of cross-blocking any of those antibodies specified herein and in particular an antibody that cross-blocks any of Ab-13, Ab-C and Ab-D referred to herein. In this regard, the anti-sclerostin antibody optionally cross-blocks the binding of a second antibody to sclerostin of SEQ ID NO: 1 or is cross-blocked from binding to sclerostin of SEQ ID NO: 1 by the second antibody, wherein the second antibody comprises light chains comprising the amino acid sequence set forth in SEQ ID NO: 205 and heavy chains comprising the amino acid sequence set forth in SEQ ID NO: 209; light chains comprising the amino acid sequence set forth in SEQ ID NO: 15 and heavy chains comprising the amino acid sequence set forth in SEQ ID NO: 19; or light chains comprising the amino acid sequence set forth in SEQ ID NO: 7 and heavy chains comprising the amino acid sequence set forth in SEQ ID NO: 11 (provided in the Sequence Listing).

Additional Treatments for Bone Disorders

In some instances, the subject may be administered an additional agent to treat their bone disorder. The subject may be, for instance, treated with any other therapy for treating bone disorders. For example, the additional treatment may be at the same time, overlapping with, or alternating with, the anti-sclerostin antibody treatment of the invention. In one instance, the subject may be administered vitamin D.

In one preferred instance, the second therapeutic agent is given in the dosing holiday for the anti-sclerostin antibody. Hence, whilst the dosing holiday allows resistance to the anti-sclerostin antibody to diminish, the subject is treated with the second therapeutic agent in the dosing holiday. Alternating treatments in that way may, in some instances, helps avoid possible detrimental effects associated with giving the other treatment for an extended, unbroken, period.

In one instance, the other therapeutic agent may be a bone resorption inhibitor. For instance, any suitable anti-resorptive may be employed. In one preferred instance, the bone resorption inhibitor is a bisphosphonate, particularly a nitrogen containing bisphosphonate. Examples of bisphosphonates include, but are not limited to, Alendronate, bonefos ciodronate, etidronate, ibandronic acid, olpadronate, neridronate, risedronate sodium, skelid, and zoledronic acid. In one preferred instance, the bisphosphonate is zoledronic acid. Bisphosphonates which may be employed include, for instance, Actonel™, Aclasta™/Reclast™, Boniva™/Bonviva™, Fosamax™, and Zometa™. An advantage of alternating between the anti-sclerostin antibody and bisphosphonate is that it may help avoid possible side effects arising from the subject being treated with bisphosphonates for a prolonged period. Hence, alternating helps avoid such side-effects, whilst also addressing the problem of resistance developing to the antibody.

Selected estrogen receptor modulators may be employed as bone resorption inhibitors, for instance, arzoxifene, bazedoxifene, FC 1271, lasofoxifene, raloxifene, and Tibolone are examples of suitable SERMs. Other bone resorption inhibitors which may be used include estrogen and calcitonin, with examples of calcitonin including salmon calcitonins, such as Miacalcin™.

Strontium compounds may be employed as the bone resorption inhibitor and in one particular instance the compound is strontium ranelate. In other instances, the additional treatment administered may be PTH, in particular recombinant parathyroid hormone releasing peptide.

In various embodiments, the bone resorption inhibitor is a RANKL inhibitor, such as an anti-RANKL antibody. In one preferred instance, the bone resorption inhibitor employed may be denosumab.

In some instances the anti-resorptive employed is not a bisphosphonate. Examples, of such agents which may be employed include PROLIA®, calcitonin, and cathepsin K inhibitors (e.g., odanacatib).

In various embodiments, the second therapeutic agent is an anabolic agent, such as parathyroid hormone or analogs thereof (e.g., teriparatide (FORTEO®).

In one case, a bone resorption inhibitor may be administered at the same time, or approximately the same time, as the antibody, or so the two therapies overlap. It may be that the bone resorption inhibitor is given to help prolong further the effect of the anti-sclerostin antibody by reducing the breakdown of bone that the antibody has stimulated and in particular where the compound is a bisphosphonate.

Disorders to be Treated

The invention is typically used to treat or help prevent a bone disorder. The invention may be, for example, employed to increase at least one of bone formation, bone mineral density, bone mineral content, bone mass, bone quality and bone strength. Hence, in one instance, the disorder to be treated via the invention is a bone disorder associated with at least one of low bone formation, low bone mineral density, low bone mineral content, low bone mass, low bone quality and low bone strength in a mammalian subject.

The disorder may be a bone-related disorder associated with abnormal osteoblast or osteoclast activity. Examples of disorders associated with bone loss which may be treated include achondroplasia, cleidocranial dysostosis, enchondromatosis, fibrous dysplasia, Gaucher's Disease, hypophosphatemic rickets, Marfan's syndrome, multiple hereditary exotoses, neurofibromatosis, osteogenesis imperfecta, osteopetrosis, osteopoikilosis, sclerotic lesions, pseudoarthrosis, pyogenic osteomyelitis, periodontal disease, anti-epileptic drug induced bone loss, primary and secondary hyperparathyroidism, familial hyperparathyroidism syndromes, weightlessness induced bone loss, osteoporosis in men, postmenopausal bone loss, osteoarthritis, renal osteodystrophy, infiltrative disorders of bone, oral bone loss, osteonecrosis of the jaw, juvenile Paget's disease, melorheostosis, metabolic bone diseases, mastocytosis, sickle cell anemia/disease, organ transplant related bone loss, kidney transplant related bone loss, systemic lupus erythematosus, ankylosing spondylitis, epilepsy, juvenile arthritides, thalassemia, mucopolysaccharidoses, Fabry Disease, Turner Syndrome, Down Syndrome, Klinefelter Syndrome, leprosy, Perthe's Disease, adolescent idiopathic scoliosis, infantile onset multi-system inflammatory disease, Winchester Syndrome, Menkes Disease, Wilson's Disease, ischemic bone disease (such as Legg-Calve-Perthes disease and regional migratory osteoporosis), anemic states, conditions caused by steroids, glucocorticoid-induced bone loss, heparin-induced bone loss, bone marrow disorders, scurvy, malnutrition, calcium deficiency, osteoporosis, osteopenia, alcoholism, chronic liver disease, postmenopausal state, chronic inflammatory conditions, rheumatoid arthritis, inflammatory bowel disease, ulcerative colitis, inflammatory colitis, Crohn's disease, oligomenorrhea, amenorrhea, diabetes mellitus, hyperthyroidism, thyroid disorders, parathyroid disorders, Cushing's disease, acromegaly, hypogonadism, immobilization or disuse, reflex sympathetic dystrophy syndrome, regional osteoporosis, osteomalacia, bone loss associated with joint replacement, HIV associated bone loss, bone loss associated with loss of growth hormone, bone loss associated with cystic fibrosis, chemotherapy-associated bone loss, tumor-induced bone loss, cancer-related bone loss, hormone ablative bone loss, multiple myeloma, drug-induced bone loss, anorexia nervosa, disease-associated facial bone loss, disease-associated cranial bone loss, disease-associated bone loss of the jaw, disease-associated bone loss of the skull, bone loss associated with aging, facial bone loss associated with aging, cranial bone loss associated with aging, jaw bone loss associated with aging, skull bone loss associated with aging, and bone loss associated with space travel. Bone loss, decreased bone mineral density, decreased bone volume, and/or decreased bone mineral content associated with these disorders may be treated in the context of the invention. In one instance, the subject to be treated may be pregnant. For instance, the invention may be employed to help in pregnancy-related bone loss. The invention may be used to slow, or reverse, bone loss in general.

In one instance, the condition to be treated is not bone fracture. In one particularly preferred instance, the condition to be treated is osteoporosis or osteopenia. In one instance, the subject to be treated is a postmenopausal woman, for instance, one with osteoporosis, particularly such a subject who is at increased, or high risk, for fracture, or has failed or is intolerant to other available osteoporosis therapy. In further instances, the invention may be employed in improving the outcome in a mammal undergoing one or more of an orthopedic procedure, dental procedure, implant surgery, joint replacement, bone grafting, bone cosmetic surgery and bone repair such as fracture healing, nonunion healing, delayed union healing and facial reconstruction.

Administration

Various routes of administering an antibody to a subject are known in the art and discussed in, e.g., U.S. Patent Publication No. 20070110747. For example, in various embodiments, it is desirable to deliver a pharmaceutical composition comprising the anti-sclerostin antibody subcutaneously, parenterally, intravenously, intramuscularly, or even intraperitoneally. Such approaches are well known to the skilled artisan, some of which are further described, for example, in U.S. Pat. Nos. 5,543,158; 5,641,515; and 5,399,363. Optionally, the anti-sclerostin antibody is administered subcutaneously.

Illustrative physiologically-acceptable (e.g., pharmaceutical) forms suitable for use include sterile aqueous solutions or dispersions and sterile powders for the extemporaneous preparation of sterile injectable solutions or dispersions (for example, see U.S. Pat. No. 5,466,468). The form must be sterile and is desirably fluid to the extent that easy syringability exists (i.e., is not excessively viscous so as to prevent passage through a syringe). A pharmaceutical composition comprising the anti-sclerostin antibody may be placed within containers (e.g., vials or syringes), along with packaging material that provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) that may be necessary to reconstitute the pharmaceutical composition. In one instance, where the antibody is to be administered with an additional treatment for the bone disorder, the two may be formulated or packaged together, optionally with instructions setting out a method of the invention.

All of the references cited herein, including patents, patent applications, literature publications, and the like, are hereby incorporated by reference.

While this invention has been described with an emphasis upon preferred embodiments, it will be obvious to those of ordinary skill in the art that variations of the preferred compounds and methods may be used and that it is intended that the invention may be practiced otherwise than as specifically described herein. Accordingly, this invention includes all modifications encompassed within the spirit and scope of the invention as defined by the following claims.

The invention is further described in the following examples. The example serves only to illustrate the invention and is not intended to limit the scope of the invention in any way.

EXAMPLES

Materials and Methods

Animals

Balb/c female mice obtained from Charles River UK (8-10 weeks of age at the start of the experiments) were maintained and studied in a manner in compliance with UK Home Office regulations.

The antibody employed in the present Examples was Scl-AbI (Eddleston et al, 2009, *J Bone MinerRes,* 24:1662-71—which is incorporated herein in its entirety). Scl-AbI was dosed at 10 mg/kg subcutaneously (control animals received PBS) at the time points showed in the Figures. Blood samples (tail tip bleeds) were taken mid-morning where indicated and frozen at −20° C. until assayed. At certain time points terminal blood samples were removed from euthanized animals to provide larger blood samples for assay.

Measurement of P1NP

P1NP was measured using a kit supplied ImmunoDiagnostic Systems (catalogue no. AC-33F1) according to the manufacturers recommended method.

Measurement of BMD

Animals were anesthetized by isofluorane inhalation. After being placed under general anesthesia, the mice were scanned on a Lunar PIXImus (GE Medical Systems) at the times shown.

Results

Determining P1NP Peak Levels Following Dosing

A preliminary experiment established that, following a subcutaneous dose of the anti-sclerostin antibody (10 mg/kg), peak P1NP levels were seen at day 4. This time point was used to monitor the P1NP response in animals subject to multiple doses of Scl-Ab, as discussed further below.

FIG. 1 shows the results of the preliminary experiment. P1NP levels for two mice dosed subcutaneously with 10 mg/kg of anti-sclerostin on day 0 are shown (square and diamond symbols). The kinetics of Scl-AbI following a single subcutaneous dose of 10 mg/kg are also shown in FIG. 1 (triangular symbols).

Multiple Dosing Experiments

Three groups of mice were established, the first group of mice (group A, n=10) was dosed with PBS on days 0, 7, 14, 21 and 28. The second group of mice (group B, n=20) was dosed with Scl-AbI (10 mg/kg, s.c.) on days 0, 7, 14, 21, and 28. The third group of mice (group C) provided a pool of aged matched control animals to determine the P1NP response in mice that had not previously been exposed to Scl-Ab1.

Mice in group C were generally dosed with PBS on the same schedule as animals in groups A and B, except that on days 14 and 28 a subgroup of mice from group C (n=5 at each time point) were dosed with Scl-AbI (10 mg/kg s.c.) and the circulating P1NP levels measured 4 days later. These subgroups allowed assessment of the P1NP response in animals that were aged matched with the animals in group B, but were receiving Scl-AbI for the first time (as opposed to the repeat dosing of group B animals).

Figure 2:
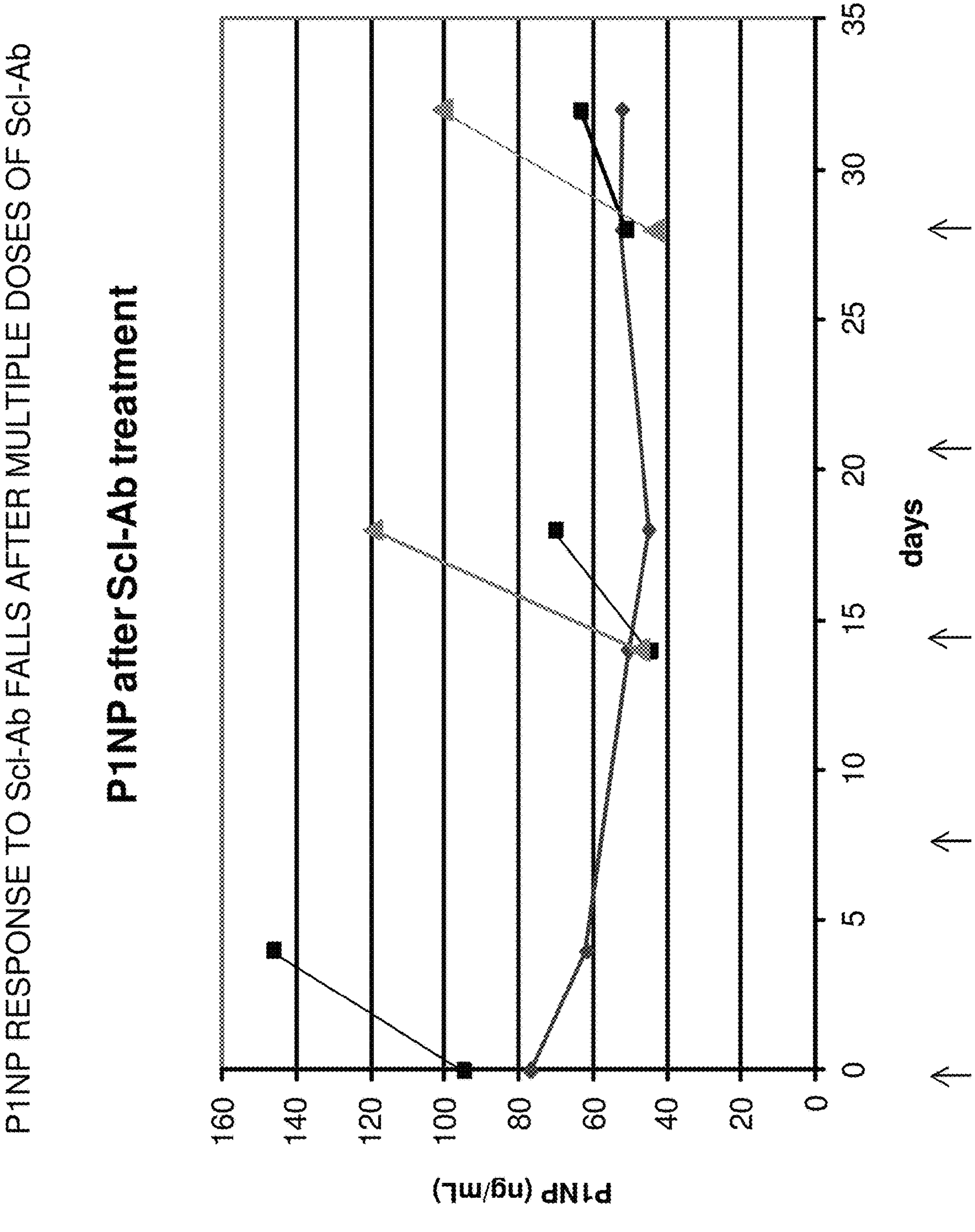
FIG. 2 shows how P1NP response to anti-sclerostin antibodies falls after multiple doses of antibody. P1NP levels are shown for group A mice administered saline alone (diamond symbols), group B mice (square symbols) administered subcutaneously 10 mg/kg anti-sclerostin antibody at the time points indicated at the bottom of the graph and group C mice (triangular symbols) administered saline, except for a single dose of antibody at the time-point depicted. The statistics use an unpaired T test (two tailed) looking at difference of absolute values at day of test. For the results shown the group B mice were administered antibody doses at days 0, 7, 14, 21 and 28, with the single doses for the group C subgroups administered at either day 14 or 28.

Blood samples were taken on days 0, 14, 18, 28 and 32 and circulating P1NP levels measured. FIG. 2 shows the P1NP levels in the different groups of animals. The results for group A (diamond symbols), group B (square symbols) and the subgroup of group C receiving the antibody at day 14 or 28 (triangular symbols) are shown in FIG. 2.

FIG. 2 illustrates a number of points. Firstly, P1NP levels in the PBS treated group (group A) fall with time. As the rate of bone synthesis would be expected to fall with age in the control group, that result was not unexpected. Secondly, the P1NP levels in group B mice (the group receiving multiple doses of Scl-AbI) at day 18 and day 32 (both time points are 4 days after receiving a dose of Scl-Ab) are significantly lower than the levels in mice from group C dosed with Scl-AbI (for the first time) at the same time points. This indicates that the P1NP response in mice receiving multiple doses of Scl-Ab (group B) is blunted compared with the response seen in age-matched mice dosed with Scl-Ab for the first time.

Figure 3:
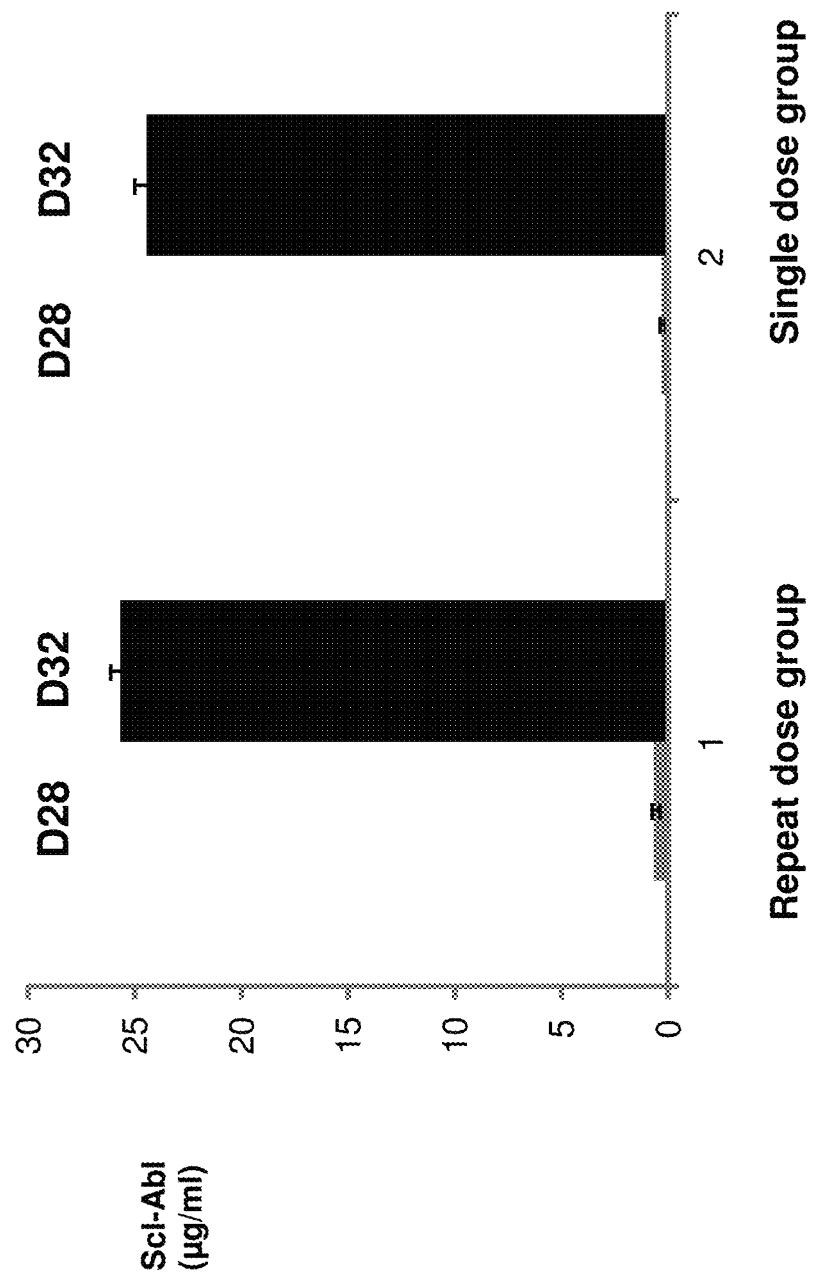
FIG. 3 shows that the decline in plasma P1NP levels after multiple doses of antibody is not due to more rapid elimination of the antibody in the multiple dosed group. The level of antibody is shown for the repeat dose group B and single dose group C immediately before a dose of 10 mg/kg of antibody given subcutaneously on day 28 and the level four days after the dose of antibody at day 32 (mean and SEM levels).

In order to determine if the result seen was due to reduced exposure to anti-sclerostin antibody in those mice receiving multiple doses, anti-sclerostin antibody levels were measured immediately prior to dosing on day 28 and four days afterwards on day 32 in mice from group B and those from group C given the single dose at day 28. FIG. 3 shows the results obtained and that the plasma levels of Scl-Ab on days 28 and 32 are not significantly different in mice from group B and group C, suggesting that the decreased P1NP response in the group B mice is not due to reduced exposure to Scl-Ab (as might happen due to rapid clearance if mice in group B mounted an immune response to Scl-Ab).

Figure 4:
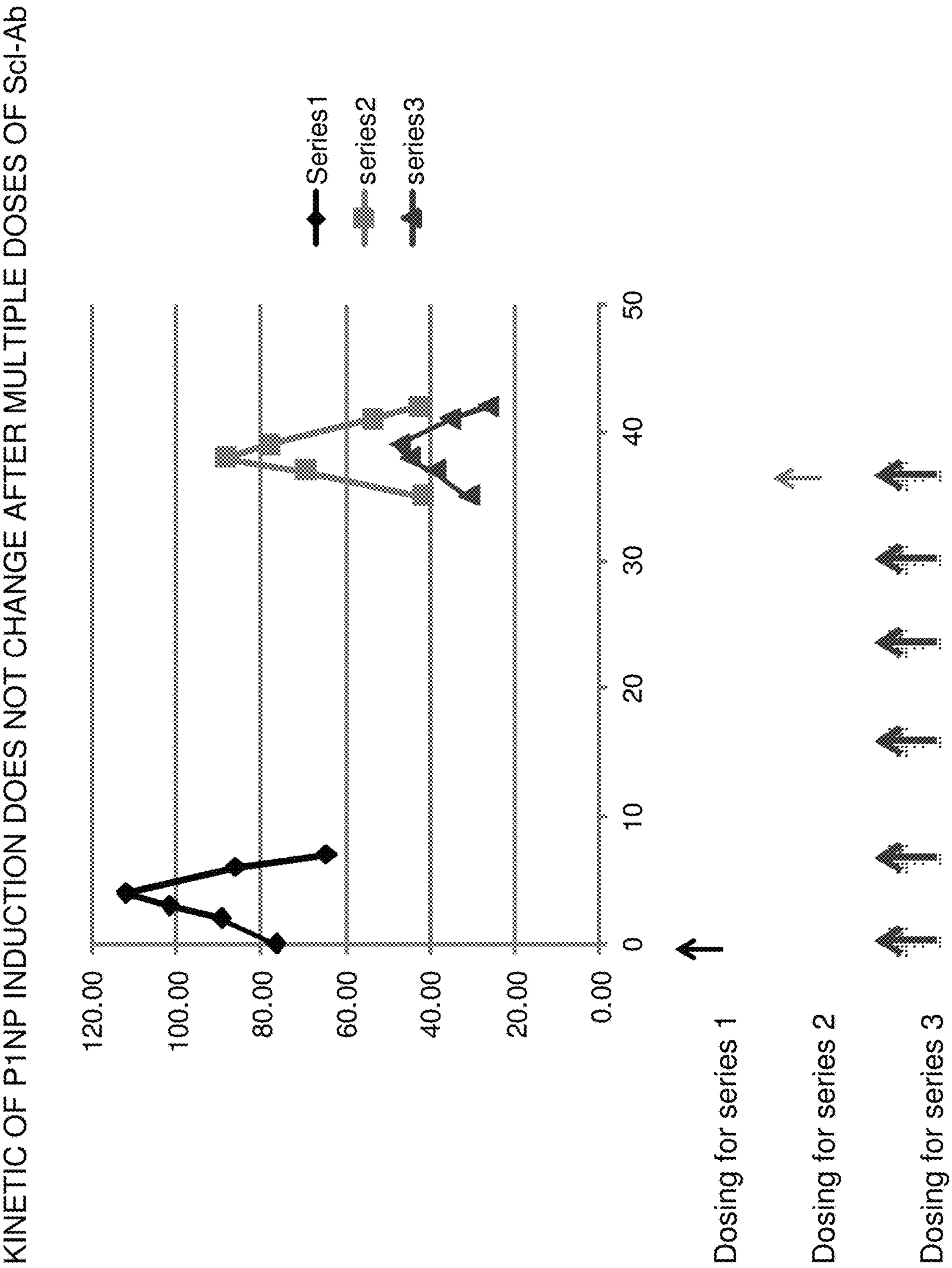
FIG. 4 shows the kinetics of P1NP induction are the same in mice given a single dose or multiple doses of anti-sclerostin antibody, only the magnitude of the P1NP induction is different between the two groups. The P1NP levels for series 1 (diamond symbols) and series 2 (square symbols) are shown where the mice were given a single dose of anti-sclerostin antibody, as well as the levels for the series 3 mice (triangular symbols) given multiple doses of anti-sclerostin antibody. The time of the administration of the antibody is shown by the arrows under the graph.

The kinetics of P1NP induction was compared, and is depicted in FIG. 4, for mice receiving a single dose of sclerostin at either day 0 or 35 (series 1—diamonds and series 2—squares), with mice receiving multiple doses (series 3—triangles). FIG. 4 shows that although the P1NP response is lower in mice receiving multiple doses of Scl-Ab, the peak of the response still occurs around day 4 and so it is not the kinetics of the P1NP response to the anti-sclerostin antibody which are changed, only the magnitude.

Dosing Holidays

Figure 5:
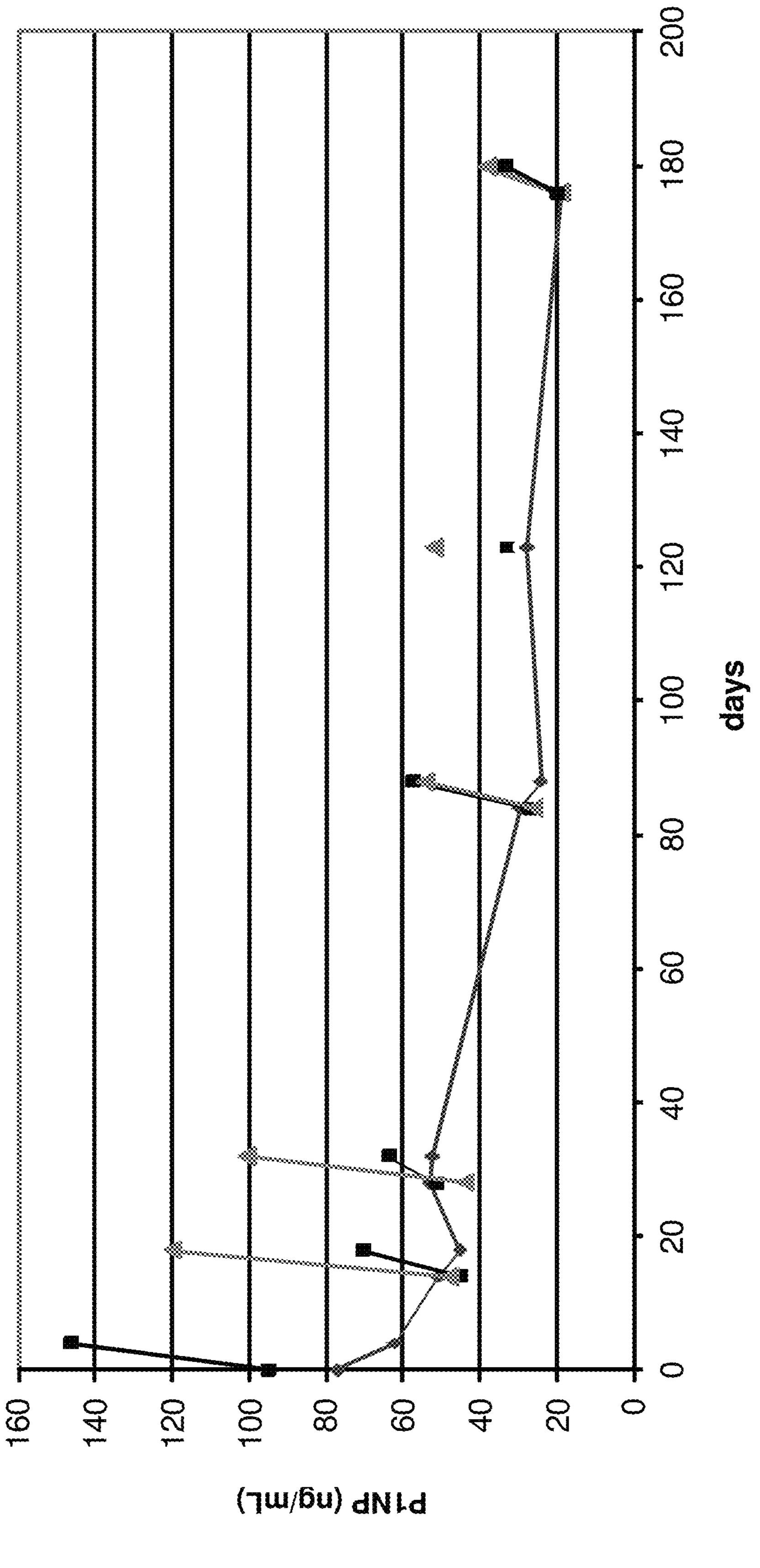
FIG. 5 shows P1NP levels in groups A, B and subgroups of group C given a single dose of antibody at the depicted time point. The symbols are the same as indicated above for FIG. 2. The dosing schedule for group B is shown by arrows at the bottom of the graph and corresponds to doses at days 0, 7, 14, 21 and 28 and days 84, 91, 98, 105, 112 119 and 176 (no baseline sample was taken on day 119). Hence, there were dosing holidays between days 28 and 84 and also days 119 and 176. The single doses for the group C subgroups were at days 14, 28, 84, 119 and 176. The statistics use an unpaired T test (two tailed) looking at difference of absolute values at day of test.

The experiment shown in FIG. 2 was continued and the data from the whole experiment is shown in FIG. 5. Again, the results for group A are shown as diamond symbols, those for group B as square symbols and the single dose subgroups of group C as triangular symbols. The arrows at the bottom of the graph show the time of dosing for the group B animals. It can be seen from FIG. 5 that in group A animals (dosed only with PBS) P1NP levels fall until day 84 after which they reach a fairly stable plateau until the end of the experiment. After the dose of Scl-Ab at day 28 mice in group B were put on a dosing holiday with no further dosing of Scl-Ab until day 84. At this time point a sub-group of aged-matched animals (from group C) were also dosed with Scl-Ab. Surprisingly, the levels of P1NP at day 88 were not significantly different in animals that had received multiple doses of Scl-Ab and those receiving Scl-Ab for the first time. The results indicates that a dosing holiday allows reversal of the resistance (or tachyphylaxis) that develops in mice exposed to multiple doses of Scl-Ab.

Mice in group B received doses of Scl-Ab (10 mg/kg s.c) at days 91, 98, 105, 112 and 119. A sub-group of mice from pool C also received Scl-Ab on day 119. FIG. 5 shows that the P1NP levels in the group B mice were significantly lower than those in the age-matched mice receiving Scl-Ab for the first time. These data show that even after an initial dosing holiday to reverse P1NP tachyphylaxis in the group B mice, the tachyphylactic state re-occurs after multiple doses of Scl-Ab.

Following the dose of Scl-Ab at day 119 the mice in group B were given a second dosing holiday until day 176 when they were dosed again with Scl-Ab (10 mg/kg s.c). At the same time point a subgroup of aged-matched animals from pool C were dosed with Scl-Ab (10 mg/kg s.c) for the first time. Measurement of circulating P1NP levels on day 180 show that there is no significant difference in the P1NP levels in the two groups indicating that a second dosing holiday again reversed the P1NP tachyphylaxis in the animals receiving multiple doses of Scl-Ab.

Figure 6:
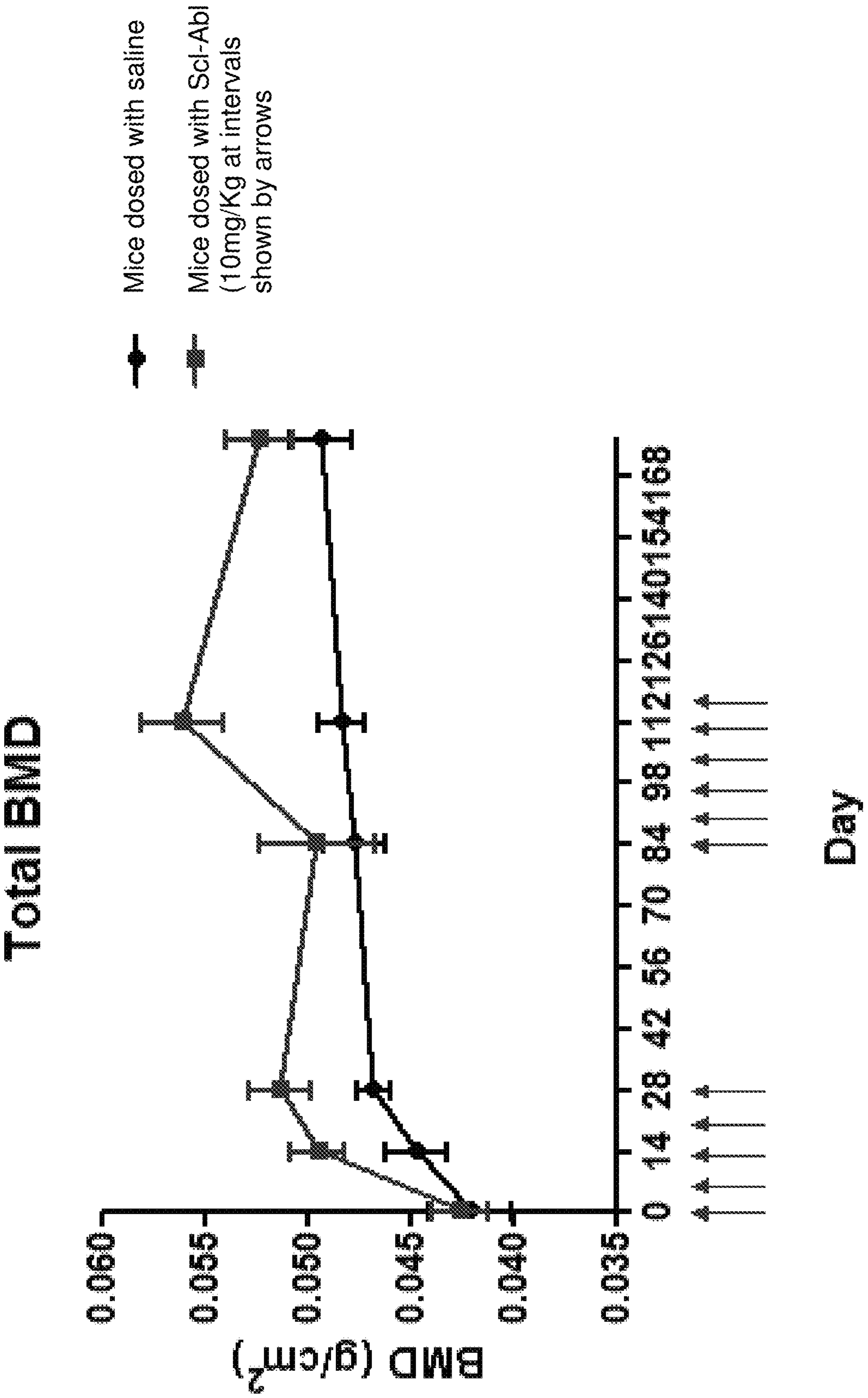
FIG. 6 shows bone mineral density in group A mice (circular symbols) and group B mice (square symbols). The dosing schedule for the group B animals is shown at the bottom of the graph.

Bone mineral density (BMD) was measure in group A and B animals. FIG. 6 shows the results obtained and illustrates that following multiple doses of Scl-Ab the BMD in group B animals increased significantly compared to animals in group A (receiving only saline). BMD declined when Scl-Ab dosing was stopped (after day 28) but again increased when dosing was re-started at day 84 after the dosing holiday.

Figure 11A:
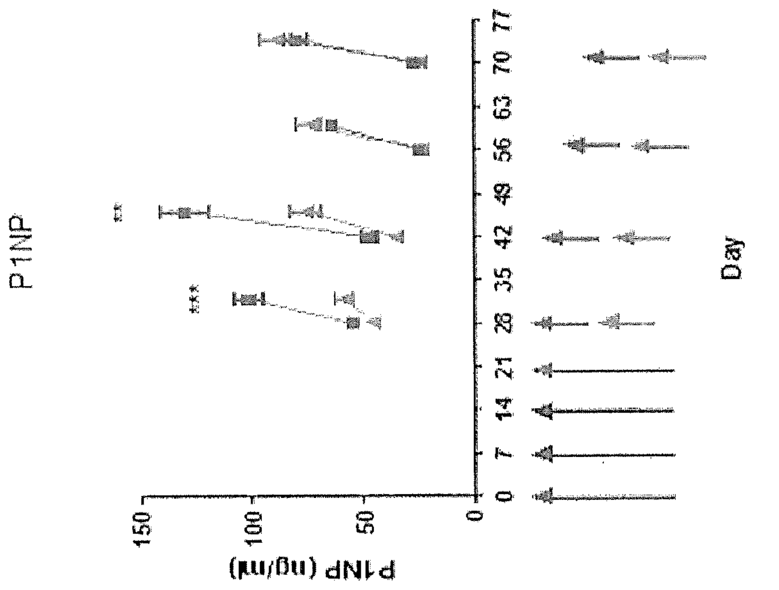
FIG. 11A is a graph illustrating P1NP levels in mice receiving five weekly doses of anti-sclerostin antibody followed by a single dose of anti-sclerostin antibody after a two week (administration on day 42), four week (administration on day 56), or six week (administration on day 70) holiday (triangle symbols) and age-matched mice receiving a single dose of anti-sclerostin antibody on day 28, day 42, day 46, or day 70 (square symbols). P1NP levels (ng/ml) are depicted on the y-axis, and day of the study is depicted on the x-axis.
Figure 11B:
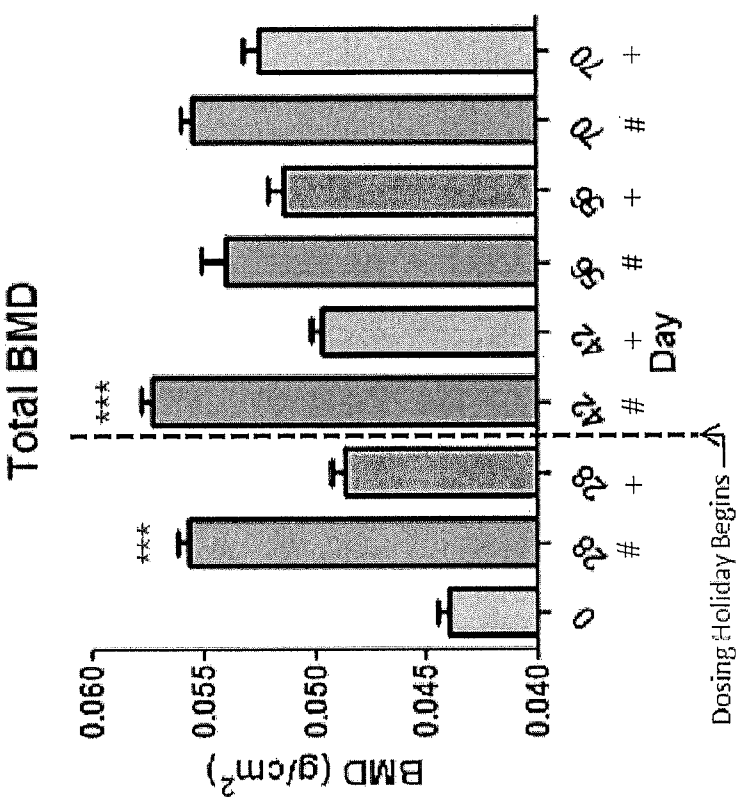
FIG. 11B is a bar graph illustrating total bone mineral density (BMD; g/cm2; y-axis) measured at various time points (days, x-axis). Bars denoted "#" correspond to measurements taken in mice receiving five weekly doses of anti-sclerostin antibody (fifth dose administered on day 28) followed by a single dose of anti-sclerostin antibody on days 42, 56, or 70 (corresponding to a two week, four week, or six week holiday, respectively). Bars denoted "+" correspond to measurements taken in mice receiving a single dose of anti-sclerostin antibody on days 28, 42, 56, or 70 of the study.

To further study the duration of tachyphylaxis associated with multiple doses of Scl-Ab, mice were given five weekly doses of Scl-Ab and a further dose after a two week, four week, or six week holiday (Group 1). In other words, subjects in Group 1 received a dose of Scl-Ab on days 0, 7, 14, 21, and 28 of the study, and a subsequent dose on one of days 42, 56, or 70. For comparison, age-matched subjects, previously treated only with saline, were administered a single dose of Scl-Ab on day 28, 42, 56, or 70 (Group 2). Thus, Group 2 mice received only one dose of Scl-Ab, whereas Group 1 mice received multiple doses, optionally with a holiday before the final dose. P1NP levels were measured the day of antibody administration and one week after, and the responses of each group was compared (FIG. 11A). While P1NP levels increased in response to antibody administration in all groups, the increase in P1NP levels in subjects receiving a first dose of Scl-Ab on days 28 and 42 (Group 2) was greater than the increase in P1NP levels in mice previously treated with antibody (Group 1). Among Group 1 subjects, Scl-Ab administration triggered a greater increase in P1NP in subjects administered the dose after a two week holiday (day 42) compared to subjects receiving the dose at the end of the five week regimen (day 28). As illustrated in FIG. 11A, full responsiveness to the Scl-Ab appeared to return after four weeks without dosing (i.e., a four week holiday). The level of marker increase in Group 1 and Group 2 subjects administered Scl-Ab at day 56 (four week holiday) and day 70 (six week holiday) was similar. FIG. 11B shows the BMD in these mice; bars denoted "#" correspond to Group 1 subjects and bars denoted "+" correspond to Group 2 subjects.

Hence, overall, the results obtained show that cycles of a series of doses followed by a dosing holiday may be employed to avoid the development of resistance to the anti-sclerostin antibody.

SEQUENCE LISTING

```
Sequence total quantity: 809
SEQ ID NO: 1            moltype = AA  length = 190
FEATURE                 Location/Qualifiers
source                  1..190
                        mol_type = protein
                        organism = Homo sapiens
SEQUENCE: 1
QGWQAFKNDA TEIIPELGEY PEPPPELENN KTMNRAENGG RPPHHPFETK DVSEYSCREL  60
HFTRYVTDGP CRSAKPVTEL VCSGQCGPAR LLPNAIGRGK WWRPSGPDFR CIPDRYRAQR  120
VQLLCPGGEA PRARKVRLVA SCKCKRLTRF HNQSELKDFG TEAARPQKGR KPRPRARSAK  180
ANQAELENAY                                                         190

SEQ ID NO: 2            moltype = AA  length = 14
FEATURE                 Location/Qualifiers
source                  1..14
                        mol_type = protein
                        organism = Homo sapiens
SEQUENCE: 2
DVSEYSCREL HFTR                                                    14

SEQ ID NO: 3            moltype = AA  length = 16
FEATURE                 Location/Qualifiers
source                  1..16
                        mol_type = protein
                        organism = Homo sapiens
SEQUENCE: 3
SAKPVTELVC SGQCGP                                                  16

SEQ ID NO: 4            moltype = AA  length = 17
FEATURE                 Location/Qualifiers
source                  1..17
                        mol_type = protein
                        organism = Homo sapiens
SEQUENCE: 4
WWRPSGPDFR CIPDRYR                                                 17

SEQ ID NO: 5            moltype = AA  length = 12
FEATURE                 Location/Qualifiers
source                  1..12
                        mol_type = protein
                        organism = Homo sapiens
SEQUENCE: 5
LVASCKCKRL TR                                                      12

SEQ ID NO: 6            moltype = AA  length = 26
FEATURE                 Location/Qualifiers
source                  1..26
                        mol_type = protein
                        organism = Homo sapiens
SEQUENCE: 6
CGPARLLPNA IGRGKWWRPS GPDFRC                                       26

SEQ ID NO: 7            moltype = AA  length = 214
FEATURE                 Location/Qualifiers
source                  1..214
                        mol_type = protein
                        organism = Mus musculus
SEQUENCE: 7
DVQMIQSPSS LSASLGDIVT MTCQASQGTS INLNWFQQKP GKAPKLLIYG SSNLEDGVPS  60
RFSGSRYGTD FTLTISSLED EDLATYFCLQ HSYLPYTFGG GTKLEIKRAD AAPTVSIFPP  120
SSEQLTSGGA SVVCFLNNFY PKDINVKWKI DGSERQNGVL NSWTDQDSKD STYSMSSTLT  180
LTKDEYERHN SYTCEATHKT STSPIVKSFN RNEC                              214

SEQ ID NO: 8            moltype = DNA  length = 645
FEATURE                 Location/Qualifiers
source                  1..645
```

mol_type = other DNA
organism = Mus musculus

SEQUENCE: 8
gatgtccaga tgattcagtc tccatcctcc ctgtctgcat ctttgggaga catagtcacc 60
atgacttgcc aggcaagtca gggcactagc attaatttaa actggtttca gcaaaaacca 120
gggaaggctc ctaagctcct gatctatggt tcaagcaact tggaagatgg ggtcccatca 180
aggttcagtg gcagtagata tgggacagat ttcactctca ccatcagcag cctggaggat 240
gaagatctgg caacttattt ctgtctacaa catagttatc tcccgtacac gttcggaggg 300
gggaccaagc tggaaataaa acgggctgat gctgcaccaa ctgtatccat cttcccacca 360
tccagtgagc agttaacatc tggaggtgcc tcagtcgtgt gcttcttgaa caacttctac 420
cccaaagaca tcaatgtcaa gtggaagatt gatggcagtg aacgacaaaa tggcgtcctg 480
aacagttgga ctgatcagga cagcaaagac agcacctaca gcatgagcag caccctcacg 540
ttgaccaagg acgagtatga acgacataac agctatacct gtgaggccac tcacaagaca 600
tcaacttcac ccattgtcaa gagcttcaac aggaatgagt gttag 645

SEQ ID NO: 9 moltype = AA length = 236
FEATURE Location/Qualifiers
source 1..236
mol_type = protein
organism = Mus musculus SEQUENCE: 9
MNTRAPAEFL GFLLLWFLGA RCDVQMIQSP SSLSASLGDI VTMTCQASQG TSINLNWFQQ 60
KPGKAPKLLI YGSSNLEDGV PSRFSGSRYG TDFTLTISSL EDEDLATYFC LQHSYLPYTF 120
GGGTKLEIKR ADAAPTVSIF PPSSEQLTSG GASVVCFLNN FYPKDINVKW KIDGSERQNG 180
VLNSWTDQDS KDSTYSMSST LTLTKDEYER HNSYTCEATH KTSTSPIVKS FNRNEC 236

SEQ ID NO: 10 moltype = DNA length = 711
FEATURE Location/Qualifiers
source 1..711
mol_type = other DNA
organism = Mus musculus SEQUENCE: 10
atgaacacga gggcccctgc tgagttcctt gggttcctgt tgctctggtt tttaggtgcc 60
agatgtgatg tccagatgat tcagtctcca tcctccctgt ctgcatcttt gggagacata 120
gtcaccatga cttgccaggc aagtcagggc actagcatta atttaaactg gtttcagcaa 180
aaaccaggga aggctcctaa gctcctgatc tatggttcaa gcaacttgga agatggggtc 240
ccatcaaggt tcagtggcag tagatatggg acagatttca ctctcaccat cagcagcctg 300
gaggatgaag atctggcaac ttatttctgt ctacaacata gttatctccc gtacacgttc 360
ggagggggga ccaagctgga aataaaacgg gctgatgctg caccaactgt atccatcttc 420
ccaccatcca gtgagcagtt aacatctgga ggtgcctcag tcgtgtgctt cttgaacaac 480
ttctacccca aagacatcaa tgtcaagtgg aagattgatg gcagtgaacg acaaaatggc 540
gtcctgaaca gttggactga tcaggacagc aaagacagca cctacagcat gagcagcacc 600
ctcacgttga ccaaggacga gtatgaacga cataacagct atacctgtga ggccactcac 660
aagacatcaa cttcacccat tgtcaagagc ttcaacagga atgagtgtta g 711

SEQ ID NO: 11 moltype = AA length = 443
FEATURE Location/Qualifiers
source 1..443
mol_type = protein
organism = Mus musculus SEQUENCE: 11
EVQLQQSGPE LVTPGASVKI SCKASGYTFT DHYMSWVKQS HGKSLEWIGD INPYSGETTY 60
NQKFKGTATL TVDKSSSIAY MEIRGLTSED SAVYYCARDD YDASPFAYWG QGTLVTVSAA 120
KTTPPSVYPL APGSAAQTNS MVTLGCLVKG YFPEPVTVTW NSGSLSSGVH TFPAVLQSDL 180
YTLSSSVTVP SSTWPSETVT CNVAHPASST KVDKKIVPRD CGCKPCICTV PEVSSVFIFP 240
PKPKDVLTIT LTPKVTCVVV DISKDDPEVQ FSWFVDDVEV HTAQTQPREE QFNSTFRSVS 300
ELPIMHQDWL NGKEFKCRVN SPAFPAPIEK TISKTKGRPK APQVYTIPPP KEQMAKDKVS 360
LTCMITDFFP EDITVEWQWN GQPAENYKNT QPIMDTDGSY FIYSKLNVQK SNWEAGNTFT 420
CSVLHEGLHN HHTEKSLSHS PGK 443

SEQ ID NO: 12 moltype = DNA length = 1332
FEATURE Location/Qualifiers
source 1..1332
mol_type = other DNA
organism = Mus musculus SEQUENCE: 12
gaggtccagc tgcaacagtc tggacctgaa ctggtgacgc ctggggcttc agtgaagata 60
tcttgtaagg cttctggata cacattcact gaccactaca tgagctgggt gaagcagagt 120
catggaaaaa gccttgagtg gattggagat attaatccct attctggtga aactacctac 180
aaccagaagt tcaagggcac ggccacattg actgtagaca agtcttccag tatagcctac 240
atggagatcc gcggcctgac atctgaggac tctgcagtct attactgtgc aagagatgat 300
tacgacgcct ctccgtttgc ttactggggc caagggactc tggtcactgt ctctgcagcc 360
aaaacgacac ccccatctgt ctatccactg gcccctggat ctgctgccca aactaactcc 420
atggtgaccc tgggatgcct ggtcaagggc tatttccctg agccagtgac agtgacctgg 480
aactctggat ccctgtccag cggtgtgcac accttcccag ctgtcctgca gtctgacctc 540
tacactctga gcagctcagt gactgtcccc tccagcacct ggcccagcga gaccgtcacc 600
tgcaacgttg cccacccggc cagcagcacc aaggtggaca agaaaattgt gcccagggat 660
tgtggttgta agccttgcat atgtacagtc ccagaagtat catctgtctt catcttcccc 720
ccaaagccca aggatgtgct caccattact ctgactccta aggtcacgtg tgttgtggta 780

```
gacatcagca aggatgatcc cgaggtccag ttcagctggt ttgtagatga tgtggaggtg  840
cacacagctc agacgcaacc ccgggaggag cagttcaaca gcactttccg ctcagtcagt  900
gaacttccca tcatgcacca ggactggctc aatggcaagg agttcaaatg cagggtcaac  960
agtccagctt tccctgcccc catcgagaaa accatctcca aaaccaaagg cagaccgaag  1020
gctccacagg tgtacaccat tccacctccc aaggagcaga tggccaagga taaagtcagt  1080
ctgacctgca tgataacaga cttcttccct gaagacatta ctgtggagtg gcagtggaat  1140
gggcagccag cggagaacta caagaacact cagcccatca tggacacaga tggctcttac  1200
ttcatctaca gcaagctcaa tgtgcagaag agcaactggg aggcaggaaa tactttcacc  1260
tgctctgtgt tacatgaggg cctgcacaac caccatactg agaagagcct ctcccactct  1320
cctggtaaat ga                                                     1332

SEQ ID NO: 13          moltype = AA  length = 462
FEATURE                Location/Qualifiers
source                 1..462
                       mol_type = protein
                       organism = Mus musculus
SEQUENCE: 13
MRCRWIFLFL LSGTAGVLSE VQLQQSGPEL VTPGASVKIS CKASGYTFTD HYMSWVKQSH  60
GKSLEWIGDI NPYSGETTYN QKFKGTATLT VDKSSSIAYM EIRGLTSEDS AVYYCARDDY  120
DASPFAYWGQ GTLVTVSAAK TTPPSVYPLA PGSAAQTNSM VTLGCLVKGY FPEPVTVTWN  180
SGSLSSGVHT FPAVLQSDLY TLSSSVTVPS STWPSETVTC NVAHPASSTK VDKKIVPRDC  240
GCKPCICTVP EVSSVFIFPP KPKDVLTITL TPKVTCVVVD ISKDDPEVQF SWFVDDVEVH  300
TAQTQPREEQ FNSTFRSVSE LPIMHQDWLN GKEFKCRVNS PAFPAPIEKT ISKTKGRPKA  360
PQVYTIPPPK EQMAKDKVSL TCMITDFFPE DITVEWQWNG QPAENYKNTQ PIMDTDGSYF  420
IYSKLNVQKS NWEAGNTFTC SVLHEGLHNH HTEKSLSHSP GK                    462

SEQ ID NO: 14          moltype = DNA  length = 1389
FEATURE                Location/Qualifiers
source                 1..1389
                       mol_type = other DNA
                       organism = Mus musculus
SEQUENCE: 14
atgagatgca ggtggatctt tctctttctc ctgtcaggaa ctgcaggtgt cctctctgag  60
gtccagctgc aacagtctgg acctgaactg gtgacgcctg gggcttcagt gaagatatct  120
tgtaaggctt ctggatacac attcactgac cactacatga gctgggtgaa gcagagtcat  180
ggaaaaagcc ttgagtggat tggagatatt aatccctatt ctggtgaaac tacctacaac  240
cagaagttca agggcacggc cacattgact gtagacaagt cttccagtat agcctacatg  300
gagatccgcg gcctgacatc tgaggactct gcagtctatt actgtgcaag agatgattac  360
gacgcctctc cgtttgctta ctggggccaa gggactctgg tcactgtctc tgcagccaaa  420
acgacacccc catctgtcta tccactggcc cctggatctg ctgcccaaac taactccatg  480
gtgaccctgg gatgcctggt caagggctat ttccctgagc cagtgacagt gacctggaac  540
tctggatccc tgtccagcgg tgtgcacacc ttcccagctg tcctgcagtc tgacctctac  600
actctgagca gctcagtgac tgtcccctcc agcacctggc ccagcgagac cgtcacctgc  660
aacgttgccc acccggccag cagcaccaag gtggacaaga aaattgtgcc cagggattgt  720
ggttgtaagc cttgcatatg tacagtccca gaagtatcat ctgtcttcat cttcccccca  780
aagcccaagg atgtgctcac cattactctg actcctaagg tcacgtgtgt tgtggtagac  840
atcagcaagg atgatcccga ggtccagttc agctggtttg tagatgatgt ggaggtgcac  900
acagctcaga cgcaaccccg ggaggagcag ttcaacagca ctttccgctc agtcagtgaa  960
cttcccatca tgcaccagga ctggctcaat ggcaaggagt tcaaatgcag ggtcaacagt  1020
ccagctttcc ctgcccccat cgagaaaacc atctccaaaa ccaaaggcag accgaaggct  1080
ccacaggtgt acaccattcc acctcccaag gagcagatgg ccaaggataa agtcagtctg  1140
acctgcatga taacagactt cttccctgaa gacattactg tggagtggca gtggaatggg  1200
cagccagcgg agaactacaa gaacactcag cccatcatgg acacagatgg ctcttacttc  1260
atctacagca agctcaatgt gcagaagagc aactgggagg caggaaatac tttcacctgc  1320
tctgtgttac atgagggcct gcacaaccac catactgaga agagcctctc ccactctcct  1380
ggtaaatga                                                         1389

SEQ ID NO: 15          moltype = AA  length = 218
FEATURE                Location/Qualifiers
source                 1..218
                       mol_type = protein
                       organism = Mus musculus
SEQUENCE: 15
DIVLTQSPAS LTVSLGLRAT ISCKASQSVD YDGDSYMNWY QQKPGQPPKL LIYAASNLES  60
GIPARFSGNG SGTDFTLNIH PVEEEDAVTY YCQQSNEDPW TFGGGTKLEI KRADAAPTVS  120
IFPPSSEQLT SGGASVVCFL NNFYPKDINV KWKIDGSERQ NGVLNSWTDQ DSKDSTYSMS  180
STLTLTKDEY ERHNSYTCEA THKTSTSPIV KSFNRNEC                          218

SEQ ID NO: 16          moltype = DNA  length = 657
FEATURE                Location/Qualifiers
source                 1..657
                       mol_type = other DNA
                       organism = Mus musculus
SEQUENCE: 16
gacattgtgc tgacccaatc tccagcttct ttgactgtgt ctctaggcct gagggccacc  60
atctcctgca aggccagcca aagtgttgat tatgatggtg atagttatat gaactggtac  120
cagcagaaac caggacagcc acccaaactc ctcatctatg ctgcatccaa tctagaatct  180
gggatcccag ccaggtttag tggcaatggg tctgggacag acttcaccct caacatccat  240
cctgtggagg aggaggatgc tgtaacctat tactgtcaac aaagtaatga ggatccgtgg  300
```

-continued

```
acgttcggtg gaggcaccaa gctggaaatc aaacgggctg atgctgcacc aactgtatcc  360
atcttcccac catccagtga gcagttaaca tctggaggtg cctcagtcgt gtgcttcttg  420
aacaacttct accccaaaga catcaatgtc aagtggaaga ttgatggcag tgaacgacaa  480
aatggcgtcc tgaacagttg gactgatcag gacagcaaag acagcaccta cagcatgagc  540
agcaccctca cgttgaccaa ggacgagtat gaacgacata acagctatac ctgtgaggcc  600
actcacaaga catcaacttc acccattgtc aagagcttca acaggaatga gtgttag     657

SEQ ID NO: 17          moltype = AA  length = 238
FEATURE                Location/Qualifiers
source                 1..238
                       mol_type = protein
                       organism = Mus musculus
SEQUENCE: 17
METDTILLWV LLLWVPGSTG DIVLTQSPAS LTVSLGLRAT ISCKASQSVD YDGDSYMNWY  60
QQKPGQPPKL LIYAASNLES GIPARFSGNG SGTDFTLNIH PVEEEDAVTY YCQQSNEDPW  120
TFGGGTKLEI KRADAAPTVS IFPPSSEQLT SGGASVVCFL NNFYPKDINV KWKIDGSERQ  180
NGVLNSWTDQ DSKDSTYSMS STLTLTKDEY ERHNSYTCEA THKTSTSPIV KSFNRNEC    238

SEQ ID NO: 18          moltype = DNA  length = 717
FEATURE                Location/Qualifiers
source                 1..717
                       mol_type = other DNA
                       organism = Mus musculus
SEQUENCE: 18
atggagacag acacaatcct gctatgggtg ctgctgctct gggttccagg ctccactggt  60
gacattgtgc tgacccaatc tccagcttct ttgactgtgt ctctaggcct gagggccacc  120
atctcctgca aggccagcca aagtgttgat tatgatggtg atagttatat gaactggtac  180
cagcagaaac caggacagcc acccaaactc ctcatctatg ctgcatccaa tctagaatct  240
gggatcccag ccaggtttag tggcaatggg tctgggacag acttcaccct caacatccat  300
cctgtggagg aggaggatgc tgtaacctat tactgtcaac aaagtaatga ggatccgtgg  360
acgttcggtg gaggcaccaa gctggaaatc aaacgggctg atgctgcacc aactgtatcc  420
atcttcccac catccagtga gcagttaaca tctggaggtg cctcagtcgt gtgcttcttg  480
aacaacttct accccaaaga catcaatgtc aagtggaaga ttgatggcag tgaacgacaa  540
aatggcgtcc tgaacagttg gactgatcag gacagcaaag acagcaccta cagcatgagc  600
agcaccctca cgttgaccaa ggacgagtat gaacgacata acagctatac ctgtgaggcc  660
actcacaaga catcaacttc acccattgtc aagagcttca acaggaatga gtgttag     717

SEQ ID NO: 19          moltype = AA  length = 449
FEATURE                Location/Qualifiers
source                 1..449
                       mol_type = protein
                       organism = Mus musculus
SEQUENCE: 19
EVQLQQSGPE LVKPGTSVKM SCKASGYTFT DCYMNWVKQS HGKSLEWIGD INPFNGGTTY  60
NQKFKGKATL TVDKSSSTAY MQLNSLTSDD SAVYYCARSH YYFDGRVPWD AMDYWGQGTS  120
VTVSSAKTTP PSVYPLAPGS AAQTNSMVTL GCLVKGYFPE PVTVTWNSGS LSSGVHTFPA  180
VLQSDLYTLS SSVTVPSSTW PSETVTCNVA HPASSTKVDK KIVPRDCGCK PCICTVPEVS  240
SVFIFPPKPK DVLTITLTPK VTCVVVDISK DDPEVQFSWF VDDVEVHTAQ TQPREEQFNS  300
TFRSVSELPI MHQDWLNGKE FKCRVNSAAF PAPIEKTISK TKGRPKAPQV YTIPPPKEQM  360
AKDKVSLTCM ITDFFPEDIT VEWQWNGQPA ENYKNTQPIM DTDGSYFIYS KLNVQKSNWE  420
AGNTFTCSVL HEGLHNHHTE KSLSHSPGK                                   449

SEQ ID NO: 20          moltype = DNA  length = 1350
FEATURE                Location/Qualifiers
source                 1..1350
                       mol_type = other DNA
                       organism = Mus musculus
SEQUENCE: 20
gaggtccagc tgcaacaatc tggacctgag ctggtgaagc ctgggacttc agtgaagatg  60
tcctgtaagg cttctggata cacattcact gactgctaca tgaactgggt gaagcagagc  120
catgggaaga gccttgaatg gattggagat attaatcctt tcaacggtgg tactacctac  180
aaccagaagt tcaagggcaa ggccacattg actgtagaca aatcctccag cacagcctac  240
atgcagctca acagcctgac atctgacgac tctgcagtct attactgtgc aagatcccat  300
tattacttcg atggtagagt cccttgggat gctatggact actggggtca aggaacctca  360
gtcaccgtct cctcagccaa aacgacaccc ccatctgtct atccactggc ccctggatct  420
gctgcccaaa ctaactccat ggtgaccctg ggatgcctgg tcaagggcta tttccctgag  480
ccagtgacag tgacctggaa ctctggatcc ctgtccagcg gtgtgcacac cttcccagct  540
gtcctgcagt ctgacctcta cactctgagc agctcagtga ctgtcccctc cagcacctgg  600
cccagcgaga ccgtcacctg caacgttgcc cacccggcca gcagcaccaa ggtggacaag  660
aaaattgtgc ccagggattg tggttgtaag ccttgcatat gtacagtccc agaagtatca  720
tctgtcttca tcttcccccc aaagcccaag gatgtgctca ccattactct gactcctaag  780
gtcacgtgtg ttgtggtaga catcagcaag gatgatcccg aggtccagtt cagctggttt  840
gtagatgatg tggaggtgca cacagctcag acgcaacccc gggaggagca gttcaacagc  900
actttccgct cagtcagtga acttcccatc atgcaccagg actggctcaa tggcaaggag  960
ttcaaatgca gggtcaacag tgcagctttc cctgccccca tcgagaaaac catctccaaa  1020
accaaaggca gaccgaaggc tccacaggtg tacaccattc cacctcccaa ggagcagatg  1080
gccaaggata aagtcagtct gacctgcatg ataacagact tcttccctga agacattact  1140
gtggagtggc agtggaatgg gcagccagcg gagaactaca agaacactca gcccatcatg  1200
gacacagatg gctcttactt catctacagc aagctcaatg tgcagaagag caactgggag  1260
```

-continued

```
gcaggaaata ctttcacctg ctctgtgtta catgagggcc tgcacaacca ccatactgag  1320
aagagcctct cccactctcc tggtaaatga                                   1350

SEQ ID NO: 21          moltype = AA  length = 468
FEATURE                Location/Qualifiers
source                 1..468
                       mol_type = protein
                       organism = Mus musculus
SEQUENCE: 21
MGWNWIFLFL LSGTAGVYSE VQLQQSGPEL VKPGTSVKMS CKASGYTFTD CYMNWVKQSH  60
GKSLEWIGDI NPFNGGTTYN QKFKGKATLT VDKSSSTAYM QLNSLTSDDS AVYYCARSHY  120
YFDGRVPWDA MDYWGQGTSV TVSSAKTTPP SVYPLAPGSA AQTNSMVTLG CLVKGYFPEP  180
VTVTWNSGSL SSGVHTFPAV LQSDLYTLSS SVTVPSSTWP SETVTCNVAH PASSTKVDKK  240
IVPRDCGCKP CICTVPEVSS VFIFPPKPKD VLTITLTPKV TCVVVDISKD DPEVQFSWFV  300
DDVEVHTAQT QPREEQFNST FRSVSELPIM HQDWLNGKEF KCRVNSAAFP APIEKTISKT  360
KGRPKAPQVY TIPPPKEQMA KDKVSLTCMI TDFFPEDITV EWQWNGQPAE NYKNTQPIMD  420
TDGSYFIYSK LNVQKSNWEA GNTFTCSVLH EGLHNHHTEK SLSHSPGK               468

SEQ ID NO: 22          moltype = DNA  length = 1407
FEATURE                Location/Qualifiers
source                 1..1407
                       mol_type = other DNA
                       organism = Mus musculus
SEQUENCE: 22
atgggatgga actggatctt tctcttcctc ttgtcaggaa ctgcaggtgt ctactctgag  60
gtccagctgc aacaatctgg acctgagctg gtgaagcctg ggacttcagt gaagatgtcc  120
tgtaaggctt ctggatacac attcactgac tgctacatga actgggtgaa gcagagccat  180
gggaagagcc ttgaatggat tggagatatt aatcctttca acggtggtac tacctacaac  240
cagaagttca agggcaaggc cacattgact gtagacaaat cctccagcac agcctacatg  300
cagctcaaca gcctgacatc tgacgactct gcagtctatt actgtgcaag atcccattat  360
tacttcgatg gtagagtccc ttgggatgct atggactact ggggtcaagg aacctcagtc  420
accgtctcct cagccaaaac gacaccccca tctgtctatc cactggcccc tggatctgct  480
gcccaaacta actccatggt gaccctggga tgcctggtca agggctattt ccctgagcca  540
gtgacagtga cctggaactc tggatccctg tccagcggtg tgcacacctt cccagctgtc  600
ctgcagtctg acctctacac tctgagcagc tcagtgactg tcccctccag cacctggccc  660
agcgagaccg tcacctgcaa cgttgcccac ccggccagca gcaccaaggt ggacaagaaa  720
attgtgccca gggattgtgg ttgtaagcct tgcatatgta cagtcccaga agtatcatct  780
gtcttcatct tccccccaaa gcccaaggat gtgctcacca ttactctgac tcctaaggtc  840
acgtgtgttg tggtagacat cagcaaggat gatcccgagg tccagttcag ctggtttgta  900
gatgatgtgg aggtgcacac agctcagacg caaccccggg aggagcagtt caacagcact  960
ttccgctcag tcagtgaact tcccatcatg caccaggact ggctcaatgg caaggagttc  1020
aaatgcaggg tcaacagtgc agctttccct gcccccatcg agaaaaccat ctccaaaacc  1080
aaaggcagac cgaaggctcc acaggtgtac accattccac ctcccaagga gcagatggcc  1140
aaggataaag tcagtctgac ctgcatgata acagacttct tccctgaaga cattactgtg  1200
gagtggcagt ggaatgggca gccagcggag aactacaaga acactcagcc catcatggac  1260
acagatggct cttacttcat ctacagcaag ctcaatgtgc agaagagcaa ctgggaggca  1320
ggaaatactt tcacctgctc tgtgttacat gagggcctgc acaaccacca tactgagaag  1380
agcctctccc actctcctgg taaatga                                      1407

SEQ ID NO: 23          moltype = AA  length = 217
FEATURE                Location/Qualifiers
REGION                 1..217
                       note = Synthetic Polypeptide
REGION                 1..217
                       note = MISC_FEATURE - Rabbit-mouse chimera
source                 1..217
                       mol_type = protein
                       organism = synthetic construct
SEQUENCE: 23
AQVLTQTPAS VSAAVGGTVT INCQSSQSVY DNNWLAWFQQ KPGQPPKLLI YDASDLASGV  60
PSRFSGSGSG TQFTLTISGV QCADAATYYC QGAYNDVIYA FGGGTEVVVK RTDAAPTVSI  120
FPPSSEQLTS GGASVVCFLN NFYPKDINVK WKIDGSERQN GVLNSWTDQD SKDSTYSMSS  180
TLTLTKDEYE RHNSYTCEAT HKTSTSPIVK SFNRNEC                           217

SEQ ID NO: 24          moltype = DNA  length = 654
FEATURE                Location/Qualifiers
misc_feature           1..654
                       note = Synthetic Polynucleotide
misc_feature           1..654
                       note = Rabbit-mouse chimera
source                 1..654
                       mol_type = other DNA
                       organism = synthetic construct
SEQUENCE: 24
gcgcaagtgc tgacccagac tccagcctcc gtgtctgcag ctgtgggagg cacagtcacc  60
atcaattgcc agtccagtca gagtgtttat gataacaact ggttagcctg gtttcagcag  120
aaaccagggc agcctcccaa gctcctgatt tatgatgcat ccgatctggc atctggggtc  180
ccatcgcggt tcagtggcag tggatctggg acacagttca ctctcaccat cagcggcgtg  240
cagtgtgccg atgctgccac ttactactgt caaggcgctt ataatgatgt tatttatgct  300
```

-continued

```
ttcggcggag ggaccgaggt ggtggtcaaa cgtacggatg ctgcaccaac tgtatccatc  360
ttcccaccat ccagtgagca gttaacatct ggaggtgcct cagtcgtgtg cttcttgaac  420
aacttctacc ccaaagacat caatgtcaag tggaagattg atggcagtga acgacaaaat  480
ggcgtcctga acagttggac tgatcaggac agcaaagaca gcacctacag catgagcagc  540
accctcacgt tgaccaagga cgagtatgaa cgacataaca gctatacctg tgaggccact  600
cacaagacat caacttcacc cattgtcaag agcttcaaca ggaatgagtg ttag        654

SEQ ID NO: 25          moltype = AA  length = 239
FEATURE                Location/Qualifiers
REGION                 1..239
                       note = Synthetic Polypeptide
REGION                 1..239
                       note = MISC_FEATURE - Rabbit-mouse chimera
source                 1..239
                       mol_type = protein
                       organism = synthetic construct
SEQUENCE: 25
MDTRAPTQLL GLLLLWLPGA TFAQVLTQTP ASVSAAVGGT VTINCQSSQS VYDNNWLAWF  60
QQKPGQPPKL LIYDASDLAS GVPSRFSGSG SGTQFTLTIS GVQCADAATY YCQGAYNDVI  120
YAFGGGTEVV VKRTDAAPTV SIFPPSSEQL TSGGASVVCF LNNFYPKDIN VKWKIDGSER  180
QNGVLNSWTD QDSKDSTYSM SSTLTLTKDE YERHNSYTCE ATHKTSTSPI VKSFNRNEC   239

SEQ ID NO: 26          moltype = DNA  length = 720
FEATURE                Location/Qualifiers
misc_feature           1..720
                       note = Synthetic Polynucleotide
misc_feature           1..720
                       note = Rabbit-mouse chimera
source                 1..720
                       mol_type = other DNA
                       organism = synthetic construct
SEQUENCE: 26
atggacacga gggcccccac tcagctgctg gggctcctgc tgctctggct cccaggtgcc  60
acatttgcgc aagtgctgac ccagactcca gcctccgtgt ctgcagctgt gggaggcaca  120
gtcaccatca attgccagtc cagtcagagt gtttatgata acaactggtt agcctggttt  180
cagcagaaac cagggcagcc tcccaagctc ctgatttatg atgcatccga tctggcatct  240
ggggtcccat cgcggttcag tggcagtgga tctgggacac agttcactct caccatcagc  300
ggcgtgcagt gtgccgatgc tgccacttac tactgtcaag gcgcttataa tgatgttatt  360
tatgctttcg gcggagggac cgaggtggtg gtcaaacgta cggatgctgc accaactgta  420
tccatcttcc caccatccag tgagcagtta acatctggag gtgcctcagt cgtgtgcttc  480
ttgaacaact tctaccccaa agacatcaat gtcaagtgga agattgatgg cagtgaacga  540
caaaatggcg tcctgaacag ttggactgat caggacagca aagacagcac ctacagcatg  600
agcagcaccc tcacgttgac caaggacgag tatgaacgac ataacagcta tacctgtgag  660
gccactcaca agacatcaac ttcacccatt gtcaagagct tcaacaggaa tgagtgttag  720

SEQ ID NO: 27          moltype = AA  length = 433
FEATURE                Location/Qualifiers
REGION                 1..433
                       note = Synthetic Polypeptide
REGION                 1..433
                       note = MISC_FEATURE - Humanized Antibody
source                 1..433
                       mol_type = protein
                       organism = synthetic construct
SEQUENCE: 27
QSLEESGGRL VTPGTPLTLT CTASGFSLSS YWMNWVRQAP GEGLEWIGTI DSGGRTDYAS  60
WAKGRFTISR TSTTMDLKMT SLTTGDTARY FCARNWNLWG QGTLVTVSSA STKGPSVYPL  120
APGSAAQTNS MVTLGCLVKG YFPEPVTVTW NSGSLSSGVH TFPAVLQSDL YTLSSSVTVP  180
SSTWPSETVT CNVAHPASST KVDKKIVPRD CGCKPCICTV PEVSSVFIFP PKPKDVLTIT  240
LTPKVTCVVV DISKDDPEVQ FSWFVDDVEV HTAQTQPREE QFNSTFRSVS ELPIMHQDWL  300
NGKEFKCRVN SAAFPAPIEK TISKTKGRPK APQVYTIPPP KEQMAKDKVS LTCMITDFFP  360
EDITVEWQWN GQPAENYKNT QPIMNTNGSY FVYSKLNVQK SNWEAGNTFT CSVLHEGLHN  420
HHTEKSLSHS PGK                                                    433

SEQ ID NO: 28          moltype = DNA  length = 1302
FEATURE                Location/Qualifiers
misc_feature           1..1302
                       note = Synthetic Polynucleotide
misc_feature           1..1302
                       note = Humanized Antibody
source                 1..1302
                       mol_type = other DNA
                       organism = synthetic construct
SEQUENCE: 28
cagtcgctgg aggagtccgg gggtcgcctg gtcacgcctg ggacacccct gacactcacc  60
tgcacagcct ctggattctc cctcagtagt tattggatga actgggtccg ccaggctcca  120
ggggaggggc tggaatggat cggaaccatt gattctggtg gtaggacgga ctacgcgagc  180
tgggcaaaag gccgattcac catctccaga acctcgacta cgatggatct gaaaatgacc  240
agtctgacga ccggggacac ggcccgttat ttctgtgcca gaaattggaa cttgtggggc  300
```

-continued

```
caaggcaccc tcgtcaccgt ctcgagcgct tctacaaagg gcccatctgt ctatccactg  360
gcccctggat ctgctgccca aactaactcc atggtgaccc tgggatgcct ggtcaagggc  420
tatttccctg agccagtgac agtgacctgg aactctggat ccctgtccag cggtgtgcac  480
accttcccag ctgtcctgca gtctgacctc tacactctga gcagctcagt gactgtcccc  540
tccagcacct ggcccagcga gaccgtcacc tgcaacgttg cccacccggc cagcagcacc  600
aaggtggaca agaaaattgt gcccagggat tgtggttgta agccttgcat atgtacagtc  660
ccagaagtat catctgtctt catcttcccc ccaaagccca aggatgtgct caccattact  720
ctgactccta aggtcacgtg tgttgtggta gacatcagca aggatgatcc cgaggtccag  780
ttcagctggt ttgtagatga tgtggaggtg cacacagctc agacgcaacc ccgggaggag  840
cagttcaaca gcactttccg ctcagtcagt gaacttccca tcatgcacca ggactggctc  900
aatggcaagg agttcaaatg cagggtcaac agtgcagctt tccctgcccc catcgagaaa  960
accatctcca aaaccaaagg cagaccgaag gctccacagg tgtacaccat tccacctccc  1020
aaggagcaga tggccaagga taaagtcagt ctgacctgca tgataacaga cttcttccct  1080
gaagacatta ctgtggagtg gcagtggaat gggcagccag cggagaacta caagaacact  1140
cagcccatca tggacacaga tggctcttac ttcgtctaca gcaagctcaa tgtgcagaag  1200
agcaactggg aggcaggaaa tactttcacc tgctctgtgt tacatgaggg cctgcacaac  1260
caccatactg agaagagcct ctcccactct cctggtaaat ga                    1302

SEQ ID NO: 29          moltype = AA  length = 452
FEATURE                Location/Qualifiers
REGION                 1..452
                       note = Synthetic Polypeptide
REGION                 1..452
                       note = MISC_FEATURE - Humanized Antibody
source                 1..452
                       mol_type = protein
                       organism = synthetic construct
SEQUENCE: 29
METGLRWLLL VAVLKGVHCQ SLEESGGRLV TPGTPLTLTC TASGFSLSSY WMNWVRQAPG  60
EGLEWIGTID SGGRTDYASW AKGRFTISRT STTMDLKMTS LTTGDTARYF CARNWNLWGQ  120
GTLVTVSSAS TKGPSVYPLA PGSAAQTNSM VTLGCLVKGY FPEPVTVTWN SGSLSSGVHT  180
FPAVLQSDLY TLSSSVTVPS STWPSETVTC NVAHPASSTK VDKKIVPRDC GCKPCICTVP  240
EVSSVFIFPP KPKDVLTITL TPKVTCVVVD ISKDDPEVQF SWFVDDVEVH TAQTQPREEQ  300
FNSTFRSVSE LPIMHQDWLN GKEFKCRVNS AAFPAPIEKT ISKTKGRPKA PQVYTIPPPK  360
EQMAKDKVSL TCMITDFFPE DITVEWQWNG QPAENYKNTQ PIMNTNGSYF VYSKLNVQKS  420
NWEAGNTFTC SVLHEGLHNH HTEKSLSHSP GK                                452

SEQ ID NO: 30          moltype = DNA  length = 1359
FEATURE                Location/Qualifiers
misc_feature           1..1359
                       note = Synthetic Polynucleotide
misc_feature           1..1359
                       note = Humanized Antibody
source                 1..1359
                       mol_type = other DNA
                       organism = synthetic construct
SEQUENCE: 30
atggagactg ggctgcgctg gcttctcctg gtcgctgtgc tcaaaggtgt ccactgtcag  60
tcgctggagg agtccggggg tcgcctggtc acgcctggga cacccctgac actcacctgc  120
acagcctctg gattctccct cagtagttat tggatgaact gggtccgcca ggctccaggg  180
gaggggctgg aatggatcgg aaccattgat tctggtggta ggacggacta cgcgagctgg  240
gcaaaaggcc gattcaccat ctccagaacc tcgactacga tggatctgaa aatgaccagt  300
ctgacgaccg gggacacggc ccgttatttc tgtgccagaa attggaactt gtggggccaa  360
ggcaccctcg tcaccgtctc gagcgcttct acaaagggcc catctgtcta tccactggcc  420
cctggatctg ctgcccaaac taactccatg gtgaccctgg gatgcctggt caagggctat  480
ttccctgagc cagtgacagt gacctggaac tctggatccc tgtccagcgg tgtgcacacc  540
ttcccagctg tcctgcagtc tgacctctac actctgagca gctcagtgac tgtcccctcc  600
agcacctggc ccagcgagac cgtcacctgc aacgttgccc acccggccag cagcaccaag  660
gtggacaaga aaattgtgcc cagggattgt ggttgtaagc cttgcatatg tacagtccca  720
gaagtatcat ctgtcttcat cttcccccca aagcccaagg atgtgctcac cattactctg  780
actcctaagg tcacgtgtgt tgtggtagac atcagcaagg atgatcccga ggtccagttc  840
agctggtttg tagatgatgt ggaggtgcac acagctcaga cgcaaccccg ggaggagcag  900
ttcaacagca ctttccgctc agtcagtgaa cttcccatca tgcaccagga ctggctcaat  960
ggcaaggagt tcaaatgcag ggtcaacagt gcagctttcc ctgcccccat cgagaaaacc  1020
atctccaaaa ccaaaggcag accgaaggct ccacaggtgt acaccattcc acctcccaag  1080
gagcagatgg ccaaggataa agtcagtctg acctgcatga taacagactt cttccctgaa  1140
gacattactg tggagtggca gtggaatggg cagccagcgg agaactacaa gaacactcag  1200
cccatcatgg acacagatgg ctcttacttc gtctacagca agctcaatgt gcagaagagc  1260
aactgggagg caggaaatac tttcacctgc tctgtgttac atgagggcct gcacaaccac  1320
catactgaga agagcctctc ccactctcct ggtaaatga                         1359

SEQ ID NO: 31          moltype = AA  length = 213
FEATURE                Location/Qualifiers
source                 1..213
                       mol_type = protein
                       organism = Mus musculus
SEQUENCE: 31
QIVLTQSPTI VSASPGEKVT LICSASSSVS FVDWFQQKPG TSPKRWIYRT SNLGFGVPAR  60
FSGGGSGTSH SLTISRMEAE DAATYYCQQR STYPPTFGAG TKLELKRADA APTVSIFPPS  120
```

-continued

```
SEQLTSGGAS VVCFLNNFYP KDINVKWKID GSERQNGVLN SWTDQDSKDS TYSMSSTLTL  180
TKDEYERHNS YTCEATHKTS TSPIVKSFNR NEC                              213

SEQ ID NO: 32          moltype = DNA  length = 642
FEATURE                Location/Qualifiers
source                 1..642
                       mol_type = other DNA
                       organism = Mus musculus
SEQUENCE: 32
caaattgttc tcacccagtc tccaacaatc gtgtctgcat ctccagggga gaaggtcacc  60
ctaatctgca gtgccagttc aagtgtaagt ttcgtggact ggttccagca gaagccaggc  120
acttctccca aacgctggat ttacagaaca tccaacctgg gttttggagt ccctgctcgc  180
ttcagtggcg gtggatctgg gacctctcac tctctcacaa tcagccgaat ggaggctgaa  240
gatgctgcca cttattactg ccagcaaagg agtacttacc cacccacgtt cggtgctggg  300
accaagctgg aactgaaacg ggctgatgct gcaccaactg tatccatctt cccaccatcc  360
agtgagcagt taacatctgg aggtgcctca gtcgtgtgct tcttgaacaa cttctacccc  420
aaagacatca atgtcaagtg gaagattgat ggcagtgaac gacaaaatgg cgtcctgaac  480
agttggactg atcaggacag caaagacagc acctacagca tgagcagcac cctcacgttg  540
accaaggacg agtatgaacg acataacagc tatacctgtg aggccactca caagacatca  600
acttcaccca ttgtcaagag cttcaacagg aatgagtgtt ag                    642

SEQ ID NO: 33          moltype = AA  length = 235
FEATURE                Location/Qualifiers
source                 1..235
                       mol_type = protein
                       organism = Mus musculus
SEQUENCE: 33
MHFQVQIFSF LLISASVIVS RGQIVLTQSP TIVSASPGEK VTLICSASSS VSFVDWFQQK  60
PGTSPKRWIY RTSNLGFGVP ARFSGGGSGT SHSLTISRME AEDAATYYCQ QRSTYPPTFG  120
AGTKLELKRA DAAPTVSIFP PSSEQLTSGG ASVVCFLNNF YPKDINVKWK IDGSERQNGV  180
LNSWTDQDSK DSTYSMSSTL TLTKDEYERH NSYTCEATHK TSTSPIVKSF NRNEC       235

SEQ ID NO: 34          moltype = DNA  length = 708
FEATURE                Location/Qualifiers
source                 1..708
                       mol_type = other DNA
                       organism = Mus musculus
SEQUENCE: 34
atgcattttc aagtgcagat tttcagcttc ctgctaatca gtgcctcagt catagtgtcc  60
agagggcaaa ttgttctcac ccagtctcca acaatcgtgt ctgcatctcc aggggagaag  120
gtcaccctaa tctgcagtgc cagttcaagt gtaagtttcg tggactggtt ccagcagaag  180
ccaggcactt ctcccaaacg ctggatttac agaacatcca acctgggttt tggagtccct  240
gctcgcttca gtggcggtgg atctgggacc tctcactctc tcacaatcag ccgaatggag  300
gctgaagatg ctgccactta ttactgccag caaaggagta cttacccacc cacgttcggt  360
gctgggacca agctggaact gaaacgggct gatgctgcac caactgtatc catcttccca  420
ccatccagtg agcagttaac atctggaggt gcctcagtcg tgtgcttctt gaacaacttc  480
taccccaaag acatcaatgt caagtggaag attgatggca gtgaacgaca aaatggcgtc  540
ctgaacagtt ggactgatca ggacagcaaa gacagcacct acagcatgag cagcaccctc  600
acgttgacca aggacgagta tgaacgacat aacagctata cctgtgaggc cactcacaag  660
acatcaactt cacccattgt caagagcttc aacaggaatg agtgttag              708

SEQ ID NO: 35          moltype = AA  length = 449
FEATURE                Location/Qualifiers
source                 1..449
                       mol_type = protein
                       organism = Mus musculus
SEQUENCE: 35
QVTLKESGPG ILQPSQTLSL TCSFSGFSLS TSGMGVGWIR HPSGKNLEWL AHIWWDDVKR  60
YNPVLKSRLT ISKDTSNSQV FLKIANVDTA DTATYYCARI EDFDYDEEYY AMDYWGQGTS  120
VIVSSAKTTP PSVYPLAPGS AAQTNSMVTL GCLVKGYFPE PVTVTWNSGS LSSGVHTFPA  180
VLQSDLYTLS SSVTVPSSTW PSETVTCNVA HPASSTKVDK KIVPRDCGCK PCICTVPEVS  240
SVFIFPPKPK DVLTITLTPK VTCVVVDISK DDPEVQFSWF VDDVEVHTAQ TQPREEQFNS  300
TFRSVSELPI MHQDWLNGKE FKCRVNSAAF PAPIEKTISK TKGRPKAPQV YTIPPPKEQM  360
AKDKVSLTCM ITDFFPEDIT VEWQWNGQPA ENYKNTQPIM DTDGSYFVYS KLNVQKSNWE  420
AGNTFTCSVL HEGLHNHHTE KSLSHSPGK                                   449

SEQ ID NO: 36          moltype = DNA  length = 1350
FEATURE                Location/Qualifiers
source                 1..1350
                       mol_type = other DNA
                       organism = Mus musculus
SEQUENCE: 36
caggttactc tgaaagagtc tggccctggg atattgcagc cctcccagac cctcagtctg  60
acttgttctt tctctgggtt ttcactgagc acttctggta tgggtgtagg ctggattcgt  120
cacccatcag ggaagaatct ggagtggctg gcacacattt ggtgggatga tgtcaagcgc  180
tataacccag tcctgaagag ccgactgact atctccaagg atacctccaa cagccaggta  240
ttcctcaaga tcgccaatgt ggacactgca gatactgcca catactactg tgctcgaata  300
gaggactttg attacgacga ggagtattat gctatggact actggggtca aggaacctca  360
gtcatcgtct cctcagccaa aacgacaccc ccatctgtct atccactggc ccctggatct  420
```

```
gctgcccaaa ctaactccat ggtgaccctg ggatgcctgg tcaagggcta tttccctgag  480
ccagtgacag tgacctggaa ctctggatcc ctgtccagcg gtgtgcacac cttcccagct  540
gtcctgcagt ctgacctcta cactctgagc agctcagtga ctgtcccctc cagcacctgg  600
cccagcgaga ccgtcacctg caacgttgcc cacccggcca gcagcaccaa ggtggacaag  660
aaaattgtgc ccagggattg tggttgtaag ccttgcatat gtacagtccc agaagtatca  720
tctgtcttca tcttcccccc aaagcccaag gatgtgctca ccattactct gactcctaag  780
gtcacgtgtg ttgtggtaga catcagcaag gatgatcccg aggtccagtt cagctggttt  840
gtagatgatg tggaggtgca cacagctcag acgcaacccc gggaggagca gttcaacagc  900
actttccgct cagtcagtga acttcccatc atgcaccagg actggctcaa tggcaaggag  960
ttcaaatgca gggtcaacag tgcagctttc cctgccccca tcgagaaaac catctccaaa  1020
accaaaggca gaccgaaggc tccacaggtg tacaccattc cacctcccaa ggagcagatg  1080
gccaaggata aagtcagtct gacctgcatg ataacagact tcttccctga agacattact  1140
gtggagtggc agtggaatgg gcagccagcg gagaactaca agaacactca gcccatcatg  1200
gacacagatg gctcttactt cgtctacagc aagctcaatg tgcagaagag caactgggag  1260
gcaggaaata ctttcacctg ctctgtgtta catgagggcc tgcacaacca ccatactgag  1320
aagagcctct cccactctcc tggtaaatga                                  1350

SEQ ID NO: 37          moltype = AA  length = 468
FEATURE                Location/Qualifiers
source                 1..468
                       mol_type = protein
                       organism = Mus musculus
SEQUENCE: 37
MGRLTSSFLL LIVPAYVLSQ VTLKESGPGI LQPSQTLSLT CSFSGFSLST SGMGVGWIRH  60
PSGKNLEWLA HIWWDDVKRY NPVLKSRLTI SKDTSNSQVF LKIANVDTAD TATYYCARIE  120
DFDYDEEYYA MDYWGQGTSV IVSSAKTTPP SVYPLAPGSA AQTNSMVTLG CLVKGYFPEP  180
VTVTWNSGSL SSGVHTFPAV LQSDLYTLSS SVTVPSSTWP SETVTCNVAH PASSTKVDKK  240
IVPRDCGCKP CICTVPEVSS VFIFPPKPKD VLTITLTPKV TCVVVDISKD DPEVQFSWFV  300
DDVEVHTAQT QPREEQFNST FRSVSELPIM HQDWLNGKEF KCRVNSAAFP APIEKTISKT  360
KGRPKAPQVY TIPPPKEQMA KDKVSLTCMI TDFFPEDITV EWQWNGQPAE NYKNTQPIMD  420
TDGSYFVYSK LNVQKSNWEA GNTFTCSVLH EGLHNHHTEK SLSHSPGK                468

SEQ ID NO: 38          moltype = DNA  length = 1407
FEATURE                Location/Qualifiers
source                 1..1407
                       mol_type = other DNA
                       organism = Mus musculus
SEQUENCE: 38
atgggcaggc ttacttcttc attcctgcta ctgattgtcc ctgcatatgt cctgtcccag  60
gttactctga aagagtctgg ccctgggata ttgcagccct cccagaccct cagtctgact  120
tgttctttct ctgggttttc actgagcact tctggtatgg gtgtaggctg gattcgtcac  180
ccatcaggga agaatctgga gtggctggca cacatttggt gggatgatgt caagcgctat  240
aacccagtcc tgaagagccg actgactatc tccaaggata cctccaacag ccaggtattc  300
ctcaagatcg ccaatgtgga cactgcagat actgccacat actactgtgc tcgaatagag  360
gactttgatt acgacgagga gtattatgct atggactact ggggtcaagg aacctcagtc  420
atcgtctcct cagccaaaac gacaccccca tctgtctatc cactggcccc tggatctgct  480
gcccaaacta actccatggt gaccctggga tgcctggtca agggctattt ccctgagcca  540
gtgacagtga cctggaactc tggatccctg tccagcggtg tgcacacctt cccagctgtc  600
ctgcagtctg acctctacac tctgagcagc tcagtgactg tcccctccag cacctggccc  660
agcgagaccg tcacctgcaa cgttgcccac ccggccagca gcaccaaggt ggacaagaaa  720
attgtgccca gggattgtgg ttgtaagcct tgcatatgta cagtcccaga agtatcatct  780
gtcttcatct tccccccaaa gcccaaggat gtgctcacca ttactctgac tcctaaggtc  840
acgtgtgttg tggtagacat cagcaaggat gatcccgagg tccagttcag ctggtttgta  900
gatgatgtgg aggtgcacac agctcagacg caaccccggg aggagcagtt caacagcact  960
ttccgctcag tcagtgaact tcccatcatg caccaggact ggctcaatgg caaggagttc  1020
aaatgcaggg tcaacagtgc agctttccct gcccccatcg agaaaaccat ctccaaaacc  1080
aaaggcagac cgaaggctcc acaggtgtac accattccac ctcccaagga gcagatggcc  1140
aaggataaag tcagtctgac ctgcatgata acagacttct tccctgaaga cattactgtg  1200
gagtggcagt ggaatgggca gccagcggag aactacaaga acactcagcc catcatggac  1260
acagatggct cttacttcgt ctacagcaag ctcaatgtgc agaagagcaa ctgggaggca  1320
ggaaatactt tcacctgctc tgtgttacat gagggcctgc acaaccacca tactgagaag  1380
agcctctccc actctcctgg taaatga                                      1407

SEQ ID NO: 39          moltype = AA  length = 5
FEATURE                Location/Qualifiers
source                 1..5
                       mol_type = protein
                       organism = Mus musculus
SEQUENCE: 39
DHYMS                                                              5

SEQ ID NO: 40          moltype = AA  length = 17
FEATURE                Location/Qualifiers
source                 1..17
                       mol_type = protein
                       organism = Mus musculus
SEQUENCE: 40
DINPYSGETT YNQKFKG                                                 17
```

-continued

```
SEQ ID NO: 41           moltype = AA  length = 10
FEATURE                 Location/Qualifiers
source                  1..10
                        mol_type = protein
                        organism = Mus musculus
SEQUENCE: 41
DDYDASPFAY                                                            10

SEQ ID NO: 42           moltype = AA  length = 11
FEATURE                 Location/Qualifiers
source                  1..11
                        mol_type = protein
                        organism = Mus musculus
SEQUENCE: 42
QASQGTSINL N                                                          11

SEQ ID NO: 43           moltype = AA  length = 7
FEATURE                 Location/Qualifiers
source                  1..7
                        mol_type = protein
                        organism = Mus musculus
SEQUENCE: 43
GSSNLED                                                               7

SEQ ID NO: 44           moltype = AA  length = 9
FEATURE                 Location/Qualifiers
source                  1..9
                        mol_type = protein
                        organism = Mus musculus
SEQUENCE: 44
LQHSYLPYT                                                             9

SEQ ID NO: 45           moltype = AA  length = 5
FEATURE                 Location/Qualifiers
source                  1..5
                        mol_type = protein
                        organism = Mus musculus
SEQUENCE: 45
DCYMN                                                                 5

SEQ ID NO: 46           moltype = AA  length = 17
FEATURE                 Location/Qualifiers
source                  1..17
                        mol_type = protein
                        organism = Mus musculus
SEQUENCE: 46
DINPFNGGTT YNQKFKG                                                    17

SEQ ID NO: 47           moltype = AA  length = 16
FEATURE                 Location/Qualifiers
source                  1..16
                        mol_type = protein
                        organism = Mus musculus
SEQUENCE: 47
SHYYFDGRVP WDAMDY                                                     16

SEQ ID NO: 48           moltype = AA  length = 15
FEATURE                 Location/Qualifiers
source                  1..15
                        mol_type = protein
                        organism = Mus musculus
SEQUENCE: 48
KASQSVDYDG DSYMN                                                      15

SEQ ID NO: 49           moltype = AA  length = 7
FEATURE                 Location/Qualifiers
source                  1..7
                        mol_type = protein
                        organism = Mus musculus
SEQUENCE: 49
AASNLES                                                               7

SEQ ID NO: 50           moltype = AA  length = 9
FEATURE                 Location/Qualifiers
source                  1..9
                        mol_type = protein
                        organism = Mus musculus
SEQUENCE: 50
QQSNEDPWT                                                             9
```

-continued

```
SEQ ID NO: 51          moltype = AA  length = 5
FEATURE                Location/Qualifiers
REGION                 1..5
                       note = Synthetic Polypeptide
REGION                 1..5
                       note = MISC_FEATURE - Rabbit-mouse chimera
source                 1..5
                       mol_type = protein
                       organism = synthetic construct
SEQUENCE: 51
SYWMN                                                                  5

SEQ ID NO: 52          moltype = AA  length = 16
FEATURE                Location/Qualifiers
REGION                 1..16
                       note = Synthetic Polypeptide
REGION                 1..16
                       note = MISC_FEATURE - Rabbit-mouse chimera
source                 1..16
                       mol_type = protein
                       organism = synthetic construct
SEQUENCE: 52
TIDSGGRTDY ASWAKG                                                      16

SEQ ID NO: 53          moltype = AA  length = 4
FEATURE                Location/Qualifiers
REGION                 1..4
                       note = Synthetic Polypeptide
REGION                 1..4
                       note = MISC_FEATURE - Rabbit-Mouse Chimera
source                 1..4
                       mol_type = protein
                       organism = synthetic construct
SEQUENCE: 53
NWNL                                                                   4

SEQ ID NO: 54          moltype = AA  length = 13
FEATURE                Location/Qualifiers
REGION                 1..13
                       note = Synthetic Polypeptide
REGION                 1..13
                       note = MISC_FEATURE - Rabbit-mouse chimera
source                 1..13
                       mol_type = protein
                       organism = synthetic construct
SEQUENCE: 54
QSSQSVYDNN WLA                                                         13

SEQ ID NO: 55          moltype = AA  length = 7
FEATURE                Location/Qualifiers
REGION                 1..7
                       note = Synthetic Polypeptide
REGION                 1..7
                       note = MISC_FEATURE - Rabbit-mouse chimera
source                 1..7
                       mol_type = protein
                       organism = synthetic construct
SEQUENCE: 55
DASDLAS                                                                7

SEQ ID NO: 56          moltype = AA  length = 10
FEATURE                Location/Qualifiers
REGION                 1..10
                       note = Synthetic Polypeptide
REGION                 1..10
                       note = MISC_FEATURE - Rabbit-mouse chimera
source                 1..10
                       mol_type = protein
                       organism = synthetic construct
SEQUENCE: 56
QGAYNDVIYA                                                             10

SEQ ID NO: 57          moltype = AA  length = 7
FEATURE                Location/Qualifiers
source                 1..7
                       mol_type = protein
                       organism = Mus musculus
SEQUENCE: 57
```

-continued

```
TSGMGVG                                                                  7

SEQ ID NO: 58          moltype = AA  length = 16
FEATURE                Location/Qualifiers
source                 1..16
                       mol_type = protein
                       organism = Mus musculus
SEQUENCE: 58
HIWWDDVKRY NPVLKS                                                       16

SEQ ID NO: 59          moltype = AA  length = 14
FEATURE                Location/Qualifiers
source                 1..14
                       mol_type = protein
                       organism = Mus musculus
SEQUENCE: 59
EDFDYDEEYY AMDY                                                         14

SEQ ID NO: 60          moltype = AA  length = 10
FEATURE                Location/Qualifiers
source                 1..10
                       mol_type = protein
                       organism = Mus musculus
SEQUENCE: 60
SASSSVSFVD                                                              10

SEQ ID NO: 61          moltype = AA  length = 7
FEATURE                Location/Qualifiers
source                 1..7
                       mol_type = protein
                       organism = Mus musculus
SEQUENCE: 61
RTSNLGF                                                                  7

SEQ ID NO: 62          moltype = AA  length = 9
FEATURE                Location/Qualifiers
source                 1..9
                       mol_type = protein
                       organism = Mus musculus
SEQUENCE: 62
QQRSTYPPT                                                                9

SEQ ID NO: 63          moltype = AA  length = 20
FEATURE                Location/Qualifiers
source                 1..20
                       mol_type = protein
                       organism = Homo sapiens
SEQUENCE: 63
CGPARLLPNA IGRGKWWRPS                                                   20

SEQ ID NO: 64          moltype = AA  length = 20
FEATURE                Location/Qualifiers
source                 1..20
                       mol_type = protein
                       organism = Homo sapiens
SEQUENCE: 64
GPARLLPNAI GRGKWWRPSG                                                   20

SEQ ID NO: 65          moltype = AA  length = 20
FEATURE                Location/Qualifiers
source                 1..20
                       mol_type = protein
                       organism = Homo sapiens
SEQUENCE: 65
PARLLPNAIG RGKWWRPSGP                                                   20

SEQ ID NO: 66          moltype = AA  length = 20
FEATURE                Location/Qualifiers
source                 1..20
                       mol_type = protein
                       organism = Homo sapiens
SEQUENCE: 66
ARLLPNAIGR GKWWRPSGPD                                                   20

SEQ ID NO: 67          moltype = AA  length = 20
FEATURE                Location/Qualifiers
source                 1..20
                       mol_type = protein
                       organism = Homo sapiens
```

```
SEQUENCE: 67
RLLPNAIGRG KWWRPSGPDF                                          20

SEQ ID NO: 68          moltype = AA  length = 20
FEATURE                Location/Qualifiers
source                 1..20
                       mol_type = protein
                       organism = Homo sapiens
SEQUENCE: 68
LLPNAIGRGK WWRPSGPDFR                                          20

SEQ ID NO: 69          moltype = AA  length = 20
FEATURE                Location/Qualifiers
source                 1..20
                       mol_type = protein
                       organism = Homo sapiens
SEQUENCE: 69
LPNAIGRGKW WRPSGPDFRC                                          20

SEQ ID NO: 70          moltype = AA  length = 14
FEATURE                Location/Qualifiers
source                 1..14
                       mol_type = protein
                       organism = Homo sapiens
SEQUENCE: 70
SAKPVTELVC SGQC                                                14

SEQ ID NO: 71          moltype = AA  length = 7
FEATURE                Location/Qualifiers
source                 1..7
                       mol_type = protein
                       organism = Homo sapiens
SEQUENCE: 71
LVASCKC                                                        7

SEQ ID NO: 72          moltype = AA  length = 8
FEATURE                Location/Qualifiers
source                 1..8
                       mol_type = protein
                       organism = Homo sapiens
SEQUENCE: 72
CRELHFTR                                                       8

SEQ ID NO: 73          moltype = AA  length = 7
FEATURE                Location/Qualifiers
source                 1..7
                       mol_type = protein
                       organism = Homo sapiens
SEQUENCE: 73
CIPDRYR                                                        7

SEQ ID NO: 74          moltype = DNA  length = 399
FEATURE                Location/Qualifiers
misc_feature           1..399
                       note = Synthetic Polynucleotide
misc_feature           1..399
                       note = Humanized Antibody Sequence
source                 1..399
                       mol_type = other DNA
                       organism = synthetic construct
SEQUENCE: 74
atggacacga gggcccccac tcagctgctg gggctcctgc tgctctggct cccaggtgcc  60
acatttgctc aagttctgac ccagagtcca agcagtctct ccgccagcgt aggcgatcgt  120
gtgactatta cctgtcaatc tagtcagagc gtgtatgata acaattggct ggcgtggtac  180
cagcaaaaac cgggcaaagc ccgaagctg ctcatctatg acgcgtccga tctggctagc  240
ggtgtgccaa gccgtttcag tggcagtggc agcggtactg actttaccct cacaatttcg  300
tctctccagc cggaagattt cgccacttac tattgtcaag gtgcttacaa cgatgtgatt  360
tatgccttcg gtcagggcac taaagtagaa atcaaacgt                     399

SEQ ID NO: 75          moltype = AA  length = 133
FEATURE                Location/Qualifiers
REGION                 1..133
                       note = Synthetic Polypeptide
REGION                 1..133
                       note = MISC_FEATURE - Humanized Antibody Sequence
source                 1..133
                       mol_type = protein
                       organism = synthetic construct
SEQUENCE: 75
```

-continued

```
MDTRAPTQLL GLLLLWLPGA TFAQVLTQSP SSLSASVGDR VTITCQSSQS VYDNNWLAWY  60
QQKPGKAPKL LIYDASDLAS GVPSRFSGSG SGTDFTLTIS SLQPEDFATY YCQGAYNDVI  120
YAFGQGTKVE IKR                                                    133

SEQ ID NO: 76          moltype = DNA  length = 393
FEATURE                Location/Qualifiers
misc_feature           1..393
                       note = Synthetic Polynucleotide
misc_feature           1..393
                       note = Humanized Antibody Sequence
source                 1..393
                       mol_type = other DNA
                       organism = synthetic construct
SEQUENCE: 76
atggagactg ggctgcgctg gcttctcctg gtcgctgtgc tcaaaggtgt ccactgtgag  60
gtgcagctgt tggagtctgg aggcgggctt gtccagcctg gagggagcct gcgtctctct  120
tgtgcagcaa gcggcttcag cttatcctct tactggatga attgggtgcg gcaggcacct  180
gggaagggcc tggagtgggt gggcaccatt gattccggag gccgtacaga ctacgcgtct  240
tgggcaaagg gccgtttcac catttcccgc gacaactcca aaaataccat gtacctccag  300
atgaactctc tccgcgcaga ggacacagca cgttattact gtgcacgcaa ctggaatctg  360
tggggtcaag gtactcttgt aacagtctcg agc                              393

SEQ ID NO: 77          moltype = AA  length = 131
FEATURE                Location/Qualifiers
REGION                 1..131
                       note = Synthetic Polypeptide
REGION                 1..131
                       note = MISC_FEATURE - Humanized Antibody Sequence
source                 1..131
                       mol_type = protein
                       organism = synthetic construct
SEQUENCE: 77
METGLRWLLL VAVLKGVHCE VQLLESGGGL VQPGGSLRLS CAASGFSLSS YWMNWVRQAP  60
GKGLEWVGTI DSGGRTDYAS WAKGRFTISR DNSKNTMYLQ MNSLRAEDTA RYYCARNWNL  120
WGQGTLVTVS S                                                      131

SEQ ID NO: 78          moltype = AA  length = 11
FEATURE                Location/Qualifiers
source                 1..11
                       mol_type = protein
                       organism = Mus musculus
SEQUENCE: 78
RASQDISNYL N                                                      11

SEQ ID NO: 79          moltype = AA  length = 7
FEATURE                Location/Qualifiers
source                 1..7
                       mol_type = protein
                       organism = Mus musculus
SEQUENCE: 79
YTSRLLS                                                           7

SEQ ID NO: 80          moltype = AA  length = 9
FEATURE                Location/Qualifiers
source                 1..9
                       mol_type = protein
                       organism = Mus musculus
SEQUENCE: 80
QQGDTLPYT                                                         9

SEQ ID NO: 81          moltype = AA  length = 11
FEATURE                Location/Qualifiers
source                 1..11
                       mol_type = protein
                       organism = Mus musculus
SEQUENCE: 81
RASQDISNYL N                                                      11

SEQ ID NO: 82          moltype = AA  length = 24
FEATURE                Location/Qualifiers
source                 1..24
                       mol_type = protein
                       organism = Rattus norvegicus
SEQUENCE: 82
QGWQAFKNDA TEIIPGLREY PEPP                                        24

SEQ ID NO: 83          moltype = AA  length = 20
FEATURE                Location/Qualifiers
source                 1..20
```

```
                        mol_type = protein
                        organism = Rattus norvegicus
SEQUENCE: 83
TEIIPGLREY PEPPQELENN                                           20

SEQ ID NO: 84           moltype = AA  length = 20
FEATURE                 Location/Qualifiers
source                  1..20
                        mol_type = protein
                        organism = Rattus norvegicus
SEQUENCE: 84
PEPPQELENN QTMNRAENGG                                           20

SEQ ID NO: 85           moltype = AA  length = 20
FEATURE                 Location/Qualifiers
source                  1..20
                        mol_type = protein
                        organism = Rattus norvegicus
SEQUENCE: 85
ENGGRPPHHP YDTKDVSEYS                                           20

SEQ ID NO: 86           moltype = AA  length = 14
FEATURE                 Location/Qualifiers
source                  1..14
                        mol_type = protein
                        organism = Rattus norvegicus
SEQUENCE: 86
CRELHYTRFV TDGP                                                 14

SEQ ID NO: 87           moltype = AA  length = 25
FEATURE                 Location/Qualifiers
source                  1..25
                        mol_type = protein
                        organism = Rattus norvegicus
SEQUENCE: 87
CRELHYTRFV TDGPSRSAKP VTELV                                     25

SEQ ID NO: 88           moltype = AA  length = 23
FEATURE                 Location/Qualifiers
source                  1..23
                        mol_type = protein
                        organism = Rattus norvegicus
SEQUENCE: 88
CRSAKPVTEL VSSGQSGPRA RLL                                       23

SEQ ID NO: 89           moltype = AA  length = 25
FEATURE                 Location/Qualifiers
source                  1..25
                        mol_type = protein
                        organism = Rattus norvegicus
SEQUENCE: 89
CGPARLLPNA IGRVKWWRPN GPDFR                                     25

SEQ ID NO: 90           moltype = AA  length = 20
FEATURE                 Location/Qualifiers
source                  1..20
                        mol_type = protein
                        organism = Rattus norvegicus
SEQUENCE: 90
RAQRVQLLCP GGAAPRSRKV                                           20

SEQ ID NO: 91           moltype = AA  length = 16
FEATURE                 Location/Qualifiers
source                  1..16
                        mol_type = protein
                        organism = Rattus norvegicus
SEQUENCE: 91
PGGAAPRSRK VRLVAS                                               16

SEQ ID NO: 92           moltype = AA  length = 23
FEATURE                 Location/Qualifiers
source                  1..23
                        mol_type = protein
                        organism = Rattus norvegicus
SEQUENCE: 92
KRLTRFHNQS ELKDFGPETA RPQ                                       23

SEQ ID NO: 93           moltype = AA  length = 16
FEATURE                 Location/Qualifiers
```

```
source                 1..16
                       mol_type = protein
                       organism = Rattus norvegicus
SEQUENCE: 93
IPDRYAQRVQ LLSPGG                                            16

SEQ ID NO: 94          moltype = AA  length = 24
FEATURE                Location/Qualifiers
source                 1..24
                       mol_type = protein
                       organism = Rattus norvegicus
SEQUENCE: 94
SELKDFGPET ARPQKGRKPR PRAR                                   24

SEQ ID NO: 95          moltype = AA  length = 23
FEATURE                Location/Qualifiers
source                 1..23
                       mol_type = protein
                       organism = Rattus norvegicus
SEQUENCE: 95
KGRKPRPRAR GAKANQAELE NAY                                    23

SEQ ID NO: 96          moltype = AA  length = 18
FEATURE                Location/Qualifiers
source                 1..18
                       mol_type = protein
                       organism = Rattus norvegicus
SEQUENCE: 96
PNAIGRVKWW RPNGPDFR                                          18

SEQ ID NO: 97          moltype = AA  length = 22
FEATURE                Location/Qualifiers
source                 1..22
                       mol_type = protein
                       organism = Rattus norvegicus
SEQUENCE: 97
KWWRPNGPDF RCIPDRYRAQ RV                                     22

SEQ ID NO: 98          moltype = AA  length = 213
FEATURE                Location/Qualifiers
source                 1..213
                       mol_type = protein
                       organism = Rattus norvegicus
SEQUENCE: 98
MQLSLAPCLA CLLVHAAFVA VESQGWQAFK NDATEIIPGL REYPEPPQEL ENNQTMNRAE  60
NGGRPPHHPY DTKDVSEYSC RELHYTRFVT DGPCRSAKPV TELVCSGQCG PARLLPNAIG  120
RVKWWRPNGP DFRCIPDRYR AQRVQLLCPG GAAPRSRKVR LVASCKCKRL TRFHNQSELK  180
DFGPETARPQ KGRKPRPRAR GAKANQAELE NAY                           213

SEQ ID NO: 99          moltype = AA  length = 7
FEATURE                Location/Qualifiers
source                 1..7
                       mol_type = protein
                       organism = Mus musculus
SEQUENCE: 99
YTSRLHS                                                      7

SEQ ID NO: 100         moltype = AA  length = 9
FEATURE                Location/Qualifiers
source                 1..9
                       mol_type = protein
                       organism = Mus musculus
SEQUENCE: 100
QQGDTLPYT                                                    9

SEQ ID NO: 101         moltype = AA  length = 11
FEATURE                Location/Qualifiers
source                 1..11
                       mol_type = protein
                       organism = Mus musculus
SEQUENCE: 101
RASQVITNYL Y                                                 11

SEQ ID NO: 102         moltype = AA  length = 7
FEATURE                Location/Qualifiers
source                 1..7
                       mol_type = protein
                       organism = Mus musculus
SEQUENCE: 102
```

-continued

```
YTSRLHS                                                          7

SEQ ID NO: 103          moltype = AA  length = 9
FEATURE                 Location/Qualifiers
source                  1..9
                        mol_type = protein
                        organism = Mus musculus
SEQUENCE: 103
QQGDTLPYT                                                        9

SEQ ID NO: 104          moltype = AA  length = 11
FEATURE                 Location/Qualifiers
source                  1..11
                        mol_type = protein
                        organism = Mus musculus
SEQUENCE: 104
RASQDISNYL N                                                     11

SEQ ID NO: 105          moltype = AA  length = 7
FEATURE                 Location/Qualifiers
source                  1..7
                        mol_type = protein
                        organism = Mus musculus
SEQUENCE: 105
YTSRLLS                                                          7

SEQ ID NO: 106          moltype = AA  length = 9
FEATURE                 Location/Qualifiers
source                  1..9
                        mol_type = protein
                        organism = Mus musculus
SEQUENCE: 106
QQGDTLPYT                                                        9

SEQ ID NO: 107          moltype = AA  length = 11
FEATURE                 Location/Qualifiers
source                  1..11
                        mol_type = protein
                        organism = Mus musculus
SEQUENCE: 107
RASQDISNYL N                                                     11

SEQ ID NO: 108          moltype = AA  length = 7
FEATURE                 Location/Qualifiers
source                  1..7
                        mol_type = protein
                        organism = Mus musculus
SEQUENCE: 108
YTSRLFS                                                          7

SEQ ID NO: 109          moltype = AA  length = 9
FEATURE                 Location/Qualifiers
source                  1..9
                        mol_type = protein
                        organism = Mus musculus
SEQUENCE: 109
QQGDTLPYT                                                        9

SEQ ID NO: 110          moltype = AA  length = 11
FEATURE                 Location/Qualifiers
source                  1..11
                        mol_type = protein
                        organism = Mus musculus
SEQUENCE: 110
RASQDISNYL N                                                     11

SEQ ID NO: 111          moltype = AA  length = 7
FEATURE                 Location/Qualifiers
source                  1..7
                        mol_type = protein
                        organism = Mus musculus
SEQUENCE: 111
YTSRLLS                                                          7

SEQ ID NO: 112          moltype = AA  length = 9
FEATURE                 Location/Qualifiers
source                  1..9
                        mol_type = protein
                        organism = Mus musculus
```

-continued

```
SEQUENCE: 112
QQGDTLPYT                                                      9

SEQ ID NO: 113          moltype = AA  length = 11
FEATURE                 Location/Qualifiers
source                  1..11
                        mol_type = protein
                        organism = Mus musculus
SEQUENCE: 113
RASQDISNYL N                                                   11

SEQ ID NO: 114          moltype = AA  length = 7
FEATURE                 Location/Qualifiers
source                  1..7
                        mol_type = protein
                        organism = Mus musculus
SEQUENCE: 114
YTSTLQS                                                        7

SEQ ID NO: 115          moltype = AA  length = 9
FEATURE                 Location/Qualifiers
source                  1..9
                        mol_type = protein
                        organism = Mus musculus
SEQUENCE: 115
QQGDTLPYT                                                      9

SEQ ID NO: 116          moltype = AA  length = 12
FEATURE                 Location/Qualifiers
source                  1..12
                        mol_type = protein
                        organism = Mus musculus
SEQUENCE: 116
SVSSSISSSN LH                                                  12

SEQ ID NO: 117          moltype = AA  length = 213
FEATURE                 Location/Qualifiers
source                  1..213
                        mol_type = protein
                        organism = Mus musculus
SEQUENCE: 117
QIVLSQSPAI LSTSPGEKVT MTCRASSSVY YMHWYQQKPG SSPKPWIYAT SNLASGVPVR  60
FSGSGSGTSY SLTITRVEAE DAATYYCQQW SSDPLTFGAG TKLELKRADA APTVSIFPPS  120
SEQLTSGGAS VVCFLNNFYP KDINVKWKID GSERQNGVLN SWTDQDSKDS TYSMSSTLTL  180
TKDEYERHNS YTCEATHKTS TSPIVKSFNR NEC                             213

SEQ ID NO: 118          moltype = DNA  length = 642
FEATURE                 Location/Qualifiers
source                  1..642
                        mol_type = other DNA
                        organism = Mus musculus
SEQUENCE: 118
caaattgttc tctcccagtc tccagcaatc ctgtctacat ctccagggga gaaggtcaca  60
atgacttgca gggccagctc aagtgtatat tacatgcact ggtaccagca gaagccagga  120
tcctccccca aaccctggat ttatgccaca tccaacctgg cttctggagt ccctgttcgc  180
ttcagtggca gtgggtctgg gacctcttac tctctcacaa tcaccagagt ggaggctgaa  240
gatgctgcca cttattactg ccagcagtgg agtagtgacc cactcacgtt cggtgctggg  300
accaagctgg agctgaaacg ggctgatgct gcaccaactg tatccatctt cccaccatcc  360
agtgagcagt taacatctgg aggtgcctca gtcgtgtgct tcttgaacaa cttctacccc  420
aaagacatca atgtcaagtg gaagattgat ggcagtgaac gacaaaatgg cgtcctgaac  480
agttggactg atcaggacag caaagacagc acctacagca tgagcagcac cctcacgttg  540
accaaggacg agtatgaacg acataacagc tatacctgtg aggccactca caagacatca  600
acttcaccca ttgtcaagag cttcaacagg aatgagtgtt ag                    642

SEQ ID NO: 119          moltype = AA  length = 235
FEATURE                 Location/Qualifiers
source                  1..235
                        mol_type = protein
                        organism = Mus musculus
SEQUENCE: 119
MDFQVQIFSF LLISASVIMS RGQIVLSQSP AILSTSPGEK VTMTCRASSS VYYMHWYQQK  60
PGSSPKPWIY ATSNLASGVP VRFSGSGSGT SYSLTITRVE AEDAATYYCQ QWSSDPLTFG  120
AGTKLELKRA DAAPTVSIFP PSSEQLTSGG ASVVCFLNNF YPKDINVKWK IDGSERQNGV  180
LNSWTDQDSK DSTYSMSSTL TLTKDEYERH NSYTCEATHK TSTSPIVKSF NRNEC       235

SEQ ID NO: 120          moltype = DNA  length = 708
FEATURE                 Location/Qualifiers
source                  1..708
                        mol_type = other DNA
```

-continued

```
                         organism = Mus musculus
SEQUENCE: 120
atggattttc aagtgcagat tttcagcttc ctgctaatca gtgcttcagt cattatgtcc  60
aggggacaaa ttgttctctc ccagtctcca gcaatcctgt ctacatctcc aggggagaag  120
gtcacaatga cttgcagggc cagctcaagt gtatattaca tgcactggta ccagcagaag  180
ccaggatcct cccccaaacc ctggatttat gccacatcca acctggcttc tggagtccct  240
gttcgcttca gtggcagtgg gtctgggacc tcttactctc tcacaatcac cagagtggag  300
gctgaagatg ctgccactta ttactgccag cagtggagta gtgacccact cacgttcggt  360
gctgggacca agctggagct gaaacgggct gatgctgcac caactgtatc catcttccca  420
ccatccagtg agcagttaac atctggaggt gcctcagtcg tgtgcttctt gaacaacttc  480
taccccaaag acatcaatgt caagtggaag attgatggca gtgaacgaca aaatggcgtc  540
ctgaacagtt ggactgatca ggacagcaaa gacagcacct acagcatgag cagcaccctc  600
acgttgacca aggacgagta tgaacgacat aacagctata cctgtgaggc cactcacaag  660
acatcaactt cacccattgt caagagcttc aacaggaatg agtgttag              708

SEQ ID NO: 121           moltype = AA  length = 445
FEATURE                  Location/Qualifiers
source                   1..445
                         mol_type = protein
                         organism = Mus musculus
SEQUENCE: 121
EVQVQQSGPE LVKPGASVKL SCTASGFNIK DYFIHWVKQR PEQGLEWIGR LDPEDGESDY  60
APKFQDKAIM TADTSSNTAY LQLRSLTSED TAIYYCERED YDGTYTFFPY WGQGTLVTVS  120
AAKTTPPSVY PLAPGSAAQT NSMVTLGCLV KGYFPEPVTV TWNSGSLSSG VHTFPAVLQS  180
DLYTLSSSVT VPSSTWPSET VTCNVAHPAS STKVDKKIVP RDCGCKPCIC TVPEVSSVFI  240
FPPKPKDVLT ITLTPKVTCV VVDISKDDPE VQFSWFVDDV EVHTAQTQPR EEQFNSTFRS  300
VSELPIMHQD WLNGKEFKCR VNSAAFPAPI EKTISKTKGR PKAPQVYTIP PPKEQMAKDK  360
VSLTCMITDF FPEDITVEWQ WNGQPAENYK NTQPIMDTDG SYFIYSKLNV QKSNWEAGNT  420
FTCSVLHEGL HNHHTEKSLS HSPGK                                       445

SEQ ID NO: 122           moltype = DNA  length = 1338
FEATURE                  Location/Qualifiers
source                   1..1338
                         mol_type = other DNA
                         organism = Mus musculus
SEQUENCE: 122
gaggttcagg tgcagcagtc tgggccagaa cttgtgaagc caggggcctc agtcaagttg  60
tcctgcacag cttctggctt caacattaaa gactacttta tacactgggt gaagcagagg  120
cctgaacagg gcctggagtg gattggaagg cttgatcctg aggatggtga aagtgattat  180
gccccgaagt tccaggacaa ggccattatg acagcagaca catcatccaa cacagcctat  240
cttcagctca gaagcctgac atctgaggac actgccatct attattgtga gagagaggac  300
tacgatggta cctacacctt ttttccttac tggggccaag ggactctggt cactgtctct  360
gcagccaaaa cgacaccccc atctgtctat ccactggccc ctggatctgc tgcccaaact  420
aactccatgg tgaccctggg atgcctggtc aagggctatt tccctgagcc agtgacagtg  480
acctggaact ctggatccct gtccagcggt gtgcacacct tcccagctgt cctgcagtct  540
gacctctaca ctctgagcag ctcagtgact gtcccctcca gcacctggcc cagcgagacc  600
gtcacctgca acgttgccca cccggccagc agcaccaagg tggacaagaa aattgtgccc  660
agggattgtg gttgtaagcc ttgcatatgt acagtcccag aagtatcatc tgtcttcatc  720
ttccccccaa agcccaagga tgtgctcacc attactctga ctcctaaggt cacgtgtgtt  780
gtggtagaca tcagcaagga tgatcccgag gtccagttca gctggtttgt agatgatgtg  840
gaggtgcaca cagctcagac gcaaccccgg gaggagcagt tcaacagcac tttccgctca  900
gtcagtgaac ttcccatcat gcaccaggac tggctcaatg gcaaggagtt caaatgcagg  960
gtcaacagtg cagctttccc tgcccccatc gagaaaacca tctccaaaac caaaggcaga  1020
ccgaaggctc cacaggtgta caccattcca cctcccaagg agcagatggc caaggataaa  1080
gtcagtctga cctgcatgat aacagacttc ttccctgaag acattactgt ggagtggcag  1140
tggaatgggc agccagcgga gaactacaag aacactcagc ccatcatgga cacagatggc  1200
tcttacttca tctacagcaa gctcaatgtg cagaagagca actgggaggc aggaaatact  1260
ttcacctgct ctgtgttaca tgagggcctg cacaaccacc atactgagaa gagcctctcc  1320
cactctcctg gtaaatga                                               1338

SEQ ID NO: 123           moltype = AA  length = 464
FEATURE                  Location/Qualifiers
source                   1..464
                         mol_type = protein
                         organism = Mus musculus
SEQUENCE: 123
MKCSWVIFFL MAVVTGVNSE VQVQQSGPEL VKPGASVKLS CTASGFNIKD YFIHWVKQRP  60
EQGLEWIGRL DPEDGESDYA PKFQDKAIMT ADTSSNTAYL QLRSLTSEDT AIYYCEREDY  120
DGTYTFFPYW GQGTLVTVSA AKTTPPSVYP LAPGSAAQTN SMVTLGCLVK GYFPEPVTVT  180
WNSGSLSSGV HTFPAVLQSD LYTLSSSVTV PSSTWPSETV TCNVAHPASS TKVDKKIVPR  240
DCGCKPCICT VPEVSSVFIF PPKPKDVLTI TLTPKVTCVV VDISKDDPEV QFSWFVDDVE  300
VHTAQTQPRE EQFNSTFRSV SELPIMHQDW LNGKEFKCRV NSAAFPAPIE KTISKTKGRP  360
KAPQVYTIPP PKEQMAKDKV SLTCMITDFF PEDITVEWQW NGQPAENYKN TQPIMDTDGS  420
YFIYSKLNVQ KSNWEAGNTF TCSVLHEGLH NHHTEKSLSH SPGK                  464

SEQ ID NO: 124           moltype = DNA  length = 1395
FEATURE                  Location/Qualifiers
source                   1..1395
                         mol_type = other DNA
```

```
                         organism = Mus musculus
SEQUENCE: 124
atgaaatgca gctgggtcat cttcttcctg atggcagtgg ttacaggggt caattcagag  60
gttcaggtgc agcagtctgg gccagaactt gtgaagccag gggcctcagt caagttgtcc  120
tgcacagctt ctggcttcaa cattaaagac tactttatac actgggtgaa gcagaggcct  180
gaacagggcc tggagtggat tggaaggctt gatcctgagg atggtgaaag tgattatgcc  240
ccgaagttcc aggacaaggc cattatgaca gcagacacat catccaacac agcctatctt  300
cagctcagaa gcctgacatc tgaggacact gccatctatt attgtgagag agaggactac  360
gatggtacct acaccttttt tccttactgg ggccaaggga ctctggtcac tgtctctgca  420
gccaaaacga cacccccatc tgtctatcca ctggcccctg gatctgctgc ccaaactaac  480
tccatggtga ccctgggatg cctggtcaag ggctatttcc ctgagccagt gacagtgacc  540
tggaactctg gatccctgtc cagcggtgtg cacaccttcc cagctgtcct gcagtctgac  600
ctctacactc tgagcagctc agtgactgtc ccctccagca cctggcccag cgagaccgtc  660
acctgcaacg ttgcccaccc ggccagcagc accaaggtgg acaagaaaat tgtgcccagg  720
gattgtggtt gtaagccttg catatgtaca gtcccagaag tatcatctgt cttcatcttc  780
cccccaaagc ccaaggatgt gctcaccatt actctgactc ctaaggtcac gtgtgttgtg  840
gtagacatca gcaaggatga tcccgaggtc cagttcagct ggtttgtaga tgatgtggag  900
gtgcacacag ctcagacgca accccgggag gagcagttca acagcacttt ccgctcagtc  960
agtgaacttc ccatcatgca ccaggactgg ctcaatggca aggagttcaa atgcagggtc  1020
aacagtgcag ctttccctgc ccccatcgag aaaaccatct ccaaaaccaa aggcagaccg  1080
aaggctccac aggtgtacac cattccacct cccaaggagc agatggccaa ggataaagtc  1140
agtctgacct gcatgataac agacttcttc cctgaagaca ttactgtgga gtggcagtgg  1200
aatgggcagc cagcggagaa ctacaagaac actcagccca tcatggacac agatggctct  1260
tacttcatct acagcaagct caatgtgcag aagagcaact gggaggcagg aaatactttc  1320
acctgctctg tgttacatga gggcctgcac aaccaccata ctgagaagag cctctcccac  1380
tctcctggta aatga                                                  1395

SEQ ID NO: 125          moltype = AA  length = 215
FEATURE                 Location/Qualifiers
source                  1..215
                        mol_type = protein
                        organism = Mus musculus
SEQUENCE: 125
EIVLTQSPAL MAASPGEKVT ITCSVSSTIS SNHLHWFQQK SDTSPKPWIY GTSNLASGVP  60
VRFSGSGSGT SYSLTISSME AEDAATYYCQ QWSSYPLTFG AGTKLELRRA DAAPTVSIFP  120
PSSEQLTSGG ASVVCFLNNF YPKDINVKWK IDGSERQNGV LNSWTDQDSK DSTYSMSSTL  180
TLTKDEYERH NSYTCEATHK TSTSPIVKSF NRNEC                            215

SEQ ID NO: 126          moltype = DNA  length = 648
FEATURE                 Location/Qualifiers
source                  1..648
                        mol_type = other DNA
                        organism = Mus musculus
SEQUENCE: 126
gaaattgtgc tcacccagtc tccagcactc atggctgcat ctccggggga gaaggtcacc  60
atcacctgca gtgtcagttc aactataagt tccaaccact tgcactggtt ccagcagaag  120
tcagacacct cccccaaacc ctggatttat ggcacatcca acctggcttc tggagtccct  180
gttcgcttca gtggcagtgg atctgggacc tcttattctc tcacaatcag cagcatggag  240
gctgaggatg ctgccactta ttactgtcaa cagtggagta gttacccact cacgttcggc  300
gctgggacca agctggagct gagacgggct gatgctgcac caactgtatc catcttccca  360
ccatccagtg agcagttaac atctggaggt gcctcagtcg tgtgcttctt gaacaacttc  420
taccccaaag acatcaatgt caagtggaag attgatggca gtgaacgaca aaatggcgtc  480
ctgaacagtt ggactgatca ggacagcaaa gacagcacct acagcatgag cagcaccctc  540
acgttgacca aggacgagta tgaacgacat aacagctata cctgtgaggc cactcacaag  600
acatcaactt cacccattgt caagagcttc aacaggaatg agtgttag              648

SEQ ID NO: 127          moltype = AA  length = 237
FEATURE                 Location/Qualifiers
source                  1..237
                        mol_type = protein
                        organism = Mus musculus
SEQUENCE: 127
MDFHVQIFSF MLISVTVILS SGEIVLTQSP ALMAASPGEK VTITCSVSST ISSNHLHWFQ  60
QKSDTSPKPW IYGTSNLASG VPVRFSGSGS GTSYSLTISS MEAEDAATYY CQQWSSYPLT  120
FGAGTKLELR RADAAPTVSI FPPSSEQLTS GGASVVCFLN NFYPKDINVK WKIDGSERQN  180
GVLNSWTDQD SKDSTYSMSS TLTLTKDEYE RHNSYTCEAT HKTSTSPIVK SFNRNEC     237

SEQ ID NO: 128          moltype = DNA  length = 714
FEATURE                 Location/Qualifiers
source                  1..714
                        mol_type = other DNA
                        organism = Mus musculus
SEQUENCE: 128
atggattttc atgtgcagat tttcagcttc atgctaatca gtgtcacagt cattttgtcc  60
agtggagaaa ttgtgctcac ccagtctcca gcactcatgg ctgcatctcc gggggagaag  120
gtcaccatca cctgcagtgt cagttcaact ataagttcca accacttgca ctggttccag  180
cagaagtcag acacctcccc caaaccctgg atttatggca catccaacct ggcttctgga  240
gtccctgttc gcttcagtgg cagtggatct gggacctctt attctctcac aatcagcagc  300
atggaggctg aggatgctgc cacttattac tgtcaacagt ggagtagtta cccactcacg  360
```

-continued

```
ttcggcgctg ggaccaagct ggagctgaga cgggctgatg ctgcaccaac tgtatccatc  420
ttcccaccat ccagtgagca gttaacatct ggaggtgcct cagtcgtgtg cttcttgaac  480
aacttctacc ccaaagacat caatgtcaag tggaagattg atggcagtga acgacaaaat  540
ggcgtcctga acagttggac tgatcaggac agcaaagaca gcacctacag catgagcagc  600
accctcacgt tgaccaagga cgagtatgaa cgacataaca gctatacctg tgaggccact  660
cacaagacat caacttcacc cattgtcaag agcttcaaca ggaatgagtg ttag        714

SEQ ID NO: 129         moltype = AA  length = 449
FEATURE                Location/Qualifiers
source                 1..449
                       mol_type = protein
                       organism = Mus musculus
SEQUENCE: 129
EVQLQQSGAE LVRPGALVKL SCTASDFNIK DFYLHWMRQR PEQGLDWIGR IDPENGDTLY  60
DPKFQDKATL TTDTSSNTAY LQLSGLTSET TAVYYCSREA DYFHDGTSYW YFDVWGAGTT  120
ITVSSAKTTP PSVYPLAPGS AAQTNSMVTL GCLVKGYFPE PVTVTWNSGS LSSGVHTFPA  180
VLQSDLYTLS SSVTVPSSTW PSETVTCNVA HPASSTKVDK KIVPRDCGCK PCICTVPEVS  240
SVFIFPPKPK DVLTITLTPK VTCVVVDISK DDPEVQFSWF VDDVEVHTAQ TQPREEQFNS  300
TFRSVSELPI MHQDWLNGKE FKCRVNSAAF PAPIEKTISK TKGRPKAPQV YTIPPPKEQM  360
AKDKVSLTCM ITDFFPEDIT VEWQWNGQPA ENYKNTQPIM DTDGSYFIYS KLNVQKSNWE  420
AGNTFTCSVL HEGLHNHHTE KSLSHSPGK                                  449

SEQ ID NO: 130         moltype = DNA  length = 1350
FEATURE                Location/Qualifiers
source                 1..1350
                       mol_type = other DNA
                       organism = Mus musculus
SEQUENCE: 130
gaggttcagc tgcagcagtc tggggctgaa cttgtgaggc caggggcctt agtcaagttg  60
tcctgcacag cttctgactt caacattaaa gacttctatc tacactggat gaggcagcgg  120
cctgaacagg gcctggactg gattggaagg attgatcctg agaatggtga tactttatat  180
gacccgaagt tccaggacaa ggccactctt acaacagaca catcctccaa cacagcctac  240
ctgcagctca gcggcctgac atctgagacc actgccgtct attactgttc tagagaggcg  300
gattatttcc acgatggtac ctcctactgg tacttcgatg tctggggcgc agggaccaca  360
atcaccgtct cctcagccaa aacgacaccc ccatctgtct atccactggc ccctggatct  420
gctgcccaaa ctaactccat ggtgaccctg ggatgcctgg tcaagggcta tttccctgag  480
ccagtgacag tgacctggaa ctctggatcc ctgtccagcg gtgtgcacac cttcccagct  540
gtcctgcagt ctgacctcta cactctgagc agctcagtga ctgtcccctc cagcacctgg  600
cccagcgaga ccgtcacctg caacgttgcc cacccggcca gcagcaccaa ggtggacaag  660
aaaattgtgc ccagggattg tggttgtaag ccttgcatat gtacagtccc agaagtatca  720
tctgtcttca tcttcccccc aaagcccaag gatgtgctca ccattactct gactcctaag  780
gtcacgtgtg ttgtggtaga catcagcaag gatgatcccg aggtccagtt cagctggttt  840
gtagatgatg tggaggtgca cacagctcag acgcaacccc gggaggagca gttcaacagc  900
actttccgct cagtcagtga acttcccatc atgcaccagg actggctcaa tggcaaggag  960
ttcaaatgca gggtcaacag tgcagctttc cctgccccca tcgagaaaac catctccaaa  1020
accaaaggca gaccgaaggc tccacaggtg tacaccattc cacctcccaa ggagcagatg  1080
gccaaggata aagtcagtct gacctgcatg ataacagact tcttccctga agacattact  1140
gtggagtggc agtggaatgg gcagccagcg gagaactaca agaacactca gcccatcatg  1200
gacacagatg gctcttactt catctacagc aagctcaatg tgcagaagag caactgggag  1260
gcaggaaata ctttcacctg ctctgtgtta catgagggcc tgcacaacca ccatactgag  1320
aagagcctct cccactctcc tggtaaatga                                  1350

SEQ ID NO: 131         moltype = AA  length = 468
FEATURE                Location/Qualifiers
source                 1..468
                       mol_type = protein
                       organism = Mus musculus
SEQUENCE: 131
MKCSWVIFFL MAVVTGVNSE VQLQQSGAEL VRPGALVKLS CTASDFNIKD FYLHWMRQRP  60
EQGLDWIGRI DPENGDTLYD PKFQDKATLT TDTSSNTAYL QLSGLTSETT AVYYCSREAD  120
YFHDGTSYWY FDVWGAGTTI TVSSAKTTPP SVYPLAPGSA AQTNSMVTLG CLVKGYFPEP  180
VTVTWNSGSL SSGVHTFPAV LQSDLYTLSS SVTVPSSTWP SETVTCNVAH PASSTKVDKK  240
IVPRDCGCKP CICTVPEVSS VFIFPPKPKD VLTITLTPKV TCVVVDISKD DPEVQFSWFV  300
DDVEVHTAQT QPREEQFNST FRSVSELPIM HQDWLNGKEF KCRVNSAAFP APIEKTISKT  360
KGRPKAPQVY TIPPPKEQMA KDKVSLTCMI TDFFPEDITV EWQWNGQPAE NYKNTQPIMD  420
TDGSYFIYSK LNVQKSNWEA GNTFTCSVLH EGLHNHHTEK SLSHSPGK              468

SEQ ID NO: 132         moltype = DNA  length = 1407
FEATURE                Location/Qualifiers
source                 1..1407
                       mol_type = other DNA
                       organism = Mus musculus
SEQUENCE: 132
atgaaatgca gctgggtcat cttcttcctg atggcagtgg ttacaggggt caattcagag  60
gttcagctgc agcagtctgg ggctgaactt gtgaggccag gggccttagt caagttgtcc  120
tgcacagctt ctgacttcaa cattaaagac ttctatctac actggatgag gcagcggcct  180
gaacagggcc tggactggat tggaaggatt gatcctgaga atggtgatac tttatatgac  240
ccgaagttcc aggacaaggc cactcttaca acagacacat cctccaacac agcctacctg  300
cagctcagcg gcctgacatc tgagaccact gccgtctatt actgttctag agaggcggat  360
```

-continued

```
tatttccacg atggtacctc ctactggtac ttcgatgtct ggggcgcagg gaccacaatc  420
accgtctcct cagccaaaac gacaccccca tctgtctatc cactggcccc tggatctgct  480
gcccaaacta actccatggt gaccctggga tgcctggtca agggctattt ccctgagcca  540
gtgacagtga cctggaactc tggatccctg tccagcggtg tgcacacctt cccagctgtc  600
ctgcagtctg acctctacac tctgagcagc tcagtgactg tcccctccag cacctggccc  660
agcgagaccg tcacctgcaa cgttgcccac ccggccagca gcaccaaggt ggacaagaaa  720
attgtgccca gggattgtgg ttgtaagcct tgcatatgta cagtcccaga agtatcatct  780
gtcttcatct tccccccaaa gcccaaggat gtgctcacca ttactctgac tcctaaggtc  840
acgtgtgttg tggtagacat cagcaaggat gatcccgagg tccagttcag ctggtttgta  900
gatgatgtgg aggtgcacac agctcagacg caaccccggg aggagcagtt caacagcact  960
ttccgctcag tcagtgaact tcccatcatg caccaggact ggctcaatgg caaggagttc  1020
aaatgcaggg tcaacagtgc agctttccct gcccccatcg agaaaaccat ctccaaaacc  1080
aaaggcagac cgaaggctcc acaggtgtac accattccac ctcccaagga gcagatggcc  1140
aaggataaag tcagtctgac ctgcatgata acagacttct tccctgaaga cattactgtg  1200
gagtggcagt ggaatgggca gccagcggag aactacaaga acactcagcc catcatggac  1260
acagatggct cttacttcat ctacagcaag ctcaatgtgc agaagagcaa ctgggaggca  1320
ggaaatactt tcacctgctc tgtgttacat gagggcctgc acaaccacca tactgagaag  1380
agcctctccc actctcctgg taaatga                                    1407

SEQ ID NO: 133          moltype = AA  length = 214
FEATURE                 Location/Qualifiers
source                  1..214
                        mol_type = protein
                        organism = Mus musculus
SEQUENCE: 133
DIQMTQITSS LSASLGDRVS ISCRASQDIS NYLNWYQQKP DGTFKLLIFY TSRLLSGVPS  60
RFSGSGSGTD YSLTIYNLEQ EDFATYFCQQ GDTLPYTFGG GTKLEIKRAD AAPTVSIFPP  120
SSEQLTSGGA SVVCFLNNFY PKDINVKWKI DGSERQNGVL NSWTDQDSKD STYSMSSTLT  180
LTKDEYERHN SYTCEATHKT STSPIVKSFN RNEC                             214

SEQ ID NO: 134          moltype = DNA  length = 645
FEATURE                 Location/Qualifiers
source                  1..645
                        mol_type = other DNA
                        organism = Mus musculus
SEQUENCE: 134
gatatccaga tgacacagat tacatcctcc ctgtctgcct ctctgggaga cagggtctcc  60
atcagttgca gggcaagtca agacattagc aattatttaa actggtatca gcagaaacca  120
gatggaactt ttaaactcct tatcttctac acatcaagat tactctcagg agtcccatca  180
aggttcagtg gcagtgggtc tggaacagat tattctctca ccatttacaa cctggagcaa  240
gaagattttg ccacttactt ttgccaacag ggagatacgc ttccgtacac tttcggaggg  300
gggaccaagc tggaaataaa acgggctgat gctgcaccaa ctgtatccat cttcccacca  360
tccagtgagc agttaacatc tggaggtgcc tcagtcgtgt gcttcttgaa caacttctac  420
cccaaagaca tcaatgtcaa gtggaagatt gatggcagtg aacgacaaaa tggcgtcctg  480
aacagttgga ctgatcagga cagcaaagac agcacctaca gcatgagcag caccctcacg  540
ttgaccaagg acgagtatga acgacataac agctatacct gtgaggccac tcacaagaca  600
tcaacttcac ccattgtcaa gagcttcaac aggaatgagt gttag                645

SEQ ID NO: 135          moltype = AA  length = 234
FEATURE                 Location/Qualifiers
source                  1..234
                        mol_type = protein
                        organism = Mus musculus
SEQUENCE: 135
MMSSAQFLGL LLLCFQGTRC DIQMTQITSS LSASLGDRVS ISCRASQDIS NYLNWYQQKP  60
DGTFKLLIFY TSRLLSGVPS RFSGSGSGTD YSLTIYNLEQ EDFATYFCQQ GDTLPYTFGG  120
GTKLEIKRAD AAPTVSIFPP SSEQLTSGGA SVVCFLNNFY PKDINVKWKI DGSERQNGVL  180
NSWTDQDSKD STYSMSSTLT LTKDEYERHN SYTCEATHKT STSPIVKSFN RNEC       234

SEQ ID NO: 136          moltype = DNA  length = 705
FEATURE                 Location/Qualifiers
source                  1..705
                        mol_type = other DNA
                        organism = Mus musculus
SEQUENCE: 136
atgatgtcct ctgctcagtt ccttggtctc ctgttgctct gttttcaagg taccagatgt  60
gatatccaga tgacacagat tacatcctcc ctgtctgcct ctctgggaga cagggtctcc  120
atcagttgca gggcaagtca agacattagc aattatttaa actggtatca gcagaaacca  180
gatggaactt ttaaactcct tatcttctac acatcaagat tactctcagg agtcccatca  240
aggttcagtg gcagtgggtc tggaacagat tattctctca ccatttacaa cctggagcaa  300
gaagattttg ccacttactt ttgccaacag ggagatacgc ttccgtacac tttcggaggg  360
gggaccaagc tggaaataaa acgggctgat gctgcaccaa ctgtatccat cttcccacca  420
tccagtgagc agttaacatc tggaggtgcc tcagtcgtgt gcttcttgaa caacttctac  480
cccaaagaca tcaatgtcaa gtggaagatt gatggcagtg aacgacaaaa tggcgtcctg  540
aacagttgga ctgatcagga cagcaaagac agcacctaca gcatgagcag caccctcacg  600
ttgaccaagg acgagtatga acgacataac agctatacct gtgaggccac tcacaagaca  660
tcaacttcac ccattgtcaa gagcttcaac aggaatgagt gttag                705

SEQ ID NO: 137          moltype = AA  length = 447
```

-continued

```
FEATURE                 Location/Qualifiers
source                  1..447
                        mol_type = protein
                        organism = Mus musculus
SEQUENCE: 137
EVQLQQSGPE LMKPGASVKM SCKASGYTFT DYNMHWVKQN QGKTLEWIGE INPNSGGAGY  60
NQKFKGKATL TVDKSSTTAY MELRSLTSED SAVYYCARLG YDDIYDDWYF DVWGAGTTVT  120
VSSAKTTPPS VYPLAPGSAA QTNSMVTLGC LVKGYFPEPV TVTWNSGSLS SGVHTFPAVL  180
QSDLYTLSSS VTVPSSTWPS ETVTCNVAHP ASSTKVDKKI VPRDCGCKPC ICTVPEVSSV  240
FIFPPKPKDV LTITLTPKVT CVVVDISKDD PEVQFSWFVD DVEVHTAQTQ PREEQFNSTF  300
RSVSELPIMH QDWLNGKEFK CRVNSAAFPA PIEKTISKTK GRPKAPQVYT IPPPKEQMAK  360
DKVSLTCMIT DFFPEDITVE WQWNGQPAEN YKNTQPIMDT DGSYFIYSKL NVQKSNWEAG  420
NTFTCSVLHE GLHNHHTEKS LSHSPGK                                     447

SEQ ID NO: 138          moltype = DNA  length = 1344
FEATURE                 Location/Qualifiers
source                  1..1344
                        mol_type = other DNA
                        organism = Mus musculus
SEQUENCE: 138
gaggtccaac tgcaacagtc tggacctgaa ctaatgaagc ctggggcttc agtgaagatg  60
tcctgcaagg cttctggata tacattcact gactacaaca tgcactgggt gaagcagaac  120
caaggaaaga ccctagagtg gataggagaa attaatccta acagtggtgg tgctggctac  180
aaccagaagt tcaagggcaa ggccacattg actgtagaca agtcctccac cacagcctac  240
atggagctcc gcagcctgac atctgaggac tctgcagtct attactgtgc aagattgggc  300
tacgatgata tctacgacga ctggtacttc gatgtctggg gcgcagggac cacggtcacc  360
gtctcctcag ccaaaacgac acccccatct gtctatccac tggcccctgg atctgctgcc  420
caaactaact ccatggtgac cctgggatgc ctggtcaagg gctatttccc tgagccagtg  480
acagtgacct ggaactctgg atccctgtcc agcggtgtgc acaccttccc agctgtcctg  540
cagtctgacc tctacactct gagcagctca gtgactgtcc cctccagcac ctggcccagc  600
gagaccgtca cctgcaacgt tgcccacccg gccagcagca ccaaggtgga caagaaaatt  660
gtgcccaggg attgtggttg taagccttgc atatgtacag tcccagaagt atcatctgtc  720
ttcatcttcc ccccaaagcc caaggatgtg ctcaccatta ctctgactcc taaggtcacg  780
tgtgttgtgg tagacatcag caaggatgat cccgaggtcc agttcagctg gtttgtagat  840
gatgtggagg tgcacacagc tcagacgcaa ccccgggagg agcagttcaa cagcactttc  900
cgctcagtca gtgaacttcc catcatgcac caggactggc tcaatggcaa ggagttcaaa  960
tgcagggtca acagtgcagc tttccctgcc cccatcgaga aaaccatctc caaaaccaaa  1020
ggcagaccga aggctccaca ggtgtacacc attccacctc ccaaggagca gatggccaag  1080
gataaagtca gtctgacctg catgataaca gacttcttcc ctgaagacat tactgtggag  1140
tggcagtgga atgggcagcc agcggagaac tacaagaaca ctcagcccat catggacaca  1200
gatggctctt acttcatcta cagcaagctc aatgtgcaga agagcaactg ggaggcagga  1260
aatactttca cctgctctgt gttacatgag ggcctgcaca accaccatac tgagaagagc  1320
ctctcccact ctcctggtaa atga                                        1344

SEQ ID NO: 139          moltype = AA  length = 466
FEATURE                 Location/Qualifiers
source                  1..466
                        mol_type = protein
                        organism = Mus musculus
SEQUENCE: 139
MGWSWTFLFL LSGTAGVLSE VQLQQSGPEL MKPGASVKMS CKASGYTFTD YNMHWVKQNQ  60
GKTLEWIGEI NPNSGGAGYN QKFKGKATLT VDKSSTTAYM ELRSLTSEDS AVYYCARLGY  120
DDIYDDWYFD VWGAGTTVTV SSAKTTPPSV YPLAPGSAAQ TNSMVTLGCL VKGYFPEPVT  180
VTWNSGSLSS GVHTFPAVLQ SDLYTLSSSV TVPSSTWPSE TVTCNVAHPA SSTKVDKKIV  240
PRDCGCKPCI CTVPEVSSVF IFPPKPKDVL TITLTPKVTC VVVDISKDDP EVQFSWFVDD  300
VEVHTAQTQP REEQFNSTFR SVSELPIMHQ DWLNGKEFKC RVNSAAFPAP IEKTISKTKG  360
RPKAPQVYTI PPPKEQMAKD KVSLTCMITD FFPEDITVEW QWNGQPAENY KNTQPIMDTD  420
GSYFIYSKLN VQKSNWEAGN TFTCSVLHEG LHNHHTEKSL SHSPGK                466

SEQ ID NO: 140          moltype = DNA  length = 1401
FEATURE                 Location/Qualifiers
source                  1..1401
                        mol_type = other DNA
                        organism = Mus musculus
SEQUENCE: 140
atgggatgga gctggacctt tctcttcctc ctgtcaggaa ctgcaggtgt cctctctgag  60
gtccaactgc aacagtctgg acctgaacta atgaagcctg gggcttcagt gaagatgtcc  120
tgcaaggctt ctggatatac attcactgac tacaacatgc actgggtgaa gcagaaccaa  180
ggaaagaccc tagagtggat aggagaaatt aatcctaaca gtggtggtgc tggctacaac  240
cagaagttca agggcaaggc cacattgact gtagacaagt cctccaccac agcctacatg  300
gagctccgca gcctgacatc tgaggactct gcagtctatt actgtgcaag attgggctac  360
gatgatatct acgacgactg gtacttcgat gtctggggcg cagggaccac ggtcaccgtc  420
tcctcagcca aaacgacacc cccatctgtc tatccactgg cccctggatc tgctgcccaa  480
actaactcca tggtgaccct gggatgcctg gtcaagggct atttccctga gccagtgaca  540
gtgacctgga actctggatc cctgtccagc ggtgtgcaca ccttcccagc tgtcctgcag  600
tctgacctct acactctgag cagctcagtg actgtcccct ccagcacctg gcccagcgag  660
accgtcacct gcaacgttgc ccacccggcc agcagcacca aggtggacaa gaaaattgtg  720
cccagggatt gtggttgtaa gccttgcata tgtacagtcc cagaagtatc atctgtcttc  780
atcttccccc caaagcccaa ggatgtgctc accattactc tgactcctaa ggtcacgtgt  840
```

-continued

```
gttgtggtag acatcagcaa ggatgatccc gaggtccagt tcagctggtt tgtagatgat  900
gtggaggtgc acacagctca gacgcaaccc cgggaggagc agttcaacag cactttccgc  960
tcagtcagtg aacttcccat catgcaccag gactggctca atggcaagga gttcaaatgc  1020
agggtcaaca gtgcagcttt ccctgccccc atcgagaaaa ccatctccaa aaccaaaggc  1080
agaccgaagg ctccacaggt gtacaccatt ccacctccca aggagcagat ggccaaggat  1140
aaagtcagtc tgacctgcat gataacagac ttcttccctg aagacattac tgtggagtgg  1200
cagtggaatg ggcagccagc ggagaactac aagaacactc agcccatcat ggacacagat  1260
ggctcttact tcatctacag caagctcaat gtgcagaaga gcaactggga ggcaggaaat  1320
actttcacct gctctgtgtt acatgagggc ctgcacaacc accatactga gaagagcctc  1380
tcccactctc ctggtaaatg a                                            1401

SEQ ID NO: 141          moltype = AA  length = 214
FEATURE                 Location/Qualifiers
REGION                  1..214
                        note = Synthetic Polypeptide
REGION                  1..214
                        note = MISC_FEATURE - Humanized Antibody Sequence
source                  1..214
                        mol_type = protein
                        organism = synthetic construct
SEQUENCE: 141
DIQMTQSPSS LSASVGDRVT ITCRASQDIS NYLNWYQQKP GKAPKLLIYY TSRLLSGVPS  60
RFSGSGSGTD FTLTISSLQP EDFATYYCQQ GDTLPYTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 142          moltype = DNA  length = 642
FEATURE                 Location/Qualifiers
misc_feature            1..642
                        note = Synthetic Polynucleotide
misc_feature            1..642
                        note = Humanized Antibody Sequence
source                  1..642
                        mol_type = other DNA
                        organism = synthetic construct
SEQUENCE: 142
gacatccaga tgacccagtc tccatcctcc ctctccgcat ccgtaggcga ccgcgtaacc  60
ataacatgta gagcatctca agatatttcc aactatttga attggtacca acaaaaaccc  120
ggcaaagcac ctaaactcct catttactat acatcaagac tcctctccgg cgttccatca  180
cgattctcag gctccggctc cggcacagat ttcacactca ctatttcctc cctccaacca  240
gaagattttg caacctatta ctgtcaacaa ggcgatacac tcccatacac attcggcggc  300
ggcacaaaag ttgaaattaa acgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                     642

SEQ ID NO: 143          moltype = AA  length = 236
FEATURE                 Location/Qualifiers
REGION                  1..236
                        note = Synthetic Polypeptide
REGION                  1..236
                        note = MISC_FEATURE - Humanized Antibody Sequence
source                  1..236
                        mol_type = protein
                        organism = synthetic construct
SEQUENCE: 143
MDMRVPAQLL GLLLLWLRGA RCDIQMTQSP SSLSASVGDR VTITCRASQD ISNYLNWYQQ  60
KPGKAPKLLI YYTSRLLSGV PSRFSGSGSG TDFTLTISSL QPEDFATYYC QQGDTLPYTF  120
GGGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC       236

SEQ ID NO: 144          moltype = DNA  length = 708
FEATURE                 Location/Qualifiers
misc_feature            1..708
                        note = Synthetic Polynucleotide
misc_feature            1..708
                        note = Humanized Antibody Sequence
source                  1..708
                        mol_type = other DNA
                        organism = synthetic construct
SEQUENCE: 144
atggacatga gggtccccgc tcagctcctg gggctcctgc tactctggct ccgaggtgcc  60
agatgtgaca tccagatgac ccagtctcca tcctccctct ccgcatccgt aggcgaccgc  120
gtaaccataa catgtagagc atctcaagat atttccaact atttgaattg gtaccaacaa  180
aaacccggca aagcacctaa actcctcatt tactatacat caagactcct ctccggcgtt  240
ccatcacgat tctcaggctc cggctccggc acagatttca cactcactat ttcctccctc  300
caaccagaag attttgcaac ctattactgt caacaaggcg atacactccc atacacattc  360
```

-continued

```
ggcggcggca caaaagttga aattaaacgt acggtggctg caccatctgt cttcatcttc  420
ccgccatctg atgagcagtt gaaatctgga actgcctctg ttgtgtgcct gctgaataac  480
ttctatccca gagaggccaa agtacagtgg aaggtggata acgccctcca atcgggtaac  540
tcccaggaga gtgtcacaga gcaggacagc aaggacagca cctacagcct cagcagcacc  600
ctgacgctga gcaaagcaga ctacgagaaa cacaaagtct acgcctgcga agtcacccat  660
cagggcctga gctcgcccgt cacaaagagc ttcaacaggg gagagtgt              708

SEQ ID NO: 145         moltype = AA  length = 449
FEATURE                Location/Qualifiers
REGION                 1..449
                       note = Synthetic Polypeptide
REGION                 1..449
                       note = MISC_FEATURE - Humanized Antibody Sequence
source                 1..449
                       mol_type = protein
                       organism = synthetic construct
SEQUENCE: 145
EVQLVQSGAE VKKPGASVKV SCKASGYTFT DYNMHWVRQA PGQGLEWMGE INPNSGGAGY  60
NQKFKGRVTM TTDTSTSTAY MELRSLRSDD TAVYYCARLG YDDIYDDWYF DVWGQGTTVT  120
VSSASTKGPS VFPLAPCSRS TSESTAALGC LVKDYFPEPV TVSWNSGALT SGVHTFPAVL  180
QSSGLYSLSS VVTVPSSNFG TQTYTCNVDH KPSNTKVDKT VERKCCVECP PCPAPPVAGP  240
SVFLFPPKPK DTLMISRTPE VTCVVVDVSH EDPEVQFNWY VDGVEVHNAK TKPREEQFNS  300
TFRVVSVLTV VHQDWLNGKE YKCKVSNKGL PAPIEKTISK TKGQPREPQV YTLPPSREEM  360
TKNQVSLTCL VKGFYPSDIA VEWESNGQPE NNYKTTPPML DSDGSFFLYS KLTVDKSRWQ  420
QGNVFSCSVM HEALHNHYTQ KSLSLSPGK                                   449

SEQ ID NO: 146         moltype = DNA  length = 1347
FEATURE                Location/Qualifiers
misc_feature           1..1347
                       note = Synthetic Polynucleotide
misc_feature           1..1347
                       note = Humanized Antibody Sequence
source                 1..1347
                       mol_type = other DNA
                       organism = synthetic construct
SEQUENCE: 146
gaggtgcagc tggtgcagag cggcgccgag gtaaaaaaac caggagcaag cgttaaagtt  60
tcttgtaaag caagcggata tacatttaca gattacaaca tgcattgggt aagacaagcg  120
ccaggacaag gattggaatg gatgggcgaa attaacccta atagtggagg agcaggctac  180
aatcaaaaat tcaaagggag agttacaatg acaacagaca caagcacttc aacagcatat  240
atggaactgc gatcacttag aagcgacgat acagctgtat actattgcgc acgacttggg  300
tatgatgata tatatgatga ctggtatttc gatgtttggg gccagggaac aacagttacc  360
gtctctagtg cctccaccaa gggcccatcg gtcttccccc tggcgccctg ctccaggagc  420
acctccgaga gcacagcggc cctgggctgc ctggtcaagg actacttccc cgaaccggtg  480
acggtgtcgt ggaactcagg cgctctgacc agcggcgtgc acaccttccc agctgtccta  540
cagtcctcag gactctactc cctcagcagc gtggtgaccg tgccctccag caacttcggc  600
acccagacct acacctgcaa cgtagatcac aagcccagca acaccaaggt ggacaagaca  660
gttgagcgca aatgttgtgt cgagtgccca ccgtgcccag caccacctgt ggcaggaccg  720
tcagtcttcc tcttcccccc aaaacccaag gacaccctca tgatctcccg gacccctgag  780
gtcacgtgcg tggtggtgga cgtgagccac gaagaccccg aggtccagtt caactggtac  840
gtggacggcg tggaggtgca taatgccaag acaaagccac gggaggagca gttcaacagc  900
acgttccgtg tggtcagcgt cctcaccgtt gtgcaccagg actggctgaa cggcaaggag  960
tacaagtgca aggtctccaa caaaggcctc ccagccccca tcgagaaaac catctccaaa  1020
accaaagggc agccccgaga accacaggtg tacaccctgc ccccatcccg ggaggagatg  1080
accaagaacc aggtcagcct gacctgcctg gtcaaaggct tctaccccag cgacatcgcc  1140
gtggagtggg agagcaatgg gcagccggag aacaactaca agaccacacc tcccatgctg  1200
gactccgacg gctccttctt cctctacagc aagctcaccg tggacaagag caggtggcag  1260
caggggaacg tcttctcatg ctccgtgatg catgaggctc tgcacaacca ctacacgcag  1320
aagagcctct ccctgtctcc gggtaaa                                     1347

SEQ ID NO: 147         moltype = AA  length = 468
FEATURE                Location/Qualifiers
REGION                 1..468
                       note = Synthetic Polypeptide
REGION                 1..468
                       note = MISC_FEATURE - Humanized Antibody Sequence
source                 1..468
                       mol_type = protein
                       organism = synthetic construct
SEQUENCE: 147
MDWTWRILFL VAAATGAHSE VQLVQSGAEV KKPGASVKVS CKASGYTFTD YNMHWVRQAP  60
GQGLEWMGEI NPNSGGAGYN QKFKGRVTMT TDTSTSTAYM ELRSLRSDDT AVYYCARLGY  120
DDIYDDWYFD VWGQGTTVTV SSASTKGPSV FPLAPCSRST SESTAALGCL VKDYFPEPVT  180
VSWNSGALTS GVHTFPAVLQ SSGLYSLSSV VTVPSSNFGT QTYTCNVDHK PSNTKVDKTV  240
ERKCCVECPP CPAPPVAGPS VFLFPPKPKD TLMISRTPEV TCVVVDVSHE DPEVQFNWYV  300
DGVEVHNAKT KPREEQFNST FRVVSVLTVV HQDWLNGKEY KCKVSNKGLP APIEKTISKT  360
KGQPREPQVY TLPPSREEMT KNQVSLTCLV KGFYPSDIAV EWESNGQPEN NYKTTPPMLD  420
SDGSFFLYSK LTVDKSRWQQ GNVFSCSVMH EALHNHYTQK SLSLSPGK              468
```

-continued

```
SEQ ID NO: 148         moltype = DNA  length = 1404
FEATURE                Location/Qualifiers
source                 1..1404
                       mol_type = other DNA
                       organism = Mus musculus
SEQUENCE: 148
atggactgga cctggaggat cctcttcttg gtggcagcag ccacaggagc ccactccgag  60
gtgcagctgg tgcagagcgg cgccgaggta aaaaaaccag gagcaagcgt taaagtttct  120
tgtaaagcaa gcggatatac atttacagat tacaacatgc attgggtaag acaagcgcca  180
ggacaaggat tggaatggat gggcgaaatt aaccctaata gtggaggagc aggctacaat  240
caaaaattca aagggagagt tacaatgaca acagacacaa gcacttcaac agcatatatg  300
gaactgcgat cacttagaag cgacgataca gctgtatact attgcgcacg acttgggtat  360
gatgatatat atgatgactg gtatttcgat gtttggggcc agggaacaac agttaccgtc  420
tctagtgcct ccaccaaggg cccatcggtc ttccccctgg cgccctgctc caggagcacc  480
tccgagagca cagcggccct gggctgcctg gtcaaggact acttccccga accggtgacg  540
gtgtcgtgga actcaggcgc tctgaccagc ggcgtgcaca ccttcccagc tgtcctacag  600
tcctcaggac tctactccct cagcagcgtg gtgaccgtgc cctccagcaa cttcggcacc  660
cagacctaca cctgcaacgt agatcacaag cccagcaaca ccaaggtgga caagacagtt  720
gagcgcaaat gttgtgtcga gtgcccaccg tgcccagcac cacctgtggc aggaccgtca  780
gtcttcctct tccccccaaa acccaaggac accctcatga tctcccggac ccctgaggtc  840
acgtgcgtgg tggtggacgt gagccacgaa gaccccgagg tccagttcaa ctggtacgtg  900
gacggcgtgg aggtgcataa tgccaagaca aagccacggg aggagcagtt caacagcacg  960
ttccgtgtgg tcagcgtcct caccgttgtg caccaggact ggctgaacgg caaggagtac  1020
aagtgcaagg tctccaacaa aggcctccca gcccccatcg agaaaaccat ctccaaaacc  1080
aaagggcagc cccgagaacc acaggtgtac accctgcccc catcccggga ggagatgacc  1140
aagaaccagg tcagcctgac ctgcctggtc aaaggcttct accccagcga catcgccgtg  1200
gagtgggaga gcaatgggca gccggagaac aactacaaga ccacacctcc catgctggac  1260
tccgacggct ccttcttcct ctacagcaag ctcaccgtgg acaagagcag gtggcagcag  1320
gggaacgtct tctcatgctc cgtgatgcat gaggctctgc acaaccacta cacgcagaag  1380
agcctctccc tgtctccggg taaa                                         1404

SEQ ID NO: 149         moltype = AA  length = 214
FEATURE                Location/Qualifiers
source                 1..214
                       mol_type = protein
                       organism = Mus musculus
SEQUENCE: 149
DIQMTQTTSS LSASLGDRVT ISCRASQDIS NYLNWFQQKP DGTLKLLIFY TSRLHSGVPS  60
RFSGSGSGTD YSLTISNLEQ EDIATYFCQQ GDTLPYTFGG GTKLEIRRAD AAPTVSIFPP  120
SSEQLTSGGA SVVCFLNNFY PKDINVKWKI DGSERQNGVL NSWTDQDSKD STYSMSSTLT  180
LTKDEYERHN SYTCEATHKT STSPIVKSFN RNEC                             214

SEQ ID NO: 150         moltype = DNA  length = 645
FEATURE                Location/Qualifiers
source                 1..645
                       mol_type = other DNA
                       organism = Mus musculus
SEQUENCE: 150
gatatccaga tgacacagac tacatcctcc ctgtctgcct ctctgggaga cagagtcacc  60
atcagttgca gggcaagtca ggacattagc aattatttaa actggtttca gcagaaacca  120
gatggaactc ttaaactcct gatcttctac acatcaagat tacactcagg agttccatca  180
aggttcagtg gcagtgggtc tggaacagat tattctctca ccattagcaa cctggagcaa  240
gaagatattg ccacttactt ttgccaacag ggtgatacgc ttccgtacac gttcgggggg  300
gggaccaagc tggaaataag acgggctgat gctgcaccaa ctgtatccat cttcccacca  360
tccagtgagc agttaacatc tggaggtgcc tcagtcgtgt gcttcttgaa caacttctac  420
cccaaagaca tcaatgtcaa gtggaagatt gatggcagtg aacgacaaaa tggcgtcctg  480
aacagttgga ctgatcagga cagcaaagac agcacctaca gcatgagcag caccctcacg  540
ttgaccaagg acgagtatga acgacataac agctatacct gtgaggccac tcacaagaca  600
tcaacttcac ccattgtcaa gagcttcaac aggaatgagt gttag                  645

SEQ ID NO: 151         moltype = AA  length = 234
FEATURE                Location/Qualifiers
source                 1..234
                       mol_type = protein
                       organism = Mus musculus
SEQUENCE: 151
MMSSAQFLGL LLLCFQGTRC DIQMTQTTSS LSASLGDRVT ISCRASQDIS NYLNWFQQKP  60
DGTLKLLIFY TSRLHSGVPS RFSGSGSGTD YSLTISNLEQ EDIATYFCQQ GDTLPYTFGG  120
GTKLEIRRAD AAPTVSIFPP SSEQLTSGGA SVVCFLNNFY PKDINVKWKI DGSERQNGVL  180
NSWTDQDSKD STYSMSSTLT LTKDEYERHN SYTCEATHKT STSPIVKSFN RNEC        234

SEQ ID NO: 152         moltype = DNA  length = 705
FEATURE                Location/Qualifiers
source                 1..705
                       mol_type = other DNA
                       organism = Mus musculus
SEQUENCE: 152
atgatgtcct ctgctcagtt ccttggtctc ctgttgctct gttttcaagg taccagatgt  60
gatatccaga tgacacagac tacatcctcc ctgtctgcct ctctgggaga cagagtcacc  120
```

-continued

```
atcagttgca gggcaagtca ggacattagc aattatttaa actggtttca gcagaaacca  180
gatggaactc ttaaactcct gatcttctac acatcaagat tacactcagg agttccatca  240
aggttcagtg gcagtgggtc tggaacagat tattctctca ccattagcaa cctggagcaa  300
gaagatattg ccacttactt ttgccaacag ggtgatacgc ttccgtacac gttcgggggg  360
gggaccaagc tggaaataag acgggctgat gctgcaccaa ctgtatccat cttcccacca  420
tccagtgagc agttaacatc tggaggtgcc tcagtcgtgt gcttcttgaa caacttctac  480
cccaaagaca tcaatgtcaa gtggaagatt gatggcagtg aacgacaaaa tggcgtcctg  540
aacagttgga ctgatcagga cagcaaagac agcacctaca gcatgagcag caccctcacg  600
ttgaccaagg acgagtatga acgacataac agctatacct gtgaggccac tcacaagaca  660
tcaacttcac ccattgtcaa gagcttcaac aggaatgagt gttag                    705

SEQ ID NO: 153         moltype = AA  length = 447
FEATURE                Location/Qualifiers
source                 1..447
                       mol_type = protein
                       organism = Mus musculus
SEQUENCE: 153
EVQLQQSGPE LMKPGASVKM SCKASGYTFT DYNMHWVKQN QGKSLEWIGE INPNSGGSGY  60
NQKFKGKATL TVDKSSSTAY MELRSLTSED SAVYYCARLV YDGSYEDWYF DVWGAGTTVT  120
VSSAKTTPPS VYPLAPGSAA QTNSMVTLGC LVKGYFPEPV TVTWNSGSLS SGVHTFPAVL  180
QSDLYTLSSS VTVPSSTWPS ETVTCNVAHP ASSTKVDKKI VPRDCGCKPC ICTVPEVSSV  240
FIFPPKPKDV LTITLTPKVT CVVVDISKDD PEVQFSWFVD DVEVHTAQTQ PREEQFNSTF  300
RSVSELPIMH QDWLNGKEFK CRVNSAAFPA PIEKTISKTK GRPKAPQVYT IPPPKEQMAK  360
DKVSLTCMIT DFFPEDITVE WQWNGQPAEN YKNTQPIMDT DGSYFIYSKL NVQKSNWEAG  420
NTFTCSVLHE GLHNHHTEKS LSHSPGK                                    447

SEQ ID NO: 154         moltype = DNA  length = 1344
FEATURE                Location/Qualifiers
source                 1..1344
                       mol_type = other DNA
                       organism = Mus musculus
SEQUENCE: 154
gaggtccagc tgcaacagtc tggacctgaa ctaatgaagc ctggggcttc agtgaagatg  60
tcctgcaagg cttctggata cacattcact gactacaaca tgcactgggt gaaacagaac  120
caaggaaaga gcctagagtg gataggagaa attaatccta acagtggtgg tagtggctac  180
aaccaaaagt tcaaaggcaa ggccacattg actgtagaca agtcttccag cacagcctac  240
atggagctcc gcagcctgac atctgaggac tctgcagtct attactgtgc aagattggtc  300
tacgatggca gctacgagga ctggtacttc gatgtctggg gcgcagggac cacggtcacc  360
gtctcctcag ccaaaacgac acccccatct gtctatccac tggcccctgg atctgctgcc  420
caaactaact ccatggtgac cctgggatgc ctggtcaagg gctatttccc tgagccagtg  480
acagtgacct ggaactctgg atccctgtcc agcggtgtgc acaccttccc agctgtcctg  540
cagtctgacc tctacactct gagcagctca gtgactgtcc cctccagcac ctggcccagc  600
gagaccgtca cctgcaacgt tgcccacccg gccagcagca ccaaggtgga caagaaaatt  660
gtgcccaggg attgtggttg taagccttgc atatgtacag tcccagaagt atcatctgtc  720
ttcatcttcc ccccaaagcc caaggatgtg ctcaccatta ctctgactcc taaggtcacg  780
tgtgttgtgg tagacatcag caaggatgat cccgaggtcc agttcagctg gtttgtagat  840
gatgtggagg tgcacacagc tcagacgcaa ccccgggagg agcagttcaa cagcactttc  900
cgctcagtca gtgaacttcc catcatgcac caggactggc tcaatggcaa ggagttcaaa  960
tgcagggtca acagtgcagc tttccctgcc cccatcgaga aaaccatctc caaaaccaaa  1020
ggcagaccga aggctccaca ggtgtacacc attccacctc ccaaggagca gatggccaag  1080
gataaagtca gtctgacctg catgataaca gacttcttcc ctgaagacat tactgtggag  1140
tggcagtgga atgggcagcc agcggagaac tacaagaaca ctcagcccat catggacaca  1200
gatggctctt acttcatcta cagcaagctc aatgtgcaga agagcaactg ggaggcagga  1260
aatactttca cctgctctgt gttacatgag ggcctgcaca accaccatac tgagaagagc  1320
ctctcccact ctcctggtaa atga                                         1344

SEQ ID NO: 155         moltype = AA  length = 466
FEATURE                Location/Qualifiers
source                 1..466
                       mol_type = protein
                       organism = Mus musculus
SEQUENCE: 155
MGWSWTFLFL LSGTAGVLSE VQLQQSGPEL MKPGASVKMS CKASGYTFTD YNMHWVKQNQ  60
GKSLEWIGEI NPNSGGSGYN QKFKGKATLT VDKSSSTAYM ELRSLTSEDS AVYYCARLVY  120
DGSYEDWYFD VWGAGTTVTV SSAKTTPPSV YPLAPGSAAQ TNSMVTLGCL VKGYFPEPVT  180
VTWNSGSLSS GVHTFPAVLQ SDLYTLSSSV TVPSSTWPSE TVTCNVAHPA SSTKVDKKIV  240
PRDCGCKPCI CTVPEVSSVF IFPPKPKDVL TITLTPKVTC VVVDISKDDP EVQFSWFVDD  300
VEVHTAQTQP REEQFNSTFR SVSELPIMHQ DWLNGKEFKC RVNSAAFPAP IEKTISKTKG  360
RPKAPQVYTI PPPKEQMAKD KVSLTCMITD FFPEDITVEW QWNGQPAENY KNTQPIMDTD  420
GSYFIYSKLN VQKSNWEAGN TFTCSVLHEG LHNHHTEKSL SHSPGK                 466

SEQ ID NO: 156         moltype = DNA  length = 1401
FEATURE                Location/Qualifiers
source                 1..1401
                       mol_type = other DNA
                       organism = Mus musculus
SEQUENCE: 156
atgggatgga gctggacctt tctcttcctc ctgtcaggaa ctgcaggtgt cctctctgag  60
gtccagctgc aacagtctgg acctgaacta atgaagcctg gggcttcagt gaagatgtcc  120
```

-continued

```
tgcaaggctt ctggatacac attcactgac tacaacatgc actgggtgaa acagaaccaa  180
ggaaagagcc tagagtggat aggagaaatt aatcctaaca gtggtggtag tggctacaac  240
caaaagttca aaggcaaggc cacattgact gtagacaagt cttccagcac agcctacatg  300
gagctccgca gcctgacatc tgaggactct gcagtctatt actgtgcaag attggtctac  360
gatggcagct acgaggactg gtacttcgat gtctggggcg cagggaccac ggtcaccgtc  420
tcctcagcca aaacgacacc cccatctgtc tatccactgg cccctggatc tgctgcccaa  480
actaactcca tggtgaccct gggatgcctg gtcaagggct atttccctga gccagtgaca  540
gtgacctgga actctggatc cctgtccagc ggtgtgcaca ccttcccagc tgtcctgcag  600
tctgacctct acactctgag cagctcagtg actgtcccct ccagcacctg gcccagcgag  660
accgtcacct gcaacgttgc ccacccggcc agcagcacca aggtggacaa gaaaattgtg  720
cccagggatt gtggttgtaa gccttgcata tgtacagtcc cagaagtatc atctgtcttc  780
atcttccccc caaagcccaa ggatgtgctc accattactc tgactcctaa ggtcacgtgt  840
gttgtggtag acatcagcaa ggatgatccc gaggtccagt tcagctggtt tgtagatgat  900
gtggaggtgc acacagctca gacgcaaccc cgggaggagc agttcaacag cactttccgc  960
tcagtcagtg aacttcccat catgcaccag gactggctca atggcaagga gttcaaatgc  1020
agggtcaaca gtgcagcttt ccctgccccc atcgagaaaa ccatctccaa aaccaaaggc  1080
agaccgaagg ctccacaggt gtacaccatt ccacctccca aggagcagat ggccaaggat  1140
aaagtcagtc tgacctgcat gataacagac ttcttccctg aagacattac tgtggagtgg  1200
cagtggaatg ggcagccagc ggagaactac aagaacactc agcccatcat ggacacagat  1260
ggctcttact tcatctacag caagctcaat gtgcagaaga gcaactggga ggcaggaaat  1320
actttcacct gctctgtgtt acatgagggc ctgcacaacc accatactga gaagagcctc  1380
tcccactctc ctggtaaatg a                                            1401

SEQ ID NO: 157          moltype = AA  length = 214
FEATURE                 Location/Qualifiers
source                  1..214
                        mol_type = protein
                        organism = Mus musculus
SEQUENCE: 157
DIQMTQTTSS LSASLGDRVT ICCRASQVIT NYLYWYQQKP DGTFKLLIYY TSRLHSGVPS  60
RFSGSGSGTD YSLTISNLEQ EDIATYFCQQ GDTLPYTFGG GTKLEIKRAD AAPTVSIFPP  120
SSEQLTSGGA SVVCFLNNFY PKDINVKWKI DGSERQNGVL NSWTDQDSKD STYSMSSTLT  180
LTKDEYERHN SYTCEATHKT STSPIVKSFN RNEC                              214

SEQ ID NO: 158          moltype = DNA  length = 642
FEATURE                 Location/Qualifiers
source                  1..642
                        mol_type = other DNA
                        organism = Mus musculus
SEQUENCE: 158
gatatccaga tgacacagac tacatcctcc ctgtctgcct ctctgggaga cagagtcacc  60
atctgttgca gggcaagtca ggtcattacc aattatttat actggtatca gcagaaacca  120
gatggaactt ttaaactcct gatctactac acatcaagat tacactcagg agtcccatca  180
aggttcagtg gcagtgggtc tggaacagat tattctctca ccattagcaa cctggaacag  240
gaagatattg ccacttactt ttgccaacag ggtgatacgc ttccgtacac gttcggaggg  300
gggaccaagc tggaaataaa acgggctgat gctgcaccaa ctgtatccat cttcccacca  360
tccagtgagc agttaacatc tggaggtgcc tcagtcgtgt gcttcttgaa caacttctac  420
cccaaagaca tcaatgtcaa gtggaagatt gatggcagtg aacgacaaaa tggcgtcctg  480
aacagttgga ctgatcagga cagcaaagac agcacctaca gcatgagcag caccctcacg  540
ttgaccaagg acgagtatga acgacataac agctatacct gtgaggccac tcacaagaca  600
tcaacttcac ccattgtcaa gagcttcaac aggaatgagt gt                     642

SEQ ID NO: 159          moltype = AA  length = 234
FEATURE                 Location/Qualifiers
source                  1..234
                        mol_type = protein
                        organism = Mus musculus
SEQUENCE: 159
MMSSAQFLGL LLLCFQGTRC DIQMTQTTSS LSASLGDRVT ICCRASQVIT NYLYWYQQKP  60
DGTFKLLIYY TSRLHSGVPS RFSGSGSGTD YSLTISNLEQ EDIATYFCQQ GDTLPYTFGG  120
GTKLEIKRAD AAPTVSIFPP SSEQLTSGGA SVVCFLNNFY PKDINVKWKI DGSERQNGVL  180
NSWTDQDSKD STYSMSSTLT LTKDEYERHN SYTCEATHKT STSPIVKSFN RNEC        234

SEQ ID NO: 160          moltype = DNA  length = 702
FEATURE                 Location/Qualifiers
source                  1..702
                        mol_type = other DNA
                        organism = Mus musculus
SEQUENCE: 160
atgatgtcct ctgctcagtt ccttggtctc ctgttgctct gttttcaagg taccagatgt  60
gatatccaga tgacacagac tacatcctcc ctgtctgcct ctctgggaga cagagtcacc  120
atctgttgca gggcaagtca ggtcattacc aattatttat actggtatca gcagaaacca  180
gatggaactt ttaaactcct gatctactac acatcaagat tacactcagg agtcccatca  240
aggttcagtg gcagtgggtc tggaacagat tattctctca ccattagcaa cctggaacag  300
gaagatattg ccacttactt ttgccaacag ggtgatacgc ttccgtacac gttcggaggg  360
gggaccaagc tggaaataaa acgggctgat gctgcaccaa ctgtatccat cttcccacca  420
tccagtgagc agttaacatc tggaggtgcc tcagtcgtgt gcttcttgaa caacttctac  480
cccaaagaca tcaatgtcaa gtggaagatt gatggcagtg aacgacaaaa tggcgtcctg  540
aacagttgga ctgatcagga cagcaaagac agcacctaca gcatgagcag caccctcacg  600
```

```
ttgaccaagg acgagtatga acgacataac agctatacct gtgaggccac tcacaagaca  660
tcaacttcac ccattgtcaa gagcttcaac aggaatgagt gt                     702

SEQ ID NO: 161         moltype = AA  length = 447
FEATURE                Location/Qualifiers
source                 1..447
                       mol_type = protein
                       organism = Mus musculus
SEQUENCE: 161
EVQLQQSGPE LMKPGASVKM SCKASGYTFT DYNMHWMKQN QGKSLEWIGE INPNSGGAGY  60
NQQFKGKATL TVDKSSRTAY MELRSLTSED SAVYYCARLG YVGNYEDWYF DVWGAGTTVT  120
VSSAKTTPPS VYPLAPGSAA QTNSMVTLGC LVKGYFPEPV TVTWNSGSLS SGVHTFPAVL  180
QSDLYTLSSS VTVPSSTWPS ETVTCNVAHP ASSTKVDKKI VPRDCGCKPC ICTVPEVSSV  240
FIFPPKPKDV LTITLTPKVT CVVVDISKDD PEVQFSWFVD DVEVHTAQTQ PREEQFNSTF  300
RSVSELPIMH QDWLNGKEFK CRVNSAAFPA PIEKTISKTK GRPKAPQVYT IPPPKEQMAK  360
DKVSLTCMIT DFFPEDITVE WQWNGQPAEN YKNTQPIMDT DGSYFIYSKL NVQKSNWEAG  420
NTFTCSVLHE GLHNHHTEKS LSHSPGK                                      447

SEQ ID NO: 162         moltype = DNA  length = 1341
FEATURE                Location/Qualifiers
source                 1..1341
                       mol_type = other DNA
                       organism = Mus musculus
SEQUENCE: 162
gaggtccagc tgcaacagtc tggacctgaa ctaatgaagc ctggggcttc agtgaagatg  60
tcctgcaagg cttctggata cacattcact gactacaaca tgcactggat gaagcagaac  120
caaggaaaga gcctagaatg gataggagaa attaatccta acagtggtgg tgctggctac  180
aaccagcagt tcaaaggcaa ggccacattg actgtagaca agtcctccag gacagcctac  240
atggagctcc gcagcctgac atctgaggac tctgcagtct attactgtgc aagattgggc  300
tacgttggta attacgagga ctggtacttc gatgtctggg gcgcagggac cacggtcacc  360
gtctcctcag ccaaaacgac acccccatct gtctatccac tggcccctgg atctgctgcc  420
caaactaact ccatggtgac cctgggatgc ctggtcaagg gctatttccc tgagccagtg  480
acagtgacct ggaactctgg atccctgtcc agcggtgtgc acaccttccc agctgtcctg  540
cagtctgacc tctacactct gagcagctca gtgactgtcc cctccagcac ctggcccagc  600
gagaccgtca cctgcaacgt tgcccacccg gccagcagca ccaaggtgga caagaaaatt  660
gtgcccaggg attgtggttg taagccttgc atatgtacag tcccagaagt atcatctgtc  720
ttcatcttcc ccccaaagcc caaggatgtg ctcaccatta ctctgactcc taaggtcacg  780
tgtgttgtgg tagacatcag caaggatgat cccgaggtcc agttcagctg gtttgtagat  840
gatgtggagg tgcacacagc tcagacgcaa ccccgggagg agcagttcaa cagcactttc  900
cgctcagtca gtgaacttcc catcatgcac caggactggc tcaatggcaa ggagttcaaa  960
tgcagggtca acagtgcagc tttccctgcc cccatcgaga aaaccatctc caaaaccaaa  1020
ggcagaccga aggctccaca ggtgtacacc attccacctc ccaaggagca gatggccaag  1080
gataaagtca gtctgacctg catgataaca gacttcttcc ctgaagacat tactgtggag  1140
tggcagtgga atgggcagcc agcggagaac tacaagaaca ctcagcccat catggacaca  1200
gatggctctt acttcatcta cagcaagctc aatgtgcaga agagcaactg ggaggcagga  1260
aatactttca cctgctctgt gttacatgag ggcctgcaca accaccatac tgagaagagc  1320
ctctcccact ctcctggtaa a                                            1341

SEQ ID NO: 163         moltype = AA  length = 466
FEATURE                Location/Qualifiers
source                 1..466
                       mol_type = protein
                       organism = Mus musculus
SEQUENCE: 163
MGWSWTFLFL LSGTAGVLSE VQLQQSGPEL MKPGASVKMS CKASGYTFTD YNMHWMKQNQ  60
GKSLEWIGEI NPNSGGAGYN QQFKGKATLT VDKSSRTAYM ELRSLTSEDS AVYYCARLGY  120
VGNYEDWYFD VWGAGTTVTV SSAKTTPPSV YPLAPGSAAQ TNSMVTLGCL VKGYFPEPVT  180
VTWNSGSLSS GVHTFPAVLQ SDLYTLSSSV TVPSSTWPSE TVTCNVAHPA SSTKVDKKIV  240
PRDCGCKPCI CTVPEVSSVF IFPPKPKDVL TITLTPKVTC VVVDISKDDP EVQFSWFVDD  300
VEVHTAQTQP REEQFNSTFR SVSELPIMHQ DWLNGKEFKC RVNSAAFPAP IEKTISKTKG  360
RPKAPQVYTI PPPKEQMAKD KVSLTCMITD FFPEDITVEW QWNGQPAENY KNTQPIMDTD  420
GSYFIYSKLN VQKSNWEAGN TFTCSVLHEG LHNHHTEKSL SHSPGK                 466

SEQ ID NO: 164         moltype = DNA  length = 1398
FEATURE                Location/Qualifiers
source                 1..1398
                       mol_type = other DNA
                       organism = Mus musculus
SEQUENCE: 164
atgggatgga gctggacctt tctcttcctc ctgtcaggaa ctgcaggtgt cctctctgag  60
gtccagctgc aacagtctgg acctgaacta atgaagcctg gggcttcagt gaagatgtcc  120
tgcaaggctt ctggatacac attcactgac tacaacatgc actggatgaa gcagaaccaa  180
ggaaagagcc tagaatggat aggagaaatt aatcctaaca gtggtggtgc tggctacaac  240
cagcagttca aaggcaaggc cacattgact gtagacaagt cctccaggac agcctacatg  300
gagctccgca gcctgacatc tgaggactct gcagtctatt actgtgcaag attgggctac  360
gttggtaatt acgaggactg gtacttcgat gtctggggcg cagggaccac ggtcaccgtc  420
tcctcagcca aaacgacacc cccatctgtc tatccactgg cccctggatc tgctgcccaa  480
actaactcca tggtgaccct gggatgcctg gtcaagggct atttccctga gccagtgaca  540
gtgacctgga actctggatc cctgtccagc ggtgtgcaca ccttcccagc tgtcctgcag  600
```

```
tctgacctct acactctgag cagctcagtg actgtcccct ccagcacctg gcccagcgag  660
accgtcacct gcaacgttgc ccacccggcc agcagcacca aggtggacaa gaaaattgtg  720
cccagggatt gtggttgtaa gccttgcata tgtacagtcc cagaagtatc atctgtcttc  780
atcttccccc caaagcccaa ggatgtgctc accattactc tgactcctaa ggtcacgtgt  840
gttgtggtag acatcagcaa ggatgatccc gaggtccagt tcagctggtt tgtagatgat  900
gtggaggtgc acacagctca gacgcaaccc cgggaggagc agttcaacag cactttccgc  960
tcagtcagtg aacttcccat catgcaccag gactggctca atggcaagga gttcaaatgc  1020
agggtcaaca gtgcagcttt ccctgccccc atcgagaaaa ccatctccaa aaccaaaggc  1080
agaccgaagg ctccacaggt gtacaccatt ccacctccca aggagcagat ggccaaggat  1140
aaagtcagtc tgacctgcat gataacagac ttcttccctg aagacattac tgtggagtgg  1200
cagtggaatg ggcagccagc ggagaactac aagaacactc agcccatcat ggacacagat  1260
ggctcttact tcatctacag caagctcaat gtgcagaaga gcaactggga ggcaggaaat  1320
actttcacct gctctgtgtt acatgagggc ctgcacaacc accatactga gaagagcctc  1380
tcccactctc ctggtaaa                                                1398

SEQ ID NO: 165         moltype = AA  length = 214
FEATURE                Location/Qualifiers
source                 1..214
                       mol_type = protein
                       organism = Mus musculus
SEQUENCE: 165
DIQMTQTTSS LSASLGDRVS ISCRASQDIS NYLNWYQQKP DGTFKLLIFY TSRLLSGVPS  60
RFSGSGSGTD YSLTIYNLEQ EDFATYFCQQ GDTLPYTFGG GTKLEIKRAD AAPTVSIFPP  120
SSEQLTSGGA SVVCFLNNFY PKDINVKWKI DGSERQNGVL NSWTDQDSKD STYSMSSTLT  180
LTKDEYERHN SYTCEATHKT STSPIVKSFN RNEC                              214

SEQ ID NO: 166         moltype = DNA  length = 645
FEATURE                Location/Qualifiers
source                 1..645
                       mol_type = other DNA
                       organism = Mus musculus
SEQUENCE: 166
gatatccaga tgacacagac tacatcctcc ctgtctgcct ctctgggaga cagggtctcc  60
atcagttgca gggcaagtca agacattagc aattatttaa actggtatca gcagaaacca  120
gatggaactt ttaaactcct tatcttctac acatcaagat tactctcagg agtcccatca  180
aggttcagtg gcagtgggtc tggaacagat tattctctca ccatttacaa cctggagcaa  240
gaagattttg ccacttactt ttgccaacag ggagatacgc ttccgtacac tttcggaggg  300
gggaccaaac tggaaataaa acgggctgat gctgcaccaa ctgtatccat cttcccacca  360
tccagtgagc agttaacatc tggaggtgcc tcagtcgtgt gcttcttgaa caacttctac  420
cccaaagaca tcaatgtcaa gtggaagatt gatggcagtg aacgacaaaa tggcgtcctg  480
aacagttgga ctgatcagga cagcaaagac agcacctaca gcatgagcag caccctcacg  540
ttgaccaagg acgagtatga acgacataac agctatacct gtgaggccac tcacaagaca  600
tcaacttcac ccattgtcaa gagcttcaac aggaatgagt gttag                  645

SEQ ID NO: 167         moltype = AA  length = 234
FEATURE                Location/Qualifiers
source                 1..234
                       mol_type = protein
                       organism = Mus musculus
SEQUENCE: 167
MMSSAQFLGL LLLCFQGTRC DIQMTQTTSS LSASLGDRVS ISCRASQDIS NYLNWYQQKP  60
DGTFKLLIFY TSRLLSGVPS RFSGSGSGTD YSLTIYNLEQ EDFATYFCQQ GDTLPYTFGG  120
GTKLEIKRAD AAPTVSIFPP SSEQLTSGGA SVVCFLNNFY PKDINVKWKI DGSERQNGVL  180
NSWTDQDSKD STYSMSSTLT LTKDEYERHN SYTCEATHKT STSPIVKSFN RNEC        234

SEQ ID NO: 168         moltype = DNA  length = 705
FEATURE                Location/Qualifiers
source                 1..705
                       mol_type = other DNA
                       organism = Mus musculus
SEQUENCE: 168
atgatgtcct ctgctcagtt ccttggtctc ctgttgctct gttttcaagg taccagatgt  60
gatatccaga tgacacagac tacatcctcc ctgtctgcct ctctgggaga cagggtctcc  120
atcagttgca gggcaagtca agacattagc aattatttaa actggtatca gcagaaacca  180
gatggaactt ttaaactcct tatcttctac acatcaagat tactctcagg agtcccatca  240
aggttcagtg gcagtgggtc tggaacagat tattctctca ccatttacaa cctggagcaa  300
gaagattttg ccacttactt ttgccaacag ggagatacgc ttccgtacac tttcggaggg  360
gggaccaaac tggaaataaa acgggctgat gctgcaccaa ctgtatccat cttcccacca  420
tccagtgagc agttaacatc tggaggtgcc tcagtcgtgt gcttcttgaa caacttctac  480
cccaaagaca tcaatgtcaa gtggaagatt gatggcagtg aacgacaaaa tggcgtcctg  540
aacagttgga ctgatcagga cagcaaagac agcacctaca gcatgagcag caccctcacg  600
ttgaccaagg acgagtatga acgacataac agctatacct gtgaggccac tcacaagaca  660
tcaacttcac ccattgtcaa gagcttcaac aggaatgagt gttag                  705

SEQ ID NO: 169         moltype = AA  length = 447
FEATURE                Location/Qualifiers
source                 1..447
                       mol_type = protein
                       organism = Mus musculus
```

-continued

```
SEQUENCE: 169
EVQLQQSGPE LMKPGASVKM SCKASGYTFT DYNMHWVKQN QGKTLDWIGE INPNSGGAGY  60
NQKFKGKATL TVDKSSTTAY MELRSLTSED SAVYYCARLG YDDIYDDWYF DVWGAGTTVT  120
VSSAKTTPPS VYPLAPGSAA QTNSMVTLGC LVKGYFPEPV TVTWNSGSLS SGVHTFPAVL  180
QSDLYTLSSS VTVPSSTWPS ETVTCNVAHP ASSTKVDKKI VPRDCGCKPC ICTVPEVSSV  240
FIFPPKPKDV LTITLTPKVT CVVVDISKDD PEVQFSWFVD DVEVHTAQTQ PREEQFNSTF  300
RSVSELPIMH QDWLNGKEFK CRVNSAAFPA PIEKTISKTK GRPKAPQVYT IPPPKEQMAK  360
DKVSLTCMIT DFFPEDITVE WQWNGQPAEN YKNTQPIMDT DGSYFIYSKL NVQKSNWEAG  420
NTFTCSVLHE GLHNHHTEKS LSHSPGK                                    447

SEQ ID NO: 170          moltype = DNA  length = 1344
FEATURE                 Location/Qualifiers
source                  1..1344
                        mol_type = other DNA
                        organism = Mus musculus
SEQUENCE: 170
gaggtccaac tgcaacagtc tggacctgaa ctaatgaagc ctggggcttc agtgaagatg  60
tcctgcaagg cttctggata tacattcact gactacaaca tgcactgggt gaagcagaac  120
caaggaaaga ccctagactg gataggagaa attaatccta acagtggtgg tgctggctac  180
aaccagaagt tcaagggcaa ggccacattg actgtagaca agtcctccac cacagcctac  240
atggagctcc gcagcctgac atctgaggac tctgcagtct attactgtgc aagattgggc  300
tacgatgata tctacgacga ctggtacttc gatgtctggg gcgcagggac cacggtcacc  360
gtctcctcag ccaaaacgac acccccatct gtctatccac tggcccctgg atctgctgcc  420
caaactaact ccatggtgac cctgggatgc ctggtcaagg gctatttccc tgagccagtg  480
acagtgacct ggaactctgg atccctgtcc agcggtgtgc acaccttccc agctgtcctg  540
cagtctgacc tctacactct gagcagctca gtgactgtcc cctccagcac ctggcccagc  600
gagaccgtca cctgcaacgt tgcccacccg gccagcagca ccaaggtgga caagaaaatt  660
gtgcccaggg attgtggttg taagccttgc atatgtacag tcccagaagt atcatctgtc  720
ttcatcttcc ccccaaagcc caaggatgtg ctcaccatta ctctgactcc taaggtcacg  780
tgtgttgtgg tagacatcag caaggatgat cccgaggtcc agttcagctg gtttgtagat  840
gatgtggagg tgcacacagc tcagacgcaa ccccgggagg agcagttcaa cagcactttc  900
cgctcagtca gtgaacttcc catcatgcac caggactggc tcaatggcaa ggagttcaaa  960
tgcagggtca acagtgcagc tttccctgcc cccatcgaga aaaccatctc caaaaccaaa  1020
ggcagaccga aggctccaca ggtgtacacc attccacctc ccaaggagca gatggccaag  1080
gataaagtca gtctgacctg catgataaca gacttcttcc ctgaagacat tactgtggag  1140
tggcagtgga atgggcagcc agcggagaac tacaagaaca ctcagcccat catggacaca  1200
gatggctctt acttcatcta cagcaagctc aatgtgcaga agagcaactg ggaggcagga  1260
aatactttca cctgctctgt gttacatgag ggcctgcaca accaccatac tgagaagagc  1320
ctctcccact ctcctggtaa atga                                       1344

SEQ ID NO: 171          moltype = AA  length = 466
FEATURE                 Location/Qualifiers
source                  1..466
                        mol_type = protein
                        organism = Mus musculus
SEQUENCE: 171
MGWSWTFLFL LSGTAGVLSE VQLQQSGPEL MKPGASVKMS CKASGYTFTD YNMHWVKQNQ  60
GKTLDWIGEI NPNSGGAGYN QKFKGKATLT VDKSSTTAYM ELRSLTSEDS AVYYCARLGY  120
DDIYDDWYFD VWGAGTTVTV SSAKTTPPSV YPLAPGSAAQ TNSMVTLGCL VKGYFPEPVT  180
VTWNSGSLSS GVHTFPAVLQ SDLYTLSSSV TVPSSTWPSE TVTCNVAHPA SSTKVDKKIV  240
PRDCGCKPCI CTVPEVSSVF IFPPKPKDVL TITLTPKVTC VVVDISKDDP EVQFSWFVDD  300
VEVHTAQTQP REEQFNSTFR SVSELPIMHQ DWLNGKEFKC RVNSAAFPAP IEKTISKTKG  360
RPKAPQVYTI PPPKEQMAKD KVSLTCMITD FFPEDITVEW QWNGQPAENY KNTQPIMDTD  420
GSYFIYSKLN VQKSNWEAGN TFTCSVLHEG LHNHHTEKSL SHSPGK                 466

SEQ ID NO: 172          moltype = DNA  length = 1401
FEATURE                 Location/Qualifiers
source                  1..1401
                        mol_type = other DNA
                        organism = Mus musculus
SEQUENCE: 172
atgggatgga gctggacctt tctcttcctc ctgtcaggaa ctgcaggtgt cctctctgag  60
gtccaactgc aacagtctgg acctgaacta atgaagcctg gggcttcagt gaagatgtcc  120
tgcaaggctt ctggatatac attcactgac tacaacatgc actgggtgaa gcagaaccaa  180
ggaaagaccc tagactggat aggagaaatt aatcctaaca gtggtggtgc tggctacaac  240
cagaagttca agggcaaggc cacattgact gtagacaagt cctccaccac agcctacatg  300
gagctccgca gcctgacatc tgaggactct gcagtctatt actgtgcaag attgggctac  360
gatgatatct acgacgactg gtacttcgat gtctggggcg cagggaccac ggtcaccgtc  420
tcctcagcca aaacgacacc cccatctgtc tatccactgg cccctggatc tgctgcccaa  480
actaactcca tggtgaccct gggatgcctg gtcaagggct atttccctga gccagtgaca  540
gtgacctgga actctggatc cctgtccagc ggtgtgcaca ccttcccagc tgtcctgcag  600
tctgacctct acactctgag cagctcagtg actgtcccct ccagcacctg gcccagcgag  660
accgtcacct gcaacgttgc ccacccggcc agcagcacca aggtggacaa gaaaattgtg  720
cccagggatt gtggttgtaa gccttgcata tgtacagtcc cagaagtatc atctgtcttc  780
atcttccccc caaagcccaa ggatgtgctc accattactc tgactcctaa ggtcacgtgt  840
gttgtggtag acatcagcaa ggatgatccc gaggtccagt tcagctggtt tgtagatgat  900
gtggaggtgc acacagctca gacgcaaccc cgggaggagc agttcaacag cactttccgc  960
tcagtcagtg aacttcccat catgcaccag gactggctca atggcaagga gttcaaatgc  1020
agggtcaaca gtgcagcttt ccctgccccc atcgagaaaa ccatctccaa aaccaaaggc  1080
```

```
agaccgaagg ctccacaggt gtacaccatt ccacctccca aggagcagat ggccaaggat  1140
aaagtcagtc tgacctgcat gataacagac ttcttccctg aagacattac tgtggagtgg  1200
cagtggaatg ggcagccagc ggagaactac aagaacactc agcccatcat ggacacagat  1260
ggctcttact tcatctacag caagctcaat gtgcagaaga gcaactggga ggcaggaaat  1320
actttcacct gctctgtgtt acatgagggc ctgcacaacc accatactga gaagagcctc  1380
tcccactctc ctggtaaatg a                                            1401

SEQ ID NO: 173         moltype = AA  length = 214
FEATURE                Location/Qualifiers
source                 1..214
                       mol_type = protein
                       organism = Mus musculus
SEQUENCE: 173
DIQMTQITSS LSASLGDRVS ISCRASQDIS NYLNWYQQKP DGTFKLLIFY TSRLFSGVPS  60
RFSGSGSGTD YSLTIYNLEQ EDFATYFCQQ GDTLPYTFGG GTKVEIKRAD AAPTVSIFPP  120
SSEQLTSGGA SVVCFLNNFY PKDINVKWKI DGSERQNGVL NSWTDQDSKD STYSMSSTLT  180
LTKDEYERHN SYTCEATHKT STSPIVKSFN RNEC                              214

SEQ ID NO: 174         moltype = DNA  length = 642
FEATURE                Location/Qualifiers
source                 1..642
                       mol_type = other DNA
                       organism = Mus musculus
SEQUENCE: 174
gatatccaga tgacacagat tacatcctcc ctgtctgcct ctctgggaga cagggtctcc  60
atcagttgca gggcaagtca agacattagc aattatttaa attggtatca gcagaaacca  120
gatggaactt ttaaactcct tatcttctac acatcaagat tattttcagg agtcccatca  180
aggttcagtg gcagtgggtc tggaacagat tattctctca ccatttacaa cctggagcaa  240
gaagattttg ccacttactt ttgccaacag ggagatacgc ttccgtacac tttcggaggg  300
gggaccaagg tggaaataaa acgggctgat gctgcaccaa ctgtatccat cttcccacca  360
tccagtgagc agttaacatc tggaggtgcc tcagtcgtgt gcttcttgaa caacttctac  420
cccaaagaca tcaatgtcaa gtggaagatt gatggcagtg aacgacaaaa tggcgtcctg  480
aacagttgga ctgatcagga cagcaaagac agcacctaca gcatgagcag caccctcacg  540
ttgaccaagg acgagtatga acgacataac agctatacct gtgaggccac tcacaagaca  600
tcaacttcac ccattgtcaa gagcttcaac aggaatgagt gt                     642

SEQ ID NO: 175         moltype = AA  length = 234
FEATURE                Location/Qualifiers
source                 1..234
                       mol_type = protein
                       organism = Mus musculus
SEQUENCE: 175
MMSSAQFLGL LLLCFQGTRC DIQMTQITSS LSASLGDRVS ISCRASQDIS NYLNWYQQKP  60
DGTFKLLIFY TSRLFSGVPS RFSGSGSGTD YSLTIYNLEQ EDFATYFCQQ GDTLPYTFGG  120
GTKVEIKRAD AAPTVSIFPP SSEQLTSGGA SVVCFLNNFY PKDINVKWKI DGSERQNGVL  180
NSWTDQDSKD STYSMSSTLT LTKDEYERHN SYTCEATHKT STSPIVKSFN RNEC        234

SEQ ID NO: 176         moltype = DNA  length = 702
FEATURE                Location/Qualifiers
source                 1..702
                       mol_type = other DNA
                       organism = Mus musculus
SEQUENCE: 176
atgatgtcct ctgctcagtt ccttggtctc ctgttgctct gttttcaagg taccagatgt  60
gatatccaga tgacacagat tacatcctcc ctgtctgcct ctctgggaga cagggtctcc  120
atcagttgca gggcaagtca agacattagc aattatttaa attggtatca gcagaaacca  180
gatggaactt ttaaactcct tatcttctac acatcaagat tattttcagg agtcccatca  240
aggttcagtg gcagtgggtc tggaacagat tattctctca ccatttacaa cctggagcaa  300
gaagattttg ccacttactt ttgccaacag ggagatacgc ttccgtacac tttcggaggg  360
gggaccaagg tggaaataaa acgggctgat gctgcaccaa ctgtatccat cttcccacca  420
tccagtgagc agttaacatc tggaggtgcc tcagtcgtgt gcttcttgaa caacttctac  480
cccaaagaca tcaatgtcaa gtggaagatt gatggcagtg aacgacaaaa tggcgtcctg  540
aacagttgga ctgatcagga cagcaaagac agcacctaca gcatgagcag caccctcacg  600
ttgaccaagg acgagtatga acgacataac agctatacct gtgaggccac tcacaagaca  660
tcaacttcac ccattgtcaa gagcttcaac aggaatgagt gt                     702

SEQ ID NO: 177         moltype = AA  length = 450
FEATURE                Location/Qualifiers
source                 1..450
                       mol_type = protein
                       organism = Mus musculus
SEQUENCE: 177
EVQLQQSGPE LMKPGTSVKM SCKASGYTFT DYNMHWVKQT QGKTLEWIGE INPNSGGAGY  60
NQKFKGKATL TVDKSSTTAY MELRSLTSED SAVYYCAKLG YDDIYDDWYF DVWGAGTTVT  120
VSSAKTTAPS VYPLAPVCGD TTGSSVTLGC LVKGYFPEPV TLTWNSGSLS SDVHTFPALL  180
QSGLYTLSSS VTVTTWPSQT ITCNVAHPAS STKVDKKIEP RGSPTHKPCP PCPAPNLLGG  240
PSVFIFPPKI KDVLMISLSP MVTCVVVDVS EDDPDVHVSW FVNNVEVHTA QTQTHREDYN  300
STIRVVSALP IQHQDWMSGK EFKCKVNNKA LPAPIERTIS KPKGPVRAPQ VYVLPPPEEE  360
MTKKQVTLTC MITDFMPEDI YVEWTNNGQT ELNYKNTEPV LDSDGSYFMY SKLRVEKKNW  420
```

-continued

```
VERNSYSCSV VHEGLHNHHT TKSFSRTPGK                                450

SEQ ID NO: 178          moltype = DNA  length = 1350
FEATURE                 Location/Qualifiers
source                  1..1350
                        mol_type = other DNA
                        organism = Mus musculus
SEQUENCE: 178
gaggtccaac tgcaacagtc tggacctgaa ctaatgaagc ctgggacttc agtgaagatg  60
tcctgcaagg cttctggata tacattcact gactacaaca tgcactgggt gaagcagacc  120
caaggaaaga ccctagagtg gataggagaa attaatccta acagtggtgg tgctggctac  180
aaccagaagt tcaagggcaa ggccacattg actgtagaca agtcctccac cacagcctac  240
atggagctcc gcagcctgac atctgaggac tctgcagtct attactgtgc aaaattgggc  300
tacgatgata tctacgacga ctggtatttc gatgtctggg gcgcagggac cacggtcacc  360
gtctcctcag ccaaaacaac agccccatcg gtctatccac tggcccctgt gtgtggagat  420
acaactggct cctcggtgac tctaggatgc ctggtcaagg gttatttccc tgagccagtg  480
accttgacct ggaactctgg atccctgtcc agtgatgtgc acaccttccc agctctcctg  540
cagtctggcc tctacaccct cagcagctca gtgactgtaa ccacctggcc cagccagacc  600
atcacctgca atgtggccca cccggcaagc agcaccaaag tggacaagaa aattgagccc  660
agagggtccc caacacataa accctgtcct ccatgcccag ctcctaacct cttgggtgga  720
ccatccgtct tcatcttccc tccaaagatc aaggatgtac tcatgatctc cctgagcccc  780
atggtcacgt gtgtggtggt ggatgtgagc gaggatgacc cagatgtcca tgtcagctgg  840
ttcgtgaaca acgtggaagt acacacagct cagacacaaa cccatagaga ggattacaac  900
agtactatcc gggtggtcag tgccctcccc atccagcacc aggactggat gagtggcaag  960
gagttcaaat gcaaggtcaa caacaaagcc ctcccagcgc ccatcgagag aaccatctca  1020
aaacccaaag ggccagtaag agctccacag gtatatgtct tgcctccacc agaagaagag  1080
atgactaaga aacaggtcac tctgacctgc atgatcacag acttcatgcc tgaagacatt  1140
tacgtggagt ggaccaacaa cggcaaaaca gagctaaact acaagaacac tgaaccagtc  1200
ctggactctg atggttctta cttcatgtac agcaagctga gagtggaaaa gaagaactgg  1260
gtggaaagaa atagctactc ctgttcagtg gtccacgagg gtctgcacaa tcaccacacg  1320
actaagagct tctcccggac tccgggtaaa                                1350

SEQ ID NO: 179          moltype = AA  length = 469
FEATURE                 Location/Qualifiers
source                  1..469
                        mol_type = protein
                        organism = Mus musculus
SEQUENCE: 179
MGWSWTFLFL LSGTAGVLSE VQLQQSGPEL MKPGTSVKMS CKASGYTFTD YNMHWVKQTQ  60
GKTLEWIGEI NPNSGGAGYN QKFKGKATLT VDKSSTTAYM ELRSLTSEDS AVYYCAKLGY  120
DDIYDDWYFD VWGAGTTVTV SSAKTTAPSV YPLAPVCGDT TGSSVTLGCL VKGYFPEPVT  180
LTWNSGSLSS DVHTFPALLQ SGLYTLSSSV TVTTWPSQTI TCNVAHPASS TKVDKKIEPR  240
GSPTHKPCPP CPAPNLLGGP SVFIFPPKIK DVLMISLSPM VTCVVVDVSE DDPDVHVSWF  300
VNNVEVHTAQ TQTHREDYNS TIRVVSALPI QHQDWMSGKE FKCKVNNKAL PAPIERTISK  360
PKGPVRAPQV YVLPPPEEEM TKKQVTLTCM ITDFMPEDIY VEWTNNGQTE LNYKNTEPVL  420
DSDGSYFMYS KLRVEKKNWV ERNSYSCSVV HEGLHNHHTT KSFSRTPGK            469

SEQ ID NO: 180          moltype = DNA  length = 1407
FEATURE                 Location/Qualifiers
source                  1..1407
                        mol_type = other DNA
                        organism = Mus musculus
SEQUENCE: 180
atgggatgga gctggacctt tctcttcctc ctgtcaggaa ctgcaggtgt cctctctgag  60
gtccaactgc aacagtctgg acctgaacta atgaagcctg ggacttcagt gaagatgtcc  120
tgcaaggctt ctggatatac attcactgac tacaacatgc actgggtgaa gcagacccaa  180
ggaaagaccc tagagtggat aggagaaatt aatcctaaca gtggtggtgc tggctacaac  240
cagaagttca agggcaaggc cacattgact gtagacaagt cctccaccac agcctacatg  300
gagctccgca gcctgacatc tgaggactct gcagtctatt actgtgcaaa attgggctac  360
gatgatatct acgacgactg gtatttcgat gtctggggcg cagggaccac ggtcaccgtc  420
tcctcagcca aaacaacagc cccatcggtc tatccactgg cccctgtgtg tggagataca  480
actggctcct cggtgactct aggatgcctg gtcaagggtt atttccctga gccagtgacc  540
ttgacctgga actctggatc cctgtccagt gatgtgcaca ccttcccagc tctcctgcag  600
tctggcctct acaccctcag cagctcagtg actgtaacca cctggcccag ccagaccatc  660
acctgcaatg tggcccaccc ggcaagcagc accaaagtgg acaagaaaat tgagcccaga  720
gggtccccaa cacataaacc ctgtcctcca tgcccagctc ctaacctctt gggtggacca  780
tccgtcttca tcttccctcc aaagatcaag gatgtactca tgatctccct gagccccatg  840
gtcacgtgtg tggtggtgga tgtgagcgag gatgacccag atgtccatgt cagctggttc  900
gtgaacaacg tggaagtaca cacagctcag acacaaaccc atagagagga ttacaacagt  960
actatccggg tggtcagtgc cctccccatc cagcaccagg actggatgag tggcaaggag  1020
ttcaaatgca aggtcaacaa caaagccctc ccagcgccca tcgagagaac catctcaaaa  1080
cccaaagggc cagtaagagc tccacaggta tatgtcttgc ctccaccaga agaagagatg  1140
actaagaaac aggtcactct gacctgcatg atcacagact tcatgcctga agacatttac  1200
gtggagtgga ccaacaacgg gcaaacagag ctaaactaca agaacactga accagtcctg  1260
gactctgatg gttcttactt catgtacagc aagctgagag tggaaaagaa gaactgggtg  1320
gaaagaaata gctactcctg ttcagtggtc cacgagggtc tgcacaatca ccacacgact  1380
aagagcttct cccggactcc gggtaaa                                   1407

SEQ ID NO: 181          moltype = AA  length = 214
```

```
FEATURE                 Location/Qualifiers
source                  1..214
                        mol_type = protein
                        organism = Mus musculus
SEQUENCE: 181
DIQMTQTTSS LSASLGDRVS ISCRASQDIS NYLNWYQQKP DGTFKLLIFY TSRLLSGVPS  60
RFSGSGSGTD YSLTIYNLEQ EDFATYFCQQ GDTLPYTFGG GTKLEIKRAD AAPTVSIFPL  120
SSEQLTSGGA SVVCFLNNFY PKDINVKWKI DGSERQNGVL NSWTDQDSKD STYSMSSTLT  180
LTKDEYERHN SYTCEATHKT STSPIVKSFN RNEC                              214

SEQ ID NO: 182          moltype = DNA  length = 645
FEATURE                 Location/Qualifiers
source                  1..645
                        mol_type = other DNA
                        organism = Mus musculus
SEQUENCE: 182
gatatccaga tgacacagac tacatcctcc ctgtctgcct ctctgggaga cagggtctcc  60
atcagttgca gggcaagtca agacattagc aattatttaa actggtatca gcagaaacca  120
gatggaactt ttaaactcct tatcttctac acatcaagat tactctcagg agtcccatca  180
aggttcagtg gcagtgggtc tggaacagat tattctctca ccatttacaa cctggagcaa  240
gaagattttg ccacttactt ttgccaacag ggagatacgc ttccgtacac tttcggaggg  300
gggaccaaac tggaaataaa acgggctgat gctgcaccaa ctgtatccat cttcccacta  360
tccagtgagc agttaacatc tggaggtgcc tcagtcgtgt gcttcttgaa caacttctac  420
cccaaagaca tcaatgtcaa gtggaagatt gatggcagtg aacgacaaaa tggcgtcctg  480
aacagttgga ctgatcagga cagcaaagac agcacctaca gcatgagcag caccctcacg  540
ttgaccaagg acgagtatga acgacataac agctatacct gtgaggccac tcacaagaca  600
tcaacttcac ccattgtcaa gagcttcaac aggaatgagt gttag                  645

SEQ ID NO: 183          moltype = AA  length = 234
FEATURE                 Location/Qualifiers
source                  1..234
                        mol_type = protein
                        organism = Mus musculus
SEQUENCE: 183
MMSSAQFLGL LLLCFQGTRC DIQMTQTTSS LSASLGDRVS ISCRASQDIS NYLNWYQQKP  60
DGTFKLLIFY TSRLLSGVPS RFSGSGSGTD YSLTIYNLEQ EDFATYFCQQ GDTLPYTFGG  120
GTKLEIKRAD AAPTVSIFPL SSEQLTSGGA SVVCFLNNFY PKDINVKWKI DGSERQNGVL  180
NSWTDQDSKD STYSMSSTLT LTKDEYERHN SYTCEATHKT STSPIVKSFN RNEC        234

SEQ ID NO: 184          moltype = DNA  length = 705
FEATURE                 Location/Qualifiers
source                  1..705
                        mol_type = other DNA
                        organism = Mus musculus
SEQUENCE: 184
atgatgtcct ctgctcagtt ccttggtctc ctgttgctct gttttcaagg taccagatgt  60
gatatccaga tgacacagac tacatcctcc ctgtctgcct ctctgggaga cagggtctcc  120
atcagttgca gggcaagtca agacattagc aattatttaa actggtatca gcagaaacca  180
gatggaactt ttaaactcct tatcttctac acatcaagat tactctcagg agtcccatca  240
aggttcagtg gcagtgggtc tggaacagat tattctctca ccatttacaa cctggagcaa  300
gaagattttg ccacttactt ttgccaacag ggagatacgc ttccgtacac tttcggaggg  360
gggaccaaac tggaaataaa acgggctgat gctgcaccaa ctgtatccat cttcccacta  420
tccagtgagc agttaacatc tggaggtgcc tcagtcgtgt gcttcttgaa caacttctac  480
cccaaagaca tcaatgtcaa gtggaagatt gatggcagtg aacgacaaaa tggcgtcctg  540
aacagttgga ctgatcagga cagcaaagac agcacctaca gcatgagcag caccctcacg  600
ttgaccaagg acgagtatga acgacataac agctatacct gtgaggccac tcacaagaca  660
tcaacttcac ccattgtcaa gagcttcaac aggaatgagt gttag                  705

SEQ ID NO: 185          moltype = AA  length = 447
FEATURE                 Location/Qualifiers
source                  1..447
                        mol_type = protein
                        organism = Mus musculus
SEQUENCE: 185
EVQLQQSGPE LMKPGASVKM SCKASGYTFT DYNMHWVKQN QGKTLEWIGE INPNSGGAGY  60
NQKFKGKATL TVDKSSTTAY MELRSLTSED SAVYYCARLG YDDIYDDWYF DVWGAGTTVT  120
VSSAKTTPPS VYPLAPGSAA QTNSMVTLGC LVKGYFPEPV TVTWNSGSLS SGVHTFPAVL  180
QSDLYTLSSS VTVPSSTWPS ETVTCNVAHP ASSTKVDKKI VPRDCGCKPC ICTVPEVSSV  240
FIFPPKPKDV LTITLTPKVT CVVVDISKDD PEVQFSWFVD DVEVHTAQTQ PREEQFNSTF  300
RSVSELPIMH QDWLNGKEFK CRVNSAAFPA PIEKTISKTK GRPKAPQVYT IPPPKEQMAK  360
DKVSLTCMIT DFFPEDITVE WQWNGQPAEN YKNTQPIMDT DGSYFIYSKL NVQKSNWEAG  420
NTFTCSVLHE GLHNHHTEKS LSHSPGK                                      447

SEQ ID NO: 186          moltype = DNA  length = 1344
FEATURE                 Location/Qualifiers
source                  1..1344
                        mol_type = other DNA
                        organism = Mus musculus
SEQUENCE: 186
```

-continued

```
gaggtccaac tgcaacagtc tggacctgaa ctaatgaagc ctggggcttc agtgaagatg  60
tcctgcaagg cttctggata tacattcact gactacaaca tgcactgggt gaagcagaac  120
caaggaaaga ccctagaatg gataggagaa attaatccta acagtggtgg tgctggctac  180
aaccagaagt tcaagggcaa ggccacattg actgtagaca agtcctccac cacagcctac  240
atggagctcc gcagcctgac atctgaggac tctgcagtct attactgtgc aagattgggc  300
tacgatgata tctacgacga ctggtacttc gatgtctggg gcgcagggac cacggtcacc  360
gtctcctcag ccaaaacgac acccccatct gtctatccac tggcccctgg atctgctgcc  420
caaactaact ccatggtgac cctgggatgc ctggtcaagg gctatttccc tgagccagtg  480
acagtgacct ggaactctgg atccctgtcc agcggtgtgc acaccttccc agctgtcctg  540
cagtctgacc tctacactct gagcagctca gtgactgtcc cctccagcac ctggcccagc  600
gagaccgtca cctgcaacgt tgcccacccg gccagcagca ccaaggtgga caagaaaatt  660
gtgcccaggg attgtggttg taagccttgc atatgtacag tcccagaagt atcatctgtc  720
ttcatcttcc ccccaaagcc caaggatgtg ctcaccatta ctctgactcc taaggtcacg  780
tgtgttgtgg tagacatcag caaggatgat cccgaggtcc agttcagctg gtttgtagat  840
gatgtggagg tgcacacagc tcagacgcaa ccccgggagg agcagttcaa cagcactttc  900
cgctcagtca gtgaacttcc catcatgcac caggactggc tcaatggcaa ggagttcaaa  960
tgcagggtca acagtgcagc tttccctgcc cccatcgaga aaaccatctc caaaaccaaa  1020
ggcagaccga aggctccaca ggtgtacacc attccacctc ccaaggagca gatggccaag  1080
gataaagtca gtctgacctg catgataaca gacttcttcc ctgaagacat tactgtggag  1140
tggcagtgga atgggcagcc agcggagaac tacaagaaca ctcagcccat catggacaca  1200
gatggctctt acttcatcta cagcaagctc aatgtgcaga agagcaactg ggaggcagga  1260
aatactttca cctgctctgt gttacatgag ggcctgcaca accaccatac tgagaagagc  1320
ctctcccact ctcctggtaa atga                                         1344

SEQ ID NO: 187          moltype = AA  length = 466
FEATURE                 Location/Qualifiers
source                  1..466
                        mol_type = protein
                        organism = Mus musculus
SEQUENCE: 187
MGWSWTFLFL LSGTAGVLSE VQLQQSGPEL MKPGASVKMS CKASGYTFTD YNMHWVKQNQ  60
GKTLEWIGEI NPNSGGAGYN QKFKGKATLT VDKSSTTAYM ELRSLTSEDS AVYYCARLGY  120
DDIYDDWYFD VWGAGTTVTV SSAKTTPPSV YPLAPGSAAQ TNSMVTLGCL VKGYFPEPVT  180
VTWNSGSLSS GVHTFPAVLQ SDLYTLSSSV TVPSSTWPSE TVTCNVAHPA SSTKVDKKIV  240
PRDCGCKPCI CTVPEVSSVF IFPPKPKDVL TITLTPKVTC VVVDISKDDP EVQFSWFVDD  300
VEVHTAQTQP REEQFNSTFR SVSELPIMHQ DWLNGKEFKC RVNSAAFPAP IEKTISKTKG  360
RPKAPQVYTI PPPKEQMAKD KVSLTCMITD FFPEDITVEW QWNGQPAENY KNTQPIMDTD  420
GSYFIYSKLN VQKSNWEAGN TFTCSVLHEG LHNHHTEKSL SHSPGK                 466

SEQ ID NO: 188          moltype = DNA  length = 1401
FEATURE                 Location/Qualifiers
source                  1..1401
                        mol_type = other DNA
                        organism = Mus musculus
SEQUENCE: 188
atgggatgga gctggacctt tctcttcctc ctgtcaggaa ctgcaggtgt cctctctgag  60
gtccaactgc aacagtctgg acctgaacta atgaagcctg gggcttcagt gaagatgtcc  120
tgcaaggctt ctggatatac attcactgac tacaacatgc actgggtgaa gcagaaccaa  180
ggaaagaccc tagaatggat aggagaaatt aatcctaaca gtggtggtgc tggctacaac  240
cagaagttca agggcaaggc cacattgact gtagacaagt cctccaccac agcctacatg  300
gagctccgca gcctgacatc tgaggactct gcagtctatt actgtgcaag attgggctac  360
gatgatatct acgacgactg gtacttcgat gtctggggcg cagggaccac ggtcaccgtc  420
tcctcagcca aaacgacacc cccatctgtc tatccactgg cccctggatc tgctgcccaa  480
actaactcca tggtgaccct gggatgcctg gtcaagggct atttccctga gccagtgaca  540
gtgacctgga actctggatc cctgtccagc ggtgtgcaca ccttcccagc tgtcctgcag  600
tctgacctct acactctgag cagctcagtg actgtcccct ccagcacctg gcccagcgag  660
accgtcacct gcaacgttgc ccacccggcc agcagcacca aggtggacaa gaaaattgtg  720
cccagggatt gtggttgtaa gccttgcata tgtacagtcc cagaagtatc atctgtcttc  780
atcttccccc caaagcccaa ggatgtgctc accattactc tgactcctaa ggtcacgtgt  840
gttgtggtag acatcagcaa ggatgatccc gaggtccagt tcagctggtt tgtagatgat  900
gtggaggtgc acacagctca gacgcaaccc cgggaggagc agttcaacag cactttccgc  960
tcagtcagtg aacttcccat catgcaccag gactggctca atggcaagga gttcaaatgc  1020
agggtcaaca gtgcagcttt ccctgccccc atcgagaaaa ccatctccaa aaccaaaggc  1080
agaccgaagg ctccacaggt gtacaccatt ccacctccca aggagcagat ggccaaggat  1140
aaagtcagtc tgacctgcat gataacagac ttcttccctg aagacattac tgtggagtgg  1200
cagtggaatg ggcagccagc ggagaactac aagaacactc agcccatcat ggacacagat  1260
ggctcttact tcatctacag caagctcaat gtgcagaaga gcaactggga ggcaggaaat  1320
actttcacct gctctgtgtt acatgagggc ctgcacaacc accatactga gaagagcctc  1380
tcccactctc ctggtaaatg a                                            1401

SEQ ID NO: 189          moltype = AA  length = 213
FEATURE                 Location/Qualifiers
source                  1..213
                        mol_type = protein
                        organism = Mus musculus
SEQUENCE: 189
QIVLSQSPAF LSVSPGDKVT MTCRASSSIS YIHWFQQKPG SSPRSWIYAT SNLASGVPGR  60
FSGSGSGTSY SLTISRVEAE DAATYYCQQW SSDPLTFGAG TKLELKRADA APTVSIFPPS  120
SEQLTSGGAS VVCFLNNFYP KDINVKWKID GSERQNGVLN SWTDQDSKDS TYSMSSTLTL  180
```

-continued

```
TKDEYERHNS YTCEATHKTS TSPIVKSFNR NEC                             213

SEQ ID NO: 190         moltype = DNA  length = 642
FEATURE                Location/Qualifiers
source                 1..642
                       mol_type = other DNA
                       organism = Mus musculus
SEQUENCE: 190
caaattgttc tctcccagtc tccagcattc ctgtctgtat ctccagggga taaggtcaca  60
atgacttgca gggccagctc aagtataagt tacatacact ggtttcagca gaagccagga  120
tcctccccca gatcctggat ttatgccaca tccaacctgg cttctggagt ccctggtcgc  180
ttcagtggca gtgggtctgg gacctcttac tctctcacaa tcagcagagt ggaggctgag  240
gatgctgcca cttattactg ccagcagtgg agtagtgacc cactcacgtt cggtgctggg  300
accaagctgg agctgaaacg ggctgatgct gcaccaactg tatccatctt cccaccatcc  360
agtgagcagt taacatctgg aggtgcctca gtcgtgtgct tcttgaacaa cttctacccc  420
aaagacatca atgtcaagtg gaagattgat ggcagtgaac gacaaaatgg cgtcctgaac  480
agttggactg atcaggacag caaagacagc acctacagca tgagcagcac cctcacgttg  540
accaaggacg agtatgaacg acataacagc tatacctgtg aggccactca caagacatca  600
acttcaccca ttgtcaagag cttcaacagg aatgagtgtt ag                   642

SEQ ID NO: 191         moltype = AA  length = 235
FEATURE                Location/Qualifiers
source                 1..235
                       mol_type = protein
                       organism = Mus musculus
SEQUENCE: 191
MDFQVQIFSF LLISASVIMS RGQIVLSQSP AFLSVSPGDK VTMTCRASSS ISYIHWFQQK  60
PGSSPRSWIY ATSNLASGVP GRFSGSGSGT SYSLTISRVE AEDAATYYCQ QWSSDPLTFG  120
AGTKLELKRA DAAPTVSIFP PSSEQLTSGG ASVVCFLNNF YPKDINVKWK IDGSERQNGV  180
LNSWTDQDSK DSTYSMSSTL TLTKDEYERH NSYTCEATHK TSTSPIVKSF NRNEC       235

SEQ ID NO: 192         moltype = DNA  length = 708
FEATURE                Location/Qualifiers
source                 1..708
                       mol_type = other DNA
                       organism = Mus musculus
SEQUENCE: 192
atggattttc aagtgcagat tttcagcttc ctgctaatca gtgcttcagt cataatgtcc  60
agaggacaaa ttgttctctc ccagtctcca gcattcctgt ctgtatctcc aggggataag  120
gtcacaatga cttgcagggc cagctcaagt ataagttaca tacactggtt tcagcagaag  180
ccaggatcct cccccagatc ctggatttat gccacatcca acctggcttc tggagtccct  240
ggtcgcttca gtggcagtgg gtctgggacc tcttactctc tcacaatcag cagagtggag  300
gctgaggatg ctgccactta ttactgccag cagtggagta gtgacccact cacgttcggt  360
gctgggacca agctggagct gaaacgggct gatgctgcac caactgtatc catcttccca  420
ccatccagtg agcagttaac atctggaggt gcctcagtcg tgtgcttctt gaacaacttc  480
taccccaaag acatcaatgt caagtggaag attgatggca gtgaacgaca aaatggcgtc  540
ctgaacagtt ggactgatca ggacagcaaa gacagcacct acagcatgag cagcaccctc  600
acgttgacca aggacgagta tgaacgacat aacagctata cctgtgaggc cactcacaag  660
acatcaactt cacccattgt caagagcttc aacaggaatg agtgttag              708

SEQ ID NO: 193         moltype = AA  length = 445
FEATURE                Location/Qualifiers
source                 1..445
                       mol_type = protein
                       organism = Mus musculus
SEQUENCE: 193
EVQLQQSGAD LVQPGASVKV SCTASGFDIK DYYIHWMKQR PDQGLEWIGR VDPDNGETEF  60
APKFPGKATF TTDTSSNTAY LQLRGLTSED TAIYYCGRED YDGTYTWFPY WGQGTLVTVS  120
AAKTTPPSVY PLAPGSAAQT NSMVTLGCLV KGYFPEPVTV TWNSGSLSSG VHTFPAVLQS  180
DLYTLSSSVT VPSSTWPSET VTCNVAHPAS STKVDKKIVP RDCGCKPCIC TVPEVSSVFI  240
FPPKPKDVLT ITLTPKVTCV VVDISKDDPE VQFSWFVDDV EVHTAQTQPR EEQFNSTFRS  300
VSELPIMHQD WLNGKEFKCR VNSAAFPAPI EKTISKTKGR PKAPQVYTIP PPKEQMAKDK  360
VSLTCMITDF FPEDITVEWQ WNGQPAENYK NTQPIMDTDG SYFIYSKLNV QKSNWEAGNT  420
FTCSVLHEGL HNHHTEKSLS HSPGK                                      445

SEQ ID NO: 194         moltype = DNA  length = 1338
FEATURE                Location/Qualifiers
source                 1..1338
                       mol_type = other DNA
                       organism = Mus musculus
SEQUENCE: 194
gaagttcagc tgcaacagtc tggggcagac cttgtgcagc caggggcctc agtcaaggtg  60
tcctgcacag cttctggctt cgacattaag gactactata tacactggat gaaacagagg  120
cctgaccagg gcctggagtg gattggaagg gttgatcctg acaatggtga gactgaattt  180
gcccccgaagt tcccgggcaa ggccactttt acaacagaca catcctccaa cacagcctac  240
ctacaactca gaggcctgac atctgaggac actgccatct attactgtgg gagagaagac  300
tacgatggta cctacacctg gtttccttat tggggccaag ggactctggt cactgtctct  360
gcagccaaaa cgacaccccc atctgtctat ccactggccc ctggatctgc tgcccaaact  420
aactccatgg tgaccctggg atgcctggtc aagggctatt tccctgagcc agtgacagtg  480
```

-continued

```
acctggaact ctggatccct gtccagcggt gtgcacacct tcccagctgt cctgcagtct  540
gacctctaca ctctgagcag ctcagtgact gtcccctcca gcacctggcc cagcgagacc  600
gtcacctgca acgttgccca cccggccagc agcaccaagg tggacaagaa aattgtgccc  660
agggattgtg gttgtaagcc ttgcatatgt acagtcccag aagtatcatc tgtcttcatc  720
ttccccccaa agcccaagga tgtgctcacc attactctga ctcctaaggt cacgtgtgtt  780
gtggtagaca tcagcaagga tgatcccgag gtccagttca gctggtttgt agatgatgtg  840
gaggtgcaca cagctcagac gcaaccccgg gaggagcagt tcaacagcac tttccgctca  900
gtcagtgaac ttcccatcat gcaccaggac tggctcaatg gcaaggagtt caaatgcagg  960
gtcaacagtg cagctttccc tgcccccatc gagaaaacca tctccaaaac caaaggcaga  1020
ccgaaggctc cacaggtgta caccattcca cctcccaagg agcagatggc caaggataaa  1080
gtcagtctga cctgcatgat aacagacttc ttccctgaag acattactgt ggagtggcag  1140
tggaatgggc agccagcgga gaactacaag aacactcagc ccatcatgga cacagatggc  1200
tcttacttca tctacagcaa gctcaatgtg cagaagagca actgggaggc aggaaatact  1260
ttcacctgct ctgtgttaca tgagggcctg cacaaccacc atactgagaa gagcctctcc  1320
cactctcctg gtaaatga                                                1338

SEQ ID NO: 195         moltype = AA  length = 464
FEATURE                Location/Qualifiers
source                 1..464
                       mol_type = protein
                       organism = Mus musculus
SEQUENCE: 195
MKCSWVIFFL MAVVTGVNSE VQLQQSGADL VQPGASVKVS CTASGFDIKD YYIHWMKQRP  60
DQGLEWIGRV DPDNGETEFA PKFPGKATFT TDTSSNTAYL QLRGLTSEDT AIYYCGREDY  120
DGTYTWFPYW GQGTLVTVSA AKTTPPSVYP LAPGSAAQTN SMVTLGCLVK GYFPEPVTVT  180
WNSGSLSSGV HTFPAVLQSD LYTLSSSVTV PSSTWPSETV TCNVAHPASS TKVDKKIVPR  240
DCGCKPCICT VPEVSSVFIF PPKPKDVLTI TLTPKVTCVV VDISKDDPEV QFSWFVDDVE  300
VHTAQTQPRE EQFNSTFRSV SELPIMHQDW LNGKEFKCRV NSAAFPAPIE KTISKTKGRP  360
KAPQVYTIPP PKEQMAKDKV SLTCMITDFF PEDITVEWQW NGQPAENYKN TQPIMDTDGS  420
YFIYSKLNVQ KSNWEAGNTF TCSVLHEGLH NHHTEKSLSH SPGK                    464

SEQ ID NO: 196         moltype = DNA  length = 1395
FEATURE                Location/Qualifiers
source                 1..1395
                       mol_type = other DNA
                       organism = Mus musculus
SEQUENCE: 196
atgaaatgca gctgggtcat cttcttcctg atggcagtgg ttacaggggt caattcagaa  60
gttcagctgc aacagtctgg ggcagacctt gtgcagccag ggcctcagt caaggtgtcc  120
tgcacagctt ctggcttcga cattaaggac tactatatac actggatgaa acagaggcct  180
gaccagggcc tggagtggat tggaagggtt gatcctgaca atggtgagac tgaatttgcc  240
ccgaagttcc cgggcaaggc cacttttaca acagacacat cctccaacac agcctaccta  300
caactcagag gcctgacatc tgaggacact gccatctatt actgtgggag agaagactac  360
gatggtacct acacctggtt tccttattgg ggccaaggga ctctggtcac tgtctctgca  420
gccaaaacga cacccccatc tgtctatcca ctggcccctg gatctgctgc ccaaactaac  480
tccatggtga ccctgggatg cctggtcaag ggctatttcc ctgagccagt gacagtgacc  540
tggaactctg gatccctgtc cagcggtgtg cacaccttcc cagctgtcct gcagtctgac  600
ctctacactc tgagcagctc agtgactgtc ccctccagca cctggcccag cgagaccgtc  660
acctgcaacg ttgcccaccc ggccagcagc accaaggtgg acaagaaaat tgtgcccagg  720
gattgtggtt gtaagccttg catatgtaca gtcccagaag tatcatctgt cttcatcttc  780
cccccaaagc ccaaggatgt gctcaccatt actctgactc ctaaggtcac gtgtgttgtg  840
gtagacatca gcaaggatga tcccgaggtc cagttcagct ggtttgtaga tgatgtggag  900
gtgcacacag ctcagacgca accccgggag gagcagttca acagcacttt ccgctcagtc  960
agtgaacttc ccatcatgca ccaggactgg ctcaatggca aggagttcaa atgcagggtc  1020
aacagtgcag ctttccctgc ccccatcgag aaaaccatct ccaaaaccaa aggcagaccg  1080
aaggctccac aggtgtacac cattccacct cccaaggagc agatggccaa ggataaagtc  1140
agtctgacct gcatgataac agacttcttc cctgaagaca ttactgtgga gtggcagtgg  1200
aatgggcagc cagcggagaa ctacaagaac actcagccca tcatggacac agatggctct  1260
tacttcatct acagcaagct caatgtgcag aagagcaact gggaggcagg aaatactttc  1320
acctgctctg tgttacatga gggcctgcac aaccaccata ctgagaagag cctctcccac  1380
tctcctggta aatga                                                   1395

SEQ ID NO: 197         moltype = AA  length = 214
FEATURE                Location/Qualifiers
source                 1..214
                       mol_type = protein
                       organism = Mus musculus
SEQUENCE: 197
DLQMTQTTSS LSASLGDRVT ISCRASQDIS NYLNWYQQKP DGTVKLLIFY TSTLQSGVPS  60
RFSGSGSGTN YSLTITNLEQ DDAATYFCQQ GDTLPYTFGG GTKLEIKRAD AAPTVSIFPP  120
SSEQLTSGGA SVVCFLNNFY PKDINVKWKI DGSERQNGVL NSWTDQDSKD STYSMSSTLT  180
LTKDEYERHN SYTCEATHKT STSPIVKSFN RNEC                              214

SEQ ID NO: 198         moltype = DNA  length = 645
FEATURE                Location/Qualifiers
source                 1..645
                       mol_type = other DNA
                       organism = Mus musculus
SEQUENCE: 198
```

```
gatctccaga tgacacagac tacttcctcc ctgtctgcct ctctgggaga cagagtcacc  60
atcagttgca gggcaagtca ggacattagc aattatttaa actggtatca gcagaaacca  120
gatggaactg ttaagctcct gatcttctac acatcaacat tacagtcagg agtcccatcg  180
aggttcagtg gcagtgggtc tggaacaaat tattctctca ccattaccaa cctggagcaa  240
gatgatgctg ccacttactt ttgccaacag ggtgatacgc ttccgtacac gttcggaggg  300
gggaccaagc tggaaataaa acgggctgat gctgcaccaa ctgtatccat cttcccacca  360
tccagtgagc agttaacatc tggaggtgcc tcagtcgtgt gcttcttgaa caacttctac  420
cccaaagaca tcaatgtcaa gtggaagatt gatggcagtg aacgacaaaa tggcgtcctg  480
aacagttgga ctgatcagga cagcaaagac agcacctaca gcatgagcag caccctcacg  540
ttgaccaagg acgagtatga acgacataac agctatacct gtgaggccac tcacaagaca  600
tcaacttcac ccattgtcaa gagcttcaac aggaatgagt gttag                   645

SEQ ID NO: 199         moltype = AA  length = 234
FEATURE                Location/Qualifiers
source                 1..234
                       mol_type = protein
                       organism = Mus musculus
SEQUENCE: 199
MMSSAQFLGL LLLCFQGSRC DLQMTQTTSS LSASLGDRVT ISCRASQDIS NYLNWYQQKP  60
DGTVKLLIFY TSTLQSGVPS RFSGSGSGTN YSLTITNLEQ DDAATYFCQQ GDTLPYTFGG  120
GTKLEIKRAD AAPTVSIFPP SSEQLTSGGA SVVCFLNNFY PKDINVKWKI DGSERQNGVL  180
NSWTDQDSKD STYSMSSTLT LTKDEYERHN SYTCEATHKT STSPIVKSFN RNEC          234

SEQ ID NO: 200         moltype = DNA  length = 705
FEATURE                Location/Qualifiers
source                 1..705
                       mol_type = other DNA
                       organism = Mus musculus
SEQUENCE: 200
atgatgtcct ctgctcagtt ccttggtctc ctgttgctct gttttcaagg ttccagatgt  60
gatctccaga tgacacagac tacttcctcc ctgtctgcct ctctgggaga cagagtcacc  120
atcagttgca gggcaagtca ggacattagc aattatttaa actggtatca gcagaaacca  180
gatggaactg ttaagctcct gatcttctac acatcaacat tacagtcagg agtcccatcg  240
aggttcagtg gcagtgggtc tggaacaaat tattctctca ccattaccaa cctggagcaa  300
gatgatgctg ccacttactt ttgccaacag ggtgatacgc ttccgtacac gttcggaggg  360
gggaccaagc tggaaataaa acgggctgat gctgcaccaa ctgtatccat cttcccacca  420
tccagtgagc agttaacatc tggaggtgcc tcagtcgtgt gcttcttgaa caacttctac  480
cccaaagaca tcaatgtcaa gtggaagatt gatggcagtg aacgacaaaa tggcgtcctg  540
aacagttgga ctgatcagga cagcaaagac agcacctaca gcatgagcag caccctcacg  600
ttgaccaagg acgagtatga acgacataac agctatacct gtgaggccac tcacaagaca  660
tcaacttcac ccattgtcaa gagcttcaac aggaatgagt gttag                   705

SEQ ID NO: 201         moltype = AA  length = 447
FEATURE                Location/Qualifiers
source                 1..447
                       mol_type = protein
                       organism = Mus musculus
SEQUENCE: 201
EVQLQQSGPE LMKPGASVKM SCKASGYTFT DYNMHWMKQN QGKSLEWIGE INPNSGGSGY  60
NQKFKGKATL TVDKSSSTAY MELRSLTSED SAVYYCARLG YYGNYEDWYF DVWGAGTTVT  120
VSSAKTTPPS VYPLAPGSAA QTNSMVTLGC LVKGYFPEPV TVTWNSGSLS SGVHTFPAVL  180
QSDLYTLSSS VTVPSSTWPS ETVTCNVAHP ASSTKVDKKI VPRDCGCKPC ICTVPEVSSV  240
FIFPPKPKDV LTITLTPKVT CVVVDISKDD PEVQFSWFVD DVEVHTAQTQ PREEQFNSTF  300
RSVSELPIMH QDWLNGKEFK CRVNSAAFPA PIEKTISKTK GRPKAPQVYT IPPPKEQMAK  360
DKVSLTCMIT DFFPEDITVE WQWNGQPAEN YKNTQPIMDT DGSYFIYSKL NVQKSNWEAG  420
NTFTCSVLHE GLHNHHTEKS LSHSPGK                                       447

SEQ ID NO: 202         moltype = DNA  length = 1344
FEATURE                Location/Qualifiers
source                 1..1344
                       mol_type = other DNA
                       organism = Mus musculus
SEQUENCE: 202
gaggtccagt tgcaacagtc tggacctgaa ctaatgaagc ctggggcttc agtgaagatg  60
tcctgcaagg cttctggata cacattcact gactacaaca tgcactggat gaagcagaac  120
caaggaaaga gcctagagtg gataggagag attaatccta acagtggtgg ttctggttac  180
aaccagaagt tcaaaggcaa ggccacattg actgtagaca agtcctccag cacagcctac  240
atggagctcc gcagcctgac atctgaggac tctgcagtct attactgtgc aagattgggc  300
tactatggta actacgagga ctggtatttc gatgtctggg gcgcagggac cacggtcacc  360
gtctcctctg ccaaaacgac acccccatct gtctatccac tggcccctgg atctgctgcc  420
caaactaact ccatggtgac cctgggatgc ctggtcaagg gctatttccc tgagccagtg  480
acagtgacct ggaactctgg atccctgtcc agcggtgtgc acaccttccc agctgtcctg  540
cagtctgacc tctacactct gagcagctca gtgactgtcc cctccagcac ctggcccagc  600
gagaccgtca cctgcaacgt tgcccacccg gccagcagca ccaaggtgga caagaaaatt  660
gtgcccaggg attgtggttg taagccttgc atatgtacag tcccagaagt atcatctgtc  720
ttcatcttcc ccccaaagcc caaggatgtg ctcaccatta ctctgactcc taaggtcacg  780
tgtgttgtgg tagacatcag caaggatgat cccgaggtcc agttcagctg gtttgtagat  840
gatgtggagg tgcacacagc tcagacgcaa ccccgggagg agcagttcaa cagcactttc  900
cgctcagtca gtgaacttcc catcatgcac caggactggc tcaatggcaa ggagttcaaa  960
```

-continued

```
tgcagggtca acagtgcagc tttccctgcc cccatcgaga aaaccatctc caaaaccaaa  1020
ggcagaccga aggctccaca ggtgtacacc attccacctc ccaaggagca gatggccaag  1080
gataaagtca gtctgacctg catgataaca gacttcttcc ctgaagacat tactgtggag  1140
tggcagtgga atgggcagcc agcggagaac tacaagaaca ctcagcccat catggacaca  1200
gatggctctt acttcatcta cagcaagctc aatgtgcaga agagcaactg ggaggcagga  1260
aatactttca cctgctctgt gttacatgag ggcctgcaca accaccatac tgagaagagc  1320
ctctcccact ctcctggtaa atga                                         1344

SEQ ID NO: 203         moltype = AA  length = 466
FEATURE                Location/Qualifiers
source                 1..466
                       mol_type = protein
                       organism = Mus musculus
SEQUENCE: 203
MGWSWTFLFL LSGTSGVLSE VQLQQSGPEL MKPGASVKMS CKASGYTFTD YNMHWMKQNQ  60
GKSLEWIGEI NPNSGGSGYN QKFKGKATLT VDKSSSTAYM ELRSLTSEDS AVYYCARLGY  120
YGNYEDWYFD VWGAGTTVTV SSAKTTPPSV YPLAPGSAAQ TNSMVTLGCL VKGYFPEPVT  180
VTWNSGSLSS GVHTFPAVLQ SDLYTLSSSV TVPSSTWPSE TVTCNVAHPA SSTKVDKKIV  240
PRDCGCKPCI CTVPEVSSVF IFPPKPKDVL TITLTPKVTC VVVDISKDDP EVQFSWFVDD  300
VEVHTAQTQP REEQFNSTFR SVSELPIMHQ DWLNGKEFKC RVNSAAFPAP IEKTISKTKG  360
RPKAPQVYTI PPPKEQMAKD KVSLTCMITD FFPEDITVEW QWNGQPAENY KNTQPIMDTD  420
GSYFIYSKLN VQKSNWEAGN TFTCSVLHEG LHNHHTEKSL SHSPGK                 466

SEQ ID NO: 204         moltype = DNA  length = 1401
FEATURE                Location/Qualifiers
source                 1..1401
                       mol_type = other DNA
                       organism = Mus musculus
SEQUENCE: 204
atgggatgga gctggacctt tctcttcctc ctgtcaggaa cttcgggtgt cctctctgag  60
gtccagttgc aacagtctgg acctgaacta atgaagcctg gggcttcagt gaagatgtcc  120
tgcaaggctt ctggatacac attcactgac tacaacatgc actggatgaa gcagaaccaa  180
ggaaagagcc tagagtggat aggagagatt aatcctaaca gtggtggttc tggttacaac  240
cagaagttca aaggcaaggc cacattgact gtagacaagt cctccagcac agcctacatg  300
gagctccgca gcctgacatc tgaggactct gcagtctatt actgtgcaag attgggctac  360
tatggtaact acgaggactg gtatttcgat gtctggggcg cagggaccac ggtcaccgtc  420
tcctctgcca aaacgacacc cccatctgtc tatccactgg cccctggatc tgctgcccaa  480
actaactcca tggtgaccct gggatgcctg gtcaagggct atttccctga gccagtgaca  540
gtgacctgga actctggatc cctgtccagc ggtgtgcaca ccttcccagc tgtcctgcag  600
tctgacctct acactctgag cagctcagtg actgtcccct ccagcacctg gcccagcgag  660
accgtcacct gcaacgttgc ccacccggcc agcagcacca aggtggacaa gaaaattgtg  720
cccagggatt gtggttgtaa gccttgcata tgtacagtcc cagaagtatc atctgtcttc  780
atcttccccc caaagcccaa ggatgtgctc accattactc tgactcctaa ggtcacgtgt  840
gttgtggtag acatcagcaa ggatgatccc gaggtccagt tcagctggtt tgtagatgat  900
gtggaggtgc acacagctca gacgcaaccc cgggaggagc agttcaacag cactttccgc  960
tcagtcagtg aacttcccat catgcaccag gactggctca atggcaagga gttcaaatgc  1020
agggtcaaca gtgcagcttt ccctgccccc atcgagaaaa ccatctccaa aaccaaaggc  1080
agaccgaagg ctccacaggt gtacaccatt ccacctccca aggagcagat ggccaaggat  1140
aaagtcagtc tgacctgcat gataacagac ttcttccctg aagacattac tgtggagtgg  1200
cagtggaatg ggcagccagc ggagaactac aagaacactc agcccatcat ggacacagat  1260
ggctcttact tcatctacag caagctcaat gtgcagaaga gcaactggga ggcaggaaat  1320
actttcacct gctctgtgtt acatgagggc ctgcacaacc accatactga gaagagcctc  1380
tcccactctc ctggtaaatg a                                            1401

SEQ ID NO: 205         moltype = AA  length = 215
FEATURE                Location/Qualifiers
source                 1..215
                       mol_type = protein
                       organism = Mus musculus
SEQUENCE: 205
QIVLTQSPAI MSASPGEKVT MTCRASSSVT SSYLNWYQQK PGSSPKLWIY STSNLASGVP  60
ARFSGSGSGT SYSLTISSVE AEDAATYYCQ QYDFFPSTFG GGTKLEIKRA DAAPTVSIFP  120
PSSEQLTSGG ASVVCFLNNF YPKDINVKWK IDGSERQNGV LNSWTDQDSK DSTYSMSSTL  180
TLTKDEYERH NSYTCEATHK TSTSPIVKSF NRNEC                             215

SEQ ID NO: 206         moltype = DNA  length = 645
FEATURE                Location/Qualifiers
source                 1..645
                       mol_type = other DNA
                       organism = Mus musculus
SEQUENCE: 206
cagattgttc tcacccagtc tccagcaatc atgtctgcat ctccagggga gaaggtcacc  60
atgacctgca gggccagctc aagtgtaact tccagttact tgaactggta ccagcagaag  120
ccaggatctt cccccaaact ctggatttat agcacatcca acctggcttc aggagtccca  180
gctcgcttca gtggcagtgg gtctgggacc tcttactctc tcacaatcag cagtgtggag  240
gctgaggatg ctgccactta ttactgccag cagtatgatt ttttcccatc gacgttcggt  300
ggaggcacca agctggaaat caagcgggct gatgctgcac caactgtatc catcttccca  360
ccatccagtg agcagttaac atctggaggt gcctcagtcg tgtgcttctt gaacaacttc  420
taccccaaag acatcaatgt caagtggaag attgatggca gtgaacgaca aaatggcgtc  480
```

-continued

```
ctgaacagtt ggactgatca ggacagcaaa gacagcacct acagcatgag cagcaccctc  540
acgttgacca aggacgagta tgaacgacat aacagctata cctgtgaggc cactcacaag  600
acatcaactt cacccatcgt caagagcttc aacaggaatg agtgt                  645

SEQ ID NO: 207          moltype = AA  length = 237
FEATURE                 Location/Qualifiers
source                  1..237
                        mol_type = protein
                        organism = Mus musculus
SEQUENCE: 207
MDSQVQIFSF LLISALVKMS RGQIVLTQSP AIMSASPGEK VTMTCRASSS VTSSYLNWYQ  60
QKPGSSPKLW IYSTSNLASG VPARFSGSGS GTSYSLTISS VEAEDAATYY CQQYDFFPST  120
FGGGTKLEIK RADAAPTVSI FPPSSEQLTS GGASVVCFLN NFYPKDINVK WKIDGSERQN  180
GVLNSWTDQD SKDSTYSMSS TLTLTKDEYE RHNSYTCEAT HKTSTSPIVK SFNRNEC     237

SEQ ID NO: 208          moltype = DNA  length = 711
FEATURE                 Location/Qualifiers
source                  1..711
                        mol_type = other DNA
                        organism = Mus musculus
SEQUENCE: 208
atggattctc aagtgcagat tttcagcttc cttctaatca gtgccttagt caaaatgtcc  60
agaggacaga ttgttctcac ccagtctcca gcaatcatgt ctgcatctcc aggggagaag  120
gtcaccatga cctgcagggc cagctcaagt gtaacttcca gttacttgaa ctggtaccag  180
cagaagccag gatcttcccc caaactctgg atttatagca catccaacct ggcttcagga  240
gtcccagctc gcttcagtgg cagtgggtct gggacctctt actctctcac aatcagcagt  300
gtggaggctg aggatgctgc cacttattac tgccagcagt atgatttttt cccatcgacg  360
ttcggtggag gcaccaagct ggaaatcaag cgggctgatg ctgcaccaac tgtatccatc  420
ttcccaccat ccagtgagca gttaacatct ggaggtgcct cagtcgtgtg cttcttgaac  480
aacttctacc ccaaagacat caatgtcaag tggaagattg atggcagtga acgacaaaat  540
ggcgtcctga acagttggac tgatcaggac agcaaagaca gcacctacag catgagcagc  600
accctcacgt tgaccaagga cgagtatgaa cgacataaca gctatacctg tgaggccact  660
cacaagacat caacttcacc catcgtcaag agcttcaaca ggaatgagtg t           711

SEQ ID NO: 209          moltype = AA  length = 445
FEATURE                 Location/Qualifiers
source                  1..445
                        mol_type = protein
                        organism = Mus musculus
SEQUENCE: 209
EVQLQQSGPE LVKPGASVKM SCKASGYTFT DYYMNWVKQS HGESLEWIGD INPYNDDTTY  60
NHKFKGKATL TVDKSSNTAY MQLNSLTSED SAVYYCARET AVITTNAMDY WGQGTSVTVS  120
SAKTTPPSVY PLAPGSAAQT NSMVTLGCLV KGYFPEPVTV TWNSGSLSSG VHTFPAVLQS  180
DLYTLSSSVT VPSSTWPSET VTCNVAHPAS STKVDKKIVP RDCGCKPCIC TVPEVSSVFI  240
FPPKPKDVLT ITLTPKVTCV VVDISKDDPE VQFSWFVDDV EVHTAQTQPR EEQFNSTFRS  300
VSELPIMHQD WLNGKEFKCR VNSAAFPAPI EKTISKTKGR PKAPQVYTIP PPKEQMAKDK  360
VSLTCMITDF FPEDITVEWQ WNGQPAENYK NTQPIMDTDG SYFIYSKLNV QKSNWEAGNT  420
FTCSVLHEGL HNHHTEKSLS HSPGK                                        445

SEQ ID NO: 210          moltype = DNA  length = 1335
FEATURE                 Location/Qualifiers
source                  1..1335
                        mol_type = other DNA
                        organism = Mus musculus
SEQUENCE: 210
gaggtccagc tgcaacaatc tggacctgag ctggtgaagc ctggggcttc agtgaagatg  60
tcctgtaagg cttctggata cacattcact gactactaca tgaactgggt gaagcagagc  120
catggagaga gccttgagtg gattggagat attaatcctt acaacgatga tactacctac  180
aaccacaagt tcaagggcaa ggccacattg actgtagaca aatcctccaa cacagcctac  240
atgcagctca acagcctgac atctgaggac tctgcagtct attactgtgc aagagagacg  300
gccgttatta ctacgaatgc tatggactac tggggtcaag gaacctcagt caccgtctcc  360
tcagccaaaa cgacaccccc atctgtctat ccactggccc ctggatctgc tgcccaaact  420
aactccatgg tgaccctggg atgcctggtc aagggctatt tccctgagcc agtgacagtg  480
acctggaact ctggatccct gtccagcggt gtgcacacct tcccagctgt cctgcagtct  540
gacctctaca ctctgagcag ctcagtgact gtcccctcca gcacctggcc cagcgagacc  600
gtcacctgca acgttgccca cccggccagc agcaccaagg tggacaagaa aattgtgccc  660
agggattgtg gttgtaagcc ttgcatatgt acagtcccag aagtatcatc tgtcttcatc  720
ttccccccaa agcccaagga tgtgctcacc attactctga ctcctaaggt cacgtgtgtt  780
gtggtagaca tcagcaagga tgatcccgag gtccagttca gctggtttgt agatgatgtg  840
gaggtgcaca cagctcagac gcaaccccgg gaggagcagt tcaacagcac tttccgctca  900
gtcagtgaac ttcccatcat gcaccaggac tggctcaatg gcaaggagtt caaatgcagg  960
gtcaacagtg cagctttccc tgcccccatc gagaaaacca tctccaaaac caaaggcaga  1020
ccgaaggctc cacaggtgta caccattcca cctcccaagg agcagatggc caaggataaa  1080
gtcagtctga cctgcatgat aacagacttc ttccctgaag acattactgt ggagtggcag  1140
tggaatgggc agccagcgga gaactacaag aacactcagc ccatcatgga cacagatggc  1200
tcttacttca tctacagcaa gctcaatgtg cagaagagca actgggaggc aggaaatact  1260
ttcacctgct ctgtgttaca tgagggcctg cacaaccacc atactgagaa gagcctctcc  1320
cactctcctg gtaaa                                                   1335
```

-continued

```
SEQ ID NO: 211         moltype = AA  length = 464
FEATURE                Location/Qualifiers
source                 1..464
                       mol_type = protein
                       organism = Mus musculus
SEQUENCE: 211
MGWNWIFLFL LSGTAGVYSE VQLQQSGPEL VKPGASVKMS CKASGYTFTD YYMNWVKQSH  60
GESLEWIGDI NPYNDDTTYN HKFKGKATLT VDKSSNTAYM QLNSLTSEDS AVYYCARETA  120
VITTNAMDYW GQGTSVTVSS AKTTPPSVYP LAPGSAAQTN SMVTLGCLVK GYFPEPVTVT  180
WNSGSLSSGV HTFPAVLQSD LYTLSSSVTV PSSTWPSETV TCNVAHPASS TKVDKKIVPR  240
DCGCKPCICT VPEVSSVFIF PPKPKDVLTI TLTPKVTCVV VDISKDDPEV QFSWFVDDVE  300
VHTAQTQPRE EQFNSTFRSV SELPIMHQDW LNGKEFKCRV NSAAFPAPIE KTISKTKGRP  360
KAPQVYTIPP PKEQMAKDKV SLTCMITDFF PEDITVEWQW NGQPAENYKN TQPIMDTDGS  420
YFIYSKLNVQ KSNWEAGNTF TCSVLHEGLH NHHTEKSLSH SPGK                  464

SEQ ID NO: 212         moltype = DNA  length = 1392
FEATURE                Location/Qualifiers
source                 1..1392
                       mol_type = other DNA
                       organism = Mus musculus
SEQUENCE: 212
atgggatgga actggatctt tctcttcctc ttgtcaggaa ctgcaggtgt ctactctgag  60
gtccagctgc aacaatctgg acctgagctg gtgaagcctg gggcttcagt gaagatgtcc  120
tgtaaggctt ctggatacac attcactgac tactacatga actgggtgaa gcagagccat  180
ggagagagcc ttgagtggat tggagatatt aatccttaca acgatgatac tacctacaac  240
cacaagttca agggcaaggc cacattgact gtagacaaat cctccaacac agcctacatg  300
cagctcaaca gcctgacatc tgaggactct gcagtctatt actgtgcaag agagacggcc  360
gttattacta cgaatgctat ggactactgg ggtcaaggaa cctcagtcac cgtctcctca  420
gccaaaacga cacccccatc tgtctatcca ctggcccctg gatctgctgc ccaaactaac  480
tccatggtga ccctgggatg cctggtcaag ggctatttcc ctgagccagt gacagtgacc  540
tggaactctg gatccctgtc cagcggtgtg cacaccttcc cagctgtcct gcagtctgac  600
ctctacactc tgagcagctc agtgactgtc ccctccagca cctggcccag cgagaccgtc  660
acctgcaacg ttgcccaccc ggccagcagc accaaggtgg acaagaaaat tgtgcccagg  720
gattgtggtt gtaagccttg catatgtaca gtcccagaag tatcatctgt cttcatcttc  780
cccccaaagc ccaaggatgt gctcaccatt actctgactc ctaaggtcac gtgtgttgtg  840
gtagacatca gcaaggatga tcccgaggtc cagttcagct ggtttgtaga tgatgtggag  900
gtgcacacag ctcagacgca accccgggag gagcagttca acagcacttt ccgctcagtc  960
agtgaacttc ccatcatgca ccaggactgg ctcaatggca aggagttcaa atgcagggtc  1020
aacagtgcag ctttccctgc ccccatcgag aaaaccatct ccaaaaccaa aggcagaccg  1080
aaggctccac aggtgtacac cattccacct cccaaggagc agatggccaa ggataaagtc  1140
agtctgacct gcatgataac agacttcttc cctgaagaca ttactgtgga gtggcagtgg  1200
aatgggcagc cagcggagaa ctacaagaac actcagccca tcatggacac agatggctct  1260
tacttcatct acagcaagct caatgtgcag aagagcaact gggaggcagg aaatactttc  1320
acctgctctg tgttacatga gggcctgcac aaccaccata ctgagaagag cctctcccac  1380
tctcctggta aa                                                      1392

SEQ ID NO: 213         moltype = AA  length = 215
FEATURE                Location/Qualifiers
REGION                 1..215
                       note = Synthetic Polypeptide
REGION                 1..215
                       note = MISC_FEATURE - Humanized Antibody Sequence
source                 1..215
                       mol_type = protein
                       organism = synthetic construct
SEQUENCE: 213
DIQLTQSPSF LSASVGDRVT ITCRASSSVT SSYLNWYQQK PGKAPKLLIY STSNLASGVP  60
SRFSGSGSGT EFTLTISSLQ PEDFATYYCQ QYDFFPSTFG GGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 214         moltype = DNA  length = 645
FEATURE                Location/Qualifiers
misc_feature           1..645
                       note = Synthetic Polynucleotide
misc_feature           1..645
                       note = Humanized Antibody Sequence
source                 1..645
                       mol_type = other DNA
                       organism = synthetic construct
SEQUENCE: 214
gacatccagc tgacccagag ccccagcttc ctttccgcat ccgttggtga ccgagtaaca  60
atcacatgcc gcgcctcatc ttcagttaca tcttcttatc ttaattggta tcaacaaaaa  120
ccaggaaaag cacctaaact tcttatatac tctacatcta atctcgcatc aggagttccc  180
tctcgatttt caggatctgg atcaggcaca gaatttacac ttactatatc atcactccaa  240
ccagaagact tcgccactta ttactgccaa caatacgatt tttttccaag cacattcgga  300
ggaggtacaa aagtagaaat caagcgtacg gtggctgcac catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
```

```
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgt                  645

SEQ ID NO: 215          moltype = AA  length = 237
FEATURE                 Location/Qualifiers
REGION                  1..237
                        note = Synthetic Polypeptide
REGION                  1..237
                        note = MISC_FEATURE - Humanized Antibody Sequence
source                  1..237
                        mol_type = protein
                        organism = synthetic construct
SEQUENCE: 215
MDMRVPAQLL GLLLLWLPGA RCDIQLTQSP SFLSASVGDR VTITCRASSS VTSSYLNWYQ  60
QKPGKAPKLL IYSTSNLASG VPSRFSGSGS GTEFTLTISS LQPEDFATYY CQQYDFFPST  120
FGGGTKVEIK RTVAAPSVFI FPPSDEQLKS GTASVVCLLN NFYPREAKVQ WKVDNALQSG  180
NSQESVTEQD SKDSTYSLSS TLTLSKADYE KHKVYACEVT HQGLSSPVTK SFNRGEC     237

SEQ ID NO: 216          moltype = DNA  length = 711
FEATURE                 Location/Qualifiers
misc_feature            1..711
                        note = Synthetic Polynucleotide
misc_feature            1..711
                        note = Humanized Antibody Sequence
source                  1..711
                        mol_type = other DNA
                        organism = synthetic construct
SEQUENCE: 216
atggacatga gggtccccgc tcagctcctg gggctcctgc tactctggct cccaggtgcc  60
agatgtgaca tccagctgac ccagagcccc agcttccttt ccgcatccgt tggtgaccga  120
gtaacaatca catgccgcgc ctcatcttca gttacatctt cttatcttaa ttggtatcaa  180
caaaaaccag gaaaagcacc taaacttctt atatactcta catctaatct cgcatcagga  240
gttccctctc gatttcagg  atctggatca ggcacagaat ttacacttac tatatcatca  300
ctccaaccag aagacttcgc cacttattac tgccaacaat acgatttttt tccaagcaca  360
ttcggaggag gtacaaaagt agaaatcaag cgtacggtgg ctgcaccatc tgtcttcatc  420
ttcccgccat ctgatgagca gttgaaatct ggaactgcct ctgttgtgtg cctgctgaat  480
aacttctatc ccagagaggc caaagtacag tggaaggtgg ataacgccct ccaatcgggt  540
aactcccagg agagtgtcac agagcaggac agcaaggaca gcacctacag cctcagcagc  600
accctgacgc tgagcaaagc agactacgag aaacacaaag tctacgcctg cgaagtcacc  660
catcagggcc tgagctcgcc cgtcacaaag agcttcaaca ggggagagtg t           711

SEQ ID NO: 217          moltype = AA  length = 447
FEATURE                 Location/Qualifiers
REGION                  1..447
                        note = Synthetic Polypeptide
REGION                  1..447
                        note = MISC_FEATURE - Humanized Antibody Sequence
source                  1..447
                        mol_type = protein
                        organism = synthetic construct
SEQUENCE: 217
EVQLVQSGAE VKKPGASVKV SCKASGYTFT DYYMNWVRQA PGQRLEWMGD INPYNDDTTY  60
NHKFKGRVTI TRDTSASTAY MELSSLRSED TAVYYCARET AVITTNAMDY WGQGTTVTVS  120
SASTKGPSVF PLAPCSRSTS ESTAALGCLV KDYFPEPVTV SWNSGALTSG VHTFPAVLQS  180
SGLYSLSSVV TVPSSNFGTQ TYTCNVDHKP SNTKVDKTVE RKCCVECPPC PAPPVAGPSV  240
FLFPPKPKDT LMISRTPEVT CVVVDVSHED PEVQFNWYVD GVEVHNAKTK PREEQFNSTF  300
RVVSVLTVVH QDWLNGKEYK CKVSNKGLPA PIEKTISKTK GQPREPQVYT LPPSREEMTK  360
NQVSLTCLVK GFYPSDIAVE WESNGQPENN YKTTPPMLDS DGSFFLYSKL TVDKSRWQQG  420
NVFSCSVMHE ALHNHYTQKS LSLSPGK                                      447

SEQ ID NO: 218          moltype = DNA  length = 1341
FEATURE                 Location/Qualifiers
misc_feature            1..1341
                        note = Synthetic Polynucleotide
misc_feature            1..1341
                        note = Humanized Antibody Sequence
source                  1..1341
                        mol_type = other DNA
                        organism = synthetic construct
SEQUENCE: 218
gaggtgcagc tggtgcagag cggcgccgag gtcaagaaac ctggagcaag cgtaaaggtt  60
agttgcaaag catctggata cacatttacc gactactaca tgaattgggt acgacaagcc  120
cctggacaaa gacttgaatg gatgggagac attaaccctt ataacgacga cactacatac  180
aatcataaat ttaaaggaag agttacaatt acaagagata catccgcatc aaccgcctat  240
atggaacttt cctcattgag atctgaagac actgctgttt attactgtgc aagagaaact  300
gccgttatta ctactaacgc tatggattac tggggtcaag gaaccactgt taccgtctct  360
agtgcctcca ccaagggccc atcggtcttc cccctggcgc cctgctccag gagcacctcc  420
gagagcacag cggccctggg ctgcctggtc aaggactact tccccgaacc ggtgacggtg  480
```

-continued

```
tcgtggaact caggcgctct gaccagcggc gtgcacacct tcccagctgt cctacagtcc  540
tcaggactct actccctcag cagcgtggtg accgtgccct ccagcaactt cggcacccag  600
acctacacct gcaacgtaga tcacaagccc agcaacacca aggtggacaa gacagttgag  660
cgcaaatgtt gtgtcgagtg cccaccgtgc ccagcaccac ctgtggcagg accgtcagtc  720
ttcctcttcc ccccaaaacc caaggacacc ctcatgatct cccggacccc tgaggtcacg  780
tgcgtggtgg tggacgtgag ccacgaagac cccgaggtcc agttcaactg gtacgtggac  840
ggcgtggagg tgcataatgc caagacaaag ccacgggagg agcagttcaa cagcacgttc  900
cgtgtggtca gcgtcctcac cgttgtgcac caggactggc tgaacggcaa ggagtacaag  960
tgcaaggtct ccaacaaagg cctcccagcc cccatcgaga aaaccatctc caaaaccaaa  1020
gggcagcccc gagaaccaca ggtgtacacc ctgcccccat cccgggagga gatgaccaag  1080
aaccaggtca gcctgacctg cctggtcaaa ggcttctacc ccagcgacat cgccgtggag  1140
tgggagagca atgggcagcc ggagaacaac tacaagacca cacctcccat gctggactcc  1200
gacggctcct tcttcctcta cagcaagctc accgtggaca agagcaggtg gcagcagggg  1260
aacgtcttct catgctccgt gatgcatgag gctctgcaca accactacac gcagaagagc  1320
ctctccctgt ctccgggtaa a                                            1341

SEQ ID NO: 219         moltype = AA  length = 466
FEATURE                Location/Qualifiers
REGION                 1..466
                       note = Synthetic Polypeptide
REGION                 1..466
                       note = MISC_FEATURE - Humanized Antibody Sequence
source                 1..466
                       mol_type = protein
                       organism = synthetic construct
SEQUENCE: 219
MDWTWRILFL VAAATGAHSE VQLVQSGAEV KKPGASVKVS CKASGYTFTD YYMNWVRQAP  60
GQRLEWMGDI NPYNDDTTYN HKFKGRVTIT RDTSASTAYM ELSSLRSEDT AVYYCARETA  120
VITTNAMDYW GQGTTVTVSS ASTKGPSVFP LAPCSRSTSE STAALGCLVK DYFPEPVTVS  180
WNSGALTSGV HTFPAVLQSS GLYSLSSVVT VPSSNFGTQT YTCNVDHKPS NTKVDKTVER  240
KCCVECPPCP APPVAGPSVF LFPPKPKDTL MISRTPEVTC VVVDVSHEDP EVQFNWYVDG  300
VEVHNAKTKP REEQFNSTFR VVSVLTVVHQ DWLNGKEYKC KVSNKGLPAP IEKTISKTKG  360
QPREPQVYTL PPSREEMTKN QVSLTCLVKG FYPSDIAVEW ESNGQPENNY KTTPPMLDSD  420
GSFFLYSKLT VDKSRWQQGN VFSCSVMHEA LHNHYTQKSL SLSPGK                 466

SEQ ID NO: 220         moltype = DNA  length = 1398
FEATURE                Location/Qualifiers
misc_feature           1..1398
                       note = Synthetic Polynucleotide
misc_feature           1..1398
                       note = Humanized Antibody Sequence
source                 1..1398
                       mol_type = other DNA
                       organism = synthetic construct
SEQUENCE: 220
atggactgga cctggaggat cctcttcttg gtggcagcag ccacaggagc ccactccgag  60
gtgcagctgg tgcagagcgg cgccgaggtc aagaaacctg gagcaagcgt aaaggttagt  120
tgcaaagcat ctggatacac atttaccgac tactacatga attgggtacg acaagcccct  180
ggacaaagac ttgaatggat gggagacatt aacccttata acgacgacac tacatacaat  240
cataaattta aaggaagagt tacaattaca agagatacat ccgcatcaac cgcctatatg  300
gaactttcct cattgagatc tgaagacact gctgtttatt actgtgcaag agaaactgcc  360
gttattacta ctaacgctat ggattactgg ggtcaaggaa ccactgttac cgtctctagt  420
gcctccacca agggcccatc ggtcttcccc ctggcgccct gctccaggag cacctccgag  480
agcacagcgg ccctgggctg cctggtcaag gactacttcc ccgaaccggt gacggtgtcg  540
tggaactcag gcgctctgac cagcggcgtg cacaccttcc cagctgtcct acagtcctca  600
ggactctact ccctcagcag cgtggtgacc gtgccctcca gcaacttcgg cacccagacc  660
tacacctgca acgtagatca caagcccagc aacaccaagg tggacaagac agttgagcgc  720
aaatgttgtg tcgagtgccc accgtgccca gcaccacctg tggcaggacc gtcagtcttc  780
ctcttccccc caaaacccaa ggacaccctc atgatctccc ggacccctga ggtcacgtgc  840
gtggtggtgg acgtgagcca cgaagacccc gaggtccagt tcaactggta cgtggacggc  900
gtggaggtgc ataatgccaa gacaaagcca cgggaggagc agttcaacag cacgttccgt  960
gtggtcagcg tcctcaccgt tgtgcaccag gactggctga acggcaagga gtacaagtgc  1020
aaggtctcca acaaaggcct cccagccccc atcgagaaaa ccatctccaa aaccaaaggg  1080
cagccccgag aaccacaggt gtacaccctg cccccatccc gggaggagat gaccaagaac  1140
caggtcagcc tgacctgcct ggtcaaaggc ttctacccca gcgacatcgc cgtggagtgg  1200
gagagcaatg ggcagccgga gaacaactac aagaccacac ctcccatgct ggactccgac  1260
ggctccttct tcctctacag caagctcacc gtggacaaga gcaggtggca gcaggggaac  1320
gtcttctcat gctccgtgat gcatgaggct ctgcacaacc actacacgca gaagagcctc  1380
tccctgtctc cgggtaaa                                                1398

SEQ ID NO: 221         moltype = AA  length = 215
FEATURE                Location/Qualifiers
REGION                 1..215
                       note = Synthetic Polypeptide
REGION                 1..215
                       note = MISC_FEATURE - Humanized Antibody Sequence
source                 1..215
                       mol_type = protein
                       organism = synthetic construct
```

-continued

```
SEQUENCE: 221
DIQMTQSPSS LSASVGDRVT ITCSVSSTIS SNHLHWFQQK PGKAPKSLIY GTSNLASGVP  60
SRFSGSGSGT DFTLTISSLQ PEDFATYYCQ QWSSYPLTFG GGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                            215

SEQ ID NO: 222          moltype = DNA  length = 645
FEATURE                 Location/Qualifiers
misc_feature            1..645
                        note = Synthetic Polynucleotide
misc_feature            1..645
                        note = Humanized Antibody Sequence
source                  1..645
                        mol_type = other DNA
                        organism = synthetic construct
SEQUENCE: 222
gacatccaga tgacccagtc tccatcctcc ctctcagcat ccgtaggcga tagagttaca  60
ataacatgca gcgtatcatc aactatatca tcaaatcatc ttcattggtt ccaacagaaa  120
cccggcaaag cacctaaatc acttatatac ggcacatcaa atctcgcatc aggcgttcct  180
tcaagatttt caggctctgg ctcaggcacc gactttactc ttacaatatc ctccctccaa  240
cccgaagact tcgcaaccta ttactgtcaa caatggtcct catatccact cacatttggc  300
ggcggcacaa aagtagaaat taaacgtacg gtggctgcac catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgt                 645

SEQ ID NO: 223          moltype = AA  length = 237
FEATURE                 Location/Qualifiers
REGION                  1..237
                        note = Synthetic Polypeptide
REGION                  1..237
                        note = MISC_FEATURE - Humanized Antibody Sequence
source                  1..237
                        mol_type = protein
                        organism = synthetic construct
SEQUENCE: 223
MDMRVPAQLL GLLLLWLRGA RCDIQMTQSP SSLSASVGDR VTITCSVSST ISSNHLHWFQ  60
QKPGKAPKSL IYGTSNLASG VPSRFSGSGS GTDFTLTISS LQPEDFATYY CQQWSSYPLT  120
FGGGTKVEIK RTVAAPSVFI FPPSDEQLKS GTASVVCLLN NFYPREAKVQ WKVDNALQSG  180
NSQESVTEQD SKDSTYSLSS TLTLSKADYE KHKVYACEVT HQGLSSPVTK SFNRGEC     237

SEQ ID NO: 224          moltype = DNA  length = 711
FEATURE                 Location/Qualifiers
misc_feature            1..711
                        note = Synthetic Polynucleotide
misc_feature            1..711
                        note = Humanized Antibody Sequence
source                  1..711
                        mol_type = other DNA
                        organism = synthetic construct
SEQUENCE: 224
atggacatga gggtccccgc tcagctcctg gggctcctgc tactctggct ccgaggtgcc  60
agatgtgaca tccagatgac ccagtctcca tcctccctct cagcatccgt aggcgataga  120
gttacaataa catgcagcgt atcatcaact atatcatcaa atcatcttca ttggttccaa  180
cagaaacccg gcaaagcacc taaatcactt atatacggca catcaaatct cgcatcaggc  240
gttccttcaa gattttcagg ctctggctca ggcaccgact ttactcttac aatatcctcc  300
ctccaacccg aagacttcgc aacctattac tgtcaacaat ggtcctcata tccactcaca  360
tttggcggcg gcacaaaagt agaaattaaa cgtacggtgg ctgcaccatc tgtcttcatc  420
ttcccgccat ctgatgagca gttgaaatct ggaactgcct ctgttgtgtg cctgctgaat  480
aacttctatc ccagagaggc caaagtacag tggaaggtgg ataacgccct ccaatcgggt  540
aactcccagg agagtgtcac agagcaggac agcaaggaca gcacctacag cctcagcagc  600
accctgacgc tgagcaaagc agactacgag aaacacaaag tctacgcctg cgaagtcacc  660
catcagggcc tgagctcgcc cgtcacaaag agcttcaaca ggggagagtg t          711

SEQ ID NO: 225          moltype = AA  length = 451
FEATURE                 Location/Qualifiers
REGION                  1..451
                        note = Synthetic Polypeptide
REGION                  1..451
                        note = MISC_FEATURE - Humanized Antibody Sequence
source                  1..451
                        mol_type = protein
                        organism = synthetic construct
SEQUENCE: 225
EVQLVQSGAE VKKPGASVKV SCKASDFNIK DFYLHWVRQA PGQGLEWIGR IDPENGDTLY  60
DPKFQDKVTM TTDTSTSTAY MELRSLRSDD TAVYYCAREA DYFHDGTSYW YFDVWGRGTL  120
VTVSSASTKG PSVFPLAPCS RSTSESTAAL GCLVKDYFPE PVTVSWNSGA LTSGVHTFPA  180
```

-continued

```
VLQSSGLYSL SSVVTVPSSN FGTQTYTCNV DHKPSNTKVD KTVERKCCVE CPPCPAPPVA  240
GPSVFLFPPK PKDTLMISRT PEVTCVVVDV SHEDPEVQFN WYVDGVEVHN AKTKPREEQF  300
NSTFRVVSVL TVVHQDWLNG KEYKCKVSNK GLPAPIEKTI SKTKGQPREP QVYTLPPSRE  360
EMTKNQVSLT CLVKGFYPSD IAVEWESNGQ PENNYKTTPP MLDSDGSFFL YSKLTVDKSR  420
WQQGNVFSCS VMHEALHNHY TQKSLSLSPG K                                451

SEQ ID NO: 226         moltype = DNA  length = 1353
FEATURE                Location/Qualifiers
misc_feature           1..1353
                       note = Synthetic Polynucleotide
source                 1..1353
                       mol_type = other DNA
                       organism = synthetic construct
SEQUENCE: 226
gaggtgcagc tggtgcagtc tggggctgag gtgaagaagc ctggggcctc agtgaaggtc  60
tcctgcaagg cttctgactt caacattaaa gacttctatc tacactgggt gcgacaggcc  120
cctggacaag ggcttgagtg gattggaagg attgatcctg agaatggtga tactttatat  180
gacccgaagt tccaggacaa ggtcaccatg accacagaca cgtccaccag cacagcctac  240
atggagctga ggagcctgag atctgacgac acggccgtgt attactgtgc gagagaggcg  300
gattatttcc acgatggtac ctcctactgg tacttcgatg tctggggccg tggcaccctg  360
gtcaccgtct ctagtgcctc caccaagggc ccatcggtct tccccctggc gccctgctcc  420
aggagcacct ccgagagcac agcggccctg ggctgcctgg tcaaggacta cttccccgaa  480
ccggtgacgg tgtcgtggaa ctcaggcgct ctgaccagcg gcgtgcacac cttcccagct  540
gtcctacagt cctcaggact ctactccctc agcagcgtgg tgaccgtgcc ctccagcaac  600
ttcggcaccc agacctacac ctgcaacgta gatcacaagc ccagcaacac caaggtggac  660
aagacagttg agcgcaaatg ttgtgtcgag tgcccaccgt gcccagcacc acctgtggca  720
ggaccgtcag tcttcctctt ccccccaaaa cccaaggaca ccctcatgat ctcccggacc  780
cctgaggtca cgtgcgtggt ggtggacgtg agccacgaag accccgaggt ccagttcaac  840
tggtacgtgg acggcgtgga ggtgcataat gccaagacaa agccacggga ggagcagttc  900
aacagcacgt tccgtgtggt cagcgtcctc accgttgtgc accaggactg gctgaacggc  960
aaggagtaca agtgcaaggt ctccaacaaa ggcctcccag cccccatcga gaaaaccatc  1020
tccaaaacca aagggcagcc ccgagaacca caggtgtaca ccctgccccc atcccgggag  1080
gagatgacca agaaccaggt cagcctgacc tgcctggtca aaggcttcta ccccagcgac  1140
atcgccgtgg agtgggagag caatgggcag ccggagaaca actacaagac cacacctccc  1200
atgctggact ccgacggctc cttcttcctc tacagcaagc tcaccgtgga caagagcagg  1260
tggcagcagg ggaacgtctt ctcatgctcc gtgatgcatg aggctctgca caaccactac  1320
acgcagaaga gcctctccct gtctccgggt aaa                              1353

SEQ ID NO: 227         moltype = AA  length = 470
FEATURE                Location/Qualifiers
REGION                 1..470
                       note = Synthetic Polypeptide
REGION                 1..470
                       note = MISC_FEATURE - Humanized Antibody Sequence
source                 1..470
                       mol_type = protein
                       organism = synthetic construct
SEQUENCE: 227
MDWTWRILFL VAAATGAHSE VQLVQSGAEV KKPGASVKVS CKASDFNIKD FYLHWVRQAP  60
GQGLEWIGRI DPENGDTLYD PKFQDKVTMT TDTSTSTAYM ELRSLRSDDT AVYYCAREAD  120
YFHDGTSYWY FDVWGRGTLV TVSSASTKGP SVFPLAPCSR STSESTAALG CLVKDYFPEP  180
VTVSWNSGAL TSGVHTFPAV LQSSGLYSLS SVVTVPSSNF GTQTYTCNVD HKPSNTKVDK  240
TVERKCCVEC PPCPAPPVAG PSVFLFPPKP KDTLMISRTP EVTCVVVDVS HEDPEVQFNW  300
YVDGVEVHNA KTKPREEQFN STFRVVSVLT VVHQDWLNGK EYKCKVSNKG LPAPIEKTIS  360
KTKGQPREPQ VYTLPPSREE MTKNQVSLTC LVKGFYPSDI AVEWESNGQP ENNYKTTPPM  420
LDSDGSFFLY SKLTVDKSRW QQGNVFSCSV MHEALHNHYT QKSLSLSPGK             470

SEQ ID NO: 228         moltype = DNA  length = 1410
FEATURE                Location/Qualifiers
misc_feature           1..1410
                       note = Synthetic Polynucleotide
misc_feature           1..1410
                       note = Humanized Antibody Sequence
source                 1..1410
                       mol_type = other DNA
                       organism = synthetic construct
SEQUENCE: 228
atggactgga cctggaggat cctcttcttg gtggcagcag ccacaggagc ccactccgag  60
gtgcagctgg tgcagtctgg ggctgaggtg aagaagcctg gggcctcagt gaaggtctcc  120
tgcaaggctt ctgacttcaa cattaaagac ttctatctac actgggtgcg acaggcccct  180
ggacaagggc ttgagtggat tggaaggatt gatcctgaga atggtgatac tttatatgac  240
ccgaagttcc aggacaaggt caccatgacc acagacacgt ccaccagcac agcctacatg  300
gagctgagga gcctgagatc tgacgacacg gccgtgtatt actgtgcgag agaggcggat  360
tatttccacg atggtacctc ctactggtac ttcgatgtct ggggccgtgg caccctggtc  420
accgtctcta gtgcctccac caagggccca tcggtcttcc ccctggcgcc ctgctccagg  480
agcacctccg agagcacagc ggccctgggc tgcctggtca aggactactt ccccgaaccg  540
gtgacggtgt cgtggaactc aggcgctctg accagcggcg tgcacacctt cccagctgtc  600
ctacagtcct caggactcta ctccctcagc agcgtggtga ccgtgccctc cagcaacttc  660
ggcacccaga cctacacctg caacgtagat cacaagccca gcaacaccaa ggtggacaag  720
```

```
acagttgagc gcaaatgttg tgtcgagtgc ccaccgtgcc cagcaccacc tgtggcagga  780
ccgtcagtct tcctcttccc cccaaaaccc aaggacaccc tcatgatctc ccggacccct  840
gaggtcacgt gcgtggtggt ggacgtgagc cacgaagacc ccgaggtcca gttcaactgg  900
tacgtggacg gcgtggaggt gcataatgcc aagacaaagc cacgggagga gcagttcaac  960
agcacgttcc gtgtggtcag cgtcctcacc gttgtgcacc aggactggct gaacggcaag  1020
gagtacaagt gcaaggtctc caacaaaggc ctcccagccc ccatcgagaa aaccatctcc  1080
aaaaccaaag ggcagccccg agaaccacag gtgtacaccc tgcccccatc ccgggaggag  1140
atgaccaaga accaggtcag cctgacctgc ctggtcaaag gcttctaccc cagcgacatc  1200
gccgtggagt gggagagcaa tgggcagccg gagaacaact acaagaccac acctcccatg  1260
ctggactccg acggctcctt cttcctctac agcaagctca ccgtggacaa gagcaggtgg  1320
cagcagggga acgtcttctc atgctccgtg atgcatgagg ctctgcacaa ccactacacg  1380
cagaagagcc tctccctgtc tccgggtaaa                                  1410

SEQ ID NO: 229          moltype = AA  length = 213
FEATURE                 Location/Qualifiers
REGION                  1..213
                        note = Synthetic Polypeptide
REGION                  1..213
                        note = MISC_FEATURE - Humanized Antibody Sequence
source                  1..213
                        mol_type = protein
                        organism = synthetic construct
SEQUENCE: 229
DIQLTQSPSF LSASVGDRVT ITCRASSSIS YIHWYQQKPG KAPKLLIYAT SNLASGVPSR  60
FSGSGSGTEF TLTISSLQPE DFATYYCQQW SSDPLTFGGG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 230          moltype = DNA  length = 639
FEATURE                 Location/Qualifiers
misc_feature            1..639
                        note = Synthetic Polynucleotide
misc_feature            1..639
                        note = Humanized Antibody Sequence
source                  1..639
                        mol_type = other DNA
                        organism = synthetic construct
SEQUENCE: 230
gacatccagt tgacccagtc tccatccttc ctgtctgcat ctgtaggaga cagagtcacc  60
atcacttgca gggccagctc aagtataagt tacatacact ggtatcagca aaaaccaggg  120
aaagccccta agctcctgat ctatgccaca tccaacctgg cttctggggt cccatcaagg  180
ttcagcggca gtggatctgg gacagaattc actctcacaa tcagcagcct gcagcctgaa  240
gattttgcaa cttattactg tcagcagtgg agtagtgacc cactcacgtt cggcggaggg  300
accaaggtgg agatcaaacg tacggtggct gcaccatctg tcttcatctt cccgccatct  360
gatgagcagt tgaaatctgg aactgcctct gttgtgtgcc tgctgaataa cttctatccc  420
agagaggcca aagtacagtg gaaggtggat aacgccctcc aatcgggtaa ctcccaggag  480
agtgtcacag agcaggacag caaggacagc acctacagcc tcagcagcac cctgacgctg  540
agcaaagcag actacgagaa acacaaagtc tacgcctgcg aagtcaccca tcagggcctg  600
agctcgcccg tcacaaagag cttcaacagg ggagagtgt                         639

SEQ ID NO: 231          moltype = AA  length = 235
FEATURE                 Location/Qualifiers
REGION                  1..235
                        note = Synthetic Polypeptide
REGION                  1..235
                        note = MISC_FEATURE - Humanized Antibody Sequence
source                  1..235
                        mol_type = protein
                        organism = synthetic construct
SEQUENCE: 231
MDMRVPAQLL GLLLLWLPGA RCDIQLTQSP SFLSASVGDR VTITCRASSS ISYIHWYQQK  60
PGKAPKLLIY ATSNLASGVP SRFSGSGSGT EFTLTISSLQ PEDFATYYCQ QWSSDPLTFG  120
GGTKVEIKRT VAAPSVFIFP PSDEQLKSGT ASVVCLLNNF YPREAKVQWK VDNALQSGNS  180
QESVTEQDSK DSTYSLSSTL TLSKADYEKH KVYACEVTHQ GLSSPVTKSF NRGEC       235

SEQ ID NO: 232          moltype = DNA  length = 705
FEATURE                 Location/Qualifiers
misc_feature            1..705
                        note = Synthetic Polynucleotide
misc_feature            1..705
                        note = Humanized Antibody Sequence
source                  1..705
                        mol_type = other DNA
                        organism = synthetic construct
SEQUENCE: 232
atggacatga gggtccccgc tcagctcctg gggctcctgc tgctctggct cccaggtgcc  60
agatgtgaca tccagttgac ccagtctcca tccttcctgt ctgcatctgt aggagacaga  120
gtcaccatca cttgcagggc cagctcaagt ataagttaca tacactggta tcagcaaaaa  180
ccagggaaag cccctaagct cctgatctat gccacatcca acctggcttc tggggtccca  240
```

```
tcaaggttca gcggcagtgg atctgggaca gaattcactc tcacaatcag cagcctgcag  300
cctgaagatt ttgcaactta ttactgtcag cagtggagta gtgacccact cacgttcggc  360
ggagggacca aggtggagat caaacgtacg gtggctgcac catctgtctt catcttcccg  420
ccatctgatg agcagttgaa atctggaact gcctctgttg tgtgcctgct gaataacttc  480
tatcccagag aggccaaagt acagtggaag gtggataacg ccctccaatc gggtaactcc  540
caggagagtg tcacagagca ggacagcaag gacagcacct acagcctcag cagcaccctg  600
acgctgagca aagcagacta cgagaaacac aaagtctacg cctgcgaagt cacccatcag  660
ggcctgagct cgcccgtcac aaagagcttc aacaggggag agtgt                705

SEQ ID NO: 233          moltype = AA  length = 447
FEATURE                 Location/Qualifiers
REGION                  1..447
                        note = Synthetic Polypeptide
REGION                  1..447
                        note = MISC_FEATURE - Humanized Antibody Sequence
source                  1..447
                        mol_type = protein
                        organism = synthetic construct
SEQUENCE: 233
EVQLVQSGAE VKKPGASVKV SCKASGFDIK DYYIHWVRQA PGQGLEWIGR VDPDNGETEF  60
APKFPGKVTM TTDTSISTAY MELSRLRSDD TAVYYCARED YDGTYTWFPY WGQGTLVTVS  120
SASTKGPSVF PLAPCSRSTS ESTAALGCLV KDYFPEPVTV SWNSGALTSG VHTFPAVLQS  180
SGLYSLSSVV TVPSSNFGTQ TYTCNVDHKP SNTKVDKTVE RKCCVECPPC PAPPVAGPSV  240
FLFPPKPKDT LMISRTPEVT CVVVDVSHED PEVQFNWYVD GVEVHNAKTK PREEQFNSTF  300
RVVSVLTVVH QDWLNGKEYK CKVSNKGLPA PIEKTISKTK GQPREPQVYT LPPSREEMTK  360
NQVSLTCLVK GFYPSDIAVE WESNGQPENN YKTTPPMLDS DGSFFLYSKL TVDKSRWQQG  420
NVFSCSVMHE ALHNHYTQKS LSLSPGK                                    447

SEQ ID NO: 234          moltype = DNA  length = 1341
FEATURE                 Location/Qualifiers
misc_feature            1..1341
                        note = Synthetic Polynucleotide
misc_feature            1..1341
                        note = Humanized Antibody Sequence
source                  1..1341
                        mol_type = other DNA
                        organism = synthetic construct
SEQUENCE: 234
gaggtgcagc tggtgcagtc tggggctgag gtgaagaagc ctggggcctc agtgaaggtc  60
tcctgcaagg cttctggatt cgacattaag gactactata tacactgggt gcgacaggcc  120
cctggacaag ggcttgagtg gatcggaagg gttgatcctg acaatggtga gactgaattt  180
gccccgaagt tcccgggcaa ggtcaccatg accacagaca cgtccatcag cacagcctac  240
atggagctga gcaggctgag atctgacgac acggccgtgt attactgtgc gagagaagac  300
tacgatggta cctacacctg gtttccttat tggggccaag ggactctggt caccgtctct  360
agtgcctcca ccaagggccc atcggtcttc cccctggcgc cctgctccag gagcacctcc  420
gagagcacag cggccctggg ctgcctggtc aaggactact tccccgaacc ggtgacggtg  480
tcgtggaact caggcgctct gaccagcggc gtgcacacct tcccagctgt cctacagtcc  540
tcaggactct actccctcag cagcgtggtg accgtgccct ccagcaactt cggcacccag  600
acctacacct gcaacgtaga tcacaagccc agcaacacca aggtggacaa gacagttgag  660
cgcaaatgtt gtgtcgagtg cccaccgtgc ccagcaccac ctgtggcagg accgtcagtc  720
ttcctcttcc ccccaaaacc caaggacacc ctcatgatct cccggacccc tgaggtcacg  780
tgcgtggtgg tggacgtgag ccacgaagac cccgaggtcc agttcaactg gtacgtggac  840
ggcgtggagg tgcataatgc caagacaaag ccacgggagg agcagttcaa cagcacgttc  900
cgtgtggtca gcgtcctcac cgttgtgcac caggactggc tgaacggcaa ggagtacaag  960
tgcaaggtct ccaacaaagg cctcccagcc cccatcgaga aaaccatctc caaaaccaaa  1020
gggcagcccc gagaaccaca ggtgtacacc ctgcccccat cccgggagga gatgaccaag  1080
aaccaggtca gcctgacctg cctggtcaaa ggcttctacc ccagcgacat cgccgtggag  1140
tgggagagca atgggcagcc ggagaacaac tacaagacca cacctcccat gctggactcc  1200
gacggctcct tcttcctcta cagcaagctc accgtggaca agagcaggtg gcagcagggg  1260
aacgtcttct catgctccgt gatgcatgag gctctgcaca accactacac gcagaagagc  1320
ctctccctgt ctccgggtaa a                                          1341

SEQ ID NO: 235          moltype = AA  length = 466
FEATURE                 Location/Qualifiers
REGION                  1..466
                        note = Synthetic Polypeptide
REGION                  1..466
                        note = MISC_FEATURE - Humanized Antibody Sequence
source                  1..466
                        mol_type = protein
                        organism = synthetic construct
SEQUENCE: 235
MDWTWRILFL VAAATGAHSE VQLVQSGAEV KKPGASVKVS CKASGFDIKD YYIHWVRQAP  60
GQGLEWIGRV DPDNGETEFA PKFPGKVTMT TDTSISTAYM ELSRLRSDDT AVYYCAREDY  120
DGTYTWFPYW GQGTLVTVSS ASTKGPSVFP LAPCSRSTSE STAALGCLVK DYFPEPVTVS  180
WNSGALTSGV HTFPAVLQSS GLYSLSSVVT VPSSNFGTQT YTCNVDHKPS NTKVDKTVER  240
KCCVECPPCP APPVAGPSVF LFPPKPKDTL MISRTPEVTC VVVDVSHEDP EVQFNWYVDG  300
VEVHNAKTKP REEQFNSTFR VVSVLTVVHQ DWLNGKEYKC KVSNKGLPAP IEKTISKTKG  360
QPREPQVYTL PPSREEMTKN QVSLTCLVKG FYPSDIAVEW ESNGQPENNY KTTPPMLDSD  420
```

-continued

```
GSFFLYSKLT VDKSRWQQGN VFSCSVMHEA LHNHYTQKSL SLSPGK                466

SEQ ID NO: 236          moltype = DNA  length = 1398
FEATURE                 Location/Qualifiers
misc_feature            1..1398
                        note = Synthetic Polynucleotide
misc_feature            1..1398
                        note = Humanized Antibody Sequence
source                  1..1398
                        mol_type = other DNA
                        organism = synthetic construct
SEQUENCE: 236
atggactgga cctggaggat cctcttcttg gtggcagcag ccacaggagc ccactccgag  60
gtgcagctgg tgcagtctgg ggctgaggtg aagaagcctg gggcctcagt gaaggtctcc  120
tgcaaggctt ctggattcga cattaaggac tactatatac actgggtgcg acaggcccct  180
ggacaagggc ttgagtggat cggaagggtt gatcctgaca atggtgagac tgaatttgcc  240
ccgaagttcc cgggcaaggt caccatgacc acagacacgt ccatcagcac agcctacatg  300
gagctgagca ggctgagatc tgacgacacg gccgtgtatt actgtgcgag agaagactac  360
gatggtacct acacctggtt tccttattgg ggccaaggga ctctggtcac cgtctctagt  420
gcctccacca agggcccatc ggtcttcccc ctggcgccct gctccaggag cacctccgag  480
agcacagcgg ccctgggctg cctggtcaag gactacttcc ccgaaccggt gacggtgtcg  540
tggaactcag gcgctctgac cagcggcgtg cacaccttcc cagctgtcct acagtcctca  600
ggactctact ccctcagcag cgtggtgacc gtgccctcca gcaacttcgg cacccagacc  660
tacacctgca acgtagatca caagcccagc aacaccaagg tggacaagac agttgagcgc  720
aaatgttgtg tcgagtgccc accgtgccca gcaccacctg tggcaggacc gtcagtcttc  780
ctcttccccc caaaacccaa ggacaccctc atgatctccc ggacccctga ggtcacgtgc  840
gtggtggtgg acgtgagcca cgaagacccc gaggtccagt tcaactggta cgtggacggc  900
gtggaggtgc ataatgccaa gacaaagcca cgggaggagc agttcaacag cacgttccgt  960
gtggtcagcg tcctcaccgt tgtgcaccag gactggctga acggcaagga gtacaagtgc  1020
aaggtctcca acaaaggcct cccagccccc atcgagaaaa ccatctccaa aaccaaaggg  1080
cagccccgag aaccacaggt gtacaccctg cccccatccc gggaggagat gaccaagaac  1140
caggtcagcc tgacctgcct ggtcaaaggc ttctacccca gcgacatcgc cgtggagtgg  1200
gagagcaatg ggcagccgga gaacaactac aagaccacac ctcccatgct ggactccgac  1260
ggctccttct tcctctacag caagctcacc gtggacaaga gcaggtggca gcaggggaac  1320
gtcttctcat gctccgtgat gcatgaggct ctgcacaacc actacacgca gaagagcctc  1380
tccctgtctc cgggtaaa                                                1398

SEQ ID NO: 237          moltype = AA  length = 7
FEATURE                 Location/Qualifiers
source                  1..7
                        mol_type = protein
                        organism = Mus musculus
SEQUENCE: 237
GTSNLAS                                                           7

SEQ ID NO: 238          moltype = AA  length = 8
FEATURE                 Location/Qualifiers
source                  1..8
                        mol_type = protein
                        organism = Mus musculus
SEQUENCE: 238
QQWTTTYT                                                          8

SEQ ID NO: 239          moltype = AA  length = 11
FEATURE                 Location/Qualifiers
source                  1..11
                        mol_type = protein
                        organism = Mus musculus
SEQUENCE: 239
RASQDISSYL N                                                      11

SEQ ID NO: 240          moltype = AA  length = 7
FEATURE                 Location/Qualifiers
source                  1..7
                        mol_type = protein
                        organism = Mus musculus
SEQUENCE: 240
STSRLNS                                                           7

SEQ ID NO: 241          moltype = AA  length = 8
FEATURE                 Location/Qualifiers
source                  1..8
                        mol_type = protein
                        organism = Mus musculus
SEQUENCE: 241
QQDIKHPT                                                          8

SEQ ID NO: 242          moltype = AA  length = 11
FEATURE                 Location/Qualifiers
```

-continued

```
source                  1..11
                        mol_type = protein
                        organism = Mus musculus
SEQUENCE: 242
KASQDVFTAV A                                                   11

SEQ ID NO: 243          moltype = AA  length = 7
FEATURE                 Location/Qualifiers
source                  1..7
                        mol_type = protein
                        organism = Mus musculus
SEQUENCE: 243
WASTRHT                                                        7

SEQ ID NO: 244          moltype = AA  length = 9
FEATURE                 Location/Qualifiers
source                  1..9
                        mol_type = protein
                        organism = Mus musculus
SEQUENCE: 244
QQYSSYPLT                                                      9

SEQ ID NO: 245          moltype = AA  length = 5
FEATURE                 Location/Qualifiers
source                  1..5
                        mol_type = protein
                        organism = Mus musculus
SEQUENCE: 245
DYNMH                                                          5

SEQ ID NO: 246          moltype = AA  length = 17
FEATURE                 Location/Qualifiers
source                  1..17
                        mol_type = protein
                        organism = Mus musculus
SEQUENCE: 246
EINPNSGGAG YNQKFKG                                             17

SEQ ID NO: 247          moltype = AA  length = 14
FEATURE                 Location/Qualifiers
source                  1..14
                        mol_type = protein
                        organism = Mus musculus
SEQUENCE: 247
LGYDDIYDDW YFDV                                                14

SEQ ID NO: 248          moltype = AA  length = 5
FEATURE                 Location/Qualifiers
source                  1..5
                        mol_type = protein
                        organism = Mus musculus
SEQUENCE: 248
DYNMH                                                          5

SEQ ID NO: 249          moltype = AA  length = 17
FEATURE                 Location/Qualifiers
source                  1..17
                        mol_type = protein
                        organism = Mus musculus
SEQUENCE: 249
EINPNSGGSG YNQKFKG                                             17

SEQ ID NO: 250          moltype = AA  length = 14
FEATURE                 Location/Qualifiers
source                  1..14
                        mol_type = protein
                        organism = Mus musculus
SEQUENCE: 250
LVYDGSYEDW YFDV                                                14

SEQ ID NO: 251          moltype = AA  length = 5
FEATURE                 Location/Qualifiers
source                  1..5
                        mol_type = protein
                        organism = Mus musculus
SEQUENCE: 251
DYNMH                                                          5

SEQ ID NO: 252          moltype = AA  length = 17
```

```
FEATURE                Location/Qualifiers
source                 1..17
                       mol_type = protein
                       organism = Mus musculus
SEQUENCE: 252
EINPNSGGAG YNQQFKG                                    17

SEQ ID NO: 253         moltype = AA  length = 14
FEATURE                Location/Qualifiers
source                 1..14
                       mol_type = protein
                       organism = Mus musculus
SEQUENCE: 253
LGYVGNYEDW YFDV                                       14

SEQ ID NO: 254         moltype = AA  length = 5
FEATURE                Location/Qualifiers
source                 1..5
                       mol_type = protein
                       organism = Mus musculus
SEQUENCE: 254
DYNMH                                                 5

SEQ ID NO: 255         moltype = AA  length = 17
FEATURE                Location/Qualifiers
source                 1..17
                       mol_type = protein
                       organism = Mus musculus
SEQUENCE: 255
EINPNSGGAG YNQKFKG                                    17

SEQ ID NO: 256         moltype = AA  length = 14
FEATURE                Location/Qualifiers
source                 1..14
                       mol_type = protein
                       organism = Mus musculus
SEQUENCE: 256
LGYDDIYDDW YFDV                                       14

SEQ ID NO: 257         moltype = AA  length = 5
FEATURE                Location/Qualifiers
source                 1..5
                       mol_type = protein
                       organism = Mus musculus
SEQUENCE: 257
DYNMH                                                 5

SEQ ID NO: 258         moltype = AA  length = 17
FEATURE                Location/Qualifiers
source                 1..17
                       mol_type = protein
                       organism = Mus musculus
SEQUENCE: 258
EINPNSGGAG YNQKFKG                                    17

SEQ ID NO: 259         moltype = AA  length = 14
FEATURE                Location/Qualifiers
source                 1..14
                       mol_type = protein
                       organism = Mus musculus
SEQUENCE: 259
LGYDDIYDDW YFDV                                       14

SEQ ID NO: 260         moltype = AA  length = 5
FEATURE                Location/Qualifiers
source                 1..5
                       mol_type = protein
                       organism = Mus musculus
SEQUENCE: 260
DYNMH                                                 5

SEQ ID NO: 261         moltype = AA  length = 17
FEATURE                Location/Qualifiers
source                 1..17
                       mol_type = protein
                       organism = Mus musculus
SEQUENCE: 261
EINPNSGGAG YNQKFKG                                    17
```

-continued

```
SEQ ID NO: 262          moltype = AA  length = 14
FEATURE                 Location/Qualifiers
source                  1..14
                        mol_type = protein
                        organism = Mus musculus
SEQUENCE: 262
LGYDDIYDDW YFDV                                                    14

SEQ ID NO: 263          moltype = AA  length = 5
FEATURE                 Location/Qualifiers
source                  1..5
                        mol_type = protein
                        organism = Mus musculus
SEQUENCE: 263
DYNMH                                                              5

SEQ ID NO: 264          moltype = AA  length = 17
FEATURE                 Location/Qualifiers
source                  1..17
                        mol_type = protein
                        organism = Mus musculus
SEQUENCE: 264
EINPNSGGSG YNQKFKG                                                 17

SEQ ID NO: 265          moltype = AA  length = 14
FEATURE                 Location/Qualifiers
source                  1..14
                        mol_type = protein
                        organism = Mus musculus
SEQUENCE: 265
LGYYGNYEDW YFDV                                                    14

SEQ ID NO: 266          moltype = AA  length = 5
FEATURE                 Location/Qualifiers
source                  1..5
                        mol_type = protein
                        organism = Mus musculus
SEQUENCE: 266
DYYIH                                                              5

SEQ ID NO: 267          moltype = AA  length = 17
FEATURE                 Location/Qualifiers
source                  1..17
                        mol_type = protein
                        organism = Mus musculus
SEQUENCE: 267
RIDPDNGEST YVPKFQG                                                 17

SEQ ID NO: 268          moltype = AA  length = 13
FEATURE                 Location/Qualifiers
source                  1..13
                        mol_type = protein
                        organism = Mus musculus
SEQUENCE: 268
EGLDYGDYYA VDY                                                     13

SEQ ID NO: 269          moltype = AA  length = 5
FEATURE                 Location/Qualifiers
source                  1..5
                        mol_type = protein
                        organism = Mus musculus
SEQUENCE: 269
DYIMH                                                              5

SEQ ID NO: 270          moltype = AA  length = 17
FEATURE                 Location/Qualifiers
source                  1..17
                        mol_type = protein
                        organism = Mus musculus
SEQUENCE: 270
YINPYNDDTE YNEKFKG                                                 17

SEQ ID NO: 271          moltype = AA  length = 11
FEATURE                 Location/Qualifiers
source                  1..11
                        mol_type = protein
                        organism = Mus musculus
SEQUENCE: 271
SIYYYDAPFA Y                                                       11
```

```
SEQ ID NO: 272          moltype = AA  length = 5
FEATURE                 Location/Qualifiers
source                  1..5
                        mol_type = protein
                        organism = Mus musculus
SEQUENCE: 272
DYYMH                                                                5

SEQ ID NO: 273          moltype = AA  length = 17
FEATURE                 Location/Qualifiers
source                  1..17
                        mol_type = protein
                        organism = Mus musculus
SEQUENCE: 273
RIDPENGDII YDPKFQG                                                   17

SEQ ID NO: 274          moltype = AA  length = 10
FEATURE                 Location/Qualifiers
source                  1..10
                        mol_type = protein
                        organism = Mus musculus
SEQUENCE: 274
DAGDPAWFTY                                                           10

SEQ ID NO: 275          moltype = AA  length = 10
FEATURE                 Location/Qualifiers
source                  1..10
                        mol_type = protein
                        organism = Mus musculus
SEQUENCE: 275
RASSSVYYMH                                                           10

SEQ ID NO: 276          moltype = AA  length = 7
FEATURE                 Location/Qualifiers
source                  1..7
                        mol_type = protein
                        organism = Mus musculus
SEQUENCE: 276
ATSNLAS                                                              7

SEQ ID NO: 277          moltype = AA  length = 9
FEATURE                 Location/Qualifiers
source                  1..9
                        mol_type = protein
                        organism = Mus musculus
SEQUENCE: 277
QQWSSDPLT                                                            9

SEQ ID NO: 278          moltype = AA  length = 12
FEATURE                 Location/Qualifiers
source                  1..12
                        mol_type = protein
                        organism = Mus musculus
SEQUENCE: 278
SVSSTISSNH LH                                                        12

SEQ ID NO: 279          moltype = AA  length = 7
FEATURE                 Location/Qualifiers
source                  1..7
                        mol_type = protein
                        organism = Mus musculus
SEQUENCE: 279
GTSNLAS                                                              7

SEQ ID NO: 280          moltype = AA  length = 9
FEATURE                 Location/Qualifiers
source                  1..9
                        mol_type = protein
                        organism = Mus musculus
SEQUENCE: 280
QQWSSYPLT                                                            9

SEQ ID NO: 281          moltype = AA  length = 10
FEATURE                 Location/Qualifiers
source                  1..10
                        mol_type = protein
                        organism = Mus musculus
SEQUENCE: 281
```

```
RASSSISYIH                                                    10

SEQ ID NO: 282          moltype = AA  length = 7
FEATURE                 Location/Qualifiers
source                  1..7
                        mol_type = protein
                        organism = Mus musculus
SEQUENCE: 282
ATSNLAS                                                       7

SEQ ID NO: 283          moltype = AA  length = 9
FEATURE                 Location/Qualifiers
source                  1..9
                        mol_type = protein
                        organism = Mus musculus
SEQUENCE: 283
QQWSSDPLT                                                     9

SEQ ID NO: 284          moltype = AA  length = 12
FEATURE                 Location/Qualifiers
source                  1..12
                        mol_type = protein
                        organism = Mus musculus
SEQUENCE: 284
RASSSVTSSY LN                                                 12

SEQ ID NO: 285          moltype = AA  length = 7
FEATURE                 Location/Qualifiers
source                  1..7
                        mol_type = protein
                        organism = Mus musculus
SEQUENCE: 285
STSNLAS                                                       7

SEQ ID NO: 286          moltype = AA  length = 9
FEATURE                 Location/Qualifiers
source                  1..9
                        mol_type = protein
                        organism = Mus musculus
SEQUENCE: 286
QQYDFFPST                                                     9

SEQ ID NO: 287          moltype = AA  length = 5
FEATURE                 Location/Qualifiers
source                  1..5
                        mol_type = protein
                        organism = Mus musculus
SEQUENCE: 287
DYFIH                                                         5

SEQ ID NO: 288          moltype = AA  length = 17
FEATURE                 Location/Qualifiers
source                  1..17
                        mol_type = protein
                        organism = Mus musculus
SEQUENCE: 288
RLDPEDGESD YAPKFQD                                            17

SEQ ID NO: 289          moltype = AA  length = 12
FEATURE                 Location/Qualifiers
source                  1..12
                        mol_type = protein
                        organism = Mus musculus
SEQUENCE: 289
EDYDGTYTFF PY                                                 12

SEQ ID NO: 290          moltype = AA  length = 5
FEATURE                 Location/Qualifiers
source                  1..5
                        mol_type = protein
                        organism = Mus musculus
SEQUENCE: 290
DFYLH                                                         5

SEQ ID NO: 291          moltype = AA  length = 17
FEATURE                 Location/Qualifiers
source                  1..17
                        mol_type = protein
                        organism = Mus musculus
```

-continued

```
SEQUENCE: 291
RIDPENGDTL YDPKFQD                                            17

SEQ ID NO: 292          moltype = AA  length = 16
FEATURE                 Location/Qualifiers
source                  1..16
                        mol_type = protein
                        organism = Mus musculus
SEQUENCE: 292
EADYFHDGTS YWYFDV                                             16

SEQ ID NO: 293          moltype = AA  length = 5
FEATURE                 Location/Qualifiers
source                  1..5
                        mol_type = protein
                        organism = Mus musculus
SEQUENCE: 293
DYYIH                                                         5

SEQ ID NO: 294          moltype = AA  length = 17
FEATURE                 Location/Qualifiers
source                  1..17
                        mol_type = protein
                        organism = Mus musculus
SEQUENCE: 294
RVDPDNGETE FAPKFPG                                            17

SEQ ID NO: 295          moltype = AA  length = 12
FEATURE                 Location/Qualifiers
source                  1..12
                        mol_type = protein
                        organism = Mus musculus
SEQUENCE: 295
EDYDGTYTWF PY                                                 12

SEQ ID NO: 296          moltype = AA  length = 5
FEATURE                 Location/Qualifiers
source                  1..5
                        mol_type = protein
                        organism = Mus musculus
SEQUENCE: 296
DYYMN                                                         5

SEQ ID NO: 297          moltype = AA  length = 17
FEATURE                 Location/Qualifiers
source                  1..17
                        mol_type = protein
                        organism = Mus musculus
SEQUENCE: 297
DINPYNDDTT YNHKFKG                                            17

SEQ ID NO: 298          moltype = AA  length = 11
FEATURE                 Location/Qualifiers
source                  1..11
                        mol_type = protein
                        organism = Mus musculus
SEQUENCE: 298
ETAVITTNAM D                                                  11

SEQ ID NO: 299          moltype = AA  length = 130
FEATURE                 Location/Qualifiers
source                  1..130
                        mol_type = protein
                        organism = Mus musculus
SEQUENCE: 299
MDFQVQIFSF MLISVTVILS SGEIVLTQSP ALMAASPGEK VTITCSVSSS ISSSNLHWSQ  60
QKSGTSPKLW IYGTSNLASG VPVRFSGSGS GTSYSLTISS MEAEDAATYY CQQWTTTYTF  120
GSGTKLELKR                                                    130

SEQ ID NO: 300          moltype = DNA  length = 390
FEATURE                 Location/Qualifiers
source                  1..390
                        mol_type = other DNA
                        organism = Mus musculus
SEQUENCE: 300
atggattttc aggtgcagat tttcagcttc atgctaatca gtgtcacagt catattgtcc  60
agtggagaaa ttgtgctcac ccagtctcca gcactcatgg ctgcatctcc aggggagaag  120
gtcaccatca cctgcagtgt cagctcgagt ataagttcca gcaacttaca ctggtcccag  180
cagaagtcag gaacctcccc caaactctgg atttatggca catccaacct tgcttctgga  240
```

```
gtccctgttc gcttcagtgg cagtggatct gggacctctt attctctcac aatcagcagc  300
atggaggctg aagatgctgc cacttattac tgtcaacagt ggactactac gtatacgttc  360
ggatcgggga ccaagctgga gctgaaacgt                                   390

SEQ ID NO: 301         moltype = AA  length = 141
FEATURE                Location/Qualifiers
source                 1..141
                       mol_type = protein
                       organism = Mus musculus
SEQUENCE: 301
MGWNWIIFFL MAVVTGVNSE VQLRQSGADL VKPGASVKLS CTASGFNIKD YYIHWVKQRP  60
EQGLEWIGRI DPDNGESTYV PKFQGKATIT ADTSSNTAYL QLRSLTSEDT AIYYCGREGL  120
DYGDYYAVDY WGQGTSVTVS S                                            141

SEQ ID NO: 302         moltype = DNA  length = 423
FEATURE                Location/Qualifiers
source                 1..423
                       mol_type = other DNA
                       organism = Mus musculus
SEQUENCE: 302
atgggatgga actggatcat cttcttcctg atggcagtgg ttacaggggt caattcagag  60
gtgcagttgc ggcagtctgg ggcagacctt gtgaagccag gggcctcagt caagttgtcc  120
tgcacagctt ctggcttcaa cattaaagac tactatatac actgggtgaa gcagaggcct  180
gaacagggcc tggagtggat tggaaggatt gatcctgata atggtgaaag tacatatgtc  240
ccgaagttcc agggcaaggc cactataaca gcagacacat catccaacac agcctaccta  300
caactcagaa gcctgacatc tgaggacact gccatctatt attgtgggag agaggggctc  360
gactatggtg actactatgc tgtggactac tggggtcaag gaacctcggt cacagtctcg  420
agc                                                                423

SEQ ID NO: 303         moltype = AA  length = 130
FEATURE                Location/Qualifiers
REGION                 1..130
                       note = Synthetic Polypeptide
REGION                 1..130
                       note = MISC_FEATURE - Humanized Antibody Sequence
source                 1..130
                       mol_type = protein
                       organism = synthetic construct
SEQUENCE: 303
MDMRVPAQLL GLLLLWLPGA RCDIQLTQSP SFLSASVGDR VTITCSVSSS ISSSNLHWYQ  60
QKPGKAPKLL IYGTSNLASG VPSRFSGSGS GTEFTLTISS LQPEDFATYY CQQWTTTYTF  120
GQGTKLEIKR                                                         130

SEQ ID NO: 304         moltype = DNA  length = 390
FEATURE                Location/Qualifiers
misc_feature           1..390
                       note = Synthetic Polynucleotide
misc_feature           1..390
                       note = Humanized Antibody Sequence
source                 1..390
                       mol_type = other DNA
                       organism = synthetic construct
SEQUENCE: 304
atggatatgc gcgtgccggc gcagctgctg ggcctgctgc tgctgtggct gccgggcgcg  60
cgctgcgata ttcagctgac ccagagcccg agctttctga gcgcgagcgt gggcgatcgc  120
gtgaccatta cctgcagcgt gagcagcagc attagcagca gcaacctgca ttggtatcag  180
cagaaaccgg gcaaagcgcc gaaactgctg atttatggca ccagcaacct ggcgagcggc  240
gtgccgagcc gctttagcgg cagcggcagc ggcaccgaat ttaccctgac cattagcagc  300
ctgcagccgg aagattttgc gacctattat tgccagcagt ggaccaccac ctatacctttt  360
ggccagggca ccaaactgga aattaaacgt                                   390

SEQ ID NO: 305         moltype = AA  length = 141
FEATURE                Location/Qualifiers
REGION                 1..141
                       note = Synthetic Polypeptide
REGION                 1..141
                       note = MISC_FEATURE - Humanized Antibody Sequence
source                 1..141
                       mol_type = protein
                       organism = synthetic construct
SEQUENCE: 305
MDWTWSILFL VAAPTGAHSE VQLVQSGAEV KKPGASVKVS CKASGFNIKD YYIHWVRQAP  60
GQGLEWMGRI DPDNGESTYV PKFQGRVTMT TDTSTSTAYM ELRSLRSDDT AVYYCAREGL  120
DYGDYYAVDY WGQGTLVTVS S                                            141

SEQ ID NO: 306         moltype = DNA  length = 423
FEATURE                Location/Qualifiers
misc_feature           1..423
                       note = Synthetic Polynucleotide
```

-continued

```
misc_feature          1..423
                      note = Humanized Antibody Sequence
source                1..423
                      mol_type = other DNA
                      organism = synthetic construct
SEQUENCE: 306
atggattgga cctggagcat tctgtttctg gtggcggcgc cgaccggcgc gcatagcgaa  60
gtgcagctgg tgcagagcgg cgcggaagtg aaaaaaccgg gcgcgagcgt gaaagtgagc  120
tgcaaagcga gcggctttaa cattaaagat tattatattc attgggtgcg ccaggcgccg  180
ggccagggcc tggaatggat gggccgcatt gatccggata acggcgaaag cacctatgtg  240
ccgaaatttc agggccgcgt gaccatgacc accgatacca gcaccagcac cgcgtatatg  300
gaactgcgca gcctgcgcag cgatgatacc gcggtgtatt attgcgcgcg cgaaggcctg  360
gattatggcg attattatgc ggtggattat tggggccagg gcaccctggt gaccgtctcg  420
agc                                                                423

SEQ ID NO: 307        moltype = AA  length = 127
FEATURE               Location/Qualifiers
REGION                1..127
                      note = Synthetic Polypeptide
REGION                1..127
                      note = MISC_FEATURE - Humanized Antibody Sequence
source                1..127
                      mol_type = protein
                      organism = synthetic construct
SEQUENCE: 307
MMSSAQFLGL LLLCFQGTRC DIQMTQTTSS LSASLGDRVN ISCRASQDIS SYLNWYQQKP  60
DGTVKLLIYS TSRLNSGVPS RFSGSGSGTD YSLTISNLAQ EDIATYFCQQ DIKHPTFGGG  120
TKLELKR                                                            127

SEQ ID NO: 308        moltype = DNA  length = 381
FEATURE               Location/Qualifiers
source                1..381
                      mol_type = other DNA
                      organism = Mus musculus
SEQUENCE: 308
atgatgtcct ctgctcagtt ccttggtctc ctgttgctct gttttcaagg taccagatgt  60
gatatccaga tgacacagac tacatcctcc ctgtctgcct ctctgggaga cagagtcaac  120
atcagctgca gggcaagtca ggacattagc agttatttaa actggtatca gcagaaacca  180
gatggaactg ttaaactcct gatctactcc acatcaagat taaactcagg agtcccatca  240
aggttcagtg gcagtgggtc tgggacagat tattctctca ctattagcaa cctggcacaa  300
gaagatattg ccacttactt ttgccaacag gatattaagc atccgacgtt cggtggaggc  360
accaagttgg agctgaaacg t                                            381

SEQ ID NO: 309        moltype = AA  length = 139
FEATURE               Location/Qualifiers
source                1..139
                      mol_type = protein
                      organism = Mus musculus
SEQUENCE: 309
MEWIWIFLFL LSGTAGVHSE VQLQQSGPEL VKPGASVKMS CKASGFTFTD YIMHWVKQKP  60
GQGLEWIGYI NPYNDDTEYN EKFKGKATLT SDKSSSTAYM DLSSLTSEGS AVYYCARSIY  120
YYDAPFAYWG QGTLVTVSS                                               139

SEQ ID NO: 310        moltype = DNA  length = 417
FEATURE               Location/Qualifiers
source                1..417
                      mol_type = other DNA
                      organism = Mus musculus
SEQUENCE: 310
atggaatgga tctggatatt tctcttcctc ctgtcaggaa ctgcaggtgt ccactctgag  60
gtccagctgc agcagtctgg acctgagctg gtaaagcctg gggcttcagt gaagatgtcc  120
tgcaaggctt ctgggttcac attcactgac tacattatgc actgggtgaa gcagaagcct  180
gggcagggcc ttgagtggat tggatatatt aatccttaca atgatgatac tgaatacaat  240
gagaagttca aaggcaaggc cacactgact tcagacaaat cctccagcac agcctacatg  300
gatctcagca gtctgacctc tgagggctct gcggtctatt actgtgcaag atcgatttat  360
tactacgatg ccccgtttgc ttactggggc caagggactc tggtcacagt ctcgagc     417

SEQ ID NO: 311        moltype = AA  length = 127
FEATURE               Location/Qualifiers
REGION                1..127
                      note = Synthetic Polypeptide
REGION                1..127
                      note = MISC_FEATURE - Humanized Antibody Sequence
source                1..127
                      mol_type = protein
                      organism = synthetic construct
SEQUENCE: 311
MMSSAQFLGL LLLCFQGTRC DIQMTQSPSS LSASVGDRVT ITCRASQDIS SYLNWYQQKP  60
GKAPKLLIYS TSRLNSGVPS RFSGSGSGTD FTLTISSLQP EDFATYYCQQ DIKHPTFGQG  120
```

```
TKVEIKR                                                        127

SEQ ID NO: 312          moltype = DNA  length = 381
FEATURE                 Location/Qualifiers
misc_feature            1..381
                        note = Synthetic Polynucleotide
misc_feature            1..381
                        note = Humanized Antibody Sequence
source                  1..381
                        mol_type = other DNA
                        organism = synthetic construct
SEQUENCE: 312
atgatgtcct ctgctcagtt ccttggtctc ctgttgctct gttttcaagg taccagatgt  60
gatatccaga tgacccagtc tccatcctcc ctgtctgcat ctgtaggtga ccgtgtcacc  120
atcacttgcc gcgcaagtca ggatattagc agctatttaa attggtatca gcagaaacca  180
gggaaagccc ctaagctcct gatctattct acttcccgtt tgaatagtgg ggtcccatca  240
cgcttcagtg gcagtggctc tgggacagat ttcactctca ccatcagcag tctgcaacct  300
gaagattttg caacttacta ctgtcaacag gatattaaac accctacgtt cggtcaaggc  360
accaaggtgg agatcaaacg t                                        381

SEQ ID NO: 313          moltype = AA  length = 139
FEATURE                 Location/Qualifiers
REGION                  1..139
                        note = Synthetic Polypeptide
REGION                  1..139
                        note = MISC_FEATURE - Humanized Antibody Sequence
source                  1..139
                        mol_type = protein
                        organism = synthetic construct
SEQUENCE: 313
MEWIWIFLFL LSGTAGVHSE VQLVQSGAEV KKPGSSVKVS CKASGFTFTD YIMHWVRQAP  60
GQGLEWMGYI NPYNDDTEYN EKFKGRVTIT ADKSTSTAYM ELSSLRSEDT AVYYCARSIY  120
YYDAPFAYWG QGTLVTVSS                                           139

SEQ ID NO: 314          moltype = AA  length = 107
FEATURE                 Location/Qualifiers
source                  1..107
                        mol_type = protein
                        organism = Mus musculus
SEQUENCE: 314
DIQMTQTTSS LSASLGDRVN ISCRASQDIS SYLNWYQQKP DGTVKLLIYS TSRLNSGVPS  60
RFSGSGSGTD YSLTISNLAQ EDIATYFCQQ DIKHPTFGGG TKLELKR            107

SEQ ID NO: 315          moltype = AA  length = 128
FEATURE                 Location/Qualifiers
source                  1..128
                        mol_type = protein
                        organism = Mus musculus
SEQUENCE: 315
MKSQTQVFVY MLLWLSGVEG DIVMTQSHKF MSTSVGDRVT ITCKASQDVF TAVAWYQQKP  60
GQSPKLLIYW ASTRHTGVPD RFTGSGSGTD FTLTISNVQS EDLADYFCQQ YSSYPLTFGA  120
GTKLELKR                                                       128

SEQ ID NO: 316          moltype = DNA  length = 381
FEATURE                 Location/Qualifiers
source                  1..381
                        mol_type = other DNA
                        organism = Mus musculus
SEQUENCE: 316
atgaagtcac agacccaggt ctttgtatac atgttgctgt ggttgtctgg tgttgaagga  60
gacattgtga tgacccagtc tcacaaattc atgtccacgt cagtaggaga cagggtcacc  120
atcacctgca aggccagtca ggatgtcttt actgctgtag cctggtatca acagaaacca  180
ggacaatctc ctaaactact gatttactgg gcatccaccc ggcacactgg agtccctgat  240
cgcttcacag gcagtggatc tgggacagat ttcactctca ccattagcaa tgtgcagtct  300
gaagacttgg cagattattt ctgtcaacaa tatagcagct atcctctcac gttcggtgct  360
gggaccaagt tggagctgaa a                                        381

SEQ ID NO: 317          moltype = AA  length = 138
FEATURE                 Location/Qualifiers
source                  1..138
                        mol_type = protein
                        organism = Mus musculus
SEQUENCE: 317
MGWNWIIFFL MAVVTGVNSE VQLQQSGAEL VRPGALVKLS CKASGFNIKD YYMHWVKQRP  60
EQGLEWIGRI DPENGDIIYD PKFQGKASIT TDTSSNTAYL QLSSLTSEDT AVYYCAYDAG  120
DPAWFTYWGQ GTLVTVSS                                            138

SEQ ID NO: 318          moltype = DNA  length = 411
FEATURE                 Location/Qualifiers
```

-continued

```
source                  1..411
                        mol_type = other DNA
                        organism = Mus musculus
SEQUENCE: 318
atgggatgga actggatcat cttcttcctg atggcagtgg ttacaggggt caattcagag  60
gttcagctgc agcagtctgg ggctgagctt gtgaggccag ggccttagt caagttgtcc  120
tgcaaagctt ctggcttcaa tattaaagac tactatatgc actgggtgaa gcagaggcct  180
gaacagggcc tggagtggat tggaaggatt gatcctgaga atggtgatat tatatatgac  240
ccgaagttcc agggcaaggc cagtataaca acagacacat cctccaacac agcctacctg  300
cagctcagca gcctgacgtc tgaggacact gccgtctatt actgtgctta cgatgctggt  360
gaccccgcct ggtttactta ctggggccaa gggactctgg tcaccgtctc g          411

SEQ ID NO: 319          moltype = AA  length = 130
FEATURE                 Location/Qualifiers
source                  1..130
                        mol_type = protein
                        organism = Mus musculus
SEQUENCE: 319
MDMRVPAQLL GLLLLWLRGA RCDIQMTQSP SSLSASVGDR VTITCKASQD VFTAVAWYQQ  60
KPGKAPKLLI YWASTRHTGV PSRFSGSGSG TDFTLTISSL QPEDFATYYC QQYSSYPLTF  120
GGGTKVEIKR                                                         130

SEQ ID NO: 320          moltype = DNA  length = 390
FEATURE                 Location/Qualifiers
source                  1..390
                        mol_type = other DNA
                        organism = Mus musculus
SEQUENCE: 320
atggatatgc gcgtgccggc gcagctgctg ggcctgctgc tgctgtggct gcgcggcgcg  60
cgctgcgata tccagatgac ccagagcccg agcagcctga gcgcgagcgt gggcgatcgc  120
gtgaccatta cctgcaaagc gagccaggat gtgtttaccg cggtggcgtg gtatcagcag  180
aaaccgggca aagcgccgaa actgctgatt tattgggcga gcacccgcca taccggcgtg  240
ccgagtcgct ttagcggcag cggcagcggc accgatttta ccctgaccat tagcagcctg  300
cagccggaag attttgcgac ctattattgc cagcagtata gcagctatcc gctgaccttt  360
ggcggcggca ccaaagtgga aattaaacgt                                   390

SEQ ID NO: 321          moltype = AA  length = 138
FEATURE                 Location/Qualifiers
REGION                  1..138
                        note = Synthetic Polypeptide
REGION                  1..138
                        note = MISC_FEATURE - Humanized Antibody Sequence
source                  1..138
                        mol_type = protein
                        organism = synthetic construct
SEQUENCE: 321
MDWTWSILFL VAAPTGAHSE VQLVQSGAEV KKPGASVKVS CKASGFNIKD YYMHWVRQAP  60
GQGLEWIGRI DPENGDIIYD PKFQGRVTMT TDTSTSTAYM ELRSLRSDDT AVYYCAYDAG  120
DPAWFTYWGQ GTLVTVSS                                                138

SEQ ID NO: 322          moltype = DNA  length = 414
FEATURE                 Location/Qualifiers
misc_feature            1..414
                        note = Synthetic Polynucleotide
misc_feature            1..414
                        note = Humanized Antibody Sequence
source                  1..414
                        mol_type = other DNA
                        organism = synthetic construct
SEQUENCE: 322
atggattgga cctggagcat tctgtttctg gtggcggcgc cgaccggcgc gcatagcgaa  60
gtgcagctgg tgcagagcgg cgcggaagtg aaaaaaccgg gcgcgagcgt gaaagtgagc  120
tgcaaagcga gcggctttaa cattaaagat tattatatgc attgggtgcg ccaggcgccg  180
ggccagggcc tggaatggat cggccgcatt gatccggaaa acggcgatat tatttatgat  240
ccgaaatttc agggccgcgt gaccatgacc accgatacca gcaccagcac cgcgtatatg  300
gaactgcgca gcctgcgcag cgatgatacc gcggtgtatt attgcgcgta tgatgcgggc  360
gatccggcgt ggtttaccta ttggggccag ggcaccctgg tgaccgtctc gagc        414

SEQ ID NO: 323          moltype = AA  length = 106
FEATURE                 Location/Qualifiers
source                  1..106
                        mol_type = protein
                        organism = Mus musculus
SEQUENCE: 323
TDAAPTVSIF PPSSEQLTSG GASVVCFLNN FYPKDINVKW KIDGSERQNG VLNSWTDQDS  60
KDSTYSMSST LTLTKDEYER HNSYTCEATH KTSTSPIVKS FNRNEC                 106

SEQ ID NO: 324          moltype = AA  length = 320
FEATURE                 Location/Qualifiers
```

```
source                  1..320
                        mol_type = protein
                        organism = Mus musculus
SEQUENCE: 324
AKTTPPSVYP LAPGSAAQTN SMVTLGCLVK GYFPEPVTVT WNSGSLSSGV HTFPAVLQSD  60
LYTLSSSVTV PSSTWPSETV TCNVAHPASS TKVDKKIVPR DCGCKPCICT VPEVSSVFIF  120
PPKPKDVLTI TLTPKVTCVV VDISKDDPEV QFSWFVDDVE VHTAQTQPRE EQFNSTFRSV  180
SELPIMHQDW LNGKEFKCRV NSAAFPAPIE KTISKTKGRP KAPQVYTIPP PKEQMAKDKV  240
SLTCMITDFF PEDITVEWQW NGQPAENYKN TQPIMDTDGS YFVYSKLNVQ KSNWEAGNTF  300
TCSVLHEGLH NHHTEKSLSH                                              320

SEQ ID NO: 325          moltype = AA  length = 106
FEATURE                 Location/Qualifiers
source                  1..106
                        mol_type = protein
                        organism = Homo sapiens
SEQUENCE: 325
TVAAPSVFIF PPSDEQLKSG TASVVCLLNN FYPREAKVQW KVDNALQSGN SQESVTEQDS  60
KDSTYSLSST LTLSKADYEK HKVYACEVTH QGLSSPVTKS FNRGEC                 106

SEQ ID NO: 326          moltype = AA  length = 327
FEATURE                 Location/Qualifiers
source                  1..327
                        mol_type = protein
                        organism = Homo sapiens
SEQUENCE: 326
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                      327

SEQ ID NO: 327          moltype = AA  length = 120
FEATURE                 Location/Qualifiers
source                  1..120
                        mol_type = protein
                        organism = Mus musculus
SEQUENCE: 327
EVQLQQSGPE LVKPGASVKM SCKASGFTFT DYIMHWVKQK PGQGLEWIGY INPYNDDTEY  60
NEKFKGKATL TSDKSSSTAY MDLSSLTSEG SAVYYCARSI YYYDAPFAYW GQGTLVTVSS  120

SEQ ID NO: 328          moltype = AA  length = 120
FEATURE                 Location/Qualifiers
source                  1..120
                        mol_type = protein
                        organism = Mus musculus
SEQUENCE: 328
EVQLQQSGPE LVKPGASVKM SCKASGFTFT DYIMHWVKQK PGQGLEWIGY INPYNDDTEY  60
NEKFKGKATL TSDKSSSTAY MDLSSLTSEG SAVYYCARSI YYYDAPFAYW GQGTLVTVSS  120

SEQ ID NO: 329          moltype = AA  length = 120
FEATURE                 Location/Qualifiers
source                  1..120
                        mol_type = protein
                        organism = Mus musculus
SEQUENCE: 329
EVQLVQSGAE VKKPGSSVKV SCKASGFTFT DYIMHWVRQA PGQGLEWMGY INPYNDDTEY  60
NEKFKGRVTI TADKSTSTAY MELSSLRSED TAVYYCARSI YYYDAPFAYW GQGTLVTVSS  120

SEQ ID NO: 330          moltype = AA  length = 226
FEATURE                 Location/Qualifiers
source                  1..226
                        mol_type = protein
                        organism = Mus musculus
SEQUENCE: 330
EVQLQQSGPE LVKPGASVKM SCKASGFTFT DYIMHWVKQK PGQGLEWIGY INPYNDDTEY  60
NEKFKGKATL TSDKSSSTAY MDLSSLTSEG SAVYYCARSI YYYDAPFAYW GQGTLVTVSS  120
TVAAPSVFIF PPSDEQLKSG TASVVCLLNN FYPREAKVQW KVDNALQSGN SQESVTEQDS  180
KDSTYSLSST LTLSKADYEK HKVYACEVTH QGLSSPVTKS FNRGEC                 226

SEQ ID NO: 331          moltype = AA  length = 447
FEATURE                 Location/Qualifiers
source                  1..447
                        mol_type = protein
                        organism = Mus musculus
SEQUENCE: 331
EVQLVQSGAE VKKPGSSVKV SCKASGFTFT DYIMHWVRQA PGQGLEWMGY INPYNDDTEY  60
NEKFKGRVTI TADKSTSTAY MELSSLRSED TAVYYCARSI YYYDAPFAYW GQGTLVTVSS  120
```

```
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                    447

SEQ ID NO: 332          moltype = AA  length = 107
FEATURE                 Location/Qualifiers
source                  1..107
                        mol_type = protein
                        organism = Mus musculus
SEQUENCE: 332
DIQMTQITSS LSASLGDRVS ISCRASQDIS NYLNWYQQKP DGTFKLLIFY TSRLLSGVPS  60
RFSGSGSGTD YSLTIYNLEQ EDFATYFCQQ GDTLPYTFGG GTKLEIK                107

SEQ ID NO: 333          moltype = AA  length = 324
FEATURE                 Location/Qualifiers
source                  1..324
                        mol_type = protein
                        organism = Mus musculus
SEQUENCE: 333
AKTTPPSVYP LAPGSAAQTN SMVTLGCLVK GYFPEPVTVT WNSGSLSSGV HTFPAVLQSD  60
LYTLSSSVTV PSSTWPSETV TCNVAHPASS TKVDKKIVPR DCGCKPCICT VPEVSSVFIF  120
PPKPKDVLTI TLTPKVTCVV VDISKDDPEV QFSWFVDDVE VHTAQTQPRE EQFNSTFRSV  180
SELPIMHQDW LNGKEFKCRV NSAAFPAPIE KTISKTKGRP KAPQVYTIPP PKEQMAKDKV  240
SLTCMITDFF PEDITVEWQW NGQPAENYKN TQPIMDTDGS YFIYSKLNVQ KSNWEAGNTF  300
TCSVLHEGLH NHHTEKSLSH SPGK                                       324

SEQ ID NO: 334          moltype = AA  length = 213
FEATURE                 Location/Qualifiers
source                  1..213
                        mol_type = protein
                        organism = Mus musculus
SEQUENCE: 334
DIQMTQTTSS LSASLGDRVN ISCRASQDIS SYLNWYQQKP DGTVKLLIYS TSRLNSGVPS  60
RFSGSGSGTD YSLTISNLAQ EDIATYFCQQ DIKHPTFGGG TKLELKRTDA APTVSIFPPS  120
SEQLTSGGAS VVCFLNNFYP KDINVKWKID GSERQNGVLN SWTDQDSKDS TYSMSSTLTL  180
TKDEYERHNS YTCEATHKTS TSPIVKSFNR NEC                              213

SEQ ID NO: 335          moltype = AA  length = 444
FEATURE                 Location/Qualifiers
source                  1..444
                        mol_type = protein
                        organism = Mus musculus
SEQUENCE: 335
EVQLQQSGPE LVKPGASVKM SCKASGFTFT DYIMHWVKQK PGQGLEWIGY INPYNDDTEY  60
NEKFKGKATL TSDKSSSTAY MDLSSLTSEG SAVYYCARSI YYYDAPFAYW GQGTLVTVSS  120
AKTTPPSVYP LAPGSAAQTN SMVTLGCLVK GYFPEPVTVT WNSGSLSSGV HTFPAVLQSD  180
LYTLSSSVTV PSSTWPSETV TCNVAHPASS TKVDKKIVPR DCGCKPCICT VPEVSSVFIF  240
PPKPKDVLTI TLTPKVTCVV VDISKDDPEV QFSWFVDDVE VHTAQTQPRE EQFNSTFRSV  300
SELPIMHQDW LNGKEFKCRV NSAAFPAPIE KTISKTKGRP KAPQVYTIPP PKEQMAKDKV  360
SLTCMITDFF PEDITVEWQW NGQPAENYKN TQPIMDTDGS YFVYSKLNVQ KSNWEAGNTF  420
TCSVLHEGLH NHHTEKSLSH SPGK                                       444

SEQ ID NO: 336          moltype = AA  length = 108
FEATURE                 Location/Qualifiers
source                  1..108
                        mol_type = protein
                        organism = Mus musculus
SEQUENCE: 336
DIQMTQSPSS LSASVGDRVT ITCKASQDVF TAVAWYQQKP GKAPKLLIYW ASTRHTGVPS  60
RFSGSGSGTD FTLTISSLQP EDFATYYCQQ YSSYPLTFGG GTKVEIKR               108

SEQ ID NO: 337          moltype = DNA  length = 324
FEATURE                 Location/Qualifiers
source                  1..324
                        mol_type = other DNA
                        organism = Mus musculus
SEQUENCE: 337
gatatccaga tgacccagag cccgagcagc ctgagcgcga gcgtgggcga tcgcgtgacc  60
attacctgca aagcgagcca ggatgtgttt accgcggtgg cgtggtatca gcagaaaccg  120
ggcaaagcgc cgaaactgct gatttattgg gcgagcaccc gccataccgg cgtgccgagt  180
cgctttagcg gcagcggcag cggcaccgat tttaccctga ccattagcag cctgcagccg  240
gaagattttg cgacctatta ttgccagcag tatagcagct atccgctgac ctttggcggc  300
ggcaccaaag tggaaattaa acgt                                       324

SEQ ID NO: 338          moltype = AA  length = 119
FEATURE                 Location/Qualifiers
```

-continued

```
source                  1..119
                        mol_type = protein
                        organism = Mus musculus
SEQUENCE: 338
EVQLVQSGAE VKKPGASVKV SCKASGFNIK DYYMHWVRQA PGQGLEWIGR IDPENGDIIY  60
DPKFQGRVTM TTDTSTSTAY MELRSLRSDD TAVYYCAYDA GDPAWFTYWG QGTLVTVSS   119

SEQ ID NO: 339          moltype = DNA  length = 357
FEATURE                 Location/Qualifiers
source                  1..357
                        mol_type = other DNA
                        organism = Mus musculus
SEQUENCE: 339
gaagtgcagc tggtgcagag cggcgcggaa gtgaaaaaac cgggcgcgag cgtgaaagtg  60
agctgcaaag cgagcggctt taacattaaa gattattata tgcattgggt gcgccaggcg  120
ccgggccagg gcctggaatg gatcggccgc attgatccgg aaaacggcga tattatttat  180
gatccgaaat ttcagggccg cgtgaccatg accaccgata ccagcaccag caccgcgtat  240
atggaactgc gcagcctgcg cagcgatgat accgcggtgt attattgcgc gtatgatgcg  300
ggcgatccgg cgtggtttac ctattggggc cagggcaccc tggtgaccgt ctcgagc     357

SEQ ID NO: 340          moltype = DNA  length = 1395
FEATURE                 Location/Qualifiers
source                  1..1395
                        mol_type = other DNA
                        organism = Mus musculus
SEQUENCE: 340
atggactgga cctggaggat cctcttcttg gtggcagcag ccacaggagc ccactccgag  60
gtgcagctgg tgcagtctgg ggctgaggtg aagaagcctg ggtcctcggt gaaggtctcc  120
tgcaaggctt ctggttttac cttcaccgac tatattatgc actgggtgcg tcaggcccct  180
ggtcaagggc ttgagtggat gggctatatc aacccttata atgatgacac cgaatacaac  240
gagaagttca agggccgtgt cacgattacc gcggacaaat ccacgagcac agcctacatg  300
gagctgagca gcctgcgctc tgaggacacg gccgtgtatt actgtgcgcg ttcgatttat  360
tactacgatg ccccgtttgc ttactggggc caagggactc tggtcaccgt ctctagtgcc  420
tccaccaagg gcccatcggt cttccccctg gcgccctgct ccaggagcac ctccgagagc  480
acagcggccc tgggctgcct ggtcaaggac tacttccccg aaccggtgac ggtgtcgtgg  540
aactcaggcg ctctgaccag cggcgtgcac accttcccag ctgtcctaca gtcctcagga  600
ctctactccc tcagcagcgt ggtgaccgtg ccctccagca acttcggcac ccagacctac  660
acctgcaacg tagatcacaa gcccagcaac accaaggtgg acaagacagt tgagcgcaaa  720
tgttgtgtcg agtgcccacc gtgcccagca ccacctgtgg caggaccgtc agtcttcctc  780
ttccccccaa aacccaagga caccctcatg atctcccgga cccctgaggt cacgtgcgtg  840
gtggtggacg tgagccacga agaccccgag gtccagttca actggtacgt ggacggcgtg  900
gaggtgcata atgccaagac aaagccacgg gaggagcagt tcaacagcac gttccgtgtg  960
gtcagcgtcc tcaccgttgt gcaccaggac tggctgaacg gcaaggagta caagtgcaag  1020
gtctccaaca aaggcctccc agcccccatc gagaaaacca tctccaaaac caaagggcag  1080
ccccgagaac cacaggtgta caccctgccc ccatcccggg aggagatgac caagaaccag  1140
gtcagcctga cctgcctggt caaaggcttc taccccagcg acatcgccgt ggagtgggag  1200
agcaatgggc agccggagaa caactacaag accacacctc ccatgctgga ctccgacggc  1260
tccttcttcc tctacagcaa gctcaccgtg gacaagagca ggtggcagca ggggaacgtc  1320
ttctcatgct ccgtgatgca tgaggctctg cacaaccact acacgcagaa gagcctctcc  1380
ctgtctccgg gtaaa                                                   1395

SEQ ID NO: 341          moltype = AA  length = 213
FEATURE                 Location/Qualifiers
source                  1..213
                        mol_type = protein
                        organism = Mus musculus
SEQUENCE: 341
DIQMTQSPSS LSASVGDRVT ITCRASQDIS SYLNWYQQKP GKAPKLLIYS TSRLNSGVPS  60
RFSGSGSGTD FTLTISSLQP EDFATYYCQQ DIKHPTFGQG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 342          moltype = DNA  length = 639
FEATURE                 Location/Qualifiers
source                  1..639
                        mol_type = other DNA
                        organism = Mus musculus
SEQUENCE: 342
gacatccaga tgacccagtc tccatcctcc ctgtctgcat ctgtaggtga ccgtgtcacc  60
atcacttgcc gcgcaagtca ggatattagc agctatttaa attggtatca gcagaaacca  120
gggaaagccc ctaagctcct gatctattct acttcccgtt tgaatagtgg ggtcccatca  180
cgcttcagtg gcagtggctc tgggacagat ttcactctca ccatcagcag tctgcaacct  240
gaagattttg caacttacta ctgtcaacag gatattaaac accctacgtt cggtcaaggc  300
accaaggtgg agatcaaacg tacggtggct gcaccatctg tcttcatctt cccgccatct  360
gatgagcagt tgaaatctgg aactgcctct gttgtgtgcc tgctgaataa cttctatccc  420
agagaggcca aagtacagtg gaaggtggat aacgccctcc aatcgggtaa ctcccaggag  480
agtgtcacag agcaggacag caaggacagc acctacagcc tcagcagcac cctgacgctg  540
agcaaagcag actacgagaa acacaaagtc tacgcctgcg aagtcaccca tcagggcctg  600
agctcgcccg tcacaaagag cttcaacagg ggagagtgt                         639
```

```
SEQ ID NO: 343         moltype = AA  length = 235
FEATURE                Location/Qualifiers
source                 1..235
                       mol_type = protein
                       organism = Mus musculus
SEQUENCE: 343
MDMRVPAQLL GLLLLWLRGA RCDIQMTQSP SSLSASVGDR VTITCRASQD ISSYLNWYQQ  60
KPGKAPKLLI YSTSRLNSGV PSRFSGSGSG TDFTLTISSL QPEDFATYYC QQDIKHPTFG  120
QGTKVEIKRT VAAPSVFIFP PSDEQLKSGT ASVVCLLNNF YPREAKVQWK VDNALQSGNS  180
QESVTEQDSK DSTYSLSSTL TLSKADYEKH KVYACEVTHQ GLSSPVTKSF NRGEC       235

SEQ ID NO: 344         moltype = DNA  length = 705
FEATURE                Location/Qualifiers
source                 1..705
                       mol_type = other DNA
                       organism = Mus musculus
SEQUENCE: 344
atggacatga gggtgcccgc tcagctcctg gggctcctgc tgctgtggct gagaggtgcc  60
agatgtgaca tccagatgac ccagtctcca tcctccctgt ctgcatctgt aggtgaccgt  120
gtcaccatca cttgccgcgc aagtcaggat attagcagct atttaaattg gtatcagcag  180
aaaccaggga aagcccctaa gctcctgatc tattctactt cccgtttgaa tagtggggtc  240
ccatcacgct tcagtggcag tggctctggg acagatttca ctctcaccat cagcagtctg  300
caacctgaag attttgcaac ttactactgt caacaggata ttaaacaccc tacgttcggt  360
caaggcacca aggtggagat caaacgtacg gtggctgcac catctgtctt catcttcccg  420
ccatctgatg agcagttgaa atctggaact gcctctgttg tgtgcctgct gaataacttc  480
tatcccagag aggccaaagt acagtggaag gtggataacg ccctccaatc gggtaactcc  540
caggagagtg tcacagagca ggacagcaag gacagcacct acagcctcag cagcaccctg  600
acgctgagca aagcagacta cgagaaacac aaagtctacg cctgcgaagt cacccatcag  660
ggcctgagct cgcccgtcac aaagagcttc aacaggggag agtgt                  705

SEQ ID NO: 345         moltype = AA  length = 446
FEATURE                Location/Qualifiers
source                 1..446
                       mol_type = protein
                       organism = Mus musculus
SEQUENCE: 345
EVQLVQSGAE VKKPGSSVKV SCKASGFTFT DYIMHWVRQA PGQGLEWMGY INPYNDDTEY  60
NEKFKGRVTI TADKSTSTAY MELSSLRSED TAVYYCARSI YYYDAPFAYW GQGTLVTVSS  120
ASTKGPSVFP LAPCSRSTSE STAALGCLVK DYFPEPVTVS WNSGALTSGV HTFPAVLQSS  180
GLYSLSSVVT VPSSNFGTQT YTCNVDHKPS NTKVDKTVER KCCVECPPCP APPVAGPSVF  240
LFPPKPKDTL MISRTPEVTC VVVDVSHEDP EVQFNWYVDG VEVHNAKTKP REEQFNSTFR  300
VVSVLTVVHQ DWLNGKEYKC KVSNKGLPAP IEKTISKTKG QPREPQVYTL PPSREEMTKN  360
QVSLTCLVKG FYPSDIAVEW ESNGQPENNY KTTPPMLDSD GSFFLYSKLT VDKSRWQQGN  420
VFSCSVMHEA LHNHYTQKSL SLSPGK                                       446

SEQ ID NO: 346         moltype = DNA  length = 1338
FEATURE                Location/Qualifiers
source                 1..1338
                       mol_type = other DNA
                       organism = Mus musculus
SEQUENCE: 346
gaggtgcagc tggtgcagtc tggggctgag gtgaagaagc ctgggtcctc ggtgaaggtc  60
tcctgcaagg cttctggttt taccttcacc gactatatta tgcactgggt gcgtcaggcc  120
cctggtcaag ggcttgagtg gatgggctat atcaacccct ataatgatga caccgaatac  180
aacgagaagt tcaagggccg tgtcacgatt accgcggaca aatccacgag cacagcctac  240
atggagctga gcagcctgcg ctctgaggac acggccgtgt attactgtgc gcgttcgatt  300
tattactacg atgccccgtt tgcttactgg ggccaaggga ctctggtcac cgtctctagt  360
gcctccacca agggcccatc ggtcttcccc ctggcgccct gctccaggag cacctccgag  420
agcacagcgg ccctgggctg cctggtcaag gactacttcc ccgaaccggt gacggtgtcg  480
tggaactcag gcgctctgac cagcggcgtg cacaccttcc cagctgtcct acagtcctca  540
ggactctact ccctcagcag cgtggtgacc gtgccctcca gcaacttcgg cacccagacc  600
tacacctgca acgtagatca caagcccagc aacaccaagg tggacaagac agttgagcgc  660
aaatgttgtg tcgagtgccc accgtgccca gcaccacctg tggcaggacc gtcagtcttc  720
ctcttccccc caaaacccaa ggacaccctc atgatctccc ggacccctga ggtcacgtgc  780
gtggtggtgg acgtgagcca cgaagacccc gaggtccagt tcaactggta cgtggacggc  840
gtggaggtgc ataatgccaa gacaaagcca cgggaggagc agttcaacag cacgttccgt  900
gtggtcagcg tcctcaccgt tgtgcaccag gactggctga acggcaagga gtacaagtgc  960
aaggtctcca acaaaggcct cccagccccc atcgagaaaa ccatctccaa aaccaaaggg  1020
cagccccgag aaccacaggt gtacaccctg cccccatccc gggaggagat gaccaagaac  1080
caggtcagcc tgacctgcct ggtcaaaggc ttctacccca gcgacatcgc cgtggagtgg  1140
gagagcaatg ggcagccgga gaacaactac aagaccacac ctcccatgct ggactccgac  1200
ggctccttct tcctctacag caagctcacc gtggacaaga gcaggtggca gcaggggaac  1260
gtcttctcat gctccgtgat gcatgaggct ctgcacaacc actacacgca gaagagcctc  1320
tccctgtctc cgggtaaa                                                1338

SEQ ID NO: 347         moltype = AA  length = 465
FEATURE                Location/Qualifiers
source                 1..465
```

```
                         mol_type = protein
                         organism = Mus musculus
SEQUENCE: 347
MDWTWRILFL VAAATGAHSE VQLVQSGAEV KKPGSSVKVS CKASGFTFTD YIMHWVRQAP  60
GQGLEWMGYI NPYNDDTEYN EKFKGRVTIT ADKSTSTAYM ELSSLRSEDT AVYYCARSIY  120
YYDAPFAYWG QGTLVTVSSA STKGPSVFPL APCSRSTSES TAALGCLVKD YFPEPVTVSW  180
NSGALTSGVH TFPAVLQSSG LYSLSSVVTV PSSNFGTQTY TCNVDHKPSN TKVDKTVERK  240
CCVECPPCPA PPVAGPSVFL FPPKPKDTLM ISRTPEVTCV VVDVSHEDPE VQFNWYVDGV  300
EVHNAKTKPR EEQFNSTFRV VSVLTVVHQD WLNGKEYKCK VSNKGLPAPI EKTISKTKGQ  360
PREPQVYTLP PSREEMTKNQ VSLTCLVKGF YPSDIAVEWE SNGQPENNYK TTPPMLDSDG  420
SFFLYSKLTV DKSRWQQGNV FSCSVMHEAL HNHYTQKSLS LSPGK                465

SEQ ID NO: 348           moltype = DNA  length = 1395
FEATURE                  Location/Qualifiers
source                   1..1395
                         mol_type = other DNA
                         organism = Mus musculus
SEQUENCE: 348
atggactgga cctggaggat cctcttcttg gtggcagcag ccacaggagc ccactccgag  60
gtgcagctgg tgcagtctgg ggctgaggtg aagaagcctg ggtcctcggt gaaggtctcc  120
tgcaaggctt ctggttttac cttcaccgac tatattatgc actgggtgcg tcaggcccct  180
ggtcaagggc ttgagtggat gggctatatc aacccttata atgatgacac cgaatacaac  240
gagaagttca agggccgtgt cacgattacc gcggacaaat ccacgagcac agcctacatg  300
gagctgagca gcctgcgctc tgaggacacg gccgtgtatt actgtgcgcg ttcgatttat  360
tactacgatg ccccgtttgc ttactggggc caagggactc tggtcaccgt ctctagtgcc  420
tccaccaagg gcccatcggt cttccccctg gcgccctgct ccaggagcac ctccgagagc  480
acagcggccc tgggctgcct ggtcaaggac tacttccccg aaccggtgac ggtgtcgtgg  540
aactcaggcg ctctgaccag cggcgtgcac accttcccag ctgtcctaca gtcctcagga  600
ctctactccc tcagcagcgt ggtgaccgtg ccctccagca acttcggcac ccagacctac  660
acctgcaacg tagatcacaa gcccagcaac accaaggtgg acaagacagt tgagcgcaaa  720
tgttgtgtcg agtgcccacc gtgcccagca ccacctgtgg caggaccgtc agtcttcctc  780
ttccccccaa aacccaagga caccctcatg atctcccgga cccctgaggt cacgtgcgtg  840
gtggtggacg tgagccacga agaccccgag gtccagttca actggtacgt ggacggcgtg  900
gaggtgcata atgccaagac aaagccacgg gaggagcagt tcaacagcac gttccgtgtg  960
gtcagcgtcc tcaccgttgt gcaccaggac tggctgaacg gcaaggagta caagtgcaag  1020
gtctccaaca aaggcctccc agcccccatc gagaaaacca tctccaaaac caaagggcag  1080
ccccgagaac cacaggtgta caccctgccc ccatcccggg aggagatgac caagaaccag  1140
gtcagcctga cctgcctggt caaaggcttc taccccagcg acatcgccgt ggagtgggag  1200
agcaatgggc agccggagaa caactacaag accacacctc ccatgctgga ctccgacggc  1260
tccttcttcc tctacagcaa gctcaccgtg gacaagagca ggtggcagca ggggaacgtc  1320
ttctcatgct ccgtgatgca tgaggctctg cacaaccact acacgcagaa gagcctctcc  1380
ctgtctccgg gtaaa                                                 1395

SEQ ID NO: 349           moltype = DNA  length = 417
FEATURE                  Location/Qualifiers
source                   1..417
                         mol_type = other DNA
                         organism = Mus musculus
SEQUENCE: 349
atggaatgga tctggatatt tctcttcctc ctgtcaggaa ctgcaggtgt ccactctgag  60
gtgcagctgg tgcagtctgg ggctgaggtg aagaagcctg ggtcctcggt gaaggtctcc  120
tgcaaggctt ctggttttac cttcaccgac tatattatgc actgggtgcg tcaggcccct  180
ggtcaagggc ttgagtggat gggctatatc aacccttata atgatgacac cgaatacaac  240
gagaagttca agggccgtgt cacgattacc gcggacaaat ccacgagcac agcctacatg  300
gagctgagca gcctgcgctc tgaggacacg gccgtgtatt actgtgcgcg ttcgatttat  360
tactacgatg ccccgtttgc ttactggggc caagggactc tggtcacagt ctcgagc    417

SEQ ID NO: 350           moltype = AA  length = 218
FEATURE                  Location/Qualifiers
source                   1..218
                         mol_type = protein
                         organism = Mus musculus
SEQUENCE: 350
DIVLTQSPAS LAVSLGQRAT IACKASQSVD YDGTSYMNWY QQKPGQPPKL LIYAASNLES  60
EIPARFSGTG SGTDFTLNIH PVEEEDITTY YCQQSNEDPF TFGGGTKLEI KRADAAPTVS  120
IFPPSSEQLT SGGASVVCFL NNFYPKDINV KWKIDGSERQ NGVLNSWTDQ DSKDSTYSMS  180
STLTLTKDEY ERHNSYTCEA THKTSTSPIV KSFNRNEC                         218

SEQ ID NO: 351           moltype = AA  length = 15
FEATURE                  Location/Qualifiers
source                   1..15
                         mol_type = protein
                         organism = Mus musculus
SEQUENCE: 351
KASQSVDYDG TSYMN                                                 15

SEQ ID NO: 352           moltype = AA  length = 7
FEATURE                  Location/Qualifiers
source                   1..7
```

```
                        mol_type = protein
                        organism = Mus musculus
SEQUENCE: 352
AASNLES                                                                  7

SEQ ID NO: 353          moltype = AA  length = 9
FEATURE                 Location/Qualifiers
source                  1..9
                        mol_type = protein
                        organism = Mus musculus
SEQUENCE: 353
QQSNEDPFT                                                                9

SEQ ID NO: 354          moltype = DNA  length = 657
FEATURE                 Location/Qualifiers
source                  1..657
                        mol_type = other DNA
                        organism = Mus musculus
SEQUENCE: 354
gacattgtgt tgacccagtc tccagcttct ttggctgtgt ctctagggca gagggccacc  60
atcgcctgca aggccagcca aagtgttgat tatgatggta ctagttatat gaattggtac  120
caacagaaac caggacagcc acccaaactc ctcatctatg ctgcatccaa tctagaatct  180
gagatcccag ccaggtttag tggcactggg tctgggacag acttcaccct caacatccat  240
cctgtggagg aggaggatat cacaacctat tactgtcagc aaagtaatga ggatccgttc  300
acgttcggag gggggaccaa gttggaaata aaacgggctg atgctgcacc aactgtatcc  360
atcttcccac catccagtga gcagttaaca tctggaggtg cctcagtcgt gtgcttcttg  420
aacaacttct accccaaaga catcaatgtc aagtggaaga ttgatggcag tgaacgacaa  480
aatggcgtcc tgaacagttg gactgatcag gacagcaaag acagcaccta cagcatgagc  540
agcaccctca cgttgaccaa ggacgagtat gaacgacata acagctatac ctgtgaggcc  600
actcacaaga catcaacttc acccattgtc aagagcttca acaggaatga gtgttag     657

SEQ ID NO: 355          moltype = AA  length = 238
FEATURE                 Location/Qualifiers
source                  1..238
                        mol_type = protein
                        organism = Mus musculus
SEQUENCE: 355
METDTILLWV LLLWVPGSTG DIVLTQSPAS LAVSLGQRAT IACKASQSVD YDGTSYMNWY  60
QQKPGQPPKL LIYAASNLES EIPARFSGTG SGTDFTLNIH PVEEEDITTY YCQQSNEDPF  120
TFGGGTKLEI KRADAAPTVS IFPPSSEQLT SGGASVVCFL NNFYPKDINV KWKIDGSERQ  180
NGVLNSWTDQ DSKDSTYSMS STLTLTKDEY ERHNSYTCEA THKTSTSPIV KSFNRNEC    238

SEQ ID NO: 356          moltype = DNA  length = 717
FEATURE                 Location/Qualifiers
source                  1..717
                        mol_type = other DNA
                        organism = Mus musculus
SEQUENCE: 356
atggagacag acacaatcct gctatgggtg ctgctgctct gggttccagg ctccactggt  60
gacattgtgt tgacccagtc tccagcttct ttggctgtgt ctctagggca gagggccacc  120
atcgcctgca aggccagcca aagtgttgat tatgatggta ctagttatat gaattggtac  180
caacagaaac caggacagcc acccaaactc ctcatctatg ctgcatccaa tctagaatct  240
gagatcccag ccaggtttag tggcactggg tctgggacag acttcaccct caacatccat  300
cctgtggagg aggaggatat cacaacctat tactgtcagc aaagtaatga ggatccgttc  360
acgttcggag gggggaccaa gttggaaata aaacgggctg atgctgcacc aactgtatcc  420
atcttcccac catccagtga gcagttaaca tctggaggtg cctcagtcgt gtgcttcttg  480
aacaacttct accccaaaga catcaatgtc aagtggaaga ttgatggcag tgaacgacaa  540
aatggcgtcc tgaacagttg gactgatcag gacagcaaag acagcaccta cagcatgagc  600
agcaccctca cgttgaccaa ggacgagtat gaacgacata acagctatac ctgtgaggcc  660
actcacaaga catcaacttc acccattgtc aagagcttca acaggaatga gtgttag     717

SEQ ID NO: 357          moltype = AA  length = 442
FEATURE                 Location/Qualifiers
source                  1..442
                        mol_type = protein
                        organism = Mus musculus
SEQUENCE: 357
QVQLQQPGTE LVRPGTSVKL SCKASGYIFT TYWMNWVKQR PGQGLEWIGM IHPSASEIRL  60
DQKFKDKATL TLDKSSSTAY MHLSGPTSVD SAVYYCARSG EWGSMDYWGQ GTSVTVSSAK  120
TTPPSVYPLA PGSAAQTNSM VTLGCLVKGY FPEPVTVTWN SGSLSSGVHT FPAVLQSDLY  180
TLSSSVTVPS STWPSETVTC NVAHPASSTK VDKKIVPRDC GCKPCICTVP EVSSVFIFPP  240
KPKDVLTITL TPKVTCVVVD ISKDDPEVQF SWFVDDVEVH TAQTQPREEQ FNSTFRSVSE  300
LPIMHQDWLN GKEFKCRVNS AAFPAPIEKT ISKTKGRPKA PQVYTIPPPK EQMAKDKVSL  360
TCMITDFFPE DITVEWQWNG QPAENYKNTQ PIMDTDGSYF IYSKLNVQKS NWEAGNTFTC  420
SVLHEGLHNH HTEKSLSHSP GK                                             442

SEQ ID NO: 358          moltype = AA  length = 5
FEATURE                 Location/Qualifiers
source                  1..5
```

```
                         mol_type = protein
                         organism = Mus musculus
SEQUENCE: 358
TYWMN                                                                   5

SEQ ID NO: 359           moltype = AA  length = 17
FEATURE                  Location/Qualifiers
source                   1..17
                         mol_type = protein
                         organism = Mus musculus
SEQUENCE: 359
MIHPSASEIR LDQKFKD                                                      17

SEQ ID NO: 360           moltype = AA  length = 9
FEATURE                  Location/Qualifiers
source                   1..9
                         mol_type = protein
                         organism = Mus musculus
SEQUENCE: 360
SGEWGSMDY                                                               9

SEQ ID NO: 361           moltype = DNA  length = 1329
FEATURE                  Location/Qualifiers
source                   1..1329
                         mol_type = other DNA
                         organism = Mus musculus
SEQUENCE: 361
caggtccaac tacagcagcc tggactgag ctggtgaggc ctggaacttc agtgaagttg  60
tcctgtaagg cttctggcta catcttcacc acctactgga tgaactgggt gaaacagagg  120
cctggacaag gccttgagtg gattggcatg attcatcctt ccgcaagtga aattaggttg  180
gatcagaaat tcaaggacaa ggccacattg actcttgaca aatcctccag cacagcctat  240
atgcacctca gcggcccgac atctgtggat tctgcggtct attactgtgc aagatcaggg  300
gaatgggggt ctatggacta ctggggtcaa ggaacctcag tcaccgtctc ctcagccaaa  360
acgacacccc catctgtcta tccactggcc cctggatctg ctgcccaaac taactccatg  420
gtgaccctgg gatgcctggt caagggctat ttccctgagc cagtgacagt gacctggaac  480
tctggatccc tgtccagcgg tgtgcacacc ttcccagctg tcctgcagtc tgacctctac  540
actctgagca gctcagtgac tgtcccctcc agcacctggc ccagcgagac cgtcacctgc  600
aacgttgccc acccggccag cagcaccaag gtggacaaga aaattgtgcc cagggattgt  660
ggttgtaagc cttgcatatg tacagtccca gaagtatcat ctgtcttcat cttcccccca  720
aagcccaagg atgtgctcac cattactctg actcctaagg tcacgtgtgt tgtggtagac  780
atcagcaagg atgatcccga ggtccagttc agctggtttg tagatgatgt ggaggtgcac  840
acagctcaga cgcaaccccg ggaggagcag ttcaacagca ctttccgctc agtcagtgaa  900
cttcccatca tgcaccagga ctggctcaat ggcaaggagt tcaaatgcag ggtcaacagt  960
gcagctttcc ctgcccccat cgagaaaacc atctccaaaa ccaaaggcag accgaaggct  1020
ccacaggtgt acaccattcc acctcccaag gagcagatgg ccaaggataa agtcagtctg  1080
acctgcatga taacagactt cttccctgaa gacattactg tggagtggca gtggaatggg  1140
cagccagcgg agaactacaa gaacactcag cccatcatgg acacagatgg ctcttacttc  1200
atctacagca agctcaatgt gcagaagagc aactgggagg caggaaatac tttcacctgc  1260
tctgtgttac atgagggcct gcacaaccac catactgaga agagcctctc ccactctcct  1320
ggtaaatga                                                               1329

SEQ ID NO: 362           moltype = AA  length = 461
FEATURE                  Location/Qualifiers
source                   1..461
                         mol_type = protein
                         organism = Mus musculus
SEQUENCE: 362
MGWSSIILFL VATATGVHSQ VQLQQPGTEL VRPGTSVKLS CKASGYIFTT YWMNWVKQRP  60
GQGLEWIGMI HPSASEIRLD QKFKDKATLT LDKSSSTAYM HLSGPTSVDS AVYYCARSGE  120
WGSMDYWGQG TSVTVSSAKT TPPSVYPLAP GSAAQTNSMV TLGCLVKGYF PEPVTVTWNS  180
GSLSSGVHTF PAVLQSDLYT LSSSVTVPSS TWPSETVTCN VAHPASSTKV DKKIVPRDCG  240
CKPCICTVPE VSSVFIFPPK PKDVLTITLT PKVTCVVVDI SKDDPEVQFS WFVDDVEVHT  300
AQTQPREEQF NSTFRSVSEL PIMHQDWLNG KEFKCRVNSA AFPAPIEKTI SKTKGRPKAP  360
QVYTIPPPKE QMAKDKVSLT CMITDFFPED ITVEWQWNGQ PAENYKNTQP IMDTDGSYFI  420
YSKLNVQKSN WEAGNTFTCS VLHEGLHNHH TEKSLSHSPG K                       461

SEQ ID NO: 363           moltype = DNA  length = 1386
FEATURE                  Location/Qualifiers
source                   1..1386
                         mol_type = other DNA
                         organism = Mus musculus
SEQUENCE: 363
atgggatgga gctctatcat cctcttcttg gtagcaacag ctacaggtgt ccactcccag  60
gtccaactac agcagcctgg gactgagctg gtgaggcctg gaacttcagt gaagttgtcc  120
tgtaaggctt ctggctacat cttcaccacc tactggatga actgggtgaa acagaggcct  180
ggacaaggcc ttgagtggat tggcatgatt catccttccg caagtgaaat taggttggat  240
cagaaattca aggacaaggc cacattgact cttgacaaat cctccagcac agcctatatg  300
cacctcagcg gcccgacatc tgtggattct gcggtctatt actgtgcaag atcaggggaa  360
tgggggtcta tggactactg gggtcaagga acctcagtca ccgtctcctc agccaaaacg  420
```

-continued

```
acacccccat ctgtctatcc actggcccct ggatctgctg cccaaactaa ctccatggtg  480
accctgggat gcctggtcaa gggctatttc cctgagccag tgacagtgac ctggaactct  540
ggatccctgt ccagcggtgt gcacaccttc ccagctgtcc tgcagtctga cctctacact  600
ctgagcagct cagtgactgt cccctccagc acctggccca gcgagaccgt cacctgcaac  660
gttgcccacc cggccagcag caccaaggtg gacaagaaaa ttgtgcccag ggattgtggt  720
tgtaagcctt gcatatgtac agtcccagaa gtatcatctg tcttcatctt ccccccaaag  780
cccaaggatg tgctcaccat tactctgact cctaaggtca cgtgtgttgt ggtagacatc  840
agcaaggatg atcccgaggt ccagttcagc tggtttgtag atgatgtgga ggtgcacaca  900
gctcagacgc aaccccggga ggagcagttc aacagcactt tccgctcagt cagtgaactt  960
cccatcatgc accaggactg gctcaatggc aaggagttca aatgcagggt caacagtgca  1020
gctttccctg cccccatcga gaaaaccatc tccaaaacca aaggcagacc gaaggctcca  1080
caggtgtaca ccattccacc tcccaaggag cagatggcca aggataaagt cagtctgacc  1140
tgcatgataa cagacttctt ccctgaagac attactgtgg agtggcagtg gaatgggcag  1200
ccagcggaga actacaagaa cactcagccc atcatggaca cagatggctc ttacttcatc  1260
tacagcaagc tcaatgtgca gaagagcaac tgggaggcag gaaatacttt cacctgctct  1320
gtgttacatg agggcctgca caaccaccat actgagaaga gcctctccca ctctcctggt  1380
aaatga                                                             1386

SEQ ID NO: 364          moltype = AA  length = 106
FEATURE                 Location/Qualifiers
source                  1..106
                        mol_type = protein
                        organism = Mus musculus
SEQUENCE: 364
DIQMTQSPSS LSASVGDRVT ITCRASQDIS SYLNWYQQKP GKAPKLLIYS TSRLNSGVPS  60
RFSGSGSGTD FTLTISSLQP EDFATYYCQQ DIKHPTFGQG TKVEIK                 106

SEQ ID NO: 365          moltype = DNA  length = 318
FEATURE                 Location/Qualifiers
source                  1..318
                        mol_type = other DNA
                        organism = Mus musculus
SEQUENCE: 365
gacatccaga tgacccagtc tccatcctcc ctgtctgcat ctgtaggtga ccgtgtcacc  60
atcacttgcc gcgcaagtca ggatattagc agctatttaa attggtatca gcagaaacca  120
gggaaagccc ctaagctcct gatctattct acttcccgtt tgaatagtgg ggtcccatca  180
cgcttcagtg gcagtggctc tgggacagat ttcactctca ccatcagcag tctgcaacct  240
gaagattttg caacttacta ctgtcaacag gatattaaac accctacgtt cggtcaaggc  300
accaaggtgg agatcaaa                                                318

SEQ ID NO: 366          moltype = AA  length = 120
FEATURE                 Location/Qualifiers
source                  1..120
                        mol_type = protein
                        organism = Mus musculus
SEQUENCE: 366
EVQLVQSGAE VKKPGSSVKV SCKASGFTFT DYIMHWVRQA PGQGLEWMGY INPYNDDTEY  60
NEKFKGRVTI TADKSTSTAY MELSSLRSED TAVYYCARSI YYYDAPFAYW GQGTLVTVSS  120

SEQ ID NO: 367          moltype = DNA  length = 360
FEATURE                 Location/Qualifiers
source                  1..360
                        mol_type = other DNA
                        organism = Mus musculus
SEQUENCE: 367
gaggtgcagc tggtgcagtc tggggctgag gtgaagaagc ctgggtcctc ggtgaaggtc  60
tcctgcaagg cttctggttt taccttcacc gactatatta tgcactgggt gcgtcaggcc  120
cctggtcaag gcttgagtgg gatgggctat atcaacccctt ataatgatga caccgaatac  180
aacgagaagt tcaagggccg tgtcacgatt accgcggaca aatccacgag cacagcctac  240
atggagctga gcagcctgcg ctctgaggac acggccgtgt attactgtgc gcgttcgatt  300
tattactacg atgccccgtt tgcttactgg ggccaaggga ctctggtcac cgtctctagt  360

SEQ ID NO: 368          moltype = AA  length = 108
FEATURE                 Location/Qualifiers
source                  1..108
                        mol_type = protein
                        organism = Mus musculus
SEQUENCE: 368
DIQMTQSPSS LSASVGDRVT ITCKASQDVF TAVAWYQQKP GKAPKLLIYW ASTRHTGVPS  60
RFSGSGSGTD FTLTISSLQP EDFATYYCQQ YSSYPLTFGG GTKVEIKR               108

SEQ ID NO: 369          moltype = DNA  length = 324
FEATURE                 Location/Qualifiers
source                  1..324
                        mol_type = other DNA
                        organism = Mus musculus
SEQUENCE: 369
gatatccaga tgacccagag cccgagcagc ctgagcgcga gcgtgggcga tcgcgtgacc  60
attacctgca aagcgagcca ggatgtgttt accgcggtgg cgtggtatca gcagaaaccg  120
```

-continued

```
ggcaaagcgc cgaaactgct gatttattgg gcgagcaccc gccataccgg cgtgccgagt  180
cgctttagcg gcagcggcag cggcaccgat tttaccctga ccattagcag cctgcagccg  240
gaagattttg cgacctatta ttgccagcag tatagcagct atccgctgac ctttggcggc  300
ggcaccaaag tggaaattaa acgt                                         324

SEQ ID NO: 370         moltype = AA  length = 119
FEATURE                Location/Qualifiers
source                 1..119
                       mol_type = protein
                       organism = Mus musculus
SEQUENCE: 370
EVQLVQSGAE VKKPGASVKV SCKASGFNIK DYYMHWVRQA PGQGLEWIGR IDPENGDIIY  60
DPKFQGRVTM TTDTSTSTAY MELRSLRSDD TAVYYCAYDA GDPAWFTYWG QGTLVTVSS   119

SEQ ID NO: 371         moltype = DNA  length = 357
FEATURE                Location/Qualifiers
source                 1..357
                       mol_type = other DNA
                       organism = Mus musculus
SEQUENCE: 371
gaagtgcagc tggtgcagag cggcgcggaa gtgaaaaaac cgggcgcgag cgtgaaagtg  60
agctgcaaag cgagcggctt taacattaaa gattattata tgcattgggt gcgccaggcg  120
ccgggccagg gcctggaatg gatcggccgc attgatccgg aaaacggcga tattatttat  180
gatccgaaat ttcagggccg cgtgaccatg accaccgata ccagcaccag caccgcgtat  240
atggaactgc gcagcctgcg cagcgatgat accgcggtgt attattgcgc gtatgatgcg  300
ggcgatccgg cgtggtttac ctattggggc cagggcaccc tggtgaccgt ctcgagc     357

SEQ ID NO: 372         moltype = AA  length = 108
FEATURE                Location/Qualifiers
source                 1..108
                       mol_type = protein
                       organism = Mus musculus
SEQUENCE: 372
DIQLTQSPSF LSASVGDRVT ITCSVSSSIS SSNLHWYQQK PGKAPKLLIY GTSNLASGVP  60
SRFSGSGSGT EFTLTISSLQ PEDFATYYCQ QWTTTYTFGQ GTKLEIKR               108

SEQ ID NO: 373         moltype = DNA  length = 324
FEATURE                Location/Qualifiers
source                 1..324
                       mol_type = other DNA
                       organism = Mus musculus
SEQUENCE: 373
gatattcagc tgacccagag cccgagcttt ctgagcgcga gcgtgggcga tcgcgtgacc  60
attacctgca gcgtgagcag cagcattagc agcagcaacc tgcattggta tcagcagaaa  120
ccgggcaaag cgccgaaact gctgatttat ggcaccagca acctggcgag cggcgtgccg  180
agccgcttta gcggcagcgg cagcggcacc gaatttaccc tgaccattag cagcctgcag  240
ccggaagatt ttgcgaccta ttattgccag cagtggacca ccacctatac ctttggccag  300
ggcaccaaac tggaaattaa acgt                                         324

SEQ ID NO: 374         moltype = AA  length = 122
FEATURE                Location/Qualifiers
source                 1..122
                       mol_type = protein
                       organism = Mus musculus
SEQUENCE: 374
EVQLVQSGAE VKKPGASVKV SCKASGFNIK DYYIHWVRQA PGQGLEWMGR IDPDNGESTY  60
VPKFQGRVTM TTDTSTSTAY MELRSLRSDD TAVYYCAREG LDYGDYYAVD YWGQGTLVTV  120
SS                                                                 122

SEQ ID NO: 375         moltype = DNA  length = 366
FEATURE                Location/Qualifiers
source                 1..366
                       mol_type = other DNA
                       organism = Mus musculus
SEQUENCE: 375
gaagtgcagc tggtgcagag cggcgcggaa gtgaaaaaac cgggcgcgag cgtgaaagtg  60
agctgcaaag cgagcggctt taacattaaa gattattata ttcattgggt gcgccaggcg  120
ccgggccagg gcctggaatg gatgggccgc attgatccgg ataacggcga aagcacctat  180
gtgccgaaat ttcagggccg cgtgaccatg accaccgata ccagcaccag caccgcgtat  240
atggaactgc gcagcctgcg cagcgatgat accgcggtgt attattgcgc gcgcgaaggc  300
ctggattatg gcgattatta tgcggtggat tattggggcc agggcaccct ggtgaccgtc  360
tcgagc                                                             366

SEQ ID NO: 376         moltype = AA  length = 107
FEATURE                Location/Qualifiers
source                 1..107
                       mol_type = protein
                       organism = Mus musculus
SEQUENCE: 376
```

-continued

```
DIQMTQSPSS LSASVGDRVT ITCRASQDIS NYLNWYQQKP GKAPKLLIYY TSRLLSGVPS  60
RFSGSGSGTD FTLTISSLQP EDFATYYCQQ GDTLPYTFGG GTKVEIK                107

SEQ ID NO: 377         moltype = DNA  length = 321
FEATURE                Location/Qualifiers
source                 1..321
                       mol_type = other DNA
                       organism = Mus musculus
SEQUENCE: 377
gacatccaga tgacccagtc tccatcctcc ctctccgcat ccgtaggcga ccgcgtaacc  60
ataacatgta gagcatctca agatatttcc aactatttga attggtacca acaaaaaccc  120
ggcaaagcac ctaaactcct catttactat acatcaagac tcctctccgg cgttccatca  180
cgattctcag gctccggctc cggcacagat ttcacactca ctatttcctc cctccaacca  240
gaagattttg caacctatta ctgtcaacaa ggcgatacac tcccatacac attcggcggc  300
ggcacaaaag ttgaaattaa a                                            321

SEQ ID NO: 378         moltype = AA  length = 123
FEATURE                Location/Qualifiers
source                 1..123
                       mol_type = protein
                       organism = Mus musculus
SEQUENCE: 378
EVQLVQSGAE VKKPGASVKV SCKASGYTFT DYNMHWVRQA PGQGLEWMGE INPNSGGAGY  60
NQKFKGRVTM TTDTSTSTAY MELRSLRSDD TAVYYCARLG YDDIYDDWYF DVWGQGTTVT  120
VSS                                                                123

SEQ ID NO: 379         moltype = DNA  length = 369
FEATURE                Location/Qualifiers
source                 1..369
                       mol_type = other DNA
                       organism = Mus musculus
SEQUENCE: 379
gaggtgcagc tggtgcagag cggcgccgag gtaaaaaaac caggagcaag cgttaaagtt  60
tcttgtaaag caagcggata tacatttaca gattacaaca tgcattgggt aagacaagcg  120
ccaggacaag gattggaatg gatgggcgaa attaacccta atagtggagg agcaggctac  180
aatcaaaaat tcaaagggag agttacaatg acaacagaca caagcacttc aacagcatat  240
atggaactgc gatcacttag aagcgacgat acagctgtat actattgcgc acgacttggg  300
tatgatgata tatatgatga ctggtatttc gatgtttggg gccagggaac aacagttacc  360
gtctctagt                                                          369

SEQ ID NO: 380         moltype = AA  length = 108
FEATURE                Location/Qualifiers
source                 1..108
                       mol_type = protein
                       organism = Mus musculus
SEQUENCE: 380
DIQLTQSPSF LSASVGDRVT ITCRASSSVT SSYLNWYQQK PGKAPKLLIY STSNLASGVP  60
SRFSGSGSGT EFTLTISSLQ PEDFATYYCQ QYDFFPSTFG GGTKVEIK               108

SEQ ID NO: 381         moltype = DNA  length = 324
FEATURE                Location/Qualifiers
source                 1..324
                       mol_type = other DNA
                       organism = Mus musculus
SEQUENCE: 381
gacatccagc tgacccagag ccccagcttc ctttccgcat ccgttggtga ccgagtaaca  60
atcacatgcc gcgcctcatc ttcagttaca tcttcttatc ttaattggta tcaacaaaaa  120
ccaggaaaag cacctaaact tcttatatac tctacatcta atctcgcatc aggagttccc  180
tctcgatttt caggatctgg atcaggcaca gaatttacac ttactatatc atcactccaa  240
ccagaagact tcgccactta ttactgccaa caatacgatt tttttccaag cacattcgga  300
ggaggtacaa aagtagaaat caag                                         324

SEQ ID NO: 382         moltype = AA  length = 121
FEATURE                Location/Qualifiers
source                 1..121
                       mol_type = protein
                       organism = Mus musculus
SEQUENCE: 382
EVQLVQSGAE VKKPGASVKV SCKASGYTFT DYYMNWVRQA PGQRLEWMGD INPYNDDTTY  60
NHKFKGRVTI TRDTSASTAY MELSSLRSED TAVYYCARET AVITTNAMDY WGQGTTVTVS  120
S                                                                  121

SEQ ID NO: 383         moltype = DNA  length = 363
FEATURE                Location/Qualifiers
source                 1..363
                       mol_type = other DNA
                       organism = Mus musculus
SEQUENCE: 383
gaggtgcagc tggtgcagag cggcgccgag gtcaagaaac ctggagcaag cgtaaaggtt  60
```

-continued

```
agttgcaaag catctggata cacatttacc gactactaca tgaattgggt acgacaagcc  120
cctggacaaa gacttgaatg gatgggagac attaaccctt ataacgacga cactacatac  180
aatcataaat ttaaaggaag agttacaatt acaagagata catccgcatc aaccgcctat  240
atggaacttt cctcattgag atctgaagac actgctgttt attactgtgc aagagaaact  300
gccgttatta ctactaacgc tatggattac tggggtcaag gaaccactgt taccgtctct  360
agt                                                                363

SEQ ID NO: 384          moltype = AA  length = 108
FEATURE                 Location/Qualifiers
source                  1..108
                        mol_type = protein
                        organism = Mus musculus
SEQUENCE: 384
DIQMTQSPSS LSASVGDRVT ITCSVSSTIS SNHLHWFQQK PGKAPKSLIY GTSNLASGVP  60
SRFSGSGSGT DFTLTISSLQ PEDFATYYCQ QWSSYPLTFG GGTKVEIK               108

SEQ ID NO: 385          moltype = DNA  length = 324
FEATURE                 Location/Qualifiers
source                  1..324
                        mol_type = other DNA
                        organism = Mus musculus
SEQUENCE: 385
gacatccaga tgacccagtc tccatcctcc ctctcagcat ccgtaggcga tagagttaca  60
ataacatgca gcgtatcatc aactatatca tcaaatcatc ttcattggtt ccaacagaaa  120
cccggcaaag cacctaaatc acttatatac ggcacatcaa atctcgcatc aggcgttcct  180
tcaagatttt caggctctgg ctcaggcacc gactttactc ttacaatatc ctccctccaa  240
cccgaagact tcgcaaccta ttactgtcaa caatggtcct catatccact cacatttggc  300
ggcggcacaa aagtagaaat taaa                                         324

SEQ ID NO: 386          moltype = AA  length = 125
FEATURE                 Location/Qualifiers
source                  1..125
                        mol_type = protein
                        organism = Mus musculus
SEQUENCE: 386
EVQLVQSGAE VKKPGASVKV SCKASDFNIK DFYLHWVRQA PGQGLEWIGR IDPENGDTLY  60
DPKFQDKVTM TTDTSTSTAY MELRSLRSDD TAVYYCAREA DYFHDGTSYW YFDVWGRGTL  120
VTVSS                                                              125

SEQ ID NO: 387          moltype = DNA  length = 375
FEATURE                 Location/Qualifiers
source                  1..375
                        mol_type = other DNA
                        organism = Mus musculus
SEQUENCE: 387
gaggtgcagc tggtgcagtc tggggctgag gtgaagaagc ctggggcctc agtgaaggtc  60
tcctgcaagg cttctgactt caacattaaa gacttctatc tacactgggt gcgacaggcc  120
cctggacaag ggcttgagtg gattggaagg attgatcctg agaatggtga tactttatat  180
gacccgaagt tccaggacaa ggtcaccatg accacagaca cgtccaccag cacagcctac  240
atggagctga ggagcctgag atctgacgac acggccgtgt attactgtgc gagagaggcg  300
gattatttcc acgatggtac ctcctactgg tacttcgatg tctggggccg tggcaccctg  360
gtcaccgtct ctagt                                                   375

SEQ ID NO: 388          moltype = AA  length = 106
FEATURE                 Location/Qualifiers
source                  1..106
                        mol_type = protein
                        organism = Mus musculus
SEQUENCE: 388
DIQLTQSPSF LSASVGDRVT ITCRASSSIS YIHWYQQKPG KAPKLLIYAT SNLASGVPSR  60
FSGSGSGTEF TLTISSLQPE DFATYYCQQW SSDPLTFGGG TKVEIK                 106

SEQ ID NO: 389          moltype = DNA  length = 318
FEATURE                 Location/Qualifiers
source                  1..318
                        mol_type = other DNA
                        organism = Mus musculus
SEQUENCE: 389
gacatccagt tgacccagtc tccatccttc ctgtctgcat ctgtaggaga cagagtcacc  60
atcacttgca gggccagctc aagtataagt tacatacact ggtatcagca aaaaccaggg  120
aaagccccta agctcctgat ctatgccaca tccaacctgg cttctggggt cccatcaagg  180
ttcagcggca gtggatctgg gacagaattc actctcacaa tcagcagcct gcagcctgaa  240
gattttgcaa cttattactg tcagcagtgg agtagtgacc cactcacgtt cggcggaggg  300
accaaggtgg agatcaaa                                                318

SEQ ID NO: 390          moltype = AA  length = 121
FEATURE                 Location/Qualifiers
source                  1..121
                        mol_type = protein
```

```
                         organism = Mus musculus
SEQUENCE: 390
EVQLVQSGAE VKKPGASVKV SCKASGFDIK DYYIHWVRQA PGQGLEWIGR VDPDNGETEF  60
APKFPGKVTM TTDTSISTAY MELSRLRSDD TAVYYCARED YDGTYTWFPY WGQGTLVTVS  120
S                                                                121

SEQ ID NO: 391           moltype = DNA  length = 363
FEATURE                  Location/Qualifiers
source                   1..363
                         mol_type = other DNA
                         organism = Mus musculus
SEQUENCE: 391
gaggtgcagc tggtgcagtc tggggctgag gtgaagaagc ctggggcctc agtgaaggtc  60
tcctgcaagg cttctggatt cgacattaag gactactata tacactgggt gcgacaggcc  120
cctggacaag ggcttgagtg gatcggaagg gttgatcctg acaatggtga gactgaattt  180
gccccgaagt tcccgggcaa ggtcaccatg accacagaca cgtccatcag cacagcctac  240
atggagctga gcaggctgag atctgacgac acggccgtgt attactgtgc gagagaagac  300
tacgatggta cctacacctg gtttccttat tggggccaag ggactctggt caccgtctct  360
agt                                                              363

SEQ ID NO: 392           moltype = AA  length = 448
FEATURE                  Location/Qualifiers
REGION                   1..448
                         note = Synthetic Polypeptide
REGION                   1..448
                         note = MISC_FEATURE - Humanized Antibody Sequence
source                   1..448
                         mol_type = protein
                         organism = synthetic construct
SEQUENCE: 392
EVQLVQSGAE VKKPGASVKV SCKASGYTFT DYNMHWVRQA PGQGLEWMGE INPNSGGAGY  60
NQKFKGRVTM TTDTSTSTAY MELRSLRSDD TAVYYCARLG YDDIYDDWYF DVWGQGTTVT  120
VSSASTKGPS VFPLAPCSRS TSESTAALGC LVKDYFPEPV TVSWNSGALT SGVHTFPAVL  180
QSSGLYSLSS VVTVPSSNFG TQTYTCNVDH KPSNTKVDKT VERKCCVECP PCPAPPVAGP  240
SVFLFPPKPK DTLMISRTPE VTCVVVDVSH EDPEVQFNWY VDGVEVHNAK TKPREEQFNS  300
TFRVVSVLTV VHQDWLNGKE YKCKVSNKGL PAPIEKTISK TKGQPREPQV YTLPPSREEM  360
TKNQVSLTCL VKGFYPSDIA VEWESNGQPE NNYKTTPPML DSDGSFFLYS KLTVDKSRWQ  420
QGNVFSCSVM HEALHNHYTQ KSLSLSPG                                   448

SEQ ID NO: 393           moltype = AA  length = 446
FEATURE                  Location/Qualifiers
REGION                   1..446
                         note = Synthetic Polypeptide
REGION                   1..446
                         note = MISC_FEATURE - Humanized Antibody Sequence
source                   1..446
                         mol_type = protein
                         organism = synthetic construct
SEQUENCE: 393
EVQLVQSGAE VKKPGASVKV SCKASGYTFT DYYMNWVRQA PGQRLEWMGD INPYNDDTTY  60
NHKFKGRVTI TRDTSASTAY MELSSLRSED TAVYYCARET AVITTNAMDY WGQGTTVTVS  120
SASTKGPSVF PLAPCSRSTS ESTAALGCLV KDYFPEPVTV SWNSGALTSG VHTFPAVLQS  180
SGLYSLSSVV TVPSSNFGTQ TYTCNVDHKP SNTKVDKTVE RKCCVECPPC PAPPVAGPSV  240
FLFPPKPKDT LMISRTPEVT CVVVDVSHED PEVQFNWYVD GVEVHNAKTK PREEQFNSTF  300
RVVSVLTVVH QDWLNGKEYK CKVSNKGLPA PIEKTISKTK GQPREPQVYT LPPSREEMTK  360
NQVSLTCLVK GFYPSDIAVE WESNGQPENN YKTTPPMLDS DGSFFLYSKL TVDKSRWQQG  420
NVFSCSVMHE ALHNHYTQKS LSLSPG                                     446

SEQ ID NO: 394           moltype = AA  length = 450
FEATURE                  Location/Qualifiers
REGION                   1..450
                         note = Synthetic Polypeptide
REGION                   1..450
                         note = MISC_FEATURE - Humanized Antibody Sequence
source                   1..450
                         mol_type = protein
                         organism = synthetic construct
SEQUENCE: 394
EVQLVQSGAE VKKPGASVKV SCKASDFNIK DFYLHWVRQA PGQGLEWIGR IDPENGDTLY  60
DPKFQDKVTM TTDTSTSTAY MELRSLRSDD TAVYYCAREA DYFHDGTSYW YFDVWGRGTL  120
VTVSSASTKG PSVFPLAPCS RSTSESTAAL GCLVKDYFPE PVTVSWNSGA LTSGVHTFPA  180
VLQSSGLYSL SSVVTVPSSN FGTQTYTCNV DHKPSNTKVD KTVERKCCVE CPPCPAPPVA  240
GPSVFLFPPK PKDTLMISRT PEVTCVVVDV SHEDPEVQFN WYVDGVEVHN AKTKPREEQF  300
NSTFRVVSVL TVVHQDWLNG KEYKCKVSNK GLPAPIEKTI SKTKGQPREP QVYTLPPSRE  360
EMTKNQVSLT CLVKGFYPSD IAVEWESNGQ PENNYKTTPP MLDSDGSFFL YSKLTVDKSR  420
WQQGNVFSCS VMHEALHNHY TQKSLSLSPG                                 450

SEQ ID NO: 395           moltype = AA  length = 446
FEATURE                  Location/Qualifiers
```

```
REGION                 1..446
                       note = Synthetic Polypeptide
REGION                 1..446
                       note = MISC_FEATURE - Humanized Antibody Sequence
source                 1..446
                       mol_type = protein
                       organism = synthetic construct
SEQUENCE: 395
EVQLVQSGAE VKKPGASVKV SCKASGFDIK DYYIHWVRQA PGQGLEWIGR VDPDNGETEF  60
APKFPGKVTM TTDTSISTAY MELSRLRSDD TAVYYCARED YDGTYTWFPY WGQGTLVTVS  120
SASTKGPSVF PLAPCSRSTS ESTAALGCLV KDYFPEPVTV SWNSGALTSG VHTFPAVLQS  180
SGLYSLSSVV TVPSSNFGTQ TYTCNVDHKP SNTKVDKTVE RKCCVECPPC PAPPVAGPSV  240
FLFPPKPKDT LMISRTPEVT CVVVDVSHED PEVQFNWYVD GVEVHNAKTK PREEQFNSTF  300
RVVSVLTVVH QDWLNGKEYK CKVSNKGLPA PIEKTISKTK GQPREPQVYT LPPSREEMTK  360
NQVSLTCLVK GFYPSDIAVE WESNGQPENN YKTTPPMLDS DGSFFLYSKL TVDKSRWQQG  420
NVFSCSVMHE ALHNHYTQKS LSLSPG                                      446

SEQ ID NO: 396         moltype = AA  length = 445
FEATURE                Location/Qualifiers
REGION                 1..445
                       note = Synthetic Polypeptide
REGION                 1..445
                       note = MISC_FEATURE - Humanized Antibody Sequence
source                 1..445
                       mol_type = protein
                       organism = synthetic construct
SEQUENCE: 396
EVQLVQSGAE VKKPGSSVKV SCKASGFTFT DYIMHWVRQA PGQGLEWMGY INPYNDDTEY  60
NEKFKGRVTI TADKSTSTAY MELSSLRSED TAVYYCARSI YYYDAPFAYW GQGTLVTVSS  120
ASTKGPSVFP LAPCSRSTSE STAALGCLVK DYFPEPVTVS WNSGALTSGV HTFPAVLQSS  180
GLYSLSSVVT VPSSNFGTQT YTCNVDHKPS NTKVDKTVER KCCVECPPCP APPVAGPSVF  240
LFPPKPKDTL MISRTPEVTC VVVDVSHEDP EVQFNWYVDG VEVHNAKTKP REEQFNSTFR  300
VVSVLTVVHQ DWLNGKEYKC KVSNKGLPAP IEKTISKTKG QPREPQVYTL PPSREEMTKN  360
QVSLTCLVKG FYPSDIAVEW ESNGQPENNY KTTPPMLDSD GSFFLYSKLT VDKSRWQQGN  420
VFSCSVMHEA LHNHYTQKSL SLSPG                                       445

SEQ ID NO: 397         moltype = AA  length = 213
FEATURE                Location/Qualifiers
source                 1..213
                       mol_type = protein
                       organism = Homo sapiens
SEQUENCE: 397
MQLPLALCLV CLLVHTAFRV VEGQGWQAFK NDATEIIPEL GEYPEPPPEL ENNKTMNRAE  60
NGGRPPHHPF ETKDVSEYSC RELHFTRYVT DGPCRSAKPV TELVCSGQCG PARLLPNAIG  120
RGKWWRPSGP DFRCIPDRYR AQRVQLLCPG GEAPRARKVR LVASCKCKRL TRFHNQSELK  180
DFGTEAARPQ KGRKPRPRAR SAKANQAELE NAY                               213

SEQ ID NO: 398         moltype = AA  length = 444
FEATURE                Location/Qualifiers
REGION                 1..444
                       note = Miscellaneous construct
source                 1..444
                       mol_type = protein
                       organism = synthetic construct
SEQUENCE: 398
QVQLVQSGAE VKKPGSSVKV SCKASGYTFT DYFLNWVRQA PGQGLEWMGT IYPYHDGTTY  60
SQKFKGRVTI TADKSTSTAY MELSSLRSED TAVYYCAREE EDGQFDYWGQ GTTVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP EFLGGPSVFL  240
FPPKPKDTLM ISRTPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PSQEEMTKNQ  360
VSLTCLVKGF YPSDIAVEWE SNGQPENNYK TTPPVLDSDG SFFLYSRLTV DKSRWQEGNV  420
FSCSVMHEAL HNHYTQKSLS LSLG                                        444

SEQ ID NO: 399         moltype = AA  length = 444
FEATURE                Location/Qualifiers
REGION                 1..444
                       note = Miscellaneous construct
source                 1..444
                       mol_type = protein
                       organism = synthetic construct
SEQUENCE: 399
QVQLVQSGAE VKKPGASVKV SCKVSGFPIK DTFQHWVRQA PGKGLEWMGW SDPEIGDTEY  60
ASKFQGRVTM TEDTSTDTAY MELSSLRSED TAVYYCATGD TTYKFDFWGQ GTTVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP EFLGGPSVFL  240
FPPKPKDTLM ISRTPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PSQEEMTKNQ  360
VSLTCLVKGF YPSDIAVEWE SNGQPENNYK TTPPVLDSDG SFFLYSRLTV DKSRWQEGNV  420
```

```
FSCSVMHEAL HNHYTQKSLS LSLG                                        444

SEQ ID NO: 400         moltype = AA  length = 450
FEATURE                Location/Qualifiers
REGION                 1..450
                       note = Miscellaneous construct
source                 1..450
                       mol_type = protein
                       organism = synthetic construct
SEQUENCE: 400
EVQLVQSGAE VKKPGESLKI SCKGSDFEIK DYYIHWVRQM PGKGLEWMGQ IDAEDGETEY  60
APRFQGQVTI SADKSISTAY LQWSSLKASD TAMYYCAREG YYYDGRDYWY FDVWGQGTTV  120
TVSSASTKGP SVFPLAPCSR STSESTAALG CLVKDYFPEP VTVSWNSGAL TSGVHTFPAV  180
LQSSGLYSLS SVVTVPSSSL GTKTYTCNVD HKPSNTKVDK RVESKYGPPC PPCPAPEFLG  240
GPSVFLFPPK PKDTLMISRT PEVTCVVVDV SQEDPEVQFN WYVDGVEVHN AKTKPREEQF  300
NSTYRVVSVL TVLHQDWLNG KEYKCKVSNK GLPSSIEKTI SKAKGQPREP QVYTLPPSQE  360
EMTKNQVSLT CLVKGFYPSD IAVEWESNGQ PENNYKTTPP VLDSDGSFFL YSRLTVDKSR  420
WQEGNVFSCS VMHEALHNHY TQKSLSLSLG                                  450

SEQ ID NO: 401         moltype = AA  length = 214
FEATURE                Location/Qualifiers
REGION                 1..214
                       note = Miscellaneous construct
source                 1..214
                       mol_type = protein
                       organism = synthetic construct
SEQUENCE: 401
DIQMTQSPSS LSASVGDRVT ITCSASQGIQ WYLNWYQQKP GKAPKLLIYY TSSLHSGVPS  60
RFSGSGSGTD FTLTISSLQP EDFATYYCQQ HSKLPRTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 402         moltype = AA  length = 214
FEATURE                Location/Qualifiers
REGION                 1..214
                       note = Miscellaneous construct
source                 1..214
                       mol_type = protein
                       organism = synthetic construct
SEQUENCE: 402
DIQMTQSPSS LSASVGDRVT ITCKASQDVH TAVAWYQQKP GKAPKLLIYW ASTRWTGVPS  60
RFSGSGSGTD FTLTISSLQP EDFATYYCQQ YSDYPWTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 403         moltype = AA  length = 213
FEATURE                Location/Qualifiers
REGION                 1..213
                       note = Miscellaneous construct
source                 1..213
                       mol_type = protein
                       organism = synthetic construct
SEQUENCE: 403
EIVLTQSPAT LSLSPGERAT LSCSASSSVS YIHWYQQKPG QAPRLLIYST SELASGIPAR  60
FSGSGSGTDF TLTISSLEPE DFAVYYCQQL SHLPLTFGGG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 404         moltype = DNA  length = 1332
FEATURE                Location/Qualifiers
misc_feature           1..1332
                       note = Miscellaneous construct
source                 1..1332
                       mol_type = other DNA
                       organism = synthetic construct
SEQUENCE: 404
caggtgcagc tggtgcagtc tggggctgag gtgaagaagc ctgggtcctc agtgaaggtt  60
tcctgcaagg catctggata cacattcact gactactttc tgaactgggt gcgacaggcc  120
cctggacaag ggcttgagtg gatgggaact atttatcctt accatgatgg tactacctac  180
tctcagaagt tcaagggcag agtcaccatt accgcggaca aatccacgag cacagcctac  240
atggagctga gcagcctgag atctgaggac acggccgtgt attactgtgc gagagaggaa  300
gaggatggtc agttcgacta ctggggccaa ggaaccacgg tcaccgtctc ctcagcctcc  360
accaagggcc catcggtctt cccgctagcg ccctgctcca ggagcacctc cgagagcaca  420
gccgccctgg gctgcctggt caaggactac ttccccgaac cggtgacggt gtcgtggaac  480
tcaggcgccc tgaccagcgg cgtgcacacc ttcccggctg tcctacagtc ctcaggactc  540
tactccctca gcagcgtggt gaccgtgccc tccagcagct tgggcacgaa gacctacacc  600
tgcaacgtag atcacaagcc cagcaacacc aaggtggaca agagagttga gtccaaatat  660
ggtcccccat gcccaccctg cccagcacct gagttcctgg ggggaccatc agtcttcctg  720
ttccccccaa aacccaagga cactctcatg atctcccgga cccctgaggt cacgtgcgtg  780
```

```
gtggtggacg tgagccagga agaccccgag gtccagttca actggtacgt ggatggcgtg  840
gaggtgcata atgccaagac aaagccgcgg gaggagcagt tcaacagcac gtaccgtgtg  900
gtcagcgtcc tcaccgtcct gcaccaggac tggctgaacg gcaaggagta caagtgcaag  960
gtctccaaca aaggcctccc gtcctccatc gagaaaacca tctccaaagc caaagggcag  1020
ccccgagagc cacaggtgta caccctgccc ccatcccagg aggagatgac caagaaccag  1080
gtcagcctga cctgcctggt caaaggcttc taccccagcg acatcgccgt ggagtgggaa  1140
agcaatgggc agccggagaa caactacaag accacgcctc ccgtgctgga ctccgacggc  1200
tccttcttcc tctacagcag gctaaccgtg gacaagagca ggtggcagga ggggaatgtc  1260
ttctcatgct ccgtgatgca tgaggctctg cacaaccact acacacagaa gagcctctcc  1320
ctgtctctgg gt                                                     1332

SEQ ID NO: 405          moltype = DNA  length = 1332
FEATURE                 Location/Qualifiers
misc_feature            1..1332
                        note = Miscellaneous construct
source                  1..1332
                        mol_type = other DNA
                        organism = synthetic construct
SEQUENCE: 405
caggttcagc tggtgcagtc tggggctgag gtgaagaagc ctggggcctc agtgaaggtc  60
tcctgcaagg tttccggctt ccccattaag gacacctttc agcactgggt gcgacaggct  120
cctggaaaag ggcttgagtg gatgggatgg agcgatcctg agatcggtga tactgaatat  180
gcctcgaagt tccagggcag agtcaccatg accgaggaca catctacaga cacagcctac  240
atggagctga gcagcctgag atctgaggac acggccgtgt attactgtgc aacaggcgac  300
accacataca agtttgactt ctgggggcaa gggaccacgg tcaccgtctc ctcagcctcc  360
accaagggcc catcggtctt cccgctagcg ccctgctcca ggagcacctc cgagagcaca  420
gccgccctgg gctgcctggt caaggactac ttccccgaac cggtgacggt gtcgtggaac  480
tcaggcgccc tgaccagcgg cgtgcacacc ttcccggctg tcctacagtc ctcaggactc  540
tactccctca gcagcgtggt gaccgtgccc tccagcagct tgggcacgaa gacctacacc  600
tgcaacgtag atcacaagcc cagcaacacc aaggtggaca agagagttga gtccaaatat  660
ggtcccccat gcccaccctg cccagcacct gagttcctgg ggggaccatc agtcttcctg  720
ttccccccaa aacccaagga cactctcatg atctcccgga cccctgaggt cacgtgcgtg  780
gtggtggacg tgagccagga agaccccgag gtccagttca actggtacgt ggatggcgtg  840
gaggtgcata atgccaagac aaagccgcgg gaggagcagt tcaacagcac gtaccgtgtg  900
gtcagcgtcc tcaccgtcct gcaccaggac tggctgaacg gcaaggagta caagtgcaag  960
gtctccaaca aaggcctccc gtcctccatc gagaaaacca tctccaaagc caaagggcag  1020
ccccgagagc cacaggtgta caccctgccc ccatcccagg aggagatgac caagaaccag  1080
gtcagcctga cctgcctggt caaaggcttc taccccagcg acatcgccgt ggagtgggaa  1140
agcaatgggc agccggagaa caactacaag accacgcctc ccgtgctgga ctccgacggc  1200
tccttcttcc tctacagcag gctaaccgtg gacaagagca ggtggcagga ggggaatgtc  1260
ttctcatgct ccgtgatgca tgaggctctg cacaaccact acacacagaa gagcctctcc  1320
ctgtctctgg gt                                                     1332

SEQ ID NO: 406          moltype = DNA  length = 1350
FEATURE                 Location/Qualifiers
misc_feature            1..1350
                        note = Miscellaneous construct
source                  1..1350
                        mol_type = other DNA
                        organism = synthetic construct
SEQUENCE: 406
gaggtgcagc tggtgcagtc tggagcagag gtgaaaaagc ccggggagtc tctgaagatc  60
tcctgtaagg gttctgactt cgagattaaa gactactata tacattgggt gcgccagatg  120
cccgggaaag gcctggagtg gatggggcag attgatgctg aggatggtga aactgaatat  180
gccccgaggt tccagggcca ggtcaccatc tcagccgaca agtccatcag caccgcctac  240
ctgcagtgga gcagcctgaa ggcctcggac accgccatgt attactgtgc gagagagggt  300
tattactacg atgggcgcga ctactggtac ttcgatgtct ggggccaagg gaccacggtc  360
accgtctcct cagcctccac caagggccca tcggtcttcc cgctagcgcc ctgctccagg  420
agcacctccg agagcacagc cgccctgggc tgcctggtca aggactactt ccccgaaccg  480
gtgacggtgt cgtggaactc aggcgccctg accagcggcg tgcacacctt cccggctgtc  540
ctacagtcct caggactcta ctccctcagc agcgtggtga ccgtgccctc cagcagcttg  600
ggcacgaaga cctacacctg caacgtagat cacaagccca gcaacaccaa ggtggacaag  660
agagttgagt ccaaatatgg tcccccatgc ccaccctgcc cagcacctga gttcctgggg  720
ggaccatcag tcttcctgtt ccccccaaaa cccaaggaca ctctcatgat ctcccggacc  780
cctgaggtca cgtgcgtggt ggtggacgtg agccaggaag accccgaggt ccagttcaac  840
tggtacgtgg atggcgtgga ggtgcataat gccaagacaa agccgcggga ggagcagttc  900
aacagcacgt accgtgtggt cagcgtcctc accgtcctgc accaggactg gctgaacggc  960
aaggagtaca agtgcaaggt ctccaacaaa ggcctcccgt cctccatcga gaaaaccatc  1020
tccaaagcca aagggcagcc ccgagagcca caggtgtaca ccctgccccc atcccaggag  1080
gagatgacca agaaccaggt cagcctgacc tgcctggtca aaggcttcta ccccagcgac  1140
atcgccgtgg agtgggaaag caatgggcag ccggagaaca actacaagac cacgcctccc  1200
gtgctggact ccgacggctc cttcttcctc tacagcaggc taaccgtgga caagagcagg  1260
tggcaggagg ggaatgtctt ctcatgctcc gtgatgcatg aggctctgca caaccactac  1320
acacagaaga gcctctccct gtctctgggt                                  1350

SEQ ID NO: 407          moltype = DNA  length = 642
FEATURE                 Location/Qualifiers
misc_feature            1..642
                        note = Miscellaneous construct
```

-continued

```
source                  1..642
                        mol_type = other DNA
                        organism = synthetic construct
SEQUENCE: 407
gacatccaga tgacccagtc tccatcctct ctgtctgcat ctgtaggaga cagagtcacc  60
atcacttgca gtgcaagtca gggcattcag tggtatttaa actggtatca gcagaaacca  120
gggaaagccc ctaagctcct gatctattac acatcaagtt tacactcagg ggtcccatca  180
aggttcagtg gcagtggatc tgggacagat ttcactctca ccatcagcag tctgcaacct  240
gaagattttg caacttacta ctgtcagcag catagtaaac ttcctcggac gttcggcgga  300
gggaccaagg tggagatcaa acggactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gc                     642

SEQ ID NO: 408          moltype = DNA  length = 642
FEATURE                 Location/Qualifiers
misc_feature            1..642
                        note = Miscellaneous construct
source                  1..642
                        mol_type = other DNA
                        organism = synthetic construct
SEQUENCE: 408
gacatccaga tgacccagtc tccatcctcc ctgtctgcat ctgtaggaga cagagtcacc  60
atcacttgca aggccagtca ggatgtgcac actgctgtag cctggtatca gcagaaacca  120
gggaaagccc ctaagctcct gatctattgg gcatccaccc ggtggactgg agtcccatca  180
aggttcagtg gcagtggatc tgggacagat ttcactctca ccatcagcag tctgcaacct  240
gaagattttg caacttacta ctgtcagcaa tatagcgatt atccgtggac gttcggcgga  300
gggaccaagg tggagatcaa acggactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gc                     642

SEQ ID NO: 409          moltype = DNA  length = 639
FEATURE                 Location/Qualifiers
misc_feature            1..639
                        note = Miscellaneous construct
source                  1..639
                        mol_type = other DNA
                        organism = synthetic construct
SEQUENCE: 409
gaaattgtgt tgacacagtc tccagccacc ctgtctttgt ctccagggga aagagccacc  60
ctctcctgca gtgccagctc aagtgtaagt tacatccact ggtaccaaca gaaacctggc  120
caggctccca ggctcctcat ctatagcaca tccgagctgg cttctggcat cccagccagg  180
ttcagtggca gtgggtctgg gacagacttc actctcacca tcagcagcct agagcctgaa  240
gattttgcag tttattactg tcagcagctt agtcatctcc cgctcacgtt cggcggaggg  300
accaaggtgg agatcaaacg aactgtggct gcaccatctg tcttcatctt cccgccatct  360
gatgagcagt tgaaatctgg aactgcctct gttgtgtgcc tgctgaataa cttctatccc  420
agagaggcca aagtacagtg gaaggtggat aacgccctcc aatcgggtaa ctcccaggag  480
agtgtcacag agcaggacag caaggacagc acctacagcc tcagcagcac cctgacgctg  540
agcaaagcag actacgagaa acacaaagtc tacgcctgcg aagtcaccca tcagggcctg  600
agctcgcccg tcacaaagag cttcaacagg ggagagtgc                         639

SEQ ID NO: 410          moltype = AA  length = 118
FEATURE                 Location/Qualifiers
REGION                  1..118
                        note = Miscellaneous construct
source                  1..118
                        mol_type = protein
                        organism = synthetic construct
SEQUENCE: 410
QVQLVQSGAE VKKPGSSVKV SCKASGYTFT DYFLNWVRQA PGQGLEWMGT IYPYHDGTTY  60
SQKFKGRVTI TADKSTSTAY MELSSLRSED TAVYYCAREE EDGQFDYWGQ GTTVTVSS    118

SEQ ID NO: 411          moltype = AA  length = 118
FEATURE                 Location/Qualifiers
REGION                  1..118
                        note = Miscellaneous construct
source                  1..118
                        mol_type = protein
                        organism = synthetic construct
SEQUENCE: 411
QVQLVQSGAE VKKPGASVKV SCKVSGFPIK DTFQHWVRQA PGKGLEWMGW SDPEIGDTEY  60
ASKFQGRVTM TEDTSTDTAY MELSSLRSED TAVYYCATGD TTYKFDFWGQ GTTVTVSS    118

SEQ ID NO: 412          moltype = AA  length = 124
```

-continued

```
FEATURE                Location/Qualifiers
REGION                 1..124
                       note = Miscellaneous construct
source                 1..124
                       mol_type = protein
                       organism = synthetic construct
SEQUENCE: 412
EVQLVQSGAE VKKPGESLKI SCKGSDFEIK DYYIHWVRQM PGKGLEWMGQ IDAEDGETEY  60
APRFQGQVTI SADKSISTAY LQWSSLKASD TAMYYCAREG YYYDGRDYWY FDVWGQGTTV  120
TVSS                                                              124

SEQ ID NO: 413         moltype = AA  length = 107
FEATURE                Location/Qualifiers
REGION                 1..107
                       note = Miscellaneous construct
source                 1..107
                       mol_type = protein
                       organism = synthetic construct
SEQUENCE: 413
DIQMTQSPSS LSASVGDRVT ITCSASQGIQ WYLNWYQQKP GKAPKLLIYY TSSLHSGVPS  60
RFSGSGSGTD FTLTISSLQP EDFATYYCQQ HSKLPRTFGG GTKVEIK               107

SEQ ID NO: 414         moltype = AA  length = 107
FEATURE                Location/Qualifiers
REGION                 1..107
                       note = Miscellaneous construct
source                 1..107
                       mol_type = protein
                       organism = synthetic construct
SEQUENCE: 414
DIQMTQSPSS LSASVGDRVT ITCKASQDVH TAVAWYQQKP GKAPKLLIYW ASTRWTGVPS  60
RFSGSGSGTD FTLTISSLQP EDFATYYCQQ YSDYPWTFGG GTKVEIK               107

SEQ ID NO: 415         moltype = AA  length = 106
FEATURE                Location/Qualifiers
REGION                 1..106
                       note = Miscellaneous construct
source                 1..106
                       mol_type = protein
                       organism = synthetic construct
SEQUENCE: 415
EIVLTQSPAT LSLSPGERAT LSCSASSSVS YIHWYQQKPG QAPRLLIYST SELASGIPAR  60
FSGSGSGTDF TLTISSLEPE DFAVYYCQQL SHLPLTFGGG TKVEIK                106

SEQ ID NO: 416         moltype = AA  length = 10
FEATURE                Location/Qualifiers
REGION                 1..10
                       note = Miscellaneous construct
source                 1..10
                       mol_type = protein
                       organism = synthetic construct
SEQUENCE: 416
GYTFTDYFLN                                                        10

SEQ ID NO: 417         moltype = AA  length = 17
FEATURE                Location/Qualifiers
REGION                 1..17
                       note = Miscellaneous construct
source                 1..17
                       mol_type = protein
                       organism = synthetic construct
SEQUENCE: 417
TIYPYHDGTT YSQKFKG                                                17

SEQ ID NO: 418         moltype = AA  length = 9
FEATURE                Location/Qualifiers
REGION                 1..9
                       note = Miscellaneous construct
source                 1..9
                       mol_type = protein
                       organism = synthetic construct
SEQUENCE: 418
EEEDGQFDY                                                         9

SEQ ID NO: 419         moltype = AA  length = 11
FEATURE                Location/Qualifiers
REGION                 1..11
                       note = Miscellaneous construct
source                 1..11
```

-continued

```
                         mol_type = protein
                         organism = synthetic construct
SEQUENCE: 419
SASQGIQWYL N                                                      11

SEQ ID NO: 420           moltype = AA  length = 7
FEATURE                  Location/Qualifiers
REGION                   1..7
                         note = Miscellaneous construct
source                   1..7
                         mol_type = protein
                         organism = synthetic construct
SEQUENCE: 420
YTSSLHS                                                           7

SEQ ID NO: 421           moltype = AA  length = 9
FEATURE                  Location/Qualifiers
REGION                   1..9
                         note = Miscellaneous construct
source                   1..9
                         mol_type = protein
                         organism = synthetic construct
SEQUENCE: 421
QQHSKLPRT                                                         9

SEQ ID NO: 422           moltype = AA  length = 10
FEATURE                  Location/Qualifiers
REGION                   1..10
                         note = Miscellaneous construct
source                   1..10
                         mol_type = protein
                         organism = synthetic construct
SEQUENCE: 422
GFPIKDTFQH                                                        10

SEQ ID NO: 423           moltype = AA  length = 17
FEATURE                  Location/Qualifiers
REGION                   1..17
                         note = Miscellaneous construct
source                   1..17
                         mol_type = protein
                         organism = synthetic construct
SEQUENCE: 423
WSDPEIGDTE YASKFQG                                                17

SEQ ID NO: 424           moltype = AA  length = 9
FEATURE                  Location/Qualifiers
REGION                   1..9
                         note = Miscellaneous construct
source                   1..9
                         mol_type = protein
                         organism = synthetic construct
SEQUENCE: 424
GDTTYKFDF                                                         9

SEQ ID NO: 425           moltype = AA  length = 11
FEATURE                  Location/Qualifiers
REGION                   1..11
                         note = Miscellaneous construct
source                   1..11
                         mol_type = protein
                         organism = synthetic construct
SEQUENCE: 425
KASQDVHTAV A                                                      11

SEQ ID NO: 426           moltype = AA  length = 7
FEATURE                  Location/Qualifiers
REGION                   1..7
                         note = Miscellaneous construct
source                   1..7
                         mol_type = protein
                         organism = synthetic construct
SEQUENCE: 426
WASTRWT                                                           7

SEQ ID NO: 427           moltype = AA  length = 9
FEATURE                  Location/Qualifiers
REGION                   1..9
                         note = Miscellaneous construct
```

```
source                  1..9
                        mol_type = protein
                        organism = synthetic construct
SEQUENCE: 427
QQYSDYPWT                                                        9

SEQ ID NO: 428          moltype = AA  length = 10
FEATURE                 Location/Qualifiers
REGION                  1..10
                        note = Miscellaneous construct
source                  1..10
                        mol_type = protein
                        organism = synthetic construct
SEQUENCE: 428
DFEIKDYYIH                                                       10

SEQ ID NO: 429          moltype = AA  length = 17
FEATURE                 Location/Qualifiers
REGION                  1..17
                        note = Miscellaneous construct
source                  1..17
                        mol_type = protein
                        organism = synthetic construct
SEQUENCE: 429
QIDAEDGETE YAPRFQG                                               17

SEQ ID NO: 430          moltype = AA  length = 17
FEATURE                 Location/Qualifiers
REGION                  1..17
                        note = Miscellaneous construct
source                  1..17
                        mol_type = protein
                        organism = synthetic construct
SEQUENCE: 430
QIDAEDGETE YAPRFQG                                               17

SEQ ID NO: 431          moltype = AA  length = 17
FEATURE                 Location/Qualifiers
REGION                  1..17
                        note = Miscellaneous construct
source                  1..17
                        mol_type = protein
                        organism = synthetic construct
SEQUENCE: 431
QIDAEDGETE YAPRFQG                                               17

SEQ ID NO: 432          moltype = AA  length = 7
FEATURE                 Location/Qualifiers
REGION                  1..7
                        note = Miscellaneous construct
source                  1..7
                        mol_type = protein
                        organism = synthetic construct
SEQUENCE: 432
STSELAS                                                          7

SEQ ID NO: 433          moltype = AA  length = 9
FEATURE                 Location/Qualifiers
REGION                  1..9
                        note = Miscellaneous construct
source                  1..9
                        mol_type = protein
                        organism = synthetic construct
SEQUENCE: 433
QQLSHLPLT                                                        9

SEQ ID NO: 434          moltype = AA  length = 322
FEATURE                 Location/Qualifiers
REGION                  1..322
                        note = Miscellaneous construct
source                  1..322
                        mol_type = protein
                        organism = synthetic construct
SEQUENCE: 434
GPSVFPLAPC SRSTSESTAA LGCLVKDYFP EPVTVSWNSG ALTSGVHTFP AVLQSSGLYS  60
LSSVVTVPSS SLGTKTYTCN VDHKPSNTKV DKRVESKYGP PCPPCPAPEF LGGPSVFLFP  120
PKPKDTLMIS RTPEVTCVVV DVSQEDPEVQ FNWYVDGVEV HNAKTKPREE QFNSTYRVVS  180
VLTVLHQDWL NGKEYKCKVS NKGLPSSIEK TISKAKGQPR EPQVYTLPPS QEEMTKNQVS  240
LTCLVKGFYP SDIAVEWESN GQPENNYKTT PPVLDSDGSF FLYSRLTVDK SRWQEGNVFS  300
```

```
CSVMHEALHN HYTQKSLSLS LG                                    322

SEQ ID NO: 435         moltype = DNA  length = 970
FEATURE                Location/Qualifiers
misc_feature           1..970
                       note = Miscellaneous construct
source                 1..970
                       mol_type = other DNA
                       organism = synthetic construct
SEQUENCE: 435
ggcccatcgg tcttcccgct agcgccctgc tccaggagca cctccgagag cacagccgcc  60
ctgggctgcc tggtcaagga ctacttcccc gaaccggtga cggtgtcgtg gaactcaggc  120
gccctgacca gcggcgtgca caccttcccg gctgtcctac agtcctcagg actctactcc  180
gctcagcagc gtggtgaccg tgccctccag cagcttgggc acgaagacct acacctgcaa  240
cgtagatcac aagcccagca acaccaaggt ggacaagaga gttgagtcca aatatggtcc  300
cccatgccca ccctgcccag cacctgagtt cctgggggga ccatcagtct tcctgttccc  360
cccaaaaccc aaggacactc tcatgatctc ccggacccct gaggtcacgt gcgtggtggt  420
ggacgtgagc caggaagacc ccgaggtcca gttcaactgg tacgtggatg gcgtggaggt  480
gcataatgcc aagacaaagc cgcgggagga gcagttcaac agcacgtacc gtgtggtcag  540
cgtcctcacc gtcctgcacc aggactggct gaacggcaag gagtacaagt gcaaggtctc  600
caacaaaggc ctcccgtcct ccatcgagaa aaccatctcc aaagccaaag ggcagccccg  660
agagccacag gtgtacaccc tgcccccatc ccaggaggag atgaccaaga accaggtcag  720
cctgacctgc ctggtcaaag gcttctaccc cagcgacatc gccgtggagt gggaaagcaa  780
tgggcagccg gagaacaact acaagaccac gcctcccgtg ctggactccg acggctcctt  840
cttcctctac agcaggctaa ccgtggacaa gagcaggtgg caggagggga atgtcttctc  900
atgctccgtg atgcatgagg ctctgcacaa ccactacaca cagaagagcc tctccctgtc  960
tctgggttga                                                  970

SEQ ID NO: 436         moltype = AA  length = 444
FEATURE                Location/Qualifiers
REGION                 1..444
                       note = Miscellaneous construct
source                 1..444
                       mol_type = protein
                       organism = synthetic construct
SEQUENCE: 436
EVQLQQSVAE LVRPGASVKL SCTASGFNIK STFMHWVKQR PDQGLEWIGW IDPENGDTEY  60
ASKFQGKATM TADTSSNTAY LQLSSLTSED TAVYYCTTGE SNYDFDFWGL GTTLTVSSAK  120
TTPPSVYPLA PGTALKSNSM VTLGCLVKGY FPEPVTVTWN SGALSSGVHT FPAVLQSGLY  180
TLTSSVTVPS STWPSQTVTC NVAHPASSTK VDKKIVPRNC GGDCKPCICT GSEVSSVFIF  240
PPKPKDVLTI TLTPKVTCVV VDISQDDPEV HFSWFVDDVE VHTAQTRPPE EQFNSTFRSV  300
SELPILHQDW LNGRTFRCKV TSAAFPSPIE KTISKPEGRT QVPHVYTMSP TKEEMTQNEV  360
SITCMVKGFY PPDIYVEWQM NGQPQENYKN TPPTMDTDGS YFLYSKLNVK KEKWQQGNTF  420
TCSVLHEGLH NHHTEKSLSH SPGK                                  444

SEQ ID NO: 437         moltype = AA  length = 214
FEATURE                Location/Qualifiers
REGION                 1..214
                       note = Miscellaneous construct
source                 1..214
                       mol_type = protein
                       organism = synthetic construct
SEQUENCE: 437
DIVMTQSHKF MSTSVGDRVS ITCKASQDVS TAVAWYQQKP GQSPKLLIYW ASTRHTGVPD  60
RFTGSGSGTD YTLTISDVQS EDLADYFCQQ YSNYPWTFGG GTKLEIKRAD AAPTVSIFPP  120
STEQLATGGA SVVCLMNNFY PRDISVKWKI DGTERRDGVL DSVTDQDSKD STYSMSSTLS  180
LSKADYESHN LYTCEVVHKT SSSPVVKSFN RNEC                        214

SEQ ID NO: 438         moltype = AA  length = 450
FEATURE                Location/Qualifiers
REGION                 1..450
                       note = Miscellaneous construct
source                 1..450
                       mol_type = protein
                       organism = synthetic construct
SEQUENCE: 438
EVQLQQSGAE HVKPGASVKL SCTASDFNIK DYYIHWVKQR TAQGLEWIGR IDPEDGETEY  60
APRFQGKATI IADTSSNTAY LQLSSLTSED TAVYYCAREG YYYDSRDYWY FDVWGTGTTV  120
TVSSAKTTPP SVYPLAPGTA LKSNSMVTLG CLVKGYFPEP VTVTWNSGAL SSGVHTFPAV  180
LQSGLYTLTS SVTVPSSTWP SQTVTCNVAH PASSTKVDKK IVPRNCGGDC KPCICTGSEV  240
SSVFIFPPKP KDVLTITLTP KVTCVVVDIS QDDPEVHFSW FVDDVEVHTA QTRPPEEQFN  300
STFRSVSELP ILHQDWLNGR TFRCKVTSAA FPSPIEKTIS KPEGRTQVPH VYTMSPTKEE  360
MTQNEVSITC MVKGFYPPDI YVEWQMNGQP QENYKNTPPT MDTDGSYFLY SKLNVKKEKW  420
QQGNTFTCSV LHEGLHNHHT EKSLSHSPGK                            450

SEQ ID NO: 439         moltype = AA  length = 213
FEATURE                Location/Qualifiers
REGION                 1..213
                       note = Miscellaneous construct
```

```
source                  1..213
                        mol_type = protein
                        organism = synthetic construct
SEQUENCE: 439
EIVLTQSPAL MSASPGEKVT MTCSASSSVS YMHWFQQKPG TSPKLWIYST SNLASGVPAR  60
FSGSGSGTSY SLTISSMEAE DAATYYCQQW SSNPLTFGAG TKLELKRADA APTVSIFPPS  120
TEQLATGGAS VVCLMNNFYP RDISVKWKID GTERRDGVLD SVTDQDSKDS TYSMSSTLSL  180
SKADYESHNL YTCEVVHKTS SSPVVKSFNR NEC                              213

SEQ ID NO: 440          moltype = AA  length = 10
FEATURE                 Location/Qualifiers
source                  1..10
                        mol_type = protein
                        organism = Homo sapiens
SEQUENCE: 440
GFTFSSYVMN                                                        10

SEQ ID NO: 441          moltype = AA  length = 10
FEATURE                 Location/Qualifiers
source                  1..10
                        mol_type = protein
                        organism = Homo sapiens
SEQUENCE: 441
GFTFRSHWLS                                                        10

SEQ ID NO: 442          moltype = AA  length = 10
FEATURE                 Location/Qualifiers
source                  1..10
                        mol_type = protein
                        organism = Homo sapiens
SEQUENCE: 442
GFTFSSYVMN                                                        10

SEQ ID NO: 443          moltype = AA  length = 10
FEATURE                 Location/Qualifiers
source                  1..10
                        mol_type = protein
                        organism = Homo sapiens
SEQUENCE: 443
GFTFRSHWLS                                                        10

SEQ ID NO: 444          moltype = AA  length = 10
FEATURE                 Location/Qualifiers
source                  1..10
                        mol_type = protein
                        organism = Homo sapiens
SEQUENCE: 444
GFTFRSHWLS                                                        10

SEQ ID NO: 445          moltype = AA  length = 10
FEATURE                 Location/Qualifiers
source                  1..10
                        mol_type = protein
                        organism = Homo sapiens
SEQUENCE: 445
GFTFRSHWLS                                                        10

SEQ ID NO: 446          moltype = AA  length = 10
FEATURE                 Location/Qualifiers
source                  1..10
                        mol_type = protein
                        organism = Homo sapiens
SEQUENCE: 446
GFTFRSHWLS                                                        10

SEQ ID NO: 447          moltype = AA  length = 10
FEATURE                 Location/Qualifiers
source                  1..10
                        mol_type = protein
                        organism = Homo sapiens
SEQUENCE: 447
GFTFRSHWLS                                                        10

SEQ ID NO: 448          moltype = AA  length = 10
FEATURE                 Location/Qualifiers
source                  1..10
                        mol_type = protein
                        organism = Homo sapiens
SEQUENCE: 448
```

-continued

```
GFTFRSHWLS                                                                10

SEQ ID NO: 449          moltype = AA  length = 10
FEATURE                 Location/Qualifiers
source                  1..10
                        mol_type = protein
                        organism = Homo sapiens
SEQUENCE: 449
GFTFRSHWLS                                                                10

SEQ ID NO: 450          moltype = AA  length = 10
FEATURE                 Location/Qualifiers
source                  1..10
                        mol_type = protein
                        organism = Homo sapiens
SEQUENCE: 450
GFTFRSHWLS                                                                10

SEQ ID NO: 451          moltype = AA  length = 20
FEATURE                 Location/Qualifiers
source                  1..20
                        mol_type = protein
                        organism = Homo sapiens
SEQUENCE: 451
WVSFISGDSS NTYYADSVKG                                                     20

SEQ ID NO: 452          moltype = AA  length = 20
FEATURE                 Location/Qualifiers
source                  1..20
                        mol_type = protein
                        organism = Homo sapiens
SEQUENCE: 452
WVSNINYDGS STYYADSVKG                                                     20

SEQ ID NO: 453          moltype = AA  length = 20
FEATURE                 Location/Qualifiers
source                  1..20
                        mol_type = protein
                        organism = Homo sapiens
SEQUENCE: 453
WVSFISGDSS NTYYADSVKG                                                     20

SEQ ID NO: 454          moltype = AA  length = 20
FEATURE                 Location/Qualifiers
source                  1..20
                        mol_type = protein
                        organism = Homo sapiens
SEQUENCE: 454
WVSNINYDGS STYYADSVKG                                                     20

SEQ ID NO: 455          moltype = AA  length = 19
FEATURE                 Location/Qualifiers
source                  1..19
                        mol_type = protein
                        organism = Homo sapiens
SEQUENCE: 455
WVSVTGVHGD TYYADSVKG                                                      19

SEQ ID NO: 456          moltype = AA  length = 19
FEATURE                 Location/Qualifiers
source                  1..19
                        mol_type = protein
                        organism = Homo sapiens
SEQUENCE: 456
WVSVIGNWGD TYYADSVKG                                                      19

SEQ ID NO: 457          moltype = AA  length = 19
FEATURE                 Location/Qualifiers
source                  1..19
                        mol_type = protein
                        organism = Homo sapiens
SEQUENCE: 457
WVSVTTHQGY TYYADSVKG                                                      19

SEQ ID NO: 458          moltype = AA  length = 19
FEATURE                 Location/Qualifiers
source                  1..19
                        mol_type = protein
                        organism = Homo sapiens
```

```
SEQUENCE: 458
WVSATNRYGY TYYADSVKG                                            19

SEQ ID NO: 459          moltype = AA  length = 20
FEATURE                 Location/Qualifiers
source                  1..20
                        mol_type = protein
                        organism = Homo sapiens
SEQUENCE: 459
WVSNINYDGS STYYADSVKG                                           20

SEQ ID NO: 460          moltype = AA  length = 19
FEATURE                 Location/Qualifiers
source                  1..19
                        mol_type = protein
                        organism = Homo sapiens
SEQUENCE: 460
WVSVITPYGD TYYADSVKG                                            19

SEQ ID NO: 461          moltype = AA  length = 19
FEATURE                 Location/Qualifiers
source                  1..19
                        mol_type = protein
                        organism = Homo sapiens
SEQUENCE: 461
WVSVITPYGD TYYADSVKG                                            19

SEQ ID NO: 462          moltype = AA  length = 15
FEATURE                 Location/Qualifiers
source                  1..15
                        mol_type = protein
                        organism = Homo sapiens
SEQUENCE: 462
TFMHGHLGGG LSMDF                                                15

SEQ ID NO: 463          moltype = AA  length = 8
FEATURE                 Location/Qualifiers
source                  1..8
                        mol_type = protein
                        organism = Homo sapiens
SEQUENCE: 463
DTYLHFDY                                                        8

SEQ ID NO: 464          moltype = AA  length = 15
FEATURE                 Location/Qualifiers
source                  1..15
                        mol_type = protein
                        organism = Homo sapiens
SEQUENCE: 464
TFMHGHLGGG LSMDF                                                15

SEQ ID NO: 465          moltype = AA  length = 8
FEATURE                 Location/Qualifiers
source                  1..8
                        mol_type = protein
                        organism = Homo sapiens
SEQUENCE: 465
DTYLHFDY                                                        8

SEQ ID NO: 466          moltype = AA  length = 8
FEATURE                 Location/Qualifiers
source                  1..8
                        mol_type = protein
                        organism = Homo sapiens
SEQUENCE: 466
DTYLHFDY                                                        8

SEQ ID NO: 467          moltype = AA  length = 8
FEATURE                 Location/Qualifiers
source                  1..8
                        mol_type = protein
                        organism = Homo sapiens
SEQUENCE: 467
DTYLHFDY                                                        8

SEQ ID NO: 468          moltype = AA  length = 8
FEATURE                 Location/Qualifiers
source                  1..8
                        mol_type = protein
```

```
                        organism = Homo sapiens
SEQUENCE: 468
DTYLHFDY                                                                  8

SEQ ID NO: 469          moltype = AA  length = 8
FEATURE                 Location/Qualifiers
source                  1..8
                        mol_type = protein
                        organism = Homo sapiens
SEQUENCE: 469
DTYLHFDY                                                                  8

SEQ ID NO: 470          moltype = AA  length = 8
FEATURE                 Location/Qualifiers
source                  1..8
                        mol_type = protein
                        organism = Homo sapiens
SEQUENCE: 470
DTYLHFDY                                                                  8

SEQ ID NO: 471          moltype = AA  length = 8
FEATURE                 Location/Qualifiers
source                  1..8
                        mol_type = protein
                        organism = Homo sapiens
SEQUENCE: 471
DTYLHFDY                                                                  8

SEQ ID NO: 472          moltype = AA  length = 8
FEATURE                 Location/Qualifiers
source                  1..8
                        mol_type = protein
                        organism = Homo sapiens
SEQUENCE: 472
DTYLHFDY                                                                  8

SEQ ID NO: 473          moltype = AA  length = 11
FEATURE                 Location/Qualifiers
source                  1..11
                        mol_type = protein
                        organism = Homo sapiens
SEQUENCE: 473
SGDNIGSFYV H                                                              11

SEQ ID NO: 474          moltype = AA  length = 20
FEATURE                 Location/Qualifiers
source                  1..20
                        mol_type = protein
                        organism = Homo sapiens
SEQUENCE: 474
WVSNINYDGS STYYADSVKG                                                     20

SEQ ID NO: 475          moltype = AA  length = 20
FEATURE                 Location/Qualifiers
source                  1..20
                        mol_type = protein
                        organism = Homo sapiens
SEQUENCE: 475
WVSNINYDGS STYYADSVKG                                                     20

SEQ ID NO: 476          moltype = AA  length = 11
FEATURE                 Location/Qualifiers
source                  1..11
                        mol_type = protein
                        organism = Homo sapiens
SEQUENCE: 476
SGDNIGSFYV H                                                              11

SEQ ID NO: 477          moltype = AA  length = 14
FEATURE                 Location/Qualifiers
source                  1..14
                        mol_type = protein
                        organism = Homo sapiens
SEQUENCE: 477
TGTSSDVGDI NDVS                                                           14

SEQ ID NO: 478          moltype = AA  length = 14
FEATURE                 Location/Qualifiers
source                  1..14
```

```
                        mol_type = protein
                        organism = Homo sapiens
SEQUENCE: 478
TGTSSDVGDI NDVS                                                      14

SEQ ID NO: 479          moltype = AA  length = 14
FEATURE                 Location/Qualifiers
source                  1..14
                        mol_type = protein
                        organism = Homo sapiens
SEQUENCE: 479
TGTSSDVGDI NDVS                                                      14

SEQ ID NO: 480          moltype = AA  length = 14
FEATURE                 Location/Qualifiers
source                  1..14
                        mol_type = protein
                        organism = Homo sapiens
SEQUENCE: 480
TGTSSDVGDI NDVS                                                      14

SEQ ID NO: 481          moltype = AA  length = 14
FEATURE                 Location/Qualifiers
source                  1..14
                        mol_type = protein
                        organism = Homo sapiens
SEQUENCE: 481
TGTSSDVGDI NDVS                                                      14

SEQ ID NO: 482          moltype = AA  length = 14
FEATURE                 Location/Qualifiers
source                  1..14
                        mol_type = protein
                        organism = Homo sapiens
SEQUENCE: 482
TGTSSDVGDI NDVS                                                      14

SEQ ID NO: 483          moltype = AA  length = 14
FEATURE                 Location/Qualifiers
source                  1..14
                        mol_type = protein
                        organism = Homo sapiens
SEQUENCE: 483
TGTSSDVGDI NDVS                                                      14

SEQ ID NO: 484          moltype = AA  length = 11
FEATURE                 Location/Qualifiers
source                  1..11
                        mol_type = protein
                        organism = Homo sapiens
SEQUENCE: 484
LVIYDDNNRP S                                                         11

SEQ ID NO: 485          moltype = AA  length = 11
FEATURE                 Location/Qualifiers
source                  1..11
                        mol_type = protein
                        organism = Homo sapiens
SEQUENCE: 485
LMIYDVNNRP S                                                         11

SEQ ID NO: 486          moltype = AA  length = 11
FEATURE                 Location/Qualifiers
source                  1..11
                        mol_type = protein
                        organism = Homo sapiens
SEQUENCE: 486
LVIYDDNNRP S                                                         11

SEQ ID NO: 487          moltype = AA  length = 11
FEATURE                 Location/Qualifiers
source                  1..11
                        mol_type = protein
                        organism = Homo sapiens
SEQUENCE: 487
LMIYDVNNRP S                                                         11

SEQ ID NO: 488          moltype = AA  length = 11
FEATURE                 Location/Qualifiers
```

```
source                1..11
                      mol_type = protein
                      organism = Homo sapiens
SEQUENCE: 488
LMIYDVNNRP S                                                    11

SEQ ID NO: 489        moltype = AA  length = 11
FEATURE               Location/Qualifiers
source                1..11
                      mol_type = protein
                      organism = Homo sapiens
SEQUENCE: 489
LMIYDVNNRP S                                                    11

SEQ ID NO: 490        moltype = AA  length = 11
FEATURE               Location/Qualifiers
source                1..11
                      mol_type = protein
                      organism = Homo sapiens
SEQUENCE: 490
LMIYDVNNRP S                                                    11

SEQ ID NO: 491        moltype = AA  length = 11
FEATURE               Location/Qualifiers
source                1..11
                      mol_type = protein
                      organism = Homo sapiens
SEQUENCE: 491
LMIYDVNNRP S                                                    11

SEQ ID NO: 492        moltype = AA  length = 11
FEATURE               Location/Qualifiers
source                1..11
                      mol_type = protein
                      organism = Homo sapiens
SEQUENCE: 492
LMIYDVNNRP S                                                    11

SEQ ID NO: 493        moltype = AA  length = 11
FEATURE               Location/Qualifiers
source                1..11
                      mol_type = protein
                      organism = Homo sapiens
SEQUENCE: 493
LMIYDVNNRP S                                                    11

SEQ ID NO: 494        moltype = AA  length = 11
FEATURE               Location/Qualifiers
source                1..11
                      mol_type = protein
                      organism = Homo sapiens
SEQUENCE: 494
LMIYDVNNRP S                                                    11

SEQ ID NO: 495        moltype = AA  length = 10
FEATURE               Location/Qualifiers
source                1..10
                      mol_type = protein
                      organism = Homo sapiens
SEQUENCE: 495
GSWAGSSGSY                                                      10

SEQ ID NO: 496        moltype = AA  length = 10
FEATURE               Location/Qualifiers
source                1..10
                      mol_type = protein
                      organism = Homo sapiens
SEQUENCE: 496
SSYGESLTSY                                                      10

SEQ ID NO: 497        moltype = AA  length = 10
FEATURE               Location/Qualifiers
source                1..10
                      mol_type = protein
                      organism = Homo sapiens
SEQUENCE: 497
ASWTGVEPDY                                                      10

SEQ ID NO: 498        moltype = AA  length = 10
```

```
FEATURE                Location/Qualifiers
source                 1..10
                       mol_type = protein
                       organism = Homo sapiens
SEQUENCE: 498
QSYAGSYLSE                                                              10

SEQ ID NO: 499         moltype = AA  length = 10
FEATURE                Location/Qualifiers
source                 1..10
                       mol_type = protein
                       organism = Homo sapiens
SEQUENCE: 499
SSYGESLTSY                                                              10

SEQ ID NO: 500         moltype = AA  length = 10
FEATURE                Location/Qualifiers
source                 1..10
                       mol_type = protein
                       organism = Homo sapiens
SEQUENCE: 500
SSYGESLTSY                                                              10

SEQ ID NO: 501         moltype = AA  length = 10
FEATURE                Location/Qualifiers
source                 1..10
                       mol_type = protein
                       organism = Homo sapiens
SEQUENCE: 501
SSYGESLTSY                                                              10

SEQ ID NO: 502         moltype = AA  length = 10
FEATURE                Location/Qualifiers
source                 1..10
                       mol_type = protein
                       organism = Homo sapiens
SEQUENCE: 502
SSYGESLTSY                                                              10

SEQ ID NO: 503         moltype = AA  length = 10
FEATURE                Location/Qualifiers
source                 1..10
                       mol_type = protein
                       organism = Homo sapiens
SEQUENCE: 503
STYDGPGLSE                                                              10

SEQ ID NO: 504         moltype = AA  length = 10
FEATURE                Location/Qualifiers
source                 1..10
                       mol_type = protein
                       organism = Homo sapiens
SEQUENCE: 504
SSYGESLTSY                                                              10

SEQ ID NO: 505         moltype = AA  length = 10
FEATURE                Location/Qualifiers
source                 1..10
                       mol_type = protein
                       organism = Homo sapiens
SEQUENCE: 505
SSYGESLTSY                                                              10

SEQ ID NO: 506         moltype = AA  length = 124
FEATURE                Location/Qualifiers
source                 1..124
                       mol_type = protein
                       organism = Homo sapiens
SEQUENCE: 506
QVQLVESGGG LVQPGGSLRL SCAASGFTFS SYVMNWVRQA PGKGLEWVSF ISGDSSNTYY  60
ADSVKGRFTI SRDNSKNTLY LQMNSLRAED TAVYYCARTF MHGHLGGGLS MDFWGQGTLV  120
TVSS                                                                124

SEQ ID NO: 507         moltype = AA  length = 117
FEATURE                Location/Qualifiers
source                 1..117
                       mol_type = protein
                       organism = Homo sapiens
SEQUENCE: 507
```

```
QVQLVESGGG LVQPGGSLRL SCAASGFTFR SHWLSWVRQA PGKGLEWVSN INYDGSSTYY  60
ADSVKGRFTI SRDNSKNTLY LQMNSLRAED TAVYYCARDT YLHFDYWGQG TLVTVSS     117

SEQ ID NO: 508         moltype = AA  length = 124
FEATURE                Location/Qualifiers
source                 1..124
                       mol_type = protein
                       organism = Homo sapiens
SEQUENCE: 508
QVQLVESGGG LVQPGGSLRL SCAASGFTFS SYVMNWVRQA PGKGLEWVSF ISGDSSNTYY  60
ADSVKGRFTI SRDNSKNTLY LQMNSLRAED TAVYYCARTF MHGHLGGGLS MDFWGQGTLV  120
TVSS                                                              124

SEQ ID NO: 509         moltype = AA  length = 117
FEATURE                Location/Qualifiers
source                 1..117
                       mol_type = protein
                       organism = Homo sapiens
SEQUENCE: 509
QVQLVESGGG LVQPGGSLRL SCAASGFTFR SHWLSWVRQA PGKGLEWVSN INYDGSSTYY  60
ADSVKGRFTI SRDNSKNTLY LQMNSLRAED TAVYYCARDT YLHFDYWGQG TLVTVSS     117

SEQ ID NO: 510         moltype = AA  length = 116
FEATURE                Location/Qualifiers
source                 1..116
                       mol_type = protein
                       organism = Homo sapiens
SEQUENCE: 510
QVQLVESGGG LVQPGGSLRL SCAASGFTFR SHWLSWVRQA PGKGLEWVSV TGVHGDTYYA  60
DSVKGRFTIS RDNSKNTLYL QMNSLRAEDT AVYYCARDTY LHFDYWGQGT LVTVSS      116

SEQ ID NO: 511         moltype = AA  length = 116
FEATURE                Location/Qualifiers
source                 1..116
                       mol_type = protein
                       organism = Homo sapiens
SEQUENCE: 511
QVQLVESGGG LVQPGGSLRL SCAASGFTFR SHWLSWVRQA PGKGLEWVSV IGNWGDTYYA  60
DSVKGRFTIS RDNSKNTLYL QMNSLRAEDT AVYYCARDTY LHFDYWGQGT LVTVSS      116

SEQ ID NO: 512         moltype = AA  length = 116
FEATURE                Location/Qualifiers
source                 1..116
                       mol_type = protein
                       organism = Homo sapiens
SEQUENCE: 512
QVQLVESGGG LVQPGGSLRL SCAASGFTFR SHWLSWVRQA PGKGLEWVSV TTHQGYTYYA  60
DSVKGRFTIS RDNSKNTLYL QMNSLRAEDT AVYYCARDTY LHFDYWGQGT LVTVSS      116

SEQ ID NO: 513         moltype = AA  length = 116
FEATURE                Location/Qualifiers
source                 1..116
                       mol_type = protein
                       organism = Homo sapiens
SEQUENCE: 513
QVQLVESGGG LVQPGGSLRL SCAASGFTFR SHWLSWVRQA PGKGLEWVSA TNRYGYTYYA  60
DSVKGRFTIS RDNSKNTLYL QMNSLRAEDT AVYYCARDTY LHFDYWGQGT LVTVSS      116

SEQ ID NO: 514         moltype = AA  length = 117
FEATURE                Location/Qualifiers
source                 1..117
                       mol_type = protein
                       organism = Homo sapiens
SEQUENCE: 514
QVQLVESGGG LVQPGGSLRL SCAASGFTFR SHWLSWVRQA PGKGLEWVSN INYDGSSTYY  60
ADSVKGRFTI SRDNSKNTLY LQMNSLRAED TAVYYCARDT YLHFDYWGQG TLVTVSS     117

SEQ ID NO: 515         moltype = AA  length = 116
FEATURE                Location/Qualifiers
source                 1..116
                       mol_type = protein
                       organism = Homo sapiens
SEQUENCE: 515
QVQLVESGGG LVQPGGSLRL SCAASGFTFR SHWLSWVRQA PGKGLEWVSV ITPYGDTYYA  60
DSVKGRFTIS RDNSKNTLYL QMNSLRAEDT AVYYCARDTY LHFDYWGQGT LVTVSS      116

SEQ ID NO: 516         moltype = AA  length = 116
FEATURE                Location/Qualifiers
source                 1..116
```

-continued

```
                        mol_type = protein
                        organism = Homo sapiens
SEQUENCE: 516
QVQLVESGGG LVQPGGSLRL SCAASGFTFR SHWLSWVRQA PGKGLEWVSV ITPYGDTYYA  60
DSVKGRFTIS RDNSKNTLYL QMNSLRAEDT AVYYCARDTY LHFDYWGQGT LVTVSS      116

SEQ ID NO: 517          moltype = AA  length = 110
FEATURE                 Location/Qualifiers
source                  1..110
                        mol_type = protein
                        organism = Homo sapiens
SEQUENCE: 517
DIELTQPPSV SVAPGQTARI SCSGDNIGSF YVHWYQQKPG QAPVLVIYDD NNRPSGIPER  60
FSGSNSGNTA TLTISGTQAE DEADYYCGSW AGSSGSYVFG GRTKLTVLGQ             110

SEQ ID NO: 518          moltype = AA  length = 113
FEATURE                 Location/Qualifiers
source                  1..113
                        mol_type = protein
                        organism = Homo sapiens
SEQUENCE: 518
DIALTQPASV SGSPGQSITI SCTGTSSDVG DINDVSWYQQ HPGKAPKLMI YDVNNRPSGV  60
SNRFSGSKSG NTASLTISGL QAEDEADYYC SSYGESLTSY VFGGGTKLTV LGQ        113

SEQ ID NO: 519          moltype = AA  length = 110
FEATURE                 Location/Qualifiers
source                  1..110
                        mol_type = protein
                        organism = Homo sapiens
SEQUENCE: 519
DIELTQPPSV SVAPGQTARI SCSGDNIGSF YVHWYQQKPG QAPVLVIYDD NNRPSGIPER  60
FSGSNSGNTA TLTISGTQAE DEADYYCASW TGVEPDYVFG GGTKLTVLGQ             110

SEQ ID NO: 520          moltype = AA  length = 113
FEATURE                 Location/Qualifiers
source                  1..113
                        mol_type = protein
                        organism = Homo sapiens
SEQUENCE: 520
DIALTQPASV SGSPGQSITI SCTGTSSDVG DINDVSWYQQ HPGKAPKLMI YDVNNRPSGV  60
SNRFSGSKSG NTASLTISGL QAEDEADYYC QSYAGSYLSE VFGGGTKLTV LGQ        113

SEQ ID NO: 521          moltype = AA  length = 113
FEATURE                 Location/Qualifiers
source                  1..113
                        mol_type = protein
                        organism = Homo sapiens
SEQUENCE: 521
DIALTQPASV SGSPGQSITI SCTGTSSDVG DINDVSWYQQ HPGKAPKLMI YDVNNRPSGV  60
SNRFSGSKSG NTASLTISGL QAEDEADYYC SSYGESLTSY VFGGGTKLTV LGQ        113

SEQ ID NO: 522          moltype = AA  length = 113
FEATURE                 Location/Qualifiers
source                  1..113
                        mol_type = protein
                        organism = Homo sapiens
SEQUENCE: 522
DIALTQPASV SGSPGQSITI SCTGTSSDVG DINDVSWYQQ HPGKAPKLMI YDVNNRPSGV  60
SNRFSGSKSG NTASLTISGL QAEDEADYYC SSYGESLTSY VFGGGTKLTV LGQ        113

SEQ ID NO: 523          moltype = AA  length = 113
FEATURE                 Location/Qualifiers
source                  1..113
                        mol_type = protein
                        organism = Homo sapiens
SEQUENCE: 523
DIALTQPASV SGSPGQSITI SCTGTSSDVG DINDVSWYQQ HPGKAPKLMI YDVNNRPSGV  60
SNRFSGSKSG NTASLTISGL QAEDEADYYC SSYGESLTSY VFGGGTKLTV LGQ        113

SEQ ID NO: 524          moltype = AA  length = 113
FEATURE                 Location/Qualifiers
source                  1..113
                        mol_type = protein
                        organism = Homo sapiens
SEQUENCE: 524
DIALTQPASV SGSPGQSITI SCTGTSSDVG DINDVSWYQQ HPGKAPKLMI YDVNNRPSGV  60
SNRFSGSKSG NTASLTISGL QAEDEADYYC SSYGESLTSY VFGGGTKLTV LGQ        113

SEQ ID NO: 525          moltype = AA  length = 113
```

```
FEATURE                Location/Qualifiers
source                 1..113
                       mol_type = protein
                       organism = Homo sapiens
SEQUENCE: 525
DIALTQPASV SGSPGQSITI SCTGTSSDVG DINDVSWYQQ HPGKAPKLMI YDVNNRPSGV  60
SNRFSGSKSG NTASLTISGL QAEDEADYYC STYDGPGLSE VFGGGTKLTV LGQ         113

SEQ ID NO: 526         moltype = AA  length = 113
FEATURE                Location/Qualifiers
source                 1..113
                       mol_type = protein
                       organism = Homo sapiens
SEQUENCE: 526
DIALTQPASV SGSPGQSITI SCTGTSSDVG DINDVSWYQQ HPGKAPKLMI YDVNNRPSGV  60
SNRFSGSKSG NTASLTISGL QAEDEADYYC SSYGESLTSY VFGGGTKLTV LGQ         113

SEQ ID NO: 527         moltype = AA  length = 113
FEATURE                Location/Qualifiers
source                 1..113
                       mol_type = protein
                       organism = Homo sapiens
SEQUENCE: 527
DIALTQPASV SGSPGQSITI SCTGTSSDVG DINDVSWYQQ HPGKAPKLMI YDVNNRPSGV  60
SNRFSGSKSG NTASLTISGL QAEDEADYYC STYDGPGLSE VFGGGTKLTV LGQ         113

SEQ ID NO: 528         moltype = DNA  length = 372
FEATURE                Location/Qualifiers
source                 1..372
                       mol_type = other DNA
                       organism = Homo sapiens
SEQUENCE: 528
caggtgcaat tggtggaaag cggcggcggc ctggtgcaac cgggcggcag cctgcgtctg  60
agctgcgcgg cctccggatt taccttttct tcttatgtta tgaattgggt gcgccaagcc  120
cctgggaagg gtctcgagtg ggtgagcttt atctctggtg attctagcaa tacctattat  180
gcggatagcg tgaaaggccg ttttaccatt tcacgtgata attcgaaaaa caccctgtat  240
ctgcaaatga acagcctgcg tgcggaagat acggccgtgt attattgcgc gcgtactttt  300
atgcatggtc atcttggtgg tggtctttct atggattttt ggggccaagg caccctggtg  360
acggttagct ca                                                      372

SEQ ID NO: 529         moltype = DNA  length = 350
FEATURE                Location/Qualifiers
source                 1..350
                       mol_type = other DNA
                       organism = Homo sapiens
SEQUENCE: 529
caggtgcaat tggtggaaag cggcggcggc ctggtgcaac cgggcggcag cctgcgtcta  60
gctgcgcggc ctccggattt acctttcgtt ctcattggct ttcttgggtg cgccaagccc  120
ctgggaaggg tctcgagtgg gtgagcaata tcaattatga tggtagctct acctattatg  180
cggatagcgt gaaaggccgt tttaccattt cacgtgataa ttcgaaaaac accctgtatc  240
tgcaaatgaa cagcctgcgt gcggaagata cggccgtgta ttattgcgcg cgtgatactt  300
atcttcattt tgattattgg ggccaaggca ccctggtgac ggttagctca             350

SEQ ID NO: 530         moltype = DNA  length = 372
FEATURE                Location/Qualifiers
source                 1..372
                       mol_type = other DNA
                       organism = Homo sapiens
SEQUENCE: 530
caggtgcaat tggtggaaag cggcggcggc ctggtgcaac cgggcggcag cctgcgtctg  60
agctgcgcgg cctccggatt taccttttct tcttatgtta tgaattgggt gcgccaagcc  120
cctgggaagg gtctcgagtg ggtgagcttt atctctggtg attctagcaa tacctattat  180
gcggatagcg tgaaaggccg ttttaccatt tcacgtgata attcgaaaaa caccctgtat  240
ctgcaaatga acagcctgcg tgcggaagat acggccgtgt attattgcgc gcgtactttt  300
atgcatggtc atcttggtgg tggtctttct atggattttt ggggccaagg caccctggtg  360
acggttagct ca                                                      372

SEQ ID NO: 531         moltype = DNA  length = 351
FEATURE                Location/Qualifiers
source                 1..351
                       mol_type = other DNA
                       organism = Homo sapiens
SEQUENCE: 531
caggtgcaat tggtggaaag cggcggcggc ctggtgcaac cgggcggcag cctgcgtctg  60
agctgcgcgg cctccggatt tacctttcgt tctcattggc tttcttgggt gcgccaagcc  120
cctgggaagg gtctcgagtg ggtgagcaat atcaattatg atggtagctc tacctattat  180
gcggatagcg tgaaaggccg ttttaccatt tcacgtgata attcgaaaaa caccctgtat  240
ctgcaaatga acagcctgcg tgcggaagat acggccgtgt attattgcgc gcgtgatact  300
tatcttcatt ttgattattg gggccaaggc accctggtga cggttagctc a           351
```

```
SEQ ID NO: 532         moltype = DNA  length = 348
FEATURE                Location/Qualifiers
source                 1..348
                       mol_type = other DNA
                       organism = Homo sapiens
SEQUENCE: 532
caggtgcaat tggtggaaag cggcggcggc ctggtgcaac cgggcggcag cctgcgtctg  60
agctgcgcgg cctccggatt tacctttcgt tctcattggc tttcttgggt gcgccaagcc  120
cctgggaagg gtctcgagtg ggtgagcgtt actggtgttc atggtgatac ttattatgct  180
gattctgtta agggtcgttt taccatttca cgtgataatt cgaaaaacac cctgtatctg  240
caaatgaaca gcctgcgtgc ggaagatacg gccgtgtatt attgcgcgcg tgatacttat  300
cttcattttg attattgggg ccaaggcacc ctggtgacgg ttagctca               348

SEQ ID NO: 533         moltype = DNA  length = 348
FEATURE                Location/Qualifiers
source                 1..348
                       mol_type = other DNA
                       organism = Homo sapiens
SEQUENCE: 533
caggtgcaat tggtggaaag cggcggcggc ctggtgcaac cgggcggcag cctgcgtctg  60
agctgcgcgg cctccggatt tacctttcgt tctcattggc tttcttgggt gcgccaagcc  120
cctgggaagg gtctcgagtg ggtgagcgtt attggtaatt ggggtgatac ttattatgct  180
gattctgtta agggtcgttt taccatttca cgtgataatt cgaaaaacac cctgtatctg  240
caaatgaaca gcctgcgtgc ggaagatacg gccgtgtatt attgcgcgcg tgatacttat  300
cttcattttg attattgggg ccaaggcacc ctggtgacgg ttagctca               348

SEQ ID NO: 534         moltype = DNA  length = 348
FEATURE                Location/Qualifiers
source                 1..348
                       mol_type = other DNA
                       organism = Homo sapiens
SEQUENCE: 534
caggtgcaat tggtggaaag cggcggcggc ctggtgcaac cgggcggcag cctgcgtctg  60
agctgcgcgg cctccggatt tacctttcgt tctcattggc tttcttgggt gcgccaagcc  120
cctgggaagg gtctcgagtg ggtgagcgtt actactcatc agggttatac ttattatgct  180
gattctgtta agggtcgttt taccatttca cgtgataatt cgaaaaacac cctgtatctg  240
caaatgaaca gcctgcgtgc ggaagatacg gccgtgtatt attgcgcgcg tgatacttat  300
cttcattttg attattgggg ccaaggcacc ctggtgacgg ttagctca               348

SEQ ID NO: 535         moltype = DNA  length = 348
FEATURE                Location/Qualifiers
source                 1..348
                       mol_type = other DNA
                       organism = Homo sapiens
SEQUENCE: 535
caggtgcaat tggtggaaag cggcggcggc ctggtgcaac cgggcggcag cctgcgtctg  60
agctgcgcgg cctccggatt tacctttcgt tctcattggc tttcttgggt gcgccaagcc  120
cctgggaagg gtctcgagtg ggtgagcgct actaatcgtt atggttatac ttattatgct  180
gattctgtta agggtcgttt taccatttca cgtgataatt cgaaaaacac cctgtatctg  240
caaatgaaca gcctgcgtgc ggaagatacg gccgtgtatt attgcgcgcg tgatacttat  300
cttcattttg attattgggg ccaaggcacc ctggtgacgg ttagctca               348

SEQ ID NO: 536         moltype = DNA  length = 351
FEATURE                Location/Qualifiers
source                 1..351
                       mol_type = other DNA
                       organism = Homo sapiens
SEQUENCE: 536
caggtgcaat tggtggaaag cggcggcggc ctggtgcaac cgggcggcag cctgcgtctg  60
agctgcgcgg cctccggatt tacctttcgt tctcattggc tttcttgggt gcgccaagcc  120
cctgggaagg gtctcgagtg ggtgagcaat atcaattatg atggtagctc tacctattat  180
gcggatagcg tgaaaggccg ttttaccatt tcacgtgata attcgaaaaa caccctgtat  240
ctgcaaatga acagcctgcg tgcggaagat acggccgtgt attattgcgc gcgtgatact  300
tatcttcatt ttgattattg gggccaaggc accctggtga cggttagctc a           351

SEQ ID NO: 537         moltype = DNA  length = 348
FEATURE                Location/Qualifiers
source                 1..348
                       mol_type = other DNA
                       organism = Homo sapiens
SEQUENCE: 537
caggtgcaat tggtggaaag cggcggcggc ctggtgcaac cgggcggcag cctgcgtctg  60
agctgcgcgg cctccggatt tacctttcgt tctcattggc tttcttgggt gcgccaagcc  120
cctgggaagg gtctcgagtg ggtgagcgtt attactcctt atggtgatac ttattatgct  180
gattctgtta agggtcgttt taccatttca cgtgataatt cgaaaaacac cctgtatctg  240
caaatgaaca gcctgcgtgc ggaagatacg gccgtgtatt attgcgcgcg tgatacttat  300
cttcattttg attattgggg ccaaggcacc ctggtgacgg ttagctca               348
```

```
SEQ ID NO: 538          moltype = DNA  length = 348
FEATURE                 Location/Qualifiers
source                  1..348
                        mol_type = other DNA
                        organism = Homo sapiens
SEQUENCE: 538
caggtgcaat tggtggaaag cggcggcggc ctggtgcaac cgggcggcag cctgcgtctg  60
agctgcgcgg cctccggatt tacctttcgt tctcattggc tttcttgggt gcgccaagcc  120
cctgggaagg gtctcgagtg ggtgagcgtt attactcctt atggtgatac ttattatgct  180
gattctgtta agggtcgttt taccatttca cgtgataatt cgaaaaacac cctgtatctg  240
caaatgaaca gcctgcgtgc ggaagatacg gccgtgtatt attgcgcgcg tgatacttat  300
cttcattttg attattgggg ccaaggcacc ctggtgacgg ttagctca               348

SEQ ID NO: 539          moltype = DNA  length = 330
FEATURE                 Location/Qualifiers
source                  1..330
                        mol_type = other DNA
                        organism = Homo sapiens
SEQUENCE: 539
gatatcgaac tgacccagcc gccttcagtg agcgttgcac caggtcagac cgcgcgtatc  60
tcgtgtagcg gcgataatat tggttctttt tatgttcatt ggtaccagca gaaacccggg  120
caggcgccag ttcttgtgat ttatgatgat aataatcgtc cctcaggcat cccggaacgc  180
tttagcggat ccaacagcgg caacaccgcg accctgacca ttagcggcac tcaggcggaa  240
gacgaagcgg attattattg cggttcttgg gctggttctt ctggttctta tgtgtttggc  300
ggccgcacga agttaaccgt tcttggccag                                   330

SEQ ID NO: 540          moltype = DNA  length = 339
FEATURE                 Location/Qualifiers
source                  1..339
                        mol_type = other DNA
                        organism = Homo sapiens
SEQUENCE: 540
gatatcgcac tgacccagcc agcttcagtg agcggctcac caggtcagag cattaccatc  60
tcgtgtacgg gtactagcag cgatgttggt gatattaatg atgtgtcttg gtaccagcag  120
catcccggga aggcgccgaa acttatgatt tatgatgtta ataatcgtcc ctcaggcgtg  180
agcaaccgtt ttagcggatc caaaagcggc aacaccgcga gcctgaccat tagcggcctg  240
caagcggaag acgaagcgga ttattattgc tcttcttatg gtgagtctct tacttcttat  300
gtgtttggcg gcggcacgaa gttaaccgtt cttggccag                         339

SEQ ID NO: 541          moltype = DNA  length = 330
FEATURE                 Location/Qualifiers
source                  1..330
                        mol_type = other DNA
                        organism = Homo sapiens
SEQUENCE: 541
gatatcgaac tgacccagcc gccttcagtg agcgttgcac caggtcagac cgcgcgtatc  60
tcgtgtagcg gcgataatat tggttctttt tatgttcatt ggtaccagca gaaacccggg  120
caggcgccag ttcttgtgat ttatgatgat aataatcgtc cctcaggcat cccggaacgc  180
tttagcggat ccaacagcgg caacaccgcg accctgacca ttagcggcac tcaggcggaa  240
gacgaagcgg attattattg cgcttcttgg actggtgttg agcctgatta tgtgtttggc  300
ggcggcacga agttaaccgt tcttggccag                                   330

SEQ ID NO: 542          moltype = DNA  length = 339
FEATURE                 Location/Qualifiers
source                  1..339
                        mol_type = other DNA
                        organism = Homo sapiens
SEQUENCE: 542
gatatcgcac tgacccagcc agcttcagtg agcggctcac caggtcagag cattaccatc  60
tcgtgtacgg gtactagcag cgatgttggt gatattaatg atgtgtcttg gtaccagcag  120
catcccggga aggcgccgaa acttatgatt tatgatgtta ataatcgtcc ctcaggcgtg  180
agcaaccgtt ttagcggatc caaaagcggc aacaccgcga gcctgaccat tagcggcctg  240
caagcggaag acgaagcgga ttattattgc cagtcttatg ctggttctta tctttctgag  300
gtgtttggcg gcggcacgaa gttaaccgtt cttggccag                         339

SEQ ID NO: 543          moltype = DNA  length = 339
FEATURE                 Location/Qualifiers
source                  1..339
                        mol_type = other DNA
                        organism = Homo sapiens
SEQUENCE: 543
gatatcgcac tgacccagcc agcttcagtg agcggctcac caggtcagag cattaccatc  60
tcgtgtacgg gtactagcag cgatgttggt gatattaatg atgtgtcttg gtaccagcag  120
catcccggga aggcgccgaa acttatgatt tatgatgtta ataatcgtcc ctcaggcgtg  180
agcaaccgtt ttagcggatc caaaagcggc aacaccgcga gcctgaccat tagcggcctg  240
caagcggaag acgaagcgga ttattattgc tcttcttatg gtgagtctct tacttcttat  300
gtgtttggcg gcggcacgaa gttaaccgtt cttggccag                         339

SEQ ID NO: 544          moltype = DNA  length = 339
```

-continued

```
FEATURE               Location/Qualifiers
source                1..339
                      mol_type = other DNA
                      organism = Homo sapiens
SEQUENCE: 544
gatatcgcac tgacccagcc agcttcagtg agcggctcac caggtcagag cattaccatc  60
tcgtgtacgg gtactagcag cgatgttggt gatattaatg atgtgtcttg gtaccagcag  120
catcccggga aggcgccgaa acttatgatt tatgatgtta ataatcgtcc ctcaggcgtg  180
agcaaccgtt ttagcggatc caaaagcggc aacaccgcga gcctgaccat tagcggcctg  240
caagcggaag acgaagcgga ttattattgc tcttcttatg gtgagtctct tacttcttat  300
gtgtttggcg gcggcacgaa gttaaccgtt cttggccag                         339

SEQ ID NO: 545        moltype = DNA  length = 339
FEATURE               Location/Qualifiers
source                1..339
                      mol_type = other DNA
                      organism = Homo sapiens
SEQUENCE: 545
gatatcgcac tgacccagcc agcttcagtg agcggctcac caggtcagag cattaccatc  60
tcgtgtacgg gtactagcag cgatgttggt gatattaatg atgtgtcttg gtaccagcag  120
catcccggga aggcgccgaa acttatgatt tatgatgtta ataatcgtcc ctcaggcgtg  180
agcaaccgtt ttagcggatc caaaagcggc aacaccgcga gcctgaccat tagcggcctg  240
caagcggaag acgaagcgga ttattattgc tcttcttatg gtgagtctct tacttcttat  300
gtgtttggcg gcggcacgaa gttaaccgtt cttggccag                         339

SEQ ID NO: 546        moltype = DNA  length = 339
FEATURE               Location/Qualifiers
source                1..339
                      mol_type = other DNA
                      organism = Homo sapiens
SEQUENCE: 546
gatatcgcac tgacccagcc agcttcagtg agcggctcac caggtcagag cattaccatc  60
tcgtgtacgg gtactagcag cgatgttggt gatattaatg atgtgtcttg gtaccagcag  120
catcccggga aggcgccgaa acttatgatt tatgatgtta ataatcgtcc ctcaggcgtg  180
agcaaccgtt ttagcggatc caaaagcggc aacaccgcga gcctgaccat tagcggcctg  240
caagcggaag acgaagcgga ttattattgc tcttcttatg gtgagtctct tacttcttat  300
gtgtttggcg gcggcacgaa gttaaccgtt cttggccag                         339

SEQ ID NO: 547        moltype = DNA  length = 339
FEATURE               Location/Qualifiers
source                1..339
                      mol_type = other DNA
                      organism = Homo sapiens
SEQUENCE: 547
gatatcgcac tgacccagcc agcttcagtg agcggctcac caggtcagag cattaccatc  60
tcgtgtacgg gtactagcag cgatgttggt gatattaatg atgtgtcttg gtaccagcag  120
catcccggga aggcgccgaa acttatgatt tatgatgtta ataatcgtcc ctcaggcgtg  180
agcaaccgtt ttagcggatc caaaagcggc aacaccgcga gcctgaccat tagcggcctg  240
caagcggaag acgaagcgga ttattattgc tctacttatg atggtcctgg tctttctgag  300
gtgtttggcg gcggcacgaa gttaaccgtt cttggccag                         339

SEQ ID NO: 548        moltype = DNA  length = 339
FEATURE               Location/Qualifiers
source                1..339
                      mol_type = other DNA
                      organism = Homo sapiens
SEQUENCE: 548
gatatcgcac tgacccagcc agcttcagtg agcggctcac caggtcagag cattaccatc  60
tcgtgtacgg gtactagcag cgatgttggt gatattaatg atgtgtcttg gtaccagcag  120
catcccggga aggcgccgaa acttatgatt tatgatgtta ataatcgtcc ctcaggcgtg  180
agcaaccgtt ttagcggatc caaaagcggc aacaccgcga gcctgaccat tagcggcctg  240
caagcggaag acgaagcgga ttattattgc tcttcttatg gtgagtctct tacttcttat  300
gtgtttggcg gcggcacgaa gttaaccgtt cttggccag                         339

SEQ ID NO: 549        moltype = DNA  length = 339
FEATURE               Location/Qualifiers
source                1..339
                      mol_type = other DNA
                      organism = Homo sapiens
SEQUENCE: 549
gatatcgcac tgacccagcc agcttcagtg agcggctcac caggtcagag cattaccatc  60
tcgtgtacgg gtactagcag cgatgttggt gatattaatg atgtgtcttg gtaccagcag  120
catcccggga aggcgccgaa acttatgatt tatgatgtta ataatcgtcc ctcaggcgtg  180
agcaaccgtt ttagcggatc caaaagcggc aacaccgcga gcctgaccat tagcggcctg  240
caagcggaag acgaagcgga ttattattgc tctacttatg atggtcctgg tctttctgag  300
gtgtttggcg gcggcacgaa gttaaccgtt cttggccag                         339

SEQ ID NO: 550        moltype = AA  length = 469
FEATURE               Location/Qualifiers
```

```
source                  1..469
                        mol_type = protein
                        organism = Homo sapiens
SEQUENCE: 550
MAWVWTLPFL MAAAQSVQAQ VQLVESGGGL VQPGGSLRLS CAASGFTFSS YVMNWVRQAP  60
GKGLEWVSFI SGDSSNTYYA DSVKGRFTIS RDNSKNTLYL QMNSLRAEDT AVYYCARTFM  120
HGHLGGGLSM DFWGQGTLVT VSSASTKGPS VFPLAPCSRS TSESTAALGC LVKDYFPEPV  180
TVSWNSGALT SGVHTFPAVL QSSGLYSLSS VVTVPSSNFG TQTYTCNVDH KPSNTKVDKT  240
VERKCCVECP PCPAPPVAGP SVFLFPPKPK DTLMISRTPE VTCVVVDVSH EDPEVQFNWY  300
VDGVEVHNAK TKPREEQFNS TFRVVSVLTV VHQDWLNGKE YKCKVSNKGL PAPIEKTISK  360
TKGQPREPQV YTLPPSREEM TKNQVSLTCL VKGFYPSDIA VEWESNGQPE NNYKTTPPML  420
DSDGSFFLYS KLTVDKSRWQ QGNVFSCSVM HEALHNHYTQ KSLSLSPGK             469

SEQ ID NO: 551          moltype = AA  length = 462
FEATURE                 Location/Qualifiers
source                  1..462
                        mol_type = protein
                        organism = Homo sapiens
SEQUENCE: 551
MAWVWTLPFL MAAAQSVQAQ VQLVESGGGL VQPGGSLRLS CAASGFTFRS HWLSWVRQAP  60
GKGLEWVSNI NYDGSSTYYA DSVKGRFTIS RDNSKNTLYL QMNSLRAEDT AVYYCARDTY  120
LHFDYWGQGT LVTVSSASTK GPSVFPLAPC SRSTSESTAA LGCLVKDYFP EPVTVSWNSG  180
ALTSGVHTFP AVLQSSGLYS LSSVVTVPSS NFGTQTYTCN VDHKPSNTKV DKTVERKCCV  240
ECPPCPAPPV AGPSVFLFPP KPKDTLMISR TPEVTCVVVD VSHEDPEVQF NWYVDGVEVH  300
NAKTKPREEQ FNSTFRVVSV LTVVHQDWLN GKEYKCKVSN KGLPAPIEKT ISKTKGQPRE  360
PQVYTLPPSR EEMTKNQVSL TCLVKGFYPS DIAVEWESNG QPENNYKTTP PMLDSDGSFF  420
LYSKLTVDKS RWQQGNVFSC SVMHEALHNH YTQKSLSLSP GK                    462

SEQ ID NO: 552          moltype = AA  length = 469
FEATURE                 Location/Qualifiers
source                  1..469
                        mol_type = protein
                        organism = Homo sapiens
SEQUENCE: 552
MAWVWTLPFL MAAAQSVQAQ VQLVESGGGL VQPGGSLRLS CAASGFTFSS YVMNWVRQAP  60
GKGLEWVSFI SGDSSNTYYA DSVKGRFTIS RDNSKNTLYL QMNSLRAEDT AVYYCARTFM  120
HGHLGGGLSM DFWGQGTLVT VSSASTKGPS VFPLAPCSRS TSESTAALGC LVKDYFPEPV  180
TVSWNSGALT SGVHTFPAVL QSSGLYSLSS VVTVPSSNFG TQTYTCNVDH KPSNTKVDKT  240
VERKCCVECP PCPAPPVAGP SVFLFPPKPK DTLMISRTPE VTCVVVDVSH EDPEVQFNWY  300
VDGVEVHNAK TKPREEQFNS TFRVVSVLTV VHQDWLNGKE YKCKVSNKGL PAPIEKTISK  360
TKGQPREPQV YTLPPSREEM TKNQVSLTCL VKGFYPSDIA VEWESNGQPE NNYKTTPPML  420
DSDGSFFLYS KLTVDKSRWQ QGNVFSCSVM HEALHNHYTQ KSLSLSPGK             469

SEQ ID NO: 553          moltype = AA  length = 462
FEATURE                 Location/Qualifiers
source                  1..462
                        mol_type = protein
                        organism = Homo sapiens
SEQUENCE: 553
MAWVWTLPFL MAAAQSVQAQ VQLVESGGGL VQPGGSLRLS CAASGFTFRS HWLSWVRQAP  60
GKGLEWVSNI NYDGSSTYYA DSVKGRFTIS RDNSKNTLYL QMNSLRAEDT AVYYCARDTY  120
LHFDYWGQGT LVTVSSASTK GPSVFPLAPC SRSTSESTAA LGCLVKDYFP EPVTVSWNSG  180
ALTSGVHTFP AVLQSSGLYS LSSVVTVPSS NFGTQTYTCN VDHKPSNTKV DKTVERKCCV  240
ECPPCPAPPV AGPSVFLFPP KPKDTLMISR TPEVTCVVVD VSHEDPEVQF NWYVDGVEVH  300
NAKTKPREEQ FNSTFRVVSV LTVVHQDWLN GKEYKCKVSN KGLPAPIEKT ISKTKGQPRE  360
PQVYTLPPSR EEMTKNQVSL TCLVKGFYPS DIAVEWESNG QPENNYKTTP PMLDSDGSFF  420
LYSKLTVDKS RWQQGNVFSC SVMHEALHNH YTQKSLSLSP GK                    462

SEQ ID NO: 554          moltype = AA  length = 461
FEATURE                 Location/Qualifiers
source                  1..461
                        mol_type = protein
                        organism = Homo sapiens
SEQUENCE: 554
MAWVWTLPFL MAAAQSVQAQ VQLVESGGGL VQPGGSLRLS CAASGFTFRS HWLSWVRQAP  60
GKGLEWVSVT GVHGDTYYAD SVKGRFTISR DNSKNTLYLQ MNSLRAEDTA VYYCARDTYL  120
HFDYWGQGTL VTVSSASTKG PSVFPLAPCS RSTSESTAAL GCLVKDYFPE PVTVSWNSGA  180
LTSGVHTFPA VLQSSGLYSL SSVVTVPSSN FGTQTYTCNV DHKPSNTKVD KTVERKCCVE  240
CPPCPAPPVA GPSVFLFPPK PKDTLMISRT PEVTCVVVDV SHEDPEVQFN WYVDGVEVHN  300
AKTKPREEQF NSTFRVVSVL TVVHQDWLNG KEYKCKVSNK GLPAPIEKTI SKTKGQPREP  360
QVYTLPPSRE EMTKNQVSLT CLVKGFYPSD IAVEWESNGQ PENNYKTTPP MLDSDGSFFL  420
YSKLTVDKSR WQQGNVFSCS VMHEALHNHY TQKSLSLSPG K                     461

SEQ ID NO: 555          moltype = AA  length = 461
FEATURE                 Location/Qualifiers
source                  1..461
                        mol_type = protein
                        organism = Homo sapiens
SEQUENCE: 555
```

```
MAWVWTLPFL MAAAQSVQAQ VQLVESGGGL VQPGGSLRLS CAASGFTFRS HWLSWVRQAP  60
GKGLEWVSVI GNWGDTYYAD SVKGRFTISR DNSKNTLYLQ MNSLRAEDTA VYYCARDTYL  120
HFDYWGQGTL VTVSSASTKG PSVFPLAPCS RSTSESTAAL GCLVKDYFPE PVTVSWNSGA  180
LTSGVHTFPA VLQSSGLYSL SSVVTVPSSN FGTQTYTCNV DHKPSNTKVD KTVERKCCVE  240
CPPCPAPPVA GPSVFLFPPK PKDTLMISRT PEVTCVVVDV SHEDPEVQFN WYVDGVEVHN  300
AKTKPREEQF NSTFRVVSVL TVVHQDWLNG KEYKCKVSNK GLPAPIEKTI SKTKGQPREP  360
QVYTLPPSRE EMTKNQVSLT CLVKGFYPSD IAVEWESNGQ PENNYKTTPP MLDSDGSFFL  420
YSKLTVDKSR WQQGNVFSCS VMHEALHNHY TQKSLSLSPG K                    461

SEQ ID NO: 556          moltype = AA  length = 461
FEATURE                 Location/Qualifiers
source                  1..461
                        mol_type = protein
                        organism = Homo sapiens
SEQUENCE: 556
MAWVWTLPFL MAAAQSVQAQ VQLVESGGGL VQPGGSLRLS CAASGFTFRS HWLSWVRQAP  60
GKGLEWVSVT THQGYTYYAD SVKGRFTISR DNSKNTLYLQ MNSLRAEDTA VYYCARDTYL  120
HFDYWGQGTL VTVSSASTKG PSVFPLAPCS RSTSESTAAL GCLVKDYFPE PVTVSWNSGA  180
LTSGVHTFPA VLQSSGLYSL SSVVTVPSSN FGTQTYTCNV DHKPSNTKVD KTVERKCCVE  240
CPPCPAPPVA GPSVFLFPPK PKDTLMISRT PEVTCVVVDV SHEDPEVQFN WYVDGVEVHN  300
AKTKPREEQF NSTFRVVSVL TVVHQDWLNG KEYKCKVSNK GLPAPIEKTI SKTKGQPREP  360
QVYTLPPSRE EMTKNQVSLT CLVKGFYPSD IAVEWESNGQ PENNYKTTPP MLDSDGSFFL  420
YSKLTVDKSR WQQGNVFSCS VMHEALHNHY TQKSLSLSPG K                    461

SEQ ID NO: 557          moltype = AA  length = 465
FEATURE                 Location/Qualifiers
source                  1..465
                        mol_type = protein
                        organism = Homo sapiens
SEQUENCE: 557
MKHLWFFLLL VAAPRWVLSQ VQLVESGGGL VQPGGSLRLS CAASGFTFRS HWLSWVRQAP  60
GKGLEWVSAT NRYGYTYYAD SVKGRFTISR DNSKNTLYLQ MNSLRAEDTA VYYCARDTYL  120
HFDYWGQGTL VTVSSAKTTA PSVYPLAPVC GDTTGSSVTL GCLVKGYFPE PVTLTWNSGS  180
LSSGVHTFPA VLQSDLYTLS SSVTVTSSTW PSQSITCNVA HPASSTKVDK KIEPRGPTIK  240
PCPPCKCPAP NLLGGPSVFI FPPKIKDVLM ISLSPIVTCV VVDVSEDDPD VQISWFVNNV  300
EVHTAQTQTH REDYNSTLRV VSALPIQHQD WMSGKEFKCK VNNKDLPAPI ERTISKPKGS  360
VRAPQVYVLP PPEEEMTKKQ VTLTCMVTDF MPEDIYVEWT NNGKTELNYK NTEPVLDSDG  420
SYFMYSKLRV EKKNWVERNS YSCSVVHEGL HNHHTTKSFS RTPGK                465

SEQ ID NO: 558          moltype = AA  length = 462
FEATURE                 Location/Qualifiers
source                  1..462
                        mol_type = protein
                        organism = Homo sapiens
SEQUENCE: 558
MAWVWTLPFL MAAAQSVQAQ VQLVESGGGL VQPGGSLRLS CAASGFTFRS HWLSWVRQAP  60
GKGLEWVSNI NYDGSSTYYA DSVKGRFTIS RDNSKNTLYL QMNSLRAEDT AVYYCARDTY  120
LHFDYWGQGT LVTVSSASTK GPSVFPLAPC SRSTSESTAA LGCLVKDYFP EPVTVSWNSG  180
ALTSGVHTFP AVLQSSGLYS LSSVVTVPSS NFGTQTYTCN VDHKPSNTKV DKTVERKCCV  240
ECPPCPAPPV AGPSVFLFPP KPKDTLMISR TPEVTCVVVD VSHEDPEVQF NWYVDGVEVH  300
NAKTKPREEQ FNSTFRVVSV LTVVHQDWLN GKEYKCKVSN KGLPAPIEKT ISKTKGQPRE  360
PQVYTLPPSR EEMTKNQVSL TCLVKGFYPS DIAVEWESNG QPENNYKTTP PMLDSDGSFF  420
LYSKLTVDKS RWQQGNVFSC SVMHEALHNH YTQKSLSLSP GK                   462

SEQ ID NO: 559          moltype = AA  length = 461
FEATURE                 Location/Qualifiers
source                  1..461
                        mol_type = protein
                        organism = Homo sapiens
SEQUENCE: 559
MAWVWTLPFL MAAAQSVQAQ VQLVESGGGL VQPGGSLRLS CAASGFTFRS HWLSWVRQAP  60
GKGLEWVSVI TPYGDTYYAD SVKGRFTISR DNSKNTLYLQ MNSLRAEDTA VYYCARDTYL  120
HFDYWGQGTL VTVSSASTKG PSVFPLAPCS RSTSESTAAL GCLVKDYFPE PVTVSWNSGA  180
LTSGVHTFPA VLQSSGLYSL SSVVTVPSSN FGTQTYTCNV DHKPSNTKVD KTVERKCCVE  240
CPPCPAPPVA GPSVFLFPPK PKDTLMISRT PEVTCVVVDV SHEDPEVQFN WYVDGVEVHN  300
AKTKPREEQF NSTFRVVSVL TVVHQDWLNG KEYKCKVSNK GLPAPIEKTI SKTKGQPREP  360
QVYTLPPSRE EMTKNQVSLT CLVKGFYPSD IAVEWESNGQ PENNYKTTPP MLDSDGSFFL  420
YSKLTVDKSR WQQGNVFSCS VMHEALHNHY TQKSLSLSPG K                    461

SEQ ID NO: 560          moltype = AA  length = 461
FEATURE                 Location/Qualifiers
source                  1..461
                        mol_type = protein
                        organism = Homo sapiens
SEQUENCE: 560
MAWVWTLPFL MAAAQSVQAQ VQLVESGGGL VQPGGSLRLS CAASGFTFRS HWLSWVRQAP  60
GKGLEWVSVI TPYGDTYYAD SVKGRFTISR DNSKNTLYLQ MNSLRAEDTA VYYCARDTYL  120
HFDYWGQGTL VTVSSASTKG PSVFPLAPCS RSTSESTAAL GCLVKDYFPE PVTVSWNSGA  180
LTSGVHTFPA VLQSSGLYSL SSVVTVPSSN FGTQTYTCNV DHKPSNTKVD KTVERKCCVE  240
```

```
CPPCPAPPVA GPSVFLFPPK PKDTLMISRT PEVTCVVVDV SHEDPEVQFN WYVDGVEVHN  300
AKTKPREEQF NSTFRVVSVL TVVHQDWLNG KEYKCKVSNK GLPAPIEKTI SKTKGQPREP  360
QVYTLPPSRE EMTKNQVSLT CLVKGFYPSD IAVEWESNGQ PENNYKTTPP MLDSDGSFFL  420
YSKLTVDKSR WQQGNVFSCS VMHEALHNHY TQKSLSLSPG K                      461

SEQ ID NO: 561          moltype = AA  length = 130
FEATURE                 Location/Qualifiers
source                  1..130
                        mol_type = protein
                        organism = Homo sapiens
SEQUENCE: 561
MSVLTQVLAL LLLWLTGTRC DIELTQPPSV SVAPGQTARI SCSGDNIGSF YVHWYQQKPG  60
QAPVLVIYDD NNRPSGIPER FSGSNSGNTA TLTISGTQAE DEADYYCGSW AGSSGSYVFG  120
GRTKLTVLGQ                                                        130

SEQ ID NO: 562          moltype = AA  length = 237
FEATURE                 Location/Qualifiers
source                  1..237
                        mol_type = protein
                        organism = Homo sapiens
SEQUENCE: 562
MSVLTQVLAL LLLWLTGTRC DIALTQPASV SGSPGQSITI SCTGTSSDVG DINDVSWYQQ  60
HPGKAPKLMI YDVNNRPSGV SNRFSGSKSG NTASLTISGL QAEDEADYYC SSYGESLTSY  120
VFGGGTKLTV LGQPKAAPSV TLFPPSSEEL QANKATLVCL ISDFYPGAVT VAWKADSSPV  180
KAGVETTTPS KQSNNKYAAS SYLSLTPEQW KSHRSYSCQV THEGSTVEKT VAPTECS     237

SEQ ID NO: 563          moltype = AA  length = 234
FEATURE                 Location/Qualifiers
source                  1..234
                        mol_type = protein
                        organism = Homo sapiens
SEQUENCE: 563
MSVLTQVLAL LLLWLTGTRC DIELTQPPSV SVAPGQTARI SCSGDNIGSF YVHWYQQKPG  60
QAPVLVIYDD NNRPSGIPER FSGSNSGNTA TLTISGTQAE DEADYYCASW TGVEPDYVFG  120
GGTKLTVLGQ PKAAPSVTLF PPSSEELQAN KATLVCLISD FYPGAVTVAW KADSSPVKAG  180
VETTTPSKQS NNKYAASSYL SLTPEQWKSH RSYSCQVTHE GSTVEKTVAP TECS        234

SEQ ID NO: 564          moltype = AA  length = 237
FEATURE                 Location/Qualifiers
source                  1..237
                        mol_type = protein
                        organism = Homo sapiens
SEQUENCE: 564
MSVLTQVLAL LLLWLTGTRC DIALTQPASV SGSPGQSITI SCTGTSSDVG DINDVSWYQQ  60
HPGKAPKLMI YDVNNRPSGV SNRFSGSKSG NTASLTISGL QAEDEADYYC QSYAGSYLSE  120
VFGGGTKLTV LGQPKAAPSV TLFPPSSEEL QANKATLVCL ISDFYPGAVT VAWKADSSPV  180
KAGVETTTPS KQSNNKYAAS SYLSLTPEQW KSHRSYSCQV THEGSTVEKT VAPTECS     237

SEQ ID NO: 565          moltype = AA  length = 237
FEATURE                 Location/Qualifiers
source                  1..237
                        mol_type = protein
                        organism = Homo sapiens
SEQUENCE: 565
MSVLTQVLAL LLLWLTGTRC DIALTQPASV SGSPGQSITI SCTGTSSDVG DINDVSWYQQ  60
HPGKAPKLMI YDVNNRPSGV SNRFSGSKSG NTASLTISGL QAEDEADYYC SSYGESLTSY  120
VFGGGTKLTV LGQPKAAPSV TLFPPSSEEL QANKATLVCL ISDFYPGAVT VAWKADSSPV  180
KAGVETTTPS KQSNNKYAAS SYLSLTPEQW KSHRSYSCQV THEGSTVEKT VAPTECS     237

SEQ ID NO: 566          moltype = AA  length = 237
FEATURE                 Location/Qualifiers
source                  1..237
                        mol_type = protein
                        organism = Homo sapiens
SEQUENCE: 566
MSVLTQVLAL LLLWLTGTRC DIALTQPASV SGSPGQSITI SCTGTSSDVG DINDVSWYQQ  60
HPGKAPKLMI YDVNNRPSGV SNRFSGSKSG NTASLTISGL QAEDEADYYC SSYGESLTSY  120
VFGGGTKLTV LGQPKAAPSV TLFPPSSEEL QANKATLVCL ISDFYPGAVT VAWKADSSPV  180
KAGVETTTPS KQSNNKYAAS SYLSLTPEQW KSHRSYSCQV THEGSTVEKT VAPTECS     237

SEQ ID NO: 567          moltype = AA  length = 237
FEATURE                 Location/Qualifiers
source                  1..237
                        mol_type = protein
                        organism = Homo sapiens
SEQUENCE: 567
MSVLTQVLAL LLLWLTGTRC DIALTQPASV SGSPGQSITI SCTGTSSDVG DINDVSWYQQ  60
HPGKAPKLMI YDVNNRPSGV SNRFSGSKSG NTASLTISGL QAEDEADYYC SSYGESLTSY  120
VFGGGTKLTV LGQPKAAPSV TLFPPSSEEL QANKATLVCL ISDFYPGAVT VAWKADSSPV  180
```

```
KAGVETTTPS KQSNNKYAAS SYLSLTPEQW KSHRSYSCQV THEGSTVEKT VAPTECS     237

SEQ ID NO: 568          moltype = AA  length = 237
FEATURE                 Location/Qualifiers
source                  1..237
                        mol_type = protein
                        organism = Homo sapiens
SEQUENCE: 568
MSVLTQVLAL LLLWLTGTRC DIALTQPASV SGSPGQSITI SCTGTSSDVG DINDVSWYQQ  60
HPGKAPKLMI YDVNNRPSGV SNRFSGSKSG NTASLTISGL QAEDEADYYC SSYGESLTSY  120
VFGGGTKLTV LGQPKAAPSV TLFPPSSEEL QANKATLVCL ISDFYPGAVT VAWKADSSPV  180
KAGVETTTPS KQSNNKYAAS SYLSLTPEQW KSHRSYSCQV THEGSTVEKT VAPTECS     237

SEQ ID NO: 569          moltype = AA  length = 237
FEATURE                 Location/Qualifiers
source                  1..237
                        mol_type = protein
                        organism = Homo sapiens
SEQUENCE: 569
MSVLTQVLAL LLLWLTGTRC DIALTQPASV SGSPGQSITI SCTGTSSDVG DINDVSWYQQ  60
HPGKAPKLMI YDVNNRPSGV SNRFSGSKSG NTASLTISGL QAEDEADYYC STYDGPGLSE  120
VFGGGTKLTV LGQPKAAPSV TLFPPSSEEL QANKATLVCL ISDFYPGAVT VAWKADSSPV  180
KAGVETTTPS KQSNNKYAAS SYLSLTPEQW KSHRSYSCQV THEGSTVEKT VAPTECS     237

SEQ ID NO: 570          moltype = AA  length = 237
FEATURE                 Location/Qualifiers
source                  1..237
                        mol_type = protein
                        organism = Homo sapiens
SEQUENCE: 570
MSVLTQVLAL LLLWLTGTRC DIALTQPASV SGSPGQSITI SCTGTSSDVG DINDVSWYQQ  60
HPGKAPKLMI YDVNNRPSGV SNRFSGSKSG NTASLTISGL QAEDEADYYC SSYGESLTSY  120
VFGGGTKLTV LGQPKAAPSV TLFPPSSEEL QANKATLVCL ISDFYPGAVT VAWKADSSPV  180
KAGVETTTPS KQSNNKYAAS SYLSLTPEQW KSHRSYSCQV THEGSTVEKT VAPTECS     237

SEQ ID NO: 571          moltype = AA  length = 237
FEATURE                 Location/Qualifiers
source                  1..237
                        mol_type = protein
                        organism = Homo sapiens
SEQUENCE: 571
MSVLTQVLAL LLLWLTGTRC DIALTQPASV SGSPGQSITI SCTGTSSDVG DINDVSWYQQ  60
HPGKAPKLMI YDVNNRPSGV SNRFSGSKSG NTASLTISGL QAEDEADYYC STYDGPGLSE  120
VFGGGTKLTV LGQPKAAPSV TLFPPSSEEL QANKATLVCL ISDFYPGAVT VAWKADSSPV  180
KAGVETTTPS KQSNNKYAAS SYLSLTPEQW KSHRSYSCQV THEGSTVEKT VAPTECS     237

SEQ ID NO: 572          moltype = DNA  length = 1410
FEATURE                 Location/Qualifiers
source                  1..1410
                        mol_type = other DNA
                        organism = Homo sapiens
SEQUENCE: 572
atggcttggg tgtggacctt gccattcctg atggcagctg cccaaagcgt gcaggcccag  60
gtgcagctgg tcgagtctgg cggcggactg gtgcagcctg gcggcagcct gagactgagc  120
tgcgccgcca gcggcttcac cttcagcagc tacgtgatga actgggtgcg gcaggcccct  180
ggcaagggcc tggagtgggt gtccttcatc agcggcgaca gcagcaacac ctactacgcc  240
gacagcgtga agggccggtt caccatcagc cgggacaaca gcaagaacac cctgtacctg  300
cagatgaaca gcctgcgggc cgaggacacc gccgtgtact actgcgcccg gaccttcatg  360
cacggccacc tgggcggagg actgagcatg gatttctggg gccagggcac cctggtcacc  420
gtctcctcag cttccaccaa gggcccatcc gtcttccccc tggcgccctg ctccaggagc  480
acctccgaga gcacagcggc cctgggctgc ctggtcaagg actacttccc cgaaccggtg  540
acggtgtcgt ggaactcagg cgctctgacc agcggcgtgc acaccttccc agctgtccta  600
cagtcctcag gactctactc cctcagcagc gtggtgacag tgccctccag caacttcggc  660
acccagacct acacctgcaa cgtagatcac aagcccagca acaccaaggt ggacaagaca  720
gttgagcgca aatgttgtgt cgagtgccca ccgtgcccag caccacctgt ggcaggaccg  780
tcagtcttcc tcttcccccc aaaacccaag gacaccctca tgatctcccg gacccctgag  840
gtcacgtgcg tggtggtgga cgtgagccac gaagaccccg aggtccagtt caactggtac  900
gtggacggcg tggaggtgca taatgccaag acaaagccac gggaggagca gttcaacagc  960
acgttccgtg tggtcagcgt cctcaccgtt gtgcaccagg actggctgaa cggcaaggag  1020
tacaagtgca aggtctccaa caaaggcctc ccagccccca tcgagaaaac catctccaaa  1080
accaaagggc agccccgaga accacaggtg tacaccctgc ccccatcccg ggaggagatg  1140
accaagaacc aggtcagcct gacctgcctg gtcaaaggct tctaccccag cgacatcgcc  1200
gtggagtggg agagcaatgg gcagccggag aacaactaca agaccacacc tcccatgctg  1260
gactccgacg gctccttctt cctctacagc aagctcaccg tggacaagag caggtggcag  1320
caggggaacg tcttctcatg ctccgtgatg catgaggctc tgcacaacca ctacacgcag  1380
aagagcctct ccctgtctcc gggtaaatga                                   1410

SEQ ID NO: 573          moltype = DNA  length = 1389
FEATURE                 Location/Qualifiers
```

```
source                  1..1389
                        mol_type = other DNA
                        organism = Homo sapiens
SEQUENCE: 573
atggcttggg tgtggacctt gccattcctg atggcagctg cccaaggtgt ccaggcccag  60
gtgcagctgg tcgagagcgg cggagggctg gtgcagcctg gcggcagcct gagactgagc  120
tgcgccgcca gcggcttcac cttcagaagc cactggctgt cctgggtgcg gcaggcccct  180
ggcaagggcc tggaatgggt gtccaacatc aactacgacg gcagcagcac ctactacgcc  240
gacagcgtga agggccggtt caccatcagc cgggacaaca gcaagaacac cctgtacctg  300
cagatgaaca gcctgcgggc cgaggacacc gccgtgtact actgcgccag ggacacctac  360
ctgcacttcg actactgggg ccagggcacc ctggtcaccg tctcctcagc ttccaccaag  420
ggcccatccg tcttcccct ggcgccctgc tccaggagca cctccgagag cacagcggcc  480
ctgggctgcc tggtcaagga ctacttcccc gaaccggtga cggtgtcgtg gaactcaggc  540
gctctgacca gcggcgtgca caccttccca gctgtcctac agtcctcagg actctactcc  600
ctcagcagcg tggtgacagt gccctccagc aacttcggca cccagaccta cacctgcaac  660
gtagatcaca agcccagcaa caccaaggtg gacaagacag ttgagcgcaa atgttgtgtc  720
gagtgcccac cgtgcccagc accacctgtg gcaggaccgt cagtcttcct cttcccccca  780
aaacccaagg acaccctcat gatctcccgg acccctgagg tcacgtgcgt ggtggtggac  840
gtgagccacg aagaccccga ggtccagttc aactggtacg tggacggcgt ggaggtgcat  900
aatgccaaga caaagccacg ggaggagcag ttcaacagca cgttccgtgt ggtcagcgtc  960
ctcaccgttg tgcaccagga ctggctgaac ggcaaggagt acaagtgcaa ggtctccaac  1020
aaaggcctcc cagcccccat cgagaaaacc atctccaaaa ccaaagggca gccccgagaa  1080
ccacaggtgt acaccctgcc cccatcccgg gaggagatga ccaagaacca ggtcagcctg  1140
acctgcctgg tcaaaggctt ctaccccagc gacatcgccg tggagtggga gagcaatggg  1200
cagccggaga acaactacaa gaccacacct cccatgctgg actccgacgg ctccttcttc  1260
ctctacagca agctcaccgt ggacaagagc aggtggcagc aggggaacgt cttctcatgc  1320
tccgtgatgc atgaggctct gcacaaccac tacacgcaga agagcctctc cctgtctccg  1380
ggtaaatga                                                          1389

SEQ ID NO: 574          moltype = DNA  length = 1410
FEATURE                 Location/Qualifiers
source                  1..1410
                        mol_type = other DNA
                        organism = Homo sapiens
SEQUENCE: 574
atggcttggg tgtggacctt gccattcctg atggcagctg cccaaagcgt gcaggcccag  60
gtgcagctgg tcgagtctgg cggcggactg gtgcagcctg gcggcagcct gagactgagc  120
tgcgccgcca gcggcttcac cttcagcagc tacgtgatga actgggtgcg gcaggcccct  180
ggcaagggcc tggagtgggt gtccttcatc agcggcgaca gcagcaacac ctactacgcc  240
gacagcgtga agggccggtt caccatcagc cgggacaaca gcaagaacac cctgtacctg  300
cagatgaaca gcctgcgggc cgaggacacc gccgtgtact actgcgcccg gaccttcatg  360
cacggccacc tgggcggagg actgagcatg gatttctggg gccagggcac cctggtcacc  420
gtctcctcag cttccaccaa gggcccatcc gtcttccccc tggcgccctg ctccaggagc  480
acctccgaga gcacagcggc cctgggctgc ctggtcaagg actacttccc cgaaccggtg  540
acggtgtcgt ggaactcagg cgctctgacc agcggcgtgc acaccttccc agctgtccta  600
cagtcctcag gactctactc cctcagcagc gtggtgacag tgccctccag caacttcggc  660
acccagacct acacctgcaa cgtagatcac aagcccagca acaccaaggt ggacaagaca  720
gttgagcgca aatgttgtgt cgagtgccca ccgtgcccag caccacctgt ggcaggaccg  780
tcagtcttcc tcttcccccc aaaacccaag gacaccctca tgatctcccg gacccctgag  840
gtcacgtgcg tggtggtgga cgtgagccac gaagaccccg aggtccagtt caactggtac  900
gtggacggcg tggaggtgca taatgccaag acaaagccac gggaggagca gttcaacagc  960
acgttccgtg tggtcagcgt cctcaccgtt gtgcaccagg actggctgaa cggcaaggag  1020
tacaagtgca aggtctccaa caaaggcctc ccagccccca tcgagaaaac catctccaaa  1080
accaaagggc agccccgaga accacaggtg tacaccctgc ccccatcccg ggaggagatg  1140
accaagaacc aggtcagcct gacctgcctg gtcaaaggct tctaccccag cgacatcgcc  1200
gtggagtggg agagcaatgg gcagccggag aacaactaca agaccacacc tcccatgctg  1260
gactccgacg gctccttctt cctctacagc aagctcaccg tggacaagag caggtggcag  1320
caggggaacg tcttctcatg ctccgtgatg catgaggctc tgcacaacca ctacacgcag  1380
aagagcctct ccctgtctcc gggtaaatga                                   1410

SEQ ID NO: 575          moltype = DNA  length = 1389
FEATURE                 Location/Qualifiers
source                  1..1389
                        mol_type = other DNA
                        organism = Homo sapiens
SEQUENCE: 575
atggcttggg tgtggacctt gccattcctg atggcagctg cccaaggtgt ccaggcccag  60
gtgcagctgg tcgagagcgg cggagggctg gtgcagcctg gcggcagcct gagactgagc  120
tgcgccgcca gcggcttcac cttcagaagc cactggctgt cctgggtgcg gcaggcccct  180
ggcaagggcc tggaatgggt gtccaacatc aactacgacg gcagcagcac ctactacgcc  240
gacagcgtga agggccggtt caccatcagc cgggacaaca gcaagaacac cctgtacctg  300
cagatgaaca gcctgcgggc cgaggacacc gccgtgtact actgcgccag ggacacctac  360
ctgcacttcg actactgggg ccagggcacc ctggtcaccg tctcctcagc ttccaccaag  420
ggcccatccg tcttcccct ggcgccctgc tccaggagca cctccgagag cacagcggcc  480
ctgggctgcc tggtcaagga ctacttcccc gaaccggtga cggtgtcgtg gaactcaggc  540
gctctgacca gcggcgtgca caccttccca gctgtcctac agtcctcagg actctactcc  600
ctcagcagcg tggtgacagt gccctccagc aacttcggca cccagaccta cacctgcaac  660
gtagatcaca agcccagcaa caccaaggtg gacaagacag ttgagcgcaa atgttgtgtc  720
gagtgcccac cgtgcccagc accacctgtg gcaggaccgt cagtcttcct cttcccccca  780
```

```
aaacccaagg acaccctcat gatctcccgg acccctgagg tcacgtgcgt ggtggtggac  840
gtgagccacg aagaccccga ggtccagttc aactggtacg tggacggcgt ggaggtgcat  900
aatgccaaga caaagccacg ggaggagcag ttcaacagca cgttccgtgt ggtcagcgtc  960
ctcaccgttg tgcaccagga ctggctgaac ggcaaggagt acaagtgcaa ggtctccaac  1020
aaaggcctcc cagcccccat cgagaaaacc atctccaaaa ccaaagggca gccccgagaa  1080
ccacaggtgt acaccctgcc cccatcccgg gaggagatga ccaagaacca ggtcagcctg  1140
acctgcctgg tcaaaggctt ctaccccaga gacatcgccg tggagtggga gagcaatggg  1200
cagccggaga acaactacaa gaccacacct cccatgctgg actccgacgg ctccttcttc  1260
ctctacagca agctcaccgt ggacaagagc aggtggcagc aggggaacgt cttctcatgc  1320
tccgtgatgc atgaggctct gcacaaccac tacacgcaga agagcctctc cctgtctccg  1380
ggtaaatga                                                          1389

SEQ ID NO: 576          moltype = DNA  length = 1386
FEATURE                 Location/Qualifiers
source                  1..1386
                        mol_type = other DNA
                        organism = Homo sapiens
SEQUENCE: 576
atggcttggg tgtggacctt gccattcctg atggcagctg cccaaagtgt ccaggcccag  60
gtgcagctgg tcgagagcgg cggagggctg gtgcagcctg gcggcagcct gagactgagc  120
tgcgccgcca gcggcttcac cttcagaagc cactggctgt cctgggtgcg gcaggcccct  180
ggcaagggcc tggaatgggt gtccgtgacc ggcgtgcacg gcgacaccta ctacgccgac  240
agcgtgaagg gccggttcac catcagccgg gacaacagca agaacaccct gtacctgcag  300
atgaacagcc tgcgggccga ggacaccgcc gtgtactact gcgccaggga cacctacctg  360
cacttcgact actggggcca gggcaccctg gtcaccgtct cctcagcttc caccaagggc  420
ccatccgtct tcccccctggc gccctgctcc aggagcacct ccgagagcac agcggccctg  480
ggctgcctgg tcaaggacta cttccccgaa ccggtgacgg tgtcgtggaa ctcaggcgct  540
ctgaccagcg gcgtgcacac cttcccagct gtcctacagt cctcaggact ctactccctc  600
agcagcgtgg tgacagtgcc ctccagcaac ttcggcaccc agacctacac ctgcaacgta  660
gatcacaagc ccagcaacac caaggtggac aagacagttg agcgcaaatg ttgtgtcgag  720
tgcccaccgt gcccagcacc acctgtggca ggaccgtcag tcttcctctt cccccccaaaa  780
cccaaggaca ccctcatgat ctcccggacc cctgaggtca cgtgcgtggt ggtggacgtg  840
agccacgaag accccgaggt ccagttcaac tggtacgtgg acggcgtgga ggtgcataat  900
gccaagacaa agccacggga ggagcagttc aacagcacgt tccgtgtggt cagcgtcctc  960
accgttgtgc accaggactg gctgaacggc aaggagtaca agtgcaaggt ctccaacaaa  1020
ggcctcccag cccccatcga gaaaaccatc tccaaaacca aagggcagcc ccgagaacca  1080
caggtgtaca ccctgccccc atcccgggag gagatgacca agaaccaggt cagcctgacc  1140
tgcctggtca aaggcttcta ccccagcgac atcgccgtgg agtgggagag caatgggcag  1200
ccggagaaca actacaagac cacacctccc atgctggact ccgacggctc cttcttcctc  1260
tacagcaagc tcaccgtgga caagagcagg tggcagcagg ggaacgtctt ctcatgctcc  1320
gtgatgcatg aggctctgca caaccactac acgcagaaga gcctctccct gtctccgggt  1380
aaatga                                                             1386

SEQ ID NO: 577          moltype = DNA  length = 1386
FEATURE                 Location/Qualifiers
source                  1..1386
                        mol_type = other DNA
                        organism = Homo sapiens
SEQUENCE: 577
atggcttggg tgtggacctt gccattcctg atggcagctg cccaaagtgt ccaggcccag  60
gtgcagctgg tcgagagcgg cggagggctg gtgcagcctg gcggcagcct gagactgagc  120
tgcgccgcca gcggcttcac cttcagaagc cactggctgt cctgggtgcg gcaggcccct  180
ggcaagggcc tggaatgggt gtccgtgatc ggcaactggg gcgacaccta ctacgccgac  240
agcgtgaagg gccggttcac catcagccgg gacaacagca agaacaccct gtacctgcag  300
atgaacagcc tgcgggccga ggacaccgcc gtgtactact gcgccaggga cacctacctg  360
cacttcgact actggggcca gggcaccctg gtcaccgtct cctcagcttc caccaagggc  420
ccatccgtct tcccccctggc gccctgctcc aggagcacct ccgagagcac agcggccctg  480
ggctgcctgg tcaaggacta cttccccgaa ccggtgacgg tgtcgtggaa ctcaggcgct  540
ctgaccagcg gcgtgcacac cttcccagct gtcctacagt cctcaggact ctactccctc  600
agcagcgtgg tgacagtgcc ctccagcaac ttcggcaccc agacctacac ctgcaacgta  660
gatcacaagc ccagcaacac caaggtggac aagacagttg agcgcaaatg ttgtgtcgag  720
tgcccaccgt gcccagcacc acctgtggca ggaccgtcag tcttcctctt cccccccaaaa  780
cccaaggaca ccctcatgat ctcccggacc cctgaggtca cgtgcgtggt ggtggacgtg  840
agccacgaag accccgaggt ccagttcaac tggtacgtgg acggcgtgga ggtgcataat  900
gccaagacaa agccacggga ggagcagttc aacagcacgt tccgtgtggt cagcgtcctc  960
accgttgtgc accaggactg gctgaacggc aaggagtaca agtgcaaggt ctccaacaaa  1020
ggcctcccag cccccatcga gaaaaccatc tccaaaacca aagggcagcc ccgagaacca  1080
caggtgtaca ccctgccccc atcccgggag gagatgacca agaaccaggt cagcctgacc  1140
tgcctggtca aaggcttcta ccccagcgac atcgccgtgg agtgggagag caatgggcag  1200
ccggagaaca actacaagac cacacctccc atgctggact ccgacggctc cttcttcctc  1260
tacagcaagc tcaccgtgga caagagcagg tggcagcagg ggaacgtctt ctcatgctcc  1320
gtgatgcatg aggctctgca caaccactac acgcagaaga gcctctccct gtctccgggt  1380
aaatga                                                             1386

SEQ ID NO: 578          moltype = DNA  length = 1386
FEATURE                 Location/Qualifiers
source                  1..1386
                        mol_type = other DNA
                        organism = Homo sapiens
```

```
SEQUENCE: 578
atggcttggg tgtggacctt gccattcctg atggcagctg cccaaagtgt ccaggcccag  60
gtgcagctgg tcgagagcgg cggagggctg gtgcagcctg gcggcagcct gagactgagc  120
tgcgccgcca gcggcttcac cttcagaagc cactggctgt cctgggtgcg gcaggcccct  180
ggcaagggcc tggaatgggt gtccgtgacc acccaccagg gctacaccta ctacgccgac  240
agcgtgaagg gccggttcac catcagccgg gacaacagca agaacaccct gtacctgcag  300
atgaacagcc tgcgggccga ggacaccgcc gtgtactact gcgccaggga cacctacctg  360
cacttcgact actggggcca gggcaccctg gtcaccgtct cctcagcttc caccaagggc  420
ccatccgtct tccccctggc gccctgctcc aggagcacct ccgagagcac agcggccctg  480
ggctgcctgg tcaaggacta cttccccgaa ccggtgacgg tgtcgtggaa ctcaggcgct  540
ctgaccagcg gcgtgcacac cttcccagct gtcctacagt cctcaggact ctactccctc  600
agcagcgtgg tgacagtgcc ctccagcaac ttcggcaccc agacctacac ctgcaacgta  660
gatcacaagc ccagcaacac caaggtggac aagacagttg agcgcaaatg ttgtgtcgag  720
tgcccaccgt gcccagcacc acctgtggca ggaccgtcag tcttcctctt ccccccaaaa  780
cccaaggaca ccctcatgat ctcccggacc cctgaggtca cgtgcgtggt ggtggacgtg  840
agccacgaag accccgaggt ccagttcaac tggtacgtgg acggcgtgga ggtgcataat  900
gccaagacaa agccacggga ggagcagttc aacagcacgt tccgtgtggt cagcgtcctc  960
accgttgtgc accaggactg gctgaacggc aaggagtaca agtgcaaggt ctccaacaaa  1020
ggcctcccag cccccatcga gaaaaccatc tccaaaacca aagggcagcc ccgagaacca  1080
caggtgtaca ccctgccccc atcccgggag gagatgacca agaaccaggt cagcctgacc  1140
tgcctggtca aaggcttcta ccccagcgac atcgccgtgg agtgggagag caatgggcag  1200
ccggagaaca actacaagac cacacctccc atgctggact ccgacggctc cttcttcctc  1260
tacagcaagc tcaccgtgga caagagcagg tggcagcagg ggaacgtctt ctcatgctcc  1320
gtgatgcatg aggctctgca caaccactac acgcagaaga gcctctccct gtctccgggt  1380
aaatga                                                            1386

SEQ ID NO: 579          moltype = DNA  length = 1386
FEATURE                 Location/Qualifiers
source                  1..1386
                        mol_type = other DNA
                        organism = Homo sapiens
SEQUENCE: 579
atggcttggg tgtggacctt gccattcctg atggcagctg cccaaagtgt ccaggcccag  60
gtgcagctgg tcgagagcgg cggagggctg gtgcagcctg gcggcagcct gagactgagc  120
tgcgccgcca gcggcttcac cttcagaagc cactggctgt cctgggtgcg gcaggcccct  180
ggcaagggcc tggaatgggt gtccgccacc aacagatacg gctacaccta ctacgccgac  240
agcgtgaagg gccggttcac catcagccgg gacaacagca agaacaccct gtacctgcag  300
atgaacagcc tgcgggccga ggacaccgcc gtgtactact gcgccaggga cacctacctg  360
cacttcgact actggggcca gggcaccctg gtcaccgtct cctcagcttc caccaagggc  420
ccatccgtct tccccctggc gccctgctcc aggagcacct ccgagagcac agcggccctg  480
ggctgcctgg tcaaggacta cttccccgaa ccggtgacgg tgtcgtggaa ctcaggcgct  540
ctgaccagcg gcgtgcacac cttcccagct gtcctacagt cctcaggact ctactccctc  600
agcagcgtgg tgacagtgcc ctccagcaac ttcggcaccc agacctacac ctgcaacgta  660
gatcacaagc ccagcaacac caaggtggac aagacagttg agcgcaaatg ttgtgtcgag  720
tgcccaccgt gcccagcacc acctgtggca ggaccgtcag tcttcctctt ccccccaaaa  780
cccaaggaca ccctcatgat ctcccggacc cctgaggtca cgtgcgtggt ggtggacgtg  840
agccacgaag accccgaggt ccagttcaac tggtacgtgg acggcgtgga ggtgcataat  900
gccaagacaa agccacggga ggagcagttc aacagcacgt tccgtgtggt cagcgtcctc  960
accgttgtgc accaggactg gctgaacggc aaggagtaca agtgcaaggt ctccaacaaa  1020
ggcctcccag cccccatcga gaaaaccatc tccaaaacca aagggcagcc ccgagaacca  1080
caggtgtaca ccctgccccc atcccgggag gagatgacca agaaccaggt cagcctgacc  1140
tgcctggtca aaggcttcta ccccagcgac atcgccgtgg agtgggagag caatgggcag  1200
ccggagaaca actacaagac cacacctccc atgctggact ccgacggctc cttcttcctc  1260
tacagcaagc tcaccgtgga caagagcagg tggcagcagg ggaacgtctt ctcatgctcc  1320
gtgatgcatg aggctctgca caaccactac acgcagaaga gcctctccct gtctccgggt  1380
aaatga                                                            1386

SEQ ID NO: 580          moltype = DNA  length = 1389
FEATURE                 Location/Qualifiers
source                  1..1389
                        mol_type = other DNA
                        organism = Homo sapiens
SEQUENCE: 580
atggcttggg tgtggacctt gccattcctg atggcagctg cccaaggtgt ccaggcccag  60
gtgcagctgg tcgagagcgg cggagggctg gtgcagcctg gcggcagcct gagactgagc  120
tgcgccgcca gcggcttcac cttcagaagc cactggctgt cctgggtgcg gcaggcccct  180
ggcaagggcc tggaatgggt gtccaacatc aactacgacg gcagcagcac ctactacgcc  240
gacagcgtga agggccggtt caccatcagc cgggacaaca gcaagaacac cctgtacctg  300
cagatgaaca gcctgcgggc cgaggacacc gccgtgtact actgcgccag ggacacctac  360
ctgcacttcg actactgggg ccagggcacc ctggtcaccg tctcctcagc ttccaccaag  420
ggcccatccg tcttccccct ggcgccctgc tccaggagca cctccgagag cacagcggcc  480
ctgggctgcc tggtcaagga ctacttcccc gaaccggtga cggtgtcgtg gaactcaggc  540
gctctgacca gcggcgtgca caccttccca gctgtcctac agtcctcagg actctactcc  600
ctcagcagcg tggtgacagt gccctccagc aacttcggca cccagaccta cacctgcaac  660
gtagatcaca agcccagcaa caccaaggtg gacaagacag ttgagcgcaa atgttgtgtc  720
gagtgcccac cgtgcccagc accacctgtg gcaggaccgt cagtcttcct cttcccccca  780
aaacccaagg acaccctcat gatctcccgg acccctgagg tcacgtgcgt ggtggtggac  840
gtgagccacg aagaccccga ggtccagttc aactggtacg tggacggcgt ggaggtgcat  900
aatgccaaga caaagccacg ggaggagcag ttcaacagca cgttccgtgt ggtcagcgtc  960
```

-continued

```
ctcaccgttg tgcaccagga ctggctgaac ggcaaggagt acaagtgcaa ggtctccaac  1020
aaaggcctcc cagcccccat cgagaaaacc atctccaaaa ccaaagggca gccccgagaa  1080
ccacaggtgt acaccctgcc cccatcccgg gaggagatga ccaagaacca ggtcagcctg  1140
acctgcctgg tcaaaggctt ctaccccagc gacatcgccg tggagtggga gagcaatggg  1200
cagccggaga acaactacaa gaccacacct cccatgctgg actccgacgg ctccttcttc  1260
ctctacagca agctcaccgt ggacaagagc aggtggcagc aggggaacgt cttctcatgc  1320
tccgtgatgc atgaggctct gcacaaccac tacacgcaga agagcctctc cctgtctccg  1380
ggtaaatga                                                          1389

SEQ ID NO: 581         moltype = DNA  length = 1386
FEATURE                Location/Qualifiers
source                 1..1386
                       mol_type = other DNA
                       organism = Homo sapiens
SEQUENCE: 581
atggcttggg tgtggacctt gccattcctg atggcagctg cccaaagtgt ccaggcccag  60
gtgcagctgg tcgagagcgg cggagggctg gtgcagcctg gcggcagcct gagactgagc  120
tgcgccgcca gcggcttcac cttcagaagc cactggctgt cctgggtgcg gcaggcccct  180
ggcaagggcc tggaatgggt gtccgtgatc accccctacg gcgacaccta ctacgccgac  240
agcgtgaagg gccggttcac catcagccgg gacaacagca agaacaccct gtacctgcag  300
atgaacagcc tgcgggccga ggacaccgcc gtgtactact gcgccaggga cacctacctg  360
cacttcgact actggggcca gggcaccctg gtcaccgtct cctcagcttc caccaagggc  420
ccatccgtct tcccctggc gccctgctcc aggagcacct ccgagagcac agcggccctg  480
ggctgcctgg tcaaggacta cttccccgaa ccggtgacgg tgtcgtggaa ctcaggcgct  540
ctgaccagcg gcgtgcacac cttcccagct gtcctacagt cctcaggact ctactccctc  600
agcagcgtgg tgacagtgcc ctccagcaac ttcggcaccc agacctacac ctgcaacgta  660
gatcacaagc ccagcaacac caaggtggac aagacagttg agcgcaaatg ttgtgtcgag  720
tgcccaccgt gcccagcacc acctgtggca ggaccgtcag tcttcctctt ccccccaaaa  780
cccaaggaca ccctcatgat ctcccggacc cctgaggtca cgtgcgtggt ggtggacgtg  840
agccacgaag accccgaggt ccagttcaac tggtacgtgg acggcgtgga ggtgcataat  900
gccaagacaa agccacggga ggagcagttc aacagcacgt tccgtgtggt cagcgtcctc  960
accgttgtgc accaggactg gctgaacggc aaggagtaca agtgcaaggt ctccaacaaa  1020
ggcctcccag cccccatcga gaaaaccatc tccaaaacca aagggcagcc ccgagaacca  1080
caggtgtaca ccctgccccc atcccgggag gagatgacca agaaccaggt cagcctgacc  1140
tgcctggtca aaggcttcta ccccagcgac atcgccgtgg agtgggagag caatgggcag  1200
ccggagaaca actacaagac cacacctccc atgctggact ccgacggctc cttcttcctc  1260
tacagcaagc tcaccgtgga caagagcagg tggcagcagg ggaacgtctt ctcatgctcc  1320
gtgatgcatg aggctctgca caaccactac acgcagaaga gcctctccct gtctccgggt  1380
aaatga                                                             1386

SEQ ID NO: 582         moltype = DNA  length = 1386
FEATURE                Location/Qualifiers
source                 1..1386
                       mol_type = other DNA
                       organism = Homo sapiens
SEQUENCE: 582
atggcttggg tgtggacctt gccattcctg atggcagctg cccaaagtgt ccaggcccag  60
gtgcagctgg tcgagagcgg cggagggctg gtgcagcctg gcggcagcct gagactgagc  120
tgcgccgcca gcggcttcac cttcagaagc cactggctgt cctgggtgcg gcaggcccct  180
ggcaagggcc tggaatgggt gtccgtgatc accccctacg gcgacaccta ctacgccgac  240
agcgtgaagg gccggttcac catcagccgg gacaacagca agaacaccct gtacctgcag  300
atgaacagcc tgcgggccga ggacaccgcc gtgtactact gcgccaggga cacctacctg  360
cacttcgact actggggcca gggcaccctg gtcaccgtct cctcagcttc caccaagggc  420
ccatccgtct tcccctggc gccctgctcc aggagcacct ccgagagcac agcggccctg  480
ggctgcctgg tcaaggacta cttccccgaa ccggtgacgg tgtcgtggaa ctcaggcgct  540
ctgaccagcg gcgtgcacac cttcccagct gtcctacagt cctcaggact ctactccctc  600
agcagcgtgg tgacagtgcc ctccagcaac ttcggcaccc agacctacac ctgcaacgta  660
gatcacaagc ccagcaacac caaggtggac aagacagttg agcgcaaatg ttgtgtcgag  720
tgcccaccgt gcccagcacc acctgtggca ggaccgtcag tcttcctctt ccccccaaaa  780
cccaaggaca ccctcatgat ctcccggacc cctgaggtca cgtgcgtggt ggtggacgtg  840
agccacgaag accccgaggt ccagttcaac tggtacgtgg acggcgtgga ggtgcataat  900
gccaagacaa agccacggga ggagcagttc aacagcacgt tccgtgtggt cagcgtcctc  960
accgttgtgc accaggactg gctgaacggc aaggagtaca agtgcaaggt ctccaacaaa  1020
ggcctcccag cccccatcga gaaaaccatc tccaaaacca aagggcagcc ccgagaacca  1080
caggtgtaca ccctgccccc atcccgggag gagatgacca agaaccaggt cagcctgacc  1140
tgcctggtca aaggcttcta ccccagcgac atcgccgtgg agtgggagag caatgggcag  1200
ccggagaaca actacaagac cacacctccc atgctggact ccgacggctc cttcttcctc  1260
tacagcaagc tcaccgtgga caagagcagg tggcagcagg ggaacgtctt ctcatgctcc  1320
gtgatgcatg aggctctgca caaccactac acgcagaaga gcctctccct gtctccgggt  1380
aaatga                                                             1386

SEQ ID NO: 583         moltype = DNA  length = 393
FEATURE                Location/Qualifiers
source                 1..393
                       mol_type = other DNA
                       organism = Homo sapiens
SEQUENCE: 583
atgaaaaaga cagctatcgc gattgcagtg gcactggctg gtttcgctac cgtagcgcag  60
gccgatatcg aactgaccca gccgccttca gtgagcgttg caccaggtca gaccgcgcgt  120
```

```
atctcgtgta gcggcgataa tattggttct ttttatgttc attggtacca gcagaaaccc  180
gggcaggcgc cagttcttgt gatttatgat gataataatc gtccctcagg catcccggaa  240
cgctttagcg gatccaacag cggcaacacc gcgaccctga ccattagcgg cactcaggcg  300
gaagacgaag cggattatta ttgcggttct tgggctggtt cttctggttc ttatgtgttt  360
ggcggccgca cgaagttaac cgttcttggc cag                                393

SEQ ID NO: 584          moltype = DNA  length = 714
FEATURE                 Location/Qualifiers
source                  1..714
                        mol_type = other DNA
                        organism = Homo sapiens
SEQUENCE: 584
atgagtgtgc tcactcaggt cctggcgttg ctgctgctgt ggcttacagg tacgcgttgc  60
gacatcgccc tgacccagcc cgccagcgtg agcggcagcc ctggccagag catcaccatc  120
agctgcaccg gcaccagcag cgacgtgggc gacatcaacg acgtgagctg gtatcagcag  180
caccccggca aggcccccaa gctgatgatc tacgacgtga acaaccggcc cagcggcgtg  240
agcaaccggt tcagcggcag caagagcggc aacaccgcca gcctgaccat cagcggcctc  300
caggccgagg acgaggccga ctactactgc agcagctacg gcgagagcct gaccagctac  360
gtgtttggcg gcggaaccaa gcttaccgtc ctaggtcagc ccaaggctgc cccctcggtc  420
actctgttcc cgccctcctc tgaggagctt caagccaaca aggccacact ggtgtgtctc  480
ataagtgact tctacccggg agccgtgaca gtggcctgga aggcagatag cagcccccgtc  540
aaggcgggag tggagacaac cacaccctcc aaacaaagca acaacaagta cgcggccagc  600
agctatctga gcctgacgcc tgagcagtgg aagtcccaca gaagctacag ctgccaggtc  660
acgcatgaag ggagcaccgt ggaaaagaca gtggccccta cagaatgttc atag        714

SEQ ID NO: 585          moltype = DNA  length = 705
FEATURE                 Location/Qualifiers
source                  1..705
                        mol_type = other DNA
                        organism = Homo sapiens
SEQUENCE: 585
atgagtgtgc tcactcaggt cctggcgttg ctgctgctgt ggcttacagg tacgcgttgc  60
gacatcgagc tgacccagcc ccccagcgtg agcgtggccc ctggccagac cgcccggatc  120
agctgcagcg gcgacaacat cggcagcttc tacgtgcact ggtatcagca gaagcccggc  180
caggcccccg tgctggtgat ctacgacgac aacaaccggc ccagcggcat ccccgagcgg  240
ttcagcggca gcaacagcgg caacaccgcc accctgacca tcagcggcac ccaggccgag  300
gacgaggccg actactactg cgccagctgg accggcgtgg agcccgacta cgtgtttggc  360
ggcggaacaa agcttaccgt cctaggtcag cccaaggctg ccccctcggt cactctgttc  420
ccgccctcct ctgaggagct tcaagccaac aaggccacac tggtgtgtct cataagtgac  480
ttctacccgg gagccgtgac agtggcctgg aaggcagata gcagccccgt caaggcggga  540
gtggagacaa ccacaccctc caaacaaagc aacaacaagt acgcggccag cagctatctg  600
agcctgacgc ctgagcagtg gaagtcccac agaagctaca gctgccaggt cacgcatgaa  660
gggagcaccg tggaaaagac agtggcccct acagaatgtt catag                  705

SEQ ID NO: 586          moltype = DNA  length = 714
FEATURE                 Location/Qualifiers
source                  1..714
                        mol_type = other DNA
                        organism = Homo sapiens
SEQUENCE: 586
atgagtgtgc tcactcaggt cctggcgttg ctgctgctgt ggcttacagg tacgcgttgc  60
gacatcgccc tgacccagcc cgccagcgtg agcggcagcc ctggccagag catcaccatc  120
agctgcaccg gcaccagcag cgacgtgggc gacatcaacg acgtgagctg gtatcagcag  180
caccccggca aggcccccaa gctgatgatc tacgacgtga acaaccggcc cagcggcgtg  240
agcaaccggt tcagcggcag caagagcggc aacaccgcca gcctgaccat cagcggcctc  300
caggccgagg acgaggccga ctactactgc cagagctacg ccggcagcta cctgagcgag  360
gtgttcggcg gagggaccaa gcttaccgtc ctaggtcagc ccaaggctgc cccctcggtc  420
actctgttcc cgccctcctc tgaggagctt caagccaaca aggccacact ggtgtgtctc  480
ataagtgact tctacccggg agccgtgaca gtggcctgga aggcagatag cagccccgtc  540
aaggcgggag tggagacaac cacaccctcc aaacaaagca acaacaagta cgcggccagc  600
agctatctga gcctgacgcc tgagcagtgg aagtcccaca gaagctacag ctgccaggtc  660
acgcatgaag ggagcaccgt ggaaaagaca gtggccccta cagaatgttc atag        714

SEQ ID NO: 587          moltype = DNA  length = 714
FEATURE                 Location/Qualifiers
source                  1..714
                        mol_type = other DNA
                        organism = Homo sapiens
SEQUENCE: 587
atgagtgtgc tcactcaggt cctggcgttg ctgctgctgt ggcttacagg tacgcgttgc  60
gacatcgccc tgacccagcc cgccagcgtg agcggcagcc ctggccagag catcaccatc  120
agctgcaccg gcaccagcag cgacgtgggc gacatcaacg acgtgagctg gtatcagcag  180
caccccggca aggcccccaa gctgatgatc tacgacgtga acaaccggcc cagcggcgtg  240
agcaaccggt tcagcggcag caagagcggc aacaccgcca gcctgaccat cagcggcctc  300
caggccgagg acgaggccga ctactactgc agcagctacg gcgagagcct gaccagctac  360
gtgtttggcg gcggaaccaa gcttaccgtc ctaggtcagc ccaaggctgc cccctcggtc  420
actctgttcc cgccctcctc tgaggagctt caagccaaca aggccacact ggtgtgtctc  480
ataagtgact tctacccggg agccgtgaca gtggcctgga aggcagatag cagccccgtc  540
aaggcgggag tggagacaac cacaccctcc aaacaaagca acaacaagta cgcggccagc  600
```

```
agctatctga gcctgacgcc tgagcagtgg aagtcccaca gaagctacag ctgccaggtc  660
acgcatgaag ggagcaccgt ggaaaagaca gtggccccta cagaatgttc atag        714

SEQ ID NO: 588         moltype = DNA  length = 714
FEATURE                Location/Qualifiers
source                 1..714
                       mol_type = other DNA
                       organism = Homo sapiens
SEQUENCE: 588
atgagtgtgc tcactcaggt cctggcgttg ctgctgctgt ggcttacagg tacgcgttgc  60
gacatcgccc tgacccagcc cgccagcgtg agcggcagcc ctggccagag catcaccatc  120
agctgcaccg gcaccagcag cgacgtgggc gacatcaacg acgtgagctg gtatcagcag  180
caccccggca aggcccccaa gctgatgatc tacgacgtga acaaccggcc cagcggcgtg  240
agcaaccggt tcagcggcag caagagcggc aacaccgcca gcctgaccat cagcggcctc  300
caggccgagg acgaggccga ctactactgc agcagctacg gcgagagcct gaccagctac  360
gtgtttggcg gcggaaccaa gcttaccgtc ctaggtcagc ccaaggctgc cccctcggtc  420
actctgttcc cgccctcctc tgaggagctt caagccaaca aggccacact ggtgtgtctc  480
ataagtgact tctacccggg agccgtgaca gtggcctgga aggcagatag cagccccgtc  540
aaggcgggag tggagacaac cacaccctcc aaacaaagca acaacaagta cgcggccagc  600
agctatctga gcctgacgcc tgagcagtgg aagtcccaca gaagctacag ctgccaggtc  660
acgcatgaag ggagcaccgt ggaaaagaca gtggccccta cagaatgttc atag        714

SEQ ID NO: 589         moltype = DNA  length = 714
FEATURE                Location/Qualifiers
source                 1..714
                       mol_type = other DNA
                       organism = Homo sapiens
SEQUENCE: 589
atgagtgtgc tcactcaggt cctggcgttg ctgctgctgt ggcttacagg tacgcgttgc  60
gacatcgccc tgacccagcc cgccagcgtg agcggcagcc ctggccagag catcaccatc  120
agctgcaccg gcaccagcag cgacgtgggc gacatcaacg acgtgagctg gtatcagcag  180
caccccggca aggcccccaa gctgatgatc tacgacgtga acaaccggcc cagcggcgtg  240
agcaaccggt tcagcggcag caagagcggc aacaccgcca gcctgaccat cagcggcctc  300
caggccgagg acgaggccga ctactactgc agcagctacg gcgagagcct gaccagctac  360
gtgtttggcg gcggaaccaa gcttaccgtc ctaggtcagc ccaaggctgc cccctcggtc  420
actctgttcc cgccctcctc tgaggagctt caagccaaca aggccacact ggtgtgtctc  480
ataagtgact tctacccggg agccgtgaca gtggcctgga aggcagatag cagccccgtc  540
aaggcgggag tggagacaac cacaccctcc aaacaaagca acaacaagta cgcggccagc  600
agctatctga gcctgacgcc tgagcagtgg aagtcccaca gaagctacag ctgccaggtc  660
acgcatgaag ggagcaccgt ggaaaagaca gtggccccta cagaatgttc atag        714

SEQ ID NO: 590         moltype = DNA  length = 714
FEATURE                Location/Qualifiers
source                 1..714
                       mol_type = other DNA
                       organism = Homo sapiens
SEQUENCE: 590
atgagtgtgc tcactcaggt cctggcgttg ctgctgctgt ggcttacagg tacgcgttgc  60
gacatcgccc tgacccagcc cgccagcgtg agcggcagcc ctggccagag catcaccatc  120
agctgcaccg gcaccagcag cgacgtgggc gacatcaacg acgtgagctg gtatcagcag  180
caccccggca aggcccccaa gctgatgatc tacgacgtga acaaccggcc cagcggcgtg  240
agcaaccggt tcagcggcag caagagcggc aacaccgcca gcctgaccat cagcggcctc  300
caggccgagg acgaggccga ctactactgc agcagctacg gcgagagcct gaccagctac  360
gtgtttggcg gcggaaccaa gcttaccgtc ctaggtcagc ccaaggctgc cccctcggtc  420
actctgttcc cgccctcctc tgaggagctt caagccaaca aggccacact ggtgtgtctc  480
ataagtgact tctacccggg agccgtgaca gtggcctgga aggcagatag cagccccgtc  540
aaggcgggag tggagacaac cacaccctcc aaacaaagca acaacaagta cgcggccagc  600
agctatctga gcctgacgcc tgagcagtgg aagtcccaca gaagctacag ctgccaggtc  660
acgcatgaag ggagcaccgt ggaaaagaca gtggccccta cagaatgttc atag        714

SEQ ID NO: 591         moltype = DNA  length = 714
FEATURE                Location/Qualifiers
source                 1..714
                       mol_type = other DNA
                       organism = Homo sapiens
SEQUENCE: 591
atgagtgtgc tcactcaggt cctggcgttg ctgctgctgt ggcttacagg tacgcgttgc  60
gacatcgccc tgacccagcc cgccagcgtg agcggcagcc ctggccagag catcaccatc  120
agctgcaccg gcaccagcag cgacgtgggc gacatcaacg acgtgagctg gtatcagcag  180
caccccggca aggcccccaa gctgatgatc tacgacgtga acaaccggcc cagcggcgtg  240
agcaaccggt tcagcggcag caagagcggc aacaccgcca gcctgaccat cagcggcctc  300
caggccgagg acgaggccga ctactactgc agcacctacg acggccctgg cctgagcgag  360
gtgttcggcg gagggaccaa gcttaccgtc ctaggtcagc ccaaggctgc cccctcggtc  420
actctgttcc cgccctcctc tgaggagctt caagccaaca aggccacact ggtgtgtctc  480
ataagtgact tctacccggg agccgtgaca gtggcctgga aggcagatag cagccccgtc  540
aaggcgggag tggagacaac cacaccctcc aaacaaagca acaacaagta cgcggccagc  600
agctatctga gcctgacgcc tgagcagtgg aagtcccaca gaagctacag ctgccaggtc  660
acgcatgaag ggagcaccgt ggaaaagaca gtggccccta cagaatgttc atag        714
```

-continued

```
SEQ ID NO: 592         moltype = DNA  length = 714
FEATURE                Location/Qualifiers
source                 1..714
                       mol_type = other DNA
                       organism = Homo sapiens
SEQUENCE: 592
atgagtgtgc tcactcaggt cctggcgttg ctgctgctgt ggcttacagg tacgcgttgc  60
gacatcgccc tgacccagcc cgccagcgtg agcggcagcc ctggccagag catcaccatc  120
agctgcaccg gcaccagcag cgacgtgggc gacatcaacg acgtgagctg gtatcagcag  180
caccccggca aggcccccaa gctgatgatc tacgacgtga acaaccggcc cagcggcgtg  240
agcaaccggt tcagcggcag caagagcggc aacaccgcca gcctgaccat cagcggcctc  300
caggccgagg acgaggccga ctactactgc agcacctacg acggccctgg cctgagcgag  360
gtgttcggcg gagggaccaa gcttaccgtc ctaggtcagc ccaaggctgc cccctcggtc  420
actctgttcc cgccctcctc tgaggagctt caagccaaca aggccacact ggtgtgtctc  480
ataagtgact tctacccggg agccgtgaca gtggcctgga aggcagatag cagccccgtc  540
aaggcgggag tggagacaac cacaccctcc aaacaaagca acaacaagta cgcggccagc  600
agctatctga gcctgacgcc tgagcagtgg aagtcccaca gaagctacag ctgccaggtc  660
acgcatgaag ggagcaccgt ggaaaagaca gtggccccta cagaatgttc atag        714

SEQ ID NO: 593         moltype = DNA  length = 714
FEATURE                Location/Qualifiers
source                 1..714
                       mol_type = other DNA
                       organism = Homo sapiens
SEQUENCE: 593
atgagtgtgc tcactcaggt cctggcgttg ctgctgctgt ggcttacagg tacgcgttgc  60
gacatcgccc tgacccagcc cgccagcgtg agcggcagcc ctggccagag catcaccatc  120
agctgcaccg gcaccagcag cgacgtgggc gacatcaacg acgtgagctg gtatcagcag  180
caccccggca aggcccccaa gctgatgatc tacgacgtga acaaccggcc cagcggcgtg  240
agcaaccggt tcagcggcag caagagcggc aacaccgcca gcctgaccat cagcggcctc  300
caggccgagg acgaggccga ctactactgc agcacctacg acggccctgg cctgagcgag  360
gtgttcggcg gagggaccaa gcttaccgtc ctaggtcagc ccaaggctgc cccctcggtc  420
actctgttcc cgccctcctc tgaggagctt caagccaaca aggccacact ggtgtgtctc  480
ataagtgact tctacccggg agccgtgaca gtggcctgga aggcagatag cagccccgtc  540
aaggcgggag tggagacaac cacaccctcc aaacaaagca acaacaagta cgcggccagc  600
agctatctga gcctgacgcc tgagcagtgg aagtcccaca gaagctacag ctgccaggtc  660
acgcatgaag ggagcaccgt ggaaaagaca gtggccccta cagaatgttc atag        714

SEQ ID NO: 594         moltype = AA  length = 213
FEATURE                Location/Qualifiers
source                 1..213
                       mol_type = protein
                       organism = Homo sapiens
SEQUENCE: 594
MQLPLALCLV CLLVHTAFRV VEGQGWQAFK NDATEIIPEL GEYPEPPPEL ENNKTMNRAE  60
NGGRPPHHPF ETKDVSEYSC RELHFTRYVT DGPCRSAKPV TELVCSGQCG PARLLPNAIG  120
RGKWWRPSGP DFRCIPDRYR AQRVQLLCPG GEAPRARKVR LVASCKCKRL TRFHNQSELK  180
DFGTEAARPQ KGRKPRPRAR SAKANQAELE NAY                                213

SEQ ID NO: 595         moltype = AA  length = 14
FEATURE                Location/Qualifiers
source                 1..14
                       mol_type = protein
                       organism = Homo sapiens
SEQUENCE: 595
ARLLNAIGRG KWWR                                                     14

SEQ ID NO: 596         moltype = AA  length = 15
FEATURE                Location/Qualifiers
source                 1..15
                       mol_type = protein
                       organism = Homo sapiens
SEQUENCE: 596
RLVASCKCKR LTRFH                                                    15

SEQ ID NO: 597         moltype = AA  length = 13
FEATURE                Location/Qualifiers
source                 1..13
                       mol_type = protein
                       organism = Homo sapiens
SEQUENCE: 597
GGGSGGGGSG GGG                                                      13

SEQ ID NO: 598         moltype = AA  length = 19
FEATURE                Location/Qualifiers
source                 1..19
                       mol_type = protein
                       organism = Homo sapiens
SEQUENCE: 598
```

```
GGGGSGGGGS GGGGSGGGG                                       19

SEQ ID NO: 599         moltype = DNA  length = 21
FEATURE                Location/Qualifiers
misc_feature           1..21
                       note = siRNA
source                 1..21
                       mol_type = other DNA
                       organism = synthetic construct
SEQUENCE: 599
taaattatca taaagtccta a                                    21

SEQ ID NO: 600         moltype = DNA  length = 21
FEATURE                Location/Qualifiers
misc_feature           1..21
                       note = siRNA
source                 1..21
                       mol_type = other DNA
                       organism = synthetic construct
SEQUENCE: 600
aggactttat gataatttat t                                    21

SEQ ID NO: 601         moltype = DNA  length = 21
FEATURE                Location/Qualifiers
misc_feature           1..21
                       note = siRNA
source                 1..21
                       mol_type = other DNA
                       organism = synthetic construct
SEQUENCE: 601
atagtggtta aataactcca g                                    21

SEQ ID NO: 602         moltype = DNA  length = 21
FEATURE                Location/Qualifiers
misc_feature           1..21
                       note = siRNA
source                 1..21
                       mol_type = other DNA
                       organism = synthetic construct
SEQUENCE: 602
ggagttattt aaccactatt t                                    21

SEQ ID NO: 603         moltype = DNA  length = 21
FEATURE                Location/Qualifiers
misc_feature           1..21
                       note = siRNA
source                 1..21
                       mol_type = other DNA
                       organism = synthetic construct
SEQUENCE: 603
taaattctcg tgatgtgcca t                                    21

SEQ ID NO: 604         moltype = DNA  length = 21
FEATURE                Location/Qualifiers
misc_feature           1..21
                       note = siRNA
source                 1..21
                       mol_type = other DNA
                       organism = synthetic construct
SEQUENCE: 604
ggcacatcac gagaatttat t                                    21

SEQ ID NO: 605         moltype = DNA  length = 21
FEATURE                Location/Qualifiers
misc_feature           1..21
                       note = siRNA
source                 1..21
                       mol_type = other DNA
                       organism = synthetic construct
SEQUENCE: 605
tttcttatag cacagctggt t                                    21

SEQ ID NO: 606         moltype = DNA  length = 21
FEATURE                Location/Qualifiers
misc_feature           1..21
                       note = siRNA
source                 1..21
                       mol_type = other DNA
                       organism = synthetic construct
```

```
SEQUENCE: 606
ccagctgtgc tataagaaat t                                         21

SEQ ID NO: 607         moltype = DNA  length = 21
FEATURE                Location/Qualifiers
misc_feature           1..21
                       note = siRNA
source                 1..21
                       mol_type = other DNA
                       organism = synthetic construct
SEQUENCE: 607
tagacctttc catccacgct g                                         21

SEQ ID NO: 608         moltype = DNA  length = 21
FEATURE                Location/Qualifiers
misc_feature           1..21
                       note = siRNA
source                 1..21
                       mol_type = other DNA
                       organism = synthetic construct
SEQUENCE: 608
gcgtggatgg aaaggtctat t                                         21

SEQ ID NO: 609         moltype = DNA  length = 29
FEATURE                Location/Qualifiers
misc_feature           1..29
                       note = siRNA
source                 1..29
                       mol_type = other DNA
                       organism = synthetic construct
SEQUENCE: 609
atgcagctcc cactggccct gtgtcttgt                                 29

SEQ ID NO: 610         moltype = DNA  length = 30
FEATURE                Location/Qualifiers
misc_feature           1..30
                       note = siRNA
source                 1..30
                       mol_type = other DNA
                       organism = synthetic construct
SEQUENCE: 610
aatcaggccg agctggagaa cgcctactag                                30

SEQ ID NO: 611         moltype = AA  length = 102
FEATURE                Location/Qualifiers
REGION                 1..102
                       note = KERE-class Nanobody
REGION                 1..102
                       note = misc_feature - Xaa is any amino acid
REGION                 31..35
                       note = misc_feature - CDR
REGION                 50..54
                       note = misc_feature - CDR
REGION                 87..91
                       note = misc_feature - CDR
source                 1..102
                       mol_type = protein
                       organism = synthetic construct
SEQUENCE: 611
EVQLVESGGG LVQPGGSLRL SCAASGIPFS XXXXXWFRQA PGKQRDSVAX XXXXRFTISR  60
DNAKNTVYLQ MNSLKPEDTA VYRCYFXXXX XWGQGTQVTV SS                     102

SEQ ID NO: 612         moltype = AA  length = 102
FEATURE                Location/Qualifiers
REGION                 1..102
                       note = KERE-class Nanobody
REGION                 1..102
                       note = misc_feature - Xaa is any amino acid
REGION                 31..35
                       note = misc_feature - CDR
REGION                 50..54
                       note = misc_feature - CDR
REGION                 87..91
                       note = misc_feature - CDR
source                 1..102
                       mol_type = protein
                       organism = synthetic construct
SEQUENCE: 612
QVKLEESGGG LVQAGGSLRL SCVGSGRTFS XXXXXWFRLA PGKEREFVAX XXXXRFTISR  60
```

```
DTASNRGYLH MNNLTPEDTA VYYCAAXXXX XWGQGTQVTV SS                    102

SEQ ID NO: 613          moltype = AA  length = 102
FEATURE                 Location/Qualifiers
REGION                  1..102
                        note = KERE-class Nanobody
REGION                  1..102
                        note = misc_feature - Xaa is any amino acid
REGION                  31..35
                        note = misc_feature - CDR
REGION                  50..54
                        note = misc_feature - CDR
REGION                  87..91
                        note = misc_feature - CDR
source                  1..102
                        mol_type = protein
                        organism = synthetic construct
SEQUENCE: 613
AVQLVDSGGG LVQAGDSLKL SCALTGGAFT XXXXXWFRQT PGREREFVAX XXXXRFTISR  60
DNAKNMVYLR MNSLIPEDAA VYSCAAXXXX XWGQGTLVTV SS                    102

SEQ ID NO: 614          moltype = AA  length = 102
FEATURE                 Location/Qualifiers
REGION                  1..102
                        note = KERE-class Nanobody
REGION                  1..102
                        note = misc_feature - Xaa is any amino acid
REGION                  31..35
                        note = misc_feature - CDR
REGION                  50..54
                        note = misc_feature - CDR
REGION                  87..91
                        note = misc_feature - CDR
source                  1..102
                        mol_type = protein
                        organism = synthetic construct
SEQUENCE: 614
QVQLVESGGG LVEAGGSLRL SCTASESPFR XXXXXWFRQT SGQEREFVAX XXXXRFTISR  60
DDAKNTVWLH GSTLKPEDTA VYYCAAXXXX XWGQGTQVTV SS                    102

SEQ ID NO: 615          moltype = AA  length = 102
FEATURE                 Location/Qualifiers
REGION                  1..102
                        note = KERE-class Nanobody
REGION                  1..102
                        note = misc_feature - Xaa is any amino acid
REGION                  31..35
                        note = misc_feature - CDR
REGION                  50..54
                        note = misc_feature - CDR
REGION                  87..91
                        note = misc_feature - CDR
REGION                  87..91
                        note = misc_feature - CDR
source                  1..102
                        mol_type = protein
                        organism = synthetic construct
SEQUENCE: 615
AVQLVESGGG LVQGGGSLRL ACAASERIFD XXXXXWYRQG PGNERELVAX XXXXRFTISM  60
DYTKQTVYLH MNSLRPEDTG LYYCKIXXXX XWGQGTQVTV SS                    102

SEQ ID NO: 616          moltype = AA  length = 102
FEATURE                 Location/Qualifiers
REGION                  1..102
                        note = KERE-class Nanobody
REGION                  1..102
                        note = misc_feature - Xaa is any amino acid
REGION                  31..35
                        note = misc_feature - CDR
REGION                  50..54
                        note = misc_feature - CDR
REGION                  87..91
                        note = misc_feature - CDR
source                  1..102
                        mol_type = protein
                        organism = synthetic construct
SEQUENCE: 616
DVKFVESGGG LVQAGGSLRL SCVASGFNFD XXXXXWFRQA PGKEREEVAX XXXXRFTISS  60
EKDKNSVYLQ MNSLKPEDTA LYICAGXXXX XWGRGTQVTV SS                    102
```

```
SEQ ID NO: 617          moltype = AA  length = 102
FEATURE                 Location/Qualifiers
REGION                  1..102
                        note = KERE-class Nanobody
REGION                  1..102
                        note = misc_feature - Xaa is any amino acid
REGION                  31..35
                        note = misc_feature - CDR
REGION                  50..54
                        note = misc_feature - CDR
REGION                  87..91
                        note = misc_feature - CDR
source                  1..102
                        mol_type = protein
                        organism = synthetic construct
SEQUENCE: 617
QVRLAESGGG LVQSGGSLRL SCVASGSTYT XXXXXWYRQY PGKQRALVAX XXXXRFTIAR  60
DSTKDTFCLQ MNNLKPEDTA VYYCYAXXXX XWGQGTQVTV SS                     102

SEQ ID NO: 618          moltype = AA  length = 102
FEATURE                 Location/Qualifiers
REGION                  1..102
                        note = KERE-class Nanobody
REGION                  1..102
                        note = misc_feature - Xaa is any amino acid
REGION                  31..35
                        note = misc_feature - CDR
REGION                  50..54
                        note = misc_feature - CDR
REGION                  87..91
                        note = misc_feature - CDR
source                  1..102
                        mol_type = protein
                        organism = synthetic construct
SEQUENCE: 618
EVQLVESGGG LVQAGGSLRL SCAASGFTSD XXXXXWFRQA PGKPREGVSX XXXXRFTIST  60
DNAKNTVHLL MNRVNAEDTA LYYCAVXXXX XWGRGTRVTV SS                     102

SEQ ID NO: 619          moltype = AA  length = 102
FEATURE                 Location/Qualifiers
REGION                  1..102
                        note = KERE-class Nanobody
REGION                  1..102
                        note = misc_feature - Xaa is any amino acid
REGION                  31..35
                        note = misc_feature - CDR
REGION                  50..54
                        note = misc_feature - CDR
REGION                  87..91
                        note = misc_feature - CDR
source                  1..102
                        mol_type = protein
                        organism = synthetic construct
SEQUENCE: 619
QVQLVESGGG LVQPGGSLRL SCQASGDIST XXXXXWYRQV PGKLREFVAX XXXXRFTISG  60
DNAKRAIYLQ MNNLKPDDTA VYYCNRXXXX XWGQGTQVTV SP                     102

SEQ ID NO: 620          moltype = AA  length = 102
FEATURE                 Location/Qualifiers
REGION                  1..102
                        note = KERE-class Nanobody
REGION                  1..102
                        note = MISC_FEATURE - Xaa is any amino acid
REGION                  31..35
                        note = misc_feature - CDR
REGION                  50..54
                        note = misc_feature - CDR
REGION                  87..91
                        note = misc_feature - CDR
source                  1..102
                        mol_type = protein
                        organism = synthetic construct
SEQUENCE: 620
QVPVVESGGG LVQAGDSLRL FCAVPSFTST XXXXXWFRQA PGKEREFVAX XXXXRFTISR  60
NATKNTLTLR MDSLKPEDTA VYYCAAXXXX XWGQGTQVTV SS                     102

SEQ ID NO: 621          moltype = AA  length = 102
FEATURE                 Location/Qualifiers
```

```
REGION                  1..102
                        note = KERE-class Nanobody
REGION                  1..102
                        note = misc_feature - Xaa is any amino acid
REGION                  31..35
                        note = misc_feature - CDR
REGION                  50..54
                        note = misc_feature - CDR
REGION                  87..91
                        note = misc_feature - CDR
source                  1..102
                        mol_type = protein
                        organism = synthetic construct
SEQUENCE: 621
EVQLVESGGG LVQAGDSLRL FCTVSGGTAS XXXXXWFRQA PGEKREFVAX XXXXRFTIAR  60
ENAGNMVYLQ MNNLKPDDTA LYTCAAXXXX XWGRGTQVTV SS                     102

SEQ ID NO: 622          moltype = AA  length = 102
FEATURE                 Location/Qualifiers
REGION                  1..102
                        note = KERE-class Nanobody
REGION                  1..102
                        note = misc_feature - Xaa is any amino acid
REGION                  31..35
                        note = misc_feature - CDR
REGION                  50..54
                        note = misc_feature - CDR
REGION                  87..91
                        note = misc_feature - CDR
source                  1..102
                        mol_type = protein
                        organism = synthetic construct
SEQUENCE: 622
AVQLVESGGD SVQPGDSQTL SCAASGRTNS XXXXXWFRQA PGKERVFLAX XXXXRFTISR  60
DSAKNMMYLQ MNNLKPQDTA VYYCAAXXXX XWGQGTQVTV SS                     102

SEQ ID NO: 623          moltype = AA  length = 102
FEATURE                 Location/Qualifiers
REGION                  1..102
                        note = KERE-class Nanobody
REGION                  1..102
                        note = misc_feature - Xaa is any amino acid
REGION                  31..35
                        note = misc_feature - CDR
REGION                  50..54
                        note = misc_feature - CDR
REGION                  87..91
                        note = misc_feature - CDR
source                  1..102
                        mol_type = protein
                        organism = synthetic construct
SEQUENCE: 623
AVQLVESGGG LVQAGGSLRL SCVVSGLTSS XXXXXWFRQT PWQERDFVAX XXXXRFTISR  60
DNYKDTVLLE MNFLKPEDTA IYYCAAXXXX XWGQGTQVTV SS                     102

SEQ ID NO: 624          moltype = AA  length = 102
FEATURE                 Location/Qualifiers
REGION                  1..102
                        note = KERE-class Nanobody
REGION                  1..102
                        note = misc_feature - Xaa is any amino acid
REGION                  31..35
                        note = misc_feature - CDR
REGION                  50..54
                        note = misc_feature - CDR
REGION                  87..91
                        note = misc_feature - CDR
source                  1..102
                        mol_type = protein
                        organism = synthetic construct
SEQUENCE: 624
AVQLVESGGG LVQAGASLRL SCATSTRTLD XXXXXWFRQA PGRDREFVAX XXXXRFTVSR  60
DSAENTVALQ MNSLKPEDTA VYYCAAXXXX XWGQGTRVTV SS                     102

SEQ ID NO: 625          moltype = AA  length = 102
FEATURE                 Location/Qualifiers
REGION                  1..102
                        note = KERE-class Nanobody
REGION                  1..102
```

```
                         note = misc_feature - Xaa is any amino acid
REGION                   31..35
                         note = misc_feature - CDR
REGION                   50..54
                         note = misc_feature - CDR
REGION                   87..91
                         note = misc_feature - CDR
source                   1..102
                         mol_type = protein
                         organism = synthetic construct
SEQUENCE: 625
QVQLVESGGG LVQPGGSLRL SCTVSRLTAH XXXXXWFRQA PGKEREAVSX XXXXRFTISR  60
DYAGNTAFLQ MDSLKPEDTG VYYCATXXXX XWGQGTQVTV SS                     102

SEQ ID NO: 626           moltype = AA  length = 102
FEATURE                  Location/Qualifiers
REGION                   1..102
                         note = KERE-class Nanobody
REGION                   1..102
                         note = misc_feature - Xaa is any amino acid
REGION                   31..35
                         note = misc_feature - CDR
REGION                   50..54
                         note = misc_feature - CDR
REGION                   87..91
                         note = misc_feature - CDR
source                   1..102
                         mol_type = protein
                         organism = synthetic construct
SEQUENCE: 626
EVQLVESGGE LVQAGGSLKL SCTASGRNFV XXXXXWFRRA PGKEREFVAX XXXXRFTVSR  60
DNGKNTAYLR MNSLKPEDTA DYYCAVXXXX XLGSGTQVTV SS                     102

SEQ ID NO: 627           moltype = AA  length = 102
FEATURE                  Location/Qualifiers
REGION                   1..102
                         note = GLEW-class Nanobody
REGION                   1..102
                         note = misc_feature - Xaa is any amino acid
REGION                   31..35
                         note = misc_feature - CDR
REGION                   50..54
                         note = misc_feature - CDR
REGION                   87..91
                         note = misc_feature - CDR
source                   1..102
                         mol_type = protein
                         organism = synthetic construct
SEQUENCE: 627
AVQLVESGGG LVQPGGSLRL SCAASGFTFS XXXXXWVRQA PGKVLEWVSX XXXXRFTISR  60
DNAKNTLYLQ MNSLKPEDTA VYYCVKXXXX XGSQGTQVTV SS                     102

SEQ ID NO: 628           moltype = AA  length = 102
FEATURE                  Location/Qualifiers
REGION                   1..102
                         note = GLEW-class Nanobody
REGION                   1..102
                         note = misc_feature - Xaa is any amino acid
REGION                   31..35
                         note = misc_feature - CDR
REGION                   50..54
                         note = misc_feature - CDR
REGION                   87..91
                         note = misc_feature - CDR
source                   1..102
                         mol_type = protein
                         organism = synthetic construct
SEQUENCE: 628
EVQLVESGGG LVQPGGSLRL SCVCVSSGCT XXXXXWVRQA PGKAEEWVSX XXXXRFKISR  60
DNAKKTLYLQ MNSLGPEDTA MYYCQRXXXX XRGQGTQVTV SS                     102

SEQ ID NO: 629           moltype = AA  length = 102
FEATURE                  Location/Qualifiers
REGION                   1..102
                         note = GLEW-class Nanobody
REGION                   1..102
                         note = misc_feature - Xaa is any amino acid
REGION                   31..35
                         note = misc_feature - CDR
```

```
REGION                  50..54
                        note = misc_feature - CDR
REGION                  87..91
                        note = misc_feature - CDR
source                  1..102
                        mol_type = protein
                        organism = synthetic construct
SEQUENCE: 629
EVQLVESGGG LALPGGSLTL SCVFSGSTFS XXXXXWVRHT PGKAEEWVSX XXXXRFTISR  60
DNAKNTLYLE MNSLSPEDTA MYYCGRXXXX XRSKGIQVTV SS                    102

SEQ ID NO: 630          moltype = AA  length = 102
FEATURE                 Location/Qualifiers
REGION                  1..102
                        note = P,R,S 103-class Nanobody
REGION                  1..102
                        note = misc_feature - CDR
REGION                  31..35
                        note = misc_feature - CDR
REGION                  50..54
                        note = misc_feature - CDR
REGION                  87..91
                        note = misc_feature - CDR
source                  1..102
                        mol_type = protein
                        organism = synthetic construct
SEQUENCE: 630
AVQLVESGGG LVQAGGSLRL SCAASGRTFS XXXXXWFRQA PGKEREFVAX XXXXRFTISR  60
DNAKNTVYLQ MNSLKPEDTA VYYCAAXXXX XRGQGTQVTV SS                    102

SEQ ID NO: 631          moltype = AA  length = 102
FEATURE                 Location/Qualifiers
REGION                  1..102
                        note = P,R,S 103-class Nanobody
REGION                  1..102
                        note = misc_feature - Xaa is any amino acid
REGION                  31..35
                        note = misc_feature - CDR
REGION                  50..54
                        note = misc_feature - CDR
REGION                  87..91
                        note = misc_feature - CDR
source                  1..102
                        mol_type = protein
                        organism = synthetic construct
SEQUENCE: 631
DVQLVESGGD LVQPGGSLRL SCAASGFSFD XXXXXWLRQT PGKGLEWVGX XXXXRFTISR  60
DNAKNMLYLH LNNLKSEDTA VYYCRRXXXX XLGQGTQVTV SS                    102

SEQ ID NO: 632          moltype = AA  length = 102
FEATURE                 Location/Qualifiers
REGION                  1..102
                        note = P,R,S 103-class Nanobody
REGION                  1..102
                        note = misc_feature - Xaa is any amino acid
REGION                  31..35
                        note = misc_feature - CDR
REGION                  50..54
                        note = misc_feature - CDR
REGION                  87..91
                        note = misc_feature - CDR
source                  1..102
                        mol_type = protein
                        organism = synthetic construct
SEQUENCE: 632
EVQLVESGGG LVQPGGSLRL SCVCVSSGCT XXXXXWVRQA PGKAEEWVSX XXXXRFKISR  60
DNAKKTLYLQ MNSLGPEDTA MYYCQRXXXX XRGQGTQVTV SS                    102

SEQ ID NO: 633          moltype = AA  length = 30
FEATURE                 Location/Qualifiers
REGION                  1..30
                        note = KERE-class Nanobody FW1 sequence
source                  1..30
                        mol_type = protein
                        organism = synthetic construct
SEQUENCE: 633
QVQRVESGGG LVQAGGSLRL SCAASGRTSS                                  30

SEQ ID NO: 634          moltype = AA  length = 30
```

-continued

```
FEATURE                 Location/Qualifiers
REGION                  1..30
                        note = KERE-class Nanobody FW1 sequence
source                  1..30
                        mol_type = protein
                        organism = synthetic construct
SEQUENCE: 634
QVQLVESGGG LVQTGDSLSL SCSASGRTFS                                    30

SEQ ID NO: 635          moltype = AA  length = 30
FEATURE                 Location/Qualifiers
REGION                  1..30
                        note = KERE-class Nanobody FW1 sequence
source                  1..30
                        mol_type = protein
                        organism = synthetic construct
SEQUENCE: 635
QVKLEESGGG LVQAGDSLRL SCAATGRAFG                                    30

SEQ ID NO: 636          moltype = AA  length = 30
FEATURE                 Location/Qualifiers
REGION                  1..30
                        note = KERE-class Nanobody FW1 sequence
source                  1..30
                        mol_type = protein
                        organism = synthetic construct
SEQUENCE: 636
AVQLVESGGG LVQPGESLGL SCVASGRDFV                                    30

SEQ ID NO: 637          moltype = AA  length = 30
FEATURE                 Location/Qualifiers
REGION                  1..30
                        note = KERE-class Nanobody FW1 sequence
source                  1..30
                        mol_type = protein
                        organism = synthetic construct
SEQUENCE: 637
EVQLVESGGG LVQAGGSLRL SCEVLGRTAG                                    30

SEQ ID NO: 638          moltype = AA  length = 30
FEATURE                 Location/Qualifiers
REGION                  1..30
                        note = KERE-class Nanobody FW1 sequence
source                  1..30
                        mol_type = protein
                        organism = synthetic construct
SEQUENCE: 638
QVQLVESGGG WVQPGGSLRL SCAASETILS                                    30

SEQ ID NO: 639          moltype = AA  length = 30
FEATURE                 Location/Qualifiers
REGION                  1..30
                        note = KERE-class Nanobody FW1 sequence
source                  1..30
                        mol_type = protein
                        organism = synthetic construct
SEQUENCE: 639
QVQLVESGGG TVQPGGSLNL SCVASGNTFN                                    30

SEQ ID NO: 640          moltype = AA  length = 30
FEATURE                 Location/Qualifiers
REGION                  1..30
                        note = KERE-class Nanobody FW1 sequence
source                  1..30
                        mol_type = protein
                        organism = synthetic construct
SEQUENCE: 640
EVQLVESGGG LAQPGGSLQL SCSAPGFTLD                                    30

SEQ ID NO: 641          moltype = AA  length = 30
FEATURE                 Location/Qualifiers
REGION                  1..30
                        note = KERE-class Nanobody FW1 sequence
source                  1..30
                        mol_type = protein
                        organism = synthetic construct
SEQUENCE: 641
AQELEESGGG LVQAGGSLRL SCAASGRTFN                                    30
```

```
SEQ ID NO: 642          moltype = AA  length = 22
FEATURE                 Location/Qualifiers
REGION                  1..22
                        note = KERE-class Nanobody FW1 sequence
source                  1..22
                        mol_type = protein
                        organism = synthetic construct
SEQUENCE: 642
VESGGGLVQP GGSLRLSCAA SG                                              22

SEQ ID NO: 643          moltype = AA  length = 22
FEATURE                 Location/Qualifiers
REGION                  1..22
                        note = KERE-class Nanobody FW1 sequence
source                  1..22
                        mol_type = protein
                        organism = synthetic construct
SEQUENCE: 643
VDSGGGLVQA GDSLKLSCAL TG                                              22

SEQ ID NO: 644          moltype = AA  length = 22
FEATURE                 Location/Qualifiers
REGION                  1..22
                        note = KERE-class Nanobody FW1 sequence
source                  1..22
                        mol_type = protein
                        organism = synthetic construct
SEQUENCE: 644
VDSGGGLVQA GDSLRLSCAA SG                                              22

SEQ ID NO: 645          moltype = AA  length = 22
FEATURE                 Location/Qualifiers
REGION                  1..22
                        note = KERE-class Nanobody FW1 sequence
source                  1..22
                        mol_type = protein
                        organism = synthetic construct
SEQUENCE: 645
VDSGGGLVEA GGSLRLSCQV SE                                              22

SEQ ID NO: 646          moltype = AA  length = 22
FEATURE                 Location/Qualifiers
REGION                  1..22
                        note = KERE-class Nanobody FW1 sequence
source                  1..22
                        mol_type = protein
                        organism = synthetic construct
SEQUENCE: 646
QDSGGGSVQA GGSLKLSCAA SG                                              22

SEQ ID NO: 647          moltype = AA  length = 22
FEATURE                 Location/Qualifiers
REGION                  1..22
                        note = KERE-class Nanobody FW1 sequence
source                  1..22
                        mol_type = protein
                        organism = synthetic construct
SEQUENCE: 647
VQSGGRLVQA GDSLRLSCAA SE                                              22

SEQ ID NO: 648          moltype = AA  length = 22
FEATURE                 Location/Qualifiers
REGION                  1..22
                        note = KERE-class Nanobody FW1 sequence
source                  1..22
                        mol_type = protein
                        organism = synthetic construct
SEQUENCE: 648
VESGGTLVQS GDSLKLSCAS ST                                              22

SEQ ID NO: 649          moltype = AA  length = 22
FEATURE                 Location/Qualifiers
REGION                  1..22
                        note = KERE-class Nanobody FW1 sequence
source                  1..22
                        mol_type = protein
                        organism = synthetic construct
SEQUENCE: 649
MESGGDSVQS GGSLTLSCVA SG                                              22
```

```
SEQ ID NO: 650          moltype = AA  length = 22
FEATURE                 Location/Qualifiers
REGION                  1..22
                        note = KERE-class Nanobody FW1 sequence
source                  1..22
                        mol_type = protein
                        organism = synthetic construct
SEQUENCE: 650
QASGGGLVQA GGSLRLSCSA SV                                              22

SEQ ID NO: 651          moltype = AA  length = 14
FEATURE                 Location/Qualifiers
REGION                  1..14
                        note = KERE-class Nanobody FW2 sequence
source                  1..14
                        mol_type = protein
                        organism = synthetic construct
SEQUENCE: 651
WFRQAPGKER EFVA                                                       14

SEQ ID NO: 652          moltype = AA  length = 14
FEATURE                 Location/Qualifiers
REGION                  1..14
                        note = KERE-class Nanobody FW2 sequence
source                  1..14
                        mol_type = protein
                        organism = synthetic construct
SEQUENCE: 652
WFRQTPGRER EFVA                                                       14

SEQ ID NO: 653          moltype = AA  length = 14
FEATURE                 Location/Qualifiers
REGION                  1..14
                        note = KERE-class Nanobody FW2 sequence
source                  1..14
                        mol_type = protein
                        organism = synthetic construct
SEQUENCE: 653
WYRQAPGKQR EMVA                                                       14

SEQ ID NO: 654          moltype = AA  length = 14
FEATURE                 Location/Qualifiers
REGION                  1..14
                        note = KERE-class Nanobody FW2 sequence
source                  1..14
                        mol_type = protein
                        organism = synthetic construct
SEQUENCE: 654
WYRQGPGKQR ELVA                                                       14

SEQ ID NO: 655          moltype = AA  length = 14
FEATURE                 Location/Qualifiers
REGION                  1..14
                        note = KERE-class Nanobody FW2 sequence
source                  1..14
                        mol_type = protein
                        organism = synthetic construct
SEQUENCE: 655
WIRQAPGKER EGVS                                                       14

SEQ ID NO: 656          moltype = AA  length = 14
FEATURE                 Location/Qualifiers
REGION                  1..14
                        note = KERE-class Nanobody FW2 sequence
source                  1..14
                        mol_type = protein
                        organism = synthetic construct
SEQUENCE: 656
WFREAPGKER EGIS                                                       14

SEQ ID NO: 657          moltype = AA  length = 14
FEATURE                 Location/Qualifiers
REGION                  1..14
                        note = KERE-class Nanobody FW2 sequence
source                  1..14
                        mol_type = protein
                        organism = synthetic construct
SEQUENCE: 657
```

```
WYRQAPGKER DLVA                                                   14

SEQ ID NO: 658          moltype = AA  length = 14
FEATURE                 Location/Qualifiers
REGION                  1..14
                        note = KERE-class Nanobody FW2 sequence
source                  1..14
                        mol_type = protein
                        organism = synthetic construct
SEQUENCE: 658
WFRQAPGKQR EEVS                                                   14

SEQ ID NO: 659          moltype = AA  length = 14
FEATURE                 Location/Qualifiers
REGION                  1..14
                        note = KERE-class Nanobody FW2 sequence
source                  1..14
                        mol_type = protein
                        organism = synthetic construct
SEQUENCE: 659
WFRQPPGKVR EFVG                                                   14

SEQ ID NO: 660          moltype = AA  length = 32
FEATURE                 Location/Qualifiers
REGION                  1..32
                        note = KERE-class Nanobody FW3 sequence
source                  1..32
                        mol_type = protein
                        organism = synthetic construct
SEQUENCE: 660
RFTISRDNAK NTVYLQMNSL KPEDTAVYRC YF                               32

SEQ ID NO: 661          moltype = AA  length = 32
FEATURE                 Location/Qualifiers
REGION                  1..32
                        note = KERE-class Nanobody FW3 sequence
source                  1..32
                        mol_type = protein
                        organism = synthetic construct
SEQUENCE: 661
RFAISRDNNK NTGYLQMNSL EPEDTAVYYC AA                               32

SEQ ID NO: 662          moltype = AA  length = 32
FEATURE                 Location/Qualifiers
REGION                  1..32
                        note = KERE-class Nanobody FW3 sequence
source                  1..32
                        mol_type = protein
                        organism = synthetic construct
SEQUENCE: 662
RFTVARNNAK NTVNLEMNSL KPEDTAVYYC AA                               32

SEQ ID NO: 663          moltype = AA  length = 32
FEATURE                 Location/Qualifiers
REGION                  1..32
                        note = KERE-class Nanobody FW3 sequence
source                  1..32
                        mol_type = protein
                        organism = synthetic construct
SEQUENCE: 663
RFTISRDIAK NTVDLLMNNL EPEDTAVYYC AA                               32

SEQ ID NO: 664          moltype = AA  length = 32
FEATURE                 Location/Qualifiers
REGION                  1..32
                        note = KERE-class Nanobody FW3 sequence
source                  1..32
                        mol_type = protein
                        organism = synthetic construct
SEQUENCE: 664
RLTISRDNAV DTMYLQMNSL KPEDTAVYYC AA                               32

SEQ ID NO: 665          moltype = AA  length = 32
FEATURE                 Location/Qualifiers
REGION                  1..32
                        note = KERE-class Nanobody FW3 sequence
source                  1..32
                        mol_type = protein
                        organism = synthetic construct
```

```
SEQUENCE: 665
RFTISRDNAK NTVYLQMDNV KPEDTAIYYC AA                               32

SEQ ID NO: 666          moltype = AA  length = 32
FEATURE                 Location/Qualifiers
REGION                  1..32
                        note = KERE-class Nanobody FW3 sequence
source                  1..32
                        mol_type = protein
                        organism = synthetic construct
SEQUENCE: 666
RFTISKDSGK NTVYLQMTSL KPEDTAVYYC AT                               32

SEQ ID NO: 667          moltype = AA  length = 32
FEATURE                 Location/Qualifiers
REGION                  1..32
                        note = KERE-class Nanobody FW3 sequence
source                  1..32
                        mol_type = protein
                        organism = synthetic construct
SEQUENCE: 667
RFTISRDSAK NMMYLQMNNL KPQDTAVYYC AA                               32

SEQ ID NO: 668          moltype = AA  length = 32
FEATURE                 Location/Qualifiers
REGION                  1..32
                        note = KERE-class Nanobody FW3 sequence
source                  1..32
                        mol_type = protein
                        organism = synthetic construct
SEQUENCE: 668
RFTISRENDK STVYLQLNSL KPEDTAVYYC AA                               32

SEQ ID NO: 669          moltype = AA  length = 32
FEATURE                 Location/Qualifiers
REGION                  1..32
                        note = KERE-class Nanobody FW3 sequence
source                  1..32
                        mol_type = protein
                        organism = synthetic construct
SEQUENCE: 669
RFTISRDYAG NTAYLQMNSL KPEDTGVYYC AT                               32

SEQ ID NO: 670          moltype = AA  length = 11
FEATURE                 Location/Qualifiers
REGION                  1..11
                        note = KERE-class Nanobody FW4 sequence
source                  1..11
                        mol_type = protein
                        organism = synthetic construct
SEQUENCE: 670
WGQGTQVTVS S                                                      11

SEQ ID NO: 671          moltype = AA  length = 11
FEATURE                 Location/Qualifiers
REGION                  1..11
                        note = KERE-class Nanobody FW4 sequence
source                  1..11
                        mol_type = protein
                        organism = synthetic construct
SEQUENCE: 671
WGKGTLVTVS S                                                      11

SEQ ID NO: 672          moltype = AA  length = 11
FEATURE                 Location/Qualifiers
REGION                  1..11
                        note = KERE-class Nanobody FW4 sequence
source                  1..11
                        mol_type = protein
                        organism = synthetic construct
SEQUENCE: 672
RGQGTRVTVS S                                                      11

SEQ ID NO: 673          moltype = AA  length = 11
FEATURE                 Location/Qualifiers
REGION                  1..11
                        note = KERE-class Nanobody FW4 sequence
source                  1..11
                        mol_type = protein
```

```
                          organism = synthetic construct
SEQUENCE: 673
WGLGTQVTIS S                                                         11

SEQ ID NO: 674            moltype = AA  length = 30
FEATURE                   Location/Qualifiers
REGION                    1..30
                          note = GLEW-class Nanobody FW1 sequence
source                    1..30
                          mol_type = protein
                          organism = synthetic construct
SEQUENCE: 674
QVQLVESGGG LVQPGGSLRL SCAASGFTFS                                     30

SEQ ID NO: 675            moltype = AA  length = 30
FEATURE                   Location/Qualifiers
REGION                    1..30
                          note = GLEW-class Nanobody FW1 sequence
source                    1..30
                          mol_type = protein
                          organism = synthetic construct
SEQUENCE: 675
EVHLVESGGG LVRPGGSLRL SCAAFGFIFK                                     30

SEQ ID NO: 676            moltype = AA  length = 30
FEATURE                   Location/Qualifiers
REGION                    1..30
                          note = GLEW-class Nanobody FW1 sequence
source                    1..30
                          mol_type = protein
                          organism = synthetic construct
SEQUENCE: 676
QVKLEESGGG LAQPGGSLRL SCVASGFTFS                                     30

SEQ ID NO: 677            moltype = AA  length = 30
FEATURE                   Location/Qualifiers
REGION                    1..30
                          note = GLEW-class Nanobody FW1 sequence
source                    1..30
                          mol_type = protein
                          organism = synthetic construct
SEQUENCE: 677
EVQLVESGGG LVQPGGSLRL SCVCVSSGCT                                     30

SEQ ID NO: 678            moltype = AA  length = 30
FEATURE                   Location/Qualifiers
REGION                    1..30
                          note = GLEW-class Nanobody FW1 sequence
source                    1..30
                          mol_type = protein
                          organism = synthetic construct
SEQUENCE: 678
EVQLVESGGG LALPGGSLTL SCVFSGSTFS                                     30

SEQ ID NO: 679            moltype = AA  length = 22
FEATURE                   Location/Qualifiers
REGION                    1..22
                          note = GLEW-class Nanobody FW1 sequence
source                    1..22
                          mol_type = protein
                          organism = synthetic construct
SEQUENCE: 679
VESGGGLVQP GGSLRLSCAA SG                                             22

SEQ ID NO: 680            moltype = AA  length = 22
FEATURE                   Location/Qualifiers
REGION                    1..22
                          note = GLEW-class Nanobody FW1 sequence
source                    1..22
                          mol_type = protein
                          organism = synthetic construct
SEQUENCE: 680
EESGGGLAQP GGSLRLSCVA SG                                             22

SEQ ID NO: 681            moltype = AA  length = 22
FEATURE                   Location/Qualifiers
REGION                    1..22
                          note = GLEW-class Nanobody FW1 sequence
source                    1..22
```

```
                        mol_type = protein
                        organism = synthetic construct
SEQUENCE: 681
VESGGGLALP GGSLTLSCVF SG                                              22

SEQ ID NO: 682          moltype = AA  length = 14
FEATURE                 Location/Qualifiers
REGION                  1..14
                        note = GLEW-class Nanobody FW2 sequence
source                  1..14
                        mol_type = protein
                        organism = synthetic construct
SEQUENCE: 682
WVRQAPGKVL EWVS                                                       14

SEQ ID NO: 683          moltype = AA  length = 14
FEATURE                 Location/Qualifiers
REGION                  1..14
                        note = GLEW-class Nanobody FW2 sequence
source                  1..14
                        mol_type = protein
                        organism = synthetic construct
SEQUENCE: 683
WVRRPPGKGL EWVS                                                       14

SEQ ID NO: 684          moltype = AA  length = 14
FEATURE                 Location/Qualifiers
REGION                  1..14
                        note = GLEW-class Nanobody FW2 sequence
source                  1..14
                        mol_type = protein
                        organism = synthetic construct
SEQUENCE: 684
WVRQAPGMGL EWVS                                                       14

SEQ ID NO: 685          moltype = AA  length = 14
FEATURE                 Location/Qualifiers
REGION                  1..14
                        note = GLEW-class Nanobody FW2 sequence
source                  1..14
                        mol_type = protein
                        organism = synthetic construct
SEQUENCE: 685
WVRQAPGKEP EWVS                                                       14

SEQ ID NO: 686          moltype = AA  length = 14
FEATURE                 Location/Qualifiers
REGION                  1..14
                        note = GLEW-class Nanobody FW2 sequence
source                  1..14
                        mol_type = protein
                        organism = synthetic construct
SEQUENCE: 686
WVRQAPGKDQ EWVS                                                       14

SEQ ID NO: 687          moltype = AA  length = 14
FEATURE                 Location/Qualifiers
REGION                  1..14
                        note = GLEW-class Nanobody FW2 sequence
source                  1..14
                        mol_type = protein
                        organism = synthetic construct
SEQUENCE: 687
WVRQAPGKAE EWVS                                                       14

SEQ ID NO: 688          moltype = AA  length = 14
FEATURE                 Location/Qualifiers
REGION                  1..14
                        note = GLEW-class Nanobody FW2 sequence
source                  1..14
                        mol_type = protein
                        organism = synthetic construct
SEQUENCE: 688
WVRQAPGKGL EWVA                                                       14

SEQ ID NO: 689          moltype = AA  length = 14
FEATURE                 Location/Qualifiers
REGION                  1..14
                        note = GLEW-class Nanobody FW2 sequence
```

-continued

```
source                  1..14
                        mol_type = protein
                        organism = synthetic construct
SEQUENCE: 689
WVRQAPGRAT EWVS                                             14

SEQ ID NO: 690          moltype = AA  length = 32
FEATURE                 Location/Qualifiers
REGION                  1..32
                        note = GLEW-class Nanobody FW3 sequence
source                  1..32
                        mol_type = protein
                        organism = synthetic construct
SEQUENCE: 690
RFTISRDNAK NTLYLQMNSL KPEDTAVYYC VK                         32

SEQ ID NO: 691          moltype = AA  length = 32
FEATURE                 Location/Qualifiers
REGION                  1..32
                        note = GLEW-class Nanobody FW3 sequence
source                  1..32
                        mol_type = protein
                        organism = synthetic construct
SEQUENCE: 691
RFTISRDNAR NTLYLQMDSL IPEDTALYYC AR                         32

SEQ ID NO: 692          moltype = AA  length = 32
FEATURE                 Location/Qualifiers
REGION                  1..32
                        note = GLEW-class Nanobody FW3 sequence
source                  1..32
                        mol_type = protein
                        organism = synthetic construct
SEQUENCE: 692
RFTSSRDNAK STLYLQMNDL KPEDTALYYC AR                         32

SEQ ID NO: 693          moltype = AA  length = 32
FEATURE                 Location/Qualifiers
REGION                  1..32
                        note = GLEW-class Nanobody FW3 sequence
source                  1..32
                        mol_type = protein
                        organism = synthetic construct
SEQUENCE: 693
RFIISRDNAK NTLYLQMNSL GPEDTAMYYC QR                         32

SEQ ID NO: 694          moltype = AA  length = 32
FEATURE                 Location/Qualifiers
REGION                  1..32
                        note = GLEW-class Nanobody FW3 sequence
source                  1..32
                        mol_type = protein
                        organism = synthetic construct
SEQUENCE: 694
RFTASRDNAK NTLYLQMNSL KSEDTARYYC AR                         32

SEQ ID NO: 695          moltype = AA  length = 32
FEATURE                 Location/Qualifiers
REGION                  1..32
                        note = GLEW-class Nanobody FW3 sequence
source                  1..32
                        mol_type = protein
                        organism = synthetic construct
SEQUENCE: 695
RFTISRDNAK NTLYLQMDDL QSEDTAMYYC GR                         32

SEQ ID NO: 696          moltype = AA  length = 11
FEATURE                 Location/Qualifiers
REGION                  1..11
                        note = GLEW-class Nanobody FW4 sequence
source                  1..11
                        mol_type = protein
                        organism = synthetic construct
SEQUENCE: 696
GSQGTQVTVS S                                                11

SEQ ID NO: 697          moltype = AA  length = 11
FEATURE                 Location/Qualifiers
REGION                  1..11
```

```
                        note = GLEW-class Nanobody FW4 sequence
source                  1..11
                        mol_type = protein
                        organism = synthetic construct
SEQUENCE: 697
LRGGTQVTVS S                                                    11

SEQ ID NO: 698          moltype = AA  length = 11
FEATURE                 Location/Qualifiers
REGION                  1..11
                        note = GLEW-class Nanobody FW4 sequence
source                  1..11
                        mol_type = protein
                        organism = synthetic construct
SEQUENCE: 698
RGQGTLVTVS S                                                    11

SEQ ID NO: 699          moltype = AA  length = 11
FEATURE                 Location/Qualifiers
REGION                  1..11
                        note = GLEW-class Nanobody FW4 sequence
source                  1..11
                        mol_type = protein
                        organism = synthetic construct
SEQUENCE: 699
RSRGIQVTVS S                                                    11

SEQ ID NO: 700          moltype = AA  length = 11
FEATURE                 Location/Qualifiers
REGION                  1..11
                        note = GLEW-class Nanobody FW4 sequence
source                  1..11
                        mol_type = protein
                        organism = synthetic construct
SEQUENCE: 700
WGKGTQVTVS S                                                    11

SEQ ID NO: 701          moltype = AA  length = 11
FEATURE                 Location/Qualifiers
REGION                  1..11
                        note = GLEW-class Nanobody FW4 sequence
source                  1..11
                        mol_type = protein
                        organism = synthetic construct
SEQUENCE: 701
WGQGTQVTVS S                                                    11

SEQ ID NO: 702          moltype = AA  length = 30
FEATURE                 Location/Qualifiers
REGION                  1..30
                        note = P,R,S 103-class Nanobody FW1 sequence
source                  1..30
                        mol_type = protein
                        organism = synthetic construct
SEQUENCE: 702
AVQLVESGGG LVQAGGSLRL SCAASGRTFS                                30

SEQ ID NO: 703          moltype = AA  length = 30
FEATURE                 Location/Qualifiers
REGION                  1..30
                        note = P,R,S 103-class Nanobody FW1 sequence
source                  1..30
                        mol_type = protein
                        organism = synthetic construct
SEQUENCE: 703
QVQLQESGGG MVQPGGSLRL SCAASGFDFG                                30

SEQ ID NO: 704          moltype = AA  length = 30
FEATURE                 Location/Qualifiers
REGION                  1..30
                        note = P,R,S 103-class Nanobody FW1 sequence
source                  1..30
                        mol_type = protein
                        organism = synthetic construct
SEQUENCE: 704
EVHLVESGGG LVRPGGSLRL SCAAFGFIFK                                30

SEQ ID NO: 705          moltype = AA  length = 30
FEATURE                 Location/Qualifiers
```

```
REGION                  1..30
                        note = P,R,S 103-class Nanobody FW1 sequence
source                  1..30
                        mol_type = protein
                        organism = synthetic construct
SEQUENCE: 705
QVQLAESGGG LVQPGGSLKL SCAASRTIVS                                   30

SEQ ID NO: 706          moltype = AA  length = 30
FEATURE                 Location/Qualifiers
REGION                  1..30
                        note = P,R,S 103-class Nanobody FW1 sequence
source                  1..30
                        mol_type = protein
                        organism = synthetic construct
SEQUENCE: 706
QEHLVESGGG LVDIGGSLRL SCAASERIFS                                   30

SEQ ID NO: 707          moltype = AA  length = 30
FEATURE                 Location/Qualifiers
REGION                  1..30
                        note = P,R,S 103-class Nanobody FW1 sequence
source                  1..30
                        mol_type = protein
                        organism = synthetic construct
SEQUENCE: 707
QVKLEESGGG LAQPGGSLRL SCVASGFTFS                                   30

SEQ ID NO: 708          moltype = AA  length = 30
FEATURE                 Location/Qualifiers
REGION                  1..30
                        note = P,R,S 103-class Nanobody FW1 sequence
source                  1..30
                        mol_type = protein
                        organism = synthetic construct
SEQUENCE: 708
EVQLVESGGG LVQPGGSLRL SCVCVSSGCT                                   30

SEQ ID NO: 709          moltype = AA  length = 30
FEATURE                 Location/Qualifiers
REGION                  1..30
                        note = P,R,S 103-class Nanobody FW1 sequence
source                  1..30
                        mol_type = protein
                        organism = synthetic construct
SEQUENCE: 709
EVQLVESGGG LALPGGSLTL SCVFSGSTFS                                   30

SEQ ID NO: 710          moltype = AA  length = 22
FEATURE                 Location/Qualifiers
REGION                  1..22
                        note = P,R,S 103-class Nanobody FW1 sequence
source                  1..22
                        mol_type = protein
                        organism = synthetic construct
SEQUENCE: 710
VESGGGLVQA GGSLRLSCAA SG                                           22

SEQ ID NO: 711          moltype = AA  length = 22
FEATURE                 Location/Qualifiers
REGION                  1..22
                        note = P,R,S 103-class Nanobody FW1 sequence
source                  1..22
                        mol_type = protein
                        organism = synthetic construct
SEQUENCE: 711
AESGGGLVQP GGSLKLSCAA SR                                           22

SEQ ID NO: 712          moltype = AA  length = 14
FEATURE                 Location/Qualifiers
REGION                  1..14
                        note = P,R,S 103-class Nanobody FW2 sequence
source                  1..14
                        mol_type = protein
                        organism = synthetic construct
SEQUENCE: 712
WFRQAPGKER EFVA                                                    14

SEQ ID NO: 713          moltype = AA  length = 14
```

```
FEATURE                Location/Qualifiers
REGION                 1..14
                       note = P,R,S 103-class Nanobody FW2 sequence
source                 1..14
                       mol_type = protein
                       organism = synthetic construct
SEQUENCE: 713
WVRQAPGKVL EWVS                                                  14

SEQ ID NO: 714         moltype = AA  length = 14
FEATURE                Location/Qualifiers
REGION                 1..14
                       note = P,R,S 103-class Nanobody FW2 sequence
source                 1..14
                       mol_type = protein
                       organism = synthetic construct
SEQUENCE: 714
WVRRPPGKGL EWVS                                                  14

SEQ ID NO: 715         moltype = AA  length = 14
FEATURE                Location/Qualifiers
REGION                 1..14
                       note = P,R,S 103-class Nanobody FW2 sequence
source                 1..14
                       mol_type = protein
                       organism = synthetic construct
SEQUENCE: 715
WIRQAPGKER EGVS                                                  14

SEQ ID NO: 716         moltype = AA  length = 14
FEATURE                Location/Qualifiers
REGION                 1..14
                       note = P,R,S 103-class Nanobody FW2 sequence
source                 1..14
                       mol_type = protein
                       organism = synthetic construct
SEQUENCE: 716
WVRQYPGKEP EWVS                                                  14

SEQ ID NO: 717         moltype = AA  length = 14
FEATURE                Location/Qualifiers
REGION                 1..14
                       note = P,R,S 103-class Nanobody FW2 sequence
source                 1..14
                       mol_type = protein
                       organism = synthetic construct
SEQUENCE: 717
WFRQPPGKEH EFVA                                                  14

SEQ ID NO: 718         moltype = AA  length = 14
FEATURE                Location/Qualifiers
REGION                 1..14
                       note = P,R,S 103-class Nanobody FW2 sequence
source                 1..14
                       mol_type = protein
                       organism = synthetic construct
SEQUENCE: 718
WYRQAPGKRT ELVA                                                  14

SEQ ID NO: 719         moltype = AA  length = 14
FEATURE                Location/Qualifiers
REGION                 1..14
                       note = P,R,S 103-class Nanobody FW2 sequence
source                 1..14
                       mol_type = protein
                       organism = synthetic construct
SEQUENCE: 719
WLRQAPGQGL EWVS                                                  14

SEQ ID NO: 720         moltype = AA  length = 14
FEATURE                Location/Qualifiers
REGION                 1..14
                       note = P,R,S 103-class Nanobody FW2 sequence
source                 1..14
                       mol_type = protein
                       organism = synthetic construct
SEQUENCE: 720
WLRQTPGKGL EWVG                                                  14
```

-continued

```
SEQ ID NO: 721          moltype = AA  length = 14
FEATURE                 Location/Qualifiers
REGION                  1..14
                        note = P,R,S 103-class Nanobody FW2 sequence
source                  1..14
                        mol_type = protein
                        organism = synthetic construct
SEQUENCE: 721
WVRQAPGKAE EFVS                                                    14

SEQ ID NO: 722          moltype = AA  length = 32
FEATURE                 Location/Qualifiers
REGION                  1..32
                        note = P,R,S 103-class Nanobody FW3 sequence
source                  1..32
                        mol_type = protein
                        organism = synthetic construct
SEQUENCE: 722
RFTISRDNAK NTVYLQMNSL KPEDTAVYYC AA                                32

SEQ ID NO: 723          moltype = AA  length = 32
FEATURE                 Location/Qualifiers
REGION                  1..32
                        note = P,R,S 103-class Nanobody FW3 sequence
source                  1..32
                        mol_type = protein
                        organism = synthetic construct
SEQUENCE: 723
RFTISRDNAR NTLYLQMDSL IPEDTALYYC AR                                32

SEQ ID NO: 724          moltype = AA  length = 32
FEATURE                 Location/Qualifiers
REGION                  1..32
                        note = P,R,S 103-class Nanobody FW3 sequence
source                  1..32
                        mol_type = protein
                        organism = synthetic construct
SEQUENCE: 724
RFTISRDNAK NEMYLQMNNL KTEDTGVYWC GA                                32

SEQ ID NO: 725          moltype = AA  length = 32
FEATURE                 Location/Qualifiers
REGION                  1..32
                        note = P,R,S 103-class Nanobody FW3 sequence
source                  1..32
                        mol_type = protein
                        organism = synthetic construct
SEQUENCE: 725
RFTISSDSNR NMIYLQMNNL KPEDTAVYYC AA                                32

SEQ ID NO: 726          moltype = AA  length = 32
FEATURE                 Location/Qualifiers
REGION                  1..32
                        note = P,R,S 103-class Nanobody FW3 sequence
source                  1..32
                        mol_type = protein
                        organism = synthetic construct
SEQUENCE: 726
RFTISRDNAK NMLYLHLNNL KSEDTAVYYC RR                                32

SEQ ID NO: 727          moltype = AA  length = 32
FEATURE                 Location/Qualifiers
REGION                  1..32
                        note = P,R,S 103-class Nanobody FW3 sequence
source                  1..32
                        mol_type = protein
                        organism = synthetic construct
SEQUENCE: 727
RFTISRDNAK KTVYLRLNSL NPEDTAVYSC NL                                32

SEQ ID NO: 728          moltype = AA  length = 32
FEATURE                 Location/Qualifiers
REGION                  1..32
                        note = P,R,S 103-class Nanobody FW3 sequence
source                  1..32
                        mol_type = protein
                        organism = synthetic construct
SEQUENCE: 728
RFKISRDNAK KTLYLQMNSL GPEDTAMYYC QR                                32
```

-continued

```
SEQ ID NO: 729          moltype = AA  length = 32
FEATURE                 Location/Qualifiers
REGION                  1..32
                        note = P,R,S 103-class Nanobody FW3 sequence
source                  1..32
                        mol_type = protein
                        organism = synthetic construct
SEQUENCE: 729
RFTVSRDNGK NTAYLRMNSL KPEDTADYYC AV                                32

SEQ ID NO: 730          moltype = AA  length = 11
FEATURE                 Location/Qualifiers
REGION                  1..11
                        note = P,R,S 103-class Nanobody FW4 sequence
source                  1..11
                        mol_type = protein
                        organism = synthetic construct
SEQUENCE: 730
RGQGTQVTVS S                                                       11

SEQ ID NO: 731          moltype = AA  length = 11
FEATURE                 Location/Qualifiers
REGION                  1..11
                        note = P,R,S 103-class Nanobody FW4 sequence
source                  1..11
                        mol_type = protein
                        organism = synthetic construct
SEQUENCE: 731
LRGGTQVTVS S                                                       11

SEQ ID NO: 732          moltype = AA  length = 11
FEATURE                 Location/Qualifiers
REGION                  1..11
                        note = P,R,S 103-class Nanobody FW4 sequence
source                  1..11
                        mol_type = protein
                        organism = synthetic construct
SEQUENCE: 732
GNKGTLVTVS S                                                       11

SEQ ID NO: 733          moltype = AA  length = 11
FEATURE                 Location/Qualifiers
REGION                  1..11
                        note = P,R,S 103-class Nanobody FW4 sequence
source                  1..11
                        mol_type = protein
                        organism = synthetic construct
SEQUENCE: 733
SSPGTQVTVS S                                                       11

SEQ ID NO: 734          moltype = AA  length = 11
FEATURE                 Location/Qualifiers
REGION                  1..11
                        note = P,R,S 103-class Nanobody FW4 sequence
source                  1..11
                        mol_type = protein
                        organism = synthetic construct
SEQUENCE: 734
SSQGTLVTVS S                                                       11

SEQ ID NO: 735          moltype = AA  length = 11
FEATURE                 Location/Qualifiers
REGION                  1..11
                        note = P,R,S 103-class Nanobody FW4 sequence
source                  1..11
                        mol_type = protein
                        organism = synthetic construct
SEQUENCE: 735
RSRGIQVTVS S                                                       11

SEQ ID NO: 736          moltype = AA  length = 30
FEATURE                 Location/Qualifiers
REGION                  1..30
                        note = FR1 sequence
source                  1..30
                        mol_type = protein
                        organism = synthetic construct
SEQUENCE: 736
```

-continued

```
EVQLVESGGG LVQPGGSLRL SCAASGSIFS                                  30

SEQ ID NO: 737          moltype = AA  length = 30
FEATURE                 Location/Qualifiers
REGION                  1..30
                        note = FR1 sequence
source                  1..30
                        mol_type = protein
                        organism = synthetic construct
SEQUENCE: 737
EVQLVESGGG LVQAGDSLRL SCTATGRTSS                                  30

SEQ ID NO: 738          moltype = AA  length = 30
FEATURE                 Location/Qualifiers
REGION                  1..30
                        note = FR1 sequence
source                  1..30
                        mol_type = protein
                        organism = synthetic construct
SEQUENCE: 738
EVQLVESGGG LVQAGGSLRL SCATSGFTFS                                  30

SEQ ID NO: 739          moltype = AA  length = 30
FEATURE                 Location/Qualifiers
REGION                  1..30
                        note = FR1 sequence
source                  1..30
                        mol_type = protein
                        organism = synthetic construct
SEQUENCE: 739
KVQLVESGGG LVQAGGSLRL SCAASGRTFS                                  30

SEQ ID NO: 740          moltype = AA  length = 30
FEATURE                 Location/Qualifiers
REGION                  1..30
                        note = FR1 sequence
source                  1..30
                        mol_type = protein
                        organism = synthetic construct
SEQUENCE: 740
EVQLVESGGG LVQAGDSLRL SCAATGRTSS                                  30

SEQ ID NO: 741          moltype = AA  length = 30
FEATURE                 Location/Qualifiers
REGION                  1..30
                        note = FR1 sequence
source                  1..30
                        mol_type = protein
                        organism = synthetic construct
SEQUENCE: 741
EVQLVESGGG LVQAGGSLRL SCVASGRTLR                                  30

SEQ ID NO: 742          moltype = AA  length = 30
FEATURE                 Location/Qualifiers
REGION                  1..30
                        note = FR1 sequence
source                  1..30
                        mol_type = protein
                        organism = synthetic construct
SEQUENCE: 742
EVQLVESGGG LVQAGGSLRL TCAASGRTFS                                  30

SEQ ID NO: 743          moltype = AA  length = 30
FEATURE                 Location/Qualifiers
REGION                  1..30
                        note = FR1 sequence
source                  1..30
                        mol_type = protein
                        organism = synthetic construct
SEQUENCE: 743
EVQLVESGGG LVQAGGSLRL SCAASGLTFN                                  30

SEQ ID NO: 744          moltype = AA  length = 30
FEATURE                 Location/Qualifiers
REGION                  1..30
                        note = FR1 sequence
source                  1..30
                        mol_type = protein
                        organism = synthetic construct
```

```
SEQUENCE: 744
EVQLVESGGG LVQAGDSLRL SCAATGRTSS                                30

SEQ ID NO: 745          moltype = AA  length = 5
FEATURE                 Location/Qualifiers
REGION                  1..5
                        note = CDR sequence
source                  1..5
                        mol_type = protein
                        organism = synthetic construct
SEQUENCE: 745
DNVMG                                                            5

SEQ ID NO: 746          moltype = AA  length = 5
FEATURE                 Location/Qualifiers
REGION                  1..5
                        note = CDR sequence
source                  1..5
                        mol_type = protein
                        organism = synthetic construct
SEQUENCE: 746
IYNMD                                                            5

SEQ ID NO: 747          moltype = AA  length = 5
FEATURE                 Location/Qualifiers
REGION                  1..5
                        note = CDR sequence
source                  1..5
                        mol_type = protein
                        organism = synthetic construct
SEQUENCE: 747
RFDMS                                                            5

SEQ ID NO: 748          moltype = AA  length = 5
FEATURE                 Location/Qualifiers
REGION                  1..5
                        note = CDR sequence
source                  1..5
                        mol_type = protein
                        organism = synthetic construct
SEQUENCE: 748
SYFMG                                                            5

SEQ ID NO: 749          moltype = AA  length = 5
FEATURE                 Location/Qualifiers
REGION                  1..5
                        note = CDR sequence
source                  1..5
                        mol_type = protein
                        organism = synthetic construct
SEQUENCE: 749
IYNMD                                                            5

SEQ ID NO: 750          moltype = AA  length = 5
FEATURE                 Location/Qualifiers
REGION                  1..5
                        note = CDR sequence
source                  1..5
                        mol_type = protein
                        organism = synthetic construct
SEQUENCE: 750
RYVTG                                                            5

SEQ ID NO: 751          moltype = AA  length = 5
FEATURE                 Location/Qualifiers
REGION                  1..5
                        note = CDR sequence
source                  1..5
                        mol_type = protein
                        organism = synthetic construct
SEQUENCE: 751
SFVIG                                                            5

SEQ ID NO: 752          moltype = AA  length = 5
FEATURE                 Location/Qualifiers
REGION                  1..5
                        note = CDR sequence
source                  1..5
                        mol_type = protein
```

```
                        organism = synthetic construct
SEQUENCE: 752
QYTIT                                                                  5

SEQ ID NO: 753          moltype = AA  length = 5
FEATURE                 Location/Qualifiers
REGION                  1..5
                        note = CDR sequence
source                  1..5
                        mol_type = protein
                        organism = synthetic construct
SEQUENCE: 753
IYNMD                                                                  5

SEQ ID NO: 754          moltype = AA  length = 14
FEATURE                 Location/Qualifiers
REGION                  1..14
                        note = FR2 sequence
source                  1..14
                        mol_type = protein
                        organism = synthetic construct
SEQUENCE: 754
WYRQAPGKQR ELVA                                                        14

SEQ ID NO: 755          moltype = AA  length = 14
FEATURE                 Location/Qualifiers
REGION                  1..14
                        note = FR2 sequence
source                  1..14
                        mol_type = protein
                        organism = synthetic construct
SEQUENCE: 755
WFRQTPGKER ELIA                                                        14

SEQ ID NO: 756          moltype = AA  length = 14
FEATURE                 Location/Qualifiers
REGION                  1..14
                        note = FR2 sequence
source                  1..14
                        mol_type = protein
                        organism = synthetic construct
SEQUENCE: 756
WFRQAPGKQR EFIA                                                        14

SEQ ID NO: 757          moltype = AA  length = 14
FEATURE                 Location/Qualifiers
REGION                  1..14
                        note = FR2 sequence
source                  1..14
                        mol_type = protein
                        organism = synthetic construct
SEQUENCE: 757
WFRQAPGKER EVVA                                                        14

SEQ ID NO: 758          moltype = AA  length = 14
FEATURE                 Location/Qualifiers
REGION                  1..14
                        note = FR2 sequence
source                  1..14
                        mol_type = protein
                        organism = synthetic construct
SEQUENCE: 758
WFLQAPGKER ELIA                                                        14

SEQ ID NO: 759          moltype = AA  length = 14
FEATURE                 Location/Qualifiers
REGION                  1..14
                        note = FR2 sequence
source                  1..14
                        mol_type = protein
                        organism = synthetic construct
SEQUENCE: 759
WFRQAPGKER EVVA                                                        14

SEQ ID NO: 760          moltype = AA  length = 14
FEATURE                 Location/Qualifiers
REGION                  1..14
                        note = FR2 sequence
source                  1..14
```

```
                        mol_type = protein
                        organism = synthetic construct
SEQUENCE: 760
WFRQAPGKQR EVVA                                              14

SEQ ID NO: 761          moltype = AA  length = 14
FEATURE                 Location/Qualifiers
REGION                  1..14
                        note = FR2 sequence
source                  1..14
                        mol_type = protein
                        organism = synthetic construct
SEQUENCE: 761
WFRQAPGKER EFVA                                              14

SEQ ID NO: 762          moltype = AA  length = 14
FEATURE                 Location/Qualifiers
REGION                  1..14
                        note = FR2 sequence
source                  1..14
                        mol_type = protein
                        organism = synthetic construct
SEQUENCE: 762
WFRQGSGKGR ELIA                                              14

SEQ ID NO: 763          moltype = AA  length = 16
FEATURE                 Location/Qualifiers
REGION                  1..16
                        note = CDR sequence
source                  1..16
                        mol_type = protein
                        organism = synthetic construct
SEQUENCE: 763
TIWSSGHTNY ADSVKG                                            16

SEQ ID NO: 764          moltype = AA  length = 17
FEATURE                 Location/Qualifiers
REGION                  1..17
                        note = CDR sequence
source                  1..17
                        mol_type = protein
                        organism = synthetic construct
SEQUENCE: 764
RLWWRSGSTY YADSVKG                                           17

SEQ ID NO: 765          moltype = AA  length = 16
FEATURE                 Location/Qualifiers
REGION                  1..16
                        note = CDR sequence
source                  1..16
                        mol_type = protein
                        organism = synthetic construct
SEQUENCE: 765
TIFSGGDTDY IDSVKG                                            16

SEQ ID NO: 766          moltype = AA  length = 17
FEATURE                 Location/Qualifiers
REGION                  1..17
                        note = CDR sequence
source                  1..17
                        mol_type = protein
                        organism = synthetic construct
SEQUENCE: 766
TIRWSDGSTY YEDSVKG                                           17

SEQ ID NO: 767          moltype = AA  length = 17
FEATURE                 Location/Qualifiers
REGION                  1..17
                        note = CDR sequence
source                  1..17
                        mol_type = protein
                        organism = synthetic construct
SEQUENCE: 767
RIWWRSGATY YADSVKG                                           17

SEQ ID NO: 768          moltype = AA  length = 17
FEATURE                 Location/Qualifiers
REGION                  1..17
                        note = CDR sequence
```

```
source                  1..17
                        mol_type = protein
                        organism = synthetic construct
SEQUENCE: 768
SISWSGESTY YADSVKG                                                 17

SEQ ID NO: 769          moltype = AA  length = 16
FEATURE                 Location/Qualifiers
REGION                  1..16
                        note = CDR sequence
source                  1..16
                        mol_type = protein
                        organism = synthetic construct
SEQUENCE: 769
SITSGGSTYY EDSGKG                                                  16

SEQ ID NO: 770          moltype = AA  length = 17
FEATURE                 Location/Qualifiers
REGION                  1..17
                        note = CDR sequence
source                  1..17
                        mol_type = protein
                        organism = synthetic construct
SEQUENCE: 770
AVSWSGSSES VSNSVKG                                                 17

SEQ ID NO: 771          moltype = AA  length = 17
FEATURE                 Location/Qualifiers
REGION                  1..17
                        note = CDR sequence
source                  1..17
                        mol_type = protein
                        organism = synthetic construct
SEQUENCE: 771
RIWWRSGETY YADSVKG                                                 17

SEQ ID NO: 772          moltype = AA  length = 32
FEATURE                 Location/Qualifiers
REGION                  1..32
                        note = FR3 sequence
source                  1..32
                        mol_type = protein
                        organism = synthetic construct
SEQUENCE: 772
RFTISRDNAK NTVYLQMNSL KPEDTAVYYC NL                                32

SEQ ID NO: 773          moltype = AA  length = 32
FEATURE                 Location/Qualifiers
REGION                  1..32
                        note = FR3 sequence
source                  1..32
                        mol_type = protein
                        organism = synthetic construct
SEQUENCE: 773
RFTISRDNAK NTVYLQMNSL KPEDTSVYIC TA                                32

SEQ ID NO: 774          moltype = AA  length = 32
FEATURE                 Location/Qualifiers
REGION                  1..32
                        note = FR3 sequence
source                  1..32
                        mol_type = protein
                        organism = synthetic construct
SEQUENCE: 774
RFTISRDNAK NTVYLQMNSL KPEDTAVYYC CP                                32

SEQ ID NO: 775          moltype = AA  length = 32
FEATURE                 Location/Qualifiers
REGION                  1..32
                        note = FR3 sequence
source                  1..32
                        mol_type = protein
                        organism = synthetic construct
SEQUENCE: 775
RFTISRDNAK NTVYLQMNSL KPEDTAVYYC AA                                32

SEQ ID NO: 776          moltype = AA  length = 32
FEATURE                 Location/Qualifiers
REGION                  1..32
```

```
                        note = FR3 sequence
source                  1..32
                        mol_type = protein
                        organism = synthetic construct
SEQUENCE: 776
RFTISRGNAK NTVYLQMNSL KPEDTGVYHC TA                                 32

SEQ ID NO: 777          moltype = AA  length = 32
FEATURE                 Location/Qualifiers
REGION                  1..32
                        note = FR3 sequence
source                  1..32
                        mol_type = protein
                        organism = synthetic construct
SEQUENCE: 777
RFAISRDNAK NAVYLQMNSL NLEDTGVYYC AE                                 32

SEQ ID NO: 778          moltype = AA  length = 32
FEATURE                 Location/Qualifiers
REGION                  1..32
                        note = FR3 sequence
source                  1..32
                        mol_type = protein
                        organism = synthetic construct
SEQUENCE: 778
RFTISRDNAK NRVYLQMNSL RPEDTAVYYC AA                                 32

SEQ ID NO: 779          moltype = AA  length = 32
FEATURE                 Location/Qualifiers
REGION                  1..32
                        note = FR3 sequence
source                  1..32
                        mol_type = protein
                        organism = synthetic construct
SEQUENCE: 779
RFTISRDNAK NTAYLAMNSL KPEDTAVYYC AA                                 32

SEQ ID NO: 780          moltype = AA  length = 32
FEATURE                 Location/Qualifiers
REGION                  1..32
                        note = FR3 sequence
source                  1..32
                        mol_type = protein
                        organism = synthetic construct
SEQUENCE: 780
RFTISRDNAK NTVYLQMNSL KPEDTNVYHC AA                                 32

SEQ ID NO: 781          moltype = AA  length = 12
FEATURE                 Location/Qualifiers
REGION                  1..12
                        note = CDR sequence
source                  1..12
                        mol_type = protein
                        organism = synthetic construct
SEQUENCE: 781
GTIVTGTWRS DY                                                       12

SEQ ID NO: 782          moltype = AA  length = 10
FEATURE                 Location/Qualifiers
REGION                  1..10
                        note = CDR sequence
source                  1..10
                        mol_type = protein
                        organism = synthetic construct
SEQUENCE: 782
GDTGGAAYGY                                                          10

SEQ ID NO: 783          moltype = AA  length = 6
FEATURE                 Location/Qualifiers
REGION                  1..6
                        note = CDR sequence
source                  1..6
                        mol_type = protein
                        organism = synthetic construct
SEQUENCE: 783
LGIEYA                                                              6

SEQ ID NO: 784          moltype = AA  length = 9
FEATURE                 Location/Qualifiers
```

```
REGION                1..9
                      note = CDR sequence
source                1..9
                      mol_type = protein
                      organism = synthetic construct
SEQUENCE: 784
AKGIGVYGY                                                  9

SEQ ID NO: 785        moltype = AA  length = 10
FEATURE               Location/Qualifiers
REGION                1..10
                      note = CDR sequence
source                1..10
                      mol_type = protein
                      organism = synthetic construct
SEQUENCE: 785
GVTGGAAYGY                                                 10

SEQ ID NO: 786        moltype = AA  length = 9
FEATURE               Location/Qualifiers
REGION                1..9
                      note = CDR sequence
source                1..9
                      mol_type = protein
                      organism = synthetic construct
SEQUENCE: 786
AELPGTYDY                                                  9

SEQ ID NO: 787        moltype = AA  length = 9
FEATURE               Location/Qualifiers
REGION                1..9
                      note = CDR sequence
source                1..9
                      mol_type = protein
                      organism = synthetic construct
SEQUENCE: 787
AEPAGVYDV                                                  9

SEQ ID NO: 788        moltype = AA  length = 15
FEATURE               Location/Qualifiers
REGION                1..15
                      note = CDR sequence
source                1..15
                      mol_type = protein
                      organism = synthetic construct
SEQUENCE: 788
DRRGLASTRA ADYDY                                           15

SEQ ID NO: 789        moltype = AA  length = 10
FEATURE               Location/Qualifiers
REGION                1..10
                      note = CDR sequence
source                1..10
                      mol_type = protein
                      organism = synthetic construct
SEQUENCE: 789
GDTGGASYGY                                                 10

SEQ ID NO: 790        moltype = AA  length = 11
FEATURE               Location/Qualifiers
REGION                1..11
                      note = FR4 sequence
source                1..11
                      mol_type = protein
                      organism = synthetic construct
SEQUENCE: 790
WGQGTQVTVS S                                               11

SEQ ID NO: 791        moltype = AA  length = 11
FEATURE               Location/Qualifiers
REGION                1..11
                      note = FR4 sequence
source                1..11
                      mol_type = protein
                      organism = synthetic construct
SEQUENCE: 791
WGQGTQVTVS S                                               11

SEQ ID NO: 792        moltype = AA  length = 11
```

```
FEATURE                Location/Qualifiers
REGION                 1..11
                       note = FR4 sequence
source                 1..11
                       mol_type = protein
                       organism = synthetic construct
SEQUENCE: 792
WGQGTQVTVS S                                                        11

SEQ ID NO: 793         moltype = AA  length = 11
FEATURE                Location/Qualifiers
REGION                 1..11
                       note = FR4 sequence
source                 1..11
                       mol_type = protein
                       organism = synthetic construct
SEQUENCE: 793
WGQGTQVTVS S                                                        11

SEQ ID NO: 794         moltype = AA  length = 11
FEATURE                Location/Qualifiers
REGION                 1..11
                       note = FR4 sequence
source                 1..11
                       mol_type = protein
                       organism = synthetic construct
SEQUENCE: 794
WGQGTQVTVS S                                                        11

SEQ ID NO: 795         moltype = AA  length = 11
FEATURE                Location/Qualifiers
REGION                 1..11
                       note = FR4 sequence
source                 1..11
                       mol_type = protein
                       organism = synthetic construct
SEQUENCE: 795
WGQGTQVTVS S                                                        11

SEQ ID NO: 796         moltype = AA  length = 11
FEATURE                Location/Qualifiers
REGION                 1..11
                       note = FR4 sequence
source                 1..11
                       mol_type = protein
                       organism = synthetic construct
SEQUENCE: 796
WGQGTQVTVS S                                                        11

SEQ ID NO: 797         moltype = AA  length = 11
FEATURE                Location/Qualifiers
REGION                 1..11
                       note = FR4 sequence
source                 1..11
                       mol_type = protein
                       organism = synthetic construct
SEQUENCE: 797
WGQGTQVTVS S                                                        11

SEQ ID NO: 798         moltype = AA  length = 11
FEATURE                Location/Qualifiers
REGION                 1..11
                       note = FR4 sequence
source                 1..11
                       mol_type = protein
                       organism = synthetic construct
SEQUENCE: 798
WGQGTQVTVS S                                                        11

SEQ ID NO: 799         moltype = AA  length = 120
FEATURE                Location/Qualifiers
REGION                 1..120
                       note = Nanobody
source                 1..120
                       mol_type = protein
                       organism = synthetic construct
SEQUENCE: 799
EVQLVESGGG LVQPGGSLRL SCAASGSIFS DNVMGWYRQA PGKQRELVAT IWSSGHTNYA  60
DSVKGRFTIS RDNAKNTVYL QMNSLKPEDT AVYYCNLGTI VTGTWRSDYW GQGTQVTVSS  120
```

```
SEQ ID NO: 800          moltype = AA  length = 119
FEATURE                 Location/Qualifiers
REGION                  1..119
                        note = Nanobody
source                  1..119
                        mol_type = protein
                        organism = synthetic construct
SEQUENCE: 800
EVQLVESGGG LVQAGDSLRL SCTATGRTSS IYNMDWFRQT PGKERELIAR LWWRSGSTYY  60
ADSVKGRFTI SRDNAKNTVY LQMNSLKPED TSVYICTAGD TGGAAYGYWG QGTQVTVSS   119

SEQ ID NO: 801          moltype = AA  length = 114
FEATURE                 Location/Qualifiers
REGION                  1..114
                        note = Nanobody
source                  1..114
                        mol_type = protein
                        organism = synthetic construct
SEQUENCE: 801
EVQLVESGGG LVQAGGSLRL SCATSGFTFS RFDMSWFRQA PGKQREFIAT IFSGGDTDYI  60
DSVKGRFTIS RDNAKNTVYL QMNSLKPEDT AVYYCCPLGI EYAWGQGTQV TVSS        114

SEQ ID NO: 802          moltype = AA  length = 118
FEATURE                 Location/Qualifiers
REGION                  1..118
                        note = Nanobody
source                  1..118
                        mol_type = protein
                        organism = synthetic construct
SEQUENCE: 802
KVQLVESGGG LVQAGGSLRL SCAASGRTFS SYFMGWFRQA PGKEREVVAT IRWSDGSTYY  60
EDSVKGRFTI SRDNAKNTVY LQMNSLKPED TAVYYCAAAK GIGVYGYWGQ GTQVTVSS    118

SEQ ID NO: 803          moltype = AA  length = 119
FEATURE                 Location/Qualifiers
REGION                  1..119
                        note = Nanobody
source                  1..119
                        mol_type = protein
                        organism = synthetic construct
SEQUENCE: 803
EVQLVESGGG LVQAGDSLRL SCAATGRTSS IYNMDWFLQA PGKERELIAR IWWRSGATYY  60
ADSVKGRFTI SRGNAKNTVY LQMNSLKPED TGVYHCTAGV TGGAAYGYWG QGTQVTVSS   119

SEQ ID NO: 804          moltype = AA  length = 118
FEATURE                 Location/Qualifiers
REGION                  1..118
                        note = Nanobody
source                  1..118
                        mol_type = protein
                        organism = synthetic construct
SEQUENCE: 804
EVQLVESGGG LVQAGGSLRL SCVASGRTLR RYVTGWFRQA PGKEREVVAS ISWSGESTYY  60
ADSVKGRFAI SRDNAKNAVY LQMNSLNLED TGVYYCAEAE LPGTYDYWGQ GTQVTVSS    118

SEQ ID NO: 805          moltype = AA  length = 117
FEATURE                 Location/Qualifiers
REGION                  1..117
                        note = Nanobody
source                  1..117
                        mol_type = protein
                        organism = synthetic construct
SEQUENCE: 805
EVQLVESGGG LVQAGGSLRL TCAASGRTFS SFVIGWFRQA PGKQREVVAS ITSGGSTYYE  60
DSGKGRFTIS RDNAKNRVYL QMNSLRPEDT AVYYCAAAEP AGVYDVWGQG TQVTVSS     117

SEQ ID NO: 806          moltype = AA  length = 124
FEATURE                 Location/Qualifiers
REGION                  1..124
                        note = Nanobody
source                  1..124
                        mol_type = protein
                        organism = synthetic construct
SEQUENCE: 806
EVQLVESGGG LVQAGGSLRL SCAASGLTFN QYTITWFRQA PGKEREFVAA VSWSGSSESV  60
SNSVKGRFTI SRDNAKNTAY LAMNSLKPED TAVYYCAADR RGLASTRAAD YDYWGQGTQV  120
TVSS                                                               124
```

-continued

```
SEQ ID NO: 807          moltype = AA  length = 119
FEATURE                 Location/Qualifiers
REGION                  1..119
                        note = Nanobody
source                  1..119
                        mol_type = protein
                        organism = synthetic construct
SEQUENCE: 807
EVQLVESGGG LVQAGDSLRL SCAATGRTSS IYNMDWFRQG SGKGRELIAR IWWRSGETYY  60
ADSVKGRFTI SRDNAKNTVY LQMNSLKPED TNVYHCAAGD TGGASYGYWG QGTQVTVSS   119

SEQ ID NO: 808          moltype = AA  length = 213
FEATURE                 Location/Qualifiers
source                  1..213
                        mol_type = protein
                        organism = Homo sapiens
SEQUENCE: 808
MQLPLALCLV CLLVHTAFRV VEGQGWQAFK NDATEIIPEL GEYPEPPPEL ENNKTMNRAE  60
NGGRPPHHPF ETKDVSEYSC RELHFTRYVT DGPCRSAKPV TELVCSGQCG PARLLPNAIG  120
RGKWWRPSGP DFRCIPDRYR AQTVQLLCPG GEAPRARKVR LVASCKCKRL TRFHNQSELK  180
DFGTEAARPQ KGRKPRPRAR SAKANQAELE NAY                              213

SEQ ID NO: 809          moltype = AA  length = 213
FEATURE                 Location/Qualifiers
REGION                  1..213
                        note = Recombinant sclerostin
source                  1..213
                        mol_type = protein
                        organism = synthetic construct
SEQUENCE: 809
MPLLLLLPLL WAGALAHHHH HHHQGWQAFK NDATEIIPEL GEYPEPPPEL ENNKTMNRAE  60
NGGRPPHHPF ETKDVSEYSC RELHFTRYVT DGPCRSAKPV TELVCSGQCG PARLLPNAIG  120
RGKWWRPSGP DFRCIPDRYR AQRVQLLCPG GEAPRARKVR LVASCKCKRL TRFHNQSELK  180
DFGTEAARPQ KGRKPRPRAR SAKANQAELE NAY                              213
```

The invention claimed is:

1. A method for treating osteogenesis imperfecta (OI) in a mammalian subject, which method comprises:

(a) administering a batch of at least five doses of an anti-sclerostin antibody to a subject in need of such treatment, wherein the doses in the batch are administered at intervals of three to six weeks;

(b) then allowing the subject a dosing holiday that is at least 12 months in length; and (c) administering to the subject at least one further dose of the anti-sclerostin antibody after the dosing holiday of (b).

2. The method of claim 1, wherein:

(i) the batch of doses in (a) comprises from five to twelve doses of the anti-sclerostin antibody; and/or (ii) in (c) the subject is administered a batch of from five to twelve doses of the anti-sclerostin antibody.

3. The method of claim 1, wherein:

(i) the batch of doses in (a) comprises from five to seven doses of the anti-sclerostin antibody; or (ii) the batch of doses in (a) comprises twelve doses, with the doses given at intervals of about monthly or four weeks.

4. The method of claim 1, wherein the method further comprises:

(d) allowing the subject a further dosing holiday that is at least 12 months in length; and (e) administering to the subject at least two further doses of the anti-sclerostin antibody; and (f) optionally repeating steps (d) and (e) one or more further times.

5. The method of claim 1, wherein the amount of the anti-sclerostin antibody administered for each dose is: (i) from about 50 to 250 mg; (ii) about 70 mg; (iii) about 140 mg; or (iv) about 210 mg.

6. The method of claim 1, wherein the anti-sclerostin antibody:

(i) is administered subcutaneously;

(ii) demonstrates a binding affinity for sclerostin of SEQ ID NO: 1 of less than or equal to $1\times10^{-7}$ M;

iii) neutralizes human sclerostin in a MC3T3 cell-based mineralization assay; iv) has an $IC_{50}$ of 100 nM or less, 50 nM or less, or 25 nM or less for neutralizing human sclerostin in a cell-based assay;

(v) has an $IC_{50}$ of 100 nM or less for neutralizing human sclerostin in a cell-based Wnt signalling assay in HEK293 cells; and/or (vi) has an $IC_{50}$ of 500 nM or less for neutralizing human sclerostin in a BMP2-induced mineralization assay in MC3T3 cells.

7. The method of claim 1, wherein the anti-sclerostin antibody binds to a sclerostin polypeptide comprising the amino acid sequence set forth in SEQ ID NO: 1, where said anti-sclerostin antibody binds to:

(i) the sequence of SEQ ID NO: 6, (ii) the sequence of at least one of SEQ ID NO: 2, SEQ ID NO: 3, SEQ ID NO: 4, or SEQ ID NO: 5; or (iii) the sequence of at least one of SEQ ID NO: 70, SEQ ID NO: 71, SEQ ID NO: 72, or SEQ ID NO: 73.

8. The method of claim 1, wherein the anti-sclerostin antibody:

(i) cross-blocks the binding of at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24 to sclerostin and/or is cross-blocked from binding to sclerostin by at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24;

(ii) comprises a CDR-H1 of SEQ ID NO:245, a CDR-H2 of SEQ ID NO:246, a CDR-H3 of SEQ ID NO:247, a CDR-L1 of SEQ ID NO:78, a CDR-L2 of SEQ ID NO: 79 and a CDR-L3 of SEQ ID NO:80;

(iii) comprises heavy chains comprising SEQ ID NO: 378 and light chains comprising SEQ ID NO 376; or (iv) has heavy chains of SEQ ID NO: 145 or SEQ ID NO: 392 and light chains of SEQ ID NO: 141.

9. A method for treating osteogenesis imperfecta (OI) in a mammalian subject, which method comprises:

(a) administering at least five doses of an anti-sclerostin antibody to a subject in need of such treatment, and monitoring the subject to identify when the subject shows a reduced response to a dose of the anti-sclerostin antibody;

(b) when such a reduced response is identified, allowing the subject a dosing holiday that is at least 12 months in length; and (c) administering to the subject at least one further dose of the anti-sclerostin antibody after the dosing holiday of (b).

10. The method of claim 9, wherein:

(i) the subject is known to have been administered at least two doses of the anti-sclerostin antibody prior to step (a); and/or (ii) the subject is one considered to be likely to display reduced responsiveness to the anti-sclerostin antibody due to previous administration of the anti-sclerostin antibody.

11. The method of claim 9, wherein the monitoring is performed using:

(a) a marker of bone resorption selected from the group consisting of C-telopeptide, N-telopeptide, deoxypyridinoline, pyridinoline, urinary hydroxyproline, galactosyl hydroxylysine, and tartrate-resistant acid phosphatase;

(b) a marker of bone formation and/or mineralization selected from the group consisting of bone-specific alkaline phosphatase, peptides released from N- and C-terminal extension of type I procollagen, and osteocalcin; and/or (c) assessing bone mineral content and/or bone density using a technique selected from the group consisting of single- and dual-energy X-ray absorptometry, ultrasound, computed tomography, radiography, and magnetic resonance imaging.

12. A method for treating osteogenesis imperfecta (OI) in a mammalian subject, which method comprises:

(a) administering to a subject in need of such treatment a batch of at least five doses of an anti-sclerostin antibody, wherein the doses in the batch are administered at intervals of three to six weeks;

(b) then allowing the subject a dosing holiday that is at least 12 months in length; wherein during the dosing holiday, the subject is administered a different treatment for OI; and (c) administering to the subject at least one further dose of the anti-sclerostin antibody after the dosing holiday of (b).

13. The method of claim 12, wherein:

(i) the different treatment is an anti-resorptive, optionally a bisphosphonate; and/or (ii) the subject is one who has been administered the different treatment prior to step (a).

* * * * *